US008524236B2

(12) United States Patent
Grant et al.

(10) Patent No.: US 8,524,236 B2
(45) **Date of Patent: *Sep. 3, 2013**

(54) METHODS OF ANTAGONIZING THE BINDING OF CD40 TO CD40L WITH CD40L-SPECIFIC MONOVALENT POLYPEPTIDES IN AUTOIMMUNE INDIVIDUALS

(75) Inventors: Steven Grant, Ely (GB); Haiqun Liu, Cambridge (GB); Kevin Moulder, Cambridge (GB)

(73) Assignee: Domantis Limited, Cambridge (GB)

( * ) Notice: Subject to any disclaimer, the term of this patent is extended or adjusted under 35 U.S.C. 154(b) by 1194 days.

This patent is subject to a terminal disclaimer.

(21) Appl. No.: 11/663,247

(22) PCT Filed: Sep. 16, 2005

(86) PCT No.: PCT/GB2005/003562

§ 371 (c)(1), (2), (4) Date: Oct. 10, 2008

(87) PCT Pub. No.: WO2006/030220

PCT Pub. Date: Mar. 23, 2006

(65) Prior Publication Data

US 2009/0297524 A1 Dec. 3, 2009

Related U.S. Application Data

(63) Continuation-in-part of application No. 11/102,512, filed on Apr. 8, 2005, now Pat. No. 7,563,443.

(60) Provisional application No. 60/610,819, filed on Sep. 17, 2004.

(51) Int. Cl.
*A61K 39/395* (2006.01)
*C07K 16/28* (2006.01)

(52) U.S. Cl.
USPC .................. 424/154.1; 424/130.1; 424/133.1; 424/135.1; 424/136.1; 424/141.1; 424/143.1; 424/144.1; 424/153.1; 424/173.1; 530/387.1; 530/387.3; 530/388.1; 530/388.2; 530/388.22; 530/388.7; 530/388.73; 530/388.75

(58) Field of Classification Search
None
See application file for complete search history.

(56) References Cited

U.S. PATENT DOCUMENTS

| | | | | |
|---|---|---|---|---|
| 5,474,771 | A | 12/1995 | Lederman et al. | |
| 5,747,037 | A | 5/1998 | Noelle et al. | |
| 5,759,808 | A | 6/1998 | Casterman et al. | |
| 5,800,988 | A | 9/1998 | Casterman et al. | |
| 5,831,012 | A | 11/1998 | Nilsson et al. | |
| 5,840,526 | A | 11/1998 | Casterman et al. | |
| 5,843,440 | A | 12/1998 | Pouletty et al. | |
| 5,869,049 | A | 2/1999 | Noelle et al. | |
| 5,874,541 | A | 2/1999 | Casterman et al. | |
| 5,876,718 | A | 3/1999 | Noelle et al. | |
| 5,876,950 | A | 3/1999 | Siadak et al. | |
| 5,922,545 | A | 7/1999 | Mattheakis et al. | |
| 5,977,307 | A | 11/1999 | Friden et al. | |
| 6,005,079 | A | 12/1999 | Casterman et al. | |
| 6,015,695 | A | 1/2000 | Casterman et al. | |
| 6,297,053 | B1 | 10/2001 | Stemmer | |
| 6,328,964 | B1 | 12/2001 | Noelle et al. | |
| 6,340,459 | B1 | 1/2002 | Yellin et al. | |
| 6,375,950 | B1 | 4/2002 | Noelle et al. | |
| 6,696,245 | B2 | 2/2004 | Winter et al. | |
| 7,122,187 | B2 * | 10/2006 | Black et al. | 424/154.1 |
| 7,563,443 | B2 * | 7/2009 | Grant et al. | 424/154.1 |
| 7,829,096 | B2 * | 11/2010 | Grant et al. | 424/154.1 |
| 7,927,596 | B2 * | 4/2011 | Grant et al. | 424/154.1 |
| 2003/0099644 | A1 * | 5/2003 | Ahuja et al. | 424/144.1 |
| 2003/0211100 | A1 * | 11/2003 | Bedian et al. | 424/144.1 |
| 2003/0219437 | A1 * | 11/2003 | Yellin et al. | 424/144.1 |
| 2005/0043519 | A1 | 2/2005 | Dooley et al. | |
| 2005/0089932 | A1 | 4/2005 | Kolkman et al. | |
| 2006/0063921 | A1 * | 3/2006 | Moulder et al. | 530/387.3 |

FOREIGN PATENT DOCUMENTS

| | | |
|---|---|---|
| EP | 0368684 | 5/1990 |
| EP | 0721469 | 7/1996 |
| EP | 0742721 | 11/1996 |
| EP | 0831906 | 4/1998 |
| EP | 1005372 | 6/2000 |
| GB | 0115841.9 | 7/1969 |

(Continued)

OTHER PUBLICATIONS

Conrath, K. et al.; β-Lactamase Inhibitors Derived from Single-Domain Antibody Fragments Elicited in the Camelidae Antimicrobial Agents and Chemotherapy, Oct. 2001, p. 2807-2812 vol. 45, No. 10.

(Continued)

*Primary Examiner* — Phillip Gambel
(74) *Attorney, Agent, or Firm* — Sunstein Kann Murphy & Timbers LLP

(57) ABSTRACT

The invention relates to antibody polypeptides that monovalently bind CD40L. Antibody polypeptides that are monovalent for binding of CD40L can inhibit CD40L activity while avoiding potential undesirable effects that can occur with antibodies capable of divalent or multivalent binding of CD40L. In one aspect, a monovalent anti-CD40L antibody polypeptide consists of or comprises a single immunoglobulin variable domain that specifically binds and antagonizes the activity of CD40L, preferably without substantially agonizing CD40 and/or CD40L activity. In another aspect, the monovalent anti-CD40L antibody polypeptide is a human antibody polypeptide. The invention further encompasses methods of antagonizing CD40/CD40L interactions in an individual and methods of treating diseases or disorders involving CD40/CD40L interactions, the methods involving administering a monovalent anti-CD40L antibody polypeptide to the individual.

43 Claims, 14 Drawing Sheets

(56) References Cited

FOREIGN PATENT DOCUMENTS

| | | | |
|---|---|---|---|
| GB | 230202.4 | | 1/1997 |
| WO | WO90/05144 | | 5/1990 |
| WO | WO-9005144 | | 5/1990 |
| WO | WO90/14430 | | 11/1990 |
| WO | WO-9014430 | | 11/1990 |
| WO | WO92/01047 | | 1/1992 |
| WO | WO-9201047 | | 1/1992 |
| WO | WO92/20791 | | 11/1992 |
| WO | WO-9220791 | | 11/1992 |
| WO | WO-9305236 | | 3/1993 |
| WO | WO93/11236 | | 6/1993 |
| WO | WO 95/06481 | | 3/1995 |
| WO | WO-95/06666 | | 3/1995 |
| WO | WO-9506480 | | 3/1995 |
| WO | WO-9506481 | | 3/1995 |
| WO | WO-9606213 | | 2/1996 |
| WO | WO-9640246 | | 6/1996 |
| WO | WO-9708320 | | 3/1997 |
| WO | WO-98/58965 | | 12/1998 |
| WO | WO 99/00143 | A1 | 1/1999 |
| WO | WO-9900143 | | 1/1999 |
| WO | WO-9920749 | | 4/1999 |
| WO | WO-9923221 | | 5/1999 |
| WO | WO-0029004 | | 5/2000 |
| WO | WO-0069907 | | 11/2000 |
| WO | WO-0101743 | | 1/2001 |
| WO | WO01/68860 | A1 | 9/2001 |
| WO | WO-0168860 | | 9/2001 |
| WO | WO-0190192 | | 11/2001 |
| WO | WO 01/94586 | | 12/2001 |
| WO | WO-0194586 | | 12/2001 |
| WO | WO 02/06485 | | 1/2002 |
| WO | WO-0206485 | | 1/2002 |
| WO | WO 02/18445 | | 3/2002 |
| WO | WO-0218445 | | 3/2002 |
| WO | WO-0248193 | | 6/2002 |
| WO | WO-03002609 | | 1/2003 |
| WO | WO-03031611 | | 4/2003 |
| WO | WO-03035694 | | 5/2003 |
| WO | WO2004/003019 | * | 1/2004 |
| WO | WO 2004/003019 | | 1/2004 |
| WO | WO-2004003019 | | 1/2004 |
| WO | WO-2004041862 | | 5/2004 |
| WO | WO-2004041865 | | 5/2004 |
| WO | WO-2004044011 | | 5/2004 |
| WO | WO 2004/058821 | | 7/2004 |
| WO | WO 2004/058822 | | 7/2004 |
| WO | WO-2004058821 | | 7/2004 |
| WO | WO-2004058822 | | 7/2004 |
| WO | WO 2005/035572 | | 4/2005 |
| WO | WO-2005035572 | | 5/2005 |
| WO | WO-2005040229 | | 5/2005 |

OTHER PUBLICATIONS

Hoogenboom, H. R.; "Mix and Match: Building Manifold Binding Sites"; Nature Biotechnology; vol. 15, p. 125-126, Feb. 1997.

Conrath, K. et al., "Camel Single-domain Antibodies as Modular Building Units in Bispecific and Bivalent Antibody Constructs", The Journal of Biological Chemistry, vol. 276, No. 10, Issue of Mar. 9, 2001, p. 7346-7350.

Smith, B. et al., "Prolonged in Vivo Residence Times of antibody Fragments Associated with Albumin"; Bioconjugate Chem, vol. 12 p. 750-756; 2001.

Reiter, Y. et al. "An Antibody Single-domain Phage Display Library of a Native Heavy Chain Variable Region: Isolation of Functional Single-domain VH Molecules with a Unique Interface", J. Mol. Biol, 1999, vol. 290, p. 685-698.

Nygren, P. et al., "In Vivo Stabilization of a Human Recombinant CD4 Derivative by Fusion to a Serum-albumin-binding Receptor", Vaccines, vol. 91, 1991, p. 363-368.

Ghahroudi, et al., "Selection and Identification of Single Domain Antibody Fragments from Camel Heavey-chain Antibodies"; Federation of European Biochemical Societies, 1997, p. 521-526.

Van Der Linden, R. et al., "Induction of Immune Responses and Molecular Cloning of the Heavy Chain Antibody Repertoire of Lama Glama",Journal of Immunological Methods 2000, p. 185-195.

Stahl, et al. "The Use of Gene Fusions to Protein a and Protein G in Immunology and Biotechnology", Biomedische Bibl, 1997, p. 66-76.

Waldmann, et al., "The Renal Handling of Low Molecular Weight Proteins"; The Journal of Clinical Investigation, vol. 51, 1972, p. 2162-2174.

Gale Encyclopedia of Medicine, Gale Research, 1999, p. 419.

Hulme & Hardwicke, , "Kidney Function and Structure", Proc Royal Soc. Medicinevol. 59, 1966, p. 509-512.

Birkett, D. "Pharmacokinetics Made Easy", 1998, p. 16-24.

Cortez-Retamozo, V., Efficient Tumor Targeting by Single-Domain Antibody Fragments of Camels; Int. J. Cancer, 2002, p. 456-462.

Patentee's Sep. 25, 2006 letter regarding EP05076402.6.

Patentee's Dec. 23, 2005 letter regarding EP03776677.1.

Ward, et al., "Binding Activities of a Repertoire of Single Immunoglobulin Variable Domains Secreted from *Escherichia coli*"; Letters to Nature; Nature; vol. 341, 1989; p. 544-546.

Van Den Beucken, et al., "Building Novel Binding Ligands to B7.1 and B7.2 Based on Human Antibody Sinigle Variable Light Chain Domains", J. Mol. Biol.; 2001, vol. 310, p. 591-601.

Holliger et al., "Retargeting Serum Immunoglobulin with Bispecific Diabodies", 1997,Nature Biotechnology, vol. 15, p. 632-638.

Mulyldermans, S., "Single Domain Camel Antibodies: Current Status", Molecular Biotechnology, 2001, vol. 74, p. 277-302.

Abuchowski et al.,Alteration of immunological properties of bovine serum albumin by covalent attachment of polyethylene glycol J. Biol. Chem. 1977, 252:3578-81; American Society for Biochemistry and Molecular Biology; .U.S.

Alderson et al., 1994,Synergistic effects of IL-4 and either GM-CSF or IL-3 on the induction of CD23 expression by human monocytes: regulatory effects of IFN-alpha and IFN-gamma; Cytokine, 6(4):407-13; Academic Press; US.

Aggarwal et al., 2003, Interleukin-23 promotes a distinct CD4 T cell activation state characterized by the production of interleukin-17; J Biol Chem., 278(3):1910-4; Publisher: American Society for Biochemistry and Molecular Biology; .U.S.

Andoh et al., 2002, Interleukin (IL)-4 and IL-17 synergistically stimulate IL-6 secretion in human colonic myofibroblasts; Int J Mol Med., 10(5):631-4; Publisher: D.A. Spandidos.

Armitage et al., 1992, Molecular and biological characterization of a murine ligand for CD40; Nature 357: 80-82; Publisher: Nature Publishing Group, England.

Asadullah et al., 2000, IL-15 and IL-16 overexpression in cutaneous T-cell lymphomas: stage-dependent increase in mycosis fungoides progression; Exp Dermatol., 9(4):248-51; Publisher: Munksgaard, Denmark.

Azuma, M. et al., 1993, B70 antigen is a second ligand for CTLA-4 and CD28. Nature 366, 76-79 ; Publisher: Nature Publishing Group, England.

Balasa et al., 1997, CD40 ligand-CD40 interactions are necessary for the initiation of insulitis and diabetes in nonobese diabetic mice; J. Immunol. 159(9): 4620-7; Publisher: American Association of Immunologists, US.

Bennett et al., 1998, Help for cytotoxic-T-cell responses is mediated by CD40 signalling. Nature 393: 478-480; Publisher: Nature Publishing Group, England.

Van Den Beuken et al.,Building novel binding ligands to B7.1 and B7.2 based on human antibody single variable light chain domains. J. Mol. Biol. (2001) 310, 591-601; Publisher: Academic Press, England.

Blair et al., 2000, CD40 ligand (CD154) triggers a short-term CD4(+) T cell activation response that results in secretion of immunomodulatory cytokines and apoptosis. J. Exp. Med. 191: 651-660 Publisher: Rockefeller University Press, U.S.

Blazar et al., 1997, Blockade of CD40 ligand-CD40 interaction impairs CD4+ T cell-mediated alloreactivity by inhibiting mature donor T cell expansion and function after bone marrow transplantation. J. Immunol. 158: 29-39; Publisher: American Association of Immunologists, US.

Bird et al., 1988, Single-chain antigen-binding proteins. Science 242:423-426; Publisher: American Association for the Advancement of Science, US.
Borset et al.,1994, TNF and IL-6 are potent growth factors for OH-2, a novel human myeloma cell line. Eur J Haematol., 53(1):31-7; Publisher: Blackwell, England.
Boumpas et al., 2003, A short course of BG9588 (anti-CD40 ligand antibody) improves serologic activity and decreases hematuria in patients with proliferative lupus glomerulonephritis. Arthritis Rheum. 48: 719-727; Publisher: Wiley-Liss, Inc., U.S.
Brach et al. 1992, Synergy of interleukin 3 and tumor necrosis factor alpha in stimulating clonal growth of acute myelogenous leukemia blasts is the result of induction of secondary hematopoietic cytokines by tumor necrosis factor alpha. Cancer Res., 52(8):2197-2201; American Association for Cancer Research, U.S.
Brenner et al., 1997, Evidence for a novel function of the CD40 ligand as a signalling molecule in T-lymphocytes. FEBS Lett. 417: 301-306; Publisher: Elsevier Science B.V. Netherlands.
Burchill et al., 2003 Inhibition of interleukin-17 prevents the development of arthritis in vaccinated mice challenged with *Borrelia burgdorferi*. Infect Immun., 71(6):3437-42; Publisher: American Society for Microbiology, U.S.
Chess, C., 2001, In Therapeutic Immunology, 2nd edition, Austen, K.F., Burakoff, S., Rosen, F. and Strom, T., eds., Blackwell Sciences, pp. 441-456.
Chiswell et al., 1992, Phage antibodies: will new 'coliclonal' antibodies replace monoclonal antibodies? Trends Biotechnol. 10: 80-84; Publisher: Elsevier Science Publishers, England.
Caryanniotis et al., 1997, Suppression of murine thyroiditis via blockade of the CD40-CD40L interaction. Immunology 90: 421-426; Publisher: Blackwell Scientific Publications, England.
Chegini et al., 2003,Differential expression of interleukins (IL)-13 and IL-15 in ectopic and eutopic endometrium of women with endometriosis and normal fertile women. Am J Reprod Immunol. 49(2):75-83.
Chen et al., 2003, Stimulation of airway mucin gene expression by interleukin (IL)-17 through IL-6 paracrine/autocrine loop. J Biol Chem. 278(19):17036-43; American Society for Biochemistry and Molecular Biology; .U.S.
Cheng et al., 2002, Am J Respir Crit Care Med., 166(3):409-16.
Chess, 2001, "Blockade of the CD40L/CD40 Pathway," in Therapeutic Immunology 2nd Edition, Austen, Burakof, Rosen and Strom, Eds., Blackwell Sciences (Pubs.), pp. 441-456.
Chothia et al., 1992, J. Mol. Biol. 227: 799; Publisher: Academic Press, England.
Chothia et al., 1989, Nature 342: 877; Publisher: Nature Publishing Group, England.
Chothia et al., 1985, J. Mol. Biol. 186: 651-663; Publisher: Academic Press, England.
Chothia and Lesk, 1987, J. Mol. Biol. 196(4):901-917; Publisher: Academic Press, England.
Clark & Ledbetter, 1986, Proc. Natl. Acad. Sci. U.S.A. 83: 4494.
Kuperman et al., 2002, Nat Med., 8(8):885-9.
Corre et al., 1999, Exp Hematol., 27(1):28-36.
Covey et al., 1994, Mol. Immunol. 31: 471-484.
Cox et al., 1994, Eur. J. Immunol. 24: 827.
Crameri et al., 1996, Nature Med., 2: 100.
Croft et al., 1999, Am J Pathol., 154(4):1149-58.
Cua et al., 2003, Nature, 421(6924):744-8.
Davies & Riechmann, 1995, Biotechnology N.Y. 13: 475-479.
Davies & Riechmann, 1994, FEBS Lett. 339: 285-290.
Davis et al., 2001, J. Rheumatol. 28: 95-101.
Deblaker-Hohe, 1995, Cell Immunol., 165(1):33-43.
Delgado et al., 1996 Br. J. Cancer, 73: 175.
Dellinger, 2003, Clin Infect Dis., 36(10):1259-65.
Deng et al., 1994, J. Biol. Chem., 269: 9533; American Society for Biochemistry and Molecular Biology; .U.S.
Denning, 1996, J. Immunol., 156(12):4807-14; Publisher: American Association of Immunologists, US.
Durie et al., 1993, Science 261: 132:p. 122; American Association for the Advancement of Science, US.
Early et al., 1996, J. Immunol. 157: 3159-3164; Publisher: American Association of Immunologists, US.
Eckenberg et al., 2000, Immunol., 165(8): 4312-8.
Eum et al., 2003, J Allergy Clin Immunol., 111(5):1049-61.
Feliciani et al., 1999, Int J Immunopathol Pharmacol., 12(2):55-61.
Ferretti et al,. 2003, J Immunol. 170(4):2106-12; Publisher: American Association of Immunologists, US.
Francis et al., Pharmaceutical Biotechnology vol. 3 (Borchardt, R. T. ed.); and Stability of Protein Pharmaceuticals: in vivo Pathways of Degradation and Strategies for Protein Stabilization 1991 pp. 235-263, Plenum, NY.
Freedman, A. S. et al., 1987, J. Immunol. 137, 3260-3267; Publisher: American Association of Immunologists, US.
Freeman, G. J. et al., 1993, J. Exp. Med. 178, 2185-2192. Publisher: Rockefeller University Press, U.S.
Freeman, G. J. et al., 1993, Science 262, 909-911; American Association for the Advancement of Science, US.
Freeman, G. J. et al., 1991, J. Exp. Med. 174, 625-631.Publisher: Rockefeller University Press, U.S.
Freeman, G. J. et al., 1989, J. Immunol. 143, 2714-2722; Publisher: American Association of Immunologists, US.
Fukao et al., 2000, J Immunol., 164(1):64-71; Publisher: American Association of Immunologists, US.
Gahroudi et al., 1997, FEBS Lett. 414: 521-526.
Garn et al., 2002, Immunobiology, 205(3):321-34.
Garrone et al., 1995, J Exp Med 182, 1265-1273. Publisher: Rockefeller University Press, U.S.
Gastinel et al., 1992, PNAS, 89:638.
Gerritse, 1996, Proc. Natl. Acad. Sci. U.S.A. 93: 2494.
Gobburu, et al., 1998, JPET, 286, 925-930.
Gordon et al., 1988, J. Immunol. 140: 1425; Publisher: American Association of Immunologists, US.
Gordon et al., 1987, Eur. J. Immunol. 17: 1535.
Gounni et al., 2000, Blood, 96(6):2163-71.
Graf et al., 1992, Eur. J. Immunol. 22: 3191-3194.
Greenberg et al. Nature 374:168-173 1995; Publisher: Nature Publishing Group, England.
Greenwald et al., 2000, Crit. Rev. Ther. Drug Carrier Syst. 17:101.
Gregory et al., 2003, J. Immunol., 170(11):5359-66; Publisher: American Association of Immunologists, US.
Grewal et al., 1996, Science 273: 186; American Association for the Advancement of Science, US.
Hahn et al., 2003, J Allergy Clin Immunol., 111(6):1361-1369.
Halász et al., 2003, Allergy Asthma Proc., 24(2):111-8.
Hamers-Casterman et al., 1993, Nature 363: 446-448; Publisher: Nature Publishing Group, England.
Hellings et al., 2003, Am J Respir Cell Mol Biol., 28(1):42-50.
Herbelin et al., 1992, J Immunol., 148(1):99-105; Publisher: American Association of Immunologists, US.
Herman et al., 1994, Macromol. Chem. Phys. 195:203.
Hermouet et al., 2002, Cytokine, 20(4):178-83.
Hershfield et al., 1991, PNAS 88:7185.
Holliger and Hudson, 2005, Nature Biotechnol., 23:1126-1136.
Holliger et al, Nat. Biotechnol. 1997, 15(7):632-6.
Holliger et al., 1993, PNAS (USA) 90:6444-6448.
Holt et al., 2003, Trends Biotech., 21(11):484-490 [ISR].
Hood et al. (1967) Cold Spring Harbor Symp. Quant. Biol., 48: 133.
Hoogenboom et al., 1991, Nucleic Acids Res. 19: 4133-4137.
Hoogenboom & Winter, 1992, J. Mol. Biol., 227: 381; Publisher: Academic Press, England.
Honorati et al., 2002, Osteoarthritis Cartilage, 10(10):799-807.
Howard et al., 1999, J. Clin . Invest. 103: 281-290.
Howells et al., 1991, Eur J Immunol., 21(1):97-101.
Huang et al., 2002, Arthritis Rheum. 46: 1554-1562.
Hudson et al., Journal Immunol Methods 231 (1999) 177-189.
Hurst et al., 2002, J Immunol., 169(1):443-53; Publisher: American Association of Immunologists, US.
Ikeda et al., 2003 Blood, 101(9):3594-6.
Itoh et al., 1994, Cell Immunol., 157(2):478-88.
Jones and Chan, 2002, Am J Respir Cell Mol Biol., 26(6):748-53.
Joosten et al., 2003, Arthritis Rheum., 48(2):339-47.
Jutel et al., 2003, Eur J Immunol., 33(5):1205-14.
Kabat et al., 1991, Sequences of proteins of immunological interest, U.S. Department of Health and Human Services.

Kalled et al., 1998, J. Immunol. 160: 2158-2165; Publisher: American Association of Immunologists, US.
Kalunian et al., 2002, Arthritis Rheum. 46: 3251-3258.
Kaneda et al., 2003, J Interferon Cytokine Res., 23(3):155-62.
Kaufmann, 2001, Rheumatology (Oxford)., 40(4):474-5.
Keates et al, 2000, Gastroenterology., 119(4):972-82.
Kelly-Welch, 2003, Science, 300(5625):1527-8; American Association for the Advancement of Science, US.
Kirk et al., 1997, Proc. Natl. Acad. Sci. U.S.A. 94: 8789-8794.
Kitamura et al., 1991, Cancer Res. 51:4310.
Kong et al., 1999, Nature, 402:304-309; Publisher: Nature Publishing Group, England.
Kotake and Kamatani, 2002, Drug News Perspect., 15(1):17-23.
Kudo et al., 2003, Bone, 32(1):1-7.
Laan et al., 2003, Eur Respir J. 21(3):387-93.
Larsen et al., 1996, Nature 381: 434-438; Publisher: Nature Publishing Group, England.
Laman et al., 1998, Mult. Scler. 4: 14.
Lankford and Frucht, 2003, J Leukoc Biol. 73(1):49-56.
Larsen et al., 1996, Transplantation 61: 4.
Lauwerys et al., 1999, Cytokine, 11(11):822-30.
Lauwerys et al., 1998, Eur J Immunol., 28(6):2017-24.
Lazenby et al., 1992, Cytokine, 4(6):479-87.
Lederman et al., 1993, Curr. Opin. Immunol. 5: 439-444.
Lederman et al., 1992, J. Exp. Med., 175: 1091-1101. Publisher: Rockefeller University Press, U.S.
Lederman et al., 1992, J. Immunol. 149: 3817-3826; Publisher: American Association of Immunologists, US.
Legrand et al., 2001, Arthritis Rheum., 44(9):2078-83.
Li et al., 2001, Nat Med., 7(1):114-8.
Liao et al., 2002, J. Immunol., 169(8):4288-97; Publisher: American Association of Immunologists, US.
Ling and Mattiasson, 1983, Immunol. Methods 59:327.
Linsley & Ledbetter, 1993, Ann. Rev. Immunol. 11: 191-212; Jenkins et al., 1993, Curr Opin. Immunol. 5: 361-367; and Boussiotis et al., 1996, Immunol. Rev. 153: 5-26.
Little et al., 2003, Am J Respir Cell Mol Biol., 28(3):354-62.
Lorenz and Bischoff, 2001, Immunol Rev., 179:57-60.
Low et al., 1996, J. Mol. Biol., 260: 359.
Lowry et al., 1951, J. Biol. Chem. 193: 265-275; American Society for Biochemistry and Molecular Biology; .U.S.
Lubberts et al., 2003, J Immunol., 170(5):2655-62; Publisher: American Association of Immunologists, US.
Mach et al., 1998, Nature 394: 200-203; Publisher: Nature Publishing Group, England.
Martin et al., 1996, J. Mol. Biol. 263: 800; Publisher: Academic Press, England.
Mathy et al., 2000, Immunology., 100(1):63-9.
Matthews et al., 2003, Am. J. Transplantation, 3:794-803.
Mehrota et al., 1995, J Immunol., 154(10):5093-102; Publisher: American Association of Immunologists, US.
Minshall and Hamid, 2000, Clin Exp Allergy., 30(3):301-303.
Mohan et al., 1995, J. Immunol. 154: 1470-1480.
Moriwaki et al., 2003, Metabolism, 52(5):605-8.
Musashi et al., 1991, Blood, 78(6):1448-51.
Mulydermans et al., 2001, Trends Biochem. Sci., 26(4):230-235 [ISR].
Mysliwiec et al., 2003, Int Immunopharmacol., 3(4):549-52.
Nielsen et al., 2003, Scand J Gastroenterol., 38(2):180-5.
Nucci et al., Adv. Drug Delivery Reviews 1991, 6:133.
Okamoto et al., 2002, Blood, 99(4):1289-98.
Padlan et al., 1994, Mol. Immunol. 31: 169-217.
Pankow et al., 2000, J. Immunol. 165(1):263-70; Publisher: American Association of Immunologists, US.
Parada et al., 1998, J Immunol., 1;160(5):2115-20; Publisher: American Association of Immunologists, US.
Parker et al., 1995, Proc. Natl. Acad. Sci. U.S.A. 92: 9560-9564.
Pedley et al., 1994, Br. J. Cancer, 70:1126.
Pflanz et al., 2002, Immunity., 16(6):779-90.
Plenum, NY; Goodson and Katre, 1990, Bio/Technology, 8:343.
Qin et al., 2001, Blood., 98(9):2778-83.
Ragab et al., 2002, Am J Physiol Cell Physiol., 283(3):C679-87.
Riechmann et al., 1995, Bio/Technology, 13: 475.
Reiter et al., 1994, Protein Eng. 7:697-704.
Rich and Kupper, 2001, Curr Biol., 11(13):R531-4.
Ridge et al., 1998, Nature 393: 474-478; Publisher: Nature Publishing Group, England.
Ridgeway et al., 1996, Protein Eng. 7:617-621.
Roopenian et al., 2003 J. Immunol. 170:3528; Publisher: American Association of Immunologists, US.
Salmaggi et al., 2003, J Neurooncol., 62(3):297-303.
Shirai et al., 1996, FEBS Letters 399: 1.
Schoenberger et al., 1998, Nature 393: 480-483; Publisher: Nature Publishing Group, England.
Scott & Smith, 1990, Science 249: 386; American Association for the Advancement of Science, US.
Sinah et al., 2002, Blood, 100(7):2642-9.
Smith, 1985, Science 228: 1315; American Association for the Advancement of Science, US.
Spadaro et al., 2003, Clin Rheumatol., 22(2):107-11.
Stemmer, 1994, Nature 370: 389-39.
Strengell et al., 2003, J Immunol., 170(11):5464-9; Publisher: American Association of Immunologists, US.
Stuber et al., 1996, J. Exp. Med. 183: 693-698;Publisher: Rockefeller University Press, U.S.
Tahar et al., 1994, Eur Cytokine Netw., 5(5):455-60.
Tain et al., 2003, Cytokine. 2003, 21(3):155-9.
Temann et al., 2002, J Clin Invest., 109(1):29-39.
Terada et al., 2000, Clin Exp Allergy., 30(3):348-55.
Thomas and Heywood, 2000, Thorax, 57(9):774-8.
Toda, 2003, J Allergy Clin Immunol., 111(4):875-81.
Tomlinson et al., 1996 J. Mol. Biol., 256: 813; Publisher: Academic Press, England.
Tomlinson et al., 1995, EMBO J. 14: 4628.
Tomlinson et al., 1992, J. Mol. Biol. 227: 7768; Publisher: Academic Press, England.
Uckun et al., 1991, J. Biol. Chem. 266:17478; American Society for Biochemistry and Molecular Biology; .U.S.
Ward et al., 1989, Nature 341: 544-546; Publisher: Nature Publishing Group, England.
Wilkinson et al., 1987, Immunol. Letters, 15: 17.
Winter et al., 1994, Ann. Rev. Immunology 12, 433-55.
Yellin et al., 1995, J. Exp. Med. 182: 1857-1864; Publisher: Rockefeller University Press, U.S.
Yellin et al., 1995, J. Leuko. Biol. 58: 209-216.
Yellin et al., 1991, J. Immunol. 147: 3389-3395; Publisher: American Association of Immunologists, US.
Yoshida et al., 2001, Cell Immunol., 207(2):75-80.
Zalipsky, 1995, Bioconjug. Chem. 6:150.
Zhu et al., 1997, Protein Science 6:781-788.
Zhang, 1995, J Exp Med., 182(3):699-709; Publisher: Rockefeller University Press, U.S.
Zhou et al., 2001, Respir Res., 2(2):80-4.
Bram, Peter et al. "A humanzied anti-human CD154 monoclonal antibody blocks CD154-CD40 mediated human B cell activation" International Immunopharmacology, vol. 1, No. 2, Feb. 2001.
Muyldermans S. et al. "Recognition of antigens by single-domain antibody fragments: the superfluous luxury of paired domains" Trends in Biochemical Sciences, Elsevier, Haywards, GB, vol. 26, No. 4, Apr. 2001.
Holt L.J. et al. "Domain antibodies: proteins for therapy" Trends in Biotechnology, Elsevier, Publications, Cambridge, GB, vol. 21, No. 11, Nov. 2003.
Durie F. et al. "Prevention of Collagen-induced arthritis with an antibody to gp39, the ligand for CD40" Science, American Association for the Advancement of Science, US, vol. 261, No. 5126, Sep. 3, 1993.
International Search Report, PCT/GB2005/003562, Nov. 23, 2005.

* cited by examiner

M 1 2

1 2

```
     E   V   Q   L   L   E   S   G   G   G   L   V   Q   P   G   G
1    GAG GTG CAG CTG TTG GAG TCT GGG GGA GGC TTG GTA CAG CCT GGG GGG
     CTC CAC GTC GAC AAC CTC AGA CCC CCT CCG AAC CAT GTC GGA CCC CCC

     S   L   R   L   S   C   A   A   S   G   F   T   F   S   S   Y
49   TCC CTG CGT CTC TCC TGT GCA GCC TCC GGA TTC ACC TTT AGC AGC TAT
     AGG GAC GCA GAG AGG ACA CGT CGG AGG CCT AAG TGG AAA TCG TCG ATA
                                                              HCDR1
     A   M   S   W   V   R   Q   A   P   G   K   G   L   E   W   V
97   GCC ATG AGC TGG GTC CGC CAG GCT CCA GGG AAG GGT CTA GAG TGG GTC
     CGG TAC TCG ACC CAG GCG GTC CGA GGT CCC TTC CCA GAT CTC ACC CAG

     S   A   I   S   G   S   G   G   S   T   Y   Y   A   D   S   V
145  TCA GCT ATT AGT GGT AGT GGT GGT AGC ACA TAC TAC GCA GAC TCC GTG
     AGT CGA TAA TCA CCA TCA CCA CCA TCG TGT ATG ATG CGT CTG AGG CAC
                                    HCDR2
     K   G   R   F   T   I   S   R   D   N   S   K   N   T   L   Y
193  AAG GGC CGG TTC ACC ATC TCC CGT GAC AAT TCC AAG AAC ACG CTG TAT
     TTC CCG GCC AAG TGG TAG AGG GCA CTG TTA AGG TTC TTG TGC GAC ATA

     L   Q   M   N   S   L   R   A   E   D   T   A   V   Y   Y   C
241  CTG CAA ATG AAC AGC CTG CGT GCC GAG GAC ACC GCG GTA TAT TAC TGT
     GAC GTT TAC TTG TCG GAC GCA CGG CTC CTG TGG CGC CAT ATA ATG ACA
```

*Figure 5*

```
         A   K   S   Y   G   A   F   D   Y   W   G   Q   G   T   L   V
289     GCG AAA AGT TAT GGT GCT TTT GAC TAC TGG GGC CAG GGA ACC CTG GTC
        CGC TTT TCA ATA CCA CGA AAA CTG ATG ACC CCG GTC CCT TGG GAC CAG
                        HCDR3

         T   V   S   S
337     ACC GTC TCG AGC
        TGG CAG AGC TCG
```

*Figure 5 (con't)*

```
    D   I   Q   M   T   Q   S   P   S   S   L   S   A   S   V   G
1   GAC ATC CAG ATG ACC CAG TCT CCA TCC TCC CTG TCT GCA TCT GTA GGA
    CTG TAG GTC TAC TGG GTC AGA GGT AGG AGG GAC AGA CGT AGA CAT CCT

    D   R   V   T   I   T   C   R   A   S   Q   S   I   S   S   Y
49  GAC CGT GTC ACC ATC ACT TGC CGG GCA AGT CAG AGC ATT AGC AGC TAT
    CTG GCA CAG TGG TAG TGA ACG GCC CGT TCA GTC TCG TAA TCG TCG ATA
                                          LCDR1
    L   N   W   Y   Q   Q   K   P   G   K   A   P   K   L   L   I
97  TTA AAT TGG TAC CAG CAG AAA CCA GGG AAA GCC CCT AAG CTC CTG ATC
    AAT TTA ACC ATG GTC GTC TTT GGT CCC TTT CGG GGA TTC GAG GAC TAG

    Y   A   A   S   S   L   Q   S   G   V   P   S   R   F   S   G
145 TAT GCT GCA TCC AGT TTG CAA AGT GGG GTC CCA TCA CGT TTC AGT GGC
    ATA CGA CGT AGG TCA AAC GTT TCA CCC CAG GGT AGT GCA AAG TCA CCG
            LCDR2
    S   G   S   G   T   D   F   T   L   T   I   S   S   L   Q   P
193 AGT GGA TCT GGG ACA GAT TTC ACT CTC ACC ATC AGC AGT CTG CAA CCT
    TCA CCT AGA CCC TGT CTA AAG TGA GAG TGG TAG TCG TCA GAC GTT GGA

    E   D   F   A   T   Y   Y   C   Q   Q   S   Y   S   T   P   N
241 GAA GAT TTT GCT ACG TAC TAC TGT CAA CAG AGT TAC AGT ACC CCT AAT
    CTT CTA AAA CGA TGC ATG ATG ACA GTT GTC TCA ATG TCA TGG GGA TTA
                                              LCDR3
    T   F   G   Q   G   T   K   V   E   I   K   R
289 ACG TTC GGC CAA GGG ACC AAG GTG GAA ATC AAA CGG
    TGC AAG CCG GTT CCC TGG TTC CAC CTT TAG TTT GCC
```

*Figure 6*

```
                       (1) 1        10        20        30        40        50              66
GAS wt                 (1) ATGTTGTTTAAATCCCTTTCAAAGTTAGCAACCGCTGCTGCTTTTTTTGCTGGCGTCGCAACTGCG
GAS leader e.coli      (1) ATGCTGTTTAAAAGCCTGAGCAAACTGGCGACCGCGGCGGCGTTTTTTGCGGGCGTGGCGACCGCG
GAS leaderAT           (1) ATGTTATTTAAATCATTATCAAAATTAGCAACCGCAGCAGCATTTTTTGCAGGCGTGGCAACAGCG
```

*Figure 8*

SEQUENCE LISTING

```
<160> NUMBER OF SEQ ID NOS: 477

<210> SEQ ID NO 1
<211> LENGTH: 116
<212> TYPE: PRT
<213> ORGANISM: Homo sapiens

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Tyr Gly Ala Phe Asp Tyr Trp Gly Gln Gly Thr Leu Val
            100                 105                 110

Thr Val Ser Ser
        115
```

<210> SEQ ID NO 2
<211> LENGTH: 288
<212> TYPE: DNA
<213> ORGANISM: Homo sapiens

<400> SEQUENCE: 2
gaggtgcagc tgttggagtc tgggggaggc ttggtacagc ctggggggtc cctgcgtctc 60
tcctgtgcag cctccggatt cacctttagc agctatgcca tgagctgggt ccgccaggct 120
ccagggaagg gtctagagtg ggtctcagct attagtggta gtggtggtag cacatactac 180
gcagactccg tgaagggccg gttcaccatc tcccgtgaca attccaagaa cacgctgtat 240
ctgcaaatga acagcctgcg tgccgaggac accgcggtat attactgt 288

<210> SEQ ID NO 3
<211> LENGTH: 108
<212> TYPE: PRT
<213> ORGANISM: Homo sapiens

<400> SEQUENCE: 3

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Pro Asn
85 90 95

Thr Phe Gly Gln Gly Thr Lys Val Glu Ile Lys Arg
100 105

<210> SEQ ID NO 4
<211> LENGTH: 324
<212> TYPE: DNA
<213> ORGANISM: Homo sapiens

<400> SEQUENCE: 4
gacatccaga tgacccagtc tccatcctcc ctgtctgcat ctgtaggaga ccgtgtcacc 60
atcacttgcc gggcaagtca gagcattagc agctatttaa attggtacca gcagaaacca 120
gggaaagccc ctaagctcct gatctatgct gcatccagtt tgcaaagtgg ggtcccatca 180
cgtttcagtg gcagtggatc tgggacagat ttcactctca ccatcagcag tctgcaacct 240
gaagattttg ctacgtacta ctgtcaacag agttacagta cccctaatac gttcggccaa 300
gggaccaagg tggaaatcaa acgg 324

<210> SEQ ID NO 5
<211> LENGTH: 120
<212> TYPE: PRT
<213> ORGANISM: Homo sapiens

<400> SEQUENCE: 5

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Arg Ile Ser Asp Glu
20 25 30

```
Asp Met Gly Trp Val Arg Gln Ala Pro Gly Lys Gly Leu Glu Trp Val
        35                  40                  45

Ser Ser Ile Tyr Gly Pro Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Ala Leu Glu Pro Leu Ser Glu Pro Leu Gly Phe Trp Gly Gln
            100                 105                 110

Gly Thr Leu Val Thr Val Ser Ser
        115                 120


<210> SEQ ID NO 6
<211> LENGTH: 108
<212> TYPE: PRT
<213> ORGANISM: Artificial
<220> FEATURE:
<223> OTHER INFORMATION: Primary amino acid sequence of Vk dummy

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Asn
                85                  90                  95

Thr Phe Gly Gln Gly Thr Lys Val Glu Ile Lys Arg
            100                 105


<210> SEQ ID NO 7
<211> LENGTH: 116
<212> TYPE: PRT
<213> ORGANISM: Homo sapiens

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Glu Met Met Trp Val Arg Gln Ala Pro Gly Lys Gly Leu Glu Trp Val
        35                  40                  45

Ser Thr Ile Thr Ser Asp Gly Ile Ser Thr Tyr Tyr Ala Asp Ser Val
    50                  55                  60

Lys Gly Arg Phe Thr Ile Phe Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Gly Arg Phe Phe Asp Tyr Trp Gly Gln Gly Thr Leu Val
            100                 105                 110

Thr Val Ser Ser
```

115

<210> SEQ ID NO 8
<211> LENGTH: 116
<212> TYPE: PRT
<213> ORGANISM: Homo sapiens

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Asn Tyr
            20                  25                  30

Glu Met Thr Trp Val Arg Gln Ala Pro Gly Lys Gly Leu Glu Trp Val
        35                  40                  45

Ser Ser Ile Thr Ser Asp Gly Thr Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Asn Pro Pro Phe Asp Tyr Trp Gly Gln Gly Thr Leu Val
            100                 105                 110

Thr Val Ser Ser
        115

<210> SEQ ID NO 9
<211> LENGTH: 116
<212> TYPE: PRT
<213> ORGANISM: Homo sapiens

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Gly Tyr
            20                  25                  30

Glu Met Ala Trp Val Arg Gln Ala Pro Gly Lys Gly Leu Glu Trp Val
        35                  40                  45

Ser Ser Ile Thr Ser Asp Gly Thr Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Gly Leu Arg Phe Asp Tyr Trp Gly Gln Gly Thr Leu Val
            100                 105                 110

Thr Val Ser Ser
        115

<210> SEQ ID NO 10
<211> LENGTH: 116
<212> TYPE: PRT
<213> ORGANISM: Homo sapiens

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Leu Tyr
            20                  25                  30

```
Glu Met Thr Trp Val Arg Gln Ala Pro Gly Lys Gly Leu Glu Trp Val
        35                  40                  45

Ser Ser Ile Thr Ser Asp Gly Val Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Gly Val Ile Phe Asp Tyr Trp Gly Gln Gly Thr Leu Val
            100                 105                 110

Thr Val Ser Ser
        115


<210> SEQ ID NO 11
<211> LENGTH: 108
<212> TYPE: PRT
<213> ORGANISM: Homo sapiens

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Phe Ile Asp Thr Ser
            20                  25                  30

Leu Glu Trp Tyr Gln Gln Lys Pro Gly Lys Ala Pro Lys Leu Leu Ile
        35                  40                  45

Tyr Asp Gly Ser His Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Leu Ala Thr Tyr Tyr Cys Gln Gln Tyr Trp Val Leu Pro Leu
                85                  90                  95

Thr Phe Gly Gln Gly Thr Lys Val Glu Ile Lys Arg
            100                 105


<210> SEQ ID NO 12
<211> LENGTH: 117
<212> TYPE: PRT
<213> ORGANISM: Homo sapiens

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ile Ala Tyr
            20                  25                  30

Asp Met Ser Trp Val Arg Gln Ala Pro Gly Lys Gly Leu Glu Trp Val
        35                  40                  45

Ser Trp Ile Asp Glu Trp Gly Leu Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Lys Thr Pro Glu Glu Phe Asp Tyr Trp Gly Gln Gly Thr Leu
            100                 105                 110

Val Thr Val Ser Ser
        115
```

<210> SEQ ID NO 13
<211> LENGTH: 116
<212> TYPE: PRT
<213> ORGANISM: Homo sapiens

<400> SEQUENCE: 13

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Asp Tyr
            20                  25                  30

Glu Met Ser Trp Val Arg Gln Ala Pro Gly Lys Gly Leu Glu Trp Val
        35                  40                  45

Ser Gly Ile Asp Gly Glu Gly Ser Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Gly Arg Ser Phe Asp Tyr Trp Gly Gln Gly Thr Leu Val
            100                 105                 110

Thr Val Ser Ser
        115
```

<210> SEQ ID NO 14
<211> LENGTH: 118
<212> TYPE: PRT
<213> ORGANISM: Homo sapiens

<400> SEQUENCE: 14

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Leu Tyr
            20                  25                  30

Glu Met Ala Trp Val Arg Gln Ala Pro Gly Lys Gly Leu Glu Trp Val
        35                  40                  45

Ser Gly Ile Asp Ile Leu Gly Ser Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Ser Trp Gln Gly Phe Asp Tyr Trp Gly Gln Gly Thr
            100                 105                 110

Leu Val Thr Val Ser Ser
        115
```

<210> SEQ ID NO 15
<211> LENGTH: 123
<212> TYPE: PRT
<213> ORGANISM: Homo sapiens

<400> SEQUENCE: 15

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Ser Met Tyr Trp Val Arg Gln Ala Pro Gly Lys Gly Leu Glu Trp Val
        35                  40                  45
```

```
Ser Ser Ile Ser Pro Phe Gly Trp Gly Thr Tyr Tyr Ala Asp Ser Val
    50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Gly Glu Thr Ser Gly Pro Ile Ser Glu Asn Phe Asp Tyr
            100                 105                 110

Trp Gly Gln Gly Thr Leu Val Thr Val Ser Ser
        115                 120


<210> SEQ ID NO 16
<211> LENGTH: 116
<212> TYPE: PRT
<213> ORGANISM: Homo sapiens

<400> SEQUENCE: 16

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Trp Ser Tyr
            20                  25                  30

Asp Met Thr Trp Val Arg Gln Ala Pro Gly Lys Gly Leu Glu Trp Val
        35                  40                  45

Ser Ser Ile Met Ala Ser Gly Asp Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Asp Arg Asp Phe Asp Tyr Trp Gly Gln Gly Thr Leu Val
            100                 105                 110

Thr Val Ser Ser
        115


<210> SEQ ID NO 17
<211> LENGTH: 120
<212> TYPE: PRT
<213> ORGANISM: Homo sapiens

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Glu Tyr
            20                  25                  30

Val Met Ser Trp Val Arg Gln Ala Pro Gly Lys Gly Leu Glu Trp Val
        35                  40                  45

Ser Thr Ile Ser Pro Ile Gly Leu Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Phe Pro Leu Ile Ile Leu Pro Asp Phe Asp Tyr Trp Gly Gln
            100                 105                 110

Gly Thr Leu Val Thr Val Ser Ser
        115                 120
```

<210> SEQ ID NO 18
<211> LENGTH: 123
<212> TYPE: PRT
<213> ORGANISM: Homo sapiens

<400> SEQUENCE: 18

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Met Glu Tyr
            20                  25                  30

Ala Met Ile Trp Val Arg Gln Ala Pro Gly Lys Gly Leu Glu Trp Val
        35                  40                  45

Ser Ile Ile Ser Pro Leu Gly Leu Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Gln Asp Ser Ser Asp Ser Gln Tyr Thr Asn Phe Asp Tyr
            100                 105                 110

Trp Gly Gln Gly Thr Leu Val Thr Val Ser Ser
        115                 120
```

<210> SEQ ID NO 19
<211> LENGTH: 121
<212> TYPE: PRT
<213> ORGANISM: Homo sapiens

<400> SEQUENCE: 19

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Asp Tyr
            20                  25                  30

Gly Met Gly Trp Ala Arg Gln Ala Pro Gly Lys Gly Leu Glu Trp Val
        35                  40                  45

Ser Ser Ile Gly Pro Leu Gly Leu Trp Thr Tyr Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Leu Glu Gly Leu Ile Thr Asn Phe Asp Tyr Trp Gly
            100                 105                 110

Gln Gly Thr Leu Val Thr Val Ser Ser
        115                 120
```

<210> SEQ ID NO 20
<211> LENGTH: 119
<212> TYPE: PRT
<213> ORGANISM: Homo sapiens

<400> SEQUENCE: 20

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Glu Tyr
            20                  25                  30

Asp Met Thr Trp Val Arg Gln Ala Pro Gly Lys Gly Leu Glu Trp Val
        35                  40                  45
```

```
Ser Tyr Ile Ser Ser Asp Gly Tyr Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro His Gly Ser Pro Arg Glu Phe Asp Tyr Trp Gly Gln Gly
            100                 105                 110

Thr Leu Val Thr Val Ser Ser
        115


<210> SEQ ID NO 21
<211> LENGTH: 116
<212> TYPE: PRT
<213> ORGANISM: Homo sapiens

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Pro Phe Pro Gln Tyr
            20                  25                  30

Gln Met Ala Trp Val Arg Gln Ala Pro Gly Lys Gly Leu Glu Trp Val
        35                  40                  45

Ser Met Ile Thr Ser Asp Gly Leu Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Glu Pro Leu Phe Asp Tyr Trp Gly Gln Gly Thr Leu Val
            100                 105                 110

Thr Val Ser Ser
        115


<210> SEQ ID NO 22
<211> LENGTH: 116
<212> TYPE: PRT
<213> ORGANISM: Homo sapiens

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Gln Met Ala Trp Val Arg Gln Ala Pro Gly Lys Gly Leu Glu Trp Val
        35                  40                  45

Ser Gly Ile Ser Ser Glu Gly Leu Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Gly Arg Arg Phe Asp Tyr Trp Gly Gln Gly Thr Leu Val
            100                 105                 110

Thr Val Ser Ser
        115
```

<210> SEQ ID NO 23
<211> LENGTH: 120
<212> TYPE: PRT
<213> ORGANISM: Homo sapiens

<400> SEQUENCE: 23

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Asn Tyr
            20                  25                  30

Glu Met Gly Trp Ala Arg Gln Ala Pro Gly Lys Gly Leu Glu Trp Val
        35                  40                  45

Ser Val Ile Ser Glu Trp Gly Tyr Ser Thr Tyr Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Val Gly Gly Thr Gln Tyr Glu Phe Asp Tyr Trp Gly Gln
            100                 105                 110

Gly Thr Leu Val Thr Val Ser Ser
        115                 120
```

<210> SEQ ID NO 24
<211> LENGTH: 116
<212> TYPE: PRT
<213> ORGANISM: Homo sapiens

<400> SEQUENCE: 24

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe His Asn Tyr
            20                  25                  30

Glu Met Ser Trp Val Arg Gln Ala Pro Gly Lys Gly Leu Glu Trp Val
        35                  40                  45

Ser Ser Ile Ser Ser Gly Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Gly Val Lys Phe Asp Tyr Trp Gly Gln Gly Thr Leu Val
            100                 105                 110

Thr Val Ser Ser
        115
```

<210> SEQ ID NO 25
<211> LENGTH: 116
<212> TYPE: PRT
<213> ORGANISM: Homo sapiens

<400> SEQUENCE: 25

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Leu Tyr
            20                  25                  30

Glu Met Thr Trp Val Arg Gln Ala Pro Gly Lys Gly Leu Glu Trp Val
        35                  40                  45
```

Ser Ser Ile Thr Gly Asp Gly Ile Ser Thr Tyr Tyr Ala Asp Ser Val
50 55 60

Lys Gly Arg Phe Thr Ile Ser Arg Asp Asn Ser Arg Asn Thr Leu Tyr
65 70 75 80

Leu Gln Met Asn Ser Leu Arg Ala Glu Asp Thr Ala Val Tyr Tyr Cys
85 90 95

Ala Lys Ala Gly Arg Lys Phe Asp Tyr Trp Gly Gln Gly Thr Leu Val
100 105 110

Thr Val Ser Ser
115

<210> SEQ ID NO 26
<211> LENGTH: 116
<212> TYPE: PRT
<213> ORGANISM: Homo sapiens

<400> SEQUENCE: 26

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Gln Met Ala Trp Val Arg Gln Ala Pro Gly Lys Gly Leu Glu Trp Val
35 40 45

Ser Ser Ile Thr Ser Glu Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Pro Gly Lys Asn Phe Asp Tyr Trp Gly Gln Gly Thr Leu Val
100 105 110

Thr Val Ser Ser
115

<210> SEQ ID NO 27
<211> LENGTH: 116
<212> TYPE: PRT
<213> ORGANISM: Homo sapiens

<400> SEQUENCE: 27

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Asp Asn Tyr
20 25 30

Glu Met Thr Trp Val Arg Gln Ala Pro Gly Lys Gly Leu Glu Trp Val
35 40 45

Ser Thr Ile Thr Ser Gln Gly Thr Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Pro Asp Arg Ser Phe Asp Tyr Trp Gly Gln Gly Thr Leu Val
100 105 110

Thr Val Ser Ser
115

<210> SEQ ID NO 28
<211> LENGTH: 116
<212> TYPE: PRT
<213> ORGANISM: Homo sapiens

<400> SEQUENCE: 28

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Glu Met Thr Trp Val Arg Gln Ala Pro Gly Lys Gly Leu Glu Trp Val
        35                  40                  45

Ser Ser Ile Thr Ser Asp Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Asp Lys Thr Phe Asp Tyr Trp Gly Gln Gly Thr Leu Val
            100                 105                 110

Thr Val Ser Ser
        115
```

<210> SEQ ID NO 29
<211> LENGTH: 116
<212> TYPE: PRT
<213> ORGANISM: Homo sapiens

<400> SEQUENCE: 29

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Leu Tyr
            20                  25                  30

Glu Met Thr Trp Val Arg Gln Ala Pro Gly Lys Gly Leu Glu Trp Val
        35                  40                  45

Ser Ser Ile Thr Ser Asp Gly Val Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Asp Ser Pro Phe Asp Tyr Trp Gly Gln Gly Thr Leu Val
            100                 105                 110

Thr Val Ser Ser
        115
```

<210> SEQ ID NO 30
<211> LENGTH: 116
<212> TYPE: PRT
<213> ORGANISM: Homo sapiens

<400> SEQUENCE: 30

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly His Tyr
            20                  25                  30

Asp Met Ala Trp Val Arg Gln Ala Pro Gly Lys Gly Leu Glu Trp Val
        35                  40                  45
```

```
Ser Thr Ile Ser Asp Asn Gly Asn Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Gly Arg Asp Phe Asp Tyr Trp Gly Gln Gly Thr Leu Val
            100                 105                 110

Thr Val Ser Ser
        115


<210> SEQ ID NO 31
<211> LENGTH: 116
<212> TYPE: PRT
<213> ORGANISM: Homo sapiens

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Arg Tyr
            20                  25                  30

Gln Met Ala Trp Val Arg Gln Ala Pro Gly Lys Gly Leu Glu Trp Val
        35                  40                  45

Ser Ser Ile Ser Ser Asp Gly Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Gly Arg Ala Phe Asp Tyr Trp Gly Gln Gly Thr Leu Val
            100                 105                 110

Thr Val Ser Ser
        115


<210> SEQ ID NO 32
<211> LENGTH: 116
<212> TYPE: PRT
<213> ORGANISM: Homo sapiens

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Arg Tyr
            20                  25                  30

Gln Met Ala Trp Val Arg Gln Ala Pro Gly Lys Gly Leu Glu Trp Val
        35                  40                  45

Ser Thr Ile Ser Asp Asp Gly Asp Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Asp Lys Leu Phe Asp Tyr Trp Gly Gln Gly Thr Leu Val
            100                 105                 110

Thr Val Ser Ser
        115
```

<210> SEQ ID NO 33
<211> LENGTH: 116
<212> TYPE: PRT
<213> ORGANISM: Homo sapiens

<400> SEQUENCE: 33

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Glu Tyr
            20                  25                  30

Gln Met Ala Trp Val Arg Gln Ala Pro Gly Lys Gly Leu Glu Trp Val
        35                  40                  45

Ser Thr Ile Ser Asp Asp Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Asp Leu Tyr Phe Asp Tyr Trp Gly Gln Gly Thr Leu Val
            100                 105                 110

Thr Val Ser Ser
        115
```

<210> SEQ ID NO 34
<211> LENGTH: 116
<212> TYPE: PRT
<213> ORGANISM: Homo sapiens

<400> SEQUENCE: 34

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Val Tyr
            20                  25                  30

Gln Met Gly Trp Val Arg Gln Ala Pro Gly Lys Gly Leu Glu Trp Val
        35                  40                  45

Ser Phe Ile Val Pro Gly Gly Asp Leu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Thr Trp Pro Glu Phe Asp Tyr Trp Gly Gln Gly Thr Leu Val
            100                 105                 110

Thr Val Ser Ser
        115
```

<210> SEQ ID NO 35
<211> LENGTH: 108
<212> TYPE: PRT
<213> ORGANISM: Homo sapiens

<400> SEQUENCE: 35

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Gly Glu Ser
            20                  25                  30

Leu His Trp Tyr Gln Gln Lys Pro Gly Lys Ala Pro Arg Leu Leu Ile
        35                  40                  45
```

Tyr Phe Ala Ser Leu Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln His His Met Leu Pro Ser
85 90 95

Thr Phe Gly Gln Gly Thr Lys Val Glu Ile Lys Arg
100 105

<210> SEQ ID NO 36
<211> LENGTH: 108
<212> TYPE: PRT
<213> ORGANISM: Homo sapiens

<400> SEQUENCE: 36

Asp Ile Gln Met Thr Gln Ser Pro Ser Ser Leu Ser Ala Ser Val Gly
1 5 10 15

Asp Arg Val Thr Ile Thr Cys Arg Ala Ser Gln Trp Ile Gly Asp Ser
20 25 30

Leu Ser Trp Tyr Gln Gln Lys Pro Gly Lys Ala Pro Lys Leu Leu Ile
35 40 45

Tyr Phe Ala Ser Tyr Leu Gln Ser Gly Val Pro Thr Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Phe Glu Asn Pro Val
85 90 95

Thr Phe Gly Gln Gly Thr Lys Val Gly Ile Lys Arg
100 105

<210> SEQ ID NO 37
<211> LENGTH: 108
<212> TYPE: PRT
<213> ORGANISM: Homo sapiens

<400> SEQUENCE: 37

Asp Ile Gln Met Thr Gln Ser Pro Ser Ser Leu Ser Ala Ser Val Gly
1 5 10 15

Asp Arg Val Thr Ile Thr Cys Arg Ala Ser Gln Phe Ile Gly Asp Ser
20 25 30

Leu Ser Trp Tyr Gln Gln Lys Pro Gly Lys Ala Pro Lys Leu Leu Ile
35 40 45

Tyr Phe Ser Ser Ile Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Met Asp Ile Pro Ile
85 90 95

Thr Phe Gly Gln Gly Thr Lys Val Glu Ile Lys Arg
100 105

<210> SEQ ID NO 38
<211> LENGTH: 108
<212> TYPE: PRT
<213> ORGANISM: Homo sapiens

<400> SEQUENCE: 38

Asp Ile Gln Met Thr Gln Ser Pro Ser Ser Leu Ser Ala Ser Val Gly
1 5 10 15

```
Asp Arg Val Thr Ile Thr Cys Arg Ala Ser Gln Asp Ile Asp His Asn
            20                  25                  30

Leu Glu Trp Tyr Gln Gln Lys Pro Gly Lys Ala Pro Lys Leu Leu Ile
        35                  40                  45

Tyr Asp Ser Ser Met Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr His Ser Ile Pro Val
                85                  90                  95

Thr Phe Gly Gln Gly Thr Lys Val Glu Ile Lys Arg
            100                 105


<210> SEQ ID NO 39
<211> LENGTH: 108
<212> TYPE: PRT
<213> ORGANISM: Homo sapiens

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gln Ile Glu Thr Asn
            20                  25                  30

Leu Glu Trp Tyr Gln Gln Lys Pro Gly Lys Ala Pro Lys Leu Leu Ile
        35                  40                  45

Tyr Asp Gly Ser Trp Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr His Ser Leu Pro Ala
                85                  90                  95

Thr Phe Gly Gln Gly Thr Lys Val Glu Ile Lys Arg
            100                 105


<210> SEQ ID NO 40
<211> LENGTH: 108
<212> TYPE: PRT
<213> ORGANISM: Homo sapiens

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Asn
            20                  25                  30

Leu Glu Trp Tyr Gln Gln Lys Pro Gly Lys Ala Pro Arg Leu Leu Ile
        35                  40                  45

Tyr His Gly Ser Trp Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Phe Asn Pro Thr
                85                  90                  95

Thr Phe Gly Gln Gly Thr Lys Val Glu Ile Lys Arg
            100                 105


<210> SEQ ID NO 41
<211> LENGTH: 108
```

<212> TYPE: PRT
<213> ORGANISM: Homo sapiens

<400> SEQUENCE: 41

Asp Ile Gln Met Thr Gln Ser Pro Ser Ser Leu Ser Ala Ser Val Gly
1               5                   10                  15

Asp Cys Val Thr Ile Thr Cys Arg Ala Ser Gln Asn Ile Asp Gly Leu
            20                  25                  30

Leu Trp Trp Tyr Gln Gln Lys Pro Gly Lys Ala Pro Lys Leu Leu Ile
        35                  40                  45

Tyr Ala Gly Ser Gly Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys Ala Phe Glu Pro Phe
                85                  90                  95

Thr Phe Gly Gln Gly Thr Lys Val Glu Ile Lys Arg
            100                 105

<210> SEQ ID NO 42
<211> LENGTH: 119
<212> TYPE: PRT
<213> ORGANISM: Homo sapiens

<400> SEQUENCE: 42

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Ala Tyr
            20                  25                  30

Asp Met Gly Trp Val Arg Gln Ala Pro Gly Lys Gly Leu Glu Trp Val
        35                  40                  45

Ser Gln Ile Gly Arg Asp Gly Ser Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Arg Arg Tyr Ala Ile Phe Thr Phe Asp Arg Gly Gln Gly
            100                 105                 110

Thr Leu Val Thr Val Ser Ser
        115

<210> SEQ ID NO 43
<211> LENGTH: 116
<212> TYPE: PRT
<213> ORGANISM: Homo sapiens

<400> SEQUENCE: 43

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Phe Glu Tyr
            20                  25                  30

Glu Met Thr Trp Val Arg Gln Ala Pro Gly Lys Gly Leu Glu Trp Val
        35                  40                  45

Ser Ser Ile Ala Asn Asp Gly Ser Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
85 90 95

Ala Lys Pro Asp Arg Gln Phe Asp Tyr Trp Gly Gln Gly Thr Leu Val
100 105 110

Thr Val Ser Ser
115

<210> SEQ ID NO 44
<211> LENGTH: 116
<212> TYPE: PRT
<213> ORGANISM: Homo sapiens

<400> SEQUENCE: 44

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Gly Pro Tyr
20 25 30

Glu Met Thr Trp Val Arg Gln Ala Pro Gly Lys Gly Leu Glu Trp Val
35 40 45

Ser Ser Ile Val Gly Asp Gly Leu Asp Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Pro Asp Arg Val Phe Asp Tyr Trp Gly Gln Gly Thr Leu Val
100 105 110

Thr Val Ser Ser
115

<210> SEQ ID NO 45
<211> LENGTH: 116
<212> TYPE: PRT
<213> ORGANISM: Homo sapiens

<400> SEQUENCE: 45

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ala Ser Tyr
20 25 30

Glu Met Ala Trp Val Arg Gln Ala Pro Gly Lys Gly Leu Glu Trp Val
35 40 45

Ser Ser Ile Gly Ser Asp Gly Gly Pro Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Ser Ala Val Tyr Tyr Cys
85 90 95

Ala Lys Pro Asp Arg Ala Phe Asp Tyr Trp Gly Gln Gly Thr Leu Val
100 105 110

Thr Val Ser Ser
115

<210> SEQ ID NO 46
<211> LENGTH: 119
<212> TYPE: PRT
<213> ORGANISM: Homo sapiens

<400> SEQUENCE: 46

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Glu Met Gly Trp Val Arg Gln Ala Pro Gly Lys Gly Leu Glu Trp Val
        35                  40                  45

Ser Ser Ile Glu Pro Thr Gly Ile Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro His Phe Thr Glu Leu Gly Phe Asp Tyr Trp Gly Gln Gly
            100                 105                 110

Thr Leu Val Thr Val Ser Ser
        115
```

<210> SEQ ID NO 47
<211> LENGTH: 120
<212> TYPE: PRT
<213> ORGANISM: Homo sapiens

<400> SEQUENCE: 47

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Asn Tyr
            20                  25                  30

Ala Met Ala Trp Val Arg Gln Ala Pro Gly Lys Gly Leu Glu Trp Val
        35                  40                  45

Ser Lys Ile Gly Ala Gln Gly Leu His Thr Tyr Tyr Ala Gly Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Thr Thr Met Asp Tyr Glu Arg Phe Asp Tyr Trp Gly Gln
            100                 105                 110

Gly Thr Leu Val Thr Val Ser Ser
        115                 120
```

<210> SEQ ID NO 48
<211> LENGTH: 122
<212> TYPE: PRT
<213> ORGANISM: Homo sapiens

<400> SEQUENCE: 48

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Leu Tyr
            20                  25                  30

Ala Met Ala Trp Val Arg Gln Ala Pro Gly Lys Gly Leu Glu Trp Val
        35                  40                  45

Ser Gly Ile Gly Ala Val Gly Glu Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
85 90 95

Ala Lys Glu Ala Asn Asn Leu Ser Asp Asn Leu Val Phe Asp Tyr Trp
100 105 110

Gly Gln Gly Thr Leu Val Thr Val Ser Ser
115 120

<210> SEQ ID NO 49
<211> LENGTH: 108
<212> TYPE: PRT
<213> ORGANISM: Homo sapiens

<400> SEQUENCE: 49

Asp Ile Gln Met Thr Gln Ser Pro Ser Ser Leu Ser Ala Ser Val Gly
1 5 10 15

Asp Arg Val Thr Ile Thr Cys Arg Ala Ser Gln Trp Ile Gly Asp Ser
20 25 30

Leu Ser Trp Tyr Gln Gln Lys Pro Gly Lys Ala Pro Lys Leu Leu Ile
35 40 45

Tyr Phe Gly Ser Tyr Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Leu His Thr Pro Ser
85 90 95

Thr Phe Gly Gln Gly Thr Lys Val Glu Ile Lys Arg
100 105

<210> SEQ ID NO 50
<211> LENGTH: 108
<212> TYPE: PRT
<213> ORGANISM: Homo sapiens

<400> SEQUENCE: 50

Asp Ile Gln Met Thr Gln Ser Pro Ser Ser Leu Ser Ala Ser Val Gly
1 5 10 15

Asp Arg Val Thr Ile Thr Cys Arg Ala Ser Gln Trp Ile Gly Asp Ser
20 25 30

Leu Ser Trp Tyr Gln Gln Lys Pro Gly Lys Ala Pro Lys Leu Leu Ile
35 40 45

Tyr Phe Gly Ser Tyr Leu Gln Asn Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Met Ile Thr Pro Thr
85 90 95

Thr Phe Gly Gln Gly Thr Lys Val Glu Ile Lys Arg
100 105

<210> SEQ ID NO 51
<211> LENGTH: 108
<212> TYPE: PRT
<213> ORGANISM: Homo sapiens

<400> SEQUENCE: 51

Asp Val Gln Met Thr Gln Ser Pro Ser Ser Leu Ser Ala Ser Val Gly
1 5 10 15

Asp Arg Val Thr Ile Thr Cys Arg Ala Ser Gln Trp Ile Gly Asp Ser

```
            20                  25                  30

Leu Ser Trp Tyr Gln Gln Lys Pro Gly Lys Ala Pro Lys Leu Leu Ile
        35                  40                  45

Tyr Phe Gly Ser Tyr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Met Ser Ala Pro Ser
                85                  90                  95

Thr Phe Gly Gln Gly Thr Lys Val Glu Ile Lys Arg
            100                 105


<210> SEQ ID NO 52
<211> LENGTH: 108
<212> TYPE: PRT
<213> ORGANISM: Homo sapiens

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Asp Ser
            20                  25                  30

Leu Ser Trp Tyr Gln Gln Lys Pro Gly Lys Ala Pro Lys Leu Leu Ile
        35                  40                  45

Tyr Phe Gly Ser Tyr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Tyr Gln Tyr Val Pro Ser
                85                  90                  95

Thr Phe Gly Gln Gly Thr Lys Val Glu Ile Lys Gln
            100                 105


<210> SEQ ID NO 53
<211> LENGTH: 108
<212> TYPE: PRT
<213> ORGANISM: Homo sapiens

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Pro Ile Val Asp Glu
            20                  25                  30

Leu Asp Trp Tyr Gln Gln Lys Pro Gly Lys Ala Pro Lys Leu Leu Ile
        35                  40                  45

Tyr Ala Ala Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Trp Ser Thr Tyr Pro Thr
                85                  90                  95

Thr Phe Gly Gln Gly Thr Lys Val Glu Ile Lys Arg
            100                 105


<210> SEQ ID NO 54
<211> LENGTH: 108
<212> TYPE: PRT
<213> ORGANISM: Homo sapiens
```

<400> SEQUENCE: 54

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Gly Ser Ala
20 25 30

Leu Arg Trp Tyr Gln Gln Lys Pro Gly Lys Ala Pro Lys Leu Leu Ile
35 40 45

Tyr Leu Gly Ser Asp Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Thr Gln Tyr Phe Pro Thr
85 90 95

Thr Phe Gly Gln Gly Thr Lys Val Glu Ile Lys Arg
100 105

<210> SEQ ID NO 55
<211> LENGTH: 108
<212> TYPE: PRT
<213> ORGANISM: Homo sapiens

<400> SEQUENCE: 55

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ala Ile Tyr Gly Gly
20 25 30

Leu Arg Trp Tyr Gln Gln Lys Pro Gly Lys Ala Pro Lys Leu Leu Ile
35 40 45

Tyr Gly Glu Ser Met Leu Gln Ser Gly Val Pro Ser Arg Phe Ser Gly
50 55 60

Ser Gly Ser Gly Thr Asp Phe Thr Leu Thr Ile Ser Ser Leu His Pro
65 70 75 80

Glu Asp Phe Ala Thr Tyr Tyr Cys Gln Gln Val Tyr His Lys Pro Phe
85 90 95

Thr Phe Gly Gln Gly Thr Lys Val Glu Ile Lys Arg
100 105

<210> SEQ ID NO 56
<211> LENGTH: 123
<212> TYPE: PRT
<213> ORGANISM: Homo sapiens

<400> SEQUENCE: 56

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Thr Ala Tyr
20 25 30

Arg Met Ala Trp Val Arg Gln Ala Pro Gly Lys Gly Leu Glu Trp Val
35 40 45

Ser Trp Ile Ser Pro Ser Gly Ser Gly Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Thr Leu Thr Asp Ser Pro Ser Gly His Tyr Glu Phe Asp Tyr

```
            100                 105                 110

Trp Gly Gln Gly Thr Leu Val Thr Val Ser Ser
        115                 120


<210> SEQ ID NO 57
<211> LENGTH: 123
<212> TYPE: PRT
<213> ORGANISM: Homo sapiens

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Arg Tyr
            20                  25                  30

Glu Met Gly Trp Val Arg Gln Ala Pro Gly Lys Gly Leu Glu Trp Val
        35                  40                  45

Ser Arg Ile Thr Ala Gln Gly Leu Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Leu Thr Asp Phe Ser Ser Gly His Gln Glu Phe Asp Tyr
            100                 105                 110

Trp Gly Gln Gly Thr Leu Val Thr Val Ser Ser
        115                 120


<210> SEQ ID NO 58
<211> LENGTH: 123
<212> TYPE: PRT
<213> ORGANISM: Homo sapiens

<400> SEQUENCE: 58

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asp Tyr
            20                  25                  30

Thr Met Gly Trp Val Arg Gln Ala Pro Gly Lys Gly Leu Glu Trp Val
        35                  40                  45

Ser Trp Ile His Gly Thr Gly Gly Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Leu Ala Asp Arg Ser Gly Gly Val Val Glu Phe Asp Tyr
            100                 105                 110

Trp Gly Gln Gly Thr Leu Val Thr Val Ser Ser
        115                 120


<210> SEQ ID NO 59
<211> LENGTH: 116
<212> TYPE: PRT
<213> ORGANISM: Homo sapiens

<400> SEQUENCE: 59

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Glu Tyr
            20                  25                  30

Asp Met Tyr Trp Val Arg Gln Ala Pro Gly Lys Gly Leu Glu Trp Val
        35                  40                  45

Ser Trp Ile Asp Thr Asp Gly Gly Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Gly Leu Lys Phe Asp Tyr Trp Gly Gln Gly Thr Leu Val
            100                 105                 110

Thr Val Ser Ser
        115


<210> SEQ ID NO 60
<211> LENGTH: 116
<212> TYPE: PRT
<213> ORGANISM: Homo sapiens

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Val Tyr
            20                  25                  30

Thr Met Ala Trp Val Arg Gln Ala Pro Gly Lys Gly Leu Glu Trp Val
        35                  40                  45

Ser Thr Ile Asp Glu Ser Gly Arg Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Gly Val Trp Phe Asp Tyr Trp Gly Gln Gly Thr Leu Val
            100                 105                 110

Thr Val Ser Ser
        115


<210> SEQ ID NO 61
<211> LENGTH: 124
<212> TYPE: PRT
<213> ORGANISM: Homo sapiens

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Leu Asp Tyr
            20                  25                  30

Ala Met Gly Trp Val Arg Gln Ala Pro Gly Lys Gly Leu Glu Trp Val
        35                  40                  45

Ser Thr Ile Ser Pro Met Gly Met Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ser Ala Ile Ser Phe Thr Ser Asp Ile Ser Asn Phe Asp
```

```
            100                 105                 110

Tyr Trp Gly Gln Gly Thr Leu Val Thr Val Ser Ser
        115                 120


<210> SEQ ID NO 62
<211> LENGTH: 120
<212> TYPE: PRT
<213> ORGANISM: Homo sapiens

<400> SEQUENCE: 62

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Ala Tyr
            20                  25                  30

Ala Met Thr Trp Val Arg Gln Ala Pro Gly Lys Gly Leu Glu Trp Val
        35                  40                  45

Ser Tyr Ile Ser Pro Asn Gly Thr Ala Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Tyr Val Gly Met Arg Trp Asn Ser Phe Asp Tyr Trp Gly Gln
            100                 105                 110

Gly Thr Leu Val Thr Val Ser Ser
        115                 120


<210> SEQ ID NO 63
<211> LENGTH: 116
<212> TYPE: PRT
<213> ORGANISM: Homo sapiens

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Ala Trp Val Arg Gln Ala Pro Gly Lys Gly Leu Glu Trp Val
        35                  40                  45

Ser Ser Ile Thr Ser Leu Gly Thr Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Gly Arg Lys Phe Asp Tyr Trp Gly Gln Gly Thr Leu Val
            100                 105                 110

Thr Val Ser Ser
        115


<210> SEQ ID NO 64
<211> LENGTH: 116
<212> TYPE: PRT
<213> ORGANISM: Homo sapiens

<400> SEQUENCE: 64

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Asn Glu Tyr
            20                  25                  30

Glu Met Thr Trp Val Arg Gln Ala Pro Gly Lys Gly Leu Glu Trp Val
        35                  40                  45

Ser Thr Ile Thr Ser Glu Gly Ser Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Asn Gly Lys Phe Asp Tyr Trp Gly Gln Gly Thr Leu Val
            100                 105                 110

Thr Val Ser Ser
        115


<210> SEQ ID NO 65
<211> LENGTH: 116
<212> TYPE: PRT
<213> ORGANISM: Homo sapiens

<400> SEQUENCE: 65

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Glu Met Leu Trp Val Arg Gln Ala Pro Gly Lys Gly Leu Glu Trp Val
        35                  40                  45

Ser Thr Ile Thr Ser Glu Gly His Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Gly Thr Ser Phe Asp Tyr Trp Gly Gln Gly Thr Leu Val
            100                 105                 110

Thr Val Ser Ser
        115


<210> SEQ ID NO 66
<211> LENGTH: 116
<212> TYPE: PRT
<213> ORGANISM: Homo sapiens

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Glu Met Ser Trp Val Arg Gln Ala Pro Gly Lys Gly Leu Glu Trp Val
        35                  40                  45

Ser Thr Ile Asp Ser Asp Gly Ser Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Gly Val Lys Phe Asp Tyr Trp Gly Gln Gly Thr Leu Val
```

```
        100                 105                 110

Thr Val Ser Ser
        115


<210> SEQ ID NO 67
<211> LENGTH: 116
<212> TYPE: PRT
<213> ORGANISM: Homo sapiens

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Asp Tyr
            20                  25                  30

Glu Met Thr Trp Val Arg Gln Ala Pro Gly Lys Gly Leu Glu Trp Val
        35                  40                  45

Ser Ser Ile Ser Ser Thr Gly Gln Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Gly Asn Lys Phe Asp Tyr Trp Gly Gln Gly Thr Leu Val
            100                 105                 110

Thr Val Ser Ser
        115


<210> SEQ ID NO 68
<211> LENGTH: 124
<212> TYPE: PRT
<213> ORGANISM: Homo sapiens

<400> SEQUENCE: 68

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Leu Asp Tyr
            20                  25                  30

Gly Met Ala Trp Val Arg Gln Ala Pro Gly Lys Gly Leu Glu Trp Val
        35                  40                  45

Ser Ala Ile Ser Pro Leu Gly Leu Ser Thr Tyr Tyr Ala Asp Ser Val
    50                  55                  60

Lys Ser Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Val Arg Val Gly Arg Gly Val His Pro Pro Lys Phe Asp
            100                 105                 110

Tyr Trp Gly Gln Gly Thr Leu Val Thr Val Ser Ser
        115                 120


<210> SEQ ID NO 69
<211> LENGTH: 123
<212> TYPE: PRT
<213> ORGANISM: Homo sapiens

<400> SEQUENCE: 69

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Glu Asn Tyr
            20                  25                  30

Ala Met Ser Trp Val Arg Gln Ala Pro Gly Lys Gly Leu Glu Trp Val
        35                  40                  45

Ser Thr Ile Ala Pro Leu Gly Val Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Lys Lys Val Gly Ala Trp Leu Gln Ser Arg Ser Phe Asp Tyr
            100                 105                 110

Trp Gly Gln Gly Thr Leu Val Thr Val Ser Ser
        115                 120


<210> SEQ ID NO 70
<211> LENGTH: 123
<212> TYPE: PRT
<213> ORGANISM: Homo sapiens

<400> SEQUENCE: 70

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Gly Tyr
            20                  25                  30

Pro Met Ser Trp Val Arg Gln Ala Pro Gly Lys Gly Leu Glu Trp Val
        35                  40                  45

Ser Thr Ile Ser Pro Leu Gly Pro Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Leu Met Gly Glu Tyr Leu Asn Ser Arg Thr Phe Asp Tyr
            100                 105                 110

Trp Gly Gln Gly Thr Leu Val Thr Val Ser Ser
        115                 120


<210> SEQ ID NO 71
<211> LENGTH: 124
<212> TYPE: PRT
<213> ORGANISM: Homo sapiens

<400> SEQUENCE: 71

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Ala Tyr
            20                  25                  30

Pro Met Ser Trp Val Arg Gln Ala Pro Gly Lys Gly Leu Glu Trp Val
        35                  40                  45

Ser Ser Ile Ser Pro Leu Gly Leu Trp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Ser Ala Gly Ala Glu Thr His Val Tyr Arg Leu Phe Asp
```

```
            100                 105                 110

Tyr Trp Gly Gln Gly Thr Leu Val Thr Val Ser Ser
        115                 120


<210> SEQ ID NO 72
<211> LENGTH: 116
<212> TYPE: PRT
<213> ORGANISM: Homo sapiens

<400> SEQUENCE: 72

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Asp Met Ser Trp Val Arg Gln Ala Pro Gly Lys Gly Leu Glu Trp Val
        35                  40                  45

Ser Thr Ile Leu Glu Asp Gly Leu Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Gly Arg Leu Phe Asp Tyr Trp Gly Gln Gly Thr Leu Val
            100                 105                 110

Thr Val Ser Ser
        115


<210> SEQ ID NO 73
<211> LENGTH: 116
<212> TYPE: PRT
<213> ORGANISM: Homo sapiens

<400> SEQUENCE: 73

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Pro Met Thr Trp Val Arg Gln Ala Pro Gly Lys Gly Leu Glu Trp Val
        35                  40                  45

Ser Thr Ile Leu Ser Pro Gly Thr Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Glu Lys Asp Phe Asp Tyr Trp Gly Gln Gly Thr Leu Val
            100                 105                 110

Thr Val Ser Ser
        115


<210> SEQ ID NO 74
<211> LENGTH: 124
<212> TYPE: PRT
<213> ORGANISM: Homo sapiens

<400> SEQUENCE: 74

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Leu Gln Tyr
20 25 30

Pro Met Gly Trp Val Arg Gln Ala Pro Gly Lys Gly Leu Glu Trp Val
35 40 45

Ser Thr Ile Ser Pro Val Gly Leu Thr Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Leu Phe Glu Gly Ser Arg Ile Gln Arg Asp Val Gly Phe Asp
100 105 110

Tyr Trp Gly Gln Gly Thr Leu Val Thr Val Ser Ser
115 120

<210> SEQ ID NO 75
<211> LENGTH: 122
<212> TYPE: PRT
<213> ORGANISM: Homo sapiens

<400> SEQUENCE: 75

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Glu Glu Tyr
20 25 30

Gly Met Ala Trp Val Arg Gln Ala Pro Gly Lys Gly Leu Glu Trp Val
35 40 45

Ser Thr Ile Ser Pro Leu Gly Ile Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys His Ala Thr Ser Gln Glu Ser Leu Arg Ser Phe Asp Tyr Trp
100 105 110

Gly Gln Gly Thr Leu Val Thr Val Ser Ser
115 120

<210> SEQ ID NO 76
<211> LENGTH: 116
<212> TYPE: PRT
<213> ORGANISM: Homo sapiens

<400> SEQUENCE: 76

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Glu Arg Tyr
20 25 30

Gln Met Ala Trp Val Arg Gln Ala Pro Gly Lys Gly Leu Glu Trp Val
35 40 45

Ser Thr Ile Ser Ser Asp Gly Gly Gly Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Pro Gly His Arg Phe Asp Tyr Trp Gly Gln Gly Thr Leu Val

```
            100                 105                 110

Thr Val Ser Ser
        115


<210> SEQ ID NO 77
<211> LENGTH: 116
<212> TYPE: PRT
<213> ORGANISM: Homo sapiens

<400> SEQUENCE: 77

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Arg Tyr
            20                  25                  30

Gln Met Ala Trp Val Arg Gln Ala Pro Gly Lys Gly Leu Glu Trp Val
        35                  40                  45

Ser Ser Ile Ser Ser Asp Gly Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Ser Arg Arg Phe Asp Tyr Trp Gly Gln Gly Thr Leu Val
            100                 105                 110

Thr Val Ser Ser
        115


<210> SEQ ID NO 78
<211> LENGTH: 123
<212> TYPE: PRT
<213> ORGANISM: Homo sapiens

<400> SEQUENCE: 78

Glu Val Gln Leu Leu Glu Ser Gly Gly Gly Leu Val Gln Pro Gly Gly
1               5                   10                  15

Phe Leu Arg Leu Ser Cys Ala Ala Ser Gly Phe Thr Phe Glu Leu Tyr
            20                  25                  30

Pro Met Ala Trp Val Arg Gln Ala Pro Gly Lys Gly Leu Glu Trp Val
        35                  40                  45

Ser Ser Ile Ser Pro Val Gly Phe Leu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly His Glu Gly Ser Tyr Thr Pro Arg Ser Ala Phe Asp Tyr
            100                 105                 110

Trp Gly Gln Gly Thr Leu Val Thr Val Ser Ser
        115                 120


<210> SEQ ID NO 79
<211> LENGTH: 123
<212> TYPE: PRT
<213> ORGANISM: Homo sapiens

<400> SEQUENCE: 79

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Val Ala Tyr
20 25 30

Pro Met Ala Trp Val Arg Gln Ala Pro Gly Lys Gly Leu Glu Trp Val
35 40 45

Ser Thr Ile Ala Pro Leu Gly Gly Asn Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Arg Pro Glu Gly Leu Gln Ile Asp Ser Gln Asn Phe Asp Tyr
100 105 110

Trp Gly Gln Gly Thr Leu Val Thr Val Ser Ser
115 120

<210> SEQ ID NO 80
<211> LENGTH: 116
<212> TYPE: PRT
<213> ORGANISM: Homo sapiens

<400> SEQUENCE: 80

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ala Leu Tyr
20 25 30

Gln Met Ala Trp Val Arg Gln Ala Pro Gly Lys Gly Leu Glu Trp Val
35 40 45

Ser Ser Ile Asp Ser Ser Gly Ser Asp Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Pro Glu Arg Asp Phe Asp Tyr Trp Gly Gln Gly Thr Leu Val
100 105 110

Thr Val Ser Ser
115

<210> SEQ ID NO 81
<211> LENGTH: 116
<212> TYPE: PRT
<213> ORGANISM: Homo sapiens

<400> SEQUENCE: 81

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Arg Gln Tyr
20 25 30

Gln Met Ala Trp Ala Arg Gln Ala Pro Gly Lys Gly Leu Glu Trp Val
35 40 45

Ser Thr Ile Ala Ser Asp Gly Val Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Val Gly Arg Asp Phe Asp Tyr Trp Gly Gln Gly Thr Leu Val

```
        100                 105                 110

Thr Val Ser Ser
        115


<210> SEQ ID NO 82
<211> LENGTH: 108
<212> TYPE: PRT
<213> ORGANISM: Homo sapiens

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Pro Ile Gly Pro Asp
            20                  25                  30

Leu Leu Trp Tyr Gln Gln Lys Pro Gly Lys Ala Pro Lys Leu Leu Ile
        35                  40                  45

Tyr Gln Thr Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Ala Phe Pro Val
                85                  90                  95

Thr Phe Gly Gln Gly Thr Lys Val Glu Ile Lys Arg
            100                 105


<210> SEQ ID NO 83
<211> LENGTH: 369
<212> TYPE: DNA
<213> ORGANISM: Homo sapiens

<400> SEQUENCE: 83

gcgtcgacgg aggtgcagct gttggagtct gggggaggct tggtacagcc tggggggtcc      60

ctgcgtctct cctgtgcagc ctccggattc acctttagta attatcagat ggcgtgggtc     120

cgccaggctc cagggaaggg tctagagtgg gtctcaagta ttactagtga gggtggttcg     180

acatactacg cagactccgt gaagggccgg ttcaccatct cccgcgacaa ttccaagaac     240

acactgtatc tgcaaatgaa cagcctgcgt gccgaggaca ccgcggtata ttactgtgcg     300

aaaccgggta agaattttga ctactggggt cagggaaccc tggtcaccgt ctcgtgctaa     360

taaggatcc                                                             369


<210> SEQ ID NO 84
<211> LENGTH: 369
<212> TYPE: DNA
<213> ORGANISM: Homo sapiens

<400> SEQUENCE: 84

cgcagctgcc tccacgtcga caacctcaga ccccctccga accatgtcgg accccccagg      60

gacgcagaga ggacacgtcg gaggcctaag tggaaatcat taatagtcta ccgcacccag     120

gcggtccgag gtcccttccc agatctcacc cagagttcat aatgatcact cccaccaagc     180

tgtatgatgc gtctgaggca cttcccggcc aagtggtaga gggcgctgtt aaggttcttg     240

tgtgacatag acgtttactt gtcggacgca cggctcctgt ggcgccatat aatgacacgc     300

tttggcccat tcttaaaact gatgacccca gtcccttggg accagtggca gagcacgatt     360

attcctagg                                                             369


<210> SEQ ID NO 85
```

<211> LENGTH: 119
<212> TYPE: PRT
<213> ORGANISM: Homo sapiens

<400> SEQUENCE: 85

```
Ala Ser Thr Glu Val Gln Leu Leu Glu Ser Gly Gly Gly Leu Val Gln
1               5                   10                  15

Pro Gly Gly Ser Leu Arg Leu Ser Cys Ala Ala Ser Gly Phe Thr Phe
            20                  25                  30

Ser Asn Tyr Gln Met Ala Trp Val Arg Gln Ala Pro Gly Lys Gly Leu
        35                  40                  45

Glu Trp Val Ser Ser Ile Thr Ser Glu Gly Gly Ser Thr Tyr Tyr Ala
    50                  55                  60

Asp Ser Val Lys Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Lys Pro Gly Lys Asn Phe Asp Tyr Trp Gly Gln Gly
            100                 105                 110

Thr Leu Val Thr Val Ser Cys
        115
```

<210> SEQ ID NO 86
<211> LENGTH: 33
<212> TYPE: DNA
<213> ORGANISM: Artificial
<220> FEATURE:
<223> OTHER INFORMATION: DOM8-24 forward PCR primer

<400> SEQUENCE: 86
agtgcgtcga cggaggtgca gctgttggag tct 33

<210> SEQ ID NO 87
<211> LENGTH: 42
<212> TYPE: DNA
<213> ORGANISM: Artificial
<220> FEATURE:
<223> OTHER INFORMATION: DOM8-24 reverse PCR primer

<400> SEQUENCE: 87
aaaggatcct tattagcacg agacggtgac cagggttccc tg 42

<210> SEQ ID NO 88
<211> LENGTH: 241
<212> TYPE: PRT
<213> ORGANISM: Homo sapiens

<400> SEQUENCE: 88

```
Leu Glu Lys Arg Glu Val Gln Leu Leu Glu Ser Gly Gly Gly Leu Val
1               5                   10                  15

Gln Pro Gly Gly Ser Leu Arg Leu Ser Cys Thr Ala Ser Gly Phe Thr
            20                  25                  30

Phe Asp Glu Tyr Asn Met Ser Trp Val Arg Gln Ala Pro Gly Lys Gly
        35                  40                  45

Leu Glu Trp Val Ser Thr Ile Leu Pro His Gly Asp Arg Thr Tyr Tyr
    50                  55                  60

Ala Asp Ser Val Lys Gly Arg Phe Thr Ile Ser Arg Asp Asn Ser Lys
65                  70                  75                  80

Asn Thr Leu Tyr Leu Gln Met Asn Ser Leu Arg Ala Glu Asp Thr Ala
                85                  90                  95
```

```
Val Tyr Tyr Cys Ala Lys Gln Asp Pro Leu Tyr Arg Phe Asp Tyr Trp
            100                 105                 110

Gly Gln Gly Thr Leu Val Thr Val Ser Ser Ala Ala Ala Glu Val Gln
        115                 120                 125

Leu Leu Glu Ser Gly Gly Gly Leu Val Gln Pro Gly Gly Ser Leu Arg
    130                 135                 140

Leu Ser Cys Ala Ala Ser Gly Phe Thr Phe Ser Asn Tyr Gln Met Ala
145                 150                 155                 160

Trp Val Arg Gln Ala Pro Gly Lys Gly Leu Glu Trp Val Ser Ser Ile
                165                 170                 175

Thr Ser Glu Gly Gly Ser Thr Tyr Tyr Ala Asp Ser Val Lys Gly Arg
            180                 185                 190

Phe Thr Ile Ser Arg Asp Asn Ser Lys Asn Thr Leu Tyr Leu Gln Met
        195                 200                 205

Asn Ser Leu Arg Ala Glu Asp Thr Ala Val Tyr Tyr Cys Ala Lys Pro
    210                 215                 220

Gly Lys Asn Phe Asp Tyr Trp Gly Gln Gly Thr Leu Val Thr Val Ser
225                 230                 235                 240

Ser


<210> SEQ ID NO 89
<211> LENGTH: 108
<212> TYPE: PRT
<213> ORGANISM: Homo sapiens

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Lys Ile Ala Thr Tyr
            20                  25                  30

Leu Asn Trp Tyr Gln Gln Lys Pro Gly Lys Ala Pro Lys Leu Leu Ile
        35                  40                  45

Tyr Arg Ser Ser Ser Leu Gln Ser Ala Val Pro Ser Arg Phe Ser Gly
    50                  55                  60

Ser Gly Ser Gly Thr Val Phe Thr Leu Thr Ile Ser Ser Leu Gln Pro
65                  70                  75                  80

Glu Asp Phe Ala Thr Tyr Tyr Cys Gln Gln Thr Tyr Ala Val Pro Pro
                85                  90                  95

Thr Phe Gly Gln Gly Thr Lys Val Glu Ile Lys Arg
            100                 105


<210> SEQ ID NO 90
<211> LENGTH: 51
<212> TYPE: DNA
<213> ORGANISM: Artificial
<220> FEATURE:
<223> OTHER INFORMATION: VH-5'-NotI PCR primer

<400> SEQUENCE: 90

gtatgtctgg cggccgcaga ggtgcagctg ttggagtctg ggggaggctt g             51


<210> SEQ ID NO 91
<211> LENGTH: 35
<212> TYPE: DNA
<213> ORGANISM: Artificial
<220> FEATURE:
<223> OTHER INFORMATION: VH-NO-XhoI PCR primer

<400> SEQUENCE: 91
```

-continued

```
tagaattctt attagctgga gacggtgacc agggt                            35


<210> SEQ ID NO 92
<211> LENGTH: 21
<212> TYPE: DNA
<213> ORGANISM: Artificial
<220> FEATURE:
<223> OTHER INFORMATION: Alpha factor sequencing primer

<400> SEQUENCE: 92

tactattgcc agcattgctg c                                           21


<210> SEQ ID NO 93
<211> LENGTH: 21
<212> TYPE: DNA
<213> ORGANISM: Artificial
<220> FEATURE:
<223> OTHER INFORMATION: AOX1 reverse primer

<400> SEQUENCE: 93

gcaaatggca ttctgacatc c                                           21


<210> SEQ ID NO 94
<211> LENGTH: 348
<212> TYPE: DNA
<213> ORGANISM: Homo sapiens

<400> SEQUENCE: 94

gaggtgcagc tgttggagtc tgggggaggc ttggtacagc ctggggggtc cctgcgtctc     60

tcctgtgcag cctccggatt caccttttct gattatgaga tgatgtgggt ccgccaggct    120

ccagggaagg gtctagagtg ggtctcaact attacttcgg atggtatttc tacatactac    180

gcagactccg tgaagggccg gttcaccatc ttccgcgaca attccaagaa cacgctgtat    240

ctgcaaatga acagcctgcg tgccgaggat accgcggtat attactgtgc gaaaagtggg    300

aggtttttg actactgggg tcagggaacc ctggtcaccg tctcgagc                 348


<210> SEQ ID NO 95
<211> LENGTH: 348
<212> TYPE: DNA
<213> ORGANISM: Homo sapiens

<400> SEQUENCE: 95

ctccacgtcg acaacctcag accccctccg aaccatgtcg gaccccccag ggacgcagag     60

aggacacgtc ggaggcctaa gtggaaaaga ctaatactct actacaccca ggcggtccga    120

ggtcccttcc cagatctcac ccagagttga taatgaagcc taccataaag atgtatgatg    180

cgtctgaggc acttcccggc caagtggtag aaggcgctgt taaggttctt gtgcgacata    240

gacgtttact tgtcggacgc acggctccta tggcgccata taatgacacg cttttcaccc    300

tccaaaaaac tgatgacccc agtcccttgg gaccagtggc agagctcg                 348


<210> SEQ ID NO 96
<211> LENGTH: 348
<212> TYPE: DNA
<213> ORGANISM: Homo sapiens

<400> SEQUENCE: 96

gaggtgcagc tgttggagtc tgggggaggc ttggtacagc ctggggggtc cctgcgtctc     60

tcctgtgcag cctccggatt cacctttgat aattatgaga tgacgtgggt ccgccaggct    120

ccagggaagg gtctagagtg ggtctcatct attacgagtg atggtacttc gacatactac    180
```

gcagactccg tgaagggccg gttcaccatc tcccgcgaca attccaagaa cacgctgtat 240
ctgcaaatga acagcctgcg tgccgaggat accgcggtat attactgtgc gaaacctaat 300
ccgccgtttg actactgggg tcagggaacc ctggtcaccg tctcgagc 348

<210> SEQ ID NO 97
<211> LENGTH: 348
<212> TYPE: DNA
<213> ORGANISM: Homo sapiens

<400> SEQUENCE: 97
ctccacgtcg acaacctcag accccctccg aaccatgtcg gaccccccag ggacgcagag 60
aggacacgtc ggaggcctaa gtggaaacta ttaatactct actgcaccca ggcggtccga 120
ggtcccttcc cagatctcac ccagagtaga taatgctcac taccatgaag ctgtatgatg 180
cgtctgaggc acttcccggc caagtggtag agggcgctgt taaggttctt gtgcgacata 240
gacgtttact tgtcggacgc acggctccta tggcgccata taatgacacg ctttggatta 300
ggcggcaaac tgatgacccc agtcccttgg gaccagtggc agagctcg 348

<210> SEQ ID NO 98
<211> LENGTH: 348
<212> TYPE: DNA
<213> ORGANISM: Homo sapiens

<400> SEQUENCE: 98
gaggtgcagc tgttggagtc tgggggaggc ttggtacagc ctggggggtc cctgcgtctc 60
tcctgtgcag cctccggatt cacctttgat gggtatgaga tggcgtgggt ccgccaggct 120
ccagggaagg gtctagagtg ggtctcatct attacgagtg atggtacgag tacatactac 180
gcagactccg tgaagggccg gttcaccatc tcccgcgaca attccaagaa cacgctgtat 240
ctgcaaatga acagcctgcg tgccgaggac accgcggtat attactgtgc gaaaccgggg 300
ctgcgttttg actactgggg tcagggaacc ctggtcaccg tctcgagc 348

<210> SEQ ID NO 99
<211> LENGTH: 348
<212> TYPE: DNA
<213> ORGANISM: Homo sapiens

<400> SEQUENCE: 99
ctccacgtcg acaacctcag accccctccg aaccatgtcg gaccccccag ggacgcagag 60
aggacacgtc ggaggcctaa gtggaaacta cccatactct accgcaccca ggcggtccga 120
ggtcccttcc cagatctcac ccagagtaga taatgctcac taccatgctc atgtatgatg 180
cgtctgaggc acttcccggc caagtggtag agggcgctgt taaggttctt gtgcgacata 240
gacgtttact tgtcggacgc acggctcctg tggcgccata taatgacacg ctttggcccc 300
gacgcaaaac tgatgacccc agtcccttgg gaccagtggc agagctcg 348

<210> SEQ ID NO 100
<211> LENGTH: 348
<212> TYPE: DNA
<213> ORGANISM: Homo sapiens

<400> SEQUENCE: 100
gaggtgcagc tgttggagtc tgggggaggc ttggtacagc ctggggggtc cctgcgtctc 60
tcctgtgcag cctccggatt cacctttaat ttgtatgaga tgacttgggt ccgccaggct 120
ccagggaagg gtctagagtg ggtctcatct attactagtg atggtgtttc tacatactac 180
gcagactccg tgaagggccg gttcaccatc tcccgcgaca attccaagaa cacgctgtat 240
ctgcaaatga acagcctgcg tgccgaggac accgcggtat attactgtgc gaaagctggg 300
gtgatttttg actactgggg tcagggaacc ctggtcaccg tctcgagc 348

<210> SEQ ID NO 101
<211> LENGTH: 348
<212> TYPE: DNA
<213> ORGANISM: Homo sapiens

<400> SEQUENCE: 101
ctccacgtcg acaacctcag accccctccg aaccatgtcg gaccccccag ggacgcagag 60
aggacacgtc ggaggcctaa gtggaaatta aacatactct actgaaccca ggcggtccga 120
ggtcccttcc cagatctcac ccagagtaga taatgatcac taccacaaag atgtatgatg 180
cgtctgaggc acttcccggc caagtggtag agggcgctgt taaggttctt gtgcgacata 240
gacgtttact tgtcggacgc acggctcctg tggcgccata taatgacacg ctttcgaccc 300
cactaaaaac tgatgacccc agtcccttgg gaccagtggc agagctcg 348

<210> SEQ ID NO 102
<211> LENGTH: 324
<212> TYPE: DNA
<213> ORGANISM: Homo sapiens

<400> SEQUENCE: 102
gacatccaga tgacccagtc tccatcctcc ctgtctgcat ctgtaggaga ccgtgtcacc 60
atcacttgcc gggcaagtca gtttattgat acgtcgttag agtggtatca gcagaaacca 120
gggaaagccc ctaagctcct gatctatgat gggtcccatt tgcaaagtgg ggtcccatca 180
cgtttcagtg gcagtggatc tgggacagat ttcactctca ccatcagcag tctgcaacct 240
gaagatttag ctacgtacta ctgtcaacag tattgggttc ttcctctgac gttcggccaa 300
gggaccaagg tggaaatcaa acgg 324

<210> SEQ ID NO 103
<211> LENGTH: 324
<212> TYPE: DNA
<213> ORGANISM: Homo sapiens

<400> SEQUENCE: 103
ctgtaggtct actgggtcag aggtaggagg gacagacgta gacatcctct ggcacagtgg 60
tagtgaacgg cccgttcagt caaataacta tgcagcaatc tcaccatagt cgtctttggt 120
ccctttcggg gattcgagga ctagatacta cccagggtaa acgtttcacc ccagggtagt 180
gcaaagtcac cgtcacctag accctgtcta aagtgagagt ggtagtcgtc agacgttgga 240
cttctaaatc gatgcatgat gacagttgtc ataacccaag aaggagactg caagccggtt 300
ccctggttcc acctttagtt tgcc 324

<210> SEQ ID NO 104
<211> LENGTH: 351
<212> TYPE: DNA
<213> ORGANISM: Homo sapiens

<400> SEQUENCE: 104
gaggtgcagc tgttggagtc tgggggaggc ttagtacagc ctggggggtc cctgcgtctc 60
tcctgtgcag cctccggatt cacctttatt gcttatgata tgagttgggt ccgccaggct 120
ccagggaagg gtctggagtg ggtctcatgg attgatgagt ggggtctgca gacatactac 180

```
gcagactccg tgaagggccg gttcaccatc tcccgcgaca attccaagaa cacgctgtat    240

ctgcaaatga acagcctgcg tgccgaggac accgcggtat attactgtgc gaaaaagacg    300

cctgaggagt ttgactactg ggtcagggga accctggtca ccgtctcgag c             351
```

<210> SEQ ID NO 105
<211> LENGTH: 351
<212> TYPE: DNA
<213> ORGANISM: Homo sapiens

<400> SEQUENCE: 105

```
ctccacgtcg acaacctcag accccctccg aatcatgtcg gaccccccag ggacgcagag     60

aggacacgtc ggaggcctaa gtggaaataa cgaatactat actcaaccca ggcggtccga    120

ggtcccttcc cagacctcac ccagagtacc taactactca ccccagacgt ctgtatgatg    180

cgtctgaggc acttcccggc caagtggtag agggcgctgt taaggttctt gtgcgacata    240

gacgtttact tgtcggacgc acggctcctg tggcgccata taatgacacg ctttttctgc    300

ggactcctca aactgatgac cccagtccct tgggaccagt ggcagagctc g             351
```

<210> SEQ ID NO 106
<211> LENGTH: 348
<212> TYPE: DNA
<213> ORGANISM: Homo sapiens

<400> SEQUENCE: 106

```
gaggtgcagc tgttggagtc tgggggaggc ttggtacagc ctggggggtc cctgcgtctc     60

tcctgtgcag cctccggatt cacctttggt gattatgaga tgagttgggt ccgccaggct    120

ccagggaagg gtctagagtg ggtctcaggg attgatggtg agggttctga tacatactac    180

gcagactccg tgaagggccg gttcaccatc tcccgcgaca attccaagaa cacgctgtat    240

ctgcaaatga acagcctgcg tgccgaggat accgcggtat attactgtgc gaaaccgggg    300

aggagttttg actactgggg tcagggaacc ctggtcaccg tctcgagc                 348
```

<210> SEQ ID NO 107
<211> LENGTH: 348
<212> TYPE: DNA
<213> ORGANISM: Homo sapiens

<400> SEQUENCE: 107

```
ctccacgtcg acaacctcag accccctccg aaccatgtcg gaccccccag ggacgcagag     60

aggacacgtc ggaggcctaa gtggaaacca ctaatactct actcaaccca ggcggtccga    120

ggtcccttcc cagatctcac ccagagtccc taactaccac tcccaagact atgtatgatg    180

cgtctgaggc acttcccggc caagtggtag agggcgctgt taaggttctt gtgcgacata    240

gacgtttact tgtcggacgc acggctccta tggcgccata taatgacacg ctttggcccc    300

tcctcaaaac tgatgacccc agtcccttgg gaccagtggc agagctcg                 348
```

<210> SEQ ID NO 108
<211> LENGTH: 354
<212> TYPE: DNA
<213> ORGANISM: Homo sapiens

<400> SEQUENCE: 108

```
gaggtgcagc tgttggagtc tgggggaggc ttggtacagc ctggggggtc cctgcgtctc     60

tcctgtgcag cctccggatt cacctttagg ttgtatgaga tggcgtgggt ccgccaggct    120

ccagggaagg gtctagagtg ggtctcaggg attgatattt tgggttcgag gacatactac    180
```

-continued gcagactccg tgaagggccg gttcaccatc tcccgcgaca attccaagaa cacgctgtat 240
ctgcaaatga acagcctgcg tgccgaggat accgcggtat attactgtgc gaaagatctg 300
tcgtggcagg gttttgacta ctggggtcag ggaaccctgg tcaccgtctc gagc 354

<210> SEQ ID NO 109
<211> LENGTH: 354
<212> TYPE: DNA
<213> ORGANISM: Homo sapiens

<400> SEQUENCE: 109
ctccacgtcg acaacctcag acccccctccg aaccatgtcg gaccccccag ggacgcagag 60
aggacacgtc ggaggcctaa gtggaaatcc aacatactct accgcaccca ggcggtccga 120
ggtcccttcc cagatctcac ccagagtccc taactataaa acccaagctc ctgtatgatg 180
cgtctgaggc acttcccggc caagtggtag agggcgctgt taaggttctt gtgcgacata 240
gacgtttact tgtcggacgc acggctccta tggcgccata taatgacacg ctttctagac 300
agcaccgtcc caaaactgat gaccccagtc ccttgggacc agtggcagag ctcg 354

<210> SEQ ID NO 110
<211> LENGTH: 369
<212> TYPE: DNA
<213> ORGANISM: Homo sapiens

<400> SEQUENCE: 110
gaggtgcagc tgttggagtc tgggggaggc ttggtacagc ctggggggtc cctgcgtctc 60
tcctgtgcag cctccggatt caccttttct tattattcga tgtattgggt ccgccaggct 120
ccagggaagg gtctagagtg ggtctcatcg atttcgcctt ttggttgggg tacatactac 180
gcagactccg tgaagggccg gttcaccatc tcccgcgaca attccaagga cacgctgtat 240
ctgcaaatga acagcctgcg tgccgaggac accgcggtat attactgtgc gaaatatggg 300
gagacgagtg gtccgatttc tgagaatttt gactactggg gtcagggaac cctggtcacc 360
gtctcgagc 369

<210> SEQ ID NO 111
<211> LENGTH: 369
<212> TYPE: DNA
<213> ORGANISM: Homo sapiens

<400> SEQUENCE: 111
ctccacgtcg acaacctcag acccccctccg aaccatgtcg gaccccccag ggacgcagag 60
aggacacgtc ggaggcctaa gtggaaaaga ataataagct acataaccca ggcggtccga 120
ggtcccttcc cagatctcac ccagagtagc taaagcggaa aaccaacccc atgtatgatg 180
cgtctgaggc acttcccggc caagtggtag agggcgctgt taaggttcct gtgcgacata 240
gacgtttact tgtcggacgc acggctcctg tggcgccata taatgacacg ctttataccc 300
ctctgctcac caggctaaag actcttaaaa ctgatgaccc cagtcccttg ggaccagtgg 360
cagagctcg 369

<210> SEQ ID NO 112
<211> LENGTH: 348
<212> TYPE: DNA
<213> ORGANISM: Homo sapiens

<400> SEQUENCE: 112
gaggtgcagc tgttggagtc tgggggaggc ttggtacagc ctggggggtc cctgcgtctc 60

-continued

```
tcctgtgcag cctccggatt caccttttgg tcttatgata tgacgtgggt ccgccaggct    120

ccagggaagg gtctagagtg ggtctcatct attatggctt cgggtgatga tacatactac    180

gcagactccg tgaagggccg gttcaccatc tcccgcgaca attccaagaa cacgctgtat    240

ctgcaaatga acagcctgcg tgccgaggat accgcggtat attactgtgc gaaatgggat    300

cgggattttg actactgggg tcagggaacc ctggtcaccg tctcgagc                 348


<210> SEQ ID NO 113
<211> LENGTH: 348
<212> TYPE: DNA
<213> ORGANISM: Homo sapiens

<400> SEQUENCE: 113

ctccacgtcg acaacctcag accccctccg aaccatgtcg gacccccag ggacgcagag      60

aggacacgtc ggaggcctaa gtggaaaacc agaatactat actgcaccca ggcggtccga    120

ggtcccttcc cagatctcac ccagagtaga taataccgaa gcccactact atgtatgatg    180

cgtctgaggc acttcccggc caagtggtag agggcgctgt taaggttctt gtgcgacata    240

gacgtttact tgtcggacgc acggctccta tggcgccata taatgacacg ctttacccta    300

gccctaaaac tgatgacccc agtcccttgg gaccagtggc agagctcg                 348


<210> SEQ ID NO 114
<211> LENGTH: 360
<212> TYPE: DNA
<213> ORGANISM: Homo sapiens

<400> SEQUENCE: 114

gaggtgcagc tgttggagtc tgggggaggc ttggtacagc ctggggggtc cctgcgtctc     60

tcctgtgcag cctccggatt cacctttgag gagtatgtta tgtcgtgggt ccgccaggct    120

ccagggaagg gtctggagtg ggtctcaact atttctccta ttggtctgac tacatactac    180

gcagactccg tgaagggccg gttcaccatc tcccgcgaca attccaagaa cacgctgtat    240

ctgcaaatga acagcctgcg tgccgaggac accgcggtat attactgtgc ggaatttcct    300

ttgattattc ttcctgattt tgactactgg ggtcagggaa ccctggtcac cgtctcgagc    360


<210> SEQ ID NO 115
<211> LENGTH: 360
<212> TYPE: DNA
<213> ORGANISM: Homo sapiens

<400> SEQUENCE: 115

ctccacgtcg acaacctcag accccctccg aaccatgtcg gacccccag ggacgcagag      60

aggacacgtc ggaggcctaa gtggaaactc ctcatacaat acagcaccca ggcggtccga    120

ggtcccttcc cagacctcac ccagagttga taaagaggat aaccagactg atgtatgatg    180

cgtctgaggc acttcccggc caagtggtag agggcgctgt taaggttctt gtgcgacata    240

gacgtttact tgtcggacgc acggctcctg tggcgccata taatgacacg ccttaaagga    300

aactaataag aaggactaaa actgatgacc ccagtccctt gggaccagtg gcagagctcg    360


<210> SEQ ID NO 116
<211> LENGTH: 369
<212> TYPE: DNA
<213> ORGANISM: Homo sapiens

<400> SEQUENCE: 116

gaggtgcagc tgttggagtc tgggggaggc ctggtacagc ctggggggtc cctgcgtctc     60
```

tcctgtgcag cctccggatt cacctttatg gagtatgcga tgatttgggt ccgccaggct 120
ccagggaagg gtctagagtg ggtctcaatt atttctccgc ttggtttgtc tacatactac 180
gcagactccg tgaagggccg gttcaccatc tcccgcgaca attccaagaa cacgctgtat 240
ctgcaaatga acagcctgcg tgccgaggac accgcggtat attactgtgc gaaatatcag 300
gattcgtctg atagtcagta tacgaatttt gactactggg gtcagggaac cctggtcacc 360
gtctcgagc 369

<210> SEQ ID NO 117
<211> LENGTH: 369
<212> TYPE: DNA
<213> ORGANISM: Homo sapiens

<400> SEQUENCE: 117
ctccacgtcg acaacctcag accccctccg gaccatgtcg gaccccccag ggacgcagag 60
aggacacgtc ggaggcctaa gtggaaatac ctcatacgct actaaaccca ggcggtccga 120
ggtcccttcc cagatctcac ccagagttaa taaagaggcg aaccaaacag atgtatgatg 180
cgtctgaggc acttcccggc caagtggtag agggcgctgt taaggttctt gtgcgacata 240
gacgtttact tgtcggacgc acggctcctg tggcgccata taatgacacg ctttatagtc 300
ctaagcagac tatcagtcat atgcttaaaa ctgatgaccc cagtcccttg ggaccagtgg 360
cagagctcg 369

<210> SEQ ID NO 118
<211> LENGTH: 363
<212> TYPE: DNA
<213> ORGANISM: Homo sapiens

<400> SEQUENCE: 118
gaggtgcagc tgttggagtc tgggggaggc ttggtacagc ctggggggtc cctgcgtctc 60
tcctgtgcag cctccggatt cacctttgag gattatggga tggggtgggc ccgccaggct 120
ccagggaagg gtctagagtg ggtctcaagt attggtcctc tgggtctttg gacatactac 180
gcagactccg cgaagggccg gttcaccatc tcccgcgaca attccaagaa cacgctgtat 240
ctgcaaatga acagcctgcg tgccgaggac accgcggtat attactgtgc gaaatctccg 300
cttgagggtt tgattacgaa ttttgactac tggggtcagg gaaccctggt caccgtctcg 360
agc 363

<210> SEQ ID NO 119
<211> LENGTH: 363
<212> TYPE: DNA
<213> ORGANISM: Homo sapiens

<400> SEQUENCE: 119
ctccacgtcg acaacctcag accccctccg aaccatgtcg gaccccccag ggacgcagag 60
aggacacgtc ggaggcctaa gtggaaactc ctaataccct accccacccg ggcggtccga 120
ggtcccttcc cagatctcac ccagagttca taaccaggag acccagaaac ctgtatgatg 180
cgtctgaggc gcttcccggc caagtggtag agggcgctgt taaggttctt gtgcgacata 240
gacgtttact tgtcggacgc acggctcctg tggcgccata taatgacacg ctttagaggc 300
gaactcccaa actaatgctt aaaactgatg accccagtcc cttgggacca gtggcagagc 360
tcg 363

<210> SEQ ID NO 120

<211> LENGTH: 357
<212> TYPE: DNA
<213> ORGANISM: Homo sapiens

<400> SEQUENCE: 120
gaggtgcagc tgttggagtc tgggggaggc ttggtacagc ctggggggtc cctgcgtctc 60
tcctgtgcag cctccggatt cacctttcct gagtatgata tgacgtgggt ccgccaggct 120
ccagggaagg gtctggagtg ggtctcatat attagttctg atggttattc tacatactac 180
gcagactccg tgaagggccg gttcaccatc tcccgcgaca attccaagaa cacgctgtat 240
ctgcaaatga acagcctgcg tgccgaggac accgcggtat attactgtgc gaaaccgcat 300
gggagtccgc gggagtttga ctactggggt cagggaaccc tggtcaccgt ctcgagc 357

<210> SEQ ID NO 121
<211> LENGTH: 357
<212> TYPE: DNA
<213> ORGANISM: Homo sapiens

<400> SEQUENCE: 121
ctccacgtcg acaacctcag accccctccg aaccatgtcg gaccccccag ggacgcagag 60
aggacacgtc ggaggcctaa gtggaaagga ctcatactat actgcaccca ggcggtccga 120
ggtcccttcc cagacctcac ccagagtata taatcaagac taccaataag atgtatgatg 180
cgtctgaggc acttcccggc caagtggtag agggcgctgt taaggttctt gtgcgacata 240
gacgtttact tgtcggacgc acggctcctg tggcgccata taatgacacg ctttggcgta 300
ccctcaggcg ccctcaaact gatgacccca gtcccttggg accagtggca gagctcg 357

<210> SEQ ID NO 122
<211> LENGTH: 348
<212> TYPE: DNA
<213> ORGANISM: Homo sapiens

<400> SEQUENCE: 122
gaggtgcagc tgttggagtc tgggggaggc ttggtacagc ctggggggtc cctgcgtctc 60
tcctgtgcag cctccggatt cccctttccg cagtatcaga tggcgtgggt ccgccaggct 120
ccagggaagg gtctagagtg ggtctcaatg attacttctg atggtcttga tacatattac 180
gcagactccg tgaagggccg gttcaccatc tcccgcgaca attccaagaa cacgctgtat 240
ctgcaaatga acagcctgcg tgccgaggat accgcggtat attactgtgc gaaacctgag 300
cctctttttg actactgggg tcagggaacc ctggtcaccg tctcgagc 348

<210> SEQ ID NO 123
<211> LENGTH: 348
<212> TYPE: DNA
<213> ORGANISM: Homo sapiens

<400> SEQUENCE: 123
ctccacgtcg acaacctcag accccctccg aaccatgtcg gaccccccag ggacgcagag 60
aggacacgtc ggaggcctaa ggggaaaggc gtcatagtct accgcaccca ggcggtccga 120
ggtcccttcc cagatctcac ccagagttac taatgaagac taccagaact atgtataatg 180
cgtctgaggc acttcccggc caagtggtag agggcgctgt taaggttctt gtgcgacata 240
gacgtttact tgtcggacgc acggctccta tggcgccata taatgacacg ctttggactc 300
ggagaaaaac tgatgacccc agtcccttgg gaccagtggc agagctcg 348

<210> SEQ ID NO 124

<211> LENGTH: 348
<212> TYPE: DNA
<213> ORGANISM: Homo sapiens

<400> SEQUENCE: 124
gaggtgcagc tgttggagtc tgggggaggc ttggtacagc ctggggggtc cctgcgtctc 60
tcctgtgcag cctccggatt cacctttcg ggttatcaga tggcttgggt ccgccaggct 120
ccagggaagg gtctagagtg ggtctcaggt attagttcgg agggtcttac tacatactac 180
gcagactccg tgaagggccg gttcaccatc tcccgcgaca attccaagaa cacgctgtat 240
ctgcaaatga acagcctgcg tgccgaggac accgcggtat attactgtgc gaaattgggg 300
cgtaggtttg actactgggg tcagggaacc ctggtcaccg tctcgagc 348

<210> SEQ ID NO 125
<211> LENGTH: 348
<212> TYPE: DNA
<213> ORGANISM: Homo sapiens

<400> SEQUENCE: 125
ctccacgtcg acaacctcag accccctccg aaccatgtcg gaccccccag ggacgcagag 60
aggacacgtc ggaggcctaa gtggaaaagc ccaatagtct accgaaccca ggcggtccga 120
ggtcccttcc cagatctcac ccagagtcca taatcaagcc tcccagaatg atgtatgatg 180
cgtctgaggc acttcccggc caagtggtag agggcgctgt taaggttctt gtgcgacata 240
gacgtttact tgtcggacgc acggctcctg tggcgccata taatgacacg ctttaacccc 300
gcatccaaac tgatgacccc agtcccttgg gaccagtggc agagctcg 348

<210> SEQ ID NO 126
<211> LENGTH: 360
<212> TYPE: DNA
<213> ORGANISM: Homo sapiens

<400> SEQUENCE: 126
gaggtgcagc tgttggagtc tgggggaggc ttggtacagc ctggggggtc cctgcgtctc 60
tcctgtgcag cctccggatt cacctttgcg aattatgaga tggggtgggc ccgccaggct 120
ccagggaagg gtctagagtg ggtctcagtt atttctgagt ggggttattc tacatactac 180
gcagactccg cgaagggccg gttcaccatc tcccgcgaca attccaagaa cacgctgtat 240
ctgcaaatga acagcctgcg tgccgaggac accgcggtat attactgtgc gaaacttgtg 300
ggtgggactc agtatgagtt tgactactgg ggtcagggaa ccctggtcac cgtctcgagc 360

<210> SEQ ID NO 127
<211> LENGTH: 360
<212> TYPE: DNA
<213> ORGANISM: Homo sapiens

<400> SEQUENCE: 127
ctccacgtcg acaacctcag accccctccg aaccatgtcg gaccccccag ggacgcagag 60
aggacacgtc ggaggcctaa gtggaaacgc ttaatactct accccacccg ggcggtccga 120
ggtcccttcc cagatctcac ccagagtcaa taaagactca ccccaataag atgtatgatg 180
cgtctgaggc gcttcccggc caagtggtag agggcgctgt taaggttctt gtgcgacata 240
gacgtttact tgtcggacgc acggctcctg tggcgccata taatgacacg ctttgaacac 300
ccaccctgag tcatactcaa actgatgacc ccagtccctt gggaccagtg gcagagctcg 360

<210> SEQ ID NO 128

<211> LENGTH: 348
<212> TYPE: DNA
<213> ORGANISM: Homo sapiens

<400> SEQUENCE: 128
gaggtgcagc tgttggagtc tgggggaggc ttggtacagc ctgggggggtc cctgcgtctc 60 tcctgtgcag cctccggatt cacctttcat aattatgaga tgtcgtgggt ccgccaggct 120
ccagggaagg gtctagagtg ggtctcaagt atttcttcgg gtggttcttc tacatactac 180
gcagactccg tgaagggccg gttcaccatc tcccgcgaca attccaagaa cacgctgtat 240
ctgcaaatga acagcctgcg tgccgaggac accgcggtat attactgtgc gaaaccgggg 300
gttaagtttg actactgggg tcagggaacc ctggtcaccg tctcgagc 348

<210> SEQ ID NO 129
<211> LENGTH: 348
<212> TYPE: DNA
<213> ORGANISM: Homo sapiens

<400> SEQUENCE: 129
ctccacgtcg acaacctcag accccctccg aaccatgtcg gaccccccag ggacgcagag 60
aggacacgtc ggaggcctaa gtggaaagta ttaatactct acagcaccca ggcggtccga 120
ggtcccttcc cagatctcac ccagagttca taaagaagcc caccaagaag atgtatgatg 180
cgtctgaggc acttcccggc caagtggtag agggcgctgt taaggttctt gtgcgacata 240
gacgtttact tgtcggacgc acggctcctg tggcgccata taatgacacg ctttggcccc 300
caattcaaac tgatgacccc agtcccttgg gaccagtggc agagctcg 348

<210> SEQ ID NO 130
<211> LENGTH: 348
<212> TYPE: DNA
<213> ORGANISM: Homo sapiens

<400> SEQUENCE: 130
gaggtgcagc tgttggagtc cgggggaggc ttggtacagc ctgggggggtc cctgcgtctc 60 tcctgtgcag cctccggatt cacctttggg ctgtatgaga tgacgtgggt ccgccaggct 120
ccagggaagg gtctagagtg ggtctcaagt attacgggtg atggtatttc gacatactac 180
gcagactccg tgaagggccg gttcaccatc tcccgcgaca attccaggaa cacgctgtat 240
ctgcaaatga acagcctgcg tgccgaggac accgcggtat attactgtgc gaaagctggg 300
aggaagtttg actactgggg tcagggaacc ctggtcaccg tctcgagc 348

<210> SEQ ID NO 131
<211> LENGTH: 348
<212> TYPE: DNA
<213> ORGANISM: Homo sapiens

<400> SEQUENCE: 131
ctccacgtcg acaacctcag gccccctccg aaccatgtcg gaccccccag ggacgcagag 60
aggacacgtc ggaggcctaa gtggaaaccc gacatactct actgcaccca ggcggtccga 120
ggtcccttcc cagatctcac ccagagttca taatgcccac taccataaag ctgtatgatg 180
cgtctgaggc acttcccggc caagtggtag agggcgctgt taaggtcctt gtgcgacata 240
gacgtttact tgtcggacgc acggctcctg tggcgccata taatgacacg ctttcgaccc 300
tccttcaaac tgatgacccc agtcccttgg gaccagtggc agagctcg 348

<210> SEQ ID NO 132

```
<211> LENGTH: 348
<212> TYPE: DNA
<213> ORGANISM: Homo sapiens

<400> SEQUENCE: 132

gaggtgcagc tgttggagtc tgggggaggc ttggtacagc ctggggggtc cctgcgtctc     60

tcctgtgcag cctccggatt cacctttagt aattatcaga tggcgtgggt ccgccaggct    120

ccagggaagg gtctagagtg ggtctcaagt attactagtg agggtggttc gacatactac    180

gcagactccg tgaagggccg gttcaccatc tcccgcgaca attccaagaa cacactgtat    240

ctgcaaatga acagcctgcg tgccgaggac accgcggtat attactgtgc gaaaccgggt    300

aagaattttg actactgggg tcagggaacc ctggtcaccg tctcgagc                348


<210> SEQ ID NO 133
<211> LENGTH: 348
<212> TYPE: DNA
<213> ORGANISM: Homo sapiens

<400> SEQUENCE: 133

ctccacgtcg acaacctcag accccctccg aaccatgtcg gaccccccag ggacgcagag     60

aggacacgtc ggaggcctaa gtggaaatca ttaatagtct accgcaccca ggcggtccga    120

ggtcccttcc cagatctcac ccagagttca taatgatcac tcccaccaag ctgtatgatg    180

cgtctgaggc acttcccggc caagtggtag agggcgctgt taaggttctt gtgtgacata    240

gacgtttact tgtcggacgc acggctcctg tggcgccata taatgacacg ctttggccca    300

ttcttaaaac tgatgacccc agtcccttgg gaccagtggc agagctcg                348


<210> SEQ ID NO 134
<211> LENGTH: 348
<212> TYPE: DNA
<213> ORGANISM: Homo sapiens

<400> SEQUENCE: 134

gaggtgcagc tgttggagtc tgggggaggc ttggtacagc ctggggggtc cctgcgtctc     60

tcctgtgcag cctccggatt cacctttgat aattatgaga tgacgtgggt ccgccaggct    120

ccagggaagg gtctagagtg ggtctcaact attacgtcgc agggtactag tacatactac    180

gcagactccg tgaagggccg gttcaccatc tcccgcgaca attccaagaa cacgctgtat    240

ctgcaaatga acagcctgcg tgccgaggac accgcggtat attactgtgc gaaacctgat    300

cgttcttttg actactgggg tcagggaacc ctggtcaccg tctcgagc                348


<210> SEQ ID NO 135
<211> LENGTH: 348
<212> TYPE: DNA
<213> ORGANISM: Homo sapiens

<400> SEQUENCE: 135

ctccacgtcg acaacctcag accccctccg aaccatgtcg gaccccccag ggacgcagag     60

aggacacgtc ggaggcctaa gtggaaacta ttaatactct actgcaccca ggcggtccga    120

ggtcccttcc cagatctcac ccagagttga taatgcagcg tcccatgatc atgtatgatg    180

cgtctgaggc acttcccggc caagtggtag agggcgctgt taaggttctt gtgcgacata    240

gacgtttact tgtcggacgc acggctcctg tggcgccata taatgacacg ctttggacta    300

gcaagaaaac tgatgacccc agtcccttgg gaccagtggc agagctcg                348


<210> SEQ ID NO 136
```

<211> LENGTH: 348
<212> TYPE: DNA
<213> ORGANISM: Homo sapiens

<400> SEQUENCE: 136
gaggtgcagc tgttggagtc tgggggaggc ttggtacagc ctggggggtc cctgcgtctc 60
tcctgtgcag cctccggatt cacctttcgt agttatgaga tgacttgggt ccgccaggct 120
ccagggaagg gtctggagtg ggtctcatct attacgtcgg atggtggtac tacatactac 180
gcagactccg tgaagggccg gttcaccatc tcccgcgaca attccaagaa cacgctgtat 240
ctgcaaatga acagcctgcg tgccgaggac accgcggtat attactgtgc gaaacctgat 300
aagacgtttg actactgggg tcagggaacc ctggtcaccg tctcgagc 348

<210> SEQ ID NO 137
<211> LENGTH: 348
<212> TYPE: DNA
<213> ORGANISM: Homo sapiens

<400> SEQUENCE: 137
ctccacgtcg acaacctcag accccctccg aaccatgtcg gacccccccag ggacgcagag 60 aggacacgtc ggaggcctaa gtggaaagca tcaatactct actgaaccca ggcggtccga 120
ggtcccttcc cagacctcac ccagagtaga taatgcagcc taccaccatg atgtatgatg 180
cgtctgaggc acttcccggc caagtggtag agggcgctgt taaggttctt gtgcgacata 240
gacgtttact tgtcggacgc acggctcctg tggcgccata taatgacacg ctttggacta 300
ttctgcaaac tgatgacccc agtcccttgg gaccagtggc agagctcg 348

<210> SEQ ID NO 138
<211> LENGTH: 348
<212> TYPE: DNA
<213> ORGANISM: Homo sapiens

<400> SEQUENCE: 138
gaggtgcagc tgttggagtc tgggggaggc ttggtacagc ctggggggtc cctgcgtctc 60
tcctgtgcag cctccggatt cacctttaat ttgtatgaga tgacttgggt ccgccaggct 120
ccagggaagg gtctagagtg ggtctcatct attactagtg atggtgtttc tacatactac 180
gcagactccg tgaagggccg gttcaccatc tcccgcgaca attccaagaa cacgctgtat 240
ctgcaaatga acagcctgcg tgccgaggac accgcggtat attactgtgc gaaaccggat 300
tctccgtttg actactgggg tcagggaacc ctggtcaccg tctcgagc 348

<210> SEQ ID NO 139
<211> LENGTH: 348
<212> TYPE: DNA
<213> ORGANISM: Homo sapiens

<400> SEQUENCE: 139
ctccacgtcg acaacctcag accccctccg aaccatgtcg gacccccccag ggacgcagag 60 aggacacgtc ggaggcctaa gtggaaatta aacatactct actgaaccca ggcggtccga 120
ggtcccttcc cagatctcac ccagagtaga taatgatcac taccacaaag atgtatgatg 180
cgtctgaggc acttcccggc caagtggtag agggcgctgt taaggttctt gtgcgacata 240
gacgtttact tgtcggacgc acggctcctg tggcgccata taatgacacg ctttggccta 300
agaggcaaac tgatgacccc agtcccttgg gaccagtggc agagctcg 348

<210> SEQ ID NO 140

<211> LENGTH: 348
<212> TYPE: DNA
<213> ORGANISM: Homo sapiens

<400> SEQUENCE: 140
gaggtgcagc tgttggagtc tgggggaggc ttggtacagc ctggggggtc cctgcgtctc 60
tcctgtgcag cctccggatt cacctttggg cattatgata tggcttgggt ccgccaggct 120
ccagggaagg gtctagagtg ggtctcaact attagtgata atggtaatgg gacatactac 180
gcagactccg tgaagggccg gttcaccatc tcccgcgaca attccaagaa cacgctgtat 240
ctgcaaatga acagcctgcg tgccgaggac accgcggtat attactgtgc gaaaccgggg 300
cgtgattttg actactgggg tcagggaacc ctggtcaccg tctcgagc 348

<210> SEQ ID NO 141
<211> LENGTH: 348
<212> TYPE: DNA
<213> ORGANISM: Homo sapiens

<400> SEQUENCE: 141
ctccacgtcg acaacctcag accccctccg aaccatgtcg gacccccccag ggacgcagag 60 aggacacgtc ggaggcctaa gtggaaaccc gtaatactat accgaaccca ggcggtccga 120
ggtcccttcc cagatctcac ccagagttga taatcactat taccattacc ctgtatgatg 180
cgtctgaggc acttcccggc caagtggtag agggcgctgt taaggttctt gtgcgacata 240
gacgtttact tgtcggacgc acggctcctg tggcgccata taatgacacg ctttggcccc 300
gcactaaaac tgatgacccc agtcccttgg gaccagtggc agagctcg 348

<210> SEQ ID NO 142
<211> LENGTH: 348
<212> TYPE: DNA
<213> ORGANISM: Homo sapiens

<400> SEQUENCE: 142
gaggtgcagc tgttggagtc tgggggaggc ttggtacagc ctggggggtc cctgcgtctc 60
tcctgtgcag cctccggatt cacctttggt cgttatcaga tggcttgggt ccgccaggct 120
ccagggaagg gtctagagtg ggtctcatct atttcttctg atggtggggg gacatactac 180
gcagactccg tgaagggccg gttcaccatc tcccgcgaca attccaagaa cacgctgtat 240
ctgcaaatga acagcctgcg tgccgaggat accgcggtat attactgtgc gaaacctggg 300
cgggcgtttg actactgggg tcagggaacc ctggtcaccg tctcgagc 348

<210> SEQ ID NO 143
<211> LENGTH: 348
<212> TYPE: DNA
<213> ORGANISM: Homo sapiens

<400> SEQUENCE: 143
ctccacgtcg acaacctcag accccctccg aaccatgtcg gacccccccag ggacgcagag 60 aggacacgtc ggaggcctaa gtggaaacca gcaatagtct accgaaccca ggcggtccga 120
ggtcccttcc cagatctcac ccagagtaga taaagaagac taccaccccc ctgtatgatg 180
cgtctgaggc acttcccggc caagtggtag agggcgctgt taaggttctt gtgcgacata 240
gacgtttact tgtcggacgc acggctccta tggcgccata taatgacacg ctttggaccc 300
gcccgcaaac tgatgacccc agtcccttgg gaccagtggc agagctcg 348

<210> SEQ ID NO 144

<211> LENGTH: 348
<212> TYPE: DNA
<213> ORGANISM: Homo sapiens

<400> SEQUENCE: 144
gaggtgcagc tgttggagtc tgggggaggc ttggtacagc ctggggggtc cctgcgtctc 60
tcctgtgcag cctccggatt cacctttgcg aggtatcaga tggcttgggt ccgccaggct 120
ccagggaagg gtctggagtg ggtctcaact atttctgatg atggtgattc gacatactac 180
gcagactccg tgaagggccg gttcaccatc tcccgcgaca attccaagaa cacgctgtat 240
ctgcaaatga acagcctgcg tgccgaggac accgcggtat attactgtgc gaaactggat 300
aagttgtttg actactgggg tcagggaacc ctggtcaccg tctcgagc 348

<210> SEQ ID NO 145
<211> LENGTH: 348
<212> TYPE: DNA
<213> ORGANISM: Homo sapiens

<400> SEQUENCE: 145
ctccacgtcg acaacctcag accccctccg aaccatgtcg gacccccccag ggacgcagag 60 aggacacgtc ggaggcctaa gtggaaacgc tccatagtct accgaaccca ggcggtccga 120
ggtcccttcc cagacctcac ccagagttga taaagactac taccactaag ctgtatgatg 180
cgtctgaggc acttcccggc caagtggtag agggcgctgt taaggttctt gtgcgacata 240
gacgtttact tgtcggacgc acggctcctg tggcgccata taatgacacg ctttgaccta 300
ttcaacaaac tgatgacccc agtcccttgg gaccagtggc agagctcg 348

<210> SEQ ID NO 146
<211> LENGTH: 348
<212> TYPE: DNA
<213> ORGANISM: Homo sapiens

<400> SEQUENCE: 146
gaggtgcagc tgttggagtc tgggggaggc ttggtacagc ctggggggtc cctgcgtctc 60
tcctgtgcag cctccggatt cacctttgag gagtatcaga tggcgtgggt ccgccaggct 120
ccagggaagg gtctagagtg ggtctcaacg atttcggatg atggttcttc gacatactac 180
gcagactccg tgaagggccg gttcaccatc tcccgcgaca attccaagaa cacgctgtat 240
ctgcaaatga acagcctgcg tgccgaggac accgcggtat attactgtgc gaaacctgat 300
ctttattttg actactgggg tcagggaacc ctggtcaccg tctcgagc 348

<210> SEQ ID NO 147
<211> LENGTH: 348
<212> TYPE: DNA
<213> ORGANISM: Homo sapiens

<400> SEQUENCE: 147
ctccacgtcg acaacctcag accccctccg aaccatgtcg gacccccccag ggacgcagag 60 aggacacgtc ggaggcctaa gtggaaactc ctcatagtct accgcaccca ggcggtccga 120
ggtcccttcc cagatctcac ccagagttgc taaagcctac taccaagaag ctgtatgatg 180
cgtctgaggc acttcccggc caagtggtag agggcgctgt taaggttctt gtgcgacata 240
gacgtttact tgtcggacgc acggctcctg tggcgccata taatgacacg ctttggacta 300
gaaataaaac tgatgacccc agtcccttgg gaccagtggc agagctcg 348

<210> SEQ ID NO 148

<211> LENGTH: 348
<212> TYPE: DNA
<213> ORGANISM: Homo sapiens

<400> SEQUENCE: 148
gaggtgcagc tgttggagtc tgggggaggc ttggtacagc ctggggggtc cctgcgtctc 60
tcctgtgcag cctccggatt cacctttgag gtgtatcaga tgggttgggt ccgccaggct 120
ccagggaagg gtctagagtg ggtctcattt attgtgcctg gggtgattt gacatactac 180 gcagactccg tgaagggccg gttcaccatc tcccgcgaca attccaagaa cacgctgtat 240
ctgcaaatga acagcctgcg tgccgaggac accgcggtat attactgtgc ggaaacgtgg 300
ccggagtttg actactgggg tcagggaacc ctggtcaccg tctcgagc 348

<210> SEQ ID NO 149
<211> LENGTH: 348
<212> TYPE: DNA
<213> ORGANISM: Homo sapiens

<400> SEQUENCE: 149
ctccacgtcg acaacctcag accccctccg aaccatgtcg gaccccccag ggacgcagag 60
aggacacgtc ggaggcctaa gtggaaactc cacatagtct acccaaccca ggcggtccga 120
ggtcccttcc cagatctcac ccagagtaaa taacacggac ccccactaaa ctgtatgatg 180
cgtctgaggc acttcccggc caagtggtag agggcgctgt taaggttctt gtgcgacata 240
gacgtttact tgtcggacgc acggctcctg tggcgccata taatgacacg cctttgcacc 300
ggcctcaaac tgatgacccc agtcccttgg gaccagtggc agagctcg 348

<210> SEQ ID NO 150
<211> LENGTH: 324
<212> TYPE: DNA
<213> ORGANISM: Homo sapiens

<400> SEQUENCE: 150
gacatccaga tgacccagtc tccatcctcc ctgtctgcat ctgtaggaga ccgtgtcacc 60
atcacttgcc gggcaagtca gacgattggg gagagtttac attggtacca gcagaaacca 120
gggaaagccc ctaggctcct gatctatttt gcttccctgt tgcaaagtgg ggtcccatcg 180
cgtttcagtg gcagtggatc tgggacagat tttactctca ccatcagcag tctgcaacct 240
gaagattttg ctacgtacta ctgtcaacag catcatatgc ttccttctac gttcggccaa 300
gggaccaagg tggaaatcaa acgg 324

<210> SEQ ID NO 151
<211> LENGTH: 324
<212> TYPE: DNA
<213> ORGANISM: Homo sapiens

<400> SEQUENCE: 151
ctgtaggtct actgggtcag aggtaggagg gacagacgta gacatcctct ggcacagtgg 60
tagtgaacgg cccgttcagt ctgctaaccc ctctcaaatg taaccatggt cgtctttggt 120
ccctttcggg gatccgagga ctagataaaa cgaagggaca acgtttcacc ccagggtagc 180
gcaaagtcac cgtcacctag accctgtcta aaatgagagt ggtagtcgtc agacgttgga 240
cttctaaaac gatgcatgat gacagttgtc gtagtatacg aaggaagatg caagccggtt 300
ccctggttcc acctttagtt tgcc 324

<210> SEQ ID NO 152

<211> LENGTH: 324
<212> TYPE: DNA
<213> ORGANISM: Homo sapiens

<400> SEQUENCE: 152
gacatccaga tgacccagtc tccatcctcc ctgtctgcat ctgtaggaga ccgtgtcacc 60
atcacttgcc gggcaagtca gtggattggt gatagtttat cttggtacca gcagaaacca 120
gggaaagccc ctaagctcct gatctatttt gcttcctatt tgcaaagtgg ggtcccaaca 180
cgtttcagtg gcagtggatc tgggacagat ttcactctca ccatcagcag tctgcaacct 240
gaagattttg ctacgtacta ctgtcaacag tattttgaga atcctgttac gttcggccaa 300
gggaccaagg tgggaatcaa acgg 324

<210> SEQ ID NO 153
<211> LENGTH: 324
<212> TYPE: DNA
<213> ORGANISM: Homo sapiens

<400> SEQUENCE: 153
ctgtaggtct actgggtcag aggtaggagg gacagacgta gacatcctct ggcacagtgg 60
tagtgaacgg cccgttcagt cacctaacca ctatcaaata gaaccatggt cgtctttggt 120
ccctttcggg gattcgagga ctagataaaa cgaaggataa acgtttcacc ccagggttgt 180
gcaaagtcac cgtcacctag accctgtcta aagtgagagt ggtagtcgtc agacgttgga 240
cttctaaaac gatgcatgat gacagttgtc ataaaactct taggacaatg caagccggtt 300
ccctggttcc acccttagtt tgcc 324

<210> SEQ ID NO 154
<211> LENGTH: 324
<212> TYPE: DNA
<213> ORGANISM: Homo sapiens

<400> SEQUENCE: 154
gacatccaaa tgacccagtc tccatcctcc ctgtctgcat ctgtaggaga ccgtgtcacc 60
atcacttgcc gggcaagtca gtttattggt gattctttat cttggtacca gcagaaacca 120
gggaaagccc ctaagctcct gatctatttt tcttccattt tgcaaagtgg ggtcccatca 180
cgtttcagtg gcagtggatc tgggacagat ttcactctca ccatcagcag tctgcaacct 240
gaagattttg ctacgtacta ctgtcaacag tatatggata ttcctattac gttcggccaa 300
gggaccaagg tggaaatcaa acgg 324

<210> SEQ ID NO 155
<211> LENGTH: 324
<212> TYPE: DNA
<213> ORGANISM: Homo sapiens

<400> SEQUENCE: 155
ctgtaggttt actgggtcag aggtaggagg gacagacgta gacatcctct ggcacagtgg 60
tagtgaacgg cccgttcagt caaataacca ctaagaaata gaaccatggt cgtctttggt 120
ccctttcggg gattcgagga ctagataaaa agaaggtaaa acgtttcacc ccagggtagt 180
gcaaagtcac cgtcacctag accctgtcta aagtgagagt ggtagtcgtc agacgttgga 240
cttctaaaac gatgcatgat gacagttgtc atatacctat aaggataatg caagccggtt 300
ccctggttcc acctttagtt tgcc 324

<210> SEQ ID NO 156

<211> LENGTH: 324
<212> TYPE: DNA
<213> ORGANISM: Homo sapiens

<400> SEQUENCE: 156
gacatccaga tgacccagtc tccatcctcc ctgtctgcat ctgtaggaga ccgtgtcacc 60
atcacttgcc gggcaagtca ggatattgat cataatttag agtggtatca gcagaaacca 120
gggaaagccc ctaagctcct gatctatgat agttccatgt tgcaaagtgg ggtcccatca 180
cgtttcagtg gcagtggatc tgggacagat ttcactctca ccatcagcag tctgcaacct 240
gaagattttg ctacgtacta ctgtcaacag tatcattcta ttcctgttac gttcggccaa 300
gggaccaagg tggaaatcaa acgg 324

<210> SEQ ID NO 157
<211> LENGTH: 324
<212> TYPE: DNA
<213> ORGANISM: Homo sapiens

<400> SEQUENCE: 157
ctgtaggtct actgggtcag aggtaggagg gacagacgta gacatcctct ggcacagtgg 60
tagtgaacgg cccgttcagt cctataacta gtattaaatc tcaccatagt cgtctttggt 120
ccctttcggg gattcgagga ctagatacta tcaaggtaca acgtttcacc ccagggtagt 180
gcaaagtcac cgtcacctag accctgtcta aagtgagagt ggtagtcgtc agacgttgga 240
cttctaaaac gatgcatgat gacagttgtc atagtaagat aaggacaatg caagccggtt 300
ccctggttcc acctttagtt tgcc 324

<210> SEQ ID NO 158
<211> LENGTH: 324
<212> TYPE: DNA
<213> ORGANISM: Homo sapiens

<400> SEQUENCE: 158
gacatccaga tgacccagtc tccatcctcc ctgtctgcat ctgtaggaga ccgtgtcacc 60
atcacttgcc gggcaagtca gcagattgag acgaatttag agtggtatca gcagaaacca 120
gggaaagccc ctaagctcct gatctatgat ggttcctggt tgcaaagtgg ggtcccatca 180
cgtttcagtg gcagtggatc tgggacagat ttcactctca ccatcagcag tctgcaacct 240
gaagattttg ctacgtacta ctgtcaacag tatcatagtt tgcctgctac gttcggccaa 300
gggaccaagg tggaaatcaa acgg 324

<210> SEQ ID NO 159
<211> LENGTH: 324
<212> TYPE: DNA
<213> ORGANISM: Homo sapiens

<400> SEQUENCE: 159
ctgtaggtct actgggtcag aggtaggagg gacagacgta gacatcctct ggcacagtgg 60
tagtgaacgg cccgttcagt cgtctaactc tgcttaaatc tcaccatagt cgtctttggt 120
ccctttcggg gattcgagga ctagatacta ccaaggacca acgtttcacc ccagggtagt 180
gcaaagtcac cgtcacctag accctgtcta aagtgagagt ggtagtcgtc agacgttgga 240
cttctaaaac gatgcatgat gacagttgtc atagtatcaa acggacgatg caagccggtt 300
ccctggttcc acctttagtt tgcc 324

<210> SEQ ID NO 160

<211> LENGTH: 324
<212> TYPE: DNA
<213> ORGANISM: Homo sapiens

<400> SEQUENCE: 160
gacatccaga tgacccagtc tccatcctcc ctgtctgcat ctgtaggaga ccgtgtcacc 60
atcacttgcc gggcaagtca ggatattggt aataatttag agtggtacca gcagaaacca 120
gggaaagccc ctaggctcct gatctatcat gggtcctggt tgcaaagtgg ggtcccatcg 180
cgtttcagtg gcagtggatc tgggacagat ttcactctta ccatcagcag tctgcaacct 240
gaagattttg ctacgtacta ctgtcaacag tatgatttta atcctactac gttcggccaa 300
gggaccaagg tggaaatcaa acgg 324

<210> SEQ ID NO 161
<211> LENGTH: 324
<212> TYPE: DNA
<213> ORGANISM: Homo sapiens

<400> SEQUENCE: 161
ctgtaggtct actgggtcag aggtaggagg gacagacgta gacatcctct ggcacagtgg 60
tagtgaacgg cccgttcagt cctataacca ttattaaatc tcaccatggt cgtctttggt 120
ccctttcggg gatccgagga ctagatagta cccaggacca acgtttcacc ccagggtagc 180
gcaaagtcac cgtcacctag accctgtcta aagtgagaat ggtagtcgtc agacgttgga 240
cttctaaaac gatgcatgat gacagttgtc atactaaaat taggatgatg caagccggtt 300
ccctggttcc acctttagtt tgcc 324

<210> SEQ ID NO 162
<211> LENGTH: 324
<212> TYPE: DNA
<213> ORGANISM: Homo sapiens

<400> SEQUENCE: 162
gacatccaga tgacccagtc tccatcctcc ctgtctgcat ctgtaggaga ctgtgtcacc 60
atcacttgcc gggcaagtca gaatattgat ggtctgttat ggtggtatca gcagaaacca 120
gggaaagccc ctaagctcct gatctatgcg gggtccgggt tgcaaagtgg ggtcccatca 180
cgtttcagtg gcagtggatc tgggacagat ttcactctca ccatcagcag tctgcaacct 240
gaagattttg ctacgtacta ctgtcaacag aaggcttttg agccttttac gttcggccaa 300
gggaccaagg tggaaatcaa acgg 324

<210> SEQ ID NO 163
<211> LENGTH: 324
<212> TYPE: DNA
<213> ORGANISM: Homo sapiens

<400> SEQUENCE: 163
ctgtaggtct actgggtcag aggtaggagg gacagacgta gacatcctct gacacagtgg 60
tagtgaacgg cccgttcagt cttataacta ccagacaata ccaccatagt cgtctttggt 120
ccctttcggg gattcgagga ctagatacgc cccaggccca acgtttcacc ccagggtagt 180
gcaaagtcac cgtcacctag accctgtcta aagtgagagt ggtagtcgtc agacgttgga 240
cttctaaaac gatgcatgat gacagttgtc ttccgaaaac tcggaaaatg caagccggtt 300
ccctggttcc acctttagtt tgcc 324

<210> SEQ ID NO 164

<211> LENGTH: 357
<212> TYPE: DNA
<213> ORGANISM: Homo sapiens

<400> SEQUENCE: 164
gaggtgcagc tgttggagtc tgggggaggc ttggtacagc ctggggggtc cctgcgtctc 60
tcctgtgcag cctccggatt cacctttaag gcgtatgata tgggttgggt ccgccaggct 120
ccagggaagg gtctagagtg ggtctcacag attgggaggg atggttcttt tacatactac 180
gcagactccg tgaagggccg gttcaccatc tcccgcgaca attccaagaa cacgctgtat 240
ctgcaaatga acagcctgcg tgccgaggac accgcggtat attactgtgc gaaacctcgt 300
cggtatgcta tttttacttt tgatcggggt cagggaaccc tggtcaccgt ctcgagc 357

<210> SEQ ID NO 165
<211> LENGTH: 357
<212> TYPE: DNA
<213> ORGANISM: Homo sapiens

<400> SEQUENCE: 165
ctccacgtcg acaacctcag acccccctccg aaccatgtcg gaccccccag ggacgcagag 60
aggacacgtc ggaggcctaa gtggaaattc cgcatactat acccaaccca ggcggtccga 120
ggtcccttcc cagatctcac ccagagtgtc taaccctccc taccaagaaa atgtatgatg 180
cgtctgaggc acttcccggc caagtggtag agggcgctgt taaggttctt gtgcgacata 240
gacgtttact tgtcggacgc acggctcctg tggcgccata taatgacacg ctttggagca 300
gccatacgat aaaaatgaaa actagcccca gtcccttggg accagtggca gagctcg 357

<210> SEQ ID NO 166
<211> LENGTH: 348
<212> TYPE: DNA
<213> ORGANISM: Homo sapiens

<400> SEQUENCE: 166
gaggtgcagc tgttggagtc tgggggaggc ttggtacagc ctggggggtc cctgcgtctc 60
tcctgtgcag cctccggatt caccttttt gagtatgaga tgacgtgggt ccgccaggct 120
ccagggaagg gtctagagtg ggtctcatct attgcgaatg atggttcgac tacatactac 180
gcagactccg tgaagggccg gttcaccatc tcccgcgaca attccaagaa cacgctgtat 240
ctgcaaatga acagcctgcg tgccgaggac accgcggtat attactgtgc gaaacctgat 300
cggcagtttg actactgggg tcagggaacc ctggtcaccg tctcgagc 348

<210> SEQ ID NO 167
<211> LENGTH: 348
<212> TYPE: DNA
<213> ORGANISM: Homo sapiens

<400> SEQUENCE: 167
ctccacgtcg acaacctcag acccccctccg aaccatgtcg gaccccccag ggacgcagag 60
aggacacgtc ggaggcctaa gtggaaaaaa ctcatactct actgcaccca ggcggtccga 120
ggtcccttcc cagatctcac ccagagtaga taacgcttac taccaagctg atgtatgatg 180
cgtctgaggc acttcccggc caagtggtag agggcgctgt taaggttctt gtgcgacata 240
gacgtttact tgtcggacgc acggctcctg tggcgccata taatgacacg ctttggacta 300
gccgtcaaac tgatgacccc agtcccttgg gaccagtggc agagctcg 348

<210> SEQ ID NO 168

<211> LENGTH: 348
<212> TYPE: DNA
<213> ORGANISM: Homo sapiens

<400> SEQUENCE: 168
gaggtgcagc tgttggagtc tgggggaggc ttggtacagc ctggggggtc cctgcgtctc 60
tcctgtgcag cctccggatt cacctttggt ccgtatgaga tgacttgggt ccgccaggct 120
ccagggaagg gtctagagtg ggtctcatcg attgttggtg atggtctgga tacatactac 180
gcagactccg tgaagggccg gttcaccatc tcccgcgaca attccaagaa cacgctgtat 240
ctgcaaatga acagcctgcg tgccgaggac accgcggtat attactgtgc gaaaccggat 300
cgggtttttg actactgggg tcagggaacc ctggtcaccg tctcgagc 348

<210> SEQ ID NO 169
<211> LENGTH: 348
<212> TYPE: DNA
<213> ORGANISM: Homo sapiens

<400> SEQUENCE: 169
ctccacgtcg acaacctcag accccctccg aaccatgtcg gaccccccag ggacgcagag 60
aggacacgtc ggaggcctaa gtggaaacca ggcatactct actgaaccca ggcggtccga 120
ggtcccttcc cagatctcac ccagagtagc taacaaccac taccagacct atgtatgatg 180
cgtctgaggc acttcccggc caagtggtag agggcgctgt taaggttctt gtgcgacata 240
gacgtttact tgtcggacgc acggctcctg tggcgccata taatgacacg ctttggccta 300
gcccaaaaac tgatgacccc agtcccttgg gaccagtggc agagctcg 348

<210> SEQ ID NO 170
<211> LENGTH: 348
<212> TYPE: DNA
<213> ORGANISM: Homo sapiens

<400> SEQUENCE: 170
gaggtgcagc tgttggagtc tgggggaggc ttggtacagc ctggggggtc cctgcgtctc 60
tcctgtgcag cctccggatt cacctttgct tcttatgaga tggcgtgggt ccgccaggct 120
ccagggaagg gtctagagtg ggtctcatcg attggtagtg atggtgggcc gacatactac 180
gcagactccg tgaagggccg gttcaccatc tcccgcgaca attccaagaa cacgctgtat 240
ctgcaaatga acagcctgcg tgccgaggac tccgcggtat attactgtgc gaaacctgat 300
agggcttttg actactgggg tcagggaacc ctggtcaccg tctcgagc 348

<210> SEQ ID NO 171
<211> LENGTH: 348
<212> TYPE: DNA
<213> ORGANISM: Homo sapiens

<400> SEQUENCE: 171
ctccacgtcg acaacctcag accccctccg aaccatgtcg gaccccccag ggacgcagag 60
aggacacgtc ggaggcctaa gtggaaacga agaatactct accgcaccca ggcggtccga 120
ggtcccttcc cagatctcac ccagagtagc taaccatcac taccacccgg ctgtatgatg 180
cgtctgaggc acttcccggc caagtggtag agggcgctgt taaggttctt gtgcgacata 240
gacgtttact tgtcggacgc acggctcctg aggcgccata taatgacacg ctttggacta 300
tcccgaaaac tgatgacccc agtcccttgg gaccagtggc agagctcg 348

<210> SEQ ID NO 172

<211> LENGTH: 357
<212> TYPE: DNA
<213> ORGANISM: Homo sapiens

<400> SEQUENCE: 172
gaggtgcagc tgttggagtc tgggggaggc ttggtacagc ctggggggtc cctgcgtctc 60
tcctgtgcag cctccggatt cacctttacg tcttatgaga tggggtgggt ccgccaggct 120
ccagggaagg gtctagagtg ggtctcatct attgagccta ctggtattac gacatactac 180
gcagactccg tgaagggccg gttcaccatc tcccgcgaca attccaagaa cacgctgtat 240
ctgcaaatga acagcctgcg tgccgaggac accgcggtat attactgtgc gaaacctcat 300
tttactgagc ttggttttga ctactggggt cagggaaccc tggtcaccgt ctcgagc 357

<210> SEQ ID NO 173
<211> LENGTH: 357
<212> TYPE: DNA
<213> ORGANISM: Homo sapiens

<400> SEQUENCE: 173
ctccacgtcg acaacctcag accccctccg aaccatgtcg gaccccccag ggacgcagag 60
aggacacgtc ggaggcctaa gtggaaatgc agaatactct accccaccca ggcggtccga 120
ggtcccttcc cagatctcac ccagagtaga taactcggat gaccataatg ctgtatgatg 180
cgtctgaggc acttcccggc caagtggtag agggcgctgt taaggttctt gtgcgacata 240
gacgtttact tgtcggacgc acggctcctg tggcgccata taatgacacg ctttggagta 300
aaatgactcg aaccaaaact gatgacccca gtcccttggg accagtggca gagctcg 357

<210> SEQ ID NO 174
<211> LENGTH: 360
<212> TYPE: DNA
<213> ORGANISM: Homo sapiens

<400> SEQUENCE: 174
gaggtgcagc tgttggagtc tgggggaggc ttggtacagc ctggggggtc cctgcgtctc 60
tcctgtgcag cctccggatt cacctttggt aattatgcga tggcgtgggt ccgccaggct 120
ccagggaagg gtctagagtg ggtctcaaag attggggcgc agggtcttca tacatactac 180
gcaggctccg tgaagggccg gttcaccatc tcccgcgaca attccaagaa cacgctgtat 240
ctgcaaatga acagcctgcg tgccgaggac accgcggtat attactgtgc gaaacagacg 300
acgatggatt atgagaggtt tgactactgg ggtcagggaa ccctggtcac cgtctcgagc 360

<210> SEQ ID NO 175
<211> LENGTH: 360
<212> TYPE: DNA
<213> ORGANISM: Homo sapiens

<400> SEQUENCE: 175
ctccacgtcg acaacctcag accccctccg aaccatgtcg gaccccccag ggacgcagag 60
aggacacgtc ggaggcctaa gtggaaacca ttaatacgct accgcaccca ggcggtccga 120
ggtcccttcc cagatctcac ccagagtttc taaccccgcg tcccagaagt atgtatgatg 180
cgtccgaggc acttcccggc caagtggtag agggcgctgt taaggttctt gtgcgacata 240
gacgtttact tgtcggacgc acggctcctg tggcgccata taatgacacg ctttgtctgc 300
tgctacctaa tactctccaa actgatgacc ccagtccctt gggaccagtg gcagagctcg 360

<210> SEQ ID NO 176

<211> LENGTH: 366
<212> TYPE: DNA
<213> ORGANISM: Homo sapiens

<400> SEQUENCE: 176
gaggtgcagc tgttggagtc tgggggaggc ttggtacagc ctggggggtc cctgcgtctc 60
tcctgtgcag cctccggatt cacctttgag ttgtatgcta tggcgtgggt ccgccaggct 120
ccagggaagg gtctagagtg ggtctcaggt attggtgctg tgggtgagac tacatactac 180
gcagactccg tgaagggccg gttcaccatc tcccgcgaca attccaagaa cacgctgtat 240
ctgcaaatga acagcctgcg tgccgaggac accgcggtat attactgtgc gaaagaggct 300
aataatcttt ctgataatct tgtgtttgac tactggggtc agggaaccct ggtcaccgtc 360
tcgagc 366

<210> SEQ ID NO 177
<211> LENGTH: 366
<212> TYPE: DNA
<213> ORGANISM: Homo sapiens

<400> SEQUENCE: 177
ctccacgtcg acaacctcag accccctccg aaccatgtcg gaccccccag ggacgcagag 60
aggacacgtc ggaggcctaa gtggaaactc aacatacgat accgcaccca ggcggtccga 120
ggtcccttcc cagatctcac ccagagtcca taaccacgac acccactctg atgtatgatg 180
cgtctgaggc acttcccggc caagtggtag agggcgctgt taaggttctt gtgcgacata 240
gacgtttact tgtcggacgc acggctcctg tggcgccata taatgacacg ctttctccga 300
ttattagaaa gactattaga acacaaactg atgaccccag tcccttggga ccagtggcag 360
agctcg 366

<210> SEQ ID NO 178
<211> LENGTH: 324
<212> TYPE: DNA
<213> ORGANISM: Homo sapiens

<400> SEQUENCE: 178
gacatccaga tgacccagtc tccatcctcc ctgtctgcat ctgtaggaga ccgtgtcacc 60
atcacttgcc gggcaagtca gtggattggg gattcgttaa gttggtacca gcagaaacca 120
gggaaagccc ctaagctcct gatctatttt ggttcctatt tgcaaagtgg ggtcccatca 180
cgtttcagtg gcagtggatc tgggacagat ttcactctca ccatcagcag tctgcaacct 240
gaagattttg ctacgtacta ctgtcaacag tatttgcata ctccttcgac gttcggccaa 300
gggaccaagg tggaaatcaa acgg 324

<210> SEQ ID NO 179
<211> LENGTH: 324
<212> TYPE: DNA
<213> ORGANISM: Homo sapiens

<400> SEQUENCE: 179
ctgtaggtct actgggtcag aggtaggagg gacagacgta gacatcctct ggcacagtgg 60
tagtgaacgg cccgttcagt cacctaaccc ctaagcaatt caaccatggt cgtctttggt 120
ccctttcggg gattcgagga ctagataaaa ccaaggataa acgtttcacc ccagggtagt 180
gcaaagtcac cgtcacctag accctgtcta aagtgagagt ggtagtcgtc agacgttgga 240
cttctaaaac gatgcatgat gacagttgtc ataaacgtat gaggaagctg caagccggtt 300

-continued ccctggttcc acctttagtt tgcc 324

<210> SEQ ID NO 180
<211> LENGTH: 324
<212> TYPE: DNA
<213> ORGANISM: Homo sapiens

<400> SEQUENCE: 180
gacatccaga tgacccagtc tccatcctcc ctgtctgcat ctgtaggaga ccgtgtcacc 60
atcacttgcc gggcaagtca gtggattggg gattcgttaa gttggtacca gcagaaacca 120
gggaaagccc ctaagctcct gatctatttt ggttcctatt tgcaaaatgg ggtcccatca 180
cgtttcagtg gcagtggatc tgggacagat ttcactctca ccatcagcag tctgcaacct 240
gaagattttg ctacgtacta ctgtcaacag tatatgatta ctcctactac gttcggccaa 300
gggaccaagg tggaaatcaa acgg 324

<210> SEQ ID NO 181
<211> LENGTH: 324
<212> TYPE: DNA
<213> ORGANISM: Homo sapiens

<400> SEQUENCE: 181
ctgtaggtct actgggtcag aggtaggagg gacagacgta gacatcctct ggcacagtgg 60
tagtgaacgg cccgttcagt cacctaaccc ctaagcaatt caaccatggt cgtctttggt 120
ccctttcggg gattcgagga ctagataaaa ccaaggataa acgttttacc ccagggtagt 180
gcaaagtcac cgtcacctag accctgtcta aagtgagagt ggtagtcgtc agacgttgga 240
cttctaaaac gatgcatgat gacagttgtc atatactaat gaggatgatg caagccggtt 300
ccctggttcc acctttagtt tgcc 324

<210> SEQ ID NO 182
<211> LENGTH: 324
<212> TYPE: DNA
<213> ORGANISM: Homo sapiens

<400> SEQUENCE: 182
gacgtccaga tgacccagtc tccatcctcc ctgtctgcat ctgtaggaga ccgtgtcacc 60
atcacttgcc gggcaagtca gtggattggg gattcgttaa gttggtacca gcagaaacca 120
gggaaagccc ctaagctcct gatctatttt ggttcctatt tgcaaagtgg ggtcccatca 180
cgtttcagtg gcagtggatc tgggacagat ttcactctca ccatcagcag tctgcaacct 240
gaagattttg ctacgtacta ctgtcaacag tatatgagtg ctccttctac gttcggccaa 300
gggaccaagg tggaaatcaa acgg 324

<210> SEQ ID NO 183
<211> LENGTH: 324
<212> TYPE: DNA
<213> ORGANISM: Homo sapiens

<400> SEQUENCE: 183
ctgcaggtct actgggtcag aggtaggagg gacagacgta gacatcctct ggcacagtgg 60
tagtgaacgg cccgttcagt cacctaaccc ctaagcaatt caaccatggt cgtctttggt 120
ccctttcggg gattcgagga ctagataaaa ccaaggataa acgtttcacc ccagggtagt 180
gcaaagtcac cgtcacctag accctgtcta aagtgagagt ggtagtcgtc agacgttgga 240
cttctaaaac gatgcatgat gacagttgtc atatactcac gaggaagatg caagccggtt 300
ccctggttcc acctttagtt tgcc 324

<210> SEQ ID NO 184
<211> LENGTH: 324
<212> TYPE: DNA
<213> ORGANISM: Homo sapiens

<400> SEQUENCE: 184
gacatccaga tgacccagtc tccatcctcc ctgtctgcat ctgtaggaga ccgtgtcacc 60
atcacttgcc gggcaagtca gtggattggg gattcgttaa gttggtacca gcagaaacca 120
gggaaagccc ctaagctcct gatctatttt ggttcctatt tgcaaagtgg ggtcccatca 180
cgtttcagtg gcagtggatc tgggacagat ttcactctca ccatcagcag tctgcaacct 240
gaagattctg ctacgtacta ctgtcaacag tatcagtatg ttccttctac gttcggccaa 300
gggaccaagg tggaaatcaa acag 324

<210> SEQ ID NO 185
<211> LENGTH: 324
<212> TYPE: DNA
<213> ORGANISM: Homo sapiens

<400> SEQUENCE: 185
ctgtaggtct actgggtcag aggtaggagg gacagacgta gacatcctct ggcacagtgg 60
tagtgaacgg cccgttcagt cacctaaccc ctaagcaatt caaccatggt cgtctttggt 120
ccctttcggg gattcgagga ctagataaaa ccaaggataa acgtttcacc ccagggtagt 180
gcaaagtcac cgtcacctag accctgtcta aagtgagagt ggtagtcgtc agacgttgga 240
cttctaagac gatgcatgat gacagttgtc atagtcatac aaggaagatg caagccggtt 300
ccctggttcc acctttagtt tgtc 324

<210> SEQ ID NO 186
<211> LENGTH: 324
<212> TYPE: DNA
<213> ORGANISM: Homo sapiens

<400> SEQUENCE: 186
gacatccaga tgacccagtc tccatcctcc ctgtctgcat ctgtaggaga ccgtgtcacc 60
atcacttgcc gggcaagtca gcctattgtt gatgagttag attggtacca gcagaaacca 120
gggaaagccc ctaagctcct gatctatgct gcgtccattt tgcaaagtgg ggtcccatca 180
cgtttcagtg gcagtggatc tgggacagat ttcactctca ccatcagcag tctgcaacct 240
gaagattttg ctacgtacta ctgtcatcag tggtctactt atcctacgac gttcggccaa 300
gggaccaagg tggaaattaa acgg 324

<210> SEQ ID NO 187
<211> LENGTH: 324
<212> TYPE: DNA
<213> ORGANISM: Homo sapiens

<400> SEQUENCE: 187
ctgtaggtct actgggtcag aggtaggagg gacagacgta gacatcctct ggcacagtgg 60
tagtgaacgg cccgttcagt cggataacaa ctactcaatc taaccatggt cgtctttggt 120
ccctttcggg gattcgagga ctagatacga cgcaggtaaa acgtttcacc ccagggtagt 180
gcaaagtcac cgtcacctag accctgtcta aagtgagagt ggtagtcgtc agacgttgga 240
cttctaaaac gatgcatgat gacagtagtc accagatgaa taggatgctg caagccggtt 300
ccctggttcc acctttaatt tgcc 324

<210> SEQ ID NO 188
<211> LENGTH: 324
<212> TYPE: DNA
<213> ORGANISM: Homo sapiens

<400> SEQUENCE: 188
gacatccaga tgacccagtc tccatcctcc ctgtctgcat ctgtaggtga ccgtgtcacc 60
atcacttgcc gggcaagtca ggatattggg tctgcgttaa ggtggtatca gcagaaacca 120
gggaaagccc ctaagctcct gatctatttg ggttccgatt tgcaaagtgg ggtcccatca 180
cgtttcagtg gcagtggatc tgggacagat ttcactctca ccatcagcag tctgcaacct 240
gaagattttg ctacgtacta ctgtcaacag acgcagtatt ttcctacgac gttcggccaa 300
gggaccaagg tggaaatcaa acgg 324

<210> SEQ ID NO 189
<211> LENGTH: 324
<212> TYPE: DNA
<213> ORGANISM: Homo sapiens

<400> SEQUENCE: 189
ctgtaggtct actgggtcag aggtaggagg gacagacgta gacatccact ggcacagtgg 60
tagtgaacgg cccgttcagt cctataaccc agacgcaatt ccaccatagt cgtctttggt 120
ccctttcggg gattcgagga ctagataaac ccaaggctaa acgtttcacc ccagggtagt 180
gcaaagtcac cgtcacctag accctgtcta aagtgagagt ggtagtcgtc agacgttgga 240
cttctaaaac gatgcatgat gacagttgtc tgcgtcataa aaggatgctg caagccggtt 300
ccctggttcc acctttagtt tgcc 324

<210> SEQ ID NO 190
<211> LENGTH: 324
<212> TYPE: DNA
<213> ORGANISM: Homo sapiens

<400> SEQUENCE: 190
gacatccaga tgacccagtc tccatcctcc ctgtctgcat ctgtaggaga ccgtgtcacc 60
atcacttgcc gggcaagtca ggcgatttat ggggggttac ggtggtacca gcagaaacca 120
gggaaagccc ctaagctcct gatctatggg gagtccatgt tgcaaagtgg ggtcccatca 180
cgtttcagtg gcagtggatc tgggacagat ttcactctca ccatcagcag tctgcatcct 240
gaagattttg ctacgtacta ctgtcaacag gtttatcata agccttttac gttcggccaa 300
gggaccaagg tggaaatcaa acgg 324

<210> SEQ ID NO 191
<211> LENGTH: 324
<212> TYPE: DNA
<213> ORGANISM: Homo sapiens

<400> SEQUENCE: 191
ctgtaggtct actgggtcag aggtaggagg gacagacgta gacatcctct ggcacagtgg 60
tagtgaacgg cccgttcagt ccgctaaata ccccccaatg ccaccatggt cgtctttggt 120
ccctttcggg gattcgagga ctagataccc ctcaggtaca acgtttcacc ccagggtagt 180
gcaaagtcac cgtcacctag accctgtcta aagtgagagt ggtagtcgtc agacgtagga 240
cttctaaaac gatgcatgat gacagttgtc caaatagtat tcggaaaatg caagccggtt 300
ccctggttcc acctttagtt tgcc 324

<210> SEQ ID NO 192
<211> LENGTH: 369
<212> TYPE: DNA
<213> ORGANISM: Homo sapiens

<400> SEQUENCE: 192
gaggtgcagc tgttggagtc tgggggaggc ttggtacagc ctgggggtc cctgcgtctc 60 tcctgtgcag cctccggatt cacctttacg gcgtatagga tggcttgggt ccgccaggct 120
ccagggaagg gtctagagtg ggtctcatgg atttcgcctt ctggttcggg gacatactac 180
gcagactccg tgaagggccg gttcaccatc tcccgcgaca attccaagaa cacgctgtat 240
ctgcaaatga acagcctgcg tgccgaggac accgcggtat attactgtgc gaaaactttg 300
acggattcgc cgtcggggca ttatgagttt gactactggg gtcagggaac cctggtcacc 360
gtctcgagc 369

<210> SEQ ID NO 193
<211> LENGTH: 369
<212> TYPE: DNA
<213> ORGANISM: Homo sapiens

<400> SEQUENCE: 193
ctccacgtcg acaacctcag accccctccg aaccatgtcg gaccccccag ggacgcagag 60
aggacacgtc ggaggcctaa gtggaaatgc cgcatatcct accgaaccca ggcggtccga 120
ggtcccttcc cagatctcac ccagagtacc taaagcggaa gaccaagccc ctgtatgatg 180
cgtctgaggc acttcccggc caagtggtag agggcgctgt taaggttctt gtgcgacata 240
gacgtttact tgtcggacgc acggctcctg tggcgccata taatgacacg cttttgaaac 300
tgcctaagcg gcagccccgt aatactcaaa ctgatgaccc cagtcccttg ggaccagtgg 360
cagagctcg 369

<210> SEQ ID NO 194
<211> LENGTH: 369
<212> TYPE: DNA
<213> ORGANISM: Homo sapiens

<400> SEQUENCE: 194
gaggtgcagc tgttggagtc tgggggaggc ttggtacagc ctgggggtc cctgcgtctc 60 tcctgtgcag cctccggatt cacctttgcg cggtatgaga tggggtgggt ccgccaggct 120
ccagggaagg gtctagagtg ggtctcacgg attactgctc agggtcttgg gacatactac 180
gcagactccg tgaagggccg gttcaccatc tcccgcgaca actccaagaa cacgctgtat 240
ctgcaaatga acagcctgcg tgccgaggat accgcggtat attactgtgc gaaatatctt 300
actgatttta gtagtgggca tcaggagttt gactactggg gtcagggaac cctggtcacc 360
gtctcgagc 369

<210> SEQ ID NO 195
<211> LENGTH: 369
<212> TYPE: DNA
<213> ORGANISM: Homo sapiens

<400> SEQUENCE: 195
ctccacgtcg acaacctcag accccctccg aaccatgtcg gaccccccag ggacgcagag 60
aggacacgtc ggaggcctaa gtggaaacgc gccatactct accccaccca ggcggtccga 120
ggtcccttcc cagatctcac ccagagtgcc taatgacgag tcccagaacc ctgtatgatg 180
cgtctgaggc acttcccggc caagtggtag agggcgctgt tgaggttctt gtgcgacata 240
gacgtttact tgtcggacgc acggctccta tggcgccata taatgacacg ctttatagaa 300
tgactaaaat catcacccgt agtcctcaaa ctgatgaccc cagtcccttg ggaccagtgg 360
cagagctcg 369

<210> SEQ ID NO 196
<211> LENGTH: 369
<212> TYPE: DNA
<213> ORGANISM: Homo sapiens

<400> SEQUENCE: 196
gaggtgcagc tgttggagtc tgggggaggc ttggtacagc ctggggggtc cctgcgtctc 60
tcctgtgcag cctccggatt cacctttaat gattatacta tgggttgggt ccgccaggct 120
ccagggaagg gtctagagtg ggtctcatgg attcatggga ctggtggtca gacatactac 180
gcagactccg tgaagggccg gttcaccatc tcccgcgaca attccaagaa cacgctgtat 240
ctgcaaatga acagcctgcg tgccgaggac accgcggtat attactgtgc gaaagctttg 300
gctgatagga gtggggggt tgttgagttt gactactggg gtcagggaac cctggtcacc 360
gtctcgagc 369

<210> SEQ ID NO 197
<211> LENGTH: 369
<212> TYPE: DNA
<213> ORGANISM: Homo sapiens

<400> SEQUENCE: 197
ctccacgtcg acaacctcag accccctccg aaccatgtcg gaccccccag ggacgcagag 60
aggacacgtc ggaggcctaa gtggaaatta ctaatatgat acccaaccca ggcggtccga 120
ggtcccttcc cagatctcac ccagagtacc taagtaccct gaccaccagt ctgtatgatg 180
cgtctgaggc acttcccggc caagtggtag agggcgctgt taaggttctt gtgcgacata 240
gacgtttact tgtcggacgc acggctcctg tggcgccata taatgacacg ctttcgaaac 300
cgactatcct caccccccca acaactcaaa ctgatgaccc cagtcccttg ggaccagtgg 360
cagagctcg 369

<210> SEQ ID NO 198
<211> LENGTH: 348
<212> TYPE: DNA
<213> ORGANISM: Homo sapiens

<400> SEQUENCE: 198
gaggtgcagc tgttggagtc tgggggaggc ttggtacagc ctggggggtc cctgcgtctc 60
tcctgtgcag cctccggatt caccttttct gagtatgata tgtattgggt ccgccaggct 120
ccagggaagg gtctagagtg ggtctcatgg attgatactg atggtgggga tacatactac 180
gcagactccg tgaagggccg gttcaccatc tcccgcgaca attccaagaa cacgctgtat 240
ctgcaaatga acagcctgcg tgccgaggac accgcggtat attactgtgc gaaacctggt 300
ctgaagtttg actactgggg tcagggaacc ctggtcaccg tctcgagc 348

<210> SEQ ID NO 199
<211> LENGTH: 348
<212> TYPE: DNA
<213> ORGANISM: Homo sapiens

<400> SEQUENCE: 199
ctccacgtcg acaacctcag accccctccg aaccatgtcg gaccccccag ggacgcagag 60
aggacacgtc ggaggcctaa gtggaaaaga ctcatactat acataaccca ggcggtccga 120
ggtcccttcc cagatctcac ccagagtacc taactatgac taccacccct atgtatgatg 180
cgtctgaggc acttcccggc caagtggtag agggcgctgt taaggttctt gtgcgacata 240
gacgtttact tgtcggacgc acggctcctg tggcgccata taatgacacg ctttggacca 300
gacttcaaac tgatgacccc agtcccttgg gaccagtggc agagctcg 348

<210> SEQ ID NO 200
<211> LENGTH: 348
<212> TYPE: DNA
<213> ORGANISM: Homo sapiens

<400> SEQUENCE: 200
gaggtgcagc tgttggagtc tgggggaggc ttggtacagc ctggggggtc cctgcgtctc 60
tcctgtgcag cctccggatt cacctttgag gtttatacta tggcgtgggt ccgccaggct 120
ccagggaagg gtctggagtg ggtctcaacg attgatgagt ctggtcgtga tacatactac 180
gcagactccg tgaagggccg gttcaccatc tcccgcgaca attccaagaa cacgctgtat 240
ctgcaaatga acagcctgcg tgccgaggac accgcggtat attactgtgc gaaacctggt 300
gtttggtttg actactgggg tcagggaacc ctggtcaccg tctcgagc 348

<210> SEQ ID NO 201
<211> LENGTH: 348
<212> TYPE: DNA
<213> ORGANISM: Homo sapiens

<400> SEQUENCE: 201
ctccacgtcg acaacctcag accccctccg aaccatgtcg gaccccccag ggacgcagag 60
aggacacgtc ggaggcctaa gtggaaactc caaatatgat accgcaccca ggcggtccga 120
ggtcccttcc cagacctcac ccagagttgc taactactca gaccagcact atgtatgatg 180
cgtctgaggc acttcccggc caagtggtag agggcgctgt taaggttctt gtgcgacata 240
gacgtttact tgtcggacgc acggctcctg tggcgccata taatgacacg ctttggacca 300
caaaccaaac tgatgacccc agtcccttgg gaccagtggc agagctcg 348

<210> SEQ ID NO 202
<211> LENGTH: 372
<212> TYPE: DNA
<213> ORGANISM: Homo sapiens

<400> SEQUENCE: 202
gaggtgcagc tgttggagtc tgggggaggc ttggtacagc ctggggggtc cctgcgtctc 60
tcctgtgcag cctccggatt cacctttctg gattatgcga tgggttgggt ccgccaggct 120
ccagggaagg gtctggagtg ggtctcaact atttctccga tgggtatggg tacatactac 180
gcagactccg tgaagggccg gttcaccatc tcccgcgaca attccaagaa cacgctgtat 240
ctgcaaatga acagcctgcg tgccgaggac accgcggtat attactgtgc gaaatcgagt 300
gctatttcgt ttacttctga tatttctaat tttgactact ggggtcaggg aaccctggtc 360
accgtctcga gc 372

<210> SEQ ID NO 203
<211> LENGTH: 372
<212> TYPE: DNA

<213> ORGANISM: Homo sapiens

<400> SEQUENCE: 203
ctccacgtcg acaacctcag acccccctccg aaccatgtcg gaccccccag ggacgcagag 60
aggacacgtc ggaggcctaa gtggaaagac ctaatacgct acccaaccca ggcggtccga 120
ggtcccttcc cagacctcac ccagagttga taaagaggct acccataccc atgtatgatg 180
cgtctgaggc acttcccggc caagtggtag agggcgctgt taaggttctt gtgcgacata 240
gacgtttact tgtcggacgc acggctcctg tggcgccata taatgacacg ctttagctca 300
cgataaagca aatgaagact ataaagatta aaactgatga ccccagtccc ttgggaccag 360
tggcagagct cg 372

<210> SEQ ID NO 204
<211> LENGTH: 360
<212> TYPE: DNA
<213> ORGANISM: Homo sapiens

<400> SEQUENCE: 204
gaggtgcagc tgttggagtc tgggggaggc ttggtacagc ctggggggtc cctgcgtctc 60
tcctgtgcag cctccggatt cacctttgct gcttatgcta tgacgtgggt ccgccaggct 120
ccagggaagg gtctagagtg ggtctcatat attagtccga atggtacggc gacatactac 180
gcagactccg tgaagggccg gttcaccatc tcccgcgaca attccaagaa cacgctgtat 240
ctgcaaatga acagcctgcg tgccgaggac accgcggtat attactgtgc ggaatatgtg 300
gggatgcgtt ggaattcttt tgactactgg ggtcagggaa ccctggtcac cgtctcgagc 360

<210> SEQ ID NO 205
<211> LENGTH: 360
<212> TYPE: DNA
<213> ORGANISM: Homo sapiens

<400> SEQUENCE: 205
ctccacgtcg acaacctcag accccctccg aaccatgtcg gaccccccag ggacgcagag 60
aggacacgtc ggaggcctaa gtggaaacga cgaatacgat actgcaccca ggcggtccga 120
ggtcccttcc cagatctcac ccagagtata taatcaggct taccatgccg ctgtatgatg 180
cgtctgaggc acttcccggc caagtggtag agggcgctgt taaggttctt gtgcgacata 240
gacgtttact tgtcggacgc acggctcctg tggcgccata taatgacacg ccttatacac 300
ccctacgcaa ccttaagaaa actgatgacc ccagtccctt gggaccagtg gcagagctcg 360

<210> SEQ ID NO 206
<211> LENGTH: 348
<212> TYPE: DNA
<213> ORGANISM: Homo sapiens

<400> SEQUENCE: 206
gaggtgcagc tgttggagtc tgggggaggc ttggtacagc ctggggggtc cctgcgtctc 60
tcctgtgcag cctccggatt caccttttcg agttatgaga tggcttgggt ccgccaggct 120
ccagggaagg gtctagagtg ggtctcatct attacgagtc ttggtacttc tacatactac 180
gcagactccg tgaagggccg gttcaccatc tcccgcgaca attccaagaa cacgctgtat 240
ctgcaaatga acagcctgcg tgccgaggac accgcggtat attactgtgc gaaaccgggt 300
aggaagtttg actactgggg tcagggaacc ctggtcaccg tctcgagc 348

<210> SEQ ID NO 207

<211> LENGTH: 348
<212> TYPE: DNA
<213> ORGANISM: Homo sapiens

<400> SEQUENCE: 207
ctccacgtcg acaacctcag accccctccg aaccatgtcg gaccccccag ggacgcagag 60
aggacacgtc ggaggcctaa gtggaaaagc tcaatactct accgaaccca ggcggtccga 120
ggtcccttcc cagatctcac ccagagtaga taatgctcag aaccatgaag atgtatgatg 180
cgtctgaggc acttcccggc caagtggtag agggcgctgt taaggttctt gtgcgacata 240
gacgtttact tgtcggacgc acggctcctg tggcgccata taatgacacg ctttggccca 300
tccttcaaac tgatgacccc agtcccttgg gaccagtggc agagctcg 348

<210> SEQ ID NO 208
<211> LENGTH: 348
<212> TYPE: DNA
<213> ORGANISM: Homo sapiens

<400> SEQUENCE: 208
gaggtgcagc tgttggagtc tgggggaggc ttggtacagc ctggggggtc cctgcgtctc 60
tcctgtgcag cctccggatt cacctttaat gagtatgaga tgacgtgggt ccgccaggct 120
ccagggaagg gtctagagtg ggtctcaacg attactagtg agggtagtgg gacatactac 180
gcagactccg taaagggccg gttcaccatc tcccgcgaca attccaagaa cacgctgtat 240
ctgcaaatga acagcctgcg tgccgaggac accgcggtat attactgtgc gaaacctaat 300
ggtaagtttg actactgggg tcagggaacc ctggtcaccg tctcgagc 348

<210> SEQ ID NO 209
<211> LENGTH: 348
<212> TYPE: DNA
<213> ORGANISM: Homo sapiens

<400> SEQUENCE: 209
ctccacgtcg acaacctcag accccctccg aaccatgtcg gaccccccag ggacgcagag 60
aggacacgtc ggaggcctaa gtggaaatta ctcatactct actgcaccca ggcggtccga 120
ggtcccttcc cagatctcac ccagagttgc taatgatcac tcccatcacc ctgtatgatg 180
cgtctgaggc atttcccggc caagtggtag agggcgctgt taaggttctt gtgcgacata 240
gacgtttact tgtcggacgc acggctcctg tggcgccata taatgacacg ctttggatta 300
ccattcaaac tgatgacccc agtcccttgg gaccagtggc agagctcg 348

<210> SEQ ID NO 210
<211> LENGTH: 348
<212> TYPE: DNA
<213> ORGANISM: Homo sapiens

<400> SEQUENCE: 210
gaggtgcagc tgttggagtc tgggggaggc ttggtacagc ctggggggtc cctgcgtctc 60
tcctgtgcag cctccggatt caccttttct gattatgaga tgttgtgggt ccgccaggct 120
ccagggaagg gtctggagtg ggtctcaact attactagtg agggtcattc tacatactac 180
gcagactccg tgaagggccg gttcaccatc tcccgcgaca attccaagaa cacgctgtat 240
ctgcaaatga acagcctgcg tgccgaggac accgcggtat attactgtgc gaaacctggg 300
acttcgtttg actactgggg tcagggaacc ctggtcaccg tctcgagc 348

<210> SEQ ID NO 211

<211> LENGTH: 348
<212> TYPE: DNA
<213> ORGANISM: Homo sapiens

<400> SEQUENCE: 211
ctccacgtcg acaacctcag accccctccg aaccatgtcg gaccccccag ggacgcagag 60
aggacacgtc ggaggcctaa gtggaaaaga ctaatactct acaacaccca ggcggtccga 120
ggtcccttcc cagacctcac ccagagttga taatgatcac tcccagtaag atgtatgatg 180
cgtctgaggc acttcccggc caagtggtag agggcgctgt taaggttctt gtgcgacata 240
gacgtttact tgtcggacgc acggctcctg tggcgccata taatgacacg ctttggaccc 300
tgaagcaaac tgatgacccc agtcccttgg gaccagtggc agagctcg 348

<210> SEQ ID NO 212
<211> LENGTH: 348
<212> TYPE: DNA
<213> ORGANISM: Homo sapiens

<400> SEQUENCE: 212
gaggtgcagc tgttggagtc tgggggaggc ttggtacagc ctggggggtc cctgcgtctc 60
tcctgtgcag cctccggatt cacctttagt gattatgaga tgagttgggt ccgccaggct 120
ccagggaagg gtctagagtg ggtctcaacg attgattctg atggtagttt tacatactac 180
gcagactccg tgaagggccg gttcaccatc tcccgcgaca attccaagaa cacgctgtat 240
ctgcaaatga acagcctgcg tgccgaggac accgcggtat attactgtgc gaaaccgggt 300
gtgaagtttg actactgggg tcagggaacc ctggtcaccg tctcgagc 348

<210> SEQ ID NO 213
<211> LENGTH: 348
<212> TYPE: DNA
<213> ORGANISM: Homo sapiens

<400> SEQUENCE: 213
ctccacgtcg acaacctcag accccctccg aaccatgtcg gaccccccag ggacgcagag 60
aggacacgtc ggaggcctaa gtggaaatca ctaatactct actcaaccca ggcggtccga 120
ggtcccttcc cagatctcac ccagagttgc taactaagac taccatcaaa atgtatgatg 180
cgtctgaggc acttcccggc caagtggtag agggcgctgt taaggttctt gtgcgacata 240
gacgtttact tgtcggacgc acggctcctg tggcgccata taatgacacg ctttggccca 300
cacttcaaac tgatgacccc agtcccttgg gaccagtggc agagctcg 348

<210> SEQ ID NO 214
<211> LENGTH: 348
<212> TYPE: DNA
<213> ORGANISM: Homo sapiens

<400> SEQUENCE: 214
gaggtgcagc tgttggagtc tgggggaggc ttggtacagc ctggggggtc cctgcgtctc 60
tcctgtgcag cctccggatt cacctttaag gattatgaga tgacttgggt ccgccaggct 120
ccagggaagg gtctagagtg ggtctcatct atttcttcta ctggtcagtc tacatactac 180
gcagactccg tgaagggccg gttcaccatc tcccgcgaca attccaagaa cacgctgtat 240
ctgcaaatga acagcctgcg tgccgaggac accgcggtat attactgtgc gaaaccgggt 300
aataagtttg actactgggg tcagggaacc ctggtcaccg tctcgagc 348

<210> SEQ ID NO 215

<211> LENGTH: 348
<212> TYPE: DNA
<213> ORGANISM: Homo sapiens

<400> SEQUENCE: 215
ctccacgtcg acaacctcag accccctccg aaccatgtcg gaccccccag ggacgcagag 60
aggacacgtc ggaggcctaa gtggaaattc ctaatactct actgaaccca ggcggtccga 120
ggtcccttcc cagatctcac ccagagtaga taaagaagat gaccagtcag atgtatgatg 180
cgtctgaggc acttcccggc caagtggtag agggcgctgt taaggttctt gtgcgacata 240
gacgtttact tgtcggacgc acggctcctg tggcgccata taatgacacg ctttggccca 300
ttattcaaac tgatgacccc agtcccttgg gaccagtggc agagctcg 348

<210> SEQ ID NO 216
<211> LENGTH: 372
<212> TYPE: DNA
<213> ORGANISM: Homo sapiens

<400> SEQUENCE: 216
gaggtgcagc tgttggagtc tgggggaggc ttggtacagc ctggggggtc cctgcgtctc 60
tcctgtgcag cctccggatt cacctttctt gattatggta tggcttgggt ccgccaggct 120
ccagggaagg gtctagagtg ggtctcagct atttcgcctc ttggtcttag tacatactac 180
gcagactccg tgaagagccg gttcaccatc tcccgcgaca attccaagaa cacgctgtat 240
ctgcaaatga acagcctgcg tgccgaggat accgcggtat attactgtgc gaaagaggtg 300
agggtgggta ggggtgttca tcctccgaag tttgactact ggggtcaggg aaccctggtc 360
accgtctcga gc 372

<210> SEQ ID NO 217
<211> LENGTH: 372
<212> TYPE: DNA
<213> ORGANISM: Homo sapiens

<400> SEQUENCE: 217
ctccacgtcg acaacctcag accccctccg aaccatgtcg gaccccccag ggacgcagag 60
aggacacgtc ggaggcctaa gtggaaagaa ctaataccat accgaaccca ggcggtccga 120
ggtcccttcc cagatctcac ccagagtcga taaagcggag aaccagaatc atgtatgatg 180
cgtctgaggc acttctcggc caagtggtag agggcgctgt taaggttctt gtgcgacata 240
gacgtttact tgtcggacgc acggctccta tggcgccata taatgacacg ctttctccac 300
tcccacccat ccccacaagt aggaggcttc aaactgatga ccccagtccc ttgggaccag 360
tggcagagct cg 372

<210> SEQ ID NO 218
<211> LENGTH: 369
<212> TYPE: DNA
<213> ORGANISM: Homo sapiens

<400> SEQUENCE: 218
gaggtgcagc tgttggagtc tgggggaggc ttggtacagc ctggggggtc cctgcgtctc 60
tcctgtgcag cctccggatt cacctttgag aattatgcta tgtcgtgggt ccgccaggct 120
ccagggaagg gtctagagtg ggtctcaacg attgctccgc tgggtgttcc gacatactac 180
gcagactccg tgaagggccg gttcaccatc tcccgcgaca attccaagaa cacgctgtat 240
ctgcaaatga acagcctgcg tgccgaggat accgcggtat attactgtgc gaaaaagaag 300
gttggggcgt ggctgcagtc gcggagtttt gactactggg gtcagggaac cctggtcacc 360
gtctcgagc 369

<210> SEQ ID NO 219
<211> LENGTH: 369
<212> TYPE: DNA
<213> ORGANISM: Homo sapiens

<400> SEQUENCE: 219
ctccacgtcg acaacctcag accccctccg aaccatgtcg gacccccag ggacgcagag 60 aggacacgtc ggaggcctaa gtggaaactc ttaatacgat acagcaccca ggcggtccga 120
ggtcccttcc cagatctcac ccagagttgc taacgaggcg acccacaagg ctgtatgatg 180
cgtctgaggc acttcccggc caagtggtag agggcgctgt taaggttctt gtgcgacata 240
gacgtttact tgtcggacgc acggctccta tggcgccata taatgacacg ctttttcttc 300
caaccccgca ccgacgtcag cgcctcaaaa ctgatgaccc cagtcccttg ggaccagtgg 360
cagagctcg 369

<210> SEQ ID NO 220
<211> LENGTH: 369
<212> TYPE: DNA
<213> ORGANISM: Homo sapiens

<400> SEQUENCE: 220
gaggtgcagc tgttggagtc tgggggaggc ttggtacagc ctggggggtc cctgcgtctc 60
tcctgtgcag cctccggatt cacctttgag ggttatccta tgtcgtgggt ccgccaggct 120
ccagggaagg gtctagagtg ggtctcaact attagtcctt tgggtcctga tacatactac 180
gcagactccg tgaagggccg gttcaccatc tcccgcgaca attccaagaa cacgctgtat 240
ctgcaaatga acagcctgcg tgccgaggat accgcggtat attactgtgc gaaactgttg 300
atgggggagt atttgaattc taggacgttt gactactggg gtcagggaac cctggtcacc 360
gtctcgagc 369

<210> SEQ ID NO 221
<211> LENGTH: 369
<212> TYPE: DNA
<213> ORGANISM: Homo sapiens

<400> SEQUENCE: 221
ctccacgtcg acaacctcag accccctccg aaccatgtcg gacccccag ggacgcagag 60 aggacacgtc ggaggcctaa gtggaaactc ccaataggat acagcaccca ggcggtccga 120
ggtcccttcc cagatctcac ccagagttga taatcaggaa acccaggact atgtatgatg 180
cgtctgaggc acttcccggc caagtggtag agggcgctgt taaggttctt gtgcgacata 240
gacgtttact tgtcggacgc acggctccta tggcgccata taatgacacg ctttgacaac 300
taccccctca taaacttaag atcctgcaaa ctgatgaccc cagtcccttg ggaccagtgg 360
cagagctcg 369

<210> SEQ ID NO 222
<211> LENGTH: 362
<212> TYPE: DNA
<213> ORGANISM: Homo sapiens

<400> SEQUENCE: 222
tgttggagtc tgggggaggc ttggtacagc ctggggggtc cctgcgtctc tcctgtgcag 60

-continued

```
cctccggatt cacctttgag gcgtatccta tgtcgtgggt ccgccaggct ccagggaagg    120

gtctagagtg ggtctcaagt atttcccctc ttggtttgtg gacatactac gcagactccg    180

tgaagggccg gttcaccatc tcccgcgaca attccaagaa cacgctgtat ctgcaaatga    240

acagcctgcg tgccgaggac accgcggtat attactgtgc gaaacttagt gctggggcgg    300

agactcatgt ttatcggctt tttgactact ggggtcaggg aaccctggtc accgtctcga    360

gc                                                                   362
```

<210> SEQ ID NO 223
<211> LENGTH: 372
<212> TYPE: DNA
<213> ORGANISM: Homo sapiens

<400> SEQUENCE: 223

```
ctccacgtcg acaacctcag aaccccctccg aaccatgtcg gaccccccag ggacgcagag     60

aggacacgtc ggaggcctaa gtggaaactc cgcataggat acagcaccca ggcggtccga    120

ggtcccttcc cagatctcac ccagagttca taaaggggag aaccaaacac ctgtatgatg    180

cgtctgaggc acttcccggc caagtggtag agggcgctgt taaggttctt gtgcgacata    240

gacgtttact tgtcggacgc acggctcctg tggcgccata taatgacacg ctttgaatca    300

cgaccccgcc tctgagtaca aatagccgaa aaactgatga ccccagtccc ttgggaccag    360

tggcagagct cg                                                        372
```

<210> SEQ ID NO 224
<211> LENGTH: 348
<212> TYPE: DNA
<213> ORGANISM: Homo sapiens

<400> SEQUENCE: 224

```
gaggtgcagc tgttggagtc tgggggaggc ttggtacagc ctggggggtc cctgcgtctc     60

tcctgtgcag cctccggatt caccttttct aagtatgata tgtcttgggt ccgccaggct    120

ccagggaagg gtctagagtg ggtctcaact attctggagg atggtctgac tacatactac    180

gcagactccg tgaagggccg gttcaccatc tcccgcgaca attccaagaa cacgctgtat    240

ctgcaaatga acagcctgcg tgccgaggac accgcggtat attactgtgc gaaaccgggg    300

cgtttgtttg actactgggg tcagggaacc ctggtcaccg tctcgagc                 348
```

<210> SEQ ID NO 225
<211> LENGTH: 348
<212> TYPE: DNA
<213> ORGANISM: Homo sapiens

<400> SEQUENCE: 225

```
ctccacgtcg acaacctcag accccctccg aaccatgtcg gaccccccag ggacgcagag     60

aggacacgtc ggaggcctaa gtggaaaaga ttcatactat acagaaccca ggcggtccga    120

ggtcccttcc cagatctcac ccagagttga taagacctcc taccagactg atgtatgatg    180

cgtctgaggc acttcccggc caagtggtag agggcgctgt taaggttctt gtgcgacata    240

gacgtttact tgtcggacgc acggctcctg tggcgccata taatgacacg ctttggcccc    300

gcaaacaaac tgatgacccc agtcccttgg gaccagtggc agagctcg                 348
```

<210> SEQ ID NO 226
<211> LENGTH: 348
<212> TYPE: DNA
<213> ORGANISM: Homo sapiens

<400> SEQUENCE: 226
gaggtgcagc tgttggagtc tgggggaggc ttggtacagc ctgggggtc cctgcgtctc 60 tcctgtgcag cctccggatt caccttttcg gattatccta tgacgtgggt ccgccaggct 120
ccagggaagg gtctggagtg ggtctcaact attctgtctc cgggtacgga gacatactac 180
gcagactccg tgaagggccg gttcaccatc tcccgcgaca attccaagaa cacgctgtat 240
ctgcaaatga acagcctgcg tgccgaggac accgcggtat attactgtgc gaaagctgag 300
aaggattttg actactgggg tcagggaacc ctggtcaccg tctcgagc 348

<210> SEQ ID NO 227
<211> LENGTH: 348
<212> TYPE: DNA
<213> ORGANISM: Homo sapiens

<400> SEQUENCE: 227
ctccacgtcg acaacctcag accccctccg aaccatgtcg gaccccccag ggacgcagag 60
aggacacgtc ggaggcctaa gtggaaaagc ctaataggat actgcaccca ggcggtccga 120
ggtcccttcc cagacctcac ccagagttga taagacagag gcccatgcct ctgtatgatg 180
cgtctgaggc acttcccggc caagtggtag agggcgctgt taaggttctt gtgcgacata 240
gacgtttact tgtcggacgc acggctcctg tggcgccata taatgacacg ctttcgactc 300
ttcctaaaac tgatgacccc agtcccttgg gaccagtggc agagctcg 348

<210> SEQ ID NO 228
<211> LENGTH: 372
<212> TYPE: DNA
<213> ORGANISM: Homo sapiens

<400> SEQUENCE: 228
gaggtgcagc tgttggagtc tgggggaggc ttggtacagc ctgggggtc cctgcgtctc 60 tcctgtgcag cctcgggatt cacctttttg cagtatccga tgggttgggt ccgccaggct 120
ccagggaagg gtctagagtg ggtctcaact atttctcctg ttggtttgac tacatactac 180
gcagactccg tgaagggccg gttcaccatc tcccgcgaca attccaagaa cacgctgtat 240
ctgcaaatga acagcctgcg tgccgaggat accgcggtat attactgtgc gaaattgttt 300
gaggggtcga ggattcagcg tgatgtgggt tttgactact ggggtcaggg aaccctggtc 360
accgtctcga gc 372

<210> SEQ ID NO 229
<211> LENGTH: 372
<212> TYPE: DNA
<213> ORGANISM: Homo sapiens

<400> SEQUENCE: 229
ctccacgtcg acaacctcag accccctccg aaccatgtcg gaccccccag ggacgcagag 60
aggacacgtc ggagccctaa gtggaaaaac gtcataggct acccaaccca ggcggtccga 120
ggtcccttcc cagatctcac ccagagttga taaagaggac aaccaaactg atgtatgatg 180
cgtctgaggc acttcccggc caagtggtag agggcgctgt taaggttctt gtgcgacata 240
gacgtttact tgtcggacgc acggctccta tggcgccata taatgacacg ctttaacaaa 300
ctccccagct cctaagtcgc actacaccca aaactgatga ccccagtccc ttgggaccag 360
tggcagagct cg 372

<210> SEQ ID NO 230

<211> LENGTH: 366
<212> TYPE: DNA
<213> ORGANISM: Homo sapiens

<400> SEQUENCE: 230
gaggtgcagc tgttggagtc tgggggaggc ttggtacagc ctggggggtc cctgcgtctc 60
tcctgtgcag cctccggatt cacctttgag gagtatggta tggcgtgggt ccgccaggct 120
ccagggaagg gtctagagtg ggtctcaact atttctccgc tgggtatttc gacatactac 180
gcagactccg tgaagggccg gttcaccatc tcccgcgaca attccaagaa cacgctgtat 240
ctgcaaatga acagcctgcg tgccgaggac accgcggtat attactgtgc gaaacatgct 300
acgtctcagg agtctttgcg gtcttttgac tactggggtc agggaaccct ggtcaccgtc 360
tcgagc 366

<210> SEQ ID NO 231
<211> LENGTH: 366
<212> TYPE: DNA
<213> ORGANISM: Homo sapiens

<400> SEQUENCE: 231
ctccacgtcg acaacctcag accccctccg aaccatgtcg gaccccccag ggacgcagag 60
aggacacgtc ggaggcctaa gtggaaactc ctcataccat accgcaccca ggcggtccga 120
ggtcccttcc cagatctcac ccagagttga taaagaggcg acccataaag ctgtatgatg 180
cgtctgaggc acttcccggc caagtggtag agggcgctgt taaggttctt gtgcgacata 240
gacgtttact tgtcggacgc acggctcctg tggcgccata taatgacacg ctttgtacga 300
tgcagagtcc tcagaaacgc cagaaaactg atgaccccag tcccttggga ccagtggcag 360
agctcg 366

<210> SEQ ID NO 232
<211> LENGTH: 348
<212> TYPE: DNA
<213> ORGANISM: Homo sapiens

<400> SEQUENCE: 232
gaggtgcagc tgttggagtc tgggggaggc ttggtacagc ctggggggtc cctgcgtctc 60
tcctgtgcag cctccggatt cacctttgag aggtatcaga tggcgtgggt ccgccaggct 120
ccggggaagg gtctagagtg ggtctcaacg attagttctg atggtggggg gacatactac 180
gcagactccg tgaagggccg gttcaccatc tcccgcgaca attccaagaa cacgctgtat 240
ctgcaaatga acagcctgcg tgccgaggac accgcggtat attactgtgc gaaacctggt 300
catcggtttg actactgggg tcagggaacc ctggtcaccg tctcgagc 348

<210> SEQ ID NO 233
<211> LENGTH: 348
<212> TYPE: DNA
<213> ORGANISM: Homo sapiens

<400> SEQUENCE: 233
ctccacgtcg acaacctcag accccctccg aaccatgtcg gaccccccag ggacgcagag 60
aggacacgtc ggaggcctaa gtggaaactc tccatagtct accgcaccca ggcggtccga 120
ggccccttcc cagatctcac ccagagttgc taatcaagac taccaccccc ctgtatgatg 180
cgtctgaggc acttcccggc caagtggtag agggcgctgt taaggttctt gtgcgacata 240
gacgtttact tgtcggacgc acggctcctg tggcgccata taatgacacg ctttggacca 300
gtagccaaac tgatgacccc agtcccttgg gaccagtggc agagctcg 348

<210> SEQ ID NO 234
<211> LENGTH: 348
<212> TYPE: DNA
<213> ORGANISM: Homo sapiens

<400> SEQUENCE: 234
gaggtgcagc tgttggagtc tgggggaggc ttggtacagc ctggggggtc cctgcgtctc 60
tcctgtgcag cctccggatt cacctttggt cgttatcaga tggcttgggt ccgccaggct 120
ccagggaagg gtctagagtg ggtctcatct atttcttctg atggtggggg gacatactac 180
gcagactccg tgaagggccg gttcaccatc tcccgcgaca attccaagaa cacgctgtat 240
ctgcaaatga acagcctgcg tgccgaggac accgcggtat attactgtgc gaaaccgtct 300
cgtcggtttg actactgggg tcagggaacc ctggtcaccg tctcgagc 348

<210> SEQ ID NO 235
<211> LENGTH: 348
<212> TYPE: DNA
<213> ORGANISM: Homo sapiens

<400> SEQUENCE: 235
ctccacgtcg acaacctcag accccctccg aaccatgtcg gaccccccag ggacgcagag 60
aggacacgtc ggaggcctaa gtggaaacca gcaatagtct accgaaccca ggcggtccga 120
ggtcccttcc cagatctcac ccagagtaga taaagaagac taccaccccc ctgtatgatg 180
cgtctgaggc acttcccggc caagtggtag agggcgctgt taaggttctt gtgcgacata 240
gacgtttact tgtcggacgc acggctcctg tggcgccata taatgacacg ctttggcaga 300
gcagccaaac tgatgacccc agtcccttgg gaccagtggc agagctcg 348

<210> SEQ ID NO 236
<211> LENGTH: 369
<212> TYPE: DNA
<213> ORGANISM: Homo sapiens

<400> SEQUENCE: 236
gaggtgcagc tgttggagtc tgggggaggc ttggtacagc ctggggggtt cctgcgtctc 60
tcctgtgcag cctccggatt cacctttgag ttgtatccga tggcgtgggt ccgccaggct 120
ccagggaagg gtctggagtg ggtctcatcg atttctccgg ttggttttct gacatactac 180
gcagactccg tgaagggccg gttcaccatc tcccgcgaca attccaagaa cacgctgtat 240
ctgcaaatga acagcctgcg tgccgaggat accgcggtat attactgtgc gaaagggcat 300
gaggggtcgt atactccgcg gtcggctttt gactactggg gtcagggaac cctggtcacc 360
gtctcgagc 369

<210> SEQ ID NO 237
<211> LENGTH: 369
<212> TYPE: DNA
<213> ORGANISM: Homo sapiens

<400> SEQUENCE: 237
ctccacgtcg acaacctcag accccctccg aaccatgtcg gaccccccaa ggacgcagag 60
aggacacgtc ggaggcctaa gtggaaactc aacataggct accgcaccca ggcggtccga 120
ggtcccttcc cagacctcac ccagagtagc taaagaggcc aaccaaaaga ctgtatgatg 180
cgtctgaggc acttcccggc caagtggtag agggcgctgt taaggttctt gtgcgacata 240
gacgtttact tgtcggacgc acggctccta tggcgccata taatgacacg ctttcccgta 300
ctccccagca tatgaggcgc cagccgaaaa ctgatgaccc cagtcccttg ggaccagtgg 360
cagagctcg 369

<210> SEQ ID NO 238
<211> LENGTH: 369
<212> TYPE: DNA
<213> ORGANISM: Homo sapiens

<400> SEQUENCE: 238
gaggtgcagc tgttggagtc tgggggaggc ttggtacagc ctggggggtc cctgcgtctc 60
tcctgtgcag cctccggatt cacctttgtg gcgtatccta tggcgtgggt ccgccaggct 120
ccagggaagg gtctggagtg ggtctcaact attgcgcctc tgggtggtaa tacatactac 180
gcagactccg tgaagggccg gttcaccatc tcccgcgaca attccaagaa cacgctgtat 240
ctgcaaatga acagcctgcg tgccgaggac accgcggtat attactgtgc gaaacggccg 300
gaggggctgc agattgattc tcagaatttt gactactggg gtcagggaac cctggtcacc 360
gtctcgagc 369

<210> SEQ ID NO 239
<211> LENGTH: 369
<212> TYPE: DNA
<213> ORGANISM: Homo sapiens

<400> SEQUENCE: 239
ctccacgtcg acaacctcag accccctccg aaccatgtcg gaccccccag ggacgcagag 60
aggacacgtc ggaggcctaa gtggaaacac cgcataggat accgcaccca ggcggtccga 120
ggtcccttcc cagacctcac ccagagttga taacgcggag acccaccatt atgtatgatg 180
cgtctgaggc acttcccggc caagtggtag agggcgctgt taaggttctt gtgcgacata 240
gacgtttact tgtcggacgc acggctcctg tggcgccata taatgacacg ctttgccggc 300
ctccccgacg tctaactaag agtcttaaaa ctgatgaccc cagtcccttg ggaccagtgg 360
cagagctcg 369

<210> SEQ ID NO 240
<211> LENGTH: 348
<212> TYPE: DNA
<213> ORGANISM: Homo sapiens

<400> SEQUENCE: 240
gaggtgcagc tgttggagtc tgggggaggc ttggtacagc ctggggggtc cctgcgtctc 60
tcctgtgcag cctccggatt cacctttgcg ttgtatcaga tggcttgggt ccgccaggct 120
ccagggaagg gtctagagtg ggtctcatcg attgattctt ctggtagtga tacatactac 180
gcagactccg tgaagggccg gttcaccatc tcccgcgaca attccaagaa cacgctgtat 240
ctgcaaatga acagcctgcg tgccgaggac accgcggtat attactgtgc gaaacctgag 300
cgtgattttg actactgggg tcagggaacc ctggtcaccg tctcgagc 348

<210> SEQ ID NO 241
<211> LENGTH: 348
<212> TYPE: DNA
<213> ORGANISM: Homo sapiens

<400> SEQUENCE: 241
ctccacgtcg acaacctcag accccctccg aaccatgtcg gacccccag ggacgcagag 60

```
aggacacgtc ggaggcctaa gtggaaacgc aacatagtct accgaaccca ggcggtccga    120

ggtcccttcc cagatctcac ccagagtagc taactaagaa gaccatcact atgtatgatg    180

cgtctgaggc acttcccggc caagtggtag agggcgctgt taaggttctt gtgcgacata    240

gacgtttact tgtcggacgc acggctcctg tggcgccata taatgacacg ctttggactc    300

gcactaaaac tgatgacccc agtcccttgg gaccagtggc agagctcg                 348
```

<210> SEQ ID NO 242
<211> LENGTH: 348
<212> TYPE: DNA
<213> ORGANISM: Homo sapiens

<400> SEQUENCE: 242

```
gaggtgcagc tgttggagtc tgggggaggc ttggtacagc ctggggggtc cctgcgtctc     60

tcctgtgcag cctccggatt cacctttagg cagtaccaga tggcttgggc ccgccaggct    120

ccagggaagg gtctagagtg ggtctcaacg attgcgtcgg atggtgtttc tacatactac    180

gcagactccg tgaagggccg gttcaccatc tcccgcgaca attccaagaa cacgctgtat    240

ctgcaaatga acagcctgcg tgccgaggac accgcggtat attactgtgc gaaagttggt    300

cgtgattttg actactgggg tcagggaacc ctggtcaccg tctcgagc                 348
```

<210> SEQ ID NO 243
<211> LENGTH: 348
<212> TYPE: DNA
<213> ORGANISM: Homo sapiens

<400> SEQUENCE: 243

```
ctccacgtcg acaacctcag accccctccg aaccatgtcg gaccccccag ggacgcagag     60

aggacacgtc ggaggcctaa gtggaaatcc gtcatggtct accgaacccg ggcggtccga    120

ggtcccttcc cagatctcac ccagagttgc taacgcagcc taccacaaag atgtatgatg    180

cgtctgaggc acttcccggc caagtggtag agggcgctgt taaggttctt gtgcgacata    240

gacgtttact tgtcggacgc acggctcctg tggcgccata taatgacacg ctttcaacca    300

gcactaaaac tgatgacccc agtcccttgg gaccagtggc agagctcg                 348
```

<210> SEQ ID NO 244
<211> LENGTH: 324
<212> TYPE: DNA
<213> ORGANISM: Homo sapiens

<400> SEQUENCE: 244

```
gacatccaga tgacccagtc tccatcctcc ctgtctgcat ctgtaggaga ccgtgtcacc     60

atcacttgcc gggcaagtca gcctattggt cctgatttac tgtggtacca gcagaaacca    120

gggaaagccc ctaagctcct gatctatcag acgtccattt tgcaaagtgg ggtcccatca    180

cgtttcagtg gcagtggatc tgggacagat ttcactctca ccatcagcag tctgcaacct    240

gaagattttg ctacgtacta ctgtcaacag tattgggctt ttcctgtgac gttcggccaa    300

gggaccaagg tggaaatcaa acgg                                           324
```

<210> SEQ ID NO 245
<211> LENGTH: 324
<212> TYPE: DNA
<213> ORGANISM: Homo sapiens

<400> SEQUENCE: 245

```
ctgtaggtct actgggtcag aggtaggagg gacagacgta gacatcctct ggcacagtgg     60
```

tagtgaacgg cccgttcagt cggataacca ggactaaatg acaccatggt cgtctttggt 120
ccctttcggg gattcgagga ctagatagtc tgcaggtaaa acgtttcacc ccagggtagt 180
gcaaagtcac cgtcacctag accctgtcta aagtgagagt ggtagtcgtc agacgttgga 240
cttctaaaac gatgcatgat gacagttgtc ataacccgaa aaggacactg caagccggtt 300
ccctggttcc acctttagtt tgcc 324

<210> SEQ ID NO 246
<211> LENGTH: 116
<212> TYPE: PRT
<213> ORGANISM: Homo sapiens

<400> SEQUENCE: 246

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Gln Tyr
            20                  25                  30

Asp Met Arg Trp Val Arg Gln Ala Pro Gly Lys Gly Leu Glu Trp Val
        35                  40                  45

Ser Trp Ile Asp Glu Ala Gly His Glu Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Met Asp Gly Phe Asp Tyr Trp Gly Gln Gly Thr Leu Val
            100                 105                 110

Thr Val Ser Ser
        115

<210> SEQ ID NO 247
<211> LENGTH: 108
<212> TYPE: PRT
<213> ORGANISM: Homo sapiens

<400> SEQUENCE: 247

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asp Ala
            20                  25                  30

Leu Phe Trp Tyr Gln Gln Lys Pro Gly Lys Ala Pro Lys Leu Leu Ile
        35                  40                  45

Tyr Tyr Ser Ser Met Leu Gln Ser Gly Val Pro Ser Arg Phe Ser Gly
    50                  55                  60

Gly Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg His Ser Thr Pro Ala
                85                  90                  95

Thr Phe Gly Gln Gly Thr Lys Val Glu Ile Lys Arg
            100                 105

<210> SEQ ID NO 248
<211> LENGTH: 108
<212> TYPE: PRT
<213> ORGANISM: Homo sapiens

<400> SEQUENCE: 248

Asp Ile Gln Met Thr Gln Ser Pro Ser Ser Leu Ser Ala Ser Val Gly

```
1               5                   10                  15

Asp Arg Val Thr Ile Thr Cys Arg Ala Ser Gln Asp Ile Asp Glu Ser
            20                  25                  30

Leu Met Trp Tyr Gln Gln Lys Pro Gly Lys Ala Pro Arg Leu Leu Ile
        35                  40                  45

Tyr Gly Val Ser Tyr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Trp Lys Ala Pro Phe
                85                  90                  95

Thr Phe Gly Gln Gly Thr Lys Val Glu Ile Lys Arg
            100                 105


<210> SEQ ID NO 249
<211> LENGTH: 108
<212> TYPE: PRT
<213> ORGANISM: Homo sapiens

<400> SEQUENCE: 249

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Val Glu Asp
            20                  25                  30

Leu Tyr Trp Tyr Gln Gln Lys Pro Gly Lys Ala Ala Lys Leu Leu Ile
        35                  40                  45

Tyr Gly Ala Ser Trp Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Arg Arg Arg Pro Tyr
                85                  90                  95

Thr Phe Gly Gln Gly Thr Lys Val Glu Ile Lys Arg
            100                 105


<210> SEQ ID NO 250
<211> LENGTH: 108
<212> TYPE: PRT
<213> ORGANISM: Homo sapiens

<400> SEQUENCE: 250

Asp Ile Gln Met Thr Gln Ser Pro Ala Ser Leu Ser Ala Ser Val Gly
1               5                   10                  15

Asp Arg Val Thr Ile Thr Cys Arg Ala Ser Gln Asp Ile Asp Pro Met
            20                  25                  30

Leu Arg Trp Tyr Gln Gln Lys Pro Gly Lys Ala Pro Lys Leu Leu Ile
        35                  40                  45

Tyr Ala Gly Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Leu Val Thr Pro Tyr
                85                  90                  95

Thr Phe Gly Gln Gly Thr Lys Val Glu Ile Lys Arg
            100                 105


<210> SEQ ID NO 251
```

<211> LENGTH: 108
<212> TYPE: PRT
<213> ORGANISM: Homo sapiens

<400> SEQUENCE: 251

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Asp Ala
20 25 30

Leu Phe Trp Tyr Gln Gln Lys Pro Gly Lys Ala Pro Arg Leu Leu Ile
35 40 45

Tyr Tyr Gly Ser Val Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Arg Phe Gln Glu Pro Val
85 90 95

Thr Phe Gly Gln Gly Thr Lys Val Glu Ile Lys Arg
100 105

<210> SEQ ID NO 252
<211> LENGTH: 108
<212> TYPE: PRT
<213> ORGANISM: Homo sapiens

<400> SEQUENCE: 252

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gln Ile Ser Asp Glu
20 25 30

Leu Asn Trp Tyr Gln Gln Lys Pro Gly Lys Ala Pro Lys Leu Leu Ile
35 40 45

Tyr Ala Val Ser Ile Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Trp Leu Ser Phe Pro Ser
85 90 95

Thr Phe Gly Gln Gly Thr Lys Val Glu Ile Lys Arg
100 105

<210> SEQ ID NO 253
<211> LENGTH: 123
<212> TYPE: PRT
<213> ORGANISM: Homo sapiens

<400> SEQUENCE: 253

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Val Asp Tyr
20 25 30

Pro Met Gly Trp Val Arg Gln Ala Pro Gly Lys Gly Leu Glu Trp Val
35 40 45

Ser Thr Ile Ser Thr Gly Gly Phe Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys

```
                85                  90                  95

Ala Lys Ala Arg Tyr Tyr Tyr Leu Ser Gln Ile Lys Asn Phe Asp Tyr
            100                 105                 110

Trp Gly Gln Gly Thr Leu Val Thr Val Ser Ser
        115                 120


<210> SEQ ID NO 254
<211> LENGTH: 120
<212> TYPE: PRT
<213> ORGANISM: Homo sapiens

<400> SEQUENCE: 254

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Ile Tyr
            20                  25                  30

Gly Met Thr Trp Val Arg Gln Ala Pro Gly Lys Gly Leu Glu Trp Val
        35                  40                  45

Ser Ser Ile Ser Pro Leu Gly Leu Val Thr Tyr Tyr Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Lys Glu His Gly Asp Val Pro Phe Asp Tyr Trp Gly Gln
            100                 105                 110

Gly Thr Leu Val Thr Val Ser Ser
        115                 120


<210> SEQ ID NO 255
<211> LENGTH: 123
<212> TYPE: PRT
<213> ORGANISM: Homo sapiens

<400> SEQUENCE: 255

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Leu Tyr
            20                  25                  30

Pro Met Ser Trp Val Arg Gln Ala Pro Gly Lys Gly Leu Glu Trp Val
        35                  40                  45

Ser Thr Ile Ser Pro Thr Gly Leu Leu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Lys Arg Ser Gly Lys Thr Asp Asp Thr Asn Phe Asp Tyr
            100                 105                 110

Trp Gly Gln Gly Thr Leu Val Thr Val Ser Ser
        115                 120


<210> SEQ ID NO 256
<211> LENGTH: 116
<212> TYPE: PRT
<213> ORGANISM: Homo sapiens

<400> SEQUENCE: 256
```

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Arg Glu Tyr
20 25 30

Asp Met Leu Trp Val Arg Gln Ala Pro Gly Lys Gly Leu Glu Trp Val
35 40 45

Ser Thr Ile Val Gly Asp Gly Asn Gly Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gln Asp Arg Gln Phe Asp Tyr Trp Gly Gln Gly Thr Leu Val
100 105 110

Thr Val Ser Ser
115

<210> SEQ ID NO 257
<211> LENGTH: 118
<212> TYPE: PRT
<213> ORGANISM: Homo sapiens

<400> SEQUENCE: 257

Glu Val Gln Pro Leu Glu Ser Gly Gly Gly Leu Val Gln Pro Gly Gly
1 5 10 15

Ser Leu Arg Leu Ser Cys Ala Ala Ser Gly Phe Thr Phe Thr Asp Tyr
20 25 30

Lys Met Leu Trp Val Arg Gln Ala Pro Gly Lys Gly Leu Glu Trp Val
35 40 45

Ser Ser Ile Ser Pro Ser Gly Arg Trp Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Ser Leu Phe Glu Gly Ser Phe Asp Tyr Trp Gly Gln Gly Thr
100 105 110

Leu Val Thr Val Ser Ser
115

<210> SEQ ID NO 258
<211> LENGTH: 120
<212> TYPE: PRT
<213> ORGANISM: Homo sapiens

<400> SEQUENCE: 258

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Glu Glu Tyr
20 25 30

Gly Met Ser Trp Val Arg Gln Ala Pro Gly Lys Gly Leu Glu Trp Val
35 40 45

Ser Thr Ile Ser Pro Ile Gly Val Thr Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys

```
                85                  90                  95

Ala Lys Asn Ala Tyr Asp Arg Lys Ser Asn Phe Asp Tyr Trp Gly Gln
            100                 105                 110

Gly Thr Leu Val Thr Val Ser Ser
        115                 120


<210> SEQ ID NO 259
<211> LENGTH: 124
<212> TYPE: PRT
<213> ORGANISM: Homo sapiens

<400> SEQUENCE: 259

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Arg Tyr
            20                  25                  30

Val Met Val Trp Val Arg Gln Ala Pro Gly Lys Asp Leu Glu Trp Val
        35                  40                  45

Ser Gly Ile Thr Pro Ser Gly Arg Arg Thr Tyr Tyr Ala Asp Ser Val
    50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Gly Arg His Phe Asp Pro Leu Leu Pro Ser Phe Asp
            100                 105                 110

Tyr Trp Gly Gln Gly Thr Leu Val Thr Val Ser Ser
        115                 120


<210> SEQ ID NO 260
<211> LENGTH: 123
<212> TYPE: PRT
<213> ORGANISM: Homo sapiens

<400> SEQUENCE: 260

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Asp Tyr
            20                  25                  30

Ala Met Ser Trp Val Arg Gln Ala Pro Gly Lys Gly Leu Glu Trp Val
        35                  40                  45

Ser Thr Ile Thr Pro Gly Gly Phe Trp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Ser Ser Gly Glu Leu Gln Leu Val Glu Asp Phe Asp Tyr
            100                 105                 110

Trp Gly Gln Gly Thr Leu Val Thr Val Ser Ser
        115                 120


<210> SEQ ID NO 261
<211> LENGTH: 108
<212> TYPE: PRT
<213> ORGANISM: Homo sapiens

<400> SEQUENCE: 261
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Lys His Ser
            20                  25                  30

Leu Arg Trp Tyr Gln Gln Lys Pro Gly Lys Ala Pro Arg Leu Leu Ile
        35                  40                  45

Tyr His Arg Ser Gln Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Arg His Arg Pro Tyr
                85                  90                  95

Thr Phe Gly Gln Gly Thr Lys Val Glu Ile Lys Arg
            100                 105


<210> SEQ ID NO 262
<211> LENGTH: 108
<212> TYPE: PRT
<213> ORGANISM: Homo sapiens

<400> SEQUENCE: 262

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Gly His Arg
            20                  25                  30

Leu Arg Trp Tyr Gln Gln Lys Pro Gly Lys Ala Pro Lys Leu Leu Ile
        35                  40                  45

Tyr His Arg Ser Lys Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Ala Leu Phe Pro Tyr
                85                  90                  95

Thr Phe Gly Gln Gly Thr Lys Val Glu Ile Lys Arg
            100                 105


<210> SEQ ID NO 263
<211> LENGTH: 108
<212> TYPE: PRT
<213> ORGANISM: Homo sapiens

<400> SEQUENCE: 263

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln His Ile Gly His His
            20                  25                  30

Leu Arg Trp Tyr Gln Gln Lys Pro Gly Lys Ala Pro Lys Leu Leu Ile
        35                  40                  45

Tyr His Arg Ser His Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Trp Asp Arg Pro Pro Tyr
                85                  90                  95

Thr Phe Gly Gln Gly Thr Lys Val Glu Ile Lys Arg
            100                 105
```

<210> SEQ ID NO 264
<211> LENGTH: 108
<212> TYPE: PRT
<213> ORGANISM: Homo sapiens

<400> SEQUENCE: 264

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Gly His Arg
            20                  25                  30

Leu Arg Trp Tyr Gln Gln Lys Pro Gly Lys Ala Pro Lys Leu Leu Ile
        35                  40                  45

Tyr His Arg Ser Lys Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Arg Ala Val Pro Tyr
                85                  90                  95

Thr Phe Gly Gln Gly Thr Lys Val Glu Ile Lys Arg
            100                 105
```

<210> SEQ ID NO 265
<211> LENGTH: 108
<212> TYPE: PRT
<213> ORGANISM: Homo sapiens

<400> SEQUENCE: 265

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Gly His Arg
            20                  25                  30

Leu Arg Trp Tyr Gln Gln Lys Pro Gly Lys Ala Pro Lys Leu Leu Ile
        35                  40                  45

Tyr His Arg Ser Lys Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Arg Phe Ser Pro Tyr
                85                  90                  95

Thr Phe Gly Gln Gly Thr Lys Val Glu Ile Lys Arg
            100                 105
```

<210> SEQ ID NO 266
<211> LENGTH: 108
<212> TYPE: PRT
<213> ORGANISM: Homo sapiens

<400> SEQUENCE: 266

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Gly His Arg
            20                  25                  30

Leu Arg Trp Tyr Gln Gln Lys Pro Gly Lys Ala Pro Lys Leu Leu Ile
        35                  40                  45

Tyr His Arg Ser Lys Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Ser Tyr Ala Arg Pro Val
85 90 95

Thr Phe Gly Gln Gly Thr Lys Val Glu Ile Lys Arg
100 105

<210> SEQ ID NO 267
<211> LENGTH: 108
<212> TYPE: PRT
<213> ORGANISM: Homo sapiens

<400> SEQUENCE: 267

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Asn His Arg
20 25 30

Leu Tyr Trp Tyr Gln Gln Lys Pro Gly Lys Ala Pro Lys Leu Leu Ile
35 40 45

Tyr His Arg Ser Arg Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Lys Val Arg Pro Asn
85 90 95

Thr Phe Gly Gln Gly Thr Lys Val Glu Ile Lys Arg
100 105

<210> SEQ ID NO 268
<211> LENGTH: 108
<212> TYPE: PRT
<213> ORGANISM: Homo sapiens

<400> SEQUENCE: 268

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ala Ile Gly His Arg
20 25 30

Leu Arg Trp Tyr Gln Gln Lys Pro Gly Lys Ala Pro Lys Leu Leu Ile
35 40 45

Tyr His Arg Ser Lys Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Thr Tyr Ser Ser Pro His
85 90 95

Thr Phe Gly Gln Gly Thr Lys Val Glu Ile Lys Arg
100 105

<210> SEQ ID NO 269
<211> LENGTH: 108
<212> TYPE: PRT
<213> ORGANISM: Homo sapiens

<400> SEQUENCE: 269

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ala Ile Gly His Arg
20 25 30

Leu Arg Trp Tyr Gln Gln Lys Pro Gly Lys Ala Pro Lys Leu Leu Ile
35 40 45

Tyr His Arg Ser Lys Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Ala Val Arg Pro Phe
                85                  90                  95

Thr Phe Gly Gln Gly Thr Lys Val Glu Ile Lys Arg
            100                 105

<210> SEQ ID NO 270
<211> LENGTH: 108
<212> TYPE: PRT
<213> ORGANISM: Homo sapiens

<400> SEQUENCE: 270

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Gly His Arg
            20                  25                  30

Leu Arg Trp Tyr Gln Gln Lys Pro Gly Lys Ala Pro Lys Leu Leu Ile
        35                  40                  45

Tyr His Arg Ser Lys Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Tyr Arg Pro Leu
                85                  90                  95

Thr Phe Gly Gln Gly Thr Lys Val Glu Ile Lys Arg
            100                 105

<210> SEQ ID NO 271
<211> LENGTH: 108
<212> TYPE: PRT
<213> ORGANISM: Homo sapiens

<400> SEQUENCE: 271

Asp Ile Gln Met Thr Gln Ser Pro Ala Ser Leu Ser Ala Ser Val Gly
1               5                   10                  15

Asp Arg Val Thr Ile Thr Cys Arg Ala Ser Gln Asp Ile Asp Pro Met
            20                  25                  30

Leu Arg Trp Tyr Gln Gln Lys Pro Gly Lys Ala Pro Lys Leu Leu Ile
        35                  40                  45

Tyr Ala Gly Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Ser Ile Arg Pro Tyr
                85                  90                  95

Thr Phe Gly Gln Gly Thr Lys Val Glu Ile Lys Arg
            100                 105

<210> SEQ ID NO 272
<211> LENGTH: 124
<212> TYPE: PRT
<213> ORGANISM: Homo sapiens

<400> SEQUENCE: 272

Glu Val Gln Leu Leu Glu Ser Gly Gly Gly Leu Val Gln Pro Gly Gly

```
1               5                   10                  15

Ser Leu Arg Leu Ser Cys Ala Ala Ser Gly Phe Thr Phe Glu Arg Tyr
            20                  25                  30

Pro Met Thr Trp Val Arg Gln Ala Pro Gly Lys Gly Leu Glu Trp Val
        35                  40                  45

Ser Thr Ile His Gly Ser Gly Ser Ala Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Tyr Thr Ser Arg His Asn Ser Leu Gly His Phe Asp
            100                 105                 110

Tyr Trp Gly Gln Gly Thr Leu Val Thr Val Ser Ser
        115                 120


<210> SEQ ID NO 273
<211> LENGTH: 123
<212> TYPE: PRT
<213> ORGANISM: Homo sapiens

<400> SEQUENCE: 273

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Met Asp Tyr
            20                  25                  30

Pro Met Gly Trp Val Arg Gln Ala Pro Gly Lys Gly Leu Glu Trp Val
        35                  40                  45

Ser Ser Ile Gly Pro Val Gly Met Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Gly Gly Thr Ser Gly Arg His Asn Thr Lys Phe Asp Tyr
            100                 105                 110

Trp Gly Gln Gly Thr Leu Val Thr Val Ser Ser
        115                 120


<210> SEQ ID NO 274
<211> LENGTH: 123
<212> TYPE: PRT
<213> ORGANISM: Homo sapiens

<400> SEQUENCE: 274

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Glu Tyr
            20                  25                  30

Pro Met Ser Trp Val Arg Gln Ala Pro Gly Lys Gly Leu Glu Trp Val
        35                  40                  45

Ser Val Ile Ser Pro Leu Gly Phe Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Lys Trp Thr Gly Gly Ser Gly Ile Leu Asn Ser Ser Phe Asp Tyr
100 105 110

Trp Gly Gln Gly Thr Leu Val Thr Val Ser Ser
115 120

<210> SEQ ID NO 275
<211> LENGTH: 123
<212> TYPE: PRT
<213> ORGANISM: Homo sapiens

<400> SEQUENCE: 275

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Arg Val Ser Asn Tyr
20 25 30

Asp Leu Thr Trp Val Arg Gln Ala Pro Gly Lys Gly Leu Glu Trp Val
35 40 45

Ser Thr Ile Ser Ala Thr Asn Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Ala Val Thr Trp Trp Leu Leu Arg His Asn Asp Asn Leu Gly Phe
100 105 110

Trp Gly Gln Gly Thr Leu Val Thr Val Ser Ser
115 120

<210> SEQ ID NO 276
<211> LENGTH: 121
<212> TYPE: PRT
<213> ORGANISM: Homo sapiens

<400> SEQUENCE: 276

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Ser Ile Ser Tyr Lys
20 25 30

Asn Met Ala Trp Val Arg Gln Ala Pro Gly Lys Gly Leu Glu Trp Val
35 40 45

Ser Ala Ile Lys Ala Ala Asn Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Thr Gly Ser Gln Lys Lys Arg Thr Tyr Thr Phe Asp Phe Trp Gly
100 105 110

Gln Gly Thr Leu Val Thr Val Ser Ser
115 120

<210> SEQ ID NO 277
<211> LENGTH: 123
<212> TYPE: PRT
<213> ORGANISM: Homo sapiens

<400> SEQUENCE: 277

Glu Val Gln Leu Leu Glu Ser Gly Gly Gly Leu Val Gln Pro Gly Gly

-continued

```
1               5                   10                  15

Ser Leu Arg Leu Ser Cys Ala Ala Ser Gly Phe Thr Phe Arg Ser Tyr
            20                  25                  30

Thr Met Gly Trp Val Arg Gln Ala Pro Gly Lys Gly Leu Glu Trp Val
        35                  40                  45

Ser Ser Ile Asn Pro Met Gly Tyr Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Gly Val Gly Lys Gly Thr Lys Pro His Asn Phe Asp Tyr
            100                 105                 110

Trp Gly Gln Gly Thr Leu Val Thr Val Ser Ser
        115                 120


<210> SEQ ID NO 278
<211> LENGTH: 123
<212> TYPE: PRT
<213> ORGANISM: Homo sapiens

<400> SEQUENCE: 278

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Leu Tyr
            20                  25                  30

Arg Met Ser Trp Val Arg Gln Ala Pro Gly Lys Gly Leu Glu Trp Val
        35                  40                  45

Ser Glu Ile Ser Gly Ser Gly Phe Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Leu His Asp Lys Thr Gln His His Gln Glu Phe Asp Tyr
            100                 105                 110

Trp Gly Gln Gly Thr Leu Val Thr Val Ser Ser
        115                 120


<210> SEQ ID NO 279
<211> LENGTH: 118
<212> TYPE: PRT
<213> ORGANISM: Homo sapiens

<400> SEQUENCE: 279

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ile Glu Tyr
            20                  25                  30

Pro Met Arg Trp Val Arg Gln Ala Pro Gly Lys Gly Leu Glu Trp Val
        35                  40                  45

Ser Leu Ile Ser Pro Ser Gly Val Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Lys Gly Asp Glu Ser Ser Thr Phe Asp Tyr Trp Gly Gln Gly Thr
100 105 110

Leu Val Thr Val Ser Ser
115

<210> SEQ ID NO 280
<211> LENGTH: 124
<212> TYPE: PRT
<213> ORGANISM: Homo sapiens

<400> SEQUENCE: 280

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Lys Arg Tyr
20 25 30

Asp Met Asp Trp Val Arg Gln Ala Pro Gly Lys Gly Leu Glu Trp Val
35 40 45

Ser Thr Ile Gly Ser Ser Gly Tyr Pro Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Glu Arg Met Pro Gly Tyr Phe Pro Gly Phe Ala Arg Gln Phe Asp
100 105 110

Tyr Trp Gly Gln Gly Thr Leu Val Thr Val Ser Ser
115 120

<210> SEQ ID NO 281
<211> LENGTH: 124
<212> TYPE: PRT
<213> ORGANISM: Homo sapiens

<400> SEQUENCE: 281

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Trp Arg Tyr
20 25 30

Ala Met Gly Trp Val Arg Gln Ala Pro Gly Lys Gly Leu Glu Trp Val
35 40 45

Ser Thr Ile Asn Asp Glu Gly Arg Glu Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Lys Arg Val Ser Ser Ser Val Asn Ala Pro Tyr Glu Phe Asp
100 105 110

Tyr Trp Gly Gln Gly Thr Leu Val Thr Val Ser Ser
115 120

<210> SEQ ID NO 282
<211> LENGTH: 123
<212> TYPE: PRT
<213> ORGANISM: Homo sapiens

<400> SEQUENCE: 282

Glu Val Gln Leu Leu Glu Ser Gly Gly Gly Leu Val Gln Pro Gly Gly 1 5 10 15

Ser Leu Arg Leu Ser Cys Ala Ala Ser Gly Phe Thr Phe Ala Asn Tyr
20 25 30

Ser Met Ser Trp Val Arg Gln Ala Pro Gly Lys Gly Leu Glu Trp Val
35 40 45

Ser Ser Ile Asp Arg Leu Gly Thr His Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Val Leu Ala Asp Leu Ile Ala Gly His Ala Glu Phe Asp Tyr
100 105 110

Trp Gly Gln Gly Thr Leu Val Thr Val Ser Ser
115 120

<210> SEQ ID NO 283
<211> LENGTH: 124
<212> TYPE: PRT
<213> ORGANISM: Homo sapiens

<400> SEQUENCE: 283

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Pro Ser Tyr
20 25 30

Asp Met Ala Trp Val Arg Gln Ala Pro Gly Lys Gly Leu Glu Trp Val
35 40 45

Ser Gly Ile Ser Arg Ser Gly Ser Met Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Val Asp Ala His Val Tyr Tyr Met Glu Pro Phe Phe Asp
100 105 110

Tyr Trp Gly Gln Gly Thr Leu Val Thr Val Ser Ser
115 120

<210> SEQ ID NO 284
<211> LENGTH: 116
<212> TYPE: PRT
<213> ORGANISM: Homo sapiens

<400> SEQUENCE: 284

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Glu Arg Tyr
20 25 30

Gln Met Ala Trp Val Arg Gln Ala Pro Gly Lys Gly Leu Glu Trp Val
35 40 45

Ser Thr Ile Ser Ser Asp Gly Gly Gly Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

```
Ala Lys Pro Gly Thr Val Phe Asp Tyr Trp Gly Gln Gly Thr Leu Val
            100                 105                 110

Thr Val Ser Ser
        115


<210> SEQ ID NO 285
<211> LENGTH: 116
<212> TYPE: PRT
<213> ORGANISM: Homo sapiens

<400> SEQUENCE: 285

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Lys Tyr
            20                  25                  30

Glu Met Ala Trp Val Arg Gln Ala Pro Gly Lys Gly Leu Glu Trp Val
        35                  40                  45

Ser Ser Ile Asp Gly Asp Gly Lys Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Asp Gln Phe Phe Asp Tyr Trp Gly Gln Gly Thr Leu Val
            100                 105                 110

Thr Val Ser Ser
        115


<210> SEQ ID NO 286
<211> LENGTH: 116
<212> TYPE: PRT
<213> ORGANISM: Homo sapiens

<400> SEQUENCE: 286

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ala Gly Tyr
            20                  25                  30

Gln Met Ser Trp Val Arg Gln Ala Pro Gly Lys Gly Leu Glu Trp Val
        35                  40                  45

Ser Ser Ile Thr Asn Glu Gly Val Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Gly Lys Tyr Phe Asp Tyr Trp Gly Gln Gly Thr Leu Val
            100                 105                 110

Thr Val Ser Ser
        115


<210> SEQ ID NO 287
<211> LENGTH: 116
<212> TYPE: PRT
<213> ORGANISM: Homo sapiens

<400> SEQUENCE: 287

Glu Val Gln Leu Leu Glu Ser Gly Gly Gly Leu Val Gln Pro Gly Gly
```

```
1               5                   10                  15

Ser Leu Arg Leu Ser Cys Ala Ala Ser Gly Phe Thr Phe Gly Glu Tyr
            20                  25                  30

Glu Met Val Trp Val Arg Gln Ala Pro Gly Lys Gly Leu Glu Trp Val
        35                  40                  45

Ser Ser Ile Thr Ser Asp Gly Leu Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Gly Ile Arg Phe Asp Tyr Trp Gly Gln Gly Thr Leu Val
            100                 105                 110

Thr Val Ser Ser
        115


<210> SEQ ID NO 288
<211> LENGTH: 116
<212> TYPE: PRT
<213> ORGANISM: Homo sapiens

<400> SEQUENCE: 288

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Asp Tyr
            20                  25                  30

Asp Met Ala Trp Val Arg Gln Ala Pro Gly Lys Gly Leu Glu Trp Val
        35                  40                  45

Ser Gly Ile Val Asp Asp Gly Leu Met Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Asp Val Ala Phe Asp Tyr Trp Gly Gln Gly Thr Leu Val
            100                 105                 110

Thr Val Ser Asn
        115


<210> SEQ ID NO 289
<211> LENGTH: 123
<212> TYPE: PRT
<213> ORGANISM: Homo sapiens

<400> SEQUENCE: 289

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ile Gly Tyr
            20                  25                  30

Ala Met Ala Trp Val Arg Gln Ala Pro Gly Lys Gly Leu Glu Trp Val
        35                  40                  45

Ser Ser Ile Gly Pro Leu Gly Ala Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Lys Leu Pro Ala Gly Thr Ser Ser His Ser Val Asp Phe Asp Tyr
100 105 110

Trp Gly Gln Gly Thr Leu Val Thr Val Ser Ser
115 120

<210> SEQ ID NO 290
<211> LENGTH: 116
<212> TYPE: PRT
<213> ORGANISM: Homo sapiens

<400> SEQUENCE: 290

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ala Asp Tyr
20 25 30

Glu Met Thr Trp Val Arg Gln Ala Pro Gly Lys Gly Leu Glu Trp Val
35 40 45

Ser Ser Ile Thr Ser Asp Gly Val Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Pro Ser Val Gln Phe Asp Tyr Trp Gly Gln Gly Thr Leu Val
100 105 110

Thr Val Ser Ser
115

<210> SEQ ID NO 291
<211> LENGTH: 121
<212> TYPE: PRT
<213> ORGANISM: Homo sapiens

<400> SEQUENCE: 291

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Arg Arg Tyr
20 25 30

Val Met Gly Trp Val Arg Gln Ala Pro Gly Lys Gly Leu Glu Trp Val
35 40 45

Ser Trp Ile Glu Ala Asp Gly Arg Thr Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Leu Thr Asp Gln His Val Ile Glu Phe Asp Tyr Trp Gly
100 105 110

Gln Gly Thr Leu Val Thr Val Ser Ser
115 120

<210> SEQ ID NO 292
<211> LENGTH: 117
<212> TYPE: PRT
<213> ORGANISM: Homo sapiens

<400> SEQUENCE: 292

Glu Val Gln Leu Leu Glu Ser Gly Gly Gly Leu Val Gln Pro Gly Gly

```
1               5                   10                  15

Ser Leu Arg Leu Ser Cys Ala Ala Ser Gly Phe Thr Phe Asp Gly Tyr
            20                  25                  30

Arg Met Gly Trp Val Arg Gln Ala Pro Gly Lys Gly Leu Glu Trp Val
        35                  40                  45

Ser Ser Ile Ala Pro Asp Gly Asn Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Trp Gly Met Gln Phe Asp Tyr Trp Gly Gln Gly Thr Leu
            100                 105                 110

Val Thr Val Ser Ser
        115


<210> SEQ ID NO 293
<211> LENGTH: 120
<212> TYPE: PRT
<213> ORGANISM: Homo sapiens

<400> SEQUENCE: 293

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Ser Tyr
            20                  25                  30

Pro Met Gly Trp Val Arg Gln Ala Pro Gly Lys Gly Leu Glu Trp Val
        35                  40                  45

Ser Ser Ile Gly Pro Ile Gly Phe Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Met Lys Ser Pro Tyr Lys Pro Gln Phe Asp Tyr Trp Gly Gln
            100                 105                 110

Gly Thr Leu Val Thr Val Ser Ser
        115                 120


<210> SEQ ID NO 294
<211> LENGTH: 120
<212> TYPE: PRT
<213> ORGANISM: Homo sapiens

<400> SEQUENCE: 294

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Leu Ala Tyr
            20                  25                  30

Trp Met Val Trp Val Arg Gln Ala Pro Gly Lys Gly Leu Glu Trp Val
        35                  40                  45

Ser Ser Ile Ser Pro Ser Gly Thr His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95
```

```
Ala Lys Tyr Thr Glu Pro Gly Leu Gly Ser Phe Asp Tyr Trp Gly Gln
            100                 105                 110

Gly Thr Leu Val Thr Val Ser Ser
        115                 120


<210> SEQ ID NO 295
<211> LENGTH: 119
<212> TYPE: PRT
<213> ORGANISM: Homo sapiens

<400> SEQUENCE: 295

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Glu Met Gly Trp Val Arg Gln Ala Pro Gly Lys Gly Leu Glu Trp Val
        35                  40                  45

Ser Val Ile Ser Glu Val Gly Ser Leu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro His Asp Ser Ser Ile Gly Phe Asp Tyr Trp Gly Gln Gly
            100                 105                 110

Thr Leu Val Thr Val Ser Ser
        115


<210> SEQ ID NO 296
<211> LENGTH: 108
<212> TYPE: PRT
<213> ORGANISM: Homo sapiens

<400> SEQUENCE: 296

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Asp Thr
            20                  25                  30

Leu Thr Trp Tyr Gln Gln Lys Leu Gly Lys Ala Pro Lys Leu Leu Ile
        35                  40                  45

Tyr Gly Gly Ser Glu Leu Gln Ser Gly Val Pro Pro Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Cys Ile Ser Ser Pro Cys
                85                  90                  95

Thr Phe Gly Gln Gly Thr Lys Val Glu Ile Lys Arg
            100                 105


<210> SEQ ID NO 297
<211> LENGTH: 108
<212> TYPE: PRT
<213> ORGANISM: Homo sapiens

<400> SEQUENCE: 297

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Phe Ile Gly Asp Ser
```

20 25 30

Leu Ser Trp Tyr Gln Gln Lys Pro Gly Lys Ala Pro Lys Leu Leu Ile
35 40 45

Tyr Phe Ser Ser Ile Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr His Thr Ser Pro Thr
85 90 95

Thr Phe Gly Arg Gly Thr Lys Val Lys Ile Lys Arg
100 105

<210> SEQ ID NO 298
<211> LENGTH: 108
<212> TYPE: PRT
<213> ORGANISM: Homo sapiens

<400> SEQUENCE: 298

Asp Ile Gln Met Thr Gln Ser Pro Ser Ser Leu Ser Ala Ser Val Gly
1 5 10 15

Asp Arg Val Thr Ile Thr Cys Arg Ala Ser Gln Thr Ile Glu Thr Asn
20 25 30

Leu Glu Trp Tyr Gln Gln Lys Pro Gly Lys Ala Pro Lys Leu Leu Ile
35 40 45

Tyr Asp Ser Ser Gln Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Leu Ala Thr Tyr Tyr Cys Gln Gln Tyr His Gly Tyr Pro Thr
85 90 95

Thr Phe Gly Gln Gly Thr Lys Val Glu Ile Lys Arg
100 105

<210> SEQ ID NO 299
<211> LENGTH: 108
<212> TYPE: PRT
<213> ORGANISM: Homo sapiens

<400> SEQUENCE: 299

Asp Ile Gln Met Thr Gln Ser Pro Ser Ser Leu Ser Ala Ser Val Gly
1 5 10 15

Asp Arg Val Thr Ile Thr Cys Arg Ala Ser Gln Met Ile Asp Gln Asp
20 25 30

Leu Glu Trp Tyr Gln Gln Lys Pro Gly Lys Ala Pro Lys Leu Leu Ile
35 40 45

Tyr Asn Ala Ser Trp Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr His Gly Tyr Pro Ile
85 90 95

Thr Phe Gly Gln Gly Thr Lys Val Glu Ile Lys Arg
100 105

<210> SEQ ID NO 300
<211> LENGTH: 108
<212> TYPE: PRT
<213> ORGANISM: Homo sapiens

<400> SEQUENCE: 300

Asp Ile Gln Met Thr Gln Ser Pro Ser Ser Leu Ser Ala Ser Val Gly
1 5 10 15

Asp Arg Val Thr Ile Thr Cys Arg Ala Ser Gln Thr Ile Tyr Thr Ser
20 25 30

Leu Ser Trp Tyr Gln Gln Lys Pro Gly Lys Ala Pro Lys Leu Leu Ile
35 40 45

His Tyr Gly Ser Val Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Ser Ala Thr Tyr Tyr Cys Gln Gln Val His Gln Ala Pro Thr
85 90 95

Thr Phe Gly Gln Gly Thr Lys Val Glu Ile Lys Arg
100 105

<210> SEQ ID NO 301
<211> LENGTH: 108
<212> TYPE: PRT
<213> ORGANISM: Homo sapiens

<400> SEQUENCE: 301

Asp Ile Arg Met Thr Gln Ser Pro Ser Ser Leu Ser Ala Ser Val Gly
1 5 10 15

Asp Arg Val Thr Ile Thr Cys Arg Ala Ser Gln Trp Ile Gly Asp Ser
20 25 30

Leu Ala Trp Tyr Gln Gln Lys Pro Gly Lys Ala Pro Lys Leu Leu Ile
35 40 45

Tyr Gly Ile Ser Glu Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Ser Ala Thr Tyr Tyr Cys Gln Leu Ser Ser Ser Met Pro His
85 90 95

Thr Phe Gly Gln Gly Thr Lys Val Glu Ile Lys Arg
100 105

<210> SEQ ID NO 302
<211> LENGTH: 108
<212> TYPE: PRT
<213> ORGANISM: Homo sapiens

<400> SEQUENCE: 302

Asp Ile Gln Met Thr Gln Ser Pro Ser Ser Leu Ser Ala Ser Val Gly
1 5 10 15

Asp Arg Val Thr Ile Thr Cys Arg Ala Ser Gln Glu Ile Glu Thr Asn
20 25 30

Leu Glu Trp Tyr Gln Gln Lys Pro Gly Lys Ala Pro Lys Leu Leu Ile
35 40 45

Tyr Asp Ser Ser His Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr His Gln Asn Pro Pro
85 90 95

Thr Phe Gly Gln Gly Thr Lys Val Glu Ile Lys Arg 100 105

<210> SEQ ID NO 303
<211> LENGTH: 108
<212> TYPE: PRT
<213> ORGANISM: Homo sapiens

<400> SEQUENCE: 303

Asp Ile Gln Met Thr Gln Ser Pro Ser Ser Leu Ser Ala Ser Val Gly
1 5 10 15

Asp Arg Val Thr Ile Thr Cys Arg Ala Ser Gln Trp Ile Gly Arg Gln
20 25 30

Leu Val Trp Tyr Gln Gln Lys Pro Gly Lys Ala Pro Lys Leu Leu Ile
35 40 45

Tyr Gly Ala Thr Glu Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Gln Ser Lys Gly Pro Leu
85 90 95

Thr Phe Gly His Gly Thr Lys Val Glu Ile Lys Arg
100 105

<210> SEQ ID NO 304
<211> LENGTH: 108
<212> TYPE: PRT
<213> ORGANISM: Homo sapiens

<400> SEQUENCE: 304

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Gly Thr Asp
20 25 30

Leu Asn Trp Tyr Gln Gln Lys Pro Gly Lys Ala Pro Lys Leu Leu Ile
35 40 45

Tyr Met Gly Ser Tyr Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ile Tyr Ser Phe Pro Ile
85 90 95

Thr Phe Gly Gln Gly Thr Lys Val Glu Ile Lys Arg
100 105

<210> SEQ ID NO 305
<211> LENGTH: 108
<212> TYPE: PRT
<213> ORGANISM: Homo sapiens

<400> SEQUENCE: 305

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Glu Glu Met
20 25 30

Leu His Trp Tyr Gln Gln Lys Pro Gly Lys Ala Pro Lys Leu Leu Ile
35 40 45

Tyr Phe Gly Ser Leu Leu Gln Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln His His Thr Arg Pro Tyr
85 90 95

Thr Phe Gly Gln Gly Thr Lys Val Glu Ile Lys Arg
100 105

<210> SEQ ID NO 306
<211> LENGTH: 108
<212> TYPE: PRT
<213> ORGANISM: Homo sapiens

<400> SEQUENCE: 306

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Gly Met Asp
20 25 30

Leu Glu Trp Tyr Gln Gln Ile Pro Gly Lys Val Pro Lys Leu Leu Ile
35 40 45

Tyr Asp Ala Ser Tyr Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr His Lys Leu Pro Ala
85 90 95

Thr Phe Gly Gln Gly Thr Lys Val Glu Ile Lys Arg
100 105

<210> SEQ ID NO 307
<211> LENGTH: 108
<212> TYPE: PRT
<213> ORGANISM: Homo sapiens

<400> SEQUENCE: 307

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Met Asp Asn
20 25 30

Leu Glu Trp Tyr Gln Gln Lys Pro Gly Lys Ala Pro Lys Leu Leu Ile
35 40 45

Tyr Ala Ala Ser Trp Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr His Lys Leu Pro Val
85 90 95

Thr Phe Gly Gln Gly Thr Lys Val Glu Ile Lys Arg
100 105

<210> SEQ ID NO 308
<211> LENGTH: 108
<212> TYPE: PRT
<213> ORGANISM: Homo sapiens

<400> SEQUENCE: 308

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asn Ile Gly Glu Asp
20 25 30

```
Leu Glu Trp Tyr Gln Gln Lys Pro Gly Asn Ala Pro Lys Leu Leu Ile
        35                  40                  45

Tyr Ser Ala Ser His Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Val
                85                  90                  95

Thr Phe Gly Gln Gly Thr Lys Val Glu Ile Lys Arg
            100                 105


<210> SEQ ID NO 309
<211> LENGTH: 108
<212> TYPE: PRT
<213> ORGANISM: Homo sapiens

<400> SEQUENCE: 309

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Pro Ile Asp Glu Asp
            20                  25                  30

Leu Glu Trp Tyr Gln Gln Lys Pro Gly Asn Ala Pro Lys Leu Leu Ile
        35                  40                  45

Tyr Ser Ala Ser Tyr Leu Gln Ser Gly Val Pro Ser Arg Phe Ser Gly
    50                  55                  60

Ser Gly Ser Gly Thr Asp Phe Thr Leu Thr Ile Ser Arg Leu Gln Pro
65                  70                  75                  80

Glu Asp Phe Ala Thr Tyr Tyr Cys Gln Gln Tyr His Leu Leu Pro Ala
                85                  90                  95

Thr Phe Gly Gln Gly Thr Lys Val Glu Ile Lys Arg
            100                 105


<210> SEQ ID NO 310
<211> LENGTH: 108
<212> TYPE: PRT
<213> ORGANISM: Homo sapiens

<400> SEQUENCE: 310

Asp Ile Gln Met Ile Gln Ser Pro Ser Ser Leu Ser Ala Ser Val Gly
1               5                   10                  15

Asp Arg Val Thr Ile Thr Cys Arg Ala Ser Gln Asp Ile Asn Glu Asp
            20                  25                  30

Leu Glu Trp Tyr Gln Gln Lys Pro Gly Lys Ala Pro Lys Leu Leu Ile
        35                  40                  45

Tyr Asn Ala Ser Met Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Lys Asp Phe Ala Thr Tyr Tyr Cys Gln Gln Tyr His Thr Asn Pro Thr
                85                  90                  95

Thr Phe Gly Gln Gly Thr Lys Val Glu Ile Lys Arg
            100                 105


<210> SEQ ID NO 311
<211> LENGTH: 108
<212> TYPE: PRT
<213> ORGANISM: Homo sapiens
```

<400> SEQUENCE: 311

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Glu Ala Asp
20 25 30

Leu Glu Trp Tyr Gln Gln Lys Pro Gly Lys Ala Pro Lys Leu Leu Ile
35 40 45

Tyr His Ser Ser Glu Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr His Met Ser Pro Val
85 90 95

Thr Phe Gly Gln Gly Thr Lys Val Glu Ile Lys Arg
100 105

<210> SEQ ID NO 312
<211> LENGTH: 108
<212> TYPE: PRT
<213> ORGANISM: Homo sapiens

<400> SEQUENCE: 312

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Asp Ser Asp
20 25 30

Leu Glu Trp Tyr Gln Gln Lys Pro Gly Lys Ala Pro Met Leu Leu Ile
35 40 45

Tyr Ser Ser Ser Asp Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr His Ser Leu Pro Val
85 90 95

Thr Phe Gly Gln Gly Thr Lys Val Glu Ile Lys Arg
100 105

<210> SEQ ID NO 313
<211> LENGTH: 108
<212> TYPE: PRT
<213> ORGANISM: Homo sapiens

<400> SEQUENCE: 313

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Ser Asp Asp
20 25 30

Leu Glu Trp Tyr Gln Gln Lys Pro Gly Lys Ala Pro Lys Leu Leu Ile
35 40 45

Tyr Asn Ser Ser Phe Leu Gln Ser Gly Val Pro Ser Arg Phe Ser Gly
50 55 60

Ser Gly Ser Gly Ala Asp Phe Thr Leu Thr Ile Ser Ser Leu Gln Pro
65 70 75 80

Glu Asp Phe Ala Thr Tyr Tyr Cys Gln Gln Tyr His Ser Leu Pro Val
85 90 95

Thr Phe Gly Gln Gly Thr Lys Val Glu Ile Lys Arg
100 105

<210> SEQ ID NO 314
<211> LENGTH: 108
<212> TYPE: PRT
<213> ORGANISM: Homo sapiens

<400> SEQUENCE: 314

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Glu Gly Asn
            20                  25                  30

Leu Glu Trp Tyr Gln Gln Lys Pro Gly Lys Ala Pro Lys Leu Leu Ile
        35                  40                  45

Tyr Asp Ser Ser Gln Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr His His Leu Pro Thr
                85                  90                  95

Thr Phe Gly Gln Gly Thr Lys Val Glu Ile Lys Arg
            100                 105
```

<210> SEQ ID NO 315
<211> LENGTH: 108
<212> TYPE: PRT
<213> ORGANISM: Homo sapiens

<400> SEQUENCE: 315

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Thr Asp
            20                  25                  30

Leu Glu Trp Tyr Gln Gln Lys Pro Gly Lys Ala Pro Lys Leu Leu Ile
        35                  40                  45

Tyr Asp Gly Ser Trp Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Arg Trp Ile Pro Val
                85                  90                  95

Thr Phe Gly Gln Gly Thr Lys Val Glu Ile Lys Arg
            100                 105
```

<210> SEQ ID NO 316
<211> LENGTH: 108
<212> TYPE: PRT
<213> ORGANISM: Homo sapiens

<400> SEQUENCE: 316

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Asp
            20                  25                  30

Leu Glu Trp Tyr Gln Gln Lys Leu Gly Lys Ala Pro Lys Leu Leu Ile
        35                  40                  45

Tyr Asp Ala Ser Leu Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
```

```
65                  70                  75                  80

Glu Asp Phe Ala Thr Tyr Tyr Cys Gln Gln Tyr Ser Ser Leu Pro Val
                85                  90                  95

Thr Phe Gly Gln Gly Thr Lys Val Glu Ile Lys Arg
            100                 105


<210> SEQ ID NO 317
<211> LENGTH: 108
<212> TYPE: PRT
<213> ORGANISM: Homo sapiens

<400> SEQUENCE: 317

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Pro Ile Thr Thr Ser
            20                  25                  30

Leu Glu Trp Tyr Gln Gln Lys Pro Gly Lys Ala Pro Lys Leu Leu Ile
        35                  40                  45

Tyr Asp Ala Ser Met Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Val Thr Pro Val
                85                  90                  95

Thr Phe Gly Gln Gly Thr Lys Val Glu Ile Lys Arg
            100                 105


<210> SEQ ID NO 318
<211> LENGTH: 108
<212> TYPE: PRT
<213> ORGANISM: Homo sapiens

<400> SEQUENCE: 318

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile His Thr Asn
            20                  25                  30

Leu Glu Trp Tyr Gln Gln Lys Pro Gly Lys Ala Pro Lys Leu Leu Ile
        35                  40                  45

Tyr Asp Gly Ser Met Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ala Asn Pro Val
                85                  90                  95

Thr Phe Gly Gln Gly Thr Lys Val Gly Ile Lys Arg
            100                 105


<210> SEQ ID NO 319
<211> LENGTH: 108
<212> TYPE: PRT
<213> ORGANISM: Homo sapiens

<400> SEQUENCE: 319

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile His Thr Asp
            20                  25                  30
```

Leu Glu Trp Tyr Gln Gln Lys Pro Gly Lys Ala Pro Lys Leu Leu Ile
35 40 45

Tyr Asp Gly Ser Met Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Ser Val Ser Pro Val
85 90 95

Thr Phe Gly Gln Gly Thr Lys Val Glu Ile Lys Arg
100 105

<210> SEQ ID NO 320
<211> LENGTH: 108
<212> TYPE: PRT
<213> ORGANISM: Homo sapiens

<400> SEQUENCE: 320

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Asp Asn Asn
20 25 30

Leu Glu Trp Tyr Gln Gln Lys Pro Gly Glu Ala Pro Lys Leu Leu Ile
35 40 45

Tyr Asp Gly Ser Leu Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr His Leu His Pro Val
85 90 95

Thr Phe Gly Gln Gly Thr Lys Val Glu Ile Lys Arg
100 105

<210> SEQ ID NO 321
<211> LENGTH: 108
<212> TYPE: PRT
<213> ORGANISM: Homo sapiens

<400> SEQUENCE: 321

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Asp Thr Asn
20 25 30

Leu Glu Trp Tyr Gln Gln Lys Pro Gly Glu Ala Pro Lys Leu Leu Ile
35 40 45

Tyr Asp Arg Ser Thr Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asp Ser Tyr Pro Val
85 90 95

Thr Phe Gly Gln Gly Thr Lys Val Glu Ile Lys Arg
100 105

<210> SEQ ID NO 322
<211> LENGTH: 108
<212> TYPE: PRT
<213> ORGANISM: Homo sapiens

<400> SEQUENCE: 322

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Ser Asn
            20                  25                  30

Leu Glu Trp Tyr Gln Gln Lys Pro Gly Lys Ala Pro Lys Leu Leu Ile
        35                  40                  45

Tyr Asn Ala Ser Glu Leu Gln Ser Gly Val Pro Ser Arg Phe Ser Gly
    50                  55                  60

Ser Gly Ser Gly Thr Asp Phe Thr Leu Thr Ile Ser Ser Leu Arg Pro
65                  70                  75                  80

Glu Asp Phe Ala Thr Tyr Tyr Cys Gln Gln Tyr Asp Gln Trp Pro Thr
                85                  90                  95

Thr Phe Gly Gln Gly Thr Lys Val Glu Ile Lys Arg
            100                 105
```

<210> SEQ ID NO 323
<211> LENGTH: 108
<212> TYPE: PRT
<213> ORGANISM: Homo sapiens

<400> SEQUENCE: 323

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Gly Asn Thr
            20                  25                  30

Leu Arg Trp Tyr Gln Gln Lys Pro Gly Lys Ala Pro Lys Leu Leu Ile
        35                  40                  45

Tyr Leu Ser Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Lys Lys Pro Pro Tyr
                85                  90                  95

Thr Phe Gly Gln Gly Thr Lys Val Glu Ile Lys Arg
            100                 105
```

<210> SEQ ID NO 324
<211> LENGTH: 108
<212> TYPE: PRT
<213> ORGANISM: Homo sapiens

<400> SEQUENCE: 324

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Lys Ile Lys Asn Arg
            20                  25                  30

Leu Ala Trp Tyr Gln Gln Lys Pro Gly Lys Ala Pro Lys Leu Leu Ile
        35                  40                  45

Tyr Glu Val Ser His Leu Gln Ser Gly Val Pro Ser Arg Phe Ser Gly
    50                  55                  60

Ser Gly Ser Gly Thr Asp Phe Thr Leu Thr Ile Gly Ser Leu Gln Pro
65                  70                  75                  80

Glu Asp Phe Ala Thr Tyr Tyr Cys Gln Gln Arg Arg Gln Ser Pro Tyr
                85                  90                  95

Thr Phe Gly Gln Gly Thr Lys Val Glu Ile Lys Arg
            100                 105
```

<210> SEQ ID NO 325
<211> LENGTH: 108
<212> TYPE: PRT
<213> ORGANISM: Homo sapiens

<400> SEQUENCE: 325

Asp Ile Gln Met Thr Gln Ser Pro Ser Ser Leu Ser Ala Ser Val Gly
1 5 10 15

Asp Arg Val Thr Ile Thr Cys Arg Ala Ser Glu Asp Ile Gly Glu Glu
20 25 30

Leu Phe Trp Tyr Gln Gln Lys Pro Gly Lys Ala Pro Lys Leu Leu Ile
35 40 45

Tyr Ser Ala Ser Thr Leu Gln Ser Glu Val Pro Ser Arg Phe Ser Gly
50 55 60

Ser Gly Ser Gly Thr Asp Phe Thr Leu Thr Ile Ser Ser Leu Gln His
65 70 75 80

Glu Asp Phe Ala Thr Tyr Tyr Cys Gln Gln Val Tyr Glu Trp Pro Tyr
85 90 95

Thr Phe Gly Gln Gly Thr Lys Val Glu Ile Lys Arg
100 105

<210> SEQ ID NO 326
<211> LENGTH: 108
<212> TYPE: PRT
<213> ORGANISM: Homo sapiens

<400> SEQUENCE: 326

Asp Ile Gln Met Thr Gln Ser Pro Ser Ser Leu Ser Ala Ser Val Gly
1 5 10 15

Asp Arg Val Thr Ile Thr Cys Arg Ala Ser Gln Pro Ile Ser Gly Gly
20 25 30

Leu Arg Trp Tyr Gln Gln Lys Pro Gly Lys Ala Pro Lys Leu Leu Ile
35 40 45

Tyr Ser Thr Ser Met Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Leu Tyr Ser Ala Pro Tyr
85 90 95

Thr Phe Gly Gln Gly Thr Lys Val Glu Ile Lys Arg
100 105

<210> SEQ ID NO 327
<211> LENGTH: 119
<212> TYPE: PRT
<213> ORGANISM: Homo sapiens

<400> SEQUENCE: 327

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Asp Ala Tyr
20 25 30

Glu Met Gly Trp Val Arg Gln Ala Pro Gly Lys Gly Leu Glu Trp Val
35 40 45

Ser Ile Ile Asp Trp Asp Gly Asn Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Pro Gly Asp Asn Val Gly Ile Phe Asp Tyr Trp Gly Gln Gly
100 105 110

Thr Leu Val Thr Val Ser Ser
115

<210> SEQ ID NO 328
<211> LENGTH: 122
<212> TYPE: PRT
<213> ORGANISM: Homo sapiens

<400> SEQUENCE: 328

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Tyr Met Val Trp Val Arg Gln Ala Pro Gly Lys Gly Leu Glu Trp Val
35 40 45

Ser Ala Ile Asp Glu Trp Gly Phe Ala Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys His Trp Glu Phe Thr Ser Asp Thr Ser Arg Phe Asp Tyr Trp
100 105 110

Gly Gln Gly Thr Leu Val Thr Val Ser Ser
115 120

<210> SEQ ID NO 329
<211> LENGTH: 116
<212> TYPE: PRT
<213> ORGANISM: Homo sapiens

<400> SEQUENCE: 329

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Glu Asp Phe
20 25 30

Asp Met Ala Trp Val Arg Gln Ala Pro Gly Lys Gly Leu Glu Trp Val
35 40 45

Ser Ser Ile Asn Asp Gln Gly Ser Leu Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Pro Asp Gln Phe Phe Asp Tyr Trp Gly Gln Gly Thr Leu Val
100 105 110

Thr Val Ser Ser
115

<210> SEQ ID NO 330
<211> LENGTH: 118
<212> TYPE: PRT
<213> ORGANISM: Homo sapiens

<400> SEQUENCE: 330

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ala Tyr
20 25 30

Asp Met Met Trp Val Arg Gln Ala Pro Gly Lys Gly Leu Glu Trp Val
35 40 45

Ser Arg Ile Ser Pro Gln Gly Gln Arg Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Ile Arg Gly Gln Ser Arg Ile Pro Met Arg Phe Asp Tyr Trp
100 105 110

Gly Gln Gly Thr Leu Val
115

<210> SEQ ID NO 331
<211> LENGTH: 116
<212> TYPE: PRT
<213> ORGANISM: Homo sapiens

<400> SEQUENCE: 331

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Thr Asp Tyr
20 25 30

Glu Met Gly Trp Val Arg Gln Ala Pro Gly Lys Gly Leu Glu Trp Val
35 40 45

Ser Thr Ile Thr Ser Leu Gly Glu Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Pro Gly Arg Ile Phe Asp Tyr Trp Gly Gln Gly Thr Leu Val
100 105 110

Thr Val Ser Ser
115

<210> SEQ ID NO 332
<211> LENGTH: 123
<212> TYPE: PRT
<213> ORGANISM: Homo sapiens

<400> SEQUENCE: 332

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ala Phe Tyr
20 25 30

Pro Met Met Trp Val Arg Gln Ala Pro Gly Lys Gly Leu Glu Trp Val
35 40 45

Ser Trp Ile Asp Ala Thr Gly Thr Arg Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Glu Gly Asn Tyr Gly Ser Ser Tyr Thr Met Gly Val Phe Asp Tyr
100 105 110

Trp Gly Gln Gly Thr Leu Val Thr Val Ser Ser
115 120

<210> SEQ ID NO 333
<211> LENGTH: 122
<212> TYPE: PRT
<213> ORGANISM: Homo sapiens

<400> SEQUENCE: 333

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Asp Glu Tyr
20 25 30

Pro Met Tyr Trp Val Arg Gln Ala Pro Gly Lys Gly Leu Glu Trp Val
35 40 45

Ser Ser Ile Gly Pro Ser Gly Pro Asn Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Ser Pro Tyr Phe Asp Val Ile Pro Ser Tyr Phe Asp Tyr Trp
100 105 110

Gly Gln Gly Thr Leu Val Thr Val Ser Ser
115 120

<210> SEQ ID NO 334
<211> LENGTH: 119
<212> TYPE: PRT
<213> ORGANISM: Homo sapiens

<400> SEQUENCE: 334

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ala Asp Tyr
20 25 30

Gly Met Gly Trp Val Arg Gln Ala Pro Gly Lys Gly Leu Glu Trp Val
35 40 45

Ser Ser Ile Gln Ser Ser Gly Leu Arg Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Arg Ala Asn Ser Arg Arg Gly Phe Asp Tyr Trp Gly Gln Gly
100 105 110

Thr Leu Val Thr Val Ser Ser
115

<210> SEQ ID NO 335
<211> LENGTH: 116
<212> TYPE: PRT
<213> ORGANISM: Homo sapiens

<400> SEQUENCE: 335

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asp Tyr
20 25 30

Glu Met Met Trp Val Arg Gln Ala Pro Gly Lys Gly Leu Glu Trp Val
35 40 45

Ser Ser Ile Thr Ser His Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Pro Asp Lys Asp Phe Asp Tyr Trp Gly Gln Gly Thr Leu Val
100 105 110

Thr Val Ser Ser
115

<210> SEQ ID NO 336
<211> LENGTH: 122
<212> TYPE: PRT
<213> ORGANISM: Homo sapiens

<400> SEQUENCE: 336

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ala His Tyr
20 25 30

Pro Met Ser Trp Val Arg Gln Ala Pro Gly Lys Gly Leu Glu Trp Val
35 40 45

Ser Ser Ile Gly Arg Leu Gly Asn Arg Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Arg Ala Thr Pro Val Pro Ile Lys Gly Leu Phe Asp Tyr Trp
100 105 110

Gly Gln Gly Thr Leu Val Thr Val Ser Ser
115 120

<210> SEQ ID NO 337
<211> LENGTH: 116
<212> TYPE: PRT
<213> ORGANISM: Homo sapiens

<400> SEQUENCE: 337

Glu Val Gln Leu Leu Glu Ser Gly Gly Gly Leu Val Gln Pro Gly Gly
1 5 10 15

Ser Leu Arg Leu Ser Cys Ala Ala Ser Gly Leu Thr Phe Gly Arg Tyr
20 25 30

Glu Met Ala Trp Val Arg Gln Ala Pro Gly Lys Gly Leu Glu Trp Val
35 40 45

Ser Ser Ile Asp Ser Asp Gly Trp Val Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Gln Pro Asp Ser Leu Phe Asp Tyr Trp Gly Gln Gly Thr Leu Val
100 105 110

Thr Val Ser Ser
115

<210> SEQ ID NO 338
<211> LENGTH: 117
<212> TYPE: PRT
<213> ORGANISM: Homo sapiens

<400> SEQUENCE: 338

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ser Met Val Trp Val Arg Gln Ala Pro Gly Lys Gly Leu Glu Trp Val
35 40 45

Ser Gly Ile Asn Arg Gly Gly Thr Arg Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Trp Arg Arg Gly Phe Asp Tyr Trp Gly Gln Gly Thr Leu
100 105 110

Val Thr Val Ser Ser
115

<210> SEQ ID NO 339
<211> LENGTH: 117
<212> TYPE: PRT
<213> ORGANISM: Homo sapiens

<400> SEQUENCE: 339

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Thr Arg Tyr
20 25 30

Arg Met Ser Trp Val Arg Gln Ala Pro Gly Lys Gly Leu Glu Trp Val
35 40 45

Ser Gly Ile Ser Arg Asp Gly Tyr Arg Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Met Thr Ala Ser Phe Asp Tyr Trp Gly Gln Gly Thr Leu
100 105 110

Val Thr Val Ser Ser
115

<210> SEQ ID NO 340
<211> LENGTH: 118
<212> TYPE: PRT
<213> ORGANISM: Homo sapiens

<400> SEQUENCE: 340

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Gln Met Tyr
20 25 30

Pro Met Gly Trp Val Arg Gln Ala Pro Gly Lys Gly Leu Glu Trp Val
35 40 45

Ser Met Ile Glu Pro Ala Gly Asp Leu Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Tyr Gln Glu Gln Pro Trp Phe Asp Tyr Trp Gly Gln Gly Thr
100 105 110

Leu Val Thr Val Ser Ser
115

<210> SEQ ID NO 341
<211> LENGTH: 116
<212> TYPE: PRT
<213> ORGANISM: Homo sapiens

<400> SEQUENCE: 341

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Met Tyr
20 25 30

Asp Met His Trp Val Arg Gln Ala Pro Gly Lys Gly Leu Glu Trp Val
35 40 45

Ser Thr Ile Leu Ser Asp Gly Thr Asp Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Tyr Gly Ala Met Phe Asp Tyr Trp Gly Gln Gly Thr Leu Val
100 105 110

Thr Val Ser Ser
115

<210> SEQ ID NO 342
<211> LENGTH: 118
<212> TYPE: PRT
<213> ORGANISM: Homo sapiens

<400> SEQUENCE: 342

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Lys Leu Tyr
20 25 30

Pro Met Thr Trp Val Arg Gln Ala Pro Gly Lys Gly Leu Glu Trp Val
35 40 45

Ser Ser Ile Asp Ala Gly Gly His Glu Thr Tyr Tyr Ala Asp Ser Val
50 55 60

Lys Gly Arg Phe Thr Ile Ser Arg Asp Asn Ser Lys Asn Thr Leu Tyr
65 70 75 80

```
Leu Gln Met Asn Ser Leu Arg Ala Glu Asp Thr Ala Val Tyr Tyr Cys
                85                  90                  95

Ala Lys Asp Trp Trp Asp Tyr Leu Phe Asp Tyr Trp Gly Gln Gly Thr
            100                 105                 110

Leu Val Thr Val Ser Ser
        115


<210> SEQ ID NO 343
<211> LENGTH: 117
<212> TYPE: PRT
<213> ORGANISM: Homo sapiens

<400> SEQUENCE: 343

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Pro Met Ser Trp Val Arg Gln Ala Pro Gly Lys Gly Leu Glu Trp Val
        35                  40                  45

Ser Ser Ile Asn Arg Ser Gly Met Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Gly His Gln Ala Pro Phe Asp Tyr Trp Gly Gln Gly Thr Leu
            100                 105                 110

Val Thr Val Ser Ser
        115


<210> SEQ ID NO 344
<211> LENGTH: 123
<212> TYPE: PRT
<213> ORGANISM: Homo sapiens

<400> SEQUENCE: 344

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Gly Tyr
            20                  25                  30

Ala Met Ser Trp Val Arg Gln Ala Pro Gly Lys Gly Leu Glu Trp Val
        35                  40                  45

Ser Thr Ile Asn Ala Asn Gly Ile Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Gly Leu Arg Ala Glu Asp Thr Ala Val Tyr Tyr Cys
                85                  90                  95

Ala Lys Gly Gly Val Trp Arg Trp Gly Thr Gly His Lys Phe Asp Tyr
            100                 105                 110

Trp Gly Gln Gly Thr Leu Val Thr Val Ser Ser
        115                 120


<210> SEQ ID NO 345
<211> LENGTH: 118
<212> TYPE: PRT
<213> ORGANISM: Homo sapiens
```

<400> SEQUENCE: 345

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Lys Gln Tyr
20 25 30

Asp Met Arg Trp Val Arg Gln Ala Pro Gly Lys Gly Leu Glu Trp Val
35 40 45

Ser Thr Ile Ser Gln Asn Gly Thr Lys Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Ser Arg Thr Gly Arg Tyr Phe Asp Tyr Trp Gly Gln Gly Thr
100 105 110

Leu Val Thr Val Ser Ser
115

<210> SEQ ID NO 346
<211> LENGTH: 123
<212> TYPE: PRT
<213> ORGANISM: Homo sapiens

<400> SEQUENCE: 346

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Gly Thr Tyr
20 25 30

Asp Met Gly Trp Val Arg Gln Ala Pro Gly Lys Gly Leu Glu Trp Val
35 40 45

Ser Arg Ile Asn Trp Gln Gly Asp Arg Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Ala Gly Phe Gly His Tyr Val Asp Gly Leu Gly Phe Asp Tyr
100 105 110

Trp Gly Gln Gly Thr Leu Val Thr Val Ser Ser
115 120

<210> SEQ ID NO 347
<211> LENGTH: 116
<212> TYPE: PRT
<213> ORGANISM: Homo sapiens

<400> SEQUENCE: 347

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Gly Tyr
20 25 30

Glu Met Ala Trp Val Arg Gln Ala Pro Gly Lys Gly Leu Glu Trp Val
35 40 45

Ser Ser Ile Thr Asp Met Gly Asp Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Pro Gly Thr Ala Phe Asp Tyr Trp Gly Pro Gly Thr Leu Val
100 105 110

Thr Val Ser Ser
115

<210> SEQ ID NO 348
<211> LENGTH: 117
<212> TYPE: PRT
<213> ORGANISM: Homo sapiens

<400> SEQUENCE: 348

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ala Lys Tyr
20 25 30

Lys Met Trp Trp Val Arg Gln Ala Pro Gly Lys Gly Leu Glu Trp Val
35 40 45

Ser Ser Ile Thr Pro Lys Gly His Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Arg Pro Met Thr Pro Phe Asp Tyr Trp Gly Gln Gly Thr Leu
100 105 110

Val Thr Val Ser Ser
115

<210> SEQ ID NO 349
<211> LENGTH: 122
<212> TYPE: PRT
<213> ORGANISM: Homo sapiens

<400> SEQUENCE: 349

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Glu Arg Tyr
20 25 30

Asn Met Ser Trp Val Arg Gln Ala Pro Gly Lys Gly Leu Glu Trp Val
35 40 45

Ser Ser Ile Arg Pro Arg Gly Gly Lys Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Trp Arg Arg Glu Gly Tyr Thr Gly Ser Lys Phe Asp Tyr Trp
100 105 110

Gly Gln Gly Thr Leu Val Thr Val Ser Ser
115 120

<210> SEQ ID NO 350
<211> LENGTH: 118
<212> TYPE: PRT
<213> ORGANISM: Homo sapiens

<400> SEQUENCE: 350

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Arg Tyr
            20                  25                  30

Gly Met Thr Trp Val Arg Gln Ala Pro Gly Lys Gly Leu Glu Trp Val
        35                  40                  45

Ser Ser Ile Trp Pro Arg Gly Gln Lys Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asn Ser Arg Tyr Val Phe Asp Tyr Trp Gly Gln Gly Thr
            100                 105                 110

Leu Val Thr Val Ser Ser
        115

<210> SEQ ID NO 351
<211> LENGTH: 120
<212> TYPE: PRT
<213> ORGANISM: Homo sapiens

<400> SEQUENCE: 351

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Ser Met Gly Trp Val Arg Gln Ala Pro Gly Lys Gly Leu Glu Trp Val
        35                  40                  45

Ser Thr Ile Arg Pro Asn Gly Thr Lys Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Ser Ser Ala His Leu Gln Arg Phe Asp Tyr Trp Gly Gln
            100                 105                 110

Gly Thr Leu Val Thr Val Ser Ser
        115                 120

<210> SEQ ID NO 352
<211> LENGTH: 119
<212> TYPE: PRT
<213> ORGANISM: Homo sapiens

<400> SEQUENCE: 352

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Asn Tyr
            20                  25                  30

Ser Met Gly Trp Val Arg Gln Ala Pro Gly Lys Gly Leu Glu Trp Val
        35                  40                  45

Ser Ser Ile Gly Arg His Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Lys Lys Gly Ser Thr Tyr Pro Arg Phe Asp Tyr Trp Gly Gln Gly
            100                 105                 110

Thr Leu Val Thr Val Ser Ser
        115


<210> SEQ ID NO 353
<211> LENGTH: 118
<212> TYPE: PRT
<213> ORGANISM: Homo sapiens

<400> SEQUENCE: 353

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser His Tyr
            20                  25                  30

Glu Met Gly Trp Val Arg Gln Ala Pro Gly Lys Gly Leu Glu Trp Val
        35                  40                  45

Ser Ser Ile Glu Pro Phe Gly Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Tyr Pro Gln Gly Ser Phe Asp Tyr Trp Gly Gln Gly Thr
            100                 105                 110

Leu Val Thr Val Ser Ser
        115


<210> SEQ ID NO 354
<211> LENGTH: 124
<212> TYPE: PRT
<213> ORGANISM: Homo sapiens

<400> SEQUENCE: 354

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Thr Met Gly Trp Val Arg Gln Ala Pro Gly Lys Gly Leu Glu Trp Val
        35                  40                  45

Ser Ser Ile Arg Pro Asp Gly Lys Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Val Tyr Ser Ser Cys Ala Met Cys Thr Pro Leu Leu Phe Asp
            100                 105                 110

Tyr Trp Gly Gln Gly Thr Leu Val Thr Val Ser Ser
        115                 120


<210> SEQ ID NO 355
<211> LENGTH: 123
<212> TYPE: PRT
<213> ORGANISM: Homo sapiens
```

<400> SEQUENCE: 355

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Lys Arg Tyr
20 25 30

Ser Met Ala Trp Val Arg Gln Ala Pro Gly Lys Gly Leu Glu Trp Val
35 40 45

Ser Asp Ile Gly Pro Arg Gly Phe Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Val Gly Arg Gly Gln Arg Asp Thr Ser Gln Pro Phe Asp Tyr
100 105 110

Trp Gly Gln Gly Thr Leu Val Thr Val Ser Ser
115 120

<210> SEQ ID NO 356
<211> LENGTH: 116
<212> TYPE: PRT
<213> ORGANISM: Homo sapiens

<400> SEQUENCE: 356

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ala Ser Tyr
20 25 30

Gln Met Ala Trp Val Arg Gln Ala Pro Gly Lys Gly Leu Glu Trp Val
35 40 45

Ser Gly Ile Thr Ser Gly Gly Leu Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Pro Gly Arg Gly Phe Asp Tyr Trp Gly Gln Gly Thr Leu Val
100 105 110

Thr Val Ser Ser
115

<210> SEQ ID NO 357
<211> LENGTH: 116
<212> TYPE: PRT
<213> ORGANISM: Homo sapiens

<400> SEQUENCE: 357

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ala Ser Tyr
20 25 30

Glu Met Thr Trp Val Arg Gln Ala Pro Gly Lys Gly Leu Glu Trp Val
35 40 45

Ser Gly Ile Ser Ser Asp Gly Leu Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Pro Gly Val Leu Phe Asp Tyr Trp Gly Gln Gly Thr Leu Val
100 105 110

Thr Val Ser Ser
115

<210> SEQ ID NO 358
<211> LENGTH: 117
<212> TYPE: PRT
<213> ORGANISM: Homo sapiens

<400> SEQUENCE: 358

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Asp Lys Tyr
20 25 30

Leu Met Ser Trp Val Arg Gln Ala Pro Gly Lys Gly Leu Glu Trp Val
35 40 45

Ser Gly Ile Glu Pro Leu Gly Asp Val Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Glu Ala Ser Gly Asp Phe Asp Tyr Trp Gly Gln Gly Thr Leu
100 105 110

Val Thr Val Ser Ser
115

<210> SEQ ID NO 359
<211> LENGTH: 116
<212> TYPE: PRT
<213> ORGANISM: Homo sapiens

<400> SEQUENCE: 359

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Thr Glu Tyr
20 25 30

Glu Met Ser Trp Val Arg Gln Ala Pro Gly Lys Gly Leu Glu Trp Val
35 40 45

Ser Ser Ile Asp Asn Val Gly Ser Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Pro Gly Lys Leu Phe Asp Tyr Trp Gly Gln Gly Thr Leu Val
100 105 110

Thr Val Ser Ser
115

<210> SEQ ID NO 360
<211> LENGTH: 118
<212> TYPE: PRT
<213> ORGANISM: Homo sapiens

<400> SEQUENCE: 360

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Asp Tyr
            20                  25                  30

Glu Met Trp Trp Val Arg Gln Ala Pro Gly Lys Gly Leu Glu Trp Val
        35                  40                  45

Ser Ala Ile Ser Arg Gln Gly Phe Ala Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Glu Arg Asp Asp Phe Asp Tyr Trp Gly Gln Gly Thr
            100                 105                 110

Leu Val Thr Val Ser Ser
        115

<210> SEQ ID NO 361
<211> LENGTH: 348
<212> TYPE: DNA
<213> ORGANISM: Homo sapiens

<400> SEQUENCE: 361
gaggtgcagc tgttggagtc tgggggaggc ttggtacagc ctggggggtc cctgcgtctc 60
tcctgtgcag cctccggatt cacctttgag cagtatgata tgaggtgggt ccgccaggct 120
ccagggaagg gtctagagtg ggtctcatgg attgatgagg cgggtcatga gacatactat 180
gcagactccg tgaagggccg gttcaccatc tcccgcgaca attccaggaa cacgctgtat 240
ctgcaaatga acagcctgcg tgccgaggac accgcggtat attactgtgc gaaagggatg 300
gatgggtttg actactgggg tcagggaacc ctggtcaccg tctcgagc 348

<210> SEQ ID NO 362
<211> LENGTH: 324
<212> TYPE: DNA
<213> ORGANISM: Homo sapiens

<400> SEQUENCE: 362
gacatccaga tgacccagtc tccatcctcc ctgtctgcat ctgtaggaga ccgtgtcacc 60
atcacttgcc gggcaagtca ggatattggg gatgctttat tttggtacca gcagaaacca 120
gggaaagccc ctaagctcct gatctattat tcttccatgt tgcaaagtgg ggtcccatca 180
cgtttcagtg gcggtggatc tgggacagat ttcactctca ccatcagcag tctgcaacct 240
gaagattttg ctacgtacta ctgtcaacag cggcatagta ctcctgctac gttcggccaa 300
gggaccaagg tggaaatcaa acgg 324

<210> SEQ ID NO 363
<211> LENGTH: 300
<212> TYPE: DNA
<213> ORGANISM: Homo sapiens

<400> SEQUENCE: 363
gacatccaga tgacccagtc tccatcctcc ctgtctgcat ctgtaggaga ccgtgtcacc 60
atcacttgcc gggcaagtca ggatattgat gagtctttaa tgtggtacca gcagaaacca 120
gggaaagccc ctaggctcct gatctatggg gtgtcctatt tgcaaagtgg ggtcccatca 180
cgtttcagtg gcagtggatc tgggacagat ttcactctca ccatcagcag tctgcaacct 240
gaagatttcg ctacgtacta ctgtcaacag cggtggaagg ctccttttac gttcggccaa 300

<210> SEQ ID NO 364
<211> LENGTH: 324
<212> TYPE: DNA
<213> ORGANISM: Homo sapiens

<400> SEQUENCE: 364
gacatccaga tgacccagtc tccatcctcc ctgtctgcat ctgtaggaga ccgtgttacc 60
atcacttgcc gggcaagtca ggagattgtg gaggatttat attggtatca gcagaaacca 120
gggaaagccg ctaagctcct gatctatggt gcgtcctggt tgcaaagtgg ggtcccatca 180
cgtttcagtg gcagtggatc tgggacagat ttcactctca ccatcagcag tctgcaacct 240
gaagattttg ctacgtacta ctgtcaacag acgcgtaggc gtccttatac gttcggccaa 300
gggaccaagg tggaaatcaa acgg 324

<210> SEQ ID NO 365
<211> LENGTH: 324
<212> TYPE: DNA
<213> ORGANISM: Homo sapiens

<400> SEQUENCE: 365
gacatccaga tgacccagtc tccagcctcc ctgtctgcat ctgtaggaga ccgtgtcacc 60
atcacttgcc gggcaagtca ggatattgat cctatgttaa ggtggtacca gcagaaacca 120
gggaaagccc ctaagctcct gatctatgcg ggttccattt tgcaaagtgg ggtcccatca 180
cgtttcagtg gcagtggatc tgggacagat ttcactctca ccatcagcag tctgcaacct 240
gaagattttg ctacgtacta ctgtcaacag acgctggtga ctccttatac gttcggccaa 300
gggaccaagg tggaaatcaa acgg 324

<210> SEQ ID NO 366
<211> LENGTH: 324
<212> TYPE: DNA
<213> ORGANISM: Homo sapiens

<400> SEQUENCE: 366
gacatccaga tgacccagtc tccatcctcc ctgtctgcat ctgtaggaga ccgtgtcacc 60
atcacttgcc gggcaagtca gtcgatttcg gatgcgttat tttggtacca gcagaaacca 120
gggaaagccc ctaggctcct gatctattat ggttccgttt tgcaaagtgg ggtcccatca 180
cgtttcagtg gcagtggatc tgggacagat ttcactctca ccatcagcag tctgcaacct 240
gaagattttg ctacgtacta ctgtcaacag cgttttcagg agcctgtgac gttcggccaa 300
gggaccaagg tggaaatcaa acgg 324

<210> SEQ ID NO 367
<211> LENGTH: 324
<212> TYPE: DNA
<213> ORGANISM: Homo sapiens

<400> SEQUENCE: 367
gacatccaga tgacccagtc tccatcctcc ctgtccgcat ctgtaggaga ccgtgtcacc 60
atcacttgcc gggcaagtca gcagattagt gatgagttaa attggtatca gcagaaacca 120
gggaaagccc ctaagctcct gatctatgct gtgtccattt tgcaaagtgg ggtcccatca 180
cgtttcagtg gcagtggatc tgggacagat ttcactctca ccatcagcag tctgcaacct 240

```
gaagatttg ctacgtacta ctgtcaacag tggttgagtt ttccttcgac gtttggccaa    300

gggaccaagg tggaaatcaa acgg                                          324


<210> SEQ ID NO 368
<211> LENGTH: 369
<212> TYPE: DNA
<213> ORGANISM: Homo sapiens

<400> SEQUENCE: 368

gaggtgcagc tgttggagtc tgggggaggc ttggtacagc ctggggggtc cctgcgtctc     60

tcctgtgcag cctccggatt cacctttgtt gattatccga tgggttgggt ccgccaggct    120

ccagggaagg gtctagagtg ggtctcaacg atttctacgg ggggtttttc gacatactac    180

gcagactccg tgaagggccg gttcaccatc tcccgcgaca attccaagaa cacgctgtat    240

ctgcaaatga acagcctgcg tgccgaggac accgcggtat attactgtgc gaaagcgcgg    300

tattattatc ttagtcagat taagaatttt gactactggg gtcagggaac cctggtcacc    360

gtctcgagc                                                            369


<210> SEQ ID NO 369
<211> LENGTH: 360
<212> TYPE: PRT
<213> ORGANISM: Homo sapiens

<400> SEQUENCE: 369

Gly Ala Gly Gly Thr Gly Cys Ala Gly Cys Thr Gly Thr Thr Gly Gly
1               5                   10                  15

Ala Gly Thr Cys Thr Gly Gly Gly Gly Gly Ala Gly Gly Cys Thr Thr
            20                  25                  30

Gly Gly Thr Ala Cys Ala Gly Cys Cys Thr Gly Gly Gly Gly Gly Gly
        35                  40                  45

Thr Cys Cys Cys Thr Gly Cys Gly Thr Cys Thr Cys Thr Cys Cys Thr
    50                  55                  60

Gly Thr Gly Cys Ala Gly Cys Cys Thr Cys Cys Gly Gly Ala Thr Thr
65                  70                  75                  80

Cys Ala Cys Cys Thr Thr Thr Gly Ala Thr Ala Thr Thr Thr Ala Thr
                85                  90                  95

Gly Gly Gly Ala Thr Gly Ala Cys Thr Thr Gly Gly Gly Thr Cys Cys
            100                 105                 110

Gly Cys Cys Ala Gly Gly Cys Thr Cys Cys Ala Gly Gly Gly Ala Ala
        115                 120                 125

Gly Gly Gly Thr Cys Thr Gly Gly Ala Gly Thr Gly Gly Gly Thr Cys
    130                 135                 140

Thr Cys Ala Ala Gly Thr Ala Thr Thr Thr Cys Gly Cys Cys Thr Cys
145                 150                 155                 160

Thr Thr Gly Gly Thr Cys Thr Thr Gly Thr Thr Ala Cys Ala Thr Ala
                165                 170                 175

Cys Thr Ala Cys Gly Cys Ala Gly Ala Cys Cys Cys Cys Gly Thr Gly
            180                 185                 190

Ala Ala Gly Gly Gly Cys Cys Gly Gly Thr Thr Cys Ala Cys Cys Ala
        195                 200                 205

Thr Cys Thr Cys Cys Cys Gly Cys Gly Ala Cys Ala Ala Thr Thr Cys
    210                 215                 220

Cys Ala Ala Gly Ala Ala Cys Ala Cys Gly Cys Thr Gly Thr Ala Thr
225                 230                 235                 240

Cys Thr Gly Cys Ala Ala Ala Thr Gly Ala Ala Cys Ala Gly Cys Cys
```

```
                245                 250                 255

Thr Gly Cys Gly Thr Gly Cys Cys Gly Ala Gly Gly Ala Cys Ala Cys
            260                 265                 270

Cys Gly Cys Gly Gly Thr Ala Thr Ala Thr Thr Ala Cys Thr Gly Thr
        275                 280                 285

Gly Cys Gly Ala Ala Ala Cys Thr Gly Ala Ala Gly Gly Ala Gly Cys
    290                 295                 300

Ala Thr Gly Gly Gly Gly Ala Thr Gly Thr Thr Cys Cys Thr Thr Thr
305                 310                 315                 320

Thr Gly Ala Cys Thr Ala Cys Thr Gly Gly Gly Gly Thr Cys Ala Gly
                325                 330                 335

Gly Gly Ala Ala Cys Cys Cys Thr Gly Gly Thr Cys Ala Cys Cys Gly
            340                 345                 350

Thr Cys Thr Cys Gly Ala Gly Cys
        355                 360


<210> SEQ ID NO 370
<211> LENGTH: 369
<212> TYPE: PRT
<213> ORGANISM: Homo sapiens

<400> SEQUENCE: 370

Gly Ala Gly Gly Thr Gly Cys Ala Gly Cys Thr Gly Thr Thr Gly Gly
1               5                   10                  15

Ala Gly Thr Cys Thr Gly Gly Gly Gly Gly Ala Gly Gly Cys Thr Thr
            20                  25                  30

Gly Gly Thr Ala Cys Ala Gly Cys Cys Thr Gly Gly Gly Gly Gly Gly
        35                  40                  45

Thr Cys Cys Cys Thr Gly Cys Gly Thr Cys Thr Cys Thr Cys Cys Thr
    50                  55                  60

Gly Thr Gly Cys Ala Gly Cys Cys Thr Cys Cys Gly Gly Ala Thr Thr
65                  70                  75                  80

Cys Ala Cys Cys Thr Thr Thr Gly Ala Gly Cys Thr Thr Thr Ala Thr
                85                  90                  95

Cys Cys Gly Ala Thr Gly Ala Gly Thr Thr Gly Gly Gly Thr Cys Cys
            100                 105                 110

Gly Cys Cys Ala Gly Gly Cys Thr Cys Cys Ala Gly Gly Gly Ala Ala
        115                 120                 125

Gly Gly Gly Thr Cys Thr Ala Gly Ala Gly Thr Gly Gly Gly Thr Cys
    130                 135                 140

Thr Cys Ala Ala Cys Thr Ala Thr Thr Thr Cys Thr Cys Cys Thr Ala
145                 150                 155                 160

Cys Gly Gly Gly Thr Thr Thr Gly Thr Thr Gly Ala Cys Ala Thr Ala
                165                 170                 175

Cys Thr Ala Cys Gly Cys Ala Gly Ala Cys Thr Cys Cys Gly Thr Gly
            180                 185                 190

Ala Ala Gly Gly Gly Cys Cys Gly Gly Thr Thr Cys Ala Cys Cys Ala
        195                 200                 205

Thr Cys Thr Cys Cys Cys Gly Cys Gly Ala Cys Ala Ala Thr Thr Cys
    210                 215                 220

Cys Ala Ala Gly Ala Ala Cys Ala Cys Gly Cys Thr Gly Thr Ala Thr
225                 230                 235                 240

Cys Thr Gly Cys Ala Ala Ala Thr Gly Ala Ala Cys Ala Gly Cys Cys
                245                 250                 255

Thr Gly Cys Gly Thr Gly Cys Cys Gly Ala Gly Gly Ala Cys Ala Cys
```

260 265 270

Cys Gly Cys Gly Gly Thr Ala Thr Ala Thr Thr Ala Cys Thr Gly Thr
275 280 285

Gly Cys Gly Ala Ala Ala Thr Thr Thr Ala Ala Gly Ala Gly Gly Ala
290 295 300

Gly Thr Gly Gly Gly Ala Ala Gly Ala Cys Thr Gly Ala Thr Gly Ala
305 310 315 320

Thr Ala Cys Thr Ala Ala Thr Thr Thr Thr Gly Ala Cys Thr Ala Cys
325 330 335

Thr Gly Gly Gly Gly Thr Cys Ala Gly Gly Gly Ala Ala Cys Cys Cys
340 345 350

Thr Gly Gly Thr Cys Ala Cys Cys Gly Thr Cys Thr Cys Gly Ala Gly
355 360 365

Cys

<210> SEQ ID NO 371
<211> LENGTH: 348
<212> TYPE: PRT
<213> ORGANISM: Homo sapiens

<400> SEQUENCE: 371

Gly Ala Gly Gly Thr Gly Cys Ala Gly Cys Thr Gly Thr Thr Gly Gly
1 5 10 15

Ala Gly Thr Cys Thr Gly Gly Gly Gly Gly Ala Gly Gly Cys Thr Thr
20 25 30

Gly Gly Thr Ala Cys Ala Gly Cys Cys Thr Gly Gly Gly Gly Gly Gly
35 40 45

Thr Cys Cys Cys Thr Gly Cys Gly Thr Cys Thr Cys Thr Cys Cys Thr
50 55 60

Gly Thr Gly Cys Ala Gly Cys Cys Thr Cys Cys Gly Gly Ala Thr Thr
65 70 75 80

Cys Ala Cys Cys Thr Thr Thr Cys Gly Gly Gly Ala Gly Thr Ala Thr
85 90 95

Gly Ala Thr Ala Thr Gly Cys Thr Gly Thr Gly Gly Gly Thr Cys Cys
100 105 110

Gly Cys Cys Ala Gly Gly Cys Thr Cys Cys Ala Gly Gly Gly Ala Ala
115 120 125

Gly Gly Gly Thr Cys Thr Ala Gly Ala Gly Thr Gly Gly Gly Thr Cys
130 135 140

Thr Cys Ala Ala Cys Gly Ala Thr Thr Gly Thr Gly Gly Gly Gly Gly
145 150 155 160

Ala Thr Gly Gly Thr Ala Ala Thr Gly Gly Thr Ala Cys Ala Thr Ala
165 170 175

Cys Thr Ala Cys Gly Cys Ala Gly Ala Cys Thr Cys Cys Gly Thr Gly
180 185 190

Ala Ala Gly Gly Gly Cys Cys Gly Gly Thr Thr Cys Ala Cys Cys Ala
195 200 205

Thr Cys Thr Cys Cys Cys Gly Cys Gly Ala Cys Ala Ala Thr Thr Cys
210 215 220

Cys Ala Ala Gly Ala Ala Cys Ala Cys Gly Cys Thr Gly Thr Ala Thr
225 230 235 240

Cys Thr Gly Cys Ala Ala Ala Thr Gly Ala Ala Cys Ala Gly Cys Cys
245 250 255

Thr Gly Cys Gly Thr Gly Cys Cys Gly Ala Gly Gly Ala Cys Ala Cys
260 265 270

```
Cys Gly Cys Gly Gly Thr Ala Thr Ala Thr Thr Ala Cys Thr Gly Thr
        275                 280                 285

Gly Cys Gly Ala Ala Ala Cys Ala Gly Gly Ala Thr Cys Gly Thr Cys
    290                 295                 300

Ala Gly Thr Thr Thr Gly Ala Cys Thr Ala Cys Thr Gly Gly Gly Gly
305                 310                 315                 320

Thr Cys Ala Gly Gly Gly Ala Ala Cys Cys Thr Gly Gly Thr Cys
                325                 330                 335

Ala Cys Cys Gly Thr Cys Thr Cys Gly Ala Gly Cys
            340                 345
```

<210> SEQ ID NO 372
<211> LENGTH: 354
<212> TYPE: DNA
<213> ORGANISM: Homo sapiens

<400> SEQUENCE: 372

```
gaggtgcagc cgttggagtc tgggggaggc ttggtacagc ctggggggtc cctgcgtctc     60

tcctgtgcag cctccggatt cacctttact gattataaga tgctttgggt ccgccaggct    120

ccagggaagg gtctagagtg ggtctcaagt atttctccta gtggtcgttg gacatactac    180

gcagactccg tgaagggccg gttcaccatc tcccgcgaca attccaagaa cacgctgtat    240

ctgcaaatga acagcctgcg tgccgaggac accgcggtat attactgtgc gaaaagtctt    300

tttgagggta gttttgacta ctggggtcag ggaaccctgg tcaccgtctc gagc          354
```

<210> SEQ ID NO 373
<211> LENGTH: 360
<212> TYPE: DNA
<213> ORGANISM: Homo sapiens

<400> SEQUENCE: 373

```
gaggtgcagc tgttggagtc tgggggaggc ttggtacagc ctggggggtc cctgcgtctc     60

tcctgtgcag cctccggatt cacctttgag gagtatggta tgagttgggt ccgccaggct    120

ccagggaagg gtctagagtg ggtctcaacg atttcgccta ttggtgttac tacatactac    180

gcagactccg tgaagggccg gttcaccatc tcccgcgaca attccaagaa cacgctgtat    240

ctgcaaatga acagcctgcg tgccgaggat accgcggtat attactgtgc gaaaaatgct    300

tatgatcgga agtctaattt tgactactgg ggtcagggaa ccctggtcac cgtctcgagc    360
```

<210> SEQ ID NO 374
<211> LENGTH: 372
<212> TYPE: DNA
<213> ORGANISM: Homo sapiens

<400> SEQUENCE: 374

```
gaggtgcagc tgttggagtc tgggggaggc ttggtacagc ctggggggtc cctgcgtctc     60

tcctgtgcag cctccggatt cacctttgat cggtatgtga tggtgtgggt ccgccaggct    120

ccagggaagg atctagagtg ggtctcaggt attactccga gtggtaggag gacatactac    180

gcagactccg tgaagggccg gttcaccatc tcccgcgaca attccaagga cacgctgtat    240

ctgcaaatga acagcctgcg tgccgaggac accgcggtat attactgtgc gaaagtgttg    300

gggcgtcatt ttgatcctct tctgccttcg tttgactact ggggtcaggg aaccctggtc    360

accgtctcga gc                                                        372
```

<210> SEQ ID NO 375

<211> LENGTH: 369
<212> TYPE: DNA
<213> ORGANISM: Homo sapiens

<400> SEQUENCE: 375
gaggtgcagc tgttggagtc tgggggaggc ttggtacagc ctgggggtc cctgcgtctc 60 tcctgtgcag cctccggatt cacctttgag gattatgcta tgagttgggt ccgccaggct 120
ccagggaagg gtctagagtg ggtctcaact attactccgg gtggtttttg gacatactac 180
gcagactccg tgaagggccg gttcaccatc tcccgcgaca attccaagaa cacgctgtat 240
ctgcaaatga acagcctgcg tgccgaggat accgcggtat attactgtgc gaaaacgtct 300
agtggggagt tgcagttggt tgaggatttt gactactggg gtcagggaac cctggtcacc 360
gtctcgagc 369

<210> SEQ ID NO 376
<211> LENGTH: 324
<212> TYPE: DNA
<213> ORGANISM: Homo sapiens

<400> SEQUENCE: 376
gacatccaga tgacccagtc tccatcctcc ctgtctgcat ctgtaggaga ccgtgtcacc 60
atcacttgcc gagcaagtca gaatattaag cattcgttac ggtggtacca gcagaaacca 120
gggaaagccc ctaggctcct gatctatcat cgttcccagt tgcaaagtgg ggtcccatca 180
cgtttcagtg gcagtggatc tgggacagat ttcactctca ccatcagcag tctgcaacct 240
gaagattttg ctacgtacta ctgtcaacag gttaggcatc gtccttatac gttcggccaa 300
gggaccaagg tggaaatcaa acgg 324

<210> SEQ ID NO 377
<211> LENGTH: 324
<212> TYPE: DNA
<213> ORGANISM: Homo sapiens

<400> SEQUENCE: 377
gacatccaga tgacccagtc tccatcctct ctgtctgcat ctgtaggaga ccgtgtcacc 60
atcacttgcc gggcaagtca ggctattggg catcggttac gttggtatca gcagaaacca 120
gggaaagccc ctaagctcct gatctatcat cggtccaagt tgcaaagtgg ggtcccatca 180
cgtttcagtg gcagtggatc tgggacagat ttcactctca ccatcagcag tctgcaacct 240
gaagattttg ctacgtacta ctgtcaacag gttgctttgt ttccctatac gttcggccaa 300
gggaccaagg tggaaatcaa acgg 324

<210> SEQ ID NO 378
<211> LENGTH: 324
<212> TYPE: PRT
<213> ORGANISM: Homo sapiens

<400> SEQUENCE: 378

Gly Ala Cys Ala Thr Cys Cys Ala Gly Ala Thr Gly Ala Cys Cys Cys
1 5 10 15

Ala Gly Thr Cys Thr Cys Cys Ala Thr Cys Cys Thr Cys Cys Cys Thr
20 25 30

Gly Thr Cys Thr Gly Cys Ala Thr Cys Thr Gly Thr Ala Gly Gly Ala
35 40 45

Gly Ala Cys Cys Gly Thr Gly Thr Cys Ala Cys Cys Ala Thr Cys Ala
50 55 60

Cys Thr Thr Gly Cys Cys Gly Gly Gly Cys Ala Ala Gly Thr Cys Ala
65 70 75 80

Gly Cys Ala Thr Ala Thr Thr Gly Gly Thr Cys Ala Thr Cys Ala Thr
85 90 95

Thr Thr Ala Ala Gly Gly Thr Gly Gly Thr Ala Cys Cys Ala Gly Cys
100 105 110

Ala Gly Ala Ala Ala Cys Cys Ala Gly Gly Gly Ala Ala Ala Gly Cys
115 120 125

Cys Cys Cys Cys Ala Ala Gly Cys Thr Cys Cys Thr Gly Ala Thr Cys
130 135 140

Thr Ala Thr Cys Ala Thr Ala Gly Gly Thr Cys Cys Cys Ala Thr Thr
145 150 155 160

Thr Gly Cys Ala Ala Ala Gly Thr Gly Gly Gly Gly Thr Cys Cys Cys
165 170 175

Ala Thr Cys Ala Cys Gly Thr Thr Thr Cys Ala Gly Thr Gly Gly Cys
180 185 190

Ala Gly Thr Gly Gly Ala Thr Cys Thr Gly Gly Gly Ala Cys Ala Gly
195 200 205

Ala Thr Thr Thr Cys Ala Cys Thr Cys Thr Cys Ala Cys Cys Ala Thr
210 215 220

Cys Ala Gly Cys Ala Gly Thr Cys Thr Gly Cys Ala Ala Cys Cys Thr
225 230 235 240

Gly Ala Ala Gly Ala Thr Thr Cys Thr Gly Cys Thr Ala Cys Gly Thr
245 250 255

Ala Cys Thr Ala Cys Thr Gly Thr Cys Ala Ala Cys Ala Gly Thr Gly
260 265 270

Gly Gly Ala Thr Ala Gly Gly Cys Cys Gly Cys Cys Thr Thr Ala Thr
275 280 285

Ala Cys Gly Thr Thr Cys Gly Gly Cys Cys Ala Ala Gly Gly Gly Ala
290 295 300

Cys Cys Ala Ala Gly Gly Thr Gly Gly Ala Ala Ala Thr Cys Ala Ala
305 310 315 320

Ala Cys Gly Gly

<210> SEQ ID NO 379
<211> LENGTH: 324
<212> TYPE: DNA
<213> ORGANISM: Homo sapiens

<400> SEQUENCE: 379
gacatccaga tgacccagtc cccatcctcc ctgtctgcat ctgtaggaga ccgtgtcacc 60
atcacttgcc gggcaagtca ggctattggg catcggttac gttggtatca gcagaaacca 120
gggaaagccc ctaagctcct gatctatcat cggtccaagt tgcaaagtgg ggtcccatca 180
cgtttcagtg gcagtggatc tgggacagat ttcactctca ccatcagcag tctgcaacct 240
gaagattttg ctacgtacta ctgtcaacag gtgcgggctg tgccttatac gtttggccaa 300
gggaccaagg tggaaattaa acgg 324

<210> SEQ ID NO 380
<211> LENGTH: 324
<212> TYPE: DNA
<213> ORGANISM: Homo sapiens

<400> SEQUENCE: 380
gacatccaga tgacccagtc tccatcctcc ctgtctgcat ctgtaggaga ccgtgtcacc 60

-continued atcacttgcc gggcaagtca ggctattggg catcggttac gttggtatca gcagaaacca 120
gggaaagccc ctaagctcct gatctatcat cggtccaagt tgcaaagtgg ggtcccatca 180
cgtttcagtg gcagtggatc tgggacagat ttcactctca ccatcagcag tctgcaacct 240
gaagattttg ctacgtacta ctgtcaacag gttcgttttt ctccttatac gttcggccaa 300
gggaccaagg tggaaatcaa acgg 324

<210> SEQ ID NO 381
<211> LENGTH: 324
<212> TYPE: DNA
<213> ORGANISM: Homo sapiens

<400> SEQUENCE: 381
gacatccaga tgacccagtc tccatcctcc ctgtctgcat ctgtaggaga ccgtgtcacc 60
atcacttgcc gggcaagtca ggctattggg catcggttac gttggtatca gcagaaacca 120
gggaaagccc ctaagctcct gatctatcat cggtccaagt tgcaaagtgg ggtcccatca 180
cgtttcagtg gcagtggatc tgggacagat ttcactctca ccatcagcag tctgcaacct 240
gaagattttg ctacgtacta ctgtcaacag tcttatgcta ggcctgtgac gttcggccaa 300
gggaccaagg tggaaatcaa acgg 324

<210> SEQ ID NO 382
<211> LENGTH: 324
<212> TYPE: DNA
<213> ORGANISM: Homo sapiens

<400> SEQUENCE: 382
gacatccaga tgacccagtc tccatcctcc ctgtctgcat ctgtaggaga ccgtgtcacc 60
atcacttgcc gggcaagtca aagtattaat cataggttat attggtacca gcagaaacca 120
gggaaagccc ctaagctcct gatctatcat cggtccaggt tgcaaagtgg ggtcccatca 180
cgtttcagtg gcagtggatc tgggacagat ttcactctca ccatcagcag tctgcaacct 240
gaggattttg ctacgtacta ctgtcaacag tataaggtta ggcctaatac gttcggccaa 300
gggaccaagg tggaaatcaa acgg 324

<210> SEQ ID NO 383
<211> LENGTH: 324
<212> TYPE: DNA
<213> ORGANISM: Homo sapiens

<400> SEQUENCE: 383
gacatccaga tgacccagtc tccatcctcc ctgtctgcat ctgtaggaga ccgtgtcacc 60
atcacttgcc gggcaagtca ggctattggg catcggttac gttggtatca gcagaaacca 120
gggaaagccc ctaagctcct gatttatcat cggtccaagt tgcaaagtgg ggtcccatca 180
cgtttcagtg gcagtggatc tgggacagat ttcactctca ccatcagcag tctgcaacct 240
gaagattttg ctacgtacta ctgtcaacag acttattcgt ctcctcatac gttcggccaa 300
gggaccaagg tggaaatcaa acgg 324

<210> SEQ ID NO 384
<211> LENGTH: 324
<212> TYPE: DNA
<213> ORGANISM: Homo sapiens

<400> SEQUENCE: 384
gacatccaga tgacccagtc tccatcctcc ctgtctgcat ctgtaggaga ccgtgtcacc 60
atcacttgcc gggcaagtca ggctattggg catcggttac gttggtatca gcagaaacca 120
gggaaagccc ctaagctcct gatctatcat cggtccaagt tgcaaagtgg ggtcccatca 180
cgtttcagtg gcagtggatc tgggacagat ttcactctca ccatcagcag tctacaacct 240
gaagattttg ctacgtacta ctgtcaacag agggcggtga ggccttttac gttcggccaa 300
gggaccaaag tggaaatcaa acgg 324

<210> SEQ ID NO 385
<211> LENGTH: 324
<212> TYPE: DNA
<213> ORGANISM: Homo sapiens

<400> SEQUENCE: 385
gacatccaga tgacccagtc tccatcctcc ctgtctgcat ctgtaggaga ccgtgtcacc 60
atcacttgcc gggcaagtca ggctattggg catcggttac gttggtatca gcagaaacca 120
gggaaagccc ctaagctcct gatctatcat cggtccaagt tgcaaagtgg ggtcccatca 180
cgtttcagtg gcagtggatc tgggacagat ttcactctca ccatcagcag tctgcaacct 240
gaagattttg ctacgtacta ctgtcaacag acttattatc gtcctcttac gttcggccaa 300
gggaccaagg tggaaatcaa acgg 324

<210> SEQ ID NO 386
<211> LENGTH: 324
<212> TYPE: DNA
<213> ORGANISM: Homo sapiens

<400> SEQUENCE: 386
gacatccaga tgacccagtc tccagcctcc ctgtctgcat ctgtaggaga ccgtgtcacc 60
atcacttgcc gggcaagtca ggatattgat cctatgttaa ggtggtacca gcagaaacca 120
gggaaagccc ctaagctcct gatctatgcg ggttccattt tgcaaagtgg ggtcccatca 180
cgtttcagtg gcagtggatc tgggacagat ttcactctca ccatcagcag tctgcaacct 240
gaagattttg ctacgtacta ctgtcaacag actagtatta ggccttatac gttcggccaa 300
gggaccaagg tggaaatcaa acgg 324

<210> SEQ ID NO 387
<211> LENGTH: 372
<212> TYPE: DNA
<213> ORGANISM: Homo sapiens

<400> SEQUENCE: 387
gaggtgcagc tgttggagtc tgggggaggc ttggtacagc ctgggggggtc cctgcgtctc 60 tcctgtgcag cctccggatt cacctttgag cgttatccta tgacgtgggt ccgccaggct 120
ccagggaagg gtctagagtg ggtctcaacg attcatggtt ctggtagtgc tacatactac 180
gcagactccg tgaagggccg gttcaccatc tcccgcgaca attccaagaa cacgctgtat 240
ctgcaaatga acagcctgcg tgccgaggac accgcggtat attactgtgc gaaagggccg 300
tatactagtc ggcataatag tcttgggcat tttgactact ggggtcaggg aaccctggtc 360
accgtctcga gc 372

<210> SEQ ID NO 388
<211> LENGTH: 369
<212> TYPE: DNA
<213> ORGANISM: Homo sapiens

<400> SEQUENCE: 388

-continued gaggtgcagc tgttggagtc tgggggaggc ttggtacagc ctggggggtc cctgcgtctc 60
tcctgtgcag cctccggatt cacctttatg gattatccta tggggtgggt ccgccaggct 120
ccagggaagg gtctagagtg ggtctcatct attgggcctg ttggtatgag tacatactac 180
gcagactccg tgaagggccg gttcaccatc tcccgcgaca attccaagaa cacgctgtat 240
ctgcaaatga acagcctgcg tgccgaggat accgcggtat attactgtgc gaaatatggg 300
gggactagtg gtaggcataa tactaagttt gactactggg gtcagggaac cctggtcacc 360
gtctcgagc 369

<210> SEQ ID NO 389
<211> LENGTH: 369
<212> TYPE: DNA
<213> ORGANISM: Homo sapiens

<400> SEQUENCE: 389
gaggtgcagc tgttggagtc tgggggaggc ttggtacagc ctggggggtc cctgcgtctc 60
tcctgtgcag cctccggatt cacctttact gagtatccta tgagttgggt ccgccaggct 120
ccagggaagg gtctagagtg ggtctcagtt atttctcctc ttggttttac gacatactac 180
gcagactccg tgaagggccg gttcaccatc tcccgcgaca attccaagaa cacgctgtat 240
ctgcaaatga acagcctgcg tgccgaggat accgcggtat attactgtgc gaaatggact 300
ggtgggagtg gtattttgaa ttcttctttt gactactggg gtcagggaac cctggtcacc 360
gtctcgagc 369

<210> SEQ ID NO 390
<211> LENGTH: 369
<212> TYPE: DNA
<213> ORGANISM: Homo sapiens

<400> SEQUENCE: 390
gaggtgcagc tgttggagtc tgggggaggc ttggtacagc ctggggggtc cctgcgtctc 60
tcctgtgcag cctccggatt tagggttagc aattacgatt tgacctgggt ccgccaggct 120
ccagggaagg gtctagagtg ggtatcaacc attagtgcca caaacggtag cacatactac 180
gcagactccg tgaagggccg gttcaccatc tcccgtgaca attccaagaa cacgctgtat 240
ctgcaaatga acagcctgcg tgccgaggac accgcggtat attattgcgc ggcagtgacg 300
tggtggttgt tgcgtcataa cgacaacttg ggttttgggg gtcagggaac cctggtcacc 360
gtctcgagc 369

<210> SEQ ID NO 391
<211> LENGTH: 363
<212> TYPE: DNA
<213> ORGANISM: Homo sapiens

<400> SEQUENCE: 391
gaggtgcagc tgttggagtc tgggggaggc ttggtacagc ctggggggtc cctgcgtctc 60
tcctgtgcag cctccggatt tagcattagc tataagaata tggcctgggt ccgccaggct 120
ccagggaagg gtctagagtg ggtatcagcc attaaggcgg caaacggtag cacatactac 180
gcagactccg tgaagggccg gttcaccatc tcccgtgaca attccaagaa cacgctgtat 240
ctgcaaatga acagcctgcg tgccgaggac accgcggtat attattgcgc gacagggagt 300
cagaagaagc ggacctacac gttcgacttt tggggtcagg gaaccctggt caccgtctcg 360
agc 363

<210> SEQ ID NO 392
<211> LENGTH: 369
<212> TYPE: DNA
<213> ORGANISM: Homo sapiens

<400> SEQUENCE: 392
gaggtgcagc tgttggagtc tgggggaggc ttggtacagc ctggggggtc cctgcgtctc 60
tcctgtgcag cctccggatt cacctttagg tcttatacga tgggttgggt ccgccaggct 120
ccagggaagg gtctagagtg ggtctcatct attaatccta tgggttatca gacatactac 180
gcagactccg tgaagggccg gttcaccatc tcccgcgaca attccaagaa cacgctgtat 240
ctgcaaatga acagcctgcg tgccgaggat accgcggtat attactgtgc gaaacatggg 300
gtggggaagg gtactaagcc gcataatttt gactactggg gtcagggaac cctggtcacc 360
gtctcgagc 369

<210> SEQ ID NO 393
<211> LENGTH: 369
<212> TYPE: DNA
<213> ORGANISM: Homo sapiens

<400> SEQUENCE: 393
gaggtgcagc tgttggagtc tgggggaggc ttggtacagc ctggggggtc cctgcgtctc 60
tcctgtgcag cctccggatt cacctttgag ctgtatagga tgtcttgggt ccgccaggct 120
ccagggaagg gtctagagtg ggtctcagag attagtggta gtggttttcc tacatactac 180
gcagactccg tgaagggccg gttcaccatc tcccgcgaca attccaagaa cacgctgtat 240
ctgcaaatga acagcctgcg tgccgaggac accgcggtat attactgtgc gaaaagtctg 300
catgataaga ctcagcatca tcaggagttt gactactggg gtcagggaac cctggtcacc 360
gtctcgagc 369

<210> SEQ ID NO 394
<211> LENGTH: 354
<212> TYPE: DNA
<213> ORGANISM: Homo sapiens

<400> SEQUENCE: 394
gaggtgcagc tgttggagtc tgggggaggc ttggtacagc ctggggggtc cctgcgtctc 60
tcctgtgcag cctccggatt cacctttatt gagtatccta tgcggtgggt ccgccaggct 120
ccagggaagg gtctagagtg ggtctcactt atttctccgt ctggtgtgtt tacatactac 180
gcagactccg tgaagggccg gttcaccatc tcccgcgaca attccaagaa cacgctgtat 240
ctgcaaatga acagcctgcg tgccgaggac accgcggtat attactgtgc gaaaggggat 300
gagtctagta cttttgacta ctggggtcag ggaaccctgg tcaccgtctc gagc 354

<210> SEQ ID NO 395
<211> LENGTH: 372
<212> TYPE: DNA
<213> ORGANISM: Homo sapiens

<400> SEQUENCE: 395
gaggtgcagc tgttggagtc tgggggaggc ttggtacagc ctggggggtc cctgcgtctc 60
tcctgtgcag cctccggatt cacctttaag cggtatgata tggattgggt ccgccaggct 120
ccagggaagg gtctagagtg ggtctcaacg attgggagtt cgggttatcc gacatactac 180
gcagactccg tgaagggccg gttcaccatc tcccgcgaca attccaagaa cacgctgtat 240

-continued

```
ctgcaaatga acagcctgcg tgccgaggac accgcggtat attactgtgc ggaaaggatg    300

cctggttatt ttcctgggtt tgctcggcag tttgactact ggggtcaggg aaccctggtc    360

accgtctcga gc                                                        372
```

<210> SEQ ID NO 396
<211> LENGTH: 372
<212> TYPE: DNA
<213> ORGANISM: Homo sapiens

<400> SEQUENCE: 396

```
gaggtgcagc tgttggagtc tgggggaggc ttggtacagc ctggggggtc cctgcgtctc     60

tcctgtgcag cctccggatt cacctttgg cggtatgcta tggggtgggt ccgccaggct    120

ccagggaagg gtctagagtg ggtctcaacg attaatgatg agggtcggga gacatactac    180

gcagactccg tgaagggccg gttcaccatc tcccgcgaca attccaagaa cacgctgtat    240

ctgcaaatga acagcctgcg tgccgaggac accgcggtat attactgtgc gaaaaagcgg    300

gtgtctagtt ctgtgaatgc tccgtatgag tttgactact ggggtcaggg aaccctggtc    360

accgtctcga gc                                                        372
```

<210> SEQ ID NO 397
<211> LENGTH: 369
<212> TYPE: DNA
<213> ORGANISM: Homo sapiens

<400> SEQUENCE: 397

```
gaggtgcagc tgttggagtc tgggggaggc ttggtacagc ctggggggtc cctgcgtctc     60

tcctgtgcag cctccggatt cacctttgcg aattatagta tgagttgggt ccgccaggcc    120

ccagggaagg gtctagagtg ggtctcatcg attgatcgtc ttggtacgca tacatactac    180

gcagactccg tgaagggccg gttcaccatc tcccgcgaca attccaagaa tacgctgtat    240

ctgcaaatga acagcctgcg tgccgaggat accgcggtat attactgtgc gaaagtgctg    300

gctgatctta ttgctgggca tgcggagttt gactactggg gtcagggaac cctggtcacc    360

gtctcgagc                                                            369
```

<210> SEQ ID NO 398
<211> LENGTH: 372
<212> TYPE: DNA
<213> ORGANISM: Homo sapiens

<400> SEQUENCE: 398

```
gaggtgcagc tgttggagtc tgggggaggc ttggtacagc ctggggggtc cctgcgtctc     60

tcctgtgcag cctccggatt cacctttccg tcgtatgata tggcgtgggt ccgccaggct    120

ccagggaagg gtctagagtg ggtctcaggg atttcgaggt ctggttctat gacatactac    180

gcagactccg tgaagggccg gttcaccatc tcccgcgaca attccaagaa cacgctgtat    240

ttgcaaatga acagcctgcg tgccgaggac accgcggtat attactgtgc gaaaggtgtt    300

gatgcgcatg tttattatat ggagcctttt tttgactact ggggtcaggg aaccctggtc    360

accgtctcga gc                                                        372
```

<210> SEQ ID NO 399
<211> LENGTH: 348
<212> TYPE: DNA
<213> ORGANISM: Homo sapiens

<400> SEQUENCE: 399
gaggtgcagc tgttggagtc tgggggaggc ttggtacagc ctggggggtc cctgcgtctc 60
tcctgtgcag cctccggatt cacctttgag aggtatcaga tggcgtgggt ccgccaggct 120
ccagggaagg gtctagagtg ggtctcaacg attagttctg atggtggggg gacatactac 180
gcagactccg tgaagggccg gttcaccatc tcccgcgaca attccaagaa cacgctgtat 240
ctgcaaatga acagcctgcg tgccgaggac accgcggtat attactgtgc gaaaccgggt 300
actgtttttg actactgggg tcagggaacc ctggtcaccg tctcgagc 348

<210> SEQ ID NO 400
<211> LENGTH: 348
<212> TYPE: DNA
<213> ORGANISM: Homo sapiens

<400> SEQUENCE: 400
gaggtgcagc tgttggagtc tgggggaggc ttggtacagc ctggggggtc cctgcgtctc 60
tcctgtgcag cctccggatt cacatttccg aagtatgaga tggcgtgggt ccgccaggct 120
ccagggaagg gtctagagtg ggtctcatct attgatggtg atggtaagtc tacatactac 180
gcagactccg tgaagggccg gttcaccatc tcccgcgaca attccaagaa cacgctgtat 240
ctgcaaatga acagcctgcg tgccgaggat accgcggtat attactgtgc gaaaccggat 300 cagtttttg actactgggg tcagggaacc ctggtcaccg tctcgagc 348

<210> SEQ ID NO 401
<211> LENGTH: 348
<212> TYPE: DNA
<213> ORGANISM: Homo sapiens

<400> SEQUENCE: 401
gaggtgcagc tgttggagtc tgggggaggc ttggtacagc ctggggggtc cctgcgtctc 60
tcctgtacag cctccggatt cacctttgcg ggttatcaga tgtcgtgggt ccgccaggct 120
ccagggaagg gtctagagtg ggtctcaagt attactaatg agggtgtttc tacatactac 180
gcagactccg tgaagggccg gttcaccatc tcccgcgaca attccaagaa cacgctgtat 240
ctgcaaatga acagcctgcg tgccgaggac accgcggtat attactgtgc gaaaccgggg 300
aagtattttg actactgggg tcagggaacc ctggtcaccg tctcgagc 348

<210> SEQ ID NO 402
<211> LENGTH: 348
<212> TYPE: DNA
<213> ORGANISM: Homo sapiens

<400> SEQUENCE: 402
gaggtgcagc tgttggagtc tgggggaggc ttggtacagc ctggggggtc cctgcgtctc 60
tcctgtgcag cctccggatt cacctttggg gagtatgaga tggtgtgggt ccgccaggct 120
ccagggaagg gtctggagtg ggtctcatct attacgtcgg atggtctgag tacatactac 180
gcagactccg tgaagggccg gttcaccatc tcccgcgaca attccaagaa cacgctgtat 240
ctgcaaatga acagcctgcg tgctgaggac accgcggtat attactgtgc gaaaccgggt 300
attcgttttg actactgggg tcagggaacc ctggtcaccg tctcgagc 348

<210> SEQ ID NO 403
<211> LENGTH: 348
<212> TYPE: DNA
<213> ORGANISM: Homo sapiens

<400> SEQUENCE: 403

-continued

```
gaggtgcagc tgttggagtc tgggggaggc ttggtacagc ctggggggtc cctgcgtctc      60

tcctgtgcag cctccggatt cacctttgct gattatgata tggcttgggt ccgccaggct     120

ccagggaagg gtctagagtg ggtctcaggt attgttgatg atggtcttat gacatactac     180

gcagactccg tgaagggccg gttcaccatc tcccgcgaca attccaagaa cacgctgtat     240

ctgcaaatga acagcctgcg tgccgaggac accgcggtat attactgtgc gaaaccggat     300

gttgcttttg actactgggg tcaggggacc ctggtcaccg tctcgaac                  348
```

<210> SEQ ID NO 404
<211> LENGTH: 369
<212> TYPE: DNA
<213> ORGANISM: Homo sapiens

<400> SEQUENCE: 404

```
gaggtgcagc tgttggagtc tgggggaggc ttggtacagc ctggggggtc cctgcgtctc      60

tcctgtgcag cctccggatt cacctttatt ggttatgcta tggcgtgggt ccgccaggct     120

ccagggaagg gtctagagtg ggtctcaagt attggtcctt tgggtgcgac tacatactac     180

gcagactccg tgaagggccg gttcaccatc tcccgcgaca attccaagaa cacgctgtat     240

ctgcaaatga acagcctgcg tgccgaggac accgcggtat attactgtgc gaaattgcct     300

gctggtacga gtagtcatag tgtggatttt gactactggg gtcagggaac cctggtcacc     360

gtctcgagc                                                             369
```

<210> SEQ ID NO 405
<211> LENGTH: 348
<212> TYPE: DNA
<213> ORGANISM: Homo sapiens

<400> SEQUENCE: 405

```
gaggtgcagc tgttggagtc tgggggaggc ttggtacagc ctggggggtc cctgcgtctc      60

tcctgtgcag cctccggatt cacctttgcg gattatgaga tgacttgggt ccgccaggct     120

ccagggaagg gtctagagtg ggtctcatct attactagtg atggtgtttc tacatactac     180

gcagactccg tgaagggccg gttcaccatc tcccgcgaca attccaagaa cacgctgtat     240

ctgcaaatga acagcctgcg tgccgaggac accgcggtat attactgtgc gaaaccgtcg     300

gttcagtttg actactgggg tcagggaacc ctggtcaccg tctcgagc                  348
```

<210> SEQ ID NO 406
<211> LENGTH: 363
<212> TYPE: DNA
<213> ORGANISM: Homo sapiens

<400> SEQUENCE: 406

```
gaggtgcagc tgttggagtc tgggggaggc ttggtacagc ctggggggtc cctgcgtctc      60

tcctgtgcag cctccggatt cacctttcgt aggtatgtta tggggtgggt ccgccaggct     120

ccagggaagg gtctagagtg ggtctcatgg attgaggctg atggtcgtac gacatactac     180

gcagactccg tgaagggccg gttcaccatc tcccgcgaca attccaagaa cacgctgtat     240

ctgcaaatga acagcctgcg tgccgaggac accgcggtat attactgtgc gaaagggctt     300

acggatcagc atgttattga gtttgactac tggggtcagg gaaccctggt caccgtctcg     360

agc                                                                   363
```

<210> SEQ ID NO 407
<211> LENGTH: 351
<212> TYPE: DNA

<213> ORGANISM: Homo sapiens

<400> SEQUENCE: 407
gaggtgcagc tgttggagtc tgggggaggc ttggtacagc ctggggggtc cctgcgtctc 60
tcctgtgcag cctccggatt cacctttgat ggttatcgta tggggtgggt ccgccaggct 120
ccagggaagg gtctagagtg ggtctcatcg attgctccgg atggtaatta tacatactac 180
gcagactccg tgaagggccg gttcaccatc tcccgcgaca attccaagaa cacgctgtat 240
ctgcaaatga acagcctgcg tgccgaggac accgcggtat attactgtgc gaaattttgg 300
gggatgcagt ttgactactg gggtcaggga accctggtca ccgtctcgag c 351

<210> SEQ ID NO 408
<211> LENGTH: 360
<212> TYPE: DNA
<213> ORGANISM: Homo sapiens

<400> SEQUENCE: 408
gaggtgcagc tgttggagtc tgggggaggc ttggtacagc ctggggggtc cctgcgtctc 60
tcctgtgcag cctccggatt cacctttgct tcgtatccga tgggttgggt ccgccaggct 120
ccagggaagg gtctagagtg ggtctcaagt attggtccta ttggttttac tacatactac 180
gcagactccg tgaagggccg gttcaccatc tcccgcgaca attccaagaa cacgctgtat 240
ctgcaaatga acagcctgcg tgccgaggac accgcggtat attactgtgc ggaaatgaag 300
tcgccttata agccgcagtt tgactactgg ggtcagggaa ccctggtcac cgtctcgagc 360

<210> SEQ ID NO 409
<211> LENGTH: 360
<212> TYPE: DNA
<213> ORGANISM: Homo sapiens

<400> SEQUENCE: 409
gaggtgcagc tgttggagtc tgggggaggc ttggtacagc ctggggggtc cctgcgtctc 60
tcctgtgcag cctccggatt caccttttg gcttattgga tggtttgggt ccgccaggct 120
ccagggaagg gtctagagtg ggtctcatct atttctccgt cgggtacgca tacatactac 180
gcagactccg tgaagggccg gttcaccatc tcccgcgaca attccaagaa cacgctgtat 240
ctgcaaatga acagcctgcg tgtcgaggac accgcggtat attactgtgc gaaatatact 300
gagccggggt tgggttcttt tgactactgg ggtcagggaa ccctggtcac cgtctcgagc 360

<210> SEQ ID NO 410
<211> LENGTH: 357
<212> TYPE: DNA
<213> ORGANISM: Homo sapiens

<400> SEQUENCE: 410
gaggtgcagc tgttggagtc tgggggaggc ttggtacagc ctggggggtc cctgcgtctc 60
tcctgtgcag cctccggatt caccttttcg aattatgaga tggggtgggt ccgccaggct 120
ccagggaagg gtctagagtg ggtctcagtg atttctgagg tgggttctct gacatactac 180
gcagactccg tgaagggccg gttcaccatc tcccgcgaca attccaagaa cacgctgtat 240
ctgcaaatga acagcctgcg tgccgaggac accgcggtat attactgtgc gaaacctcat 300
gatagttcga ttgggtttga ctactggggt cagggaaccc tggtcaccgt ctcgagc 357

<210> SEQ ID NO 411
<211> LENGTH: 324
<212> TYPE: DNA

<213> ORGANISM: Homo sapiens

<400> SEQUENCE: 411
gacatccaga tgacccagtc tccatcctcc ctgtctgcat ctgtaggaga ccgtgtcacc 60
atcacttgcc gggcaagtca gtggattggg gatacgttaa cgtggtacca gcagaaacta 120
gggaaagccc ctaagctcct gatctatggt ggttccgagt tgcaaagtgg ggtcccacca 180
cgtttcagtg gcagtggatc tgggacagat ttcactctca ccatcagcag tctgcaacct 240
gaagattttg ctacgtacta ctgtcaacag tgtattagta gtccttgtac gttcggccaa 300
gggaccaagg tggaaatcaa acgg 324

<210> SEQ ID NO 412
<211> LENGTH: 324
<212> TYPE: DNA
<213> ORGANISM: Homo sapiens

<400> SEQUENCE: 412
gacatccaga tgacccagtc tccatcctcc ctgtctgcat ctgtaggaga ccgtgtcacc 60
atcacttgcc gggcaagtca gtttattggt gattctttat cttggtacca gcagaaacca 120
gggaaagccc ctaagctcct gatctatttt tcttccattt tgcaaagtgg ggtcccatca 180
cgtttcagtg gcagtggatc tgggacagat ttcactctca ccatcagcag tctgcaacct 240
gaagattttg ctacgtacta ctgtcaacag tatcatactt cgcctactac gttcggccga 300
gggaccaagg tgaaaatcaa acgg 324

<210> SEQ ID NO 413
<211> LENGTH: 324
<212> TYPE: DNA
<213> ORGANISM: Homo sapiens

<400> SEQUENCE: 413
gacatccaga tgacccagtc tccatcctcc ctgtccgcat ctgtaggaga ccgtgtcacc 60
atcacttgcc gggcaagtca gactattgag actaatttag agtggtacca gcagaaacca 120
gggaaagccc ctaagctcct gatctatgat tcttcccagt tgcaaagtgg ggtcccatca 180
cgtttcagtg gcagtggatc tgggacagat tttactctca ccatcagcag tctgcaacct 240
gaagatttag ctacgtacta ctgtcaacag tatcatgggt atcctacgac gttcggccaa 300
gggaccaagg tggaaatcaa acgg 324

<210> SEQ ID NO 414
<211> LENGTH: 324
<212> TYPE: DNA
<213> ORGANISM: Homo sapiens

<400> SEQUENCE: 414
gacatccaga tgacccagtc tccatcctcc ctgtctgcat ctgtaggaga ccgtgtcacc 60
atcacttgcc gggcaagtca gatgattgat caggatttag agtggtacca gcagaaacca 120
gggaaagccc ctaagctcct gatctataat gcgtcctggt tgcaaagtgg ggtcccatca 180
cgtttcagcg gcagtggatc tgggacagat ttcactctca ccatcagcag tctgcaacct 240
gaagattttg ctacgtacta ctgtcaacag tatcatggtt atcctattac gttcggccaa 300
gggaccaagg tggaaatcaa acgg 324

<210> SEQ ID NO 415
<211> LENGTH: 324
<212> TYPE: DNA

<213> ORGANISM: Homo sapiens

<400> SEQUENCE: 415
gacatccaga tgacccagtc tccatcctcc ctgtctgcat ctgtaggaga ccgtgtcacc 60
atcacttgcc gggcaagtca gacgatttat acttcgttaa gttggtatca gcagaaacca 120
gggaaagccc ctaagctcct gatccattat ggttccgtgt tgcaaagtgg ggtcccatca 180
cgtttcagtg gcagtggatc tgggacagat ttcactctca ccatcagcag tctgcaacct 240
gaagattctg ctacgtacta ctgtcaacag gttcatcagg ctcctacgac gttcggccaa 300
gggaccaagg tggaaatcaa acgg 324

<210> SEQ ID NO 416
<211> LENGTH: 324
<212> TYPE: DNA
<213> ORGANISM: Homo sapiens

<400> SEQUENCE: 416
gacatccgga tgacccagtc tccatcctcc ctgtctgcat ctgtaggaga ccgtgtcacc 60
atcacttgcc gggcaagtca gtggattggg gattctttag cgtggtacca gcagaagcca 120
gggaaagccc ctaagctcct gatctatggt atttccgagt tgcaaagtgg ggtcccatca 180
cgtttcagtg gcagtggatc tgggacagat ttcactctca ccatcagcag tctgcaacct 240
gaagattctg ctacgtacta ctgtcaactg tctagtagta tgcctcatac gttcggccaa 300
gggaccaagg tggaaatcaa acgg 324

<210> SEQ ID NO 417
<211> LENGTH: 324
<212> TYPE: DNA
<213> ORGANISM: Homo sapiens

<400> SEQUENCE: 417
gacatccaga tgacccagtc tccatcctcc ctgtctgcat ctgtaggaga ccgtgtcacc 60
atcacttgcc gggcaagtca ggagattgag acgaatttag agtggtacca gcagaaacca 120
gggaaagccc ctaagctcct gatctatgat tcgtcccatt tgcaaagtgg ggtcccatca 180
cgtttcagtg gcagtggatc tgggacagat ttcactctca ccatcagcag tctgcaacct 240
gaagattttg ctacgtacta ctgtcaacag tatcatcaga atcctccgac gttcggccaa 300
ggaaccaagg tggaaatcaa acgg 324

<210> SEQ ID NO 418
<211> LENGTH: 324
<212> TYPE: DNA
<213> ORGANISM: Homo sapiens

<400> SEQUENCE: 418
gacatccaga tgacccagtc tccatcctcc ctgtctgcat ctgtaggaga ccgtgtcacc 60
atcacttgcc gggcaagtca gtggattggg aggcagttag tttggtacca gcagaaacca 120
gggaaagccc ctaagctcct gatctatggg gcgaccgagt tgcaaagtgg ggtcccatca 180
cgttttagtg gcagtggatc tgggacagat ttcactctca ccatcagcag tctgcaacct 240
gaagattttg ctacgtacta ctgtcaacag cagtcgaagg gtcctcttac gttcggccat 300
gggaccaagg tggaaatcaa acgg 324

<210> SEQ ID NO 419
<211> LENGTH: 324
<212> TYPE: DNA

<213> ORGANISM: Homo sapiens

<400> SEQUENCE: 419
gacatccaga tgacccagtc tccatcctcc ctgtctgcat ctgtaggaga ccgtgtcacc 60
atcacttgcc gggcaagtca ggggattggt actgatttaa attggtatca gcagaaacca 120
gggaaagccc ctaagctcct gatctatatg ggttcctatt tgcaaagtgg ggtcccatca 180
cgtttcagtg gcagtggatc tgggacagat ttcactctca ccatcagcag tctgcaacct 240
gaagattttg ctacgtacta ctgtcaacag atttattctt ttcctattac gttcggccaa 300
gggaccaagg tggaaatcaa acgg 324

<210> SEQ ID NO 420
<211> LENGTH: 324
<212> TYPE: DNA
<213> ORGANISM: Homo sapiens

<400> SEQUENCE: 420
gacatccaga tgacccagtc tccatcctcc ctgtctgcat ctgtaggaga ccgtgtcacc 60
atcacttgcc gggcaagtca ggatattgag gagatgttac attggtatca gcagaaacca 120
gggaaagccc ctaagctcct gatctatttt ggttccctgt tgcaaagtgg ggtcccatca 180
cgtttcagtg gcagtagatc tgggacagat ttcactctca ccatcagcag tctgcaacct 240
gaagattttg ctacgtacta ctgtcaacag catcatactc gtccttatac gttcggccaa 300
gggaccaagg tggaaatcaa acgg 324

<210> SEQ ID NO 421
<211> LENGTH: 324
<212> TYPE: DNA
<213> ORGANISM: Homo sapiens

<400> SEQUENCE: 421
gacatccaga tgacccagtc tccatcctcc ctgtctgcat ctgtaggaga ccgtgtcacc 60
atcacttgcc gggcaagtca ggatattggg atggatttag agtggtacca gcagatacca 120
gggaaagtcc ctaagctcct gatctatgat gcgtcctatt tgcaaagtgg ggtcccatca 180
cgtttcagtg gcagtggatc tgggacagat ttcactctca ccatcagcag tctgcaacct 240
gaagattttg ctacgtacta ctgtcaacag tatcataagc ttcctgcgac gtttggccaa 300
gggaccaagg tggaaatcaa acgg 324

<210> SEQ ID NO 422
<211> LENGTH: 323
<212> TYPE: DNA
<213> ORGANISM: Homo sapiens

<400> SEQUENCE: 422
gacatccaga tgacccagtc tccatcctcc ctgtctgcat ctgtaggaga ccgtgtcacc 60
atcacttgcc gggcaagtca ggatattatg gataatttag agtggtatca gcagaaacca 120
gggaaagccc ctaagctcct gatctatgcg gcgtcctggt tgcaaagtgg ggtcccatca 180
cgtttcagtg gcagtggatc tgggacagat ttcactctca ccatcagcag tctgcaacct 240
gaagattttg ctacgtacta ctgtcaacag tatcataagt tgcctgtgac gttcggccaa 300
ggaccaaggt ggaaatcaaa cgg 323

<210> SEQ ID NO 423
<211> LENGTH: 324
<212> TYPE: DNA

<213> ORGANISM: Homo sapiens

<400> SEQUENCE: 423
gacatccaga tgacccagtc tccatcctcc ctgtctgcat ctgtaggaga ccgtgtcacc 60
atcacttgcc gagcaagtca gaatattggg gaggatttag agtggtacca gcagaaacca 120
gggaatgccc ctaagctcct gatctatagt gcgtcccatt tgcaaagtgg ggtcccatca 180
cgtttcagtg gcagtggatc tgggacagat ttcactctca ccatcagcag tctgcaacct 240
gaagattttg ctacgtacta ctgtcaacag tattctagtt atcctgttac gttcggccaa 300
gggaccaagg tggaaatcaa acgg 324

<210> SEQ ID NO 424
<211> LENGTH: 324
<212> TYPE: DNA
<213> ORGANISM: Homo sapiens

<400> SEQUENCE: 424
gacatccaga tgacccagtc tccatcctcc ctgtctgcat ccgtaggaga ccgtgtcacc 60
atcacttgcc gggcaagtca gccgattgat gaggatttag agtggtacca gcagaaacca 120
gggaatgccc ctaagctcct gatctatagt gcgtcctatt tgcaaagtgg ggtcccatca 180
cgtttcagtg gcagtggatc tgggacagat ttcactctca ccatcagcag actgcaacct 240
gaagattttg ctacgtacta ctgtcaacag tatcatcttc tgcctgctac gttcggccaa 300
gggaccaagg tggaaatcaa acgg 324

<210> SEQ ID NO 425
<211> LENGTH: 324
<212> TYPE: DNA
<213> ORGANISM: Homo sapiens

<400> SEQUENCE: 425
gacatccaga tgatccagtc tccatcctcc ctgtctgcat ctgtaggaga ccgtgtcacc 60
atcacttgcc gggcaagtca ggatattaat gaggatttag agtggtatca gcagaaacca 120
gggaaagccc ctaagctcct gatctataat gcttccatgt tgcaaagcgg ggtcccatca 180
cgtttcagtg gcagtggatc tgggacagat ttcactctca ccatcagcag tctgcaacct 240
aaagattttg ctacgtacta ctgtcaacag tatcatacta atcctactac gttcggccaa 300
gggaccaagg tggaaatcaa acgg 324

<210> SEQ ID NO 426
<211> LENGTH: 324
<212> TYPE: DNA
<213> ORGANISM: Homo sapiens

<400> SEQUENCE: 426
gacatccaga tgacccagtc tccatcctcc ctgtctgcat ctgtaggaga ccgtgtcacc 60
atcacttgcc gggcaagtca ggatattgag gcggatttag agtggtacca gcagaaacca 120
gggaaagccc ctaagctcct gatctatcat tcttccgagt tgcaaagtgg ggtcccatca 180
cgtttcagtg gaagtggatc tgggacagat ttcactctca ccatcagcag tctgcaacct 240
gaagattttg ctacgtacta ctgtcaacag tatcatatgt cgcctgtgac gttcggccaa 300
gggaccaagg tggaaatcaa acgg 324

<210> SEQ ID NO 427
<211> LENGTH: 324
<212> TYPE: DNA

<213> ORGANISM: Homo sapiens

<400> SEQUENCE: 427
gacatccaga tgacccagtc tccatcctcc ctgtctgcat ctgtaggaga ccgtgtcacc 60
atcacttgcc gggcaagtca ggatattgat agtgatttag agtggtacca gcagaaacca 120
gggaaagccc ctatgctcct gatctattct tcgtccgatt tgcaaagtgg ggtcccatca 180
cgtttcagtg gcagtggatc tgggacagat ttcactctca ccatcagcag tctgcaacct 240
gaagattttg ctacgtacta ctgtcaacag tatcatagtc tgcctgttac gttcggccaa 300
gggaccaagg tggaaatcaa acgg 324

<210> SEQ ID NO 428
<211> LENGTH: 324
<212> TYPE: DNA
<213> ORGANISM: Homo sapiens

<400> SEQUENCE: 428
gacatccaga tgacccagtc tccatcctcc ctgtctgcat ctgtaggaga ccgtgtcacc 60
atcacttgcc gggcaagtca ggatatttcg gatgatttag agtggtacca gcagaaacca 120
gggaaagccc ctaagctcct gatctataat tcgtcctttt tgcaaagtgg ggtcccatca 180
cgtttcagtg gcagtggatc tggggcagat ttcactctca ccatcagcag tctgcaacct 240
gaagattttg ctacgtacta ctgtcaacag tatcatagtt tgcctgttac gttcggccaa 300
gggaccaagg tggaaatcaa acgg 324

<210> SEQ ID NO 429
<211> LENGTH: 324
<212> TYPE: DNA
<213> ORGANISM: Homo sapiens

<400> SEQUENCE: 429
gacatccaga tgacccagtc tccatcctcc ctgtctgcat ctgtaggaga ccgtgtcacc 60
atcacttgcc gggcaagtca ggatattgag ggtaatttag agtggtacca gcagaaacca 120
gggaaagccc ctaagctcct gatctatgat tcgtcccagt tgcaaagtgg ggtcccatca 180
cgtttcagtg gcagtgggtc tgggacagat ttcactctca ccatcagcag tctgcaacct 240
gaagattttg ctacgtacta ctgtcaacag tatcatcatc ttcctacgac gttcggccaa 300
gggaccaagg tggaaatcaa acgg 324

<210> SEQ ID NO 430
<211> LENGTH: 324
<212> TYPE: DNA
<213> ORGANISM: Homo sapiens

<400> SEQUENCE: 430
gacatccaga tgacccagtc tccatcctcc ctgtctgcat ctgtaggaga ccgtgtcacc 60
atcacttgcc gggcaagtca gagtattgat acggatttag agtggtatca gcagaaacca 120
gggaaagccc ctaagctcct gatctatgat gggtcctggt tgcaaagtgg ggtcccatca 180
cgtttcagtg gcagtggatc tgggacagat tttactctca ccatcagcag tctgcaacct 240
gaagattttg ctacgtacta ctgtcaacag tatcggtgga ttcctgttac gttcggccaa 300
gggaccaagg tggaaatcaa acgg 324

<210> SEQ ID NO 431
<211> LENGTH: 324
<212> TYPE: DNA

<213> ORGANISM: Homo sapiens

<400> SEQUENCE: 431
gacatccaga tgacccagtc tccatcctcc ctgtctgcat ctgtaggaga ccgtgtcacc 60
atcacttgcc gggcaagtca gagtattagt actgatttag agtggtacca gcagaaacta 120
gggaaagccc ctaagctcct gatctatgat gcttcccttt tgcaaagtgg ggtcccatca 180
cgtttcagtg gcagtggatc tgggacagat ttcactctca ccatcagcag tctgcaacct 240
gaagattttg ctacgtacta ctgtcaacag tattcgagtc tgcctgttac gttcggccaa 300
gggaccaagg tggaaatcaa acgg 324

<210> SEQ ID NO 432
<211> LENGTH: 324
<212> TYPE: DNA
<213> ORGANISM: Homo sapiens

<400> SEQUENCE: 432
gacatccaga tgacccagtc tccatcctcc ctgtctgcat ctgtaggaga ccgtgtcacc 60
atcacttgcc gggcaagtca gcctattacg acgtctttag agtggtacca gcagaaacca 120
gggaaagccc ctaagctcct gatctatgat gcgtccatgt tgcaaagtgg ggtcccatca 180
cgtttcagtg gcagtggatc tgggacagat ttcactctca ccatcagcag tctgcaacct 240
gaagattttg ctacgtacta ctgtcaacag tattgggtta cgcctgttac gttcggccaa 300
gggaccaagg tggaaatcaa acgg 324

<210> SEQ ID NO 433
<211> LENGTH: 324
<212> TYPE: DNA
<213> ORGANISM: Homo sapiens

<400> SEQUENCE: 433
gacatccaga tgacccagtc tccatcctcc ctgtctgcat ctgtaggaga ccgtgtcacc 60
atcacctgcc gggcaagtca gaatattcat acgaatttag agtggtatca gcagaaacca 120
gggaaagccc ctaagctcct gatctatgat ggttccatgt tgcaaagtgg ggtcccatca 180
cgtttcagtg gcagtggatc tgggacagat ttcactctca ccatcagcag tctgcaacct 240
gaagattttg ctacgtacta ctgtcaacag tattcggcta atcctgttac gttcggccaa 300
gggaccaagg tgggaatcaa acgg 324

<210> SEQ ID NO 434
<211> LENGTH: 324
<212> TYPE: DNA
<213> ORGANISM: Homo sapiens

<400> SEQUENCE: 434
gacatccaga tgacccagtc tccatcctcc ctgtctgcat ctgtaggaga ccgtgtcacc 60
atcacttgcc gggcaagtca gtggattcat acggatttag agtggtatca gcagaaacca 120
gggaaagccc ctaagctcct gatctatgat ggttccatgt tgcaaagtgg ggtcccatca 180
cgtttcagtg gcagtggatc tgggacagat ttcactctca ccatcagcag tctgcaacct 240
gaagattttg ctacgtacta ctgtcaacag tatagtgtgt cgcctgttac gttcggccaa 300
gggaccaagg tggaaatcaa acgg 324

<210> SEQ ID NO 435
<211> LENGTH: 324
<212> TYPE: DNA

<213> ORGANISM: Homo sapiens

<400> SEQUENCE: 435
gacatccaga tgacccagtc tccatcctcc ctgtctgcat ctgtaggaga ccgtgtcacc 60
atcacttgcc gggcaagtca gagtattgat aataatttag agtggtacca gcagaaacca 120
ggggaagccc ctaagctcct gatctatgat gggtcccttt tgcaaagtgg ggtcccatca 180
cgtttcagtg gcagtggatc tgggacagat ttcactctta ccatcagcag tctgcaacct 240
gaagattttg ctacgtacta ctgtcaacag tatcatcttc atcctgttac gttcggccaa 300
gggaccaagg tggaaatcaa acgg 324

<210> SEQ ID NO 436
<211> LENGTH: 324
<212> TYPE: DNA
<213> ORGANISM: Homo sapiens

<400> SEQUENCE: 436
gacatccaga tgacccagtc tccatcctcc ctgtctgcat ctgtaggaga ccgtgtcacc 60
atcacttgcc gggcaagtca ggatattgat acgaatttag agtggtatca gcagaaacca 120
ggggaagccc ctaagctcct gatctatgat cgttccacgt tgcaaagtgg ggtcccatca 180
cgtttcagtg gcagtggatc tgggacagat ttcactctca ccatcagcag tctgcaacct 240
gaagattttg ctacgtacta ctgtcaacag tatgattctt atcctgtgac gttcggccaa 300
gggaccaagg tggaaatcaa acgg 324

<210> SEQ ID NO 437
<211> LENGTH: 324
<212> TYPE: DNA
<213> ORGANISM: Homo sapiens

<400> SEQUENCE: 437
gacatccaga tgacccagtc tccatcctcc ctgtctgcat ctgtaggaga ccgtgtcacc 60
atcacttgcc gggcaagtca gtctattgag tctaatttag agtggtacca gcagaaacca 120
gggaaagccc ctaagctcct gatctataat gcgtccgagt tgcaaagtgg ggtcccatca 180
cgtttcagtg gcagtggatc tgggacagat ttcactctca ccatcagcag tctgcgacct 240
gaagattttg ctacgtacta ctgtcaacag tatgatcagt ggcctacgac gttcggccaa 300
gggaccaagg tggaaatcaa acgg 324

<210> SEQ ID NO 438
<211> LENGTH: 324
<212> TYPE: DNA
<213> ORGANISM: Homo sapiens

<400> SEQUENCE: 438
gacatccaga tgacccagtc tccatcctcc ctgtctgcat ctgtaggaga ccgtgtcact 60
atcacttgcc gggcaagtca ggctattggt aatactttac ggtggtacca gcagaaacca 120
gggaaagccc ctaagctcct gatctatctt agttccaggt tgcaaagtgg ggtcccatca 180
cgtttcagtg gcagtggatc tgggacagat tttactctca ccatcagcag tctgcaacct 240
gaagattttg ctacgtacta ctgtcaacag ctgaagaagc ctccttatac gttcggccaa 300
gggaccaagg tggaaatcaa acgg 324

<210> SEQ ID NO 439
<211> LENGTH: 324
<212> TYPE: DNA

<213> ORGANISM: Homo sapiens

<400> SEQUENCE: 439
gacatccaga tgacccagtc tccatcctcc ctgtctgcat ctgtaggaga ccgtgtcacc 60
atcacttgcc gggcaagtca gaagattaag aatcggttag cgtggtacca gcagaaacca 120
gggaaagccc ctaagctcct gatctatgag gtttcccatt tgcaaagtgg ggtcccatca 180
cgtttcagtg gcagtggatc tgggacagat ttcactctca ccatcggcag tctgcaacct 240
gaagattttg ctacgtacta ctgtcaacag aggaggcagt cgccttatac gttcggccaa 300
gggaccaagg tggaaatcaa acgg 324

<210> SEQ ID NO 440
<211> LENGTH: 324
<212> TYPE: DNA
<213> ORGANISM: Homo sapiens

<400> SEQUENCE: 440
gacatccaga tgacccagtc tccatcctcc ctgtctgcat ctgtaggaga ccgtgtcacc 60
atcacttgcc gggcaagtga ggatattggg gaggagttat tttggtatca gcagaaacca 120
gggaaagccc ctaagctcct gatctattcg gcgtccacgt tgcaaagtga ggtcccatca 180
cgtttcagtg gcagtggatc tgggacagat ttcactctca ccatcagcag tctgcaacat 240
gaagattttg ctacgtacta ctgtcaacag gtttatgagt ggccttatac gttcggccaa 300
gggaccaagg tggaaatcaa acgg 324

<210> SEQ ID NO 441
<211> LENGTH: 324
<212> TYPE: DNA
<213> ORGANISM: Homo sapiens

<400> SEQUENCE: 441
gacatccaga tgacccagtc tccatcctcc ctgtctgcat ctgtaggaga ccgtgtcacc 60
atcacttgcc gggcaagtca gcctatttct gggggtttaa ggtggtacca gcagaaacca 120
gggaaagccc ctaagctcct gatctattct acttccatgt tgcaaagtgg ggtcccatca 180
cgtttcagtg gcagtggatc tgggacagat ttcactctca ccatcagcag tctgcaacct 240
gaagattttg ctacgtacta ctgtcaacag ctttattctg ctccttatac gttcggccaa 300
gggaccaagg tggaaatcaa acgg 324

<210> SEQ ID NO 442
<211> LENGTH: 357
<212> TYPE: DNA
<213> ORGANISM: Homo sapiens

<400> SEQUENCE: 442
gaggtgcagc tgttggagtc tgggggaggc ttggtacagc ctggggggtc cctgcgtctc 60
tcctgtgcag cctccggatt cacctttgat gcgtatgaga tggggtgggt ccgccaggct 120
ccagggaagg gtctagagtg ggtctcaatt attgattggg atggtaattc tacatactac 180
gcagactccg tgaagggccg gttcaccatc tcccgcgaca attccaagaa cacgctgtat 240
ctgcaaatga acagcctgcg tgccgaggat accgcggtat attactgtgc gaaacctggg 300
gataatgttg gtatttttga ctactggggt cagggaaccc tggtcaccgt ctcgagc 357

<210> SEQ ID NO 443
<211> LENGTH: 366
<212> TYPE: DNA

<213> ORGANISM: Homo sapiens

<400> SEQUENCE: 443

```
gaggtgcagc tgttggagtc tgggggaggc ttggtacagc ctggggggtc cctgcgtctc    60
tcctgtgcag cctccggatt cacctttagt aattattata tggtgtgggt ccgccaggct   120
ccagggaagg gtctagagtg ggtctcagcg attgatgagt ggggttttgc gacatactac   180
gcagactccg tgaagggccg gttcaccatc tcccgcgaca attccaagaa cacgctgtat   240
ctgcaaatga acagcctgcg tgccgaggac accgcggtat attactgtgc gaaacattgg   300
gagtttacgt ctgatacgtc gcgttttgac tactggggtc agggaaccct ggtcaccgtc   360
tcgagc                                                              366
```

<210> SEQ ID NO 444
<211> LENGTH: 348
<212> TYPE: DNA
<213> ORGANISM: Homo sapiens

<400> SEQUENCE: 444

```
gaggtgcagc tgttggagtc tgggggaggc ttggtacagc ctggggggtc cctgcgtctc    60
tcctgtgcag cctccggatt cacctttgag gattttgata tggcttgggt ccgccaggct   120
ccagggaagg gtctagagtg ggtctcatct attaatgatc agggttctct gacatactac   180
gcagactccg tgaagggccg gttcaccatc tcccgcgaca attccaagaa cacgctgtat   240
ctgcaaatga acagcctgcg tgccgaggac accgcggtat attactgtgc gaaaccggat   300
cagttttttg actactgggg tcagggaacc ctggtcaccg tctcgagc                348
```

<210> SEQ ID NO 445
<211> LENGTH: 354
<212> TYPE: DNA
<213> ORGANISM: Homo sapiens

<400> SEQUENCE: 445

```
gaggtgcagc tgttggagtc tgggggaggc ttggtacagc ctggggggtc cctgcgtctc    60
tcctgtgcag cctccggatt cacctttagt gcttatgata tgatgtgggt ccgccaggct   120
ccagggaagg gtctagagtg ggtctcacgg attagtcctc agggtcagcg gacatactac   180
gcagactccg tgaagggccg gttcaccatc tcccgcgaca attccaagaa cacgctgtat   240
ctgcaaatga acagcctgcg tgccgaggac accgcggtat attactgtgc gaaaattcgt   300
gggcagtcgc ggattcctat gaggtttgac tactggggtc agggaaccct ggtc         354
```

<210> SEQ ID NO 446
<211> LENGTH: 348
<212> TYPE: DNA
<213> ORGANISM: Homo sapiens

<400> SEQUENCE: 446

```
gaggtgcagc tgttggagtc tgggggaggc ttggtacagc ctggggggtc cctgcgtctc    60
tcctgtgcag cctccggatt cacctttacg gattatgaga tggggtgggt ccgccaggct   120
ccagggaagg gtctagagtg ggtctcaacg attactagtt tgggtgagag tacatactac   180
gcagactccg tgaagggccg gttcaccatc tcccgcgaca attccaagaa cacgctgtat   240
ctgcaaatga acagcctgcg tgccgaggac accgcggtat attactgtgc gaaacctggt   300
cgtatttttg actactgggg tcagggaacc ctggtcaccg tctcgagc                348
```

<210> SEQ ID NO 447

<211> LENGTH: 369
<212> TYPE: DNA
<213> ORGANISM: Homo sapiens

<400> SEQUENCE: 447
gaggtgcagc tgttggagtc tgggggaggc ttggtacagc ctggggggtc cctgcgtctc 60
tcctgtgcag cctccggatt cacctttgct ttttatccta tgatgtgggt ccgccaggct 120
ccagggaagg gtctagagtg ggtctcatgg attgatgcta cgggtacgag gacatactac 180
gcagactccg tgaagggccg gttcaccatc tcccgcgaca attccaagaa cacgctgtat 240
ctgcaaatga acagcctgcg tgccgaggac accgcggtat attactgtgc ggaaggtaat 300
tatgggagtt cgtatactat gggggttttt gactactggg gtcagggaac cctggtcacc 360
gtctcgagc 369

<210> SEQ ID NO 448
<211> LENGTH: 366
<212> TYPE: DNA
<213> ORGANISM: Homo sapiens

<400> SEQUENCE: 448
gaggtgcagc tgttggagtc tgggggaggc ttggtacagc ctggggggtc cctgcgtctc 60
tcctgtgcag cctccggatt cacctttgat gagtatccga tgtattgggt ccgccaggct 120
ccagggaagg gtctagagtg ggtctcatcg attggtcctt ctggtccgaa tacatactac 180
gcagactccg tgaagggccg gttcaccatc tcccgcgaca attccaagaa cacgctgtat 240
ctgcaaatga acagcctgcg tgccgaggac accgcggtat attactgtgc gaaatctccg 300
tattttgatg ttattcctag ttattttgac tactggggtc agggaaccct ggtcaccgtc 360
tcgagc 366

<210> SEQ ID NO 449
<211> LENGTH: 357
<212> TYPE: DNA
<213> ORGANISM: Homo sapiens

<400> SEQUENCE: 449
gaggtgcagc tgttggagtc tgggggaggc ttggtacagc ctggggggtc cctgcgtctc 60
tcctgtgcag cctccggatt cacctttgcg gattacggta tgggttgggt ccgccaggct 120
ccagggaagg gtctagagtg ggtctcatct attcagtcgt cgggtttgcg gacatactac 180
gcagactccg tgaagggccg gttcaccatc tcccgcgaca attccaagaa cacgctgtat 240
ctgcaaatga acagcctgcg tgccgaggat accgcggtat attactgtgc gaaacgggct 300
aattctcgta ggggttttga ctactggggt cagggaaccc tggtcaccgt ctcgagc 357

<210> SEQ ID NO 450
<211> LENGTH: 348
<212> TYPE: DNA
<213> ORGANISM: Homo sapiens

<400> SEQUENCE: 450
gaggtgcagc tgttggagtc tgggggaggc ttggtacagc ctggggggtc cctgcgtctc 60
tcctgtgcag cctccggatt caccttttct gattatgaga tgatgtgggt ccgccaggct 120
ccagggaagg gtctagagtg ggtctcatct attactagtc atggtgggtc tacatactac 180
gcagactccg tgaagggccg gttcaccatc tcccgcgaca attccaagaa cacgctgtat 240
ctgcaaatga acagcctgcg tgccgaggat accgcggtat attactgtgc gaaacctgat 300
aaggattttg actactgggg tcagggaacc ctggtcaccg tctcgagc 348

<210> SEQ ID NO 451
<211> LENGTH: 366
<212> TYPE: DNA
<213> ORGANISM: Homo sapiens

<400> SEQUENCE: 451
gaggtgcagc tgttggagtc tgggggaggc ttggtacagc ctggggggtc cctgcgtctc 60
tcctgtgcag cctccggatt cacctttgcg cattatccga tgtcgtgggt ccgccaggct 120
ccagggaagg gtctagagtg ggtctcatcg attggtaggc tgggtaatcg tacatactac 180
gcagactccg tgaagggccg gttcaccatc tcccgcgaca attccaagaa cacgctgtat 240
ctgcaaatga acagcctgcg tgccgaggac accgcggtat attactgtgc gaaacgtgct 300
acgcctgtgc cgattaaggg tttgtttgac tactggggtc agggaaccct ggtcaccgtc 360
tcgagc 366

<210> SEQ ID NO 452
<211> LENGTH: 348
<212> TYPE: DNA
<213> ORGANISM: Homo sapiens

<400> SEQUENCE: 452
gaggtgcagc tgttggagtc tgggggaggc ttggtacagc ctggggggtc cctgcgtctc 60
tcctgtgcag cctccggact cacctttggg aggtatgaga tggcgtgggt ccgccaggct 120
ccagggaagg gtctagagtg ggtctcaagt attgattcgg atggttgggt gacatactac 180
gcagactccg tgaagggccg gttcaccatc tcccgcgaca attccaagaa cacgctgtat 240
ctgcaaatga acagcctgcg tgccgaggac accgcggtat attactgtgc gcaaccggat 300
tcgttgtttg actactgggg tcagggaacc ctggtcaccg tctcgagc 348

<210> SEQ ID NO 453
<211> LENGTH: 351
<212> TYPE: DNA
<213> ORGANISM: Homo sapiens

<400> SEQUENCE: 453
gaggtgcagc tgttggagtc tgggggaggc ttggtacagc ctggggggtc cctgcgtctc 60
tcctgtgcag cctccggatt caccttttct agttattcta tggtgtgggt ccgccaggct 120
ccagggaagg gtctagagtg ggtctcaggt attaatcggg gtggtactcg tacatactac 180
gcagactccg tgaagggccg gttcaccatc tcccgcgaca attccaagaa cacgctgtat 240
ctgcaaatga acagcctgcg tgccgaggac accgcggtat attactgtgc gaaaggttgg 300
aggagggggt ttgactactg gggtcaggga accctggtca ccgtctcgag c 351

<210> SEQ ID NO 454
<211> LENGTH: 351
<212> TYPE: DNA
<213> ORGANISM: Homo sapiens

<400> SEQUENCE: 454
gaggtgcagc tgttggagtc tgggggaggc ttggtacagc ctggggggtc cctgcgtctc 60
tcctgtgcag cctccggatt cacctttacg cgttatagga tgtcttgggt ccgccaggct 120
ccagggaagg gtctggagtg ggtctcaggg atttcgaggg atggttatcg gacatactac 180
gcagactccg tgaagggccg gttcaccatc tcccgcgaca attccaagaa cacgctgtat 240
ctgcaaatga acagcctgcg tgccgaggac accgcggtat attactgtgc gaaaggtatg 300
actgcgtcgt ttgactactg ggtcagggga accctggtca ccgtctcgag c 351

<210> SEQ ID NO 455
<211> LENGTH: 354
<212> TYPE: DNA
<213> ORGANISM: Homo sapiens

<400> SEQUENCE: 455
gaggtgcagc tgttggagtc tgggggaggc ttggtacagc ctggggggtc cctgcgtctc 60
tcctgtgcag cctccggatt cacctttcag atgtatccga tggggtgggt ccgccaggct 120
ccagggaagg gtctagagtg ggtctcaatg attgagccgg ctggtgatct tacatactac 180
gcagactccg tgaagggccg gttcaccatc tcccgcgaca attccaagaa cacgctgtat 240
ctgcaaatga acagcctgcg tgccgaggac accgcggtat attactgtgc gaaatatcag 300
gagcagcctt ggtttgacta ctggggtcag ggaaccctgg tcaccgtctc gagc 354

<210> SEQ ID NO 456
<211> LENGTH: 348
<212> TYPE: DNA
<213> ORGANISM: Homo sapiens

<400> SEQUENCE: 456
gaggtgcagc tgttggagtc tgggggaggc ttggtacagc ctggggggtc cctgcgtctc 60
tcctgtgcag cctccggatt cacctttagt atgtatgata tgcattgggt ccgccaggct 120
ccagggaagg gtctagagtg ggtctcaacg attttgtctg atggtacgga tacatactac 180
gcagactccg tgaagggccg gttcaccatc tcccgcgaca attccaagaa cacgctgtat 240
ctgcaaatga acagcctgcg tgccgaggac accgcggtat attactgtgc gaaatatggg 300
gctatgtttg actactgggg tcagggaacc ctggtcaccg tctcgagc 348

<210> SEQ ID NO 457
<211> LENGTH: 354
<212> TYPE: DNA
<213> ORGANISM: Homo sapiens

<400> SEQUENCE: 457
gaggtgcagc tgttggagtc tgggggaggc ttggtacagc ctggggggtc cctgcgtctc 60
tcctgtgcag cctccggatt cacctttaag ttgtatccga tgacgtgggt ccgccaggct 120
ccagggaagg gtctagagtg ggtctcatct attgatgcgg ggggtcatga gacatactac 180
gcagactccg tgaagggccg gttcaccatc tcccgcgaca attccaagaa cacgctgtat 240
ctgcaaatga acagcctgcg tgccgaggat accgcggtat attactgtgc gaaagattgg 300
tgggattatc tgtttgacta ctggggtcag ggaaccctgg tcaccgtctc gagc 354

<210> SEQ ID NO 458
<211> LENGTH: 351
<212> TYPE: DNA
<213> ORGANISM: Homo sapiens

<400> SEQUENCE: 458
gaggtgcagc tgttggagtc tgggggaggc ttggtacagc ctggggggtc cctgcgtctc 60
tcctgtgcag cctccggatt caccttttcg cggtatccga tgagttgggt ccgccaggct 120
ccagggaagg gtctagagtg ggtctcatct attaatcgtt cgggtatgcg gacatactac 180
gcagactccg tgaagggccg gttcaccatc tcccgcgaca attccaagaa cacgctgtat 240
ctgcaaatga acagcctgcg tgccgaggac accgcggtat attactgtgc ggaagggcat 300
caggcgccgt ttgactactg ggtcagggga accctggtca ccgtctcgag c 351

<210> SEQ ID NO 459
<211> LENGTH: 369
<212> TYPE: DNA
<213> ORGANISM: Homo sapiens

<400> SEQUENCE: 459
gaggtgcagc tgttggagtc tgggggaggc ttggtacagc ctggggggtc cctgcgtctc 60
tcctgtgcag cctccggatt cacctttacg ggtatgcta tgtcttgggt ccgccaggct 120
ccagggaagg gtctagagtg ggtctcaact attaatgcga atggtattcg gacatactac 180
gccgactccg tgaagggccg gttcaccatc tcccgcgaca attccaagaa cacgctgtat 240
ctgcaaatga acggcctgcg tgccgaggac accgcggtat attactgtgc gaaagggggg 300
gtttggaggt gggggactgg gcataagttt gactactggg gtcagggaac cctggtcacc 360
gtctcgagc 369

<210> SEQ ID NO 460
<211> LENGTH: 354
<212> TYPE: DNA
<213> ORGANISM: Homo sapiens

<400> SEQUENCE: 460
gaggtgcagc tgttggagtc tgggggaggc ttggtacagc ctggggggtc cctgcgtctc 60
tcctgtgcag cctccggatt cacctttaag cagtatgata tgcggtgggt ccgccaggct 120
ccagggaagg gtctagagtg ggtctcaacg atttcgcaga atggtactaa gacatactac 180
gcagactccg tgaagggccg gttcaccatc tcccgcgaca attccaagaa cacgctgtat 240
ctgcaaatga acagcctgcg tgccgaggac accgcggtat attactgtgc gaaatcgagg 300
actggtaggt attttgacta ctggggtcag ggaaccctgg tcaccgtctc gagc 354

<210> SEQ ID NO 461
<211> LENGTH: 369
<212> TYPE: DNA
<213> ORGANISM: Homo sapiens

<400> SEQUENCE: 461
gaggtgcagc tgttggagtc tgggggaggc ttggtacagc ctggggggtc cctgcgtctc 60
tcctgtgcag cctccggatt cacctttggg acttatgata tggggtgggt ccgccaggct 120
ccagggaagg gtctagagtg ggtctcaagg attaattggc agggtgatcg tacatactac 180
gcagactccg tgaagggccg gttcaccatc tcccgcgaca attccaagaa cacgctgtat 240
ctgcaaatga acagcctgcg tgccgaggac accgcggtat attactgtgc gaaagcgggg 300
tttggtcatt atgttgatgg tcttgggttt gactactggg gtcagggaac cctggtcacc 360
gtctcgagc 369

<210> SEQ ID NO 462
<211> LENGTH: 348
<212> TYPE: DNA
<213> ORGANISM: Homo sapiens

<400> SEQUENCE: 462
gaggtgcagc tgttggagtc tgggggaggc ttggtacagc ctggggggtc cctgcgtctc 60
tcctgtgcag cctccggatt cacctttagt gggtatgaga tggcgtgggt ccgccaggct 120

```
ccagggaagg gtctagagtg ggtctcatct attactgata tgggtgattc tacatactac    180

gcagactccg tgaagggccg gttcaccatc tcccgcgaca attccaagaa cacgctgtat    240

ctgcaaatga acagcctgcg tgccgaggac accgcggtat attactgtgc gaaacctggg    300

actgcgtttg actactgggg tccgggaacc ctggtcaccg tctcgagc                 348


<210> SEQ ID NO 463
<211> LENGTH: 351
<212> TYPE: DNA
<213> ORGANISM: Homo sapiens

<400> SEQUENCE: 463

gaggtgcagc tgttggagtc tgggggaggc ttggtacagc ctgggggtc cctgcgtctc      60

tcctgtgcag cctccggatt cacctttgcg aagtataaga tgtggtgggt ccgccaggct    120

ccagggaagg gtctagagtg ggtctcaagt attactccga agggtcattc tacatactac    180

gcagactccg tgaagggccg gttcaccatc tcccgcgaca attccaagaa cacgctgtat    240

ctgcaaatga acagcctgcg tgccgaggat accgcggtat attactgtgc gaaaaggccg    300

atgactccgt ttgactactg gggtcaggga accctggtca ccgtctcgag c             351


<210> SEQ ID NO 464
<211> LENGTH: 366
<212> TYPE: DNA
<213> ORGANISM: Homo sapiens

<400> SEQUENCE: 464

gaggtgcagc tgttggagtc tgggggaggc ttggtacagc ctgggggtc cctgcgtctc      60

tcctgtgcag cctccggatt cacctttgag cggtataata tgtcttgggt ccgccaggct    120

ccagggaagg gtctagagtg ggtctcatct attcggccgc ggggtgggaa gacatactac    180

gcagactccg tgaagggccg gttcaccatc tcccgcgaca attccaagaa cacgctgtat    240

ctgcaaatga acagcctgcg tgccgaggac accgcggtat attactgtgc gaaatggcgg    300

cgggaggggt atactggttc taagtttgac tactggggtc agggaaccct ggtcaccgtc    360

tcgagc                                                               366


<210> SEQ ID NO 465
<211> LENGTH: 354
<212> TYPE: DNA
<213> ORGANISM: Homo sapiens

<400> SEQUENCE: 465

gaggtgcagc tgttggagtc tgggggaggc ttggtacagc ctgggggtc cctgcgtctc      60

tcctgtgcag cctccggatt cacctttgag aggtatggta tgacttgggt ccgccaggct    120

ccagggaagg gtctggagtg ggtctcaagt atttggccga ggggtcagaa gacatactac    180

gcagactccg tgaagggccg gttcaccatc tcccgcgaca attccaagaa cacgctgtat    240

ctgcaaatga acagcctgcg tgccgaggac accgcggtat attactgtgc gaaagggaat    300

agtcggtatg tttttgacta ctggggtcag ggaaccctgg tcaccgtctc gagc          354


<210> SEQ ID NO 466
<211> LENGTH: 360
<212> TYPE: DNA
<213> ORGANISM: Homo sapiens

<400> SEQUENCE: 466

gaggtgcagc tgttggagtc tgggggaggc ttggtacagc ctgggggtc cctgcgtctc      60
```

tcctgtgcag cctccggatt cacctttact aattatagta tgggttgggt ccgccaggct 120
ccagggaagg gtctagagtg ggtctcaact attcgtccta atggtactaa gacatactac 180
gcagactccg tgaagggccg gttcaccatc tcccgcgaca attccaagaa cacgctgtat 240
ctgcaaatga acagcctgcg tgccgaggat accgcggtat attactgtgc gaaacggtcg 300
tctgcgcatc ttcagaggtt tgactactgg ggtcagggaa ccctggtcac cgtctcgagc 360

<210> SEQ ID NO 467
<211> LENGTH: 357
<212> TYPE: DNA
<213> ORGANISM: Homo sapiens

<400> SEQUENCE: 467
gaggtgcagc tgttggagtc tgggggaggc ttggtacagc ctggggggtc cctgcgtctc 60
tcctgtgcag cctccggatt cacctttggt aattattcga tgggttgggt ccgccaggct 120
ccagggaagg gtctagagtg ggtctcatcg attggtcgtc atggtgggcg tacatactac 180
gcagactccg tgaagggccg gttcaccatc tcccgcgaca attccaagaa cacgctgtat 240
ctgcaaatga acagcctgcg tgccgaggac accgcggtat attactgtgc gaaaaagggg 300
agtacttatc ctaggtttga ctactggggt cagggaaccc tggtcaccgt ctcgagc 357

<210> SEQ ID NO 468
<211> LENGTH: 354
<212> TYPE: DNA
<213> ORGANISM: Homo sapiens

<400> SEQUENCE: 468
gaggtgcagc tgttggagtc tgggggaggc ttggtacagc ctggggggtc cctgcgtctc 60
tcctgtacag cctccggatt caccttttcg cattatgaga tggggtgggt ccgccaggct 120
ccagggaagg gtctagagtg ggtctcaagt attgagcctt ttggtggtgg gacatactac 180
gcagactccg tgaagggccg gttcaccatc tcccgcgaca attccaagaa cacgctgtat 240
ctgcaaatga acagcctgcg tgccgaggat accgcggtat attactgtgc gaaagtgtat 300
cctcagggtt cttttgacta ctggggtcag ggaaccctgg tcaccgtctc gagc 354

<210> SEQ ID NO 469
<211> LENGTH: 372
<212> TYPE: DNA
<213> ORGANISM: Homo sapiens

<400> SEQUENCE: 469
gaggtgcagc tgttggagtc tgggggaggc ttggtacagc ctggggggtc cctgcgtctc 60
tcctgtgcag cctccggatt cacctttagt aattatacta tggggtgggt ccgtcaggct 120
ccagggaagg gtctagagtg ggtctcatct attcggcctg atggtaagat tacatactac 180
gcagactccg tgaagggccg gttcaccatc tcccgcgaca attccaagaa cacgctgtat 240
ctgcaaatga acagcctgcg tgccgaggac accgcggtat attactgtgc ggaagtttat 300
tcttcgtgtg cgatgtgtac tccgcttttg tttgactact ggggtcaggg aaccctggtc 360
accgtctcga gc 372

<210> SEQ ID NO 470
<211> LENGTH: 369
<212> TYPE: DNA

<213> ORGANISM: Homo sapiens

<400> SEQUENCE: 470
gaggtgcagc tgttggagtc tgggggggc ttggtacagc ctgggggtc cctgcgtctc 60 tcctgtgcag cctccggatt cacctttaag cggtattcga tggcgtgggt ccgccaggct 120
ccagggaagg gtctagagtg ggtctcagat attgggccga ggggtttttc gacatactac 180
gcagactccg tgaagggccg gttcaccatc tcccgcgaca attccaagaa cacgctgtat 240
ctgcaaatga acagcctgcg tgccgaggac accgcggtat attactgtgc gaaagtgggt 300
cgtggtcagc gtgatactag tcagccgttt gactactggg gtcagggaac cctggtcacc 360
gtctcgagc 369

<210> SEQ ID NO 471
<211> LENGTH: 348
<212> TYPE: DNA
<213> ORGANISM: Homo sapiens

<400> SEQUENCE: 471
gaggtgcagc tgttggagtc tggggggaggc ttggtacagc ctgggggtc cctgcgtctc 60 tcctgtgcag cctccggatt cacctttgct tcttatcaga tggcttgggt ccgccaggct 120
ccagggaagg gtctagagtg ggtctcaggg attacttcgg gtggtcttag tacgtactac 180
gcagactccg tgaagggccg gttcaccatc tcccgcgaca attccaagaa cacgctgtat 240
ctgcaaatga acagcctgcg tgccgaggac accgcggtat attactgtgc gaaaccgggg 300
aggggttttg actactgggg tcagggaacc ctggtcaccg tctcgagc 348

<210> SEQ ID NO 472
<211> LENGTH: 348
<212> TYPE: DNA
<213> ORGANISM: Homo sapiens

<400> SEQUENCE: 472
gaggtgcagc tgttggagtc tggggggaggc ttggtacagc ctggtgggtc cctgcgtctc 60
tcctgtgcag cctccggatt cacctttgct tcttatgaga tgacttgggt ccgccaggct 120
ccagggaagg gtctagagtg ggtctcaggg atttcttctg atggtctgtc tacatactac 180
gcagactccg tgaagggccg gttcaccatc tcccgcgaca attccaagaa cacgctgtat 240
ctgcaaatga acagcctgcg tgccgaggac accgcggtat attactgtgc gaaaccgggg 300
gtgttgtttg actactgggg tcagggaacc ctggtcaccg tctcgagc 348

<210> SEQ ID NO 473
<211> LENGTH: 351
<212> TYPE: DNA
<213> ORGANISM: Homo sapiens

<400> SEQUENCE: 473
gaggtgcagc tgttggagtc tggggggaggc ttggtacagc ctgggggtc cctgcgtctc 60 tcctgtgcag cctctggatt cacctttgat aagtatttga tgtcgtgggt ccgccaggct 120
ccagggaagg gtctggagtg ggtctcaggt attgagcctc tgggtgatgt tacatactac 180
gcagactccg tgaagggccg gttcaccatc tcccgcgaca attccaagaa cacgctgtat 240
ctgcaaatga acagcctgcg tgccgaggac accgcggtat attactgtgc gaaagaggct 300
tcgggggatt ttgactactg ggtcaggga accctggtca ccgtctcgag c 351

<210> SEQ ID NO 474
<211> LENGTH: 348
<212> TYPE: DNA
<213> ORGANISM: Homo sapiens

<400> SEQUENCE: 474
gaggtgcagc tgttggagtc tgggggaggc ttggtacagc ctggggggtc cctgcgtctc 60
tcctgtgcag cctccgggtt cacctttact gagtatgaga tgtcttgggt ccgccaggct 120
ccagggaagg gtctagagtg ggtctcaagt attgataatg tgggtagtag tacatactac 180
gcagactccg tgaagggccg gttcaccatc tcccgcgaca attccaagaa cacgctgtat 240
ctgcaaatga acagcctgcg tgccgaggat accgcggtat attactgtgc gaaacctggg 300 aagcttttg actactgggg tcagggaacc ctggtcaccg tctcgagc 348

<210> SEQ ID NO 475
<211> LENGTH: 354
<212> TYPE: DNA
<213> ORGANISM: Homo sapiens

<400> SEQUENCE: 475
gaggtgcagc tgttggagtc tgggggaggc ttggtacagc ctggggggtc cctgcgtctc 60
tcctgtgcag cctccggatt cacctttgct gattatgaga tgtggtgggt ccgccaggct 120
ccagggaagg gtctagagtg ggtctcagcg atttctaggc agggttttgc tacatactac 180
gcagactccg tgaaaggccg gttcaccatc tcccgcgaca attccaagaa cacgctgtat 240
ctgcaaatga acagcctgcg tgccgaggac accgcggtat attactgtgc gaaagatctg 300
gagcgggatg attttgacta ctggggtcag ggaaccctgg tcaccgtctc gagc 354

<210> SEQ ID NO 476
<211> LENGTH: 288
<212> TYPE: DNA
<213> ORGANISM: Homo sapiens

<400> SEQUENCE: 476
ctccacgtcg acaacctcag accccctccg aaccatgtcg gaccccccag ggacgcagag 60
aggacacgtc ggaggcctaa gtggaaatcg tcgatacggt actcgaccca ggcggtccga 120
ggtcccttcc cagatctcac ccagagtcga taatcaccat caccaccatc gtgtatgatg 180
cgtctgaggc acttcccggc caagtggtag agggcactgt taaggttctt gtgcgacata 240
gacgtttact tgtcggacgc acggctcctg tggcgccata taatgaca 288

<210> SEQ ID NO 477
<211> LENGTH: 324
<212> TYPE: DNA
<213> ORGANISM: Homo sapiens

<400> SEQUENCE: 477
ctgtaggtct actgggtcag aggtaggagg gacagacgta gacatcctct ggcacagtgg 60
tagtgaacgg cccgttcagt ctcgtaatcg tcgataaatt taaccatggt cgtctttggt 120
ccctttcggg gattcgagga ctagatacga cgtaggtcaa acgtttcacc ccagggtagt 180
gcaaagtcac cgtcacctag accctgtcta aagtgagagt ggtagtcgtc agacgttgga 240
cttctaaaac gatgcatgat gacagttgtc tcaatgtcat ggggattatg caagccggtt 300
ccctggttcc acctttagtt tgcc 324

METHODS OF ANTAGONIZING THE BINDING OF CD40 TO CD40L WITH CD40L-SPECIFIC MONOVALENT POLYPEPTIDES IN AUTOIMMUNE INDIVIDUALS

The present application is §371 application of PCT/GB2005/003562 filed 16 Sep. 2005 which claims the benefit of U.S. Provisional Application 60/610,819, filed 17 Sep. 2004 and is a continuation in part of U.S. application Ser. No. 11/102,512, filed 8 Apr. 2005, now U.S. Pat. No. 7,563,443, the entire disclosure of each being incorporated by reference herein.

BACKGROUND OF THE INVENTION

CD40 is a 50 kD cell surface glycoprotein molecule expressed on the surface of mature and immature B cells, macrophages, follicular dendritic cells, thymic epithelium, normal basal epithelium, and some tumor-derived cell lines. The CD40 molecule is a member of the TNF receptor family, and has important signaling functions leading to a variety of downstream effects in various cell types. Early studies showed that cross-linking of CD40 on the B cell surface with an antibody resulted in B cell proliferation and activation. Antibody cross linking of CD40 in the presence of IL-4 induces proliferation and class switching in vitro, B cell aggregation via LFA-1 (Gordon et al., 1988, J. Immunol. 140: 1425), and serine/threonine and tyrosine phosphorylation of a number of intracellular substrates (Gordon et al., 1988, supra; Uckun et al., 1991, J. Biol. Chem. 266:17478). Anti-CD40 monoclonal antibodies also prime B cells to proliferate in response to agents such as PMA (Gordon et al., 1987, Eur. J. Immunol. 17: 1535) and anti-CD20 antibody (Clark & Ledbetter, 1986, Proc. Natl. Acad. Sci. U.S.A. 83: 4494).

The receptor homology of CD40 and the antibody cross-linking studies showing a central role for CD40 in B cell activation prompted the search for a natural ligand. A mutant of the Jurkat T cell line was found to constitutively activate human B cells to secrete immunoglobulin (Yellin et al., 1991, J. Immunol. 147: 3389-3395). A monoclonal antibody, termed 5c8, was raised which specifically reacted with the mutant line, but not with the parental Jurkat cell line. The 5c8 antibody immunoprecipitated a 30 kD (more accurately, 29.3 kD, 261 amino acids) cell surface polypeptide and was found to specifically inhibit the B cell helper function of the mutant cell line. (Lederman et al., 1992, J. Exp. Med., 175: 1091-1101; Lederman et al., 1992, J. Immunol. 149: 3817-3826; Lederman et al., 1993, Curr. Opin. Immunol. 5: 439-444). The 30 kD polypeptide ligand of the 5c8 antibody was termed T-BAM, for T-B-cell Activating Molecule. A second line of studies used molecular cloning techniques to identify polypeptides that specifically bind the CD40 molecule. cDNA clones for a specific ligand of CD40 were identified in a CD40 binding assay and alternately termed CD40 Ligand (CD40L), gp39, CD154, or TRAP (Graf et al., 1992, Eur. J. Immunol. 22: 3191-3194; Armitage et al., 1992, Nature 357: 80-82; and Aruffo et al., 1993, Cell 72: 291-300). Subsequently, the CD40L clone was found to have the same structure as T-BAM (Covey et al., 1994, Mol. Immunol. 31: 471-484). Human CD40L protein shows 82.8% and 77.4% identity at the nucleic acid and amino acid levels, respectively, to a similar protein isolated from murine EL4 thymoma cells. Both of these proteins are ligands for CD40 cell surface antigen expressed on resting B cells. CD40L has also been described as IMD3, a protein involved in hyper-IgM immunodeficiency syndrome.

The human gene encoding CD40L maps to chromosome Xq26.3-q27. The gene contains five exons. Deletions, point mutations and frameshift mutations clustering within a limited region of the CD40L extracellular domain have been found to be the basis of a rare X-linked immunodeficiency syndrome (Hyper-IgM immunodeficiency syndrome, HIGM1) characterized by recurrent bacterial infections, very low or absent IgG, IgA and IgE, and normal to increased IgM and IgD serum levels. Causally-related mutations have been found to consist of clustered deletions arising by splice-donor mutations with exon skipping, splice-acceptor mutations with utilization of a cryptic splice site, and deletion/insertion events with the creation of a new splice site.

CD40L is expressed on activated, but not resting CD4+ T cells, and was found to play a particularly important role in the humoral immune response, being linked to B cell proliferation, antibody and cytokine production, and cell viability. In vivo, deletion or mutation of CD40L leads to severe immunodeficiency, both in mice and in humans, characterized by hypogammaglobulinemia and T cell deficits in cell-mediated immunity (Chess, C., 2001, in Therapeutic Immunology, $2^{nd}$ edition, Austen, K. F., Burakoff, S., Rosen, F. and Strom, T., eds., Blackwell Sciences, pp. 441-456). Human CD4+ T cells infected by HIV1, which causes severe dysfunction of cellular immunity, but paradoxically results in intense polyclonal activation of B cells, do not express CD40L. Gene and cell surface expression of the CD40L by activated T cells has been shown to be depressed in a subgroup of patients with common variable immunodeficiency (CVI). Thus, inefficient signaling via CD40 may be responsible, at least in part, for the failure of B cell differentiation in these patients.

The functional consequences of CD40L binding to CD40 include, for example, a) rescuing B cells from apoptosis induced by Fas or cross-linking of IgM, b) induction of the co-stimulator molecules CD80 (B7-1) and CD86 (B7-2) which interact with CD28 and CD152 (CTLA-4) on the surface of activated T cells; c) increased expression of other cell surface activation molecules including CD23, CD54, CD95 and lymphotoxin-a; and d) inducing immunoglobulin class switching (see Chess, supra, and references 25, 44, and 47-60 cited therein). CD40L binding to CD40 also augments the antigen-presenting functions of dendritic cells, inducing maintenance of high levels of MHC class II antigens and upregulation of accessory molecules including CD58 (LFA-3). CD40L induces cytokine production and tumoricidal activity in peripheral blood monocytes. CD40L also co-stimulates the proliferation of activated T cells, and the co-stimulation is accompanied by the production of IFN-γ, TNF-α and IL2. The expression of CD40L on murine T-helper cells and CD4+ T cells is inhibited by IFN-γ, and is inhibited on T-helper-type 2 cells by TGF-β.

CD40L upregulates the expression of CD54 by cultured Hodgkin and Reed-Sternberg cells. The increased CD54 surface expression is accompanied by increased shedding of surface-bound CD54.

CD40L has also been suggested to be important in the induction of tolerance—CD80 and CD86, which are upregulated by CD40L, interact with CD28 to provide essential co-stimulation of T cells, in concert with T cell receptor activation, that results in full activation of T cells. In the absence of CD80 and CD86-triggered activation of CD28, anergy or tolerance occurs as a consequence of antigen triggering (Linsley & Ledbetter, 1993, Ann. Rev. Immunol. 11: 191-212; Jenkins et al., 1993, Curr Opin. Immunol. 5: 361-367; and Boussiotis et al., 1996, Immunol. Rev. 153: 5-26).

The CD40L/CD40 pathway has been implicated in the in vivo priming of CD8+ cytotoxic T lymphocytes (CTSs) by CD4+ T cells. As noted, CD40L expressed on the surface of activated CD4+ T cells interacts with CD40 expressed on dendritic cells, inducing the dendritic cells to express more MHC, and signaling through CD40 can replace the requirement for CD4+ T-helper cells in priming CD8+ CTL responses. Blockade of CD40L inhibits CTL priming, emphasizing the vital role of CD40L/CD40 interactions in CTL priming by helper T cells (Ridge et al., 1998, Nature 393: 474-478; Schoenberger et al., 1998, Nature 393: 480-483; Bennett et al., 1998, Nature 393: 478-480).

CD40L can also mediate functional interactions of CD4+ T cells with other cells that express CD40, such as fibroblasts, synovial cells and endothelial cells (Yellin et al., 1995, J. Leuko. Biol. 58: 209-216; Yellin et al., 1995, J. Exp. Med. 182: 1857-1864). CD40L induces the expression of CD54 (ICAM-1) and CD106 (VCAM-1) by fibroblasts, as well as increasing fibroblast IL-6, collagenase and collagen production and inducing fibroblast proliferation. Thus, CD40L/CD40 interactions may be involved in the induction of fibrosis associated with autoimmunity and immune responses.

CD40L interaction with CD40 induces endothelial cells to express CD62E (E-selectin), ICAM-1 and VCAM-1. The upregulation of these adhesion molecules may be involved in the binding of inflammatory cells to vascular endothelium and the subsequent migration of the inflammatory cells to sites of inflammation. CD40L blockade retards the migration of leukocytes through endothelial cell barriers. In animal models of autoimmunity, antibodies to CD40L interfere with the accumulation of inflammatory cells at the site of inflammation.

CD40/CD40L interactions have been implicated in diseases having an immune or autoimmune connection. Animal models of immune-related disease in which the CD40L/CD40 pathway has been demonstrated to play a role in the pathology include, for example, murine models of systemic lupus erythematosis (Lupus or SLE; see, e.g., Kalled et al., 1998, J. Immunol. 160: 2158-2165), arthritis (collagen-induced arthritis, see, e.g., Durie et al., 1993, Science 261: 1328-1330), multiple sclerosis (experimental autoimmune encephalomyelitis, EAE; see, e.g., Howard et al., 1999, J. Clin. Invest. 103: 281-290), autoimmune thyroiditis (experimental autoimmune thyroiditis, EAT; see, e.g., Caryanniotis et al., 1997, Immunology 90: 421-426), colitis (hapten-induced colitis; see, e.g., Stuber et al., 1996, J. Exp. Med. 183: 693-698), atherosclerosis and coronary artery disease (see, e.g., Mach et al., 1998, Nature 394: 200-203), and allograft rejection (see, e.g., Parker et al., 1995, Proc. Natl. Acad. Sci. U.S.A. 92: 9560-9564; Kirk et al., 1997, Proc. Natl. Acad. Sci. U.S.A. 94: 8789-8794; Larsen et al., 1996, Nature 381: 434-438 and Blazar et al., 1997, J. Immunol. 158: 29-39).

CD40L antibody trials for treatment of human immune-related diseases include studies in patients with Lupus (see, e.g., Huang et al., 2002, Arthritis Rheum. 46: 1554-1562). A phase I trial demonstrated that anti-CD40L humanized monoclonal antibody (IDEC-131) is safe and well tolerated by patients with Lupus (Davis et al., 2001, J. Rheumatol. 28: 95-101). A phase II study with the IDEC-131 antibody showed improvement in clinical symptoms, but efficacy of the drug over placebo controls was not demonstrated (Kalunian et al., 2002, Arthritis Rheum. 46: 3251-3258). In a phase II study with BG9588 anti-CD40L antibody, clinical efficacy was demonstrated, but the study was terminated due to the occurrence of thromboembolic events (Boumpas et al., 2003, Arthritis Rheum. 48: 719-727).

U.S. Pat. Nos. 5,474,771 (Lederman et al.) and 5,876,950 (Siadak et al.) disclose murine monoclonal antibodies specific for different epitopes of human gp39. WO95/06666 (Noelle & Foy) discloses murine anti-gp39 antibodies.

U.S. Pat. No. 6,328,964 (Noelle & Claassen) discloses methods for the treatment of multiple sclerosis using gp39-specific antibodies.

U.S. Pat. No. 5,747,037 (Noelle et al.), and EP0721469B1 (Ledbetter et al.) and its U.S. counterpart U.S. Pat. No. 5,869,049 disclose anti-human monoclonal (mouse) antibodies specific for gp39. U.S. Pat. No. 5,876,718 (Noelle et al.) discloses methods of inducing T cell non-responsiveness to transplanted tissues and of treating graft-versus-host disease with anti-gp39 monoclonal (mouse) antibodies. EP0742721B1 (Noelle et al.) discloses methods of inhibiting a humoral immune response to a thymus-dependent antigen that use anti-gp39 monoclonal (mouse) antibodies. U.S. Pat. No. 6,375,950 describes methods for inducing T cell unresponsiveness to donor tissue or organs in a transplant recipient through use of anti-gp39 monoclonal (murine) antibodies.

EP1005372B1 (De Boer et al.) describes methods for the selective killing of autoreactive CD40L+ T cells using anti-CD40L monoclonal (mouse) antibody-toxin fusion proteins.

U.S. Pat. No. 6,340,459 (Yellin et al.) describes the use of murine anti gp39 monoclonal antibody 5c8 for the treatment or prevention of reperfusion injury.

EP0831906B1 (Claassen et al.) describes methods for the treatment of T cell-mediated tissue destruction in autoimmune diseases such as multiple sclerosis using anti-gp39 monoclonal (mouse) antibodies. Antibodies used in therapeutic approaches in the prior art have been divalent antibodies of murine origin.

A number of smaller antigen binding fragments of naturally occurring antibodies have been identified following protease digestion. These include, for example, the "Fab fragment" ($V_L$—$C_L$—$C_H1$-$V_H$), "Fab' fragment" (a Fab with the heavy chain hinge region) and "F(ab')$_2$ fragment" (a dimer of Fab' fragments joined by the heavy chain hinge region). Recombinant methods have been used to generate even smaller antigen-binding fragments, referred to as "single chain Fv" (variable fragment) or "scFv," consisting of $V_L$ and $V_H$ joined by a synthetic peptide linker.

While the antigen binding unit of a naturally-occurring antibody (e.g., in humans and most other mammals) is generally known to be comprised of a pair of V regions ($V_L$/$V_H$), camelid species express a large proportion of fully functional, highly specific antibodies that are devoid of light chain sequences. The camelid heavy chain antibodies are found as homodimers of a single heavy chain, dimerized via their constant regions. The variable domains of these camelid heavy chain antibodies are referred to as $V_HH$ domains and retain the ability, when isolated as fragments of the $V_H$ chain, to bind antigen with high specificity ((Hamers-Casterman et al., 1993, Nature 363: 446-448; Gahroudi et al., 1997, FEBS Lett. 414: 521-526). Antigen binding single $V_H$ domains have also been identified from, for example, a library of murine $V_H$ genes amplified from genomic DNA from the spleens of immunized mice and expressed in *E. Coli* (Ward et al., 1989, Nature 341: 544-546). Ward et al. named the isolated single $V_H$ domains "dAbs," for "domain antibodies." The term "dAb" will refer herein to an antibody single variable domain ($V_H$ or $V_L$) polypeptide that specifically binds antigen. A "dAb" binds antigen independently of other V domains; however, as the term is used herein, a "dAb" can be present in a homo- or heteromultimer with other $V_H$ or $V_L$ domains where the other domains are not required for antigen binding by the dAb, i.e., where the dAb binds antigen independently of the additional $V_H$ or $V_L$ domains.

Antibody single variable domains, for example, $V_H$H, are the smallest antigen-binding antibody unit known. For use in therapy, human antibodies are preferred, primarily because they are not as likely to provoke an immune response when administered to a patient. As noted above, isolated non-camelid $V_H$ domains tend to be relatively insoluble and are often poorly expressed. Comparisons of camelid $V_{HH}$ with the $V_H$ domains of human antibodies reveals several key differences in the framework regions of the camelid $V_{HH}$ domain corresponding to the $V_H$/$V_L$ interface of the human $V_H$ domains. Mutation of these residues of human $V_H$3 to more closely resemble the $V_{HH}$ sequence (specifically Gly 44→Glu, Leu 45→Arg and Trp 47→Gly) has been performed to produce "camelized" human $V_H$ domains that retain antigen binding activity (Davies & Riechmann, 1994, FEBS Lett. 339: 285-290) yet have improved expression and solubility. (Variable domain amino acid numbering used herein is consistent with the Kabat numbering convention (Kabat et al., 1991, Sequences of Immunological Interest, $5^{th}$ ed. U.S. Dept. Health & Human Services, Washington, D.C.)) WO 03/035694 (Muyldermans) reports that the Trp 103→Arg mutation improves the solubility of non-camelid $V_H$ domains. Davies & Riechmann (1995, Biotechnology N.Y. 13: 475-479) also report production of a phage-displayed repertoire of camelized human $V_H$ domains and selection of clones that bind hapten with affinities in the range of 100-400 nM, but clones selected for binding to protein antigen had weaker affinities.

While many antibodies and their derivatives are useful for diagnosis and therapy, the ideal pharmacokinetics of antibodies are often not achieved for a particular application. In order to provide improvement in the pharmacokinetics of antibody molecules, the present invention provides single domain variable region polypeptides that are linked to polymers which provide increased stability and half-life. The attachment of polymer molecules (e.g., polyethylene glycol; PEG) to proteins is well established and has been shown to modulate the pharmacokinetic properties of the modified proteins. For example, PEG modification of proteins has been shown to alter the in vivo circulating half-life, antigenicity, solubility, and resistance to proteolysis of the protein (Abuchowski et al., *J. Biol. Chem.* 1977, 252:3578; Nucci et al., *Adv. Drug Delivery Reviews* 1991, 6:133; Francis et al., *Pharmaceutical Biotechnology* Vol. 3 (Borchardt, R. T. ed.); and Stability of Protein Pharmaceuticals: *in vivo* Pathways of Degradation and Strategies for Protein Stabilization 1991 pp 235-263, Plenum, N.Y.).

Both site-specific and random PEGylation of protein molecules is known in the art (See, for example, Zalipsky and Lee, *Poly(ethylene glycol) Chemistry: Biotechnical and Biomedical Applications* 1992, pp 347-370, Plenum, N.Y.; Goodson and Katre, 1990, *Bio/Technology,* 8:343; Hershfield et al., 1991, *PNAS* 88:7185). More specifically, random PEGylation of antibody molecules has been described at lysine residues and thiolated derivatives (Ling and Mattiasson, 1983, *Immunol. Methods* 59: 327; Wilkinson et al., 1987, *Immunol Letters,* 15: 17; Kitamura et al., 1991, *Cancer Res.* 51:4310; Delgado et al., 1996 *Br. J. Cancer,* 73: 175; Pedley et al., 1994, *Br. J. Cancer,* 70:1126).

SUMMARY OF THE INVENTION

The invention relates to antibody polypeptides that monovalently bind CD40L. Because of the clear importance of CD40L in the production of antibodies, the CD40/CD40L interaction and pathways present important targets for the development of therapeutic approaches for the treatment of diseases and disorders that involve inappropriate or excessive antibody responses, such as autoimmune diseases. Antibody polypeptides that are monovalent for binding of CD40L can inhibit CD40L activity, including binding and activation of CD40 on the B cell surface and downstream effects, while avoiding potential undesirable effects that can occur with antibodies capable of divalent or multivalent binding of CD40L. Monovalent anti-CD40L antibody polypeptides can also be applied to any of a number of uses for which standard divalent antibodies are also used, e.g., in vivo imaging and diagnosis.

In one aspect, the antibody polypeptide consists of or comprises a single immunoglobulin variable domain that specifically binds and antagonizes the activity of CD40L, preferably without substantially agonizing CD40 and/or CD40L activity. In another aspect, because human antibodies will avoid the generation of an immune response to the antibodies when administered to human subjects for the treatment or prevention of disease, the antibody polypeptide is a human antibody polypeptide that monovalently binds CD40L, preferably without substantially agonizing CD40 and/or CD40L activity.

In summary then, in one embodiment, the invention provides an antibody polypeptide, preferably a human antibody polypeptide, that is monovalent for binding to CD40L (gp39).

In one embodiment, the human antibody polypeptide dissociates from human CD40L with a $K_d$ in the range of 50 nM to 20 pM, inclusive, as measured by surface plasmon resonance. For example, the $K_d$ for human CD40L can be 25 nM to 20 pM, 10 nM to 20 pM, 5 nm to 20 pM, 1 nM to 20 pM, 0.5 nM to 20 pM, 0.1 nM to 20 pM, 0.1 nM to 50 nM, 75 pM to 20 pM or even 50 pM to 20 pM.

Unless otherwise stated, all ranges described herein are inclusive of the specific endpoints.

In another embodiment, the antibody polypeptide inhibits the binding of CD40L to CD40.

In another embodiment, the binding of the antibody polypeptide to CD40L does not substantially agonize CD40 and/or CD40L activity.

In another embodiment, the human antibody polypeptide inhibits the binding of CD40 to CD40L, and does not substantially agonize signaling by CD40.

In another embodiment, the binding of the antibody polypeptide to CD40L does not substantially induce JNK phosphorylation in Jurkat T-cells.

In another embodiment, the binding of the antibody polypeptide to CD40L does not substantially induce IFN-γ secretion by Jurkat T-cells co-stimulated with anti-CD3 antibody.

In another embodiment, the presence of the antibody polypeptide in a standard platelet aggregation assay does not result in aggregation of more than 25% over the aggregation observed in a negative control assay performed without the addition of antibody.

In another embodiment, the human antibody polypeptide comprises a single immunoglobulin variable domain that binds CD40L. In a preferred embodiment, the single immunoglobulin variable domain is a $V_H$ or a $V_L$ domain.

In another embodiment, the antibody polypeptide is selected from the group consisting of a dAb, a FAb, an scFv, an Fv, or a disulfide-bonded Fv.

In another embodiment, the human antibody polypeptide is PEG-linked. In one embodiment, the PEG is covalently linked to the human antibody polypeptide. In one preferred embodiment, the PEG-linked human antibody polypeptide has a hydrodynamic size of at least 24 kD. In another preferred embodiment, the PEG is linked to the antibody polypeptide at a cysteine or lysine residue. In another preferred embodiment, the total PEG size is from 20 to 60 kD, inclusive. In another preferred embodiment, the PEG-linked human antibody polypeptide has a hydrodynamic size of at least 200 kD.

In one embodiment, the antibody polypeptide has an increased in vivo half-life relative to the same antibody polypeptide composition lacking polyethylene glycol.

In another embodiment, the tα-half life of the antibody polypeptide composition is increased by 10% or more. In another embodiment, the tα-half life of the antibody polypeptide composition is increased by 50% or more. In another embodiment, the tα-half life of the antibody polypeptide composition is increased by 2× or more. In another embodiment, the tα-half life of the antibody polypeptide composition is increased by 5× or more, e.g., 10×, 15×, 20×, 25×, 30×, 40×, or more. In another embodiment, the tα-half life of the antibody polypeptide composition is increased by 50× or more.

In another embodiment, the PEG-linked antibody polypeptide has a to half-life of 0.25 to 6 hours, inclusive. In another embodiment, the tα half-life is in the range of 30 minutes to 12 hours, inclusive. In another embodiment, the tα-half life of the antibody polypeptide composition is in the range of 1 to 6 hours.

In another embodiment, the tβ-half life of the antibody polypeptide composition is increased by 10% or more. In another embodiment, the tβ-half life of the antibody polypeptide composition is increased by 50% or more. In another embodiment, the tβ-half life of the antibody polypeptide composition is increased by 2× or more. In another embodiment, the tβ-half life of the antibody polypeptide composition is increased by 5× or more, e.g., 10×, 15×, 20×, 25×, 30×, 40×, or more. In another embodiment, the tβ-half life of the antibody polypeptide composition is increased by 50× or more.

In another embodiment, the antibody polypeptide composition has a tβ half-life of 1 to 170 hours, inclusive. In another embodiment, the tβ-half life is in the range of 12 to 48 hours, inclusive. In another embodiment, the tβ-half life is in the range of 12 to 26 hours, inclusive.

In addition, or alternatively to the above criteria, the present invention provides a dAb containing composition comprising a ligand according to the invention having an AUC value (area under the curve) in the range of 1 mg·min/ml or more. In one embodiment, the lower end of the range is 5, 10, 15, 20, 30, 100, 200 or 300 mg·min/ml. In addition, or alternatively, a ligand or composition according to the invention has an AUC in the range of up to 600 mg·min/ml. In one embodiment, the upper end of the range is 500, 400, 300, 200, 150, 100, 75 or 50 mg·min/ml. Advantageously a ligand according to the invention will have an AUC in the range selected from the group consisting of the following: 15 to 150 mg·min/ml, 15 to 100 mg·min/ml, 15 to 75 mg·min/ml, and 15 to 50 mg·min/ml.

In another embodiment, the antibody polypeptides described herein can be linked to human serum albumin (HSA), which also has the effect of increasing the in vivo half life of the molecule. The human serum albumin coding sequences can be obtained by PCR using primers derived from the cDNA sequence available at GenBank Accession No. NM000477. Such coding sequences can be fused to the coding sequence for a monovalent anti-CD40L antibody polypeptide as described herein, and the fusion can be expressed by one of skill in the art.

In another embodiment, the tα-half life of the HSA-linked human antibody polypeptide composition is increased by 10% or more.

In another embodiment, the tα-half life of the HSA-linked human antibody polypeptide composition is in the range of 0.25 hours to 6 hours.

In another embodiment, the tβ-half life of the HSA-linked human antibody polypeptide composition is increased by 10% or more.

In another embodiment, the tβ-half life of the HSA-linked human antibody polypeptide composition is in the range of 12 to 48 hours.

In another embodiment, the human antibody polypeptide comprises an amino acid sequence selected from the group consisting of SEQ ID NOs 7-82 and 246-360.

In another embodiment, the human antibody polypeptide inhibits binding of CD40L to CD40 with an $IC_{50}$ in the range of 20 pM to 1.5 μM, inclusive; $IC_{50}$ for inhibition of CD40L binding to CD40 in any embodiment described herein is preferably measured as described herein in Example 6. The $IC_{50}$ can preferably be in the range of 20 pM to 1 μM, 20 pM to 900 nM, 20 pM to 800 nM, 20 pM to 700 nM, 20 pM to 600 nM, 20 pM to 500 nM, 20 pM to 400 nM, 20 pM to 300 nM, 20 pM to 200 nM, 20 pM to 100 nM, or 20 pM to 50 nM. Further acceptable or preferred ranges include, for example, 50 pM to 1 μM, 100 pM to 500 nM, 125 pM to 250 nM, 150 pM to 200 nM, 150 pM to 100 nM and 200 pM to 50 nM.

In another embodiment, the antibody polypeptide is fused to a second antibody polypeptide which binds a ligand other than CD40L. In a preferred embodiment, the antibody polypeptide which binds a ligand other than CD40L binds a ligand selected from the group consisting of HSA, TNFα, IL-1, IL-2, IL-4, IL-6, IL-8, IL-12, IL-18, IFN-γ, CD2, CD4, CD8, CTLA4, LFA1, LFA3, VLA4, CD80 (B7-1), CD28, CD86 (B7-2), and CTLA-4.

In another embodiment, the human antibody polypeptide is free of an Fc domain. The limits of an Fc domain are set out in Kabat et al. (1991, Sequences of Immunological Interest, $5^{th}$ ed. U.S. Dept. Health & Human Services, Washington, D.C.; incorporated herein by reference). In the alternative, an Fc domain consists of the CH2-CH3 regions, optionally including a hinge region linked to the CH2. In a preferred embodiment, the human antibody polypeptide does not mediate platelet aggregation in a standard platelet aggregation assay.

The invention further encompasses a human antibody polypeptide which has an amino acid sequence at least 85% identical to a sequence selected from the group consisting of SEQ ID NOs 7-82 and 246-360, which antibody polypeptide specifically and monovalently binds CD40L.

The invention further encompasses an antigen-binding polypeptide, the polypeptide comprising a single immunoglobulin variable domain which specifically and monovalently binds CD40L. Recited differently, the invention further encompasses a polypeptide comprising a moiety which specifically binds CD40L, which moiety consists of a single immunoglobulin variable domain.

In one embodiment, the polypeptide consists of a human single immunoglobulin variable domain.

In another embodiment, the polypeptide has a Kd for human CD40L in the range of 50 nM to 20 pM, inclusive, as determined by surface plasmon resonance. For example, the Kd for human CD40L can be 25 nM to 20 pM, 10 nM to 20 pM, 5 nm to 20 pM, 1 nM to 20 pM, 0.5 nM to 20 pM, 0.1 nM to 20 pM, 75 pM to 20 pM or even 50 pM to 20 pM.

In another embodiment, the polypeptide inhibits the binding of CD40L to CD40.

In another embodiment, the polypeptide inhibits the binding of CD40 to CD40L and has an $IC_{50}$ in the range of 20 pM to 1.5 μM, inclusive. For example, the $IC_{50}$ can be in the range of 20 pM to 1 μM, 20 pM to 900 nM, 20 pM to 800 nM, 20 pM to 700 nM, 20 pM to 600 nM, 20 pM to 500 nM, 20 pM to 400 nM, 20 pM to 300 nM, 20 pM to 200 nM, 20 pM to 100 nM, or 20 pM to 50 nM. Further acceptable or preferred ranges include, for example, 50 pM to 1 μM, 100 pM to 500 nM, 125 pM to 250 nM, 150 pM to 200 nM, 150 pM to 100 nM and 200 pM to 50 nM.

In another embodiment, the binding of the polypeptide to CD40L does not substantially agonize CD40 and/or CD40L activity.

In another embodiment, the binding of the polypeptide to CD40L does not substantially induce JNK phosphorylation in Jurkat T-cells.

In another embodiment, the binding of the polypeptide to CD40L does not substantially induce IFN-γ secretion by Jurkat T-cells co-stimulated with anti-CD3 antibody.

In another embodiment, the presence of the antibody polypeptide in a standard platelet aggregation assay does not result in aggregation more than 25% over the aggregation observed in a negative control assay lacking antibody polypeptide.

In another embodiment, the single immunoglobulin variable domain is a human single immunoglobulin variable domain.

In another embodiment, the single immunoglobulin variable domain is a $V_H$ or a $V_L$ domain.

In one embodiment, the polypeptide is PEG-linked. In one embodiment, the PEG is covalently linked. In one preferred embodiment, the PEG-linked antigen-binding polypeptide has a hydrodynamic size of at least 24 kD. In another preferred embodiment, the PEG is linked to the antigen-binding polypeptide at a cysteine or lysine residue. In another preferred embodiment, the total PEG size is from 20 to 60 kD, inclusive. In another preferred embodiment, the PEG-linked antigen-binding polypeptide has a hydrodynamic size of at least 200 kD.

In another embodiment, the PEG-linked polypeptide has an increased in vivo half-life relative to the same polypeptide composition lacking linked polyethylene glycol. In another embodiment, the tα-half life of the polypeptide composition is increased by 10% or more. In another embodiment, the tα-half life of the polypeptide composition is increased by 50% or more. In another embodiment, the tα-half life of the polypeptide composition is increased by 2× or more. In another embodiment, the tα-half life of the polypeptide composition is increased by 5× or more, e.g., 10×, 15×, 20×, 25×, 30×, 40×, or more. In another embodiment, the tα-half life of the polypeptide composition is increased by 50× or more.

In another embodiment, the PEG-linked antibody polypeptide has a tα half-life of 0.25 to 6 hours, inclusive. In another embodiment, the tα half-life is in the range of 30 minutes to 12 hours, inclusive. In another embodiment, the tα-half life of the polypeptide composition is in the range of 1 to 6 hours.

In another embodiment, the tβ-half life of the polypeptide composition is increased by 10% or more. In another embodiment, the tβ-half life of the polypeptide composition is increased by 50% or more. In another embodiment, the tβ-half life of the polypeptide composition is increased by 2× or more. In another embodiment, the tβ-half life of the polypeptide composition is increased by 5× or more, e.g., 10×, 15×, 20×, 25×, 30×, 40×, or more. In another embodiment, the tβ-half life of the polypeptide composition is increased by 50× or more.

In another embodiment, the antibody polypeptide composition has a tβ half-life of 1 to 170 hours, inclusive. In another embodiment, the tβ-half life is in the range of 12 to 48 hours, inclusive. In another embodiment, the tβ-half life is in the range of 12 to 26 hours, inclusive.

In another embodiment, the composition has an AUC value (area under the curve) in the range of 1 mg·min/ml or more. In one embodiment, the lower end of the range is 5, 10, 15, 20, 30, 100, 200 or 300 mg·min/ml. In addition, or alternatively, a ligand or composition according to the invention has an AUC in the range of up to 600 mg·min/ml. In one embodiment, the upper end of the range is 500, 400, 300, 200, 150, 100, 75 or 50 mg·min/ml. Advantageously a ligand according to the invention will have an AUC in the range selected from the group consisting of the following: 15 to 150 mg·min/ml, 15 to 100 mg·min/ml, 15 to 75 mg·min/ml, and 15 to 50 mg·min/ml.

In another embodiment, the antibody polypeptide is linked to human serum albumin (HSA). In another embodiment, the antibody polypeptide has an increased in vivo half-life relative to the same polypeptide composition lacking linked HSA. In another embodiment, the antibody polypeptide has a tα-half life that is increased by 10% or more relative to a molecule lacking linked HSA. In another embodiment, the tα-half life of the polypeptide composition is in the range of 0.25 minutes to 6 hours. In another embodiment, the tβ-half life of the polypeptide composition is increased by 10% or more. In another embodiment, the tβ-half life is in the range of 12 to 48 hours.

In another embodiment, the antigen-binding polypeptide comprises an amino acid sequence selected from the group consisting of SEQ ID NOs 7-82 and 246-360.

In another embodiment, the antigen-binding polypeptide is free of an Fc domain.

In another aspect, the invention encompasses an immunoglobulin variable domain polypeptide which has an amino acid sequence at least 85% identical to a sequence selected from the group consisting of SEQ ID NOs 7-82 and 246-360, which polypeptide specifically and monovalently binds CD40L.

In one embodiment, the immunoglobulin variable domain polypeptide antagonizes the binding of CD40L to CD40.

In another embodiment, the immunoglobulin variable domain polypeptide inhibits the binding of CD40 to CD40L and has an $IC_{50}$ in the range of 20 pM to 1.5 μM, inclusive. For example, the $IC_{50}$ can be in the range of 20 pM to 1 μM, 20 pM to 900 nM, 20 pM to 800 nM, 20 pM to 700 nM, 20 pM to 600 nM, 20 pM to 500 nM, 20 pM to 400 nM, 20 pM to 300 nM, 20 pM to 200 nM, 20 pM to 100 nM, or 20 pM to 50 nM. Further acceptable or preferred ranges include, for example, 50 pM to 1 μM, 100 pM to 500 nM, 125 pM to 250 nM, 150 pM to 200 nM, 150 pM to 100 nM and 200 pM to 50 nM.

In another embodiment, the immunoglobulin variable domain polypeptide inhibits the interaction of CD40 with CD40L, but does not substantially agonize intracellular signaling by CD40. In a preferred embodiment, the binding of the polypeptide to CD40L does not substantially induce JNK phosphorylation in Jurkat T-cells. In another preferred embodiment, the binding of the polypeptide to CD40L does not substantially induce IFN-γ secretion by Jurkat T-cells co-stimulated with anti-CD3 antibody. In another preferred embodiment, the binding of the antibody polypeptide to CD40L does not substantially induce platelet aggregation in a platelet aggregation assay.

In another embodiment, the antigen-binding polypeptide further comprises a second antibody polypeptide which binds a ligand other than CD40L. In a preferred embodiment, the second antibody polypeptide binds a ligand selected from the group consisting of HSA, TNFα, IL-1, IL-2, IL-4, IL-6, IL-8, IL-12, IL-18, IFN-γ, CD2, CD4, CD8, CTLA4, LFA1, LFA3 and VLA4.

In one embodiment, the invention relates to an antibody polypeptide comprising an immunoglobulin variable domain which specifically and monovalently binds CD40L (e.g., an anti-CD40L dAb, FAb, an scFv, an Fv, or a disulfide-bonded Fv), and which comprises one or more framework regions comprising an amino acid sequence that is the same as the amino acid sequence of a corresponding framework region encoded by a human germline antibody gene segment, or the amino acid sequence of one or more of said framework regions collectively comprises up to 5 amino acid differences relative to the amino acid sequence of said corresponding framework region encoded by a human germline antibody gene segment.

In one embodiment, the amino acid sequences of FW1, FW2, FW3 and FW4 of the anti-CD40L variable domain or dAb are the same as the amino acid sequences of corresponding framework regions encoded by a human germline antibody gene segment, or the amino acid sequences of FW1, FW2, FW3 and FW4 collectively contain up to 10 amino acid differences relative to the amino acid sequences of corresponding framework regions encoded by said human germline antibody gene segment. In a further embodiment, the amino acid sequences of FW1, FW2 and FW3 of the anti-CD40L variable domain or dAb are the same as the amino acid sequences of corresponding framework regions encoded by human germline antibody gene segments.

In a further embodiment of the foregoing, the human germline antibody gene segment can be selected from the group consisting of DP47, DP45, DP48 and DPK9.

The invention further encompasses a method of antagonizing the binding of CD40 to CD40L in an individual, the method comprising administering a monovalent anti-CD40L antibody polypeptide as described herein to the individual, wherein the polypeptide antagonizes the binding of CD40 to CD40L in the individual.

The invention further encompasses a method of antagonizing an activity of CD40 or CD40L in an individual, the method comprising administering a monovalent anti-CD40L antibody polypeptide as described herein to the individual, wherein the polypeptide antagonizes an activity of CD40 or CD40L or both.

The invention further encompasses a composition comprising an extended release formulation comprising a monovalent anti-CD40L antibody polypeptide, preferably, but not limited to, a polypeptide comprising a single immunoglobulin variable domain that binds CD40L. In one embodiment, the single immunoglobulin variable domain is a non-human mammalian single immunoglobulin variable domain. In another embodiment, the single immunoglobulin variable domain is a human single immunoglobulin variable domain.

The invention further encompasses a method of treating or preventing a disease or disorder mediated by CD40L in an individual in need of such treatment, the method comprising administering to the individual a therapeutically effective amount of a composition comprising a monovalent anti-CD40L antibody polypeptide, preferably a composition comprising a single human immunoglobulin variable domain that binds CD40L. In one embodiment, the disease or disorder is an autoimmune disease or disorder.

The invention further encompasses a method of treating or preventing a symptom of systemic lupus erythematosus (SLE) in an individual, the method comprising administering a monovalent anti-CD40L antibody polypeptide to said individual in an amount effective to treat or prevent a symptom of SLE. The invention further encompasses a method of reducing or alleviating a symptom of a disease such as systemic lupus erythematosis, multiple sclerosis, rheumatoid arthritis, allograft rejection, xenograft rejection, and Diabetes, including insulin-dependent Type I Diabetes.

The invention further encompasses an antibody polypeptide that is monovalent for binding to CD40L, wherein the antibody polypeptide comprises a universal framework.

In one embodiment, the universal framework comprises a VH framework selected from the group consisting of DP47, DP45 and DP38, and/or the VL framework is DPK9.

In another embodiment, the antibody polypeptide comprises a generic ligand binding site. In another embodiment, the generic ligand binding site binds a generic ligand selected from the group consisting of protein A, protein L and protein G.

In another embodiment, the antibody polypeptide comprises a variable domain having one or more framework regions comprising an amino acid sequence that is the same as the amino acid sequence of a corresponding framework region encoded by a human germline antibody gene segment, or the amino acid sequences of one or more of the framework regions collectively comprises up to 5 amino acid differences relative to the amino acid sequence of the corresponding framework region encoded by a human germline antibody gene segment.

In another embodiment, the antibody polypeptide comprises a variable domain, wherein the amino acid sequences of FW1, FW2, FW3 and FW4 are the same as the amino acid sequences of corresponding framework regions encoded by a human germline antibody gene segment, or the antibody sequences of FW1, FW2, FW3 and FW4 collectively contain up to 10 amino acid differences relative to the amino acid sequences of corresponding framework regions encoded by the human germline antibody gene segment.

In another embodiment, the antibody polypeptide comprises an antibody variable domain comprising FW1, FW2 and FW3 regions, and the amino acid sequence of said FW1, FW2 and FW3 are the same as the amino acid sequences of corresponding framework regions encoded by human germline antibody gene segments. In another embodiment, the human germline antibody gene segment is selected from the group consisting of DP47, DP45, DP48 and DPK9.

The invention includes an antibody single variable domain polypeptide that binds to CD40L, wherein the polypeptide has an amino acid sequence that is identical to the amino acid sequence of DOM8-24, or differs from the amino acid sequence of DOM8-24 at no more than 25 amino acid positions and has a sequence that is at least 80% homologous to the sequence of DOM8-24. In one embodiment, the antibody single variable domain polypeptide differs form the amino acid sequence of DOM8-24 at 25 or fewer amino acid positions, 20 or fewer amino acid positions, 15 or fewer amino acid positions, 10 or fewer amino acid positions, 5 or fewer amino acid positions, 2 or fewer amino acid positions, or as few as one amino acid position. In a further embodiment, the antibody single variable domain polypeptide is at least 80% homologous to the sequence of DOM8-24, for example, at least 85% homologous, at least 90% homologous, at least 95% homologous, and up to and including 96%, 97%, 98%, or 99% homologous.

The invention includes an antibody single variable domain polypeptide that binds to CD40L, wherein the polypeptide has an amino acid sequence that is identical to the amino acid sequence of DOM8-24, or differs from the amino acid sequence of DOM8-24 at no more than 25 amino acid positions and has a CDR1 sequence that is at least 50% homologous to the CDR1 sequence of DOM8-24, or has a CDR2 sequence that is at least 50% homologous to the CDR2 sequence of DOM8-24, or has a CDR3 sequence that is at least 50% homologous to the CDR3 sequence of DOM8-24.

The invention also includes an antibody single variable domain polypeptide that binds CD40L, wherein the dAb has an amino acid sequence that is identical to the amino acid sequence of DOM8-24, or differs from the amino acid sequence of DOM8-24 at no more than 25 amino acid positions and has a CDR1 sequence that is at least 50% homologous to the CDR1 sequence of DOM8-24 and has a CDR2 sequence that is at least 50% homologous to the CDR2 sequence of DOM8-24.

The invention also includes an antibody single variable domain polypeptide that binds CD40L, wherein the dAb has an amino acid sequence that is identical to the amino acid sequence of DOM8-24, or differs from the amino acid sequence of DOM8-24 at no more than 25 amino acid positions and has a CDR2 sequence that is at least 50% homologous to the CDR2 sequence of DOM8-24 and has a CDR3 sequence that is at least 50% homologous to the CDR3 sequence of DOM8-24.

The invention also includes an antibody single variable domain polypeptide that binds CD40L, wherein the dAb has an amino acid sequence that is identical to the amino acid sequence of DOM8-24, or differs from the amino acid sequence of DOM8-24 at no more than 25 amino acid positions and has a CDR1 sequence that is at least 50% homologous to the CDR1 sequence of DOM8-24 and has a CDR3 sequence that is at least 50% homologous to the CDR3 sequence of DOM8-24.

The invention also includes an antibody single variable domain polypeptide that binds CD40L, wherein the dAb has an amino acid sequence that is identical to the amino acid sequence of DOM8-24, or differs from the amino acid sequence of DOM8-24 at no more than 25 amino acid positions and has a CDR1 sequence that is at least 50% homologous to the CDR1 sequence of DOM8-24 and has a CDR2 sequence that is at least 50% homologous to the CDR2 sequence of DOM8-24 and has a CDR3 sequence that is at least 50% homologous to the CDR3 sequence of DOM8-24.

In one embodiment, the antibody single variable domain polypeptide that binds to CD40L, if not identical in sequence to that of DOM8-24, differs form the amino acid sequence of DOM8-24 at 25 or fewer amino acid positions, 20 or fewer amino acid positions, 15 or fewer amino acid positions, 10 or fewer amino acid positions, 5 or fewer amino acid positions, 2 or fewer amino acid positions, or as few as one amino acid position.

The invention also includes a CD40L antagonist having a CDR1 sequence that is at least 50% homologous to the CDR1 sequence of DOM8-24.

The invention also includes a CD40L antagonist having a CDR2 sequence that is at least 50% homologous to the CDR2 sequence of DOM8-24.

The invention also includes a CD40L antagonist having a CDR3 sequence that is at least 50% homologous to the CDR3 sequence of DOM8-24.

The invention also includes a CD40L antagonist having a CDR1 sequence that is at least 50% homologous to the CDR1 sequence of DOM8-24 and a CDR2 sequence that is at least 50% homologous to the CDR2 sequence of DOM8-24.

The invention also includes a CD40L antagonist having a CDR2 sequence that is at least 50% homologous to the CDR2 sequence of DOM8-24 and a CDR3 sequence that is at least 50% homologous to the CDR3 sequence of DOM8-24.

The invention also includes a CD40L antagonist having a CDR1 sequence that is at least 50% homologous to the CDR1 sequence of DOM8-24 and a CDR3 sequence that is at least 50% homologous to the CDR3 sequence of DOM8-24.

The invention also includes a CD40L antagonist having a CDR1 sequence that is at least 50% homologous to the CDR1 sequence of DOM8-24 and a CDR2 sequence that is at least 50% homologous to the CDR2 sequence of DOM8-24 and a CDR3 sequence that is at least 50% homologous to the CDR3 sequence of DOM8-24.

In one embodiment the CD40L antagonist inhibits the binding of CD40 to CD40L, and/or inhibits an activity of CD40 and/or CD40L, and/or results in no more than 25% platelet aggregation in a platelet aggregation assay. In one embodiment, the antagonist results in platelet aggregation of 25% or less, 20% or less, 15% or less, 10% or less, 5% or less, and as little as zero platelet aggregation.

The invention also includes a dual specific ligand comprising a first immunoglobulin single variable domain having a binding specificity to a first antigen and a second single variable domain having a binding activity to a second antigen, wherein the first antigen is CD40L and binding of the second single variable domain to the second antigen acts to increase the half-life of the ligand in vivo. In one embodiment, the dual specific ligand is a four chain IgG immunoglobulin.

In one embodiment, the four chain IgG comprises two dual specific ligands, said dual specific ligands being different in their variable domains.

The invention also includes a dual specific ligand comprising an anti-human CD40L dAb and an anti-SA dAb.

In one embodiment, the dAbs are Camelid $V_{HH}$ domains.

In one embodiment of the dual specific ligand, either (i) the first and second immunoglobulin variable domains are heavy chain variable domains; or (ii) the first and the second immunoglobulin variable domains are light chain variable domains.

In one embodiment, the ligand is provided as an IgG immunoglobulin comprising four heavy chain single variable domains or four light chain single variable domains. The heavy chain can comprise Camelid VHH domains.

In a further embodiment of the dual specific ligand, the first and second domains bind independently, such that the dual specific ligand may simultaneously bind both the first and second antigens.

In one embodiment of the dual specific ligand, the first single variable domain has a dissociation constant ($K_d$) of $1\times10^{-8}$ M or less for human CD40L, and a $K_{off}$ rate constant of $1\times10^{-3}$ $s^{-1}$ or less, as determined by surface plasmon resonance.

In one embodiment of the dual specific ligand, the second single variable domain is specific for serum albumin (SA) and has a dissociation constant ($K_d$) of 1 nM to 500 μm for SA, as determined by surface plasmon resonance.

In a further embodiment, the second domain binds SA in a standard ligand binding assay with an IC50 of 1 nM to 500 μM. The second single variable domain may be specific for SA, and comprise the amino acid sequence of MSA-16 or a sequence that is at least 80% homologous thereto. Alternatively, the second single variable domain may be specific for SA, and comprise the amino acid sequence of MSA-26 or a sequence that is at last 80% homologous thereto.

In one embodiment of the dual specific ligand, the anti-CD40L variable domain or dAb comprises a universal framework. The anti-CD40L variable domain or dAb may also comprise a $V_H$ framework selected from the group consisting of DP47, DP45 and DP38; or a $V_L$ framework which is DPK9. In a further embodiment, the dual specific ligand or dAb can comprise a binding site for a generic ligand.

In one embodiment, the generic ligand binding site is selected from the group consisting of protein A, protein L and protein G binding site.

In one embodiment of the dual specific ligand, the anti-CD40L variable domain or dAb comprises one or more framework regions comprising an amino acid sequence that is the same as the amino acid sequence of a corresponding framework region encoded by a human germline antibody gene segment, or the amino acid sequence of one or more of said framework regions collectively comprises up to 5 amino acid differences relative to the amino acid sequence of said corresponding framework region encoded by a human germline antibody gene segment.

In one embodiment, the amino acid sequences of FW1, FW2, FW3 and FW4 of the anti-CD40L variable domain or dAb are the same as the amino acid sequences of corresponding framework regions encoded by a human germline antibody gene segment, or the amino acid sequences of FW1, FW2, FW3 and FW4 collectively contain up to 10 amino acid differences relative to the amino acid sequences of corresponding framework regions encoded by said human germline antibody gene segment.

In one embodiment, the amino acid sequences of said FW1, FW2 and FW3 of the anti-CD40L variable domain or dAb are the same as the amino acid sequences of corresponding framework regions encoded by human germline antibody gene segments. The human germline antibody gene segments are preferably selected from the group consisting of DP47, DP45, DP48 and DPK9.

The invention also includes a method for producing a dual specific ligand as described herein, comprising a first immunoglobulin single variable domain having a binding specificity for CD40L and a second single immunoglobulin single variable domain having a binding specificity for a protein which increases the half-life of the ligand in vivo, the method comprising the steps of: selecting a first variable domain by its ability to bind CD40L; selecting a second variable domain by its ability to bind to said protein; combining the variable domains; and selecting the ligand by its ability to bind to CD40L and said protein.

In one embodiment, the first variable domain is selected for binding to CD40L in absence of a complementary variable domain.

The invention also includes nucleic acid encoding a dual specific ligand described herein. The nucleic acid may comprise the nucleic acid sequence of MSA-16 or a sequence that is at least 80% homologous thereto, or alternatively may comprise, the nucleic acid sequence of MSA-26 or a sequence that is at least 70% homologous thereto. The nucleic acid may be incorporated into a vector, which may be incorporated into a host cell.

The invention also includes a pharmaceutical composition comprising a dual specific ligand as described herein and a pharmaceutically acceptable excipient, carrier or diluent.

The invention also includes a dAb monomer specific for CD40L, which monomer has a dissociation constant ($K_d$) of $1\times10^{-8}$ M or less for human CD40L, and a $K_{off}$ rate constant of $1\times10^{-3}$ $s^{-1}$ or less, as determined by surface plasmon resonance.

In one embodiment, the dAb monomer specific for CD40L has a dissociation constant ($K_d$) of $1\times10^{-7}$ M or less, as determined by surface plasmon resonance.

In one embodiment, the dAb monomer has binding specificity to CD40L with a dissociation constant ($K_d$) of $1\times10^{-8}$ M or less, as determined by surface plasmon resonance.

In one embodiment, the dAb monomer has binding specificity to CD40L with a dissociation constant ($K_d$) of 50 nM to 20 pM, as determined by surface plasmon resonance.

In one embodiment, the monomer inhibits binding of CD40 to CD40L with an $IC_{50}$ of 50 nM or less.

In a further embodiment, the dAb monomer has binding specificity to CD40L with a $K_{off}$ rate constant of $1\times10^{-3}$ $s^{-1}$ or less, $1\times10^{-4}$ $s^{-1}$ or less, $1\times10^{-5}$ $s^{-1}$ or less, or $1\times10^{-6}$ $s^{-1}$ or less, as determined by surface plasmon resonance.

In one embodiment, the dAb monomer neutralizes CD40L in a standard assay with an ND50 of 50 nM or less.

In invention also includes a dual specific ligand comprising first and second heavy chain single variable domains, or first and second light chain single variable domains, wherein the first variable domain is an anti-CD40L dAb monomer.

In one embodiment, the second variable domain has binding specificity for an antigen other than CD40L.

In a further embodiment, the second variable domain has binding specificity for an antigen selected from the group consisting of EPO receptor, ApoE, Apo-SAA, BDNF, Cardiotrophin-1, EGF, EGF receptor, ENa-78, Eotaxin, Eotaxin-2, Exodus-2, EpoR, FGF-acidic, FGF-basic, fibroblast growth factor-10, FLT3 ligand, Fractalkine (CX3C), GDNF, G-CSF, GM-CSF, GF-bl, insulin, IFN-g, IGF-I, IGF-II, IL-1a, Il-1b, IL-2, Il-3, IL-4, IL-5, IL-6, IL-7, IL-8 (72 a.a.), IL-8 (77 a.a.), IL-9, IL-10, IL-11, IL-12, IL-13, IL-15, IL-16, IL-17, IL-18 (IGIF), Inhibin a, Inhibin b, IP-10, keratinocyte growth factor-2 (KGF-2), KGF, Leptin, LIF, Lymphotactin, Mullerian inhibitory substance, monocyte colony inhibitory factor, monocyte attractant protein, M-CSF, MDC (67 a.a.), MDC (69 a.a.), MCP-1 (MCAF), MCP-2, MCP-3, MCP-4, MDC (67 a.a.), MIG, MIP-1α, MIP-1b, MIP-5a, MIP-3b, MIP-4, myeloid progenitor inhibitor factor-1 (MPIF-1), NAP-2, Neurturin, Nerve growth factor, b-NGF, NT-3, NT-4, Oncostatin M, PDGF-AA, PDGP-AB, PDGF-BB, PF-4, RANTES, SDFla, DFG1b SCF, SCGF, stem cell factor, (SCF), TARC, TGF-a, TGF-b, TGF-b2, TGF-b3, tumour necrosis factor (TNF), TNF-a, TNF-b, TNF receptor I, TNF receptor II, TNIL-1, TPO, JEGF, VEGF receptor 1, VEGF receptor 2, VEGF receptor-3, GCP-2, GRO/MGSA, GRO-b, GRO-g, HCC1, 1-309, HER 1, HER 2, HER 3, HER 4, TACE recognition site, TNF BP-1, TNF BP-II, and an antigen disclosed in Annex 2 or 3.

The invention also includes an antibody polypeptide that antagonizes or inhibits the binding of DOM8-24 to CD40L, or an antibody polypeptide that binds to the same epitope of CD40L bound by DOM8-24.

The invention also includes a dual specific ligand comprising a first immunoglobulin single variable domain having a binding specificity to a first antigen and a second single variable domain having a binding activity to a second antigen, wherein the first antigen is CD40L and the second single variable domain is an Antigen Presenting Cell surface antigen or a T cell surface antigen. The Antigen Presenting Cell surface antigen can be selected from one of the group consisting of dendritic cell surface antigens, activated macrophage surface antigens, activated B cell surface antigens, co-stimulatory signal pathway surface antigens, and MHC.

In one embodiment, the MHC is class II, and the class II can be alpha or beta.

The Antigen Presenting Cell surface antigen may be selected from the group consisting of CD28, Inducible costimulatory molecule (ICOS), CD27, CD30, OX40, CD45, CD69, CD3, CD70, Inducible costimulatory molecule ligand (ICOSL), OX40L, CD80, CD86, HVEM (Herpes Virus Entry Mediator), and LIGHT, but is preferably one of CD28, Inducible costimulatory molecule (ICOS), CD27, CD30, OX40, CD45, CD69, or CD3.

The surface antigen is preferably a B7 gene surface antigen such as B7-2 or B7-1.

DEFINITIONS

As used herein, the term "human" when applied to an antibody polypeptide or to an immunoglobulin variable domain means that the polypeptide has a sequence derived from a human immunoglobulin. A sequence is "derived from" a human immunoglobulin coding sequence when the sequence is either: a) isolated from a human individual or from cells or a cell line from a human individual; b) isolated from a library of cloned human antibody gene sequences (or a library of human antibody V domain sequences); or c) when a cloned human antibody gene sequence (or a cloned human V region sequence (including, e.g., a germline V gene segment)) was used to generate one or more diversified sequences that were then selected for binding to a desired target antigen. The term "human" as applied herein to an antibody polypeptide or to an immunoglobulin variable domain does not encompass an immunoglobulin from another species, e.g., mouse, camel, etc., that has been "humanized" through grafting of human constant region sequences onto an antibody polypeptide (i.e., replacing non-human constant regions with human constant regions) or through grafting of human V region framework sequences onto an immunoglobulin variable domain from a non-human mammal (i.e., replacing non-human framework regions of a V domain with human framework regions).

At a minimum, a human variable domain has at least 85% amino acid similarity (including, for example, 87%, 90%, 93%, 95%, 97%, 99% or higher similarity) to a naturally-occurring human immunoglobulin variable domain sequence.

As used herein, the term "domain" refers to a folded protein structure which retains its tertiary structure independently of the rest of the protein. Generally, domains are responsible for discrete functional properties of proteins, and in many cases may be added, removed or transferred to other proteins without loss of function of the remainder of the protein and/or of the domain.

By "single immunoglobulin variable domain" is meant a folded polypeptide domain which comprises a sequence characteristic of immunoglobulin variable domains and which specifically binds an antigen (e.g., dissociation constant of 500 nM or less). A "single immunoglobulin variable domain" therefore includes complete antibody variable domains as well as modified variable domains, for example in which one or more loops have been replaced by sequences which are not characteristic of antibody variable domains, or antibody variable domains which have been truncated or comprise N- or C-terminal extensions, as well as folded fragments of variable domains which retain a dissociation constant of 500 nM or less (e.g., 450 nM or less, 400 nM or less, 350 nM or less, 300 nM or less, 250 nM or less, 200 nM or less, 150 nM or less, 100 nM or less) and the target antigen specificity of the full-length domain. Where necessary or in case of any doubt, the numbering convention and boundaries set forth by Kabat et al. (1991, Supra) are applicable to immunoglobulin variable and constant domains referred to herein.

An antibody single variable domain polypeptide, as used herein refers to a mammalian single immunoglobulin variable domain polypeptide, preferably human, but also includes rodent (for example, as disclosed in WO00/29004, the contents of which are incorporated herein in their entirety) or camelid $V_{HH}$ dAbs. Camelid dAbs are antibody single variable domain polypeptides which are derived from species including camel, llama, alpaca, dromedary, and guanaco, and comprise heavy chain antibodies naturally devoid of light chain: $V_{HH}$. $V_{HH}$ molecules are about 10× smaller than IgG molecules, and as single polypeptides, they are very stable, resisting extreme pH and temperature conditions. Moreover, camelid antibody single variable domain polypeptides are resistant to the action of proteases. Camelid antibodies are described in, for example, U.S. Pat. Nos. 5,759,808; 5,800,988; 5,840,526; 5,874,541; 6,005,079; and 6,015,695, the contents of each of which are incorporated herein in their entirety. Camelid $V_{HH}$ antibody single variable domain polypeptides useful according to the invention include a class of camelid antibody single variable domain polypeptides having human-like sequences, wherein the class is characterized in that the $V_{HH}$ domains carry an amino acid from the group consisting of glycine, alanine, valine, leucine, isoleucine, proline, phenylalanine, tyrosine, tryptophan, methionine, serine, threonine, asparagine, or glutamine at position 45, such as for example L45, and further comprise a tryptophan at position 103 according to the Kabat numbering. Humanized camelid $V_{HH}$ polypeptides are taught, for example in WO04/041862, the teachings of which are incorporated herein in their entirety. It will be understood by one of skill in the art that naturally occurring camelid antibody single variable domain polypeptides may be modified according to the teachings of WO04/041862 (e.g., amino acid substitutions at positions 45 and 103) to generate humanized camelid $V_{HH}$ polypeptides. Also included in the present invention are antibody single variable domain polypeptides which are nurse shark $V_{HH}$. Nurse shark dAbs are antibody single variable domain polypeptides derived from the nurse shark, that comprise heavy chain antibodies naturally devoid of light chain: $V_{HH}$. Nurse Shark $V_{HH}$ dAbs are described, for example, in Greenberg et al. (Nature 374 pp 168-173 1995) and U.S. 20050043519.

The phrase "single immunoglobulin variable domain polypeptide" encompasses not only an isolated single immunoglobulin variable domain polypeptide, but also larger polypeptides that comprise a monomer of a single immunoglobulin variable domain polypeptide sequence. A "domain antibody" or "dAb" is equivalent to a "single immunoglobulin variable domain polypeptide" as the term is used herein. With regard to a single immunoglobulin variable domain polypeptide, the binding to antigen, e.g., CD40L, is mediated by the single immunoglobulin V domain without a requirement for a complementary V domain.

According to the invention, the terms "antibody single variable domain polypeptide", "antibody single variable domain", "single antibody variable domain", and "single immunoglobulin variable domain" are understood to be equivalent.

As used herein, the phrase "sequence characteristic of immunoglobulin variable domains" refers to an amino acid sequence that is homologous, over 20 or more, 25 or more, 30 or more, 35 or more, 40 or more, 45 or more, or even 50 or more contiguous amino acids, to a sequence comprised by an immunoglobulin variable domain sequence.

Sequences similar or homologous (e.g., at least about 70% sequence identity) to the sequences disclosed herein are also part of the invention. In some embodiments, the sequence identity at the amino acid level can be about 80%, 85%, 90%, 91%, 92%, 93%, 94%, 95%, 96%, 97%, 98%, 99% or higher. At the nucleic acid level, the sequence identity can be about 70%, 75%, 80%, 85%, 90%, 91%, 92%, 93%, 94%, 95%, 96%, 97%, 98%, 99% or higher. Alternatively, substantial identity exists when the nucleic acid segments will hybridize under selective hybridization conditions (e.g., very high stringency hybridization conditions), to the complement of the strand. The nucleic acids may be present in whole cells, in a cell lysate, or in a partially purified or substantially pure form.

As used herein, the terms "homology" or "similarity" refer to the degree with which two nucleotide or amino acid sequences structurally resemble each other. As used herein, sequence "similarity" is a measure of the degree to which amino acid sequences share similar amino acid residues at corresponding positions in an alignment of the sequences. Amino acids are similar to each other where their side chains are similar. Specifically, "similarity" encompasses amino acids that are conservative substitutes for each other. A "conservative" substitution is any substitution that has a positive score in the blosum62 substitution matrix (Hentikoff and Hentikoff, 1992, Proc. Natl. Acad. Sci. USA 89: 10915-10919). By the statement "sequence A is n % similar to sequence B" is meant that n % of the positions of an optimal global alignment between sequences A and B consists of identical amino acids or conservative substitutions. Optimal global alignments can be performed using the following parameters in the Needleman-Wunsch alignment algorithm:

For Polypeptides:

Substitution matrix: blosum62.

Gap scoring function: -A-B*LG, where A=11 (the gap penalty), B=1 (the gap length penalty) and LG is the length of the gap.

For nucleotide sequences:

Substitution matrix: 10 for matches, 0 for mismatches.

Gap scoring function: -A-B*LG where A=50 (the gap penalty), B=3 (the gap length penalty) and LG is the length of the gap.

Typical conservative substitutions are among Met, Val, Leu and Ile; among Ser and Thr; among the residues Asp, Glu and Asn; among the residues Gln, Lys and Arg; or aromatic residues Phe and Tyr.

As used herein, two sequences are "homologous" or "similar" to each other where they have at least 70%, 80%, or 85% sequence similarity to each other, including, e.g., 90%, 95%, 97%, 99% or even 100% sequence similarity, when aligned using either the Needleman-Wunsch algorithm or the "BLAST 2 sequences" algorithm described by Tatusova & Madden, 1999, FEMS Microbiol Lett. 174:247-250. Where amino acid sequences are aligned using the "BLAST 2 sequences algorithm," the Blosum 62 matrix is the default matrix.

As used herein, the terms "inhibit," "inhibits" and "inhibited" refer to a decrease in a given measurable activity (e.g., binding activity) by at least 10% relative to a reference. Where inhibition is desired, such inhibition is preferably at least 20%, 30%, 40%, 50%, 60%, 70%, 80%, 90% or more, up to and including 100%, i.e., complete inhibition or absence of the given activity. One way that inhibition of CD40L binding to CD40 is measured is as described in Example 6 herein. As used herein, the term "substantially inhibits" refers to a decrease in a given measurable activity (e.g., the binding of CD40L to CD40) by at least 50% relative to a reference. For example, "substantially inhibits" refers to a decrease in a given measurable activity of at least 50%, 55%, 60%, 65%, 70%, 75%, 80%, 85%, 90%, 95% and up to and including 100% relative to a reference. As used herein, "inhibits the binding", with reference to the binding of an antibody polypeptide binding to CD40L, or CD40 binding to CD40L, refers to a decrease in binding by at least 10% relative to a reference. "Inhibits the binding" preferably refers to a decrease in binding of at least 20%, 30%, 40%, 50%, 60%, 70%, 80%, 90% or more, up to and including 100%.

As used herein, the terms "activate," "activates" and "activated" refer to an increase in a given measurable activity by at least 5% relative to a reference, for example, at least 10%, 25%, 50%, 75% or even 100%.

As used herein, the term "antagonist" refers to an agent that inhibits at least one activity mediated by CD40L, inhibits the binding of CD40 to CD40L, and/or results in no more than 25% platelet activation and/or aggregation in a platelet aggregation assay or platelet activation assay as described herein, and preferably results in 25% or less platelet activation and/or aggregation, 20% or less, 15% or less, 10% or less, 5% or less, and as little as zero platelet activation and/or aggregation. An activity is "antagonized" if the activity (i.e., CD40L mediated activity, binding of CD40 or CD40L, or platelet activation and/or aggregation) is reduced by at least 10%, and preferably at least 20%, 30%, 40%, 50%, 60%, 70%, 80%, 90%, 95%, 97% or even 100% (i.e., no activity) in the presence, relative to the absence of an antagonist. An antagonist as the term is used herein preferably comprises a single immunoglobulin variable domain that binds monovalently to CD40L.

As used herein, the term "agonist" refers to an agent that activates at least one activity mediated by CD40L, either alone or when combined with another co-stimulus, relative to a reference. An activity is "agonized" if the activity is increased by at least 10%, e.g., 50%, in the presence, relative to the absence of an agonist.

As used herein, the term "epitope" refers to a unit of structure conventionally bound by an immunoglobulin $V_H/V_L$ pair. Epitopes define the minimum binding site for an antibody, and thus represent the target of specificity of an antibody. In the case of a single immunoglobulin variable domain, an epitope represents the unit of structure bound by a single variable domain in isolation. That is, the binding site is provided by one, single immunoglobulin variable domain.

As used herein, the term "extended release" or the equivalent terms "controlled release" or "slow release" refer to drug formulations that release active drug, such as a polypeptide drug, over a period of time following administration to an individual. Extended release of polypeptide drugs, which can occur over a range of desired times, e.g., minutes, hours, days, weeks or longer, depending upon the drug formulation, is in contrast to standard formulations in which substantially the entire dosage unit is available for immediate absorption or immediate distribution via the bloodstream. Preferred extended release formulations result in a level of circulating drug from a single administration that is sustained, for example, for 8 hours or more, 12 hours or more, 24 hours or more, 36 hours or more, 48 hours or more, 60 hours or more, 72 hours or more 84 hours or more, 96 hours or more, or even, for example, for 1 week or 2 weeks or more, for example, 1 month or more.

As used herein, a "CD40L activity" is an activity involving or resulting from the binding of CD40L to CD40, and includes, but is not limited to binding to CD40 (assayed, for example, according to the method described in Example 6), activation of Jun-N-terminal Kinase (JNK), the induction of T cells to produce and secrete cytokines including, for example, IL-10, IFN-γ and TNF-α, and the mediation of platelet activation and/or aggregation. Assays for these activities are provided herein below.

As used herein, the term "does not substantially agonize" means that a given agent, e.g., an anti-CD40L antibody polypeptide, does not activate one or more of the CD40L activities including Jun-N-terminal kinase activation (phosphorylation) in Jurkat T cells and induction of IFN-γ production or secretion in anti-CD3-stimulated Jurkat T cells, as the term "activate" is defined herein. As used herein, "does not substantially agonize" means that the agent does not activate more than 20% of the activity which is activated by CD40 binding to CD40L, preferably, the agent does not activate more than 10%, 8%, 5%, 3%, or more than 2% or less, including zero activation, of the activity which is activated by CD40 binding to CD40L.

As used herein, the term "antibody polypeptide" refers to a polypeptide which either is an antibody or is a part of an antibody, modified or unmodified, which retains the ability to specifically bind antigen. Thus, the term antibody polypeptide includes an antigen-binding heavy chain, light chain, heavy chain-light chain dimer, Fab fragment, F(ab')2 fragment, dAb, or an Fv fragment, including a single chain Fv (scFv). The phrase "antibody polypeptide" is intended to encompass recombinant fusion polypeptides that comprise an antibody polypeptide sequence that retains the ability to specifically bind antigen in the context of the fusion.

As used herein, the term "monovalent" means that a given antibody polypeptide or single immunoglobulin variable domain polypeptide can bind only a single molecule of its target. Naturally-occurring antibodies are generally divalent, in that they have two functional antigen-binding arms, each comprising a $V_H$ and a $V_L$ domain. Where steric hindrance is not an issue, a divalent antibody can bind two separate molecules of the same antigen. In contrast, a "monovalent" antibody has the capacity to bind only one such antigen molecule. As the term is used herein, a "monovalent" antibody can also comprise more than one antigen binding site, e.g., two antigen binding sites, but the binding sites must be for different antigens, such that the antibody can only bind one molecule of CD40L at a time. The antigen-binding domain of a monovalent antibody can comprise a $V_H$ and a $V_L$ domain, but preferably comprises only a single immunoglobulin variable domain, i.e., a $V_H$ or a $V_L$ domain, that has the capacity to bind CD40L without the need for a corresponding $V_L$ or $V_H$ domain, respectively. A monovalent antibody lacks the capacity to cross link molecules of a single antigen.

As used herein, the term "standard platelet aggregation assay" means the assay described in the section herein below, entitled "Platelet Aggregation Assay."

As used herein, the terms "$V_H$ domain" and "$V_L$ domain" refer to immunoglobulin variable regions as defined by Kabat et al. (supra), which is incorporated herein by reference.

As used herein, "linked" refers to the attachment of a polymer moiety, such as PEG to an amino acid residue of an antibody polypeptide. Attachment of a PEG polymer to an amino acid residue of an antibody polypeptide, e.g., an anti-CD40L dAb, is referred to as "PEGylation" and may be achieved using several PEG attachment moieties including, but not limited to N-hydroxylsuccinimide (NHS) active ester, succinimidyl propionate (SPA), maleimide (MAL), vinyl sulfone (VS), or thiol. A PEG polymer, or other polymer, can be linked to an antibody polypeptide at either a predetermined position, or may be randomly linked to the an antibody polypeptide molecule. It is preferred, however, that the PEG polymer be linked to an antibody polypeptide at a predetermined position. A PEG polymer may be linked to any residue in the an antibody polypeptide, however, it is preferable that the polymer is linked to either a lysine or cysteine, which is either naturally occurring in the antibody polypeptide, or which has been engineered into the antibody polypeptide, for example, by mutagenesis of a naturally occurring residue in the antibody polypeptide to either a cysteine or lysine. PEG-linkage can also be mediated through a peptide linker attached to an antibody polypeptide. That is, the PEG moiety can be attached to a peptide linker fused to an antibody polypeptide, where the linker provides the site, e.g., a free cysteine or lysine, for PEG attachment. As used herein, "linked" can also refer to the association of two or more antibody polypeptides, e.g., dAb monomers, to form a dimer, trimer, tetramer, or other multimer. Antibody polypeptide monomers can be linked to form a multimer by several methods known in the art, including, but not limited to, expression of the antibody polypeptide monomers as a fusion protein, linkage of two or more monomers via a peptide linker between monomers, or by chemically joining monomers after translation, either to each other directly, or through a linker by disulfide bonds, or by linkage to a di-, tri- or multivalent linking moiety (e.g., a multi-arm PEG). While dAb multimers are specifically contemplated herein, e.g., in the context of dual- or multi-specific antibody polypeptide constructs, it is emphasized that for any given antibody polypeptide construct, the construct should only be able to bind one molecule of CD40L, i.e., the constructs can have only one CD40L-binding element, and cannot cross link CD40L.

As used herein, "polymer" refers to a macromolecule made up of repeating monomeric units, and can refer to a synthetic or naturally occurring polymer such as an optionally substituted straight or branched chain polyalkylene, polyalkenylene, or polyoxyalkylene polymer or a branched or unbranched polysaccharide. A "polymer" as used herein, specifically refers to an optionally substituted or branched chain poly(ethylene glycol), poly(propylene glycol), or poly(vinyl alcohol) and derivatives thereof.

As used herein, "PEG" or "PEG polymer" refers to polyethylene glycol, and more specifically can refer to a derivatized form of PEG, including, but not limited to N-hydroxylsuccinimide (NHS) active esters of PEG such as succinimidyl propionate, benzotriazole active esters, PEG derivatized with maleimide, vinyl sulfones, or thiol groups. Particular PEG formulations can include PEG-O—$CH_2CH_2CH_2$—$CO_2$—NHS; PEG-O—$CH_2$—NHS; PEG-O—$CH_2CH_2$—$CO_2$—NHS; PEG-S—$CH_2CH_2$—CO—NHS; PEG-$O_2$CNH—CH(R)—$CO_2$—NHS; PEG-NHCO—$CH_2CH_2$—CO—NHS; and PEG-O—$CH_2$—$CO_2$—NHS; where R is $(CH_2)_4)NHCO_2$(mPEG). PEG polymers useful in the invention may be linear molecules, or may be branched wherein multiple PEG moieties are present in a single polymer. Some particularly preferred PEG conformations that are useful in the invention include, but are not limited to the following:

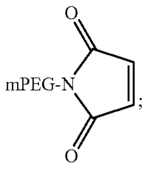

mPEG-MAL

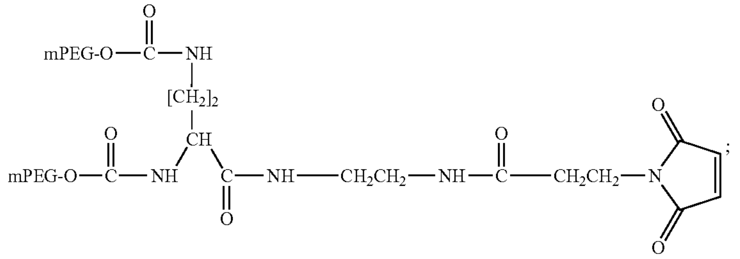

mPEG2-MAL

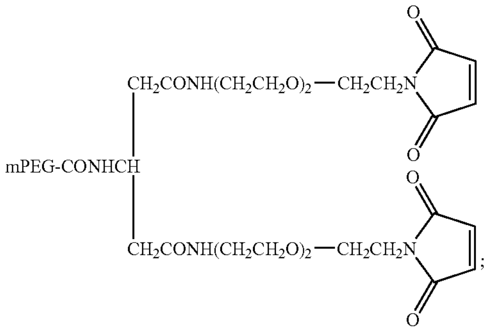

mPEG-(MAL)2

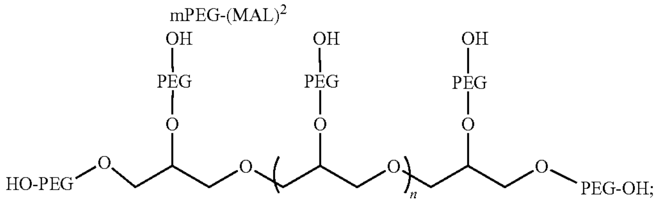

multi-arm PEG n = 0.4

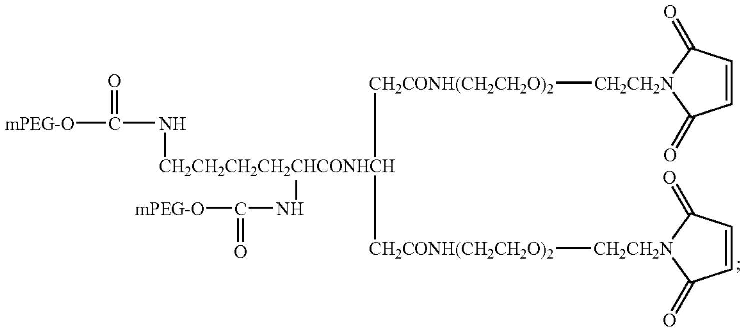

mPEG-(MAL)2

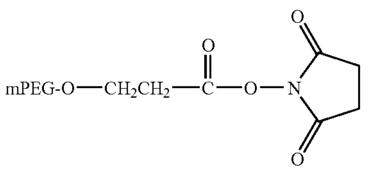

mPEG-SPA

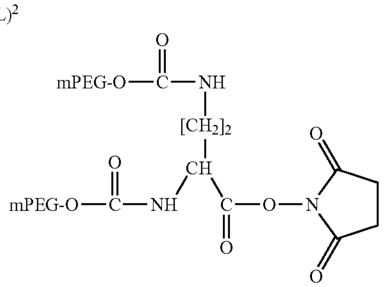

mPEG2-NHS

As used herein, a "sulfhydryl-selective reagent" is a reagent which is useful for the attachment of a PEG polymer to a thiol-containing amino acid. Thiol groups on the amino acid residue cysteine are particularly useful for interaction with a sulfhydryl-selective reagent. Sulfhydryl-selective reagents which are useful for such attachment include, but are not limited to maleimide, vinyl sulfone, and thiol. The use of sulfhydryl-selective reagents for coupling to cysteine residues is known in the art and may be adapted as needed according to the present invention (See Eg., Zalipsky, 1995, *Bioconjug. Chem.* 6:150; Greenwald et al., 2000, *Crit. Rev. Ther. Drug Carrier Syst.* 17:101; Herman et al., 1994, *Macromol. Chem. Phys.* 195:203).

The attachment of PEG or another agent, e.g., HSA, to an antibody polypeptide or to a single immunoglobulin variable domain polypeptide as described herein will preferably not impair the ability of the polypeptide to specifically bind CD40L. That is, the PEG-linked antibody polypeptide or single immunoglobulin variable domain polypeptide will retain its binding activity relative to a non-PEG-linked counterpart. As used herein, "retains activity" refers to a level of activity of a PEG-linked antibody polypeptide which is at least 10% of the level of activity of a non-PEG-linked antibody polypeptide, preferably at least 20%, 30%, 40%, 50%, 60%, 70%, 80% and up to 90%, preferably up to 95%, 98%, and up to 100% of the activity of a non-PEG-linked antibody polypeptide comprising the same antigen-binding domain or domains. More specifically, the activity of a PEG-linked antibody polypeptide compared to a non-PEG linked antibody variable domain should be determined on an antibody polypeptide molar basis; that is equivalent numbers of moles of each of the PEG-linked and non-PEG-linked antibody polypeptides should be used in each trial. In determining whether a particular PEG-linked antibody polypeptide "retains activity", it is preferred that the activity of a PEG-linked antibody polypeptide be compared with the activity of the same antibody polypeptide in the absence of PEG.

As used herein, the term "in vivo half-life" refers to the time taken for the serum concentration of a ligand (e.g., a single immunoglobulin variable domain) to reduce by 50%, in vivo, for example due to degradation of the ligand and/or clearance or sequestration of the ligand by natural mechanisms. The anti CD40L antibody polypeptides or single immunoglobulin variable domain polypeptides described herein can be stabilized in vivo and their half-life increased by binding to molecules, such as PEG, which resist degradation and/or clearance or sequestration. The half-life of an antibody polypeptide is increased if its functional activity persists, in vivo, for a longer period than a similar antibody polypeptide which is not linked to a PEG polymer. Typically, the half life of a PEGylated antibody polypeptide is increased by 10%, 20%, 30%, 40%, 50% or more relative to a non-PEGylated antibody polypeptide. Increases in the range of 2×, 3×, 4×, 5×, 10×, 20×, 30×, 40×, 50× or more of the half life are possible. Alternatively, or in addition, increases in the range of up to 30×, 40×, 50×, 60×, 70×, 80×, 90×, 100×, 150× of the half life are possible.

According to the invention, a PEG-linked antibody single variable domain has a half-life of between 0.25 and 170 hours, preferably between 1 and 100 hours, more preferably between 30 and 100 hours, and still more preferably between 50 and 100 hours, and up to 170, 180, 190, and 200 hours or more.

As used herein, "resistant to degradation" or "resists degradation" with respect to a PEG or other polymer-linked antibody polypeptide monomer or multimer means that the PEG- or other polymer-linked antibody polypeptide monomer or multimer is degraded by no more than 10% when exposed to pepsin at pH 2.0 for 30 minutes and preferably not degraded at all.

As used herein, "hydrodynamic size" refers to the apparent size of a molecule (e.g., a protein molecule) based on the diffusion of the molecule through an aqueous solution. The diffusion, or motion of a protein through solution can be processed to derive an apparent size of the protein, where the size is given by the "Stokes radius" or "hydrodynamic radius" of the protein particle. The "hydrodynamic size" of a protein depends on both mass and shape (conformation), such that two proteins having the same molecular mass may have differing hydrodynamic sizes based on the overall conformation of the protein. Hydrodynamic size is measured, for example, by size exclusion chromatography. The hydrodynamic size of a PEG-linked antibody polypeptide, e.g., a single immunoglobulin variable domain (including antibody variable domain multimers as described herein), can be in the range of 24 kDa to 500 kDa; 30 to 500 kDa; 40 to 500 kDa; 50 to 500 kDa; 100 to 500 kDa; 150 to 500 kDa; 200 to 500 kDa; 250 to 500 kDa; 300 to 500 kDa; 350 to 500 kDa; 400 to 500 kDa and 450 to 500 kDa. Preferably the hydrodynamic size of a PEGylated antibody polypeptide of the invention is 30 to 40 kDa; 70 to 80 kDa or 200 to 300 kDa. Where a single immunoglobulin variable domain polypeptide is desired for use in imaging applications, the polypeptide should have a hydrodynamic size of between 50 and 100 kDa. Alternatively, where a single immunoglobulin variable domain polypeptide is desired for therapeutic applications, the polypeptide preparation should have a hydrodynamic size of greater than 200 kDa.

As used herein, the term "$IC_{50}$" refers to the concentration of an inhibitor necessary to inhibit a given activity by 50%. $IC_{50}$ is determined by assaying a given activity, e.g., binding of CD40L to CD40, in the presence of varying amounts of the inhibitor (e.g., monovalent anti-CD40L antibody polypeptide), and plotting the inhibitor concentration versus the activity being targeted. Binding of CD40L to CD40 is measured herein by the method described in Example 6. Alternatively, SPR can be used.

As used herein, the term "fused to an antibody polypeptide" means that a polypeptide is fused to a given antibody through use of recombinant DNA techniques. Thus, an antibody "fused to" another polypeptide, e.g., to another antibody of different binding specificity, does not exist in nature and is generated through recombinant means. The term "fused to an antibody polypeptide" also encompasses the linkage of a polypeptide to a given antibody polypeptide through, for example, disulfide or other chemical linkages, where the fused polypeptide is not naturally found fused to the antibody polypeptide. Recombinant and chemical methods of fusing a polypeptide to another polypeptide, e.g., to an antibody, are well known in the art.

As used herein, the term "Fc domain" refers to the constant region antibody sequences comprising CH2 and CH3 constant domains as delimited according to Kabat et al., supra. The Fc portion of the heavy chain polypeptide has the ability to self-associate, a function which facilitates the formation of divalent antibodies. The term "lacks an Fc domain" means that a given antibody polypeptide lacks at least the portion of an immunoglobulin Fc domain (as such domains are defined according to Kabat et al., Supra) sufficient to mediate the dimerization of Fc-containing antibody polypeptides. Dimerization of Fc-containing antibody polypeptides is measured, for example, by chromatographic methods or by surface plasmon resonance. An antibody polypeptide lacking an Fc domain avoids Fc-platelet interactions and therefore avoids induction of platelet aggregation.

As used herein "treat", "reduce", "prevent", or "alleviate" as it relates to a symptom of disease refer to a decrease of the a symptom by at least 10% based on a clinically measurable parameter, or by at least one point on a clinically-accepted scale of disease or symptom severity. As used herein, the term "symptom of systemic lupus erythematosus" refers to any of the clinically relevant symptoms of SLE known to those of skill in the art. Non-limiting examples include the accumulation of IgG autoantibodies (e.g., against nuclear antigens such as chromatin, snRNPs (especially U1, Sm, Ro/SSA and La/SSB), phospholipids and cell surface molecules), hemolytic anemia, thrombocytopenia, leukopenia, glomerulonephritis, vasculitis, arthritis, and serositis). A reduction in such a symptom is a reduction by at least 10% in a clinically measurable parameter, or by at least one point on a clinically-accepted scale of disease severity.

As used herein, the phrase "specifically binds" refers to the binding of an antigen by an immunoglobulin variable domain with a dissociation constant ($K_d$) of 1 μM or lower as measured by surface plasmon resonance analysis using, for example, a BIAcore™ surface plasmon resonance system and BIAcore™ kinetic evaluation software (e.g., version 2.1). The affinity or $K_d$ for a specific binding interaction is preferably about 500 nM or lower, more preferably about 300 nM or lower.

As used herein, a "generic ligand" is a ligand that binds a substantial proportion of functional members in a given repertoire, e.g., in a phage display library. Thus, the same generic ligand can bind many members of the repertoire regardless of their target ligand specificities. In general, the presence of a functional generic ligand binding site indicates that the repertoire member is expressed and folded correctly. Thus, binding of the generic ligand to its binding site provides a method for preselecting functional polypeptides from a repertoire of polypeptides. Generic ligands include, for example, Protein A, Protein G and Protein L.

As used herein, the term "universal framework" refers to a single antibody framework sequence corresponding to the regions of an antibody conserved in sequence as defined by Kabat (supra) or corresponding to the human germline immunoglobulin repertoire or structure as defined by Chothia and Lesk, (1987) J. Mol. Biol. 196:910-917. The invention provides for the use of a single framework, or a set of such frameworks, which has been found to permit the derivation of virtually any binding specificity though variation in the hypervariable regions alone.

BRIEF DESCRIPTION OF THE FIGURES

FIG. 5 shows the sequence of the $V_H$ framework based on germline sequence DP47-JH4b (SEQ ID NO: 1, amino acid sequence; SEQ ID NO: 2, nucleotide sequence—both sense and antisense strands are shown—SEQ ID NO: 2 is the top strand (sense) and SEQ ID NO: 476 is the lower strand (antisense)). HCDRs 1-3 are indicated by underlining.

FIG. 6 shows the sequence of the $V_κ$ framework based on germline sequence DPK9-$J_K$1 (SEQ ID NO: 3, amino acid sequence; SEQ ID NO: 4, nucleotide sequence—both sense and antisense strands are shown—SEQ ID NO: 4 is the top strand (sense) and SEQ ID NO: 477 is the lower strand (antisense)). LCDRs 1-3 are indicated by underlining.

FIG. 8 shows various GAS1 secretion signal peptide coding sequences.

GAS wt: The natural occurring sequence in yeast. GAS *E. Coli*: The nucleotide sequence according to optimal *E. Coli* codon usage (Wada et al. 1992 NAR 20 p 2111). GAS leader AT: AT rich nucleotide sequence. All nucleotide sequences encode the same amino acid sequence. Yellow (light grey in greyscale) indicates nucleotides that are similar for all sequences. Blue (dark grey in greyscale) indicates nucleotides that are similar to the wt sequence. White (white in greyscale) indicates nucleotides that are different from the wt sequence.

Figure 9:
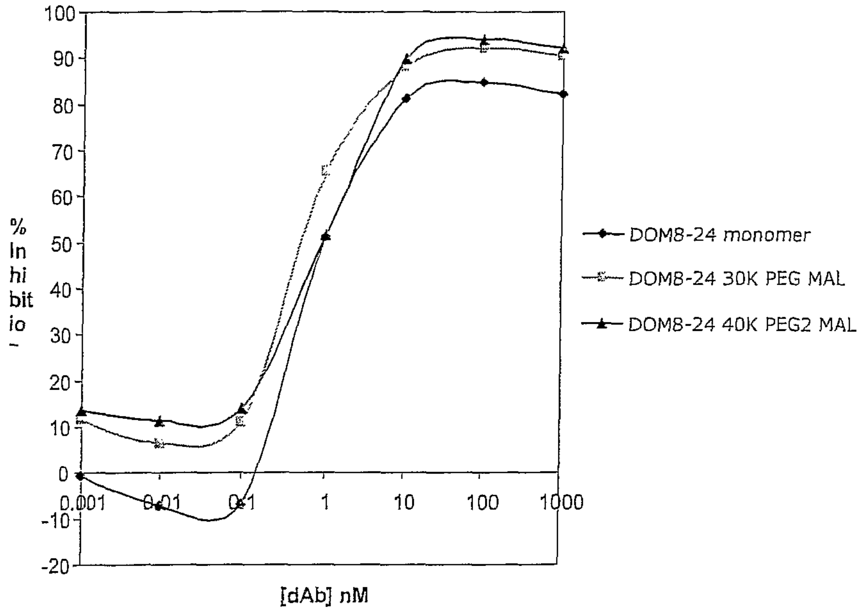

FIG. 9 shows the results of a receptor binding assay which demonstrates the affinity of PEGylated DOM8-24cys with either 30K PEG MAL or 40K PEG2-MAL.

Figure 10:
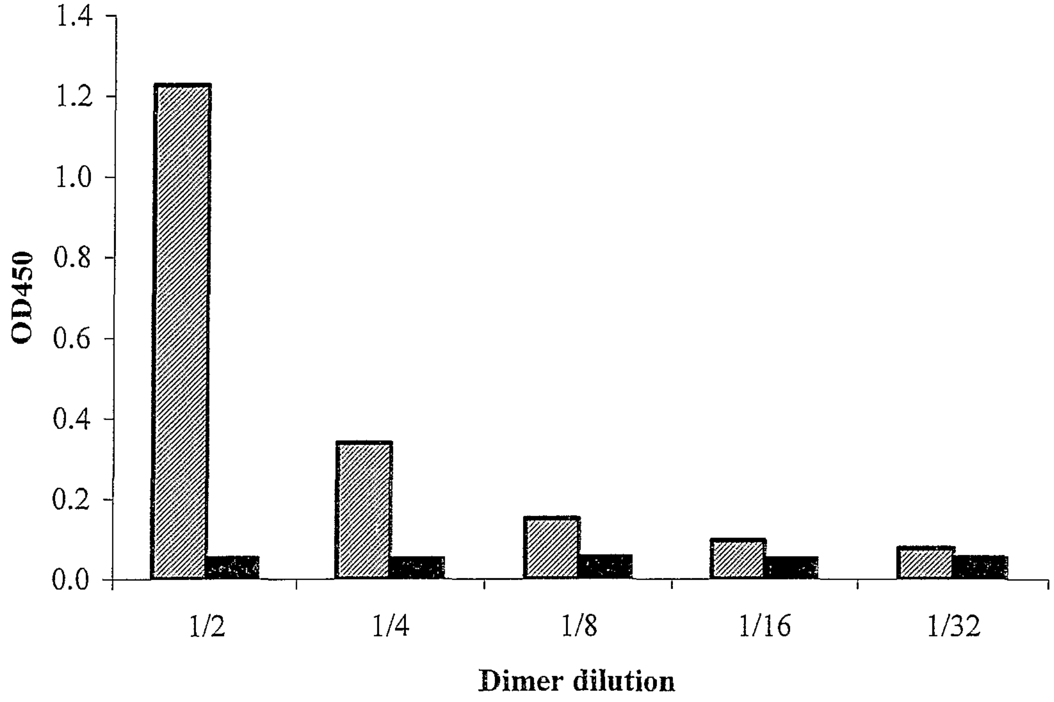

FIG. 10 shows the results of an assay to assess the simultaneous binding of a dual specific dimer to HSA and CD40L (shaded bars). Binding to control BSA antigen is also shown (solid bars).

Figure 11:
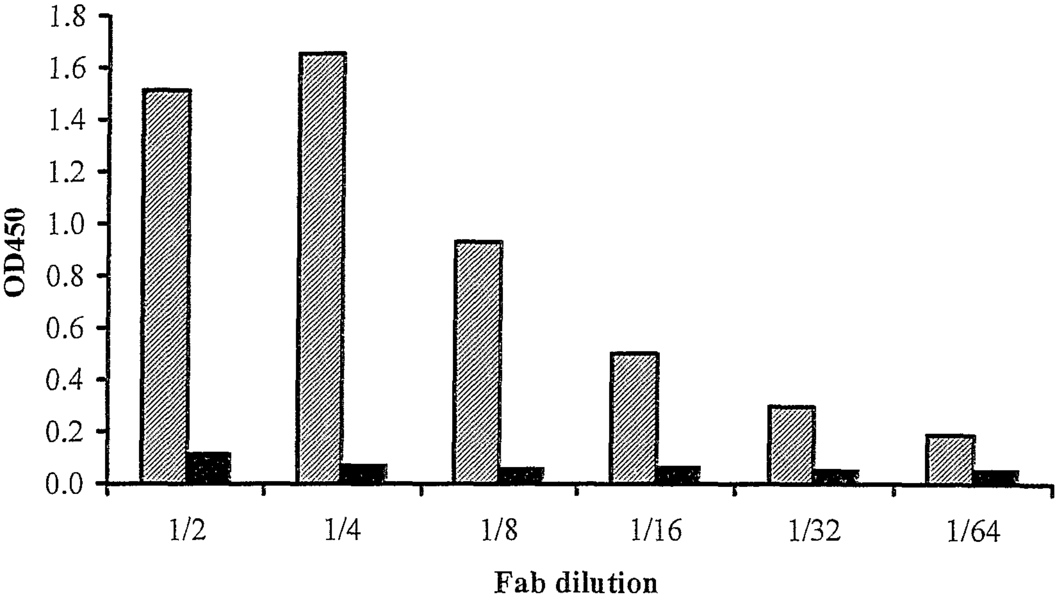

FIG. 11 shows the results of an assay to assess the simultaneous binding of a dual specific Fab to HSA and CD40L (shaded bars). Binding to control skimmed mild powder antigen is also shown (solid bars).

Figure 12:
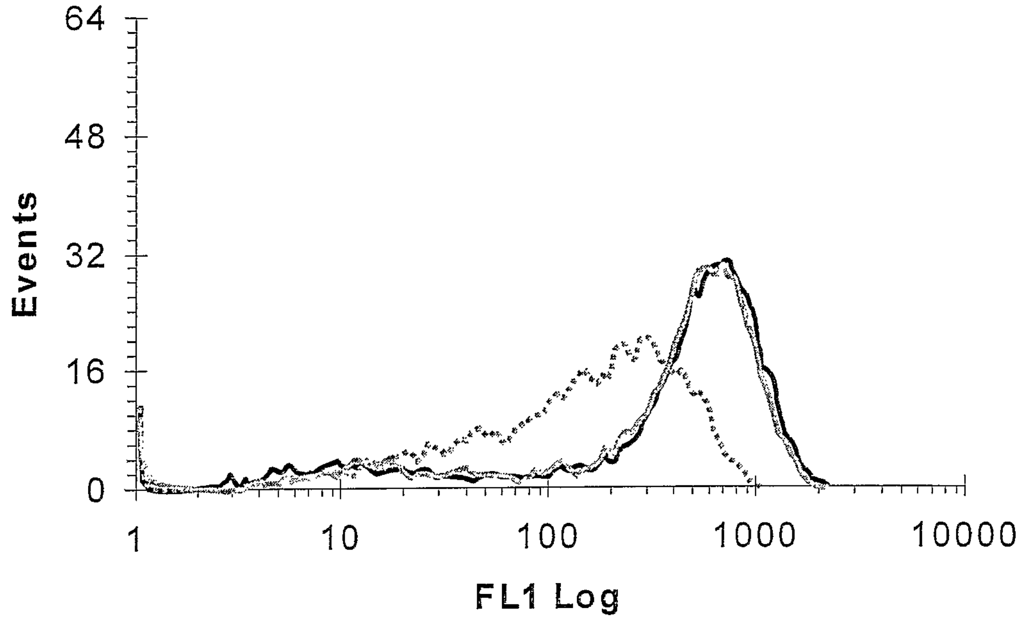

FIG. 12 shows the results of FACS analysis of the inhibitory effect of monomeric DOM-24 (grey dotted line). Control stimulated cells are shown as the solid black line and a control dAb is shown as the grey solid line.

Figure 13:
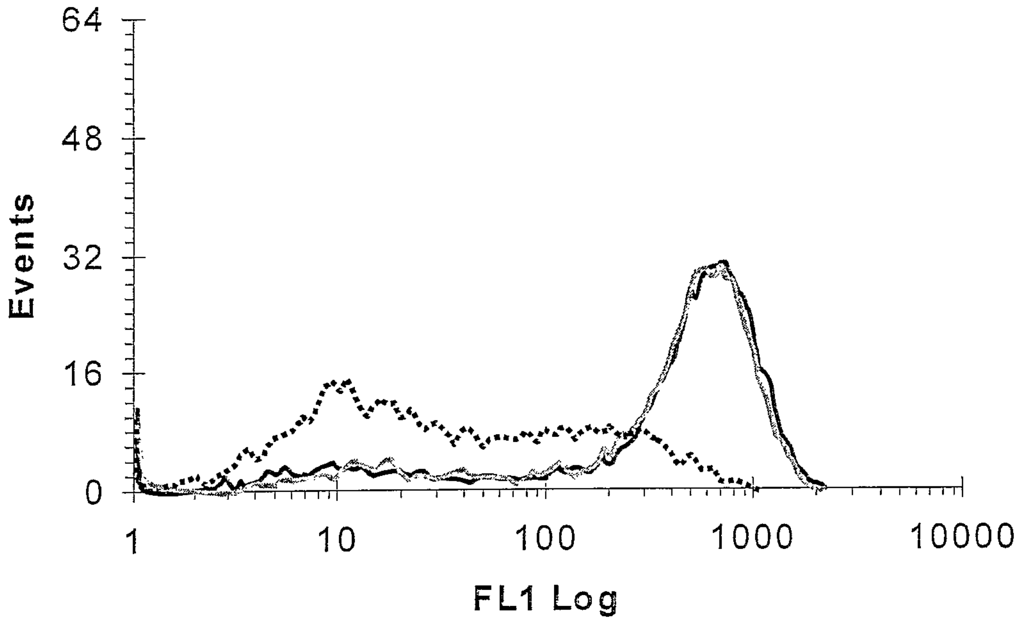

FIG. 13 shows the results of FACS analysis of the inhibitory effect of the Vk dAb DOM-116 (dotted line). Control stimulated cells are shown as the solid black line and a control dAb is shown as the grey solid line.

DETAILED DESCRIPTION

The invention provides antibody polypeptides that are monovalent for binding to CD40L. Monovalency for CD40L binding removes the possibility for cross-linking that occurs with prior art antibodies, and which plays a role in undesirable side effects observed with anti-CD40L monoclonal antibodies. Further, while not wishing to be limited to any specific mechanism or theory, because antibody polypeptides monovalent for CD40L cannot cross link CD40L, the possibility is eliminated that cross-linked CD40L may in turn cross-link cell surface CD40 and result in agonism of CD40 signaling activity. Thus, in a preferred aspect, the anti-CD40L antibodies disclosed herein not only inhibit or antagonize the binding of CD40L to CD40, they do not substantially agonize CD40 and/or CD40L activity.

In one aspect, the antibodies monovalent for CD40L binding are human antibody polypeptides. Human antibody polypeptides can be administered to human patients while largely avoiding the anti-antibody immune response often provoked by the administration of antibodies from other species, e.g., mouse. While murine antibodies can be "humanized" by grafting human constant domains onto the murine antigen-binding domains, human antibodies as disclosed herein are produced without the need for laborious and time-consuming genetic manipulation of a murine antibody sequence.

Monovalent Antibody Polypeptides:

The heavy and light polypeptide chains of antibodies comprise variable (V) regions that directly participate in antigen interactions, and constant (C) regions that provide structural support and function in non-antigen-specific interactions with immune effectors. The antigen binding domain of a conventional antibody is comprised of two separate domains: a heavy chain variable domain ($V_H$) and a light chain variable domain ($V_L$: which can be either $V_\kappa$ or $V_\lambda$). The antigen binding site itself is formed by six polypeptide loops: three from the $V_H$ domain (H1, H2 and H3) and three from the $V_L$ domain (L1, L2 and L3). In vivo, a diverse primary repertoire of V genes that encode the $V_H$ and $V_L$ domains is produced by the combinatorial rearrangement of gene segments. C regions include the light chain C regions (referred to as $C_L$ regions) and the heavy chain C regions (referred to as $C_H1$, $C_H2$ and $C_H3$ regions). A naturally-occurring antibody generally comprises two antigen binding domains and is therefore divalent.

A number of smaller antigen binding fragments of naturally occurring antibodies have been identified following protease digestion. These include, for example, the "Fab fragment" ($V_L$—$C_L$—$C_H1$-$V_H$), "Fab' fragment" (a Fab with the heavy chain hinge region), and "F(ab')$_2$ fragment" (a dimer of Fab' fragments joined by the heavy chain hinge region). Recombinant methods have been used to generate such fragments and to generate even smaller antigen-binding fragments, e.g., those referred to as "single chain Fv" (variable fragment) or "scFv," consisting of $V_L$ and $V_H$ joined by a synthetic peptide linker ($V_L$-linker-$V_H$). Fab fragments, Fab' fragments and scFv fragments are monovalent for antigen binding, as they each comprise only one antigen binding domain comprising one $V_H$/$V_L$ dimer. Even smaller monovalent antibody fragments are the "domain antibodies," or "dAbs," which comprise only a single immunoglobulin variable domain, e.g., $V_H$ or $V_L$, that alone specifically binds antigen, i.e., without the need for a complementary $V_L$ or $V_H$ domain, respectively.

The term "dAb" will refer herein to a single immunoglobulin variable domain ($V_H$ or $V_L$) polypeptide that specifically binds antigen. A "dAb" binds antigen independently of other V domains; however, a "dAb" can be present in a homo- or heteromultimer with other $V_H$ or $V_L$ domains where the other domains are not required for antigen binding by the dAb, i.e., where the dAb binds antigen independently of the additional $V_H$ or $V_L$ domains. The preparation of single immunoglobulin variable domains is described and exemplified herein below.

Monovalent antibody polypeptides can be generated in several different ways. For example, the nucleic acid sequence encoding heavy and light chains of an antibody known to bind CD40L can be manipulated to generate a number of different antibody polypeptides that are monovalent for CD40L binding. Thus, given the sequences encoding the heavy and light chain polypeptides that constitute an antibody and standard molecular cloning methodologies, one can generate monovalent antigen-binding polypeptide constructs such as Fab fragments, scFv, dAbs, or even bispecific antibodies (i.e., antibodies that comprise two different antigen-binding moieties and can therefore bind two separate antigens, preferably simultaneously) that are monovalent for CD40L.

Thus, one means of generating monovalent antibody polypeptides specific for CD40L is to amplify and express the $V_H$ and $V_L$ regions of the heavy chain and light chain gene sequences isolated, for example, from a hybridoma (e.g., a mouse hybridoma) that expresses anti-CD40L monoclonal antibody. The boundaries of $V_H$ and $V_L$ domains are set out by Kabat et al. (1991, supra). The information regarding the boundaries of the $V_H$ and $V_L$ domains of heavy and light chain genes is used to design PCR primers that amplify the V domain from a heavy or light chain coding sequence encoding an antibody known to bind CD40L. The amplified V domains are inserted into a suitable expression vector, e.g., pHEN-1 (Hoogenboom et al., 1991, Nucleic Acids Res. 19: 4133-4137) and expressed, e.g., as a fusion of the $V_H$ and $V_L$ in an scFv or other suitable monovalent format. The resulting polypeptide is then screened for high affinity monovalent binding to CD40L. For all aspects of the present invention, screening for binding is performed as known in the art or as described herein below.

Alternatively, library screening methods can be used to identify monovalent CD40L-specific binding proteins. Phage display technology (see, e.g., Smith, 1985, Science 228: 1315; Scott & Smith, 1990, Science 249: 386; McCafferty et al., 1990, Nature 348: 552) provides an approach for the selection of antibody polypeptides which bind a desired target from among large, diverse repertoires of antibody polypeptides. These phage-antibody libraries can be grouped into two categories: natural libraries which use rearranged V genes harvested from human B cells (Marks et al., 1991, J. Mol. Biol., 222: 581; Vaughan et al., 1996, Nature Biotech., 14: 309) or synthetic libraries whereby germline V gene segments or other antibody polypeptide coding sequences are 'rearranged' in vitro (Hoogenboom & Winter, 1992, J. Mol. Biol., 227: 381; Nissim et al., 1994, EMBO J., 13: 692; Griffiths et al., 1994, EMBO J., 13: 3245; De Kruif et al., 1995, J. Mol. Biol., 248: 97) or where synthetic CDRs are incorporated into a single rearranged V gene (Barbas et al., 1992. Proc. Natl. Acad. Sci. USA, 89: 4457). Methods involving genetic display packages (e.g., phage display, polysome display) are well-suited for the selection of monovalent CD40L-specific antibody constructs because they generally express only monovalent fragments, rather than whole, divalent antibodies, on the display packages. Methods for the preparation of phage display libraries displaying various antibody fragments are described in the preceding references. Such methods are also described, for example, in U.S. Pat. No. 6,696,245, which is incorporated herein by reference. The methods described in the '245 patent generally involve the randomization of selected regions of immunoglobulin gene coding regions, in particular $V_H$ and $V_L$ coding regions, while leaving other regions non-randomized (see below). The '245 patent also describes the generation of scFv constructs comprising individually randomized $V_H$ and $V_L$ domains.

The $V_H$ gene is produced by the recombination of three gene segments, $V_H$, D and $J_H$. In humans, there are approximately 51 functional $V_H$ segments (Cook and Tomlinson (1995) Immunol Today 16: 237), 25 functional D segments (Corbett et al. (1997) J. Mol. Biol. 268: 69) and 6 functional $J_H$ segments (Ravetch et al. (1981) Cell 27: 583), depending on the haplotype. The $V_H$ segment encodes the region of the polypeptide chain which forms the first and second antigen binding loops of the $V_H$ domain (H1 and H2), while the $V_H$, D and $J_H$ segments combine to form the third antigen binding loop of the $V_H$ domain (H3).

The $V_L$ gene is produced by the recombination of only two gene segments, $V_L$ and $J_L$. In humans, there are approximately 40 functional $V_\kappa$ segments (Schable and Zachau (1993) Biol.

Chem. Hoppe-Seyler 374: 1001), 31 functional $V_\lambda$ segments (Williams et al. (1996) J. Mol. Biol. 264: 220; Kawasaki et al. (1997) Genome Res. 7: 250), 5 functional $J_\kappa$ segments (Hieter et al. (1982) J. Biol. Chem. 257: 1516) and 4 functional $J_\lambda$, segments (Vasicek and Leder (1990) J. Exp. Med. 172: 609), depending on the haplotype. The $V_L$ segment encodes the region of the polypeptide chain which forms the first and second antigen binding loops of the $V_L$ domain (L1 and L2), while the $V_L$ and $J_L$ segments combine to form the third antigen binding loop of the $V_L$ domain (L3). Antibodies selected from this primary repertoire are believed to be sufficiently diverse to bind almost all antigens with at least moderate affinity. High affinity antibodies are produced in vivo by "affinity maturation" of the rearranged genes, in which point mutations are generated and selected by the immune system on the basis of improved binding.

Analysis of the structures and sequences of antibodies has shown that five of the six antigen binding loops (H1, H2, L1, L2, L3) possess a limited number of main-chain conformations or canonical structures (Chothia and Lesk (1987) J. Mol. Biol. 196: 901; Chothia et al. (1989) Nature 342: 877). The main-chain conformations are determined by (i) the length of the antigen binding loop, and (ii) particular residues, or types of residue, at certain key positions in the antigen binding loop and the antibody framework. Analysis of the loop lengths and key residues has enabled the prediction of the main-chain conformations of H1, H2, L1, L2 and L3 encoded by the majority of human antibody sequences (Chothia et al. (1992) J. Mol. Biol. 227: 799; Tomlinson et al. (1995) EMBO J. 14: 4628; Williams et al. (1996) J. Mol. Biol. 264: 220). Although the H3 region is much more diverse in terms of sequence, length and structure (due to the use of D segments), it also forms a limited number of main-chain conformations for short loop lengths which depend on the length and the presence of particular residues, or types of residue, at key positions in the loop and the antibody framework (Martin et al. (1996) J. Mol. Biol. 263: 800; Shirai et al. (1996) FEBS Letters 399: 1.

While, in one approach, diversity can be added to synthetic repertoires at any site in the CDRs of the various antigen-binding loops, this approach results in a greater proportion of V domains that do not properly fold and therefore contribute to a lower proportion of molecules with the potential to bind antigen. An understanding of the residues contributing to the main chain conformation of the antigen-binding loops permits the identification of specific residues to diversify in a synthetic repertoire of $V_H$ or $V_L$ domains. That is, diversity is best introduced in residues that are not essential to maintaining the main chain conformation. As an example, for the diversification of loop L2, the conventional approach would be to diversify all the residues in the corresponding CDR (CDR2) as defined by Kabat et al. (1991, supra), some seven residues. However, for L2, it is known that positions 50 and 53 are diverse in naturally occurring antibodies and are observed to make contact with the antigen. The preferred approach would be to diversify only those two residues in this loop. This represents a significant improvement in terms of the functional diversity required to create a range of antigen binding specificities.

Immunoglobulin polypeptide libraries can advantageously be designed to be based on predetermined variable domain main chain conformation. Such libraries may be constructed as described in International Patent Application WO 99/20749, the contents of which are incorporated herein by reference. Thus, in one aspect, an antibody polypeptide comprises the amino acid sequence of a given human germline V region gene segment, e.g., $V_H$ germline gene segment DP-47, or $V_\kappa$ germline gene segment DPK9. Such variable region polypeptides can be used for the production of scFvs or Fabs, e.g., an scFv or Fab comprising (i) an antibody heavy chain variable domain ($V_H$), or antigen binding fragment thereof, which comprises the amino acid sequence of germline $V_H$ segment DP-47 and (ii) an antibody light chain variable domain ($V_L$), or antigen binding fragment thereof, which comprises the amino acid sequence of germline $V_\kappa$ segment DPK9. Diversification of sequences within the context of the selected heavy and light chain germline gene segments, e.g., DP-47, DPK 9, DP45, DP38, etc. can generate a repertoire of diverse immunoglobulin coding sequences. One approach to diversification is described below in the context of generating a library of diversified dAb or scFv sequences. These variable region polypeptides can also be expressed as dAbs and screened for high affinity binding to CD40L. The repertoire can be cloned into or generated in a vector suitable for phage display, e.g., a lambda or filamentous bacteriophage display vector and is then screened for binding to a given target antigen, e.g., CD40L.

Preparation of Human Single Immunoglobulin Variable Domain Polypeptides:

A single immunoglobulin variable domain is a folded polypeptide domain which comprises sequences characteristic of immunoglobulin variable domains and which specifically binds an antigen (e.g., dissociation constant of 500 nM or less), and which binds antigen as a single variable domain; that is, there is one binding site provided by a single immunoglobulin variable domain without any complementary variable domain. A single immunoglobulin variable domain therefore includes complete antibody variable domains as well as modified variable domains, for example in which one or more loops have been replaced by sequences which are not characteristic of antibody variable domains or antibody variable domains which have been truncated or comprise N- or C-terminal extensions, as well as folded fragments of variable domains which retain a dissociation constant of 500 nM or less (e.g., 450 nM or less, 400 nM or less, 350 nM or less, 300 nM or less, 250 nM or less, 200 nM or less, 150 nM or less, 100 nM or less) and the target antigen specificity of the full-length domain. Preferably an antibody single variable domain useful in the invention is selected from the group of $V_H$ and $V_L$, including $V_{kappa}$ and $V_{lambda}$. The single immunoglobulin variable domains of use herein are preferably "human" as that term is defined herein.

Preparation of Single Immunoglobulin Variable Domains:

Single immunoglobulin variable domains are prepared in a number of ways. For each of these approaches, well-known methods of preparing (e.g., amplifying, mutating, etc.) and manipulating nucleic acid sequences are applicable.

One means of preparing single immunoglobulin variable domains is to amplify and express the $V_H$ or $V_L$ region of a heavy chain or light chain gene for a cloned antibody known to bind the desired antigen. That is, the $V_H$ or $V_L$ domain of a known anti-CD40L antibody coding region can be amplified and expressed as a single domain (or as a fusion of a single domain) and evaluated for binding to CD40L. The boundaries of $V_H$ and $V_L$ domains are set out by Kabat et al. (1991, supra). The information regarding the boundaries of the $V_H$ and $V_L$ domains of heavy and light chain genes is used to design PCR primers that amplify the V domain from a cloned heavy or light chain coding sequence encoding an antibody known to bind CD40L. The amplified V domain is inserted into a suitable expression vector, e.g., pHEN-1 (Hoogenboom et al., 1991, Nucleic Acids Res. 19: 4133-4137) and expressed, either alone or as a fusion with another polypeptide sequence.

In a preferred approach, a repertoire of $V_H$ or $V_L$ domains, preferably human $V_H$ or $V_L$ domains, is screened by, for example, phage display, panning against the desired antigen. Methods for the construction of bacteriophage display libraries and lambda phage expression libraries are well known in the art, and taught, for example, by: McCafferty et al., 1990, Nature 348: 552; Kang et al., 1991, Proc. Natl. Acad. Sci. U.S.A., 88: 4363; Clackson et al., 1991, Nature 352: 624; Lowman et al., 1991, Biochemistry 30: 10832; Burton et al., 1991, Proc. Natl. Acad. Sci. U.S.A. 88: 10134; Hoogenboom et al., 1991, Nucleic Acids Res. 19: 4133; Chang et al., 1991, J. Immunol. 147: 3610; Breitling et al., 1991, Gene 104: 147; Marks et al., 1991, J. Mol. Biol. 222: 581; Barbas et al., 1992, Proc. Natl. Acad. Sci. U.S.A. 89: 4457; Hawkins and Winter (1992) J. Immunol., 22: 867; Marks et al. (1992) J. Biol. Chem., 267: 16007; and Lerner et al. (1992) Science, 258: 1313. Fab phage display libraries are taught, for example, by U.S. Pat. No. 5,922,545. scFv phage libraries are taught, for example, by Huston et al., 1988, Proc. Natl. Acad. Sci. U.S.A. 85: 5879-5883; Chaudhary et al., 1990, Proc. Natl. Acad. Sci. U.S.A. 87: 1066-1070; McCafferty et al., 1990, supra; Clackson et al., 1991, supra; Marks et al., 1991, supra; Chiswell et al., 1992, Trends Biotech. 10: 80; and Marks et al., 1992, supra. Various embodiments of scFv libraries displayed on bacteriophage coat proteins have been described. Refinements of phage display approaches are also known, for example as described in WO96/06213 and WO92/01047 (Medical Research Council et al.) and WO97/08320 (Morphosys, supra).

The repertoire of $V_H$ or $V_L$ domains can be a naturally-occurring repertoire of immunoglobulin sequences or a synthetic repertoire. A naturally-occurring repertoire is one prepared, for example, from immunoglobulin-expressing cells harvested from one or more individuals. Such repertoires can be "naïve," i.e., prepared, for example, from human fetal or newborn immunoglobulin-expressing cells, or rearranged, i.e., prepared from, for example, adult human B cells. Natural repertoires are described, for example, by Marks et al., 1991, J. Mol. Biol. 222: 581 and Vaughan et al., 1996, Nature Biotech. 14: 309. If desired, clones identified from a natural repertoire, or any repertoire, for that matter, that bind the target antigen are then subjected to mutagenesis and further screening in order to produce and select variants with improved binding characteristics.

Synthetic repertoires of single immunoglobulin variable domains are prepared by artificially introducing diversity into a cloned V domain. Synthetic repertoires are described, for example, by Hoogenboom & Winter, 1992, J. Mol. Biol. 227: 381; Barbas et al., 1992, Proc. Natl. Acad. Sci. U.S.A. 89: 4457; Nissim et al., 1994, EMBO J. 13: 692; Griffiths et al., 1994, EMBO J. 13: 3245; DeKriuf et al., 1995, J. Mol. Biol. 248: 97; and WO 99/20749.

In one aspect, synthetic variable domain repertoires are prepared in $V_H$ or $V_\kappa$ backgrounds, based on artificially diversified germline $V_H$ or $V_\kappa$ sequences. For example, the $V_H$ domain repertoire can be based on cloned germline $V_H$ gene segments V3-23/DP47 (Tomlinson et al., 1992, J. Mol. Biol. 227: 7768) and JH4b. The $V_\kappa$ domain repertoire can be based, for example, on germline $V_\kappa$ gene segments O2/O12/DPK9 (Cox et al., 1994, Eur. J. Immunol. 24: 827) and $J_\kappa$1. Diversity is introduced into these or other gene segments by, for example, PCR mutagenesis. Diversity can be randomly introduced, for example, by error prone PCR (Hawkins, et al., 1992, J. Mol. Biol. 226: 889) or chemical mutagenesis. As discussed above, however it is preferred that the introduction of diversity is targeted to particular residues. It is further preferred that the desired residues are targeted by introduction of the codon NNK using mutagenic primers (using the TUPAC nomenclature, where N=G, A, T or C, and K=G or T), which encodes all amino acids and the TAG stop codon. Other codons which achieve similar ends are also of use, including the NNN codon (which leads to the production of the additional stop codons TGA and TAA), DVT codon ((A/G/T)(A/G/C)T), DVC codon ((A/G/T)(A/G/C)C), and DVY codon ((A/G/T)(A/G/C)(C/T). The DVT codon encodes 22% serine and 11% tyrosine, aspargine, glycine, alanine, aspartate, threonine and cysteine, which most closely mimics the distribution of amino acid residues for the antigen binding sites of natural human antibodies. Repertoires are made using PCR primers having the selected degenerate codon or codons at each site to be diversified. PCR mutagenesis is well known in the art.

In one aspect, diversity is introduced into the sequence of human germline $V_H$ gene segments V3-23/DP47 (Tomlinson et al., 1992, J. Mol. Biol. 227: 7768) and JH4b using the NNK codon at sites H30, H31, H33, H35, H50, H52, H52a, H53, H55, H56, H58, H95, H97 and H98, corresponding to diversity in CDRs 1, 2 and 3, with the numbering as used in U.S. Pat. No. 6,696,245.

In another aspect, diversity is also introduced into the sequence of human germline $V_H$ gene segments V3-23/DP47 and JH4b, for example, using the NNK codon at sites H30, H31, H33, H35, H50, H52, H52a, H53, H55, H56, H58, H95, H97, H98, H99, H100, H100a and H100b, corresponding to diversity in CDRs 1, 2 and 3, with the numbering as used in U.S. Pat. No. 6,696,245.

In another aspect, diversity is introduced into the sequence of human germline $V_\kappa$ gene segments O2/O12/DPK9 and $J_\kappa$1, for example, using the NNK codon at sites L30, L31, L32, L34, L50, L53, L91, L92, L93, L94 and L96, corresponding to diversity in CDRs 1, 2 and 3, with the numbering as used in U.S. Pat. No. 6,696,245.

Diversified repertoires are cloned into phage display vectors as known in the art and as described, for example, in WO 99/20749. In general, the nucleic acid molecules and vector constructs required for the performance of the present invention are available in the art and are constructed and manipulated as set forth in standard laboratory manuals, such as Sambrook et al. (1989). Molecular Cloning: A Laboratory Manual, Cold Spring Harbor, USA.

The manipulation of nucleic acids in the present invention is typically carried out in recombinant vectors. As used herein, "vector" refers to a discrete element that is used to introduce heterologous DNA into cells for the expression and/or replication thereof. Methods by which to select or construct and, subsequently, use such vectors are well known to one of skill in the art. Numerous vectors are publicly available, including bacterial plasmids, bacteriophage, artificial chromosomes and episomal vectors. Such vectors may be used for simple cloning and mutagenesis; alternatively, as is typical of vectors in which repertoire (or pre-repertoire) members of the invention are carried, a gene expression vector is employed. A vector of use according to the invention is selected to accommodate a polypeptide coding sequence of a desired size, typically from 0.25 kilobase (kb) to 40 kb in length. A suitable host cell is transformed with the vector after in vitro cloning manipulations. Each vector contains various functional components, which generally include a cloning (or "polylinker") site, an origin of replication and at least one selectable marker gene. If a given vector is an expression vector, it additionally possesses one or more of the following: enhancer element, promoter, transcription termination and signal sequences, each positioned in the vicinity of the cloning site, such that they are operatively linked to the gene encoding a polypeptide repertoire member according to the invention.

Both cloning and expression vectors generally contain nucleic acid sequences that enable the vector to replicate in one or more selected host cells. Typically in cloning vectors, this sequence is one that enables the vector to replicate independently of the host chromosomal DNA and includes origins of replication or autonomously replicating sequences. Such sequences are well known for a variety of bacteria, yeast and viruses. The origin of replication from the plasmid pBR322 is suitable for most Gram-negative bacteria, the 2 micron plasmid origin is suitable for yeast, and various viral origins (e.g. SV 40, adenovirus) are useful for cloning vectors in mammalian cells. Generally, the origin of replication is not needed for mammalian expression vectors unless these are used in mammalian cells able to replicate high levels of DNA, such as COS cells.

Advantageously, a cloning or expression vector also contains a selection gene also referred to as selectable marker. This gene encodes a protein necessary for the survival or growth of transformed host cells grown in a selective culture medium. Host cells not transformed with the vector containing the selection gene will therefore not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available in the growth media.

Because the replication of vectors according to the present invention is most conveniently performed in *E. coli*, an *E. coli-selectable* marker, for example, the β-lactamase gene that confers resistance to the antibiotic ampicillin, is of use. These can be obtained from *E. coli* plasmids, such as pBR322 or a pUC plasmid such as pUC18 or pUC19.

Expression vectors usually contain a promoter that is recognized by the host organism and is operably linked to the coding sequence of interest. Such a promoter may be inducible or constitutive. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences.

Promoters suitable for use with prokaryotic hosts include, for example, the β-lactamase and lactose promoter systems, alkaline phosphatase, the tryptophan (trp) promoter system and hybrid promoters such as the tac promoter. Promoters for use in bacterial systems will also generally contain a Shine-Dalgarno sequence operably linked to the coding sequence.

In libraries or repertoires as described herein, the preferred vectors are expression vectors that enable the expression of a nucleotide sequence corresponding to a polypeptide library member. Thus, selection is performed by separate propagation and expression of a single clone expressing the polypeptide library member or by use of any selection display system. As described above, a preferred selection display system uses bacteriophage display. Thus, phage or phagemid vectors can be used. Preferred vectors are phagemid vectors, which have an *E. coli* origin of replication (for double stranded replication) and also a phage origin of replication (for production of single-stranded DNA). The manipulation and expression of such vectors is well known in the art (Hoogenboom and Winter (1992) supra; Nissim et al. (1994) supra). Briefly, the vector contains a β-lactamase or other selectable marker gene to confer selectivity on the phagemid, and a lac promoter upstream of a expression cassette that consists (N to C terminal) of a pelB leader sequence (which directs the expressed polypeptide to the periplasmic space), a multiple cloning site (for cloning the nucleotide version of the library member), optionally, one or more peptide tags (for detection), optionally, one or more TAG stop codons and the phage protein pII. In one embodiment, the vector encodes, rather than the pelB leader sequence, a eukaryotic GAS1 leader sequence which serves to direct the secretion of the fusion polypeptide to the periplasmic space in *E. coli* or to the medium in eukaryotic cell systems. Using various suppressor and non-suppressor strains of *E. coli* and with the addition of glucose, iso-propyl thio-β-D-galactoside (IPTG) or a helper phage, such as VCS M13, the vector is able to replicate as a plasmid with no expression, produce large quantities of the polypeptide library member only, or produce phage, some of which contain at least one copy of the polypeptide-pIII fusion on their surface.

An example of a preferred vector is the pHEN1 phagemid vector (Hoogenboom et al., 1991, Nucl. Acids Res. 19: 4133-4137; sequence is available, e.g., as SEQ ID NO: 7 in WO 03/031611), in which the production of pIII fusion protein is under the control of the LacZ promoter, which is inhibited in the presence of glucose and induced with IPTG. When grown in -suppressor strains of *E. coli*, e.g., TG1, the gene III fusion protein is produced and packaged into phage, while growth in non-suppressor strains, e.g., HB2151, permits the secretion of soluble fusion protein into the bacterial periplasm and into the culture medium. Because the expression of gene III prevents later infection with helper phage, the bacteria harboring the phagemid vectors are propagated in the presence of glucose before infection with VCSM13 helper phage for phage rescue.

Construction of vectors according to the invention employs conventional ligation techniques. Isolated vectors or DNA fragments are cleaved, tailored, and re-ligated in the form desired to generate the required vector. If desired, sequence analysis to confirm that the correct sequences are present in the constructed vector is performed using standard methods. Suitable methods for constructing expression vectors, preparing in vitro transcripts, introducing DNA into host cells, and performing analyses for assessing expression and function are known to those skilled in the art. The presence of a gene sequence in a sample is detected, or its amplification and/or expression quantified by conventional methods, such as Southern or Northern analysis, Western blotting, dot blotting of DNA, RNA or protein, in situ hybridization, immunocytochemistry or sequence analysis of nucleic acid or protein molecules. Those skilled in the art will readily envisage how these methods may be modified, if desired.

Screening Single Immunoglobulin Variable Domains for Antigen Binding:

Following expression of a repertoire of single immunoglobulin variable domains on the surface of phage, selection is performed by contacting the phage repertoire with immobilized target antigen (e.g., CD40L and/or an epitope bound by DOM8-24), washing to remove unbound phage, and propagation of the bound phage, the whole process frequently referred to as "panning." This process is applicable to the screening of single immunoglobulin variable domains as well as other antibody fragments that can be expressed on a display library, e.g., scFv, Fab, etc. Alternatively, phage are pre-selected for the expression of properly folded member variants by panning against an immobilized generic ligand (e.g., protein A or protein L) that is only bound by folded members. This has the advantage of reducing the proportion of non-functional members, thereby increasing the proportion of members likely to bind a target antigen. Pre-selection with generic ligands is taught in WO 99/20749. The screening of phage antibody libraries is generally described, for example, by Harrison et al., 1996, Meth. Enzymol. 267: 83-109.

Screening is commonly performed using purified antigen immobilized on a solid support, for example, plastic tubes or wells, or on a chromatography matrix, for example Sepharose™ (Pharmacia). Screening or selection can also be performed on complex antigens, such as the surface of cells (Marks et al., 1993, BioTechnology 11: 1145; de Kruif et al., 1995, Proc. Natl. Acad. Sci. U.S.A. 92: 3938). Another alternative involves selection by binding biotinylated antigen in solution, followed by capture on streptavidin-coated beads.

In a preferred aspect, panning is performed by immobilizing antigen (generic or specific) on tubes or wells in a plate, e.g., Nunc MAXISORP™ immunotube 8 well strips. Wells are coated with 150 µl of antigen (100 µg/ml in PBS) and incubated overnight. The wells are then washed 3 times with PBS and blocked with 400 µl PBS-2% skim milk (2% MPBS) at 37° C. for 2 hr. The wells are rinsed 3 times with PBS and phage are added in 2% MPBS. The mixture is incubated at room temperature for 90 minutes and the liquid, containing unbound phage, is removed. Wells are rinsed 10 times with PBS-0.1% tween 20, and then 10 times with PBS to remove detergent. Bound phage are eluted by adding 200 µl of freshly prepared 100 mM triethylamine, mixing well and incubating for 10 min at room temperature. Eluted phage are transferred to a tube containing 100 µl of 1M Tris-HCl, pH 7.4 and vortexed to neutralize the triethylamine. Exponentially-growing *E. coli* host cells (e.g., TG1) are infected with, for example, 150 ml of the eluted phage by incubating for 30 min at 37° C. Infected cells are spun down, resuspended in fresh medium and plated in top agarose. Phage plaques are eluted or picked into fresh cultures of host cells to propagate for analysis or for further rounds of selection. One or more rounds of plaque purification are performed if necessary to ensure pure populations of selected phage. Other screening approaches are described by Harrison et al., 1996, supra.

Following identification of phage expressing a single immunoglobulin variable domain that binds a desired target, if a phagemid vector such as pHEN1 has been used, the variable domain fusion proteins are easily produced in soluble form by infecting non-suppressor strains of bacteria, e.g., HB2151 that permit the secretion of soluble gene III fusion protein. If a GAS1 secretion signal peptide is encoded by the vector, the fusion polypeptide can be secreted by eukaryotic (e.g., yeast or mammalian) or prokaryotic (e.g., *E. coli*) cells. Alternatively, the V domain sequence can be subcloned into an appropriate expression vector to produce soluble protein according to methods known in the art.

Purification and Concentration of Single Immunoglobulin Variable Domains:

Single immunoglobulin variable domain polypeptides or other monovalent antibody polypeptides secreted into the periplasmic space or into the medium of bacteria are harvested and purified according to known methods (Harrison et al., 1996, supra). Skerra & Pluckthun (1988, Science 240: 1038) and Breitling et al. (1991, Gene 104: 147) describe the harvest of antibody polypeptides from the periplasm, and Better et al. (1988, Science 240: 1041) describes harvest from the culture supernatant. For some antibody polypeptides, purification can also be achieved by binding to generic ligands, such as protein A or Protein L. Alternatively, the variable domains can be expressed with a peptide tag, e.g., the Myc, HA or 6X-His tags, which facilitates purification by affinity chromatography.

If necessary, monovalent anti-CD40L antibody polypeptides are concentrated by any of several methods well known in the art, including, for example, ultrafiltration, diafiltration and tangential flow filtration. The process of ultrafiltration uses semi-permeable membranes and pressure to separate molecular species on the basis of size and shape. The pressure is provided by gas pressure or by centrifugation. Commercial ultrafiltration products are widely available, e.g., from Millipore (Bedford, Mass.; examples include the Centricon™ and Microcon™ concentrators) and Vivascience (Hanover, Germany; examples include the Vivaspin™ concentrators). By selection of a molecular weight cutoff smaller than the target polypeptide (usually ⅓ to ⅙ the molecular weight of the target polypeptide, although differences of as little as 10 kD can be used successfully), the polypeptide is retained when solvent and smaller solutes pass through the membrane. Thus, a molecular weight cutoff of about 5 kD is useful for concentration of anti-CD40L single immunoglobulin variable domain polypeptides described herein.

Diafiltration, which uses ultrafiltration membranes with a "washing" process, is used where it is desired to remove or exchange the salt or buffer in a polypeptide preparation. The polypeptide is concentrated by the passage of solvent and small solutes through the membrane, and remaining salts or buffer are removed by dilution of the retained polypeptide with a new buffer or salt solution or water, as desired, accompanied by continued ultrafiltration. In continuous diafiltration, new buffer is added at the same rate that filtrate passes through the membrane. A diafiltration volume is the volume of polypeptide solution prior to the start of diafiltration—using continuous diafiltration, greater than 99.5% of a fully permeable solute can be removed by washing through six diafiltration volumes with the new buffer. Alternatively, the process can be performed in a discontinuous manner, wherein the sample is repeatedly diluted and then filtered back to its original volume to remove or exchange salt or buffer and ultimately concentrate the polypeptide. Equipment for diafiltration and detailed methodologies for its use are available, for example, from Pall Life Sciences (Ann Arbor, Mich.) and Sartorius AG/Vivascience (Hannover, Germany).

Tangential flow filtration (TFF), also known as "cross-flow filtration," also uses ultrafiltration membrane. Fluid containing the target polypeptide is pumped tangentially along the surface of the membrane. The pressure causes a portion of the fluid to pass through the membrane while the target polypeptide is retained above the filter. In contrast to standard ultrafiltration, however, the retained molecules do not accumulate on the surface of the membrane, but are carried along by the tangential flow. The solution that does not pass through the filter (containing the target polypeptide) can be repeatedly circulated across the membrane to achieve the desired degree of concentration. Equipment for TFF and detailed methodologies for its use are available, for example, from Millipore (e.g., the ProFlux M12™ Benchtop TFF system and the Pellicon™ systems), Pall Life Sciences (e.g., the Minim™ Tangential Flow Filtration system).

Protein concentration is measured in a number of ways that are well known in the art. These include, for example, amino acid analysis, absorbance at 280 nm, the "Bradford" and "Lowry" methods, and SDS-PAGE. The most accurate method is total hydrolysis followed by amino acid analysis by HPLC, concentration is then determined then comparison with the known sequence of the single immunoglobulin variable domain polypeptide. While this method is the most accurate, it is expensive and time-consuming. Protein determination by measurement of UV absorbance at 280 nm faster and much less expensive, yet relatively accurate and is preferred as a compromise over amino acid analysis. Absorbance at 280 nm was used to determine protein concentrations reported in the Examples described herein.

"Bradford" and "Lowry" protein assays (Bradford, 1976, Anal. Biochem. 72: 248-254; Lowry et al., 1951, J. Biol. Chem. 193: 265-275) compare sample protein concentration to a standard curve most often based on bovine serum albumin (BSA). These methods are less accurate, tending to underestimate the concentration of single immunoglobulin variable domains. Their accuracy could be improved, however, by using a $V_H$ or $V_\kappa$ single domain polypeptide as a standard.

An additional protein assay method is the bicinchoninic acid assay described in U.S. Pat. No. 4,839,295 (incorporated herein by reference) and marketed by Pierce Biotechnology (Rockford, Ill.) as the "BCA Protein Assay" (e.g., Pierce Catalog No. 23227).

The SDS-PAGE method uses gel electrophoresis and Coomassie Blue staining in comparison to known concentration standards, e.g., known amounts of a single immunoglobulin variable domain polypeptide. Quantitation can be done by eye or by densitometry.

Single human immunoglobulin variable domain antigen-binding polypeptides described herein retain solubility at high concentration (e.g., at least 4.8 mg (~400 μM) in aqueous solution (e.g., PBS), and preferably at least 5 mg/ml (~417 μM), 10 mg/ml (~833 μM), 20 mg/ml (~1.7 mM), 25 mg/ml (~2.1 mM), 30 mg/ml (~2.5 mM), 35 mg/ml (~2.9 mM), 40 mg/ml (~3.3 mM), 45 mg/ml (~3.75 mM), 50 mg/ml (~4.2 mM), 55 mg/ml (~4.6 mM), 60 mg/ml (~5.0 mM), 65 mg/ml (~5.4 mM), 70 mg/ml (~5.8 mM), 75 mg/ml (~6.3 mM), 100 mg/ml (~8.33 mM), 150 mg/ml (~12.5 mM), 200 mg/ml (~16.7 mM), 240 mg/ml (~20 mM) or higher). One structural feature that promotes high solubility is the relatively small size of the single immunoglobulin variable domain polypeptides. A full length conventional four chain antibody, e.g., IgG is about 150 kD in size. In contrast, single immunoglobulin variable domains, which all have a general structure comprising 4 framework (FW) regions and 3 CDRs, have a size of approximately 12 kD, or less than 1/10 the size of a conventional antibody. Similarly, single immunoglobulin variable domains are approximately ½ the size of an scFv molecule (~26 kD), and approximately ⅕ the size of a Fab molecule (~60 kD). It is preferred that the size of a single immunoglobulin variable domain-containing structure disclosed herein is 100 kD or less, including structures of, for example, about 90% or less, 80 kD or less, 70 kD or less, 60 kD or less, 50 kD or less, 40 kD or less, 301 kD or less, 20 kD or less, down to and including about 12 kD, or a single immunoglobulin variable domain in isolation.

The solubility of a polypeptide is primarily determined by the interactions of the amino acid side chains with the surrounding solvent. Hydrophobic side chains tend to be localized internally as a polypeptide folds, away from the solvent-interacting surfaces of the polypeptide. Conversely, hydrophilic residues tend to be localized at the solvent-interacting surfaces of a polypeptide. Generally, polypeptides having a primary sequence that permits the molecule to fold to expose more hydrophilic residues to the aqueous environment are more soluble than one that folds to expose fewer hydrophilic residues to the surface. Thus, the arrangement and number of hydrophobic and hydrophilic residues is an important determinant of solubility. Other parameters that determine polypeptide solubility include solvent pH, temperature, and ionic strength. In a common practice, the solubility of polypeptides can be maintained or enhanced by the addition of glycerol (e.g., 10% v/v) to the solution.

As discussed above, specific amino acid residues have been identified in conserved residues of human $V_H$ domains that vary in the $V_H$ domains of camelid species, which are generally more soluble than human $V_H$ domains. These include, for example, Gly 44 (Glu in camelids), Leu 45 (Arg in camelids) and Trp 47 (Gly in camelids). Amino acid residue 103 of $V_H$ is also implicated in solubility, with mutation from Trp to Arg tending to confer increased $V_H$ solubility.

In preferred aspects of the invention, single immunoglobulin variable domain polypeptides are based on the DP47 germline $V_H$ gene segment or the DPK9 germline $V_\kappa$ gene segment. Thus, these germline gene segments are capable, particularly when diversified at selected structural locations described herein, of producing specific binding single immunoglobulin variable domain polypeptides that are highly soluble. In particular, the four framework regions, which are preferably not diversified, can contribute to the high solubility of the resulting proteins.

It is expected that a single human immunoglobulin variable domain that is highly homologous to one having a known high solubility will also tend to be highly soluble. Thus, as one means of prediction or recognition that a given single immunoglobulin variable domain would have the high solubility recited herein, one can compare the sequence of a single immunoglobulin variable domain polypeptide to one or more single immunoglobulin variable domain polypeptides having known solubility. Thus, when a single immunoglobulin variable domain polypeptide is identified that has high binding affinity but unknown solubility, comparison of its amino acid sequence with that of one or more (preferably more) human single immunoglobulin variable domain polypeptides known to have high solubility (e.g., a dAb sequence disclosed herein) can permit prediction of its solubility. While it is not an absolute predictor, where there is a high degree of similarity to a known highly soluble sequence, e.g., 90-95% or greater similarity, and particularly where there is a high degree of similarity with respect to hydrophilic amino acid residues, or residues likely to be exposed at the solvent interface, it is more likely that a newly identified binding polypeptide will have solubility similar to that of the known highly soluble sequence.

Molecular modeling software can also be used to predict the solubility of a polypeptide sequence relative to that of a polypeptide of known solubility. For example, the substitution or addition of a hydrophobic residue at the solvent-exposed surface, relative to a molecule of known solubility that has a less hydrophobic or even hydrophilic residue exposed in that position is expected to decrease the relative solubility of the polypeptide. Similarly, the substitution or addition of a more hydrophilic residue at such a location is expected to increase the relative solubility. That is, a change in the net number of hydrophilic or hydrophobic residues located at the surface of the molecule (or the overall hydrophobic or hydrophilic nature of the surface-exposed residues) relative to a single immunoglobulin variable domain polypeptide structure with known solubility can predict the relative solubility of a single immunoglobulin variable domain polypeptide.

Alternatively, or in conjunction with such prediction, one can determine limits of a single immunoglobulin variable domain polypeptide's solubility by simply concentrating the polypeptide.

Affinity Determination:

Isolated single immunoglobulin variable domain- and antibody polypeptide-containing polypeptides as described herein preferably have affinities (dissociation constant, $K_d$, $=K_{off}/K_{on}$) of at least 500 nM or less, and preferably at least 400 nM-50 pM, 300 nM-50 pM, 200 nM-50 pM, and more preferably at least 100 nM-50 pM, 75 nM-50 pM, 50 nM-50 pM, 25 nM-50 pM, 10 nM-50 pM, 5 nM-50 pM, 1 nM-50 pM, 950 pM-50 pM, 900 pM-50 pM, 850 pM-50 pM, 800 pM-50 pM, 750 pM-50 pM, 700 pM-50 pM, 650 pM-50 pM, 600 pM-50 pM, 550 pM-50 pM, 500 pM-50 pM, 450 pM-50 pM, 400 pM-50 pM, 350 pM-50 pM, 300 pM-50 pM, 250 pM-50 pM, 200 pM-50 pM, 150 pM-50 pM, 100 pM-50 pM, 90 pM-50 pM, 80 pM-50 pM, 70 pM-5 pM, 60 pM-5 pM, or even as low as 50 pM.

The antigen-binding affinity of an antibody polypeptide, e.g., a single immunoglobulin variable domain polypeptide or other monovalent antibody polypeptide, can be conveniently measured by SPR using the BLAcore system (Pharmacia Biosensor, Piscataway, N.J.). In this method, antigen is coupled to the BLAcore chip at known concentrations, and variable domain polypeptides are introduced. Specific binding between the variable domain polypeptide and the immobilized antigen results in increased protein concentration on the chip matrix and a change in the SPR signal. Changes in SPR signal are recorded as resonance units (RU) and displayed with respect to time along the Y axis of a sensorgram. Baseline signal is taken with solvent alone (e.g., PBS) passing over the chip. The net difference between baseline signal and signal after completion of antibody polypeptide injection represents the binding value of a given sample. To determine the off rate ($K_{off}$), on rate ($K_{on}$) and dissociation rate ($K_d$) constants, BIAcore kinetic evaluation software (e.g., version 2.1) is used.

Thus, SPR can be used to monitor antagonism of CD40L binding to CD40 by a monovalent anti-CD40L antibody preparation by measuring the displacement or inhibition of binding of CD40L to CD40 caused the monovalent antibody preparation. SPR can also be used to monitor the dimerization, or preferably, the lack of dimerization, occurring via Fc region in antibody preparations as described herein.

High affinity is dependent upon the complementarity between a surface of the antigen and the CDRs of the antibody or antibody fragment. Complementarity is determined by the type and strength of the molecular interactions possible between portions of the target and the CDR, for example, the potential ionic interactions, van der Waals attractions, hydrogen bonding or other interactions that can occur. CDR3 tends to contribute more to antigen binding interactions than CDRs 1 and 2, probably due to its generally larger size, which provides more opportunity for favorable surface interactions. (See, e.g., Padlan et al., 1994, Mol. Immunol. 31: 169-217; Chothia & Lesk, 1987, J. Mol. Biol. 196: 904-917; and Chothia et al., 1985, J. Mol. Biol. 186: 651-663.) High affinity indicates antibody polypeptide/antigen pairings that have a high degree of complementarity, which is directly related to the structures of the variable domain and the target.

In one aspect, a monovalent anti-CD40L antibody polypeptide, e.g., a single immunoglobulin variable domain polypeptide, is linked to another antibody polypeptide to form a heterodimer in which each individual antibody polypeptide is capable of binding a different cognate antigen. Fusing antibody polypeptides, such as single immunoglobulin variable domains, as heterodimers, wherein each monomer binds a different target antigen, can produce a dual-specific ligand capable, for example, of bridging the respective target antigens. Such dual specific ligands may be used to target cytokines and other molecules which cooperate synergistically in therapeutic situations in the body of an organism. Thus, there is provided a method for synergising the activity of two or more cytokines, comprising administering a dual specific antibody heterodimer capable of binding to the two or more cytokines.

Non-limiting examples of second targets for anti-CD40L dual specific antibody polypeptides include the following: TNF-α; IL-1; IL-2; IL-4; IL-6; IL-8; IL-12; IL-18; IFN-γ; CD2; CD4; CD8; CTLA4; LFA1; LFA3, VLA4, CD80, B7-1, CD28, CD86, B7-2, and CTLA-4. In particular, second targets useful according to the invention include CD80, B7-1, CD28, CD86, B7-2, and CTLA-4. These targets are thought to be involved in a co-stimulatory pathway critical for T-cell activation (termed, co-stimulatory signal pathway antigens). This pathway includes activation of the molecule CD28 on the surface of T cells. This molecule can receive a costimulatory signal delivered by a ligand on B cells or other APCs. Ligands for CD28 include members of the B7 family of B lymphocyte activation antigens, such as B7-1 and/or B7-2 (Freedman, A. S. et al. (1987) J. Immunol. 137, 3260-3267; Freeman, G. J. et al. (1989) J. Immunol. 143, 2714-2722; Freeman, G. J. et al. (1991) J. Exp. Med. 174, 625-631; Freeman, G. J. et al. (1993) Science 262, 909-911; Azuma, M. et al. (1993) Nature 366, 76-79; Freeman, G. J. et al. (1993) J. Exp. Med. 178, 2185-2192). B7-1 and B7-2 are also ligands for another molecule, CTLA4, present on the surface of activated T cells. Accordingly, the present invention contemplates that members of the CD28 signalling pathway may be useful second targets for the dual-specific format anti-CD40L antibody polypeptides.

Homologous Sequences:

The invention encompasses anti-CD40L antibody polypeptides, e.g., CD40L-binding single immunoglobulin variable domain clones, and clones with substantial sequence similarity or homology to them that also bind target antigen with high affinity. As used herein, "substantial" sequence similarity or homology is at least 85% similarity or homology.

Calculations of "homology" or "sequence identity" between two sequences (the terms are equivalent and used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "homology" is equivalent to amino acid or nucleic acid "identity"). The percent identity between the two sequences is a function of the number of identical positions shared by the sequences, taking into account the number of gaps, and the length of each gap, which need to be introduced for optimal alignment of the two sequences.

As used herein, sequence "similarity" is a measure of the degree to which amino acid sequences share similar amino acid residues at corresponding positions in an alignment of the sequences. Amino acids are similar to each other where their side chains are similar. Specifically, "similarity" encompasses amino acids that are conservative substitutes for each other. A "conservative" substitution is any substitution that has a positive score in the blosum62 substitution matrix (Hentikoff and Hentikoff, 1992, Proc. Natl. Acad. Sci. USA 89: 10915-10919). By the statement "sequence A is n % similar to sequence B" is meant that n % of the positions of an optimal global alignment between sequences A and B consists of identical amino acids or conservative substitutions. Optimal global alignments can be performed using the following parameters in the Needleman-Wunsch alignment algorithm:

For Polypeptides:

Substitution matrix: blosum62.

Gap scoring function: -A-B*LG, where A=11 (the gap penalty), B=1 (the gap length penalty) and LG is the length of the gap.

For Nucleotide Sequences:

Substitution matrix: 10 for matches, 0 for mismatches.

Gap scoring function: -A-B*LG where A=50 (the gap penalty), B=3 (the gap length penalty) and LG is the length of the gap.

Typical conservative substitutions are among Met, Val, Leu and Ile; among Ser and Thr; among the residues Asp, Glu and Asn; among the residues Gln, Lys and Arg; or aromatic residues Phe and Tyr. In calculating the degree (most often as a percentage) of similarity between two polypeptide sequences, one considers the number of positions at which identity or similarity is observed between corresponding amino acid residues in the two polypeptide sequences in relation to the entire lengths of the two molecules being compared.

Alternatively, the BLAST (Basic Local Alignment Search Tool) algorithm is employed for sequence alignment, with parameters set to default values. The BLAST algorithm "BLAST 2 Sequences" is available at the world wide web site ("www") of the National Center for Biotechnology Information (".ncbi"), of the National Library of Medicine (".nim") of the National Institutes of Health ("nih") of the U.S. government (".gov"), in the "/blast/" directory, sub-directories "bl2seq/bl2.html." This algorithm aligns two sequences for comparison and is described by Tatusova & Madden, 1999, FEMS Microbiol Lett. 174:247-250.

An additional measure of homology or similarity is the ability to hybridize under highly stringent hybridization conditions. Thus, a first sequence encoding a single immunoglobulin variable domain polypeptide is substantially similar to a second coding sequence if the first sequence hybridizes to the second sequence (or its complement) under highly stringent hybridization conditions (such as those described by Sambrook et al., Molecular Cloning, Laboratory Manuel, Cold Spring, Harbor Laboratory press, New York). "Highly stringent hybridization conditions" refer to hybridization in 6×SSC at about 45° C., followed by one or more washes in 0.2×SSC, 0.1% SDS at 65° C. "Very highly stringent hybridization conditions" refer to hybridization in 0.5M sodium phosphate, 7% SDS at 65° C., followed by one or more washes at 0.2×SSC, 1% SDS at 65° C.

Assays for CD40L Activities:

It is preferred that a monovalent anti-CD40L antibody polypeptides as described herein bind to CD40L yet do not substantially agonize CD40 signaling. Activation of the CD40L/CD40 pathway manifests a number of different outcomes that can be measured in order to assess the effect of a given monovalent anti-CD40L antibody polypeptide on the activity of the pathway. However, for the assessment of the antagonist or agonist function of monovalent anti-CD40L antibody polypeptides described herein, at least one of the following CD40L assays can be used:

1) Activation of Jun-N-Terminal Kinase (JNK):

Stimulation of T-lymphocytes via CD40L induces strong activation of JNK. The ability of a monovalent anti-CD40L antibody polypeptide to activate this signaling pathway is measured as follows. Human leukemic Jurkat cells are stimulated with a positive control agonistic anti-CD40L antibody (2 μg/ml monoclonal anti-human or anti-mouse gp39/CD40L antibody (Pharmingen, San Diego, Calif., USA) or isotype matched hamster or mouse immunoglobulins (Dianova, Hamburg, Germany)), monovalent anti-CD40L antibody polypeptide, or a negative control irrelevant antibody as described by Brenner et al., 1997, FEBS Lett. 417: 301-306, which is incorporated herein by reference. The cells are lysed and the extract assayed for phosphorylated JNK via colorimetric assay (e.g., Titerzyme™ colorimetric (EIA) phospho-JNK1/2 immunoassay kit, by Assay Designs Inc., Catalog #900-106). An increase in phospho-JNK (e.g., by 5% or more) for anti-CD40L-stimulated cells over non-stimulated cells indicates agonism of CD40L activity by the antibody polypeptide.

2. Induction of Cytokine Secretion:

Co-stimulation of T cells with anti-CD3 Ab and CD40L has been shown to upregulate the production of IL-10, IFN-γ and TNF-α by those cells. The ability of a monovalent anti-CD40L antibody polypeptide to activate this signaling pathway is measured as follows. Human leukemic Jurkat T cells (or freshly isolated CD4+ T cells) are plated into 96 well plates containing immobilized anti-CD3 antibody. The cells are then cultured for 72 hours in the presence of a positive control agonistic anti-CD40L antibody, CD40L, monovalent anti-CD40L antibody polypeptide, or a negative control irrelevant antibody, as described by Blair et al., 2000, J. Exp. Med. 191: 651-660. IFN-γ (or IL-10 of TNF-α) is then quantitated in the supernatant by sandwich ELISA using an IFN-g standard to generate a standard curve from which all other unknowns can be calculated. An increase in IFN-g (e.g., by 5% or more) for anti-CD40L-stimulated cells over non-stimulated cells indicates agonism by the antibody polypeptide.

3. Platelet Aggregation Assay:

Divalent anti-CD40L antibodies tend to cause platelet aggregation, which is likely associated with the thromboembolic events observed in clinical trials of divalent anti-CD40L antibodies in the prior art. Monovalent anti-CD40L antibody polypeptides as described herein preferably do not substantially mediate or agonize CD40L-mediated platelet aggregation. With regard to this aspect, the "standard platelet aggregation assay" is as follows:

Platelets are prepared at $2.5\times10^5$/ml and left stirring in a 500-Ca lumi-aggregometer (or its equivalent, e.g., a Platelet Aggregation Profiler (BioData, Horsham, Pa.)). Platelets are partially activated by the addition of a dilution series of 0.1-10 μM ADP (the 10 μM ADP induces aggregation, and is used as a positive control—lower concentrations activate platelets but do not induce aggregation). CD40L mediated platelet aggregation is stimulated by addition of either anti-CD40L monoclonal antibodies (i.e., divalent monoclonal antibodies, available from, e.g., Pharmingen, San Diego, Calif., USA) or soluble CD40/Fc fusion protein (available from R&D Systems). The reaction is allowed to proceed for between 3 and 5 minutes. Stimulation of platelet aggregation above the minimal aggregation/activation achieved with ADP alone is plotted against stimulating anti-CD40L or CD40/Fc concentration. The percentage of platelet aggregation is measured by the change in light transmittance following addition of antibody polypeptide being tested or positive control peptide. A value greater than that observed for negative control lacking antibody and amounting to 25% or more of the positive control value (divalent anti-CD40L or CD40/Fc fusion) is considered to be indicative of induction of platelet aggregation.

Other methods to assess platelet aggregation and/or activation, including events which precede aggregation, or which are downstream from platelet aggregation, include assays which determine various indicators of platelet activation, and are known in the art. For example, platelet activation (and, thus, CD40/CD40L activity) can be determined by assaying for CD62P expression in platelets (e.g., using anti-CD26P antibodies and flow cytometry), assaying for monocyte-platelet-conjugate formation, assaying for platelet closure time under high shear conditions (e.g., using a PFA-100, Dade Behring, Newark, Del.), and assaying for platelet dense granule release. Methods for performing such assays are known in the art and can be found, for example, in Langer et al., 2005 Thromb. Haemost. 93: 1137-46.

PEGylation of Monovalent Anti-CD40L Antibody Polypeptides

The present invention provides PEGylated monovalent anti-CD40L antibody polypeptides which have increased half-life and preferably also resistance to degradation without a loss in activity (e.g., binding affinity) relative to non-PEGylated antibody polypeptides.

Monovalent anti-CD40L antibody polypeptides according to this aspect can be coupled, using methods known in the art to polymer molecules (preferably PEG) useful for achieving the increased half-life and degradation resistance properties encompassed by the present invention. Polymer moieties which can be utilized in the invention can be synthetic or naturally occurring and include, but are not limited to straight or branched chain polyalkylene, polyalkenylene or polyoxyalkylene polymers, or a branched or unbranched polysaccharide such as a homo- or heteropolysaccharide. Preferred examples of synthetic polymers which may be used in the invention include straight or branched chain poly(ethylene glycol) (PEG), poly(propylene glycol), or poly(vinyl alcohol) and derivatives or substituted forms thereof. Particularly preferred substituted polymers useful in the invention include substituted PEG, including methoxy(polyethylene glycol). Naturally occurring polymer moieties which may be used according to the invention in addition to or in place of PEG include lactose, amylose, dextran, or glycogen, as well as derivatives thereof which would be recognized by one of skill in the art. Derivatized forms of polymer molecules of the invention include, for example, derivatives which have additional moieties or reactive groups present therein to permit interaction with amino acid residues of the dAb polypeptides described herein. Such derivatives include N-hydroxylsuccinimide (NHS) active esters, succinimidyl propionate polymers, and sulfhydryl-selective reactive agents such as maleimide, vinyl sulfone, and thiol. Particularly preferred derivatized polymers include, but are not limited to PEG polymers having the formulae: PEG-O—$CH_2CH_2CH_2$—$CO_2$—NHS; PEG-O—$CH_2$—NHS; PEG-O—$CH_2CH_2$—$CO_2$—NHS; PEG-S—$CH_2CH_2$—CO—NHS; PEG-$O_2$CNH—CH(R)—$CO_2$—NHS; PEG-NHCO—$CH_2CH_2$—CO—NHS; and PEG-O—$CH_2$—$CO_2$—NHS; where R is $(CH_2)_4)NHCO_2$(mPEG). PEG polymers useful in the invention may be linear molecules, or may be branched wherein multiple PEG moieties are present in a single polymer. Some particularly preferred PEG derivatives which are useful in the invention include, but are not limited to the following:

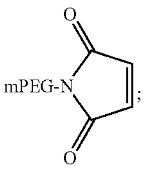

mPEG-MAL

;

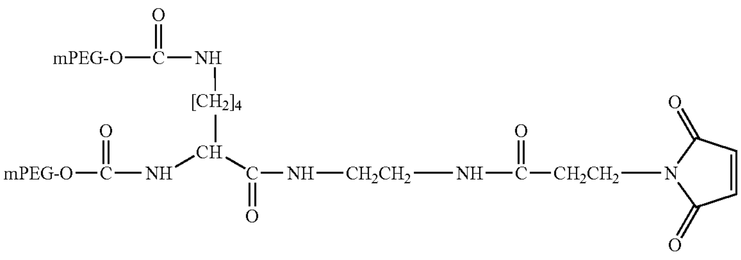

mPEG2-MAL

;

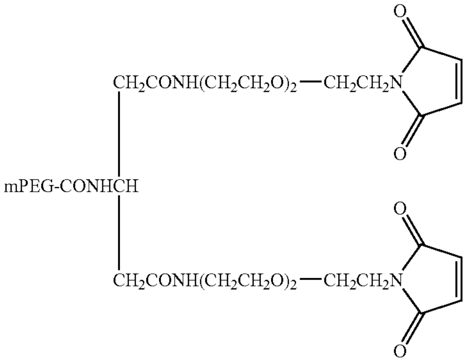

mPEG-(MAL)$^2$

;

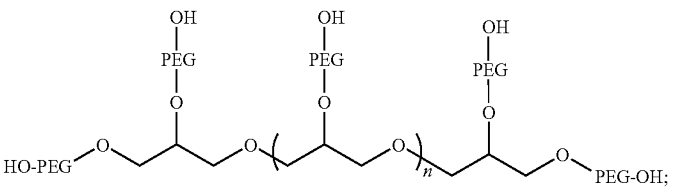

n = 0-4 multi-arm PEG

-continued

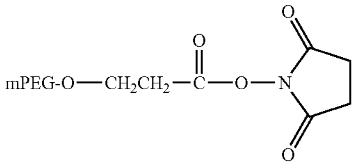

mPEG-SPA

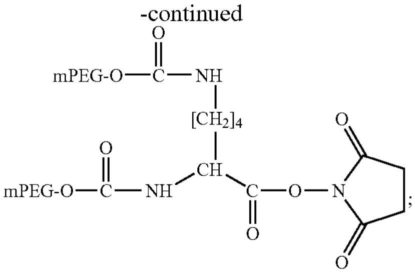

;

mPEG2-NHS

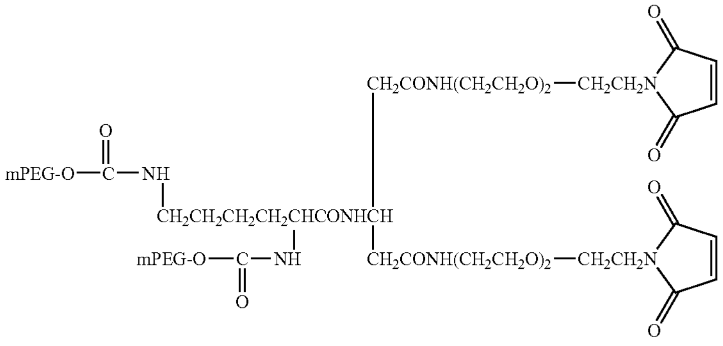

; and mPEG2-(MAL)$^2$

The reactive group (e.g., MAL, NHS, SPA, VS, or Thiol) may be attached directly to the PEG polymer or may be attached to PEG via a linker molecule.

The size of polymers useful in the invention can be in the range of between 500 Da to 60 kDa, for example, between 1000 Da and 60 kDa, 10 kDa and 60 kDa, 20 kDa and 60 kDa, 30 kDa and 60 kDa, 40 kDa and 60 kDa, and up to between 50 kDa and 60 kDa. The polymers used in the invention, particularly PEG, can be straight chain polymers or can possess a branched conformation. Depending on the combination of molecular weight and conformation, the polymer molecules useful in the invention, when attached to a monovalent anti-CD40L antibody polypeptide, will yield a molecule having an average hydrodynamic size of between 24 and 500 kDa. The hydrodynamic size of a polymer molecule used herein refers to the apparent size of a molecule (e.g., a protein molecule) based on the diffusion of the molecule through an aqueous solution. The diffusion, or motion of a protein through solution can be processed to derive an apparent size of the protein, where the size is given by the Stokes radius or hydrodynamic radius of the protein particle. The "hydrodynamic size" of a protein depends on both mass and shape (conformation), such that two proteins having the same molecular mass may have differing hydrodynamic sizes based on the overall conformation of the protein. The hydrodynamic size of a PEG-linked monovalent anti-CD40L antibody polypeptide, e.g., an anti-CD40L single immunoglobulin variable domain as described herein, can be in the range of 24 kDa to 500 kDa; 30 to 500 kDa; 40 to 500 kDa; 50 to 500 kDa; 100 to 500 kDa; 150 to 500 kDa; 200 to 500 kDa; 250 to 500 kDa; 300 to 500 kDa; 350 to 500 kDa; 400 to 500 kDa and 450 to 500 kDa. Preferably the hydrodynamic size of a PEGylated antibody polypeptide as described herein is 30 to 40 kDa; 70 to 80 kDa or 200 to 300 kDa. The size of a polymer molecule attached to a monovalent anti-CD40L antibody polypeptide may thus be varied depending upon the desired application. For example, where the PEGylated antibody polypeptide is intended to leave the circulation and enter into peripheral tissues, it is desirable to keep the size of the attached polymer low to facilitate extravazation from the blood stream. Alternatively, where it is desired to have the PEGylated antibody polypeptide remain in the circulation for a longer period of time, a higher molecular weight polymer can be used (e.g., a 30 to 60 kDa polymer).

The polymer (PEG) molecules useful in the invention can be attached to antibody polypeptides using methods that are well known in the art. The first step in the attachment of PEG or other polymer moieties to an antibody polypeptide is the substitution of the hydroxyl end-groups of the PEG polymer by electrophile-containing functional groups. Particularly, PEG polymers are attached to either cysteine or lysine residues present in the antibody polypeptide. The cysteine and lysine residues can be naturally occurring, or can be engineered into the antibody polypeptide molecule. For example, cysteine residues can be recombinantly engineered at the C-terminus of antibody polypeptides, or residues at specific solvent accessible locations in the antibody polypeptide can be substituted with cysteine or lysine. In a preferred embodiment, a PEG moiety is attached to a cysteine residue which is present in the hinge region at the C-terminus of an antibody polypeptide.

In a further preferred embodiment a PEG moiety or other polymer is attached to a cysteine or lysine residue which is either naturally occurring at or engineered into the N-terminus of antibody single variable domain polypeptide of the invention. In a still further embodiment, a PEG moiety or other polymer is attached to an antibody single variable domain according to the invention at a cysteine or lysine residue (either naturally occurring or engineered) which is at least 2 residues away from (e.g., internal to) the C- and/or N-terminus of the antibody single variable domain polypeptide.

In one embodiment, the PEG polymer(s) is attached to one or more cysteine or lysine residues present in a framework region (FWs) and one or more heterologous CDRs of a single immunoglobulin variable domain. CDRs and framework regions (e.g., CDR1-CDR3 and FW1-FW4) are those regions of an immunoglobulin variable domain as defined in the Kabat database of Sequences of Proteins of Immunological Interest (Kabat et al., 1991, supra). In a preferred embodiment, a PEG polymer is linked to a cystine or lysine residue in the $V_H$ framework segment DP47, or the $V_k$ framework segment DPK9. Cysteine and/or lysine residues of DP47 which may be linked to PEG according to the invention include the cysteine at positions 22, or 96 and the lysine at positions 43, 65, 76, or 98 of SEQ ID NO: 1 (FIG. 5). Cysteine and/or lysine residues of DPK9 which may be linked to PEG according to the invention include the cysteine residues at positions 23, or 88 and the lysine residues at positions 39, 42, 45, 103, or 107 of SEQ ID NO: 3 (FIG. 6). In addition, specific cysteine or lysine residues may be linked to PEG in the $V_H$ canonical framework region DP38, or DP45.

In addition, specific solvent accessible sites in the antibody molecule which are not naturally occurring cysteine or lysine residues may be mutated to a cysteine or lysine for attachment of a PEG polymer. Solvent accessible residues in any given antibody, e.g., a dAb, can be determined using methods known in the art such as analysis of the crystal structure of the antibody polypeptide. For example, using the solved crystal structure of the $V_H$ dAb HEL4 (SEQ ID NO: 3; a dAb that binds hen egg lysozyme), the residues Gln-13, Pro-14, Gly-15, Pro-41, Gly-42, Lys-43, Asp-62, Lys-65, Arg-87, Ala-88, Glu-89, Gln-112, Leu-115, Thr-117, Ser-119, and Ser-120 have been identified as being solvent accessible, and according to the present invention would be attractive candidates for mutation to cysteine or lysine residues for the attachment of a PEG polymer. In addition, using the solved crystal structure of the $V_k$ dummy dAb (SEQ ID NO: 4), the residues Val-15, Pro-40, Gly-41, Ser-56, Gly-57, Ser-60, Pro-80, Glu-81, Gln-100, Lys-107, and Arg-108 have been identified as being solvent accessible, and according to the present invention would be attractive candidates for mutation to cysteine or lysine residues for the attachment of a PEG polymer. In one embodiment of the invention, a PEG polymer is linked to multiple solvent accessible cysteine or lysine residues, or to solvent accessible residues which have been mutated to a cysteine or lysine residue. Alternatively, only one solvent accessible residue is linked to PEG, either where the particular antibody polypeptide only possesses one solvent accessible cysteine or lysine (or residue modified to a cysteine or lysine) or where a particular solvent accessible residue is selected from among several such residues for PEGylation.

```
Primary amino acid sequence of HEL4 (SEQ
ID NO: 5).
   1 EVQLLESGGG LVQPGGSLRL SCAASGFRIS DEDMGWVRQA
     PGKGLEWVSS

  51 IYGPSGSTYY ADSVKGRFTI SRDNSKNTLY LQMNSLRAED
     TAVYYCASAL

 101 EPLSEPLGFW GQGTLVTVSS
```

Primary amino acid sequence of $V_k$ dummy (SEQ ID NO: 6).

```
   1 DIQMTQSPSS LSASVGDRVT ITCRASQSIS SYLNWYQQKP
     GKAPKLLIYA

  51 ASSLQSGVPS RFSGSGSGTD FTLTISSLQP EDFATYYCQQ
     SYSTPNTFGQ

 101 GTKVEIKR
```

Several PEG attachment schemes which are useful in the invention are provided by the company Nektar (SanCarlos, Calif.). For example, where attachment of PEG or other polymer to a lysine residue is desired, active esters of PEG polymers which have been derivatized with N-hydroxylsuccinimide, such as succinimidyl propionate may be used. Where attachment to a cysteine residue is intended, PEG polymers which have been derivatized with sulfhydryl-selective reagents such as maleimide, vinyl sulfone, or thiols may be used. Other examples of specific embodiments of PEG derivatives which may be used according to the invention to generate PEGylated antibodies can be found in the Nektar Catalog (available on the world wide web at nektar.com). In addition, several derivatized forms of PEG may be used according to the invention to facilitate attachment of the PEG polymer to an antibody polypeptide. PEG derivatives useful in the invention include, but are not limited to PEG-succinimidyl succinate, urethane linked PEG, PEG phenylcarbonate, PEG succinimidyl carbonate, PEG-carboxymethyl azide, dimethylmaleic anhydride PEG, PEG dithiocarbonate derivatives, PEG-tresylates (2,2,2-trifluoroethanesolfonates), MPEG imidoesters, and other as described in Zalipsky and Lee, (1992) ("Use of functionalized poly(ethylene glycol)s for modification of peptides" in *Poly(Ethylene Glycol) Chemistry: Biotechnical and Biomedical Applications*, J. Milton Harris, Ed., Plenum Press, NY).

In one embodiment, the invention provides an anti-CD40L antibody single variable domain composition comprising an antibody single variable domain and PEG polymer wherein the ratio of PEG polymer to antibody single variable domain is a molar ratio of at least 0.25:1. In a further embodiment, the molar ratio of PEG polymer to antibody single variable domain is 0.33:1 or greater. In a still further embodiment the molar ratio of PEG polymer to antibody single variable domain is 0.5:1 or greater.

Dual-Specific Ligands

The invention also provides dual-specific ligands comprising immunoglobulin single variable domains which each have different specificities; that is, the first and the second epitopes bound by the dual-specific ligand are preferably different. As used herein a "dual-specific ligand" refers to a ligand comprising a first immunoglobulin single variable domain and a second immunoglobulin single variable domain as herein defined, wherein the variable regions are capable of binding to two different antigens or two epitopes on the same antigen which are not normally bound by a monospecific immunoglobulin. For example, the two epitopes may be on the same hapten, but are not the same epitope or sufficiently adjacent to be bound by a monospecific ligand. The dual specific ligands according to the invention are composed of variable domains which have different specificities, and do not contain mutually complementary variable domain pairs which have the same specificity. Dual-specific ligands may be, or be part of, polypeptides, proteins or nucleic acids, which may be naturally occurring or synthetic. In this respect, the ligand of the invention may bind an epitope or antigen and act as an antagonist or agonist (eg, EPO receptor agonist). The epitope binding domains of the ligand in one embodiment have the same epitope specificity, and may for example simultaneously bind their epitope when multiple copies of the epitope are present on the same antigen. In another embodiment, these epitopes are provided on different antigens such that the ligand can bind the epitopes and bridge the antigens. One skilled in the art will appreciate that the choice of epitopes and antigens is large and varied. They may be for instance human or animal proteins, cytokines, cytokine receptors, enzymes co-factors for enzymes or DNA binding proteins. Suitable cytokines and growth factors include but are not limited to: ApoE, Apo-SAA, BDNF, Cardiotrophin-1, EGF, EGF receptor, ENA-78, Eotaxin, Eotaxin-2, Exodus-2, EpoR, FGF-acidic, FGF-basic, fibroblast growth factor-10, FLT3 ligand, Fractalkine (CX3C), GDNF, G-CSF, GM-CSF, GF-β1, insulin, IFN-γ, IGF-I, IGF-II, IL-1α, IL-1β, IL-2, IL-3, IL-4, IL-5, IL-6, IL-7, IL-8 (72 a.a.), IL-8 (77 a.a.), IL-9, IL-0, IL-11, IL-12, IL-13, IL-15, IL-16, IL-17, IL-18 (IGIF), Inhibin α, Inhibin β, IP-10, keratinocyte growth factor-2 (KGF-2), KGF, Leptin, LIF, Lymphotactin, Mullerian inhibitory substance, monocyte colony inhibitory factor, monocyte attractant protein, M-CSF, MDC (67 a.a.), MDC (69 a.a.), MCP-1 (MCAF), MCP-2, MCP-3, MCP-4, MDC (67 a.a.), MDC (69 a.a.), MIG, MIP-1α, MIP-1β, MIP-3α, MIP-3β, MIP-4, myeloid progenitor inhibitor factor-1 (MPIF-1), NAP-2, Neurturin, Nerve growth factor, β-NGF, NT-3, NT-4, Oncostatin M, PDGF-AA, PDGF-AB, PDGF-BB, PF-4, RANTES, SDF1α, SDF1β, SCF, SCGF, stem cell factor (SCF), TARC, TGF-α, TGF-β, TGF-β2, TGF-β3, tumour necrosis factor (TNF), TNF-α, TNF-β, TNF receptor I, TNF receptor II, TNIL-1, TPO, VEGF, VEGF receptor 1, VEGF receptor 2, VEGF receptor 3, GCP-2, GRO/MGSA, GRO-β, GRO-γ, HCC1, 1-309, HER 1, HER 2, HER 3, HER 4, TACE recognition site, TNF BP-I and TNF BP-II, as well as any target disclosed in Annex 2 or Annex 3 hereto, whether in combination as set forth in the Annexes, in a different combination or individually. Cytokine receptors include receptors for the foregoing cytokines, e.g. IL-1 R1; IL-6R; IL-10R; IL-18R, as well as receptors for cytokines set forth in Annex 2 or Annex 3 and also receptors disclosed in Annex 2 and 3. It will be appreciated that this list is by no means exhaustive. Where the multispecific ligand binds to two epitopes (on the same or different antigens), the antigen(s) may be selected from this list.

In one embodiment of the second configuration of the invention, the variable domains are derived from an antibody directed against the first and/or second antigen or epitope. In a preferred embodiment the variable domains are derived from a repertoire of single variable antibody domains. In one example, the repertoire is a repertoire that is not created in an animal or a synthetic repertoire. In another example, the single variable domains are not isolated (at least in part) by animal immunisation. Thus, the single domains can be isolated from a naïve library.

In another aspect, the invention provides a multi-specific ligand comprising a first epitope binding domain having a first epitope binding specificity and a non-complementary second epitope binding domain having a second epitope binding specificity. The first and second binding specificities may be the same or different.

In a further aspect, the present invention provides a closed conformation multi-specific ligand comprising a first epitope binding domain having a first epitope binding specificity and a non-complementary second epitope binding domain having a second epitope binding specificity wherein the first and second binding specificities are capable of competing for epitope binding such that the closed conformation multi-specific ligand cannot bind both epitopes simultaneously.

In a still further aspect, the invention provides open conformation ligands comprising non-complementary binding domains, wherein the domains are specific for a different epitope on the same target. Such ligands bind to targets with increased avidity. Similarly, the invention provides multivalent ligands comprising non-complementary binding domains specific for the same epitope and directed to targets which comprise multiple copies of said epitope.

In a similar aspect, ligands according to the invention can be configured to bind individual epitopes with low affinity, such that binding to individual epitopes is not therapeutically significant; but the increased avidity resulting from binding to two epitopes provides a therapeutic benefit. In a particular example, epitopes may be targeted which are present individually on normal cell types, but present together only on abnormal or diseased cells, such as tumour cells. In such a situation, only the abnormal or diseased cells are effectively targeted by the bispecific ligands according to the invention.

Ligand specific for multiple copies of the same epitope, or adjacent epitopes, on the same target (known as chelating dAbs) may also be trimeric or polymeric (tetrameric or more) ligands comprising three, four or more non-complementary binding domains. For example, ligands may be constructed comprising three or four $V_H$ domains or $V_L$ domains.

Moreover, ligands are provided which bind to multisubunit targets, wherein each binding domain is specific for a subunit of said target. The ligand may be dimeric, trimeric or polymeric.

The invention also includes a dual specific ligand comprising a first immunoglobulin single variable domain having a binding specificity to a first antigen and a second single variable domain having a binding activity to a second antigen, wherein the first antigen is CD40L and the second single variable domain is an Antigen Presenting Cell surface antigen or a T cell surface antigen. The Antigen Presenting Cell (APC) surface antigen can be selected from one of the group consisting of dendritic cell surface antigens, activated macrophage surface antigens, activated B cell surface antigens, co-stimulatory signal pathway surface antigens, and MHC, such as MHC II alpha or beta.

The (APC) surface antigen may be selected from the group consisting of CD28, Inducible costimulatory molecule (ICOS), CD27, CD30, OX40, CD45, CD69, CD3, CD70, Inducible costimulatory molecule ligand (ICOSL), OX40L, CD80, CD86, HVEM (Herpes Virus Entry Mediator), and LIGHT, but is preferably one of CD28, Inducible costimulatory molecule (ICOS), CD27, CD30, OX40, CD45, CD69, or CD3.

The surface antigen is preferably a B7 gene surface antigen such as B7-2 or B7-1.

Dendritic cell surface antigens are known in the art and can include but are not limited to ICAM-1, ICAM-2, LFA-1, LFA-3, DEC205, MHC class I, MHC class II, B7-1, and B7-2. Activated macrophage surface antigens include, but are not limited to, TNF receptor, CD40, MHC class I and II, and B7 molecules. Activated B-cell surface antigens are known in the art (e.g., including but not limited to CD20 and CD96) and further described above (see, for example, Janeway et al., 1999, *Immunobiology*, Garland Publishing NY, NY).

Preferably, the multi-specific ligands according to the above aspects of the invention are obtainable by the method comprising the steps of:

a) selecting a first epitope binding domain by its ability to bind to a first epitope,
b) selecting a second epitope binding domain by its ability to bind to a second epitope,
c) combining the epitope binding domains; and
d) selecting the closed conformation multispecific ligand by its ability to bind to said first second epitope and said second epitope.

Advantageously the first epitope binding domain and the second epitope binding domains are non-complementary immunoglobulin variable domains, as herein defined. That is either $V_H$—$V_H$ or $V_L$—$V_L$ variable domains.

Chelating dAbs in particular may be prepared according to a preferred aspect of the invention, namely the use of anchor dAbs, in which a library of dimeric, trimeric or multimeric dAbs is constructed using a vector which comprises a constant dAb upstream or downstream of a linker sequence, with a repertoire of second, third and further dAbs being inserted on the other side of the linker. In alternative methodologies, the use of linkers may be avoided, for example by the use of non-covalent bonding or natural affinity between binding domains such as $V_H$ and $V_\kappa$. The invention accordingly provides a method for preparing a multimeric ligand comprising the steps of:

(a) providing a vector comprising a nucleic acid sequence encoding a single binding domain specific for a first epitope on a target;

(b) providing a vector encoding a repertoire comprising second binding domains specific for a second epitope on said target, which epitope can be the same or different to the first epitope, said second epitope being adjacent to said first epitope; and (c) expressing said first and second binding domains; and (d) isolating those combinations of first and second binding domains which combine together to produce a target-binding dimer.

The first and second epitopes are adjacent such that a multimeric ligand is capable of binding to both epitopes simultaneously. This provides the ligand with the advantages of increased avidity if binding. Where the epitopes are the same, the increased avidity is obtained by the presence of multiple copies of the epitope on the target, allowing at least two copies to be simultaneously bound in order to obtain the increased avidity effect.

In an alternative embodiment of the above aspect of the second configuration of the invention, at least one epitope binding domain comprises a non-immunoglobulin 'protein scaffold' or 'protein skeleton' as herein defined. Suitable non-immunoglobulin protein scaffolds include but are not limited to any of those selected from the group consisting of: SpA, fibronectin, GroEL and other chaperones, lipocallin, CCTLA4 and affibodies, as set forth above.

According to the above aspect of the second configuration of the invention, advantageously, the epitope binding domains are attached to a 'protein skeleton'. Advantageously, a protein skeleton according to the invention is an immunoglobulin skeleton.

According to the present invention, the term 'immunoglobulin skeleton' refers to a protein which comprises at least one immunoglobulin fold and which acts as a nucleus for one or more epitope binding domains, as defined herein.

Preferred immunoglobulin skeletons as herein defined includes any one or more of those selected from the following: an immunoglobulin molecule comprising at least (i) the CL (kappa or lambda subclass) domain of an antibody; or (ii) the CH1 domain of an antibody heavy chain; an immunoglobulin molecule comprising the CH1 and CH2 domains of an antibody heavy chain; an immunoglobulin molecule comprising the CH1, CH2 and CH3 domains of an antibody heavy chain; or any of the subset (ii) in conjunction with the CL (kappa or lambda subclass) domain of an antibody. A hinge region domain may also be included. Such combinations of domains may, for example, mimic natural antibodies, such as IgG or IgM, or fragments thereof, such as Fv, scFv, Fab or $F(ab')_2$ molecules. Those skilled in the art will be aware that this list is not intended to be exhaustive.

Linking of the skeleton to the epitope binding domains, as herein defined may be achieved at the polypeptide level, that is after expression of the nucleic acid encoding the skeleton and/or the epitope binding domains. Alternatively, the linking step may be performed at the nucleic acid level. Methods of linking a protein skeleton according to the present invention, to the one or more epitope binding domains include the use of protein chemistry and/or molecular biology techniques which will be familiar to those skilled in the art and are described herein.

Advantageously, the dual- or multispecific ligand may comprise a first domain capable of binding a target molecule, and a second domain capable of binding a molecule or group which extends the half-life of the ligand. For example, the molecule or group may be a bulky agent, such as HSA or a cell matrix protein. As used herein, the phrase "molecule or group which extends the half-life of a ligand" refers to a molecule or chemical group which, when bound by a dual-specific ligand as described herein increases the in vivo half-life of such dual specific ligand when administered to an animal, relative to a ligand that does not bind that molecule or group. Examples of molecules or groups that extend the half-life of a ligand are described hereinbelow. In a preferred embodiment, the closed conformation multispecific ligand may be capable of binding the target molecule only on displacement of the half-life enhancing molecule or group. Thus, for example, a closed conformation multispecific ligand is maintained in circulation in the bloodstream of a subject by a bulky molecule such as HSA. When a target molecule is encountered, competition between the binding domains of the closed conformation multispecific ligand results in displacement of the HSA and binding of the target. Molecules which increase half-life are discussed in further detail above.

Ligands according to any aspect of the present invention, as well as dAb monomers useful in constructing such ligands, may advantageously dissociate from their cognate target(s) with a $K_d$ of 300 nM to 5 pM (ie, $3\times10^{-7}$ to $5\times10^{-12}$M), preferably 50 nM to 20 pM, or 5 nM to 200 pM or 1 nM to 100 pM, $1\times10^{-7}$ M or less, $1\times10^{-8}$ M or less, $1\times10^{-9}$ M or less, $1\times10^{-10}$ M or less, $1\times10^{-11}$ M or less; and/or a $K_{off}$ rate constant of $5\times10^{-1}$ to $1\times10^{-7}$ $S^{-1}$, preferably $1\times10^{-2}$ to $1\times10^{-6}$ $S^{-1}$, or $5\times10^{-3}$ to $1\times10^{-5}$ $S^{-1}$, or $5\times10^{-1}$ $S^{-1}$ or less, or $1\times10^{-2}$ $S^{-}$ or less, or $1\times10^{-3}$ $S^{-}$ or less, or $1\times10^{-4}$ $S^{-1}$ or less, or $1\times10^{-5}$ $S^{-1}$ or less, or $1\times10^{-6}$ $S^{-1}$ or less as determined by surface plasmon resonance. The $K_d$ rate constant is defined as $K_{off}/K_{on}$.

Furthermore, the invention provides a dAb monomer (or dual specific ligand comprising such a dAb) that binds to serum albumin (SA) with a $K_d$ of 1 nM to 500 μM (ie, $\times10^{-9}$ to $5\times10^{-4}$), preferably 100 nM to 10 μM. Preferably, for a dual specific ligand comprising a first anti-SA dAb and a second dAb to another target, the affinity (eg $K_d$ and/or $K_{off}$ as measured by surface plasmon resonance, eg using BiaCore) of the second dAb for its target is from 1 to 100000 times preferably 100 to 100000, more preferably 1000 to 100000, or 10000 to 100000 times) the affinity of the first dAb for SA. For example, the first dAb binds SA with an affinity of approximately 10 μM, while the second dAb binds its target with an affinity of 100 pM. Preferably, the serum albumin is human serum albumin (HSA).

In one embodiment, the first dAb (or a dAb monomer) binds SA (eg, HSA) with a $K_d$ of approximately 50, preferably 70, and more preferably 100, 150 or 200 nM.

The invention moreover provides dimers, trimers and polymers of the aforementioned dAb monomers, in accordance with the foregoing aspect of the present invention.

Ligands according to the invention, including dAb monomers, dimers and trimers, can be linked to an antibody Fc region, comprising one or both of $C_H2$ and $C_H3$ domains, and optionally a hinge region. For example, vectors encoding ligands linked as a single nucleotide sequence to an Fc region may be used to prepare such polypeptides. Alternatively, ligands according to the invention may be free of an Fc domain.

In a further aspect, the present invention provides one or more nucleic acid molecules encoding at least a dual- or multispecific ligand as herein defined. In one embodiment, the ligand is a closed conformation ligand. In another embodiment, it is an open conformation ligand. The multispecific ligand may be encoded on a single nucleic acid molecule; alternatively, each epitope binding domain may be encoded by a separate nucleic acid molecule. Where the ligand is encoded by a single nucleic acid molecule, the domains may be expressed as a fusion polypeptide, or may be separately expressed and subsequently linked together, for example using chemical linking agents. Ligands expressed from separate nucleic acids will be linked together by appropriate means.

The nucleic acid may further encode a signal sequence for export of the polypeptides from a host cell upon expression and may be fused with a surface component of a filamentous bacteriophage particle (or other component of a selection display system) upon expression. Leader sequences, which may be used in bacterial expression and/or phage or phagemid display, include pelB, stII, ompA, phoA, bla and pelA.

In a further aspect of the second configuration of the invention the present invention provides a vector comprising nucleic acid according to the present invention.

In a yet further aspect, the present invention provides a host cell transfected with a vector according to the present invention.

Expression from such a vector may be configured to produce, for example on the surface of a bacteriophage particle, epitope binding domains for selection. This allows selection of displayed domains and thus selection of 'multispecific ligands' using the method of the present invention.

Combining Single Variable Domains

Domains useful in the invention, once selected using methods exemplified above, may be combined by a variety of methods known in the art, including covalent and non-covalent methods.

Preferred methods include the use of polypeptide linkers, as described, for example, in connection with scFv molecules (Bird et al., (1988) Science 242:423-426). Discussion of suitable linkers is provided in Bird et al. Science 242, 423-426; Hudson et al, Journal Immunol Methods 231 (1999) 177-189; Hudson et al, Proc Nat Acad Sci USA 85, 5879-5883. Linkers are preferably flexible, allowing the two single domains to interact. One linker example is a $(Gly_4 Ser)_n$ linker, where n=1 to 8, eg, 2, 3, 4, 5 or 7. The linkers used in diabodies, which are less flexible, may also be employed (Holliger et al., (1993) PNAS (USA) 90:6444-6448).

In one embodiment, the linker employed is not an immunoglobulin hinge region.

Variable domains may be combined using methods other than linkers. For example, the use of disulphide bridges, provided through naturally-occurring or engineered cysteine residues, may be exploited to stabilise $V_H$—$V_H$, $V_L$—$V_L$ or $V_H$—$V_L$ dimers (Reiter et al., (1994) Protein Eng. 7:697-704) or by remodelling the interface between the variable domains to improve the "fit" and thus the stability of interaction (Ridgeway et al., (1996) Protein Eng. 7:617-621; Zhu et al., (1997) Protein Science 6:781-788).

Other techniques for joining or stabilizing variable domains of immunoglobulins, and in particular antibody $V_H$ domains, may be employed as appropriate.

In accordance with the present invention, dual specific ligands can be in "closed" conformations in solution. A "closed" configuration is that in which the two domains (for example $V_H$ and $V_L$) are present in associated form, such as that of an associated $V_H$—$V_L$ pair which forms an antibody binding site. For example, scFv may be in a closed conformation, depending on the arrangement of the linker used to link the $V_H$ and $V_L$ domains. If this is sufficiently flexible to allow the domains to associate, or rigidly holds them in the associated position, it is likely that the domains will adopt a closed conformation.

Similarly, $V_H$ domain pairs and $V_L$ domain pairs may exist in a closed conformation. Generally, this will be a function of close association of the domains, such as by a rigid linker, in the ligand molecule. Ligands in a closed conformation will be unable to bind both the molecule which increases the half-life of the ligand and a second target molecule. Thus, the ligand will typically only bind the second target molecule on dissociation from the molecule which increases the half-life of the ligand.

Moreover, the construction of $V_H$/$V_H$, $V_L$/$V_L$ or $V_H$/$V_L$ dimers without linkers provides for competition between the domains.

Ligands according to the invention may moreover be in an open conformation. In such a conformation, the ligands will be able to simultaneously bind both the molecule which increases the half-life of the ligand and the second target molecule. Typically, variable domains in an open configuration are (in the case of $V_H$—$V_L$ pairs) held far enough apart for the domains not to interact and form an antibody binding site and not to compete for binding to their respective epitopes. In the case of $V_H$/$V_H$ or $V_L$/$V_L$ dimers, the domains are not forced together by rigid linkers. Naturally, such domain pairings will not compete for antigen binding or form an antibody binding site.

Fab fragments and whole antibodies will exist primarily in the closed conformation, although it will be appreciated that open and closed dual specific ligands are likely to exist in a variety of equilibria under different circumstances. Binding of the ligand to a target is likely to shift the balance of the equilibrium towards the open configuration. Thus, certain ligands according to the invention can exist in two conformations in solution, one of which (the open form) can bind two antigens or epitopes independently, whilst the alternative conformation (the closed form) can only bind one antigen or epitope; antigens or epitopes thus compete for binding to the ligand in this conformation.

Although the open form of the dual specific ligand may thus exist in equilibrium with the closed form in solution, it is envisaged that the equilibrium will favor the closed form; moreover, the open form can be sequestered by target binding into a closed conformation. Preferably, therefore, certain dual specific ligands of the invention are present in an equilibrium between two (open and closed) conformations.

Dual specific ligands according to the invention may be modified in order to favor an open or closed conformation. For example, stabilisation of $V_H$—$V_L$ interactions with disulphide bonds stabilises the closed conformation. Moreover, linkers used to join the domains, including $V_H$ domain and $V_L$ domain pairs, may be constructed such that the open from is favoured; for example, the linkers may sterically hinder the association of the domains, such as by incorporation of large amino acid residues in opportune locations, or the designing of a suitable rigid structure which will keep the domains physically spaced apart.

Characterisation of the Dual-Specific Ligand.

The binding of the dual-specific ligand to its specific antigens or epitopes (e.g., CD40L and/or an epitope bound by DOM8-24) can be tested by methods which will be familiar to those skilled in the art and include ELISA. In a preferred embodiment of the invention binding is tested using monoclonal phage ELISA.

Phage ELISA may be performed according to any suitable procedure: an exemplary protocol is set forth below.

Populations of phage produced at each round of selection can be screened for binding by ELISA to the selected antigen or epitope, to identify "polyclonal" phage antibodies. Phage from single infected bacterial colonies from these populations can then be screened by ELISA to identify "monoclonal" phage antibodies. It is also desirable to screen soluble antibody fragments for binding to antigen or epitope, and this can also be undertaken by ELISA using reagents, for example, against a C- or N-terminal tag (see for example Winter et al. (1994) Ann. Rev. Immunology 12, 433-55 and references cited therein.

The diversity of the selected phage monoclonal antibodies may also be assessed by gel electrophoresis of PCR products (Marks et al. 1991, supra; Nissim et al. 1994 supra), probing (Tomlinson et al., 1992) J. Mol. Biol. 227, 776) or by sequencing of the vector DNA.

Structure of 'Dual-Specific Ligands'.

As described above, an antibody is herein defined as an antibody (for example IgG, IgM, IgA, IgA, IgE) or fragment (Fab, Fv, disulphide linked Fv, scFv, diabody) which comprises at least one heavy and a light chain variable domain, at least two heavy chain variable domains or at least two light chain variable domains. It may be at least partly derived from any species naturally producing an antibody, or created by recombinant DNA technology; whether isolated from serum, B-cells, hybridomas, transfectomas, yeast or bacteria).

In a preferred embodiment of the invention the dual-specific ligand comprises at least one single heavy chain variable domain of an antibody and one single light chain variable domain of an antibody, or two single heavy or light chain variable domains. For example, the ligand may comprise a $V_H/V_L$ pair, a pair of $V_H$ domains or a pair of $V_L$ domains.

The first and the second variable domains of such a ligand may be on the same polypeptide chain. Alternatively they may be on separate polypeptide chains. In the case that they are on the same polypeptide chain they may be linked by a linker, which is preferentially a peptide sequence, as described above.

The first and second variable domains may be covalently or non-covalently associated. In the case that they are covalently associated, the covalent bonds may be disulphide bonds.

In the case that the variable domains are selected from V-gene repertoires selected for instance using phage display technology as herein described, then these variable domains comprise a universal framework region, such that is they may be recognised by a specific generic ligand as herein defined. The use of universal frameworks, generic ligands and the like is described in WO99/20749.

Where V-gene repertoires are used variation in polypeptide sequence is preferably located within the structural loops of the variable domains. The polypeptide sequences of either variable domain may be altered by DNA shuffling or by mutation in order to enhance the interaction of each variable domain with its complementary pair. DNA shuffling is known in the art and taught, for example, by Stemmer, 1994, Nature 370: 389-391 and U.S. Pat. No. 6,297,053, both of which are incorporated herein by reference. Other methods of mutagenesis are well known to those of skill in the art.

In one embodiment of the invention the 'dual-specific ligand' is a single chain Fv fragment. In an alternative embodiment of the invention, the 'dual-specific ligand' consists of a Fab format.

In a further aspect, the present invention provides nucleic acid encoding at least a 'dual-specific ligand' as herein defined.

One skilled in the art will appreciate that, depending on the aspect of the invention, both antigens or epitopes may bind simultaneously to the same antibody molecule. Alternatively, they may compete for binding to the same antibody molecule. For example, where both epitopes are bound simultaneously, both variable domains of a dual specific ligand are able to independently bind their target epitopes. Where the domains compete, the one variable domain is capable of binding its target, but not at the same time as the other variable domain binds its cognate target; or the first variable domain is capable of binding its target, but not at the same time as the second variable domain binds its cognate target.

The variable regions may be derived from antibodies directed against target antigens or epitopes. Alternatively they may be derived from a repertoire of single antibody domains such as those expressed on the surface of filamentous bacteriophage. Selection may be performed as described below.

In general, the nucleic acid molecules and vector constructs required for the performance of the present invention may be constructed and manipulated as set forth in standard laboratory manuals, such as Sambrook et al. (1989) *Molecular Cloning: A Laboratory Manual*, Cold Spring Harbor, USA.

The manipulation of nucleic acids useful in the present invention is typically carried out in recombinant vectors.

Thus in a further aspect, the present invention provides a vector comprising nucleic acid encoding at least a 'dual-specific ligand' as herein defined.

As used herein, vector refers to a discrete element that is used to introduce heterologous DNA into cells for the expression and/or replication thereof. Methods by which to select or construct and, subsequently, use such vectors are well known to one of ordinary skill in the art. Numerous vectors are publicly available, including bacterial plasmids, bacteriophage, artificial chromosomes and episomal vectors. Such vectors may be used for simple cloning and mutagenesis; alternatively gene expression vector is employed. A vector of use according to the invention may be selected to accommodate a polypeptide coding sequence of a desired size, typically from 0.25 kilobase (kb) to 40 kb or more in length A suitable host cell is transformed with the vector after in vitro cloning manipulations. Each vector contains various functional components, which generally include a cloning (or "polylinker") site, an origin of replication and at least one selectable marker gene. If given vector is an expression vector, it additionally possesses one or more of the following: enhancer element, promoter, transcription termination and signal sequences, each positioned in the vicinity of the cloning site, such that they are operatively linked to the gene encoding a ligand according to the invention.

Both cloning and expression vectors generally contain nucleic acid sequences that enable the vector to replicate in one or more selected host cells. Typically in cloning vectors, this sequence is one that enables the vector to replicate independently of the host chromosomal DNA and includes origins of replication or autonomously replicating sequences. Such sequences are well known for a variety of bacteria, yeast and viruses. The origin of replication from the plasmid pBR322 is suitable for most Gram-negative bacteria, the 2 micron plasmid origin is suitable for yeast, and various viral origins (e.g. SV 40, adenovirus) are useful for cloning vectors in mammalian cells. Generally, the origin of replication is not needed for mammalian expression vectors unless these are used in mammalian cells able to replicate high levels of DNA, such as COS cells.

Advantageously, a cloning or expression vector may contain a selection gene also referred to as selectable marker. This gene encodes a protein necessary for the survival or growth of transformed host cells grown in a selective culture medium. Host cells not transformed with the vector containing the selection gene will therefore not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available in the growth media.

Since the replication of vectors encoding a ligand according to the present invention is most conveniently performed in *E. coli*, an *E. coli*-selectable marker, for example, the β-lactamase gene that confers resistance to the antibiotic ampicillin, is of use. These can be obtained from *E. coli* plasmids, such as pBR322 or a pUC plasmid such as pUC18 or pUC19.

Expression vectors usually contain a promoter that is recognised by the host organism and is operably linked to the coding sequence of interest. Such a promoter may be inducible or constitutive. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences.

Promoters suitable for use with prokaryotic hosts include, for example, the β-lactamase and lactose promoter systems, alkaline phosphatase, the tryptophan (trp) promoter system and hybrid promoters such as the tac promoter. Promoters for use in bacterial systems will also generally contain a Shine-Delgarno sequence operably linked to the coding sequence.

The preferred vectors are expression vectors that enables the expression of a nucleotide sequence corresponding to a polypeptide library member. Thus, selection with the first and/or second antigen or epitope can be performed by separate propagation and expression of a single clone expressing the polypeptide library member or by use of any selection display system. As described above, the preferred selection display system is bacteriophage display. Thus, phage or phagemid vectors may be used, eg pIT1 or pIT2. Leader sequences useful in the invention include pelB, stII, ompA, phoA, bla and pelA. One example are phagemid vectors which have an *E. coli* origin of replication (for double stranded replication) and also a phage origin of replication (for production of single-stranded DNA). The manipulation and expression of such vectors is well known in the art (Hoogenboom and Winter (1992) supra; Nissim et al. (1994) supra). Briefly, the vector contains a β-lactamase gene to confer selectivity on the phagemid and a lac promoter upstream of a expression cassette that consists (N to C terminal) of a pelB leader sequence (which directs the expressed polypeptide to the periplasmic space), a multiple cloning site (for cloning the nucleotide version of the library member), optionally, one or more peptide tag (for detection), optionally, one or more TAG stop codon and the phage protein pIII. Thus, using various suppressor and non-suppressor strains of *E. coli* and with the addition of glucose, iso-propyl thio-β-D-galactoside (IPTG) or a helper phage, such as VCS M13, the vector is able to replicate as a plasmid with no expression, produce large quantities of the polypeptide library member only or produce phage, some of which contain at least one copy of the polypeptide-pIII fusion on their surface.

Construction of vectors encoding ligands according to the invention employs conventional ligation techniques. Isolated vectors or DNA fragments are cleaved, tailored, and religated in the form desired to generate the required vector. If desired, analysis to confirm that the correct sequences are present in the constructed vector can be performed in a known fashion. Suitable methods for constructing expression vectors, preparing in vitro transcripts, introducing DNA into host cells, and performing analyses for assessing expression and function are known to those skilled in the art. The presence of a gene sequence in a sample is detected, or its amplification and/or expression quantified by conventional methods, such as Southern or Northern analysis, Western blotting, dot blotting of DNA, RNA or protein, in situ hybridisation, immunocytochemistry or sequence analysis of nucleic acid or protein molecules. Those skilled in the art will readily envisage how these methods may be modified, if desired.

Structure of Ligands

According to one aspect of the invention, two or more non-complementary epitope binding domains are linked so that they are in a closed conformation as herein defined. Advantageously, they may be further attached to a skeleton which may, as a alternative, or on addition to a linker described herein, facilitate the formation and/or maintenance of the closed conformation of the epitope binding sites with respect to one another. Alternatively, the monomeric anti-CD40L antibody single variable domain polypeptides of the invention may be constructed using scaffold or skeleton frameworks as discussed herein.

(I) Skeletons

Skeletons may be based on immunoglobulin molecules or may be non-immunoglobulin in origin as set forth above. Preferred immunoglobulin skeletons as herein defined includes any one or more of those selected from the following: an immunoglobulin molecule comprising at least (i) the CL (kappa or lambda subclass) domain of an antibody; or (ii) the CH1 domain of an antibody heavy chain; an immunoglobulin molecule comprising the CH1 and CH2 domains of an antibody heavy chain; an immunoglobulin molecule comprising the CH1, CH2 and CH3 domains of an antibody heavy chain; or any of the subset (ii) in conjunction with the CL (kappa or lambda subclass) domain of an antibody. A hinge region domain may also be included. Such combinations of domains may, for example, mimic natural antibodies, such as IgG or IgM, or fragments thereof, such as Fv, scFv, Fab or $F(ab')_2$ molecules. Those skilled in the art will be aware that this list is not intended to be exhaustive.

(II) Protein Scaffolds

Each epitope binding domain comprises a protein scaffold and one or more CDRs which are involved in the specific interaction of the domain with one or more epitopes. Advantageously, an epitope binding domain according to the present invention comprises three CDRs. Suitable protein scaffolds, in addition to those based on immunoglobulin domains, may also be based on protein scaffolds or skeletons other than immunoglobulin domains. For example natural bacterial receptors such as SpA have been used as scaffolds for the grafting of CDRs to generate ligands which bind specifically to one or more epitopes. Details of this procedure are described in U.S. Pat. No. 5,831,012. Other suitable scaffolds include those based on fibronectin and affibodies (Affibody, Bromma, Sweeden). Details of suitable procedures are described in WO 98/58965. Other suitable scaffolds include lipocallin and CTLA4, as described in van den Beuken et al., J. Mol. Biol. (2001) 310, 591-601, and scaffolds such as those described in WO0069907 (Medical Research Council), which are based for example on the ring structure of bacterial GroEL or other chaperone polypeptides. Other non-immunoglobulin based scaffolds which may be used according to the invention include those based on the LDL receptor class A, EGF domain monomers and multimers, and scaffolds available from Biorexis (King of Prussia, Pa.) or Avidia (Mountain View, Calif.). Other non-immunoglobulin scaffolds which may be used are described, for example, in WO05/040229, WO04/044011, and US20050089932

Scaffolds for Use in Constructing Ligands i. Selection of the Main-Chain Conformation The members of the immunoglobulin superfamily all share a similar fold for their polypeptide chain. For example, although antibodies are highly diverse in terms of their primary sequence, comparison of sequences and crystallographic structures has revealed that, contrary to expectation, five of the six antigen binding loops of antibodies (H1, H2, L1, L2, L3) adopt a limited number of main-chain conformations, or canonical structures (Chothia and Lesk (1987) *J. Mol. Biol.,* 196: 901; Chothia et al. (1989) *Nature,* 342: 877). Analysis of loop lengths and key residues has therefore enabled prediction of the main-chain conformations of H1, H2, L1, L2 and L3 found in the majority of human antibodies (Chothia et al. (1992) *J. Mol. Biol.,* 227: 799; Tomlinson et al. (1995) *EMBO J.,* 14: 4628; Williams et al. (1996) *J. Mol. Biol.,* 264: 220). Although the H3 region is much more diverse in terms of sequence, length and structure (due to the use of D segments), it also forms a limited number of main-chain conformations for short loop lengths which depend on the length and the presence of particular residues, or types of residue, at key positions in the loop and the antibody framework (Martin et al. (1996) *J. Mol. Biol.,* 263: 800; Shirai et al. (1996) *FEBS Letters,* 399: 1).

The ligands of the present invention are advantageously selected and/or assembled from libraries of domains, such as libraries of $V_H$ domains and/or libraries of $V_L$ domains. Moreover, the ligands of the invention may themselves be provided in the form of libraries. In one aspect of the present invention, libraries of ligands and/or domains are designed in which certain loop lengths and key residues have been chosen to ensure that the main-chain conformation of the members is known. Advantageously, these are real conformations of immunoglobulin superfamily molecules found in nature, to minimise the chances that they are non-functional, as discussed above. Germline V gene segments serve as one suitable basic framework for constructing antibody or T-cell receptor libraries; other sequences are also of use. Variations may occur at a low frequency, such that a small number of functional members may possess an altered main-chain conformation, which does not affect its function.

Canonical structure theory is also of use to assess the number of different main-chain conformations encoded by ligands, to predict the main-chain conformation based on ligand sequences and to chose residues for diversification which do not affect the canonical structure. It is known that, in the human $V_\kappa$ domain, the L1 loop can adopt one of four canonical structures, the L2 loop has a single canonical structure and that 90% of human $V_\kappa$ domains adopt one of four or five canonical structures for the L3 loop (Tomlinson et al. (1995) supra); thus, in the $V_\kappa$ domain alone, different canonical structures can combine to create a range of different main-chain conformations. Given that the $V_\lambda$ domain encodes a different range of canonical structures for the L1, L2 and L3 loops and that $V_\kappa$ and $V_\lambda$ domains can pair with any $V_H$ domain which can encode several canonical structures for the H1 and H2 loops, the number of canonical structure combinations observed for these five loops is very large. This implies that the generation of diversity in the main-chain conformation may be essential for the production of a wide range of binding specificities. However, by constructing an antibody library based on a single known main-chain conformation it has been found, contrary to expectation, that diversity in the main-chain conformation is not required to generate sufficient diversity to target substantially all antigens. Even more surprisingly, the single main-chain conformation need not be a consensus structure—a single naturally occurring conformation can be used as the basis for an entire library. Thus, in a preferred aspect, the ligands of the invention possess a single known main-chain conformation.

The single main-chain conformation that is chosen is preferably commonplace among molecules of the immunoglobulin superfamily type in question. A conformation is commonplace when a significant number of naturally occurring molecules are observed to adopt it. Accordingly, in a preferred aspect of the invention, the natural occurrence of the different main-chain conformations for each binding loop of an immunoglobulin domain are considered separately and then a naturally occurring variable domain is chosen which possesses the desired combination of main-chain conformations for the different loops. If none is available, the nearest equivalent may be chosen. It is preferable that the desired combination of main-chain conformations for the different loops is created by selecting germline gene segments which encode the desired main-chain conformations. It is more preferable, that the selected germline gene segments are frequently expressed in nature, and most preferable that they are the most frequently expressed of all natural germline gene segments.

In designing ligands or libraries thereof the incidence of the different main-chain conformations for each of the antigen binding loops may be considered separately. For H1, H2, L1, L2 and L3, a given conformation that is adopted by between 20% and 100% of the antigen binding loops of naturally occurring molecules is chosen. Typically, its observed incidence is above 35% (i.e. between 35% and 100%) and, ideally, above 50% or even above 65%. Since the vast majority of H3 loops do not have canonical structures, it is preferable to select a main-chain conformation which is commonplace among those loops which do display canonical structures. For each of the loops, the conformation which is observed most often in the natural repertoire is therefore selected. In human antibodies, the most popular canonical structures (CS) for each loop are as follows: H1-CS 1 (79% of the expressed repertoire), H2-CS 3 (46%), L1-CS 2 of $V_\kappa$ (39%), L2-CS 1 (100%), L3-CS 1 of $V_\kappa$ (36%) (calculation assumes a κ:λ ratio of 70:30, Hood et al. (1967) *Cold Spring Harbor Symp. Quant. Biol.,* 48: 133). For H3 loops that have canonical structures, a CDR3 length (Kabat et al. (1991) *Sequences of proteins of immunological interest*, U.S. Department of Health and Human Services) of seven residues with a salt-bridge from residue 94 to residue 101 appears to be the most common. There are at least 16 human antibody sequences in the EMBL data library with the required H3 length and key residues to form this conformation and at least two crystallographic structures in the protein data bank which can be used as a basis for antibody modelling (2cgr and 1tet). The most frequently expressed germline gene segments that this combination of canonical structures are the $V_H$ segment 3-23 (DP-47), the $J_H$ segment JH4b, the $V_\kappa$ segment O2/O12 (DPK9) and the $J_\kappa$ segment $J_\kappa 1$. $V_H$ segments DP45 and DP38 are also suitable. These segments can therefore be used in combination as a basis to construct a library with the desired single main-chain conformation.

Alternatively, instead of choosing the single main-chain conformation based on the natural occurrence of the different main-chain conformations for each of the binding loops in isolation, the natural occurrence of combinations of main-chain conformations is used as the basis for choosing the single main-chain conformation. In the case of antibodies, for example, the natural occurrence of canonical structure combinations for any two, three, four, five or for all six of the antigen binding loops can be determined. Here, it is preferable that the chosen conformation is commonplace in naturally occurring antibodies and most preferable that it observed most frequently in the natural repertoire. Thus, in human antibodies, for example, when natural combinations of the five antigen binding loops, H1, H2, L1, L2 and L3, are considered, the most frequent combination of canonical structures is determined and then combined with the most popular conformation for the H3 loop, as a basis for choosing the single main-chain conformation.

ii. Diversification of the Canonical Sequence

Having selected several known main-chain conformations or, preferably a single known main-chain conformation, ligands according to the invention or libraries for use in the invention can be constructed by varying the binding site of the molecule in order to generate a repertoire with structural and/or functional diversity. This means that variants are generated such that they possess sufficient diversity in their structure and/or in their function so that they are capable of providing a range of activities.

The desired diversity is typically generated by varying the selected molecule at one or more positions. The positions to be changed can be chosen at random or are preferably selected. The variation can then be achieved either by randomisation, during which the resident amino acid is replaced by any amino acid or analogue thereof, natural or synthetic, producing a very large number of variants or by replacing the resident amino acid with one or more of a defined subset of amino acids, producing a more limited number of variants.

Various methods have been reported for introducing such diversity. Error-prone PCR (Hawkins et al. (1992) *J. Mol. Biol.,* 226: 889), chemical mutagenesis (Deng et al. (1994) *J. Biol. Chem.,* 269: 9533) or bacterial mutator strains (Low et al. (1996) *J. Mol. Biol.,* 260: 359) can be used to introduce random mutations into the genes that encode the molecule. Methods for mutating selected positions are also well known in the art and include the use of mismatched oligonucleotides or degenerate oligonucleotides, with or without the use of PCR. For example, several synthetic antibody libraries have been created by targeting mutations to the antigen binding loops. The H3 region of a human tetanus toxoid-binding Fab has been randomised to create a range of new binding specificities (Barbas et al. (1992) *Proc. Natl. Acad. Sci. USA,* 89: 4457). Random or semi-random H3 and L3 regions have been appended to germline V gene segments to produce large libraries with unmutated framework regions (Hoogenboom & Winter (1992) *J. Mol. Biol.,* 227: 381; Barbas et al. (1992) *Proc. Natl. Acad. Sci. USA,* 89: 4457; Nissim et al. (1994) *EMBO J.,* 13: 692; Griffiths et al. (1994) *EMBO J.,* 13: 3245; De Kruif et al. (1995) *J. Mol. Biol.,* 248: 97). Such diversification has been extended to include some or all of the other antigen binding loops (Crameri et al. (1996) *Nature Med.,* 2: 100; Riechmann et al. (1995) *Bio/Technology,* 13: 475; Morphosys, WO97/08320, supra).

Since loop randomisation has the potential to create approximately more than $10^{15}$ structures for H3 alone and a similarly large number of variants for the other five loops, it is not feasible using current transformation technology or even by using cell free systems to produce a library representing all possible combinations. For example, in one of the largest libraries constructed to date, $6\times10^{10}$ different antibodies, which is only a fraction of the potential diversity for a library of this design, were generated (Griffiths et al. (1994) supra).

In a preferred embodiment, only those residues which are directly involved in creating or modifying the desired function of the molecule are diversified. For many molecules, the function will be to bind a target and therefore diversity should be concentrated in the target binding site, while avoiding changing residues which are crucial to the overall packing of the molecule or to maintaining the chosen main-chain conformation.

Diversification of the Canonical Sequence as it Applies to Antibody Domains

In the case of the ligands of the invention, the binding site for the target is most often the antigen binding site. Thus, in a highly preferred aspect, the invention provides libraries of or for the assembly of antibody ligands in which only those residues in the antigen binding site are varied. These residues are extremely diverse in the human antibody repertoire and are known to make contacts in high-resolution antibody/antigen complexes. For example, in L2 it is known that positions 50 and 53 are diverse in naturally occurring antibodies and are observed to make contact with the antigen. In contrast, the conventional approach would have been to diversify all the residues in the corresponding Complementarity Determining Region (CDR1) as defined by Kabat et al. (1991, supra), some seven residues compared to the two diversified in the library for use according to the invention. This represents a significant improvement in terms of the functional diversity required to create a range of antigen binding specificities.

In nature, antibody diversity is the result of two processes: somatic recombination of germline V, D and J gene segments to create a naive primary repertoire (so called germline and junctional diversity) and somatic hypermutation of the resulting rearranged V genes. Analysis of human antibody sequences has shown that diversity in the primary repertoire is focused at the centre of the antigen binding site whereas somatic hypermutation spreads diversity to regions at the periphery of the antigen binding site that are highly conserved in the primary repertoire (see Tomlinson et al. (1996) *J. Mol. Biol.,* 256: 813). This complementarity has probably evolved as an efficient strategy for searching sequence space and, although apparently unique to antibodies, it can easily be applied to other polypeptide repertoires. The residues which are varied are a subset of those that form the binding site for the target. Different (including overlapping) subsets of residues in the target binding site are diversified at different stages during selection, if desired.

In the case of an antibody repertoire, an initial 'naive' repertoire is created where some, but not all, of the residues in the antigen binding site are diversified. As used herein in this context, the term "naive" refers to antibody molecules that have no pre-determined target. These molecules resemble those which are encoded by the immunoglobulin genes of an individual who has not undergone immune diversification, as is the case with fetal and newborn individuals, whose immune systems have not yet been challenged by a wide variety of antigenic stimuli. This repertoire is then selected against a range of antigens or epitopes. If required, further diversity can then be introduced outside the region diversified in the initial repertoire. This matured repertoire can be selected for modified function, specificity or affinity.

The invention provides two different naive repertoires of binding domains for the construction of ligands, or a naïve library of ligands, in which some or all of the residues in the antigen binding site are varied. The "primary" library mimics the natural primary repertoire, with diversity restricted to residues at the centre of the antigen binding site that are diverse in the germline V gene segments (germline diversity) or diversified during the recombination process (junctional diversity). Those residues which are diversified include, but are not limited to, H50, H52, H52a, H53, H55, H56, H58, H95, H96, H97, H98, L50, L53, L91, L92, L93, L94 and L96. In the "somatic" library, diversity is restricted to residues that are diversified during the recombination process (junctional diversity) or are highly somatically mutated). Those residues which are diversified include, but are not limited to: H31, H33, H35, H95, H96, H97, H98, L30, L31, L32, L34 and L96. All the residues listed above as suitable for diversification in these libraries are known to make contacts in one or more antibody-antigen complexes. Since in both libraries, not all of the residues in the antigen binding site are varied, additional diversity is incorporated during selection by varying the remaining residues, if it is desired to do so. It shall be apparent to one skilled in the art that any subset of any of these residues (or additional residues which comprise the antigen binding site) can be used for the initial and/or subsequent diversification of the antigen binding site.

In the construction of libraries for use in the invention, diversification of chosen positions is typically achieved at the nucleic acid level, by altering the coding sequence which specifies the sequence of the polypeptide such that a number of possible amino acids (all 20 or a subset thereof) can be incorporated at that position. Using the IUPAC nomenclature, the most versatile codon is NNK, which encodes all amino acids as well as the TAG stop codon. The NNK codon is preferably used in order to introduce the required diversity. Other codons which achieve the same ends are also of use, including the NNN codon, which leads to the production of the additional stop codons TGA and TAA.

A feature of side-chain diversity in the antigen binding site of human antibodies is a pronounced bias which favours certain amino acid residues. If the amino acid composition of the ten most diverse positions in each of the $V_H$, $V_\kappa$ and $V_\lambda$ regions are summed, more than 76% of the side-chain diversity comes from only seven different residues, these being, serine (24%), tyrosine (14%), asparagine (11%), glycine (9%), alanine (7%), aspartate (6%) and threonine (6%). This bias towards hydrophilic residues and small residues which can provide main-chain flexibility probably reflects the evolution of surfaces which are predisposed to binding a wide range of antigens or epitopes and may help to explain the required promiscuity of antibodies in the primary repertoire.

Since it is preferable to mimic this distribution of amino acids, the distribution of amino acids at the positions to be varied preferably mimics that seen in the antigen binding site of antibodies. Such bias in the substitution of amino acids that permits selection of certain polypeptides (not just, antibody polypeptides) against a range of target antigens is easily applied to any polypeptide repertoire. There are various methods for biasing the amino acid distribution at the position to be varied (including the use of tri-nucleotide mutagenesis, see WO97/08320), of which the preferred method, due to ease of synthesis, is the use of conventional degenerate codons. By comparing the amino acid profile encoded by all combinations of degenerate codons (with single, double, triple and quadruple degeneracy in equal ratios at each position) with the natural amino acid use it is possible to calculate the most representative codon. The codons (AGT)(AGC)T, (AGT)(AGC)C and (AGT)(AGC)(CT)—that is, DVT, DVC and DVY, respectively using IUPAC nomenclature—are those closest to the desired amino acid profile: they encode 22% serine and 11% tyrosine, asparagine, glycine, alanine, aspartate, threonine and cysteine. Preferably, therefore, libraries are constructed using either the DVT, DVC or DVY codon at each of the diversified positions.

Increased Half-Life

In vivo, the PEGylated monovalent anti-CD40L antibodies as described herein confer a distinct advantage over non-PEGylated antibody polypeptides, in that the PEGylated antibody molecules will have a greatly prolonged in vivo half life. Without being bound to one particular theory, it is believed that the increased half-life of the molecules described herein is conferred by the increased hydrodynamic size of the antibody polypeptide resulting from the attachment of PEG polymer(s). More specifically, it is believed that two parameters play an important role in determining the serum half-life of PEGylated antibody polypeptides. The first criterion is the nature and size of the PEG attachment, i.e., if the polymer used is simply a linear chain or a branched/forked chain, wherein the branched/forked chain gives rise to a longer half-life. The second is the location of the PEG moiety or moieties on the antibody polypeptide in the final format and how many "free" unmodified PEG arms the molecule has. The resulting hydrodynamic size of the PEGylated antibody polypeptide, as estimated, for example, by size exclusion chromatography, reflects the serum half-life of the molecule. Accordingly, the larger the hydrodynamic size of the PEGylated molecule, the greater the serum half life.

Increased half-life is useful in vivo applications of immunoglobulins, especially antibodies and most especially antibody fragments of small size. Such fragments (Fvs, Fabs, scFvs, dAbs) suffer from rapid clearance from the body; thus, while they are able to reach most parts of the body rapidly, and are quick to produce and easier to handle, their in vivo applications have been limited by their only brief persistence in vivo.

In one aspect, a monovalent anti-CD40L antibody polypeptide as described herein is stabilized in vivo by fusion with a moiety, such as PEG, that increases the hydrodynamic size of the antibody polypeptide. Methods for pharmacokinetic analysis and determination of half-life will be familiar to those skilled in the art. Details may be found in Kenneth et al: Chemical Stability of Pharmaceuticals: A Handbook for Pharmacists and in Peters et al, Pharmacokinetic analysis: A Practical Approach (1996). Reference is also made to "Pharmacokinetics", M Gibaldi & D Perron, published by Marcel Dekker, $2^{nd}$ Rev. ex edition (1982), which describes pharmacokinetic parameters such as t alpha and t beta half lives and area under the curve (AUC).

Typically, the half life of a PEGylated antibody polypeptide as described herein is increased by 10%, 20%, 30%, 40%, 50% or more relative to a non-PEGylated dAb (wherein the antibody polypeptide of the PEGylated antibody polypeptide and non-PEGylated antibody polypeptide are the same). Increases in the range of 2×, 3×, 4×, 5×, 7×, 10×, 20×, 30×, 40×, and up to 50× or more of the half life are possible. Alternatively, or in addition, increases in the range of up to 30×, 40×, 50×, 60×, 70×, 80×, 90×, 100×, 150× of the half life are possible.

Half lives (t½ alpha and t½ beta) and AUC can be determined from a curve of serum concentration of ligand against time. The WinNonlin analysis package (available from Pharsight Corp., Mountain View, Calif. 94040, USA) can be used, for example, to model the curve. In a first phase (the alpha phase) the ligand is undergoing mainly distribution in the patient, with some elimination. A second phase (beta phase) is the terminal phase when the ligand has been distributed and the serum concentration is decreasing as the ligand is cleared from the patient. The tα half life is the half life of the first phase and the tβ half life is the half life of the second phase.

"Half-life" as used herein, unless otherwise noted, refers to the overall half-life of an antibody single variable domain of the invention determined by non-compartment modeling (as contrasted with biphasic modeling, for example). Beta half-life is a measurement of the time it takes for the amount of dAb monomer or multimer to be cleared from the mammal to which it is administered. Thus, advantageously, the present invention provides a dAb-containing composition, e.g., a dAb-effector group composition, having a tα half-life in the range of 0.25 hours to 6 hours or more. In one embodiment, the lower end of the range is 30 minutes, 45 minutes, 1 hour, 1.3 hours, 2 hours, 3 hours, 4 hours, 5 hours, 6 hours, 7 hours, 10 hours, 11 hours or 12 hours. In addition or alternatively, a dAb containing composition will have a tα half-life in the range of up to and including 12 hours. In one embodiment, the upper end of the range is 11, 10, 9, 8, 7, 6, or 5 hours. An example of a suitable range is 1.3 to 6 hours, 2 to 5 hours or 3 to 4 hours.

Advantageously, the present invention provides a dAb containing composition comprising a ligand according to the invention having a tβ half-life in the range of 1-170 hours or more. In one embodiment, the lower end of the range is 2.5 hours, 3 hours, 4 hours, 5 hours, 6 hours, 7 hours, 8 hours, 9 hours, 10 hours, 11 hours or 12 hours. In addition, or alternatively, a dAb containing composition, e.g. a dAb-effector group composition has a tβ half-life in the range of up to and including 21 days. In one embodiment, the upper end of the range is 12 hours, 24 hours, 2 days, 3 days, 5 days, 10 days, 15 days, or 20 days. Advantageously a dAb containing composition according to the invention will have a tβ half-life in the range 2-100 hours, 4-80 hours, and 10-40 hours. In a further embodiment, it will be in the range 12-48 hours. In a further embodiment still, it will be in the range 12-26 hours. The present invention provides a dAb containing composition comprising a ligand according to the invention having a half-life in the range of 1-170 hours or more. In one embodiment, the lower end of the range is 1.3 hours, 2.5 hours, 3 hours, 4 hours, 5 hours, 6 hours, 7 hours, 8 hours, 9 hours, 10 hours, 11 hours or 12 hours. In addition, or alternatively, a dAb containing composition, e.g. a dAb-effector group composition has a half-life in the range of up to and including 21 days. In one embodiment, the upper end of the range is 12 hours, 24 hours, 2 days, 3 days, 5 days, 10 days, 15 days, or 20 days.

In addition, or alternatively to the above criteria, the present invention provides a dAb containing composition comprising a ligand according to the invention having an AUC value (area under the curve) in the range of 1 mg·min/ml or more. In one embodiment, the lower end of the range is 5, 10, 15, 20, 30, 100, 200 or 300 mg·min/ml. In addition, or alternatively, a ligand or composition according to the invention has an AUC in the range of up to 600 mg·min/ml. In one embodiment, the upper end of the range is 500, 400, 300, 200, 150, 100, 75 or 50 mg·min/ml. Advantageously a ligand according to the invention will have an AUC in the range selected from the group consisting of the following: 15 to 150 mg·min/ml, 15 to 100 mg·min/ml, 15 to 75 mg·min/ml, and 15 to 50 mg·min/ml.

The ligands according to the invention, including mono-, dual- and multi-specific, in one configuration thereof, are capable of binding to one or more molecules which can increase the half-life of the ligand in vivo. Typically, such molecules are polypeptides which occur naturally in vivo and which resist degradation or removal by endogenous mechanisms which remove unwanted material from the organism. For example, the molecule which increases the half-life of the organism may be selected from the following:

Proteins from the extracellular matrix; for example collagen, laminins, integrins and fibronectin. Collagens are the major proteins of the extracellular matrix. About 15 types of collagen molecules are currently known, found in different parts of the body, eg type I collagen (accounting for 90% of body collagen) found in bone, skin, tendon, ligaments, cornea, internal organs or type II collagen found in cartilage, invertebral disc, notochord, vitreous humour of the eye.

Proteins found in blood, including:

Plasma proteins such as fibrin, α-2 macroglobulin, serum albumin, fibrinogen A, fibrinogen B, serum amyloid protein A, heptaglobin, profilin, ubiquitin, uteroglobulin and β-2-microglobulin;

Enzymes and inhibitors such as plasminogen, lysozyme, cystatin C, alpha-1-antitrypsin and pancreatic trypsin inhibitor. Plasminogen is the inactive precursor of the trypsin-like serine protease plasmin. It is normally found circulating through the blood stream. When plasminogen becomes activated and is converted to plasmin, it unfolds a potent enzymatic domain that dissolves the fibrinogen fibers that entangle the blood cells in a blood clot. This is called fibrinolysis.

Immune system proteins, such as IgE, IgG, IgM.

Transport proteins such as retinol binding protein, α-1 microglobulin.

Defensins such as beta-defensin 1, Neutrophil defensins 1, 2 and 3.

Proteins found at the blood brain barrier or in neural tissues, such as melanocortin receptor, myelin, ascorbate transporter.

Transferrin receptor specific ligand-neuropharmaceutical agent fusion proteins (see U.S. Pat. No. 5,977,307); brain capillary endothelial cell receptor, transferrin, transferrin receptor, insulin, insulin-like growth factor 1 (IGF 1) receptor, insulin-like growth factor 2 (IGF 2) receptor, insulin receptor.

Proteins localised to the kidney, such as polycystin, type IV collagen, organic anion transporter K1, Heymann's antigen.

Proteins localised to the liver, for example alcohol dehydrogenase, G250.

Blood coagulation factor X

α1 antitrypsin

HNF 1α

Proteins localised to the lung, such as secretory component (binds IgA).

Proteins localised to the Heart, for example HSP 27. This is associated with dilated cardiomyopathy.

Proteins localised to the skin, for example keratin.

Bone specific proteins, such as bone morphogenic proteins (BMPs), which are a subset of the transforming growth factor β superfamily that demonstrate osteogenic activity. Examples include BMP-2, -4, -5, -6, -7 (also referred to as osteogenic protein (OP-1) and -8 (OP-2).

Tumour specific proteins, including human trophoblast antigen, herceptin receptor, oestrogen receptor, cathepsins eg cathepsin B (found in liver and spleen).

Disease-specific proteins, such as antigens expressed only on activated T-cells: including LAG-3 (lymphocyte activation gene), osteoprotegerin ligand (OPGL) see *Nature* 402, 304-309; 1999, OX40 (a member of the TNF receptor family, expressed on activated T cells and the only costimulatory T cell molecule known to be specifically up-regulated in human T cell leukaemia virus type-I (HTLV-I)-producing cells.) See *J Immunol.* 2000 Jul. 1; 165(1):263-70; Metalloproteases (associated with arthritis/cancers), including CG6512 *Drosophila*, human paraplegin, human FtsH, human AFG3L2, murine ftsH; angiogenic growth factors, including acidic fibroblast growth factor (FGF-1), basic fibroblast growth factor (FGF-2), Vascular endothelial growth factor/vascular permeability factor (VEGF/VPF), transforming growth factor-a (TGF a), tumor necrosis factor-alpha (TNF-$\alpha$), angiogenin, interleukin-3 (IL-3), interleukin-8 (IL-8), platelet-derived endothelial growth factor (PD-ECGF), placental growth factor (PlGF), midkine platelet-derived growth factor-BB (PDGF), fractalkine.

Stress Proteins (Heat Shock Proteins)

HSPs are normally found intracellularly. When they are found extracellularly, it is an indicator that a cell has died and spilled out its contents. This unprogrammed cell death (necrosis) only occurs when as a result of trauma, disease or injury and therefore in vivo, extracellular HSPs trigger a response from the immune system that will fight infection and disease. A dual specific which binds to extracellular HSP can be localised to a disease site.

Proteins Involved in Fc Transport

Brambell receptor (also known as FcRB):

This Fc receptor has two functions, both of which are potentially useful for delivery The functions are (1) The transport of IgG from mother to child across the placenta (2) the protection of IgG from degradation thereby prolonging its serum half life of IgG. It is thought that the receptor recycles IgG from endosome.

See Holliger et al, Nat Biotechnol 1997 July; 15(7):632-6.

Other proteins involved in Fc transport include the neonatal Fc receptor (FcRn) described in Gastinel et al., 1992, PNAS 89:638; and Roopenian et al., 2003 J. Immunol. 170: 3528.

Ligands according to the invention may designed to be specific for the above targets without requiring any increase in or increasing half life in vivo. For example, ligands according to the invention can be specific for targets selected from the foregoing which are tissue-specific, thereby enabling tissue-specific targeting of the dual specific ligand, or a dAb monomer that binds a tissue-specific therapeutically relevant target, irrespective of any increase in half-life, although this may result. Moreover, where the ligand or dAb monomer targets kidney or liver, this may redirect the ligand or dAb monomer to an alternative clearance pathway in vivo (for example, the ligand may be directed away from liver clearance to kidney clearance).

Polypeptides useful for increasing half-life include, but are not limited to those shown in Annex I.

Increased Protease Stability

A further advantage of the present invention is that the PEGylated dAbs and dAb multimers described herein possess increased stability to the action of proteases. Depending on the assay conditions, dabs are generally intrinsically stable to the action of proteases. In the presence of pepsin, however, many dAbs are totally degraded at pH 2 because the protein is unfolded under the acid conditions, thus making the protein more accessible to the protease enzyme. The present invention provides PEGylated dAb molecules, including dAb multimers, wherein it is believed that the PEG polymer provides protection of the polypeptide backbone due the physical coverage of the backbone by the PEG polymer, thereby preventing the protease from gaining access to the polypeptide backbone and cleaving it. In a preferred embodiment a PEGylated dAb having a higher hydrodynamic size (e.g., 200 to 500 kDa) is generated according to the invention, because the larger hydrodynamic size will confirm a greater level of protection from protease degradation than a PEGylated dAb having a lower hydrodynamic size. In one embodiment, a PEG- or other polymer-linked antibody single variable domain monomer or multimer is degraded by no more than 10% when exposed to one or more of pepsin, trypsin, elastase, chymotrypsin, or carboxypeptidase, wherein if the protease is pepsin then exposure is carried out at pH 2.0 for 30 minutes, and if the protease is one or more of trypsin, elastase, chymotrypsin, or carboxypeptidase, then exposure is carried out at pH 8.0 for 30 minutes. In a preferred embodiment, a PEG- or other polymer-linked dAb monomer or multimer is degraded by no more than 10% when exposed to pepsin at pH 2.0 for 30 minutes, preferably no more than 5%, and preferably not degraded at all. In a further preferred embodiment, a PEG- or other polymer-linked dAb multimer (e.g., hetero- or homodimer, trimer, tetramer, octamer, etc.) of the invention is degraded by less than 5%, and is preferably not degraded at all in the presence of pepsin at pH 2.0 for 30 minutes. In a preferred embodiment, a PEG- or other polymer-linked dAb monomer or multimer is degraded by no more than 10% when exposed to trypsin, elastase, chymotrypsin, or carboxypeptidase at pH 8.0 for 30 minutes, preferably no more than 5%, and preferably not degraded at all. In a further preferred embodiment, a PEG- or other polymer-linked dAb multimer (e.g., hetero- or homodimer, trimer, tetramer, octamer, etc.) of the invention is degraded by less than 5%, and is preferably not degraded at all in the presence of trypsin, elastase, chymotrypsin, or carboxypeptidase at pH 8.0 for 30 minutes.

The relative ratios of protease:antibody single variable domain polypeptide may be altered according to the invention to achieve the desired level of degradation as described above. For example the ratio or protease to antibody single variable domain may be from about 1:30, to about 10:40, to about 20:50, to about 30:50, about 40:50, about 50:50, about 50:40, about 50:30, about 50:20, about 50:10, about 50:1, about 40:1, and about 30:1.

Accordingly, the present invention provides a method for decreasing the degradation of an antibody single variable domain comprising linking an antibody single variable domain monomer or multimer to a PEG polymer according to any of the embodiments described herein. According to this aspect of the invention, the antibody single variable domain is degraded by no more than 10% in the presence of pepsin at pH2.0 for 30 minutes. In particular, a PEG-linked dAb multimer is degraded by no more than 5%, and preferably not degraded at all in the presence of pepsin at pH 2.0 for 30 minutes. In an alternate embodiment, the antibody single variable domain is degraded by no more than 10% when exposed to trypsin, elastase, chymotrypsin, or carboxypeptidase at pH 8.0 for 30 minutes, preferably no more than 5%, and preferably not degraded at all.

Degradation of PEG-linked dAb monomers and multimers according to the invention may be measured using methods which are well known to those of skill in the art. For example, following incubation of a PEG-linked dAb with pepsin at pH 2.0 for 30 minutes, or with trypsin, elastase, chymotrypsin, or carboxypeptidase at pH 8.0 for 30 minutes, the dAb samples may be analyzed by gel filtration, wherein degradation of the dAb monomer or multimer is evidenced by a gel band of a smaller molecular weight than an un-degraded (i.e., control dAb not treated with pepsin, trypsin, chymotrypsin, elastase, or carboxypeptidase) dAb. Molecular weight of the dAb bands on the gel may be determined by comparing the migration of the band with the migration of a molecular weight ladder (see FIG. 5). Other methods of measuring protein degradation are known in the art and may be adapted to evaluate the PEG-linked dAb monomers and multimers of the present invention.

Pharmaceutical Compositions, Dosage and Administration

The antibody polypeptides of the invention can be incorporated into pharmaceutical compositions suitable for administration to a subject. Typically, the pharmaceutical composition comprises a monovalent anti-CD40L antibody polypeptide and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The term "pharmaceutically acceptable carrier" excludes tissue culture medium comprising bovine or horse serum. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable substances include minor amounts of auxiliary substances such as wetting or emulsifying agents, preservatives or buffers, which enhance the shelf life or effectiveness of the antibody polypeptide.

The compositions as described herein may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular).

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants.

The antibody polypeptides described herein can be administered by a variety of methods known in the art, although for many therapeutic applications, the preferred route/mode of administration is intravenous injection or infusion. The polypeptide can also be administered by intramuscular or subcutaneous injection.

As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Single immunoglobulin variable domains and other relatively small monovalent antibody polypeptides are well suited for formulation as extended release preparations due, in part, to their small size—the number of moles per dose can be significantly higher than the dosage of, for example, full sized antibodies. Biodegradable, biocompatible polymers can be used, such as ethylene vinyl acetate, polyanhydrides, polyglycolic acid, collagen, polyorthoesters, and polylactic acid. Prolonged absorption of injectable compositions can be brought about by including in the composition an agent that delays absorption, for example, monostearate salts and gelatin. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978. Additional methods applicable to the controlled or extended release of polypeptide agents such as the monovalent antibody polypeptides disclosed herein are described, for example, in U.S. Pat. Nos. 6,306,406 and 6,346,274, as well as, for example, in U.S. Patent Application Nos. US20020182254 and US20020051808, all of which are incorporated herein by reference.

In certain embodiments, a monovalent anti-CD40L antibody polypeptide can be orally administered, for example, with an inert diluent or an assimilable edible carrier. The compound (and other ingredients, if desired) may also be enclosed in a hard or soft shell gelatin capsule, compressed into tablets, or incorporated directly into the individual's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Additional active compounds can also be incorporated into the compositions. In certain embodiments, a monovalent anti-CD40L antibody polypeptide is coformulated with and/or coadministered with one or more additional therapeutic agents. For example, a monovalent anti-CD40L antibody polypeptide can be coformulated and/or coadministered with one or more additional antibodies that bind other targets (e.g., antibodies that bind other cytokines or that bind cell surface molecules), or, for example, one or more cytokines. Such combination therapies may utilize lower dosages of the administered therapeutic agents, thus avoiding possible toxicities or complications associated with the various monotherapies.

The pharmaceutical compositions of the invention can include a "therapeutically effective amount" or a "prophylactically effective amount" of a monovalent anti-CD40L antibody polypeptide. A "therapeutically effective amount" refers to an amount effective, at dosages and for periods of time necessary, to achieve the desired therapeutic result. A therapeutically effective amount of the antibody polypeptide can vary according to factors such as the disease state, age, sex, and weight of the individual, and the ability of the monovalent anti-CD40L antibody polypeptide to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, because a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier.

A non-limiting range for a therapeutically or prophylactically effective amount of a monovalent anti-CD40L antibody polypeptide is 0.1-20 mg/kg, more preferably 1-10 mg/kg. It is to be noted that dosage values can vary with the type and severity of the condition to be alleviated. It is to be further understood that for any particular subject, specific dosage regimens should be adjusted over time according to the individual need and the professional judgment of the administering clinician.

The efficacy of treatment with a monovalent anti-CD40L antibody polypeptide as described herein is judged by the skilled clinician on the basis of improvement in one or more symptoms or indicators of the disease state or disorder being treated. An improvement of at least 10% (increase or decrease, depending upon the indicator being measured) in one or more clinical indicators is considered "effective treatment," although greater improvements are preferred, such as 20%, 30%, 40%, 50%, 75%, 90%, or even 100%, or, depending upon the indicator being measured, more than 100% (e.g., two-fold, three-fold, ten-fold, etc., up to and including attainment of a disease-free state. Indicators can be physical measurements, e.g., enzyme, cytokine, growth factor or metabolite levels, rate of cell growth or cell death, or the presence or amount of abnormal cells. One can also measure, for example, differences in the amount of time between flare-ups of symptoms of the disease or disorder (e.g., for remitting/relapsing diseases, such as multiple sclerosis). Alternatively, non-physical measurements, such as a reported reduction in pain or discomfort or other indicator of disease status can be relied upon to gauge the effectiveness of treatment. Where non-physical measurements are made, various clinically acceptable scales or indices can be used, for example, the Crohn's Disease Activity Index, or CDAI (Best et al., 1976, Gastroenterology 70: 439), which combines both physical indicators, such as hematocrit and the number of liquid or very soft stools, among others, with patient-reported factors such as the severity of abdominal pain or cramping and general well-being, to assign a disease score.

As the term is used herein, "prophylaxis" performed using a composition as described herein is "effective" if the onset or severity of one or more symptoms is delayed or reduced by at least 10%, or abolished, relative to such symptoms in a similar individual (human or animal model) not treated with the composition.

Whereas the monovalent anti-CD40L antibody polypeptides described herein must bind human CD40L, where one is to evaluate its effect in an animal model system, the polypeptide must cross-react with one or more antigens in the animal model system, preferably at high affinity. One of skill in the art can readily determine if this condition is satisfied for a given animal model system and a given monovalent anti-CD40L antibody polypeptide. If this condition is satisfied, the efficacy of the monovalent anti-CD40L antibody polypeptide can be examined by administering it to an animal model under conditions which mimic a disease state and monitoring one or more indicators of that disease state for at least a 10% improvement.

Animal Models:

Monovalent anti-CD40L antibody polypeptides as described herein are useful for the treatment of autoimmune disorders in which CD40/CD40L signaling is inappropriately active. There are several animal models in which the therapeutic efficacy of a given monovalent anti-CD40L antibody polypeptide can be assessed, as discussed below.

Systemic Lupus Erythematosis (SLE):

Anti-CD40L antibody treatment prevents the development of lupus-like nephritis in NZB/NZW and SNF1 SLE mice. Treatment of SNF1 mice with anti-CD40L antibody reverses established nephritis and preserves kidney function. See, e.g., Mohan et al., 1995, J. Immunol. 154: 1470-1480; Early et al., 1996, J. Immunol. 157: 3159-3164; Kalled et al., 1998, J. Immunol. 160: 2158-2165, and Chess, 2001, "Blockade of the CD40L/CD40 Pathway," in Therapeutic Immunology $2^{nd}$ Edition, Austen, Burakof, Rosen and Strom, Eds., Blackwell Sciences (Pubs.), pp 441-456.

Multiple Sclerosis:

Specific blockade of CD40L at the time of immunization markedly suppresses the incidence, mortality, day of onset, and clinical scores of experimental autoimmune encephalomyelitis (EAE) in B10P1L and (PLJ×SJL)F1 mice induced by either myelin basic protein or PLP myelin antigens. See, for example, Gerritse, 1996, Proc. Natl. Acad. Sci. U.S.A. 93: 2494; Grewal et al., 1996, Science 273: 186; Laman et al., 1998, Mult. Scler. 4: 14; and Chess, 2001, supra.

Rheumatoid Arthritis:

Anti-CD40L blocks the development of joint inflammation, serum antibody titers to collagen, the infiltration of inflammatory cells into the synovial tissue, ant the erosion of cartilage and bone in collagen-induced arthritis. See, e.g., Durie et al., 1993, Science 261: 132; and Chess, 2001, supra.

Insulin-Dependent Type I Diabetes Models:

The non-obese diabetic (NOD) mouse spontaneously develops T cell dependent autoimmune diabetes. Anti-CD40L monoclonal antibody treatment of 3 to 4 week old NOD females (the age at which insulitis typically begins) completely prevented the insulitis and diabetes. Cytokine analysis revealed a dramatic decrease in IFN-g and IL-2 release without a concomitant increase in IL-4 production by T cells from anti-CD40L-treated mice. See, e.g., Balasa et al., 1997, J. Immunol. 159: 1420; and Chess, 2001, supra.

Inhibition of Allograft and Xenograft Transplant Rejection:

Anti-CD40L prevents the development of renal rejection of fully allogeneic grafts in mice. Moreover, the survival of renal allografts transplanted into nephrectomized rhesus monkeys is typically prolonged by anti-CD40L therapy alone. Similarly, anti CD40L therapy has prevented graft rejection of skin, islet cells and cardiac transplants as well as GVHD in rodents. See, e.g., Kirk et al., 1997, Proc. Natl. Acad. Sci. U.S.A. 94: 8789-8794; Parker et al., 1995, Proc. Natl. Acad. Sci. U.S.A. 92: 9560; Larsen et al., 1996, Transplantation 61: 4; and Chess, 2001, supra.

Uses of Monovalent Anti-CD40L Antibody Polypeptides

Anti-CD40L antibody polypeptides as described herein are useful for the treatment or prevention of diseases or disorders in which inappropriate activation of a CD40L/CD40- mediated pathway is involved. In particular, autoimmune diseases frequently involve inappropriate regulation or activity of CD40L/CD40 pathways. Administration of an anti-CD40L antibody polypeptide as described herein to an individual suffering from such a disease, can reduce one or more symptoms of the disease. Non-limiting examples of diseases for which the antibody polypeptides described herein can be therapeutically useful include Systemic Lupus Erythematosus (SLE), Idiotypic Thrombocytopenic Purpura (ITP), transplant rejection, Crohn's Disease, Inflammatory Bowel Disease (IBD), colitis, asthma/allergy, atherosclerosis, Myasthenia Gravis, immune response to recombinant drug products, e.g., factor VII in hemophilia, Multiple Sclerosis, Psoriasis, Rheumatoid Arthritis, Ankylosing Spondylitis, Coronary Heart Disease, and Diabetes, including Type 1 and/or Type 2 Diabetes.

The anti-CD40L antibody polypeptides described herein are additionally useful in the way that generally any antibody preparation is useful, e.g., for in vivo imaging or diagnostic uses, in vitro diagnostic uses, etc. For these and other uses it may be desirable to label the anti-CD40L antibody polypeptides, e.g., with a fluorescent, calorimetric, enzymatic or radioactive label. Methods of labeling antibody polypeptides are well known in the art.

EXAMPLES

Example 1

Biotinylation of Recombinant CD40L

Recombinant human soluble CD40L (PeproTech) was biotinylated and used during phage selections. Reagents, equipment and sources from which they are available are provided in Table 1.

Biotinylation of CD40L was performed by incubating CD40L (0.5 mg/ml) with EZ-Link™ Sulfo-NHS-LC-Biotin [Sulfosuccinimidyl-6-(biotinamido)hexanoate] (Pierce) at a molar ratio of 5:1 on ice for 2 hours according to the product instructions. The biotinylation reaction mixture was then dialysed against 3 exchanges of PBS (1000× sample volume) in a Slide-A-Lyzer® Dialysis Cassette at 4° C. to remove the unincorporated biotinylation reagent.

Figure 1A:
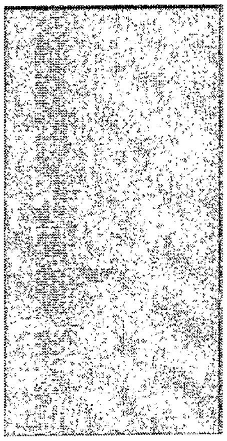
FIG. 1 shows gel analysis of the quality of biotin-labeled CD40L used in the screening procedures described herein. (a) 11 g of non-biotinylated-CD40L (Lane 1) and 0.3 μg of biotin-CD40L (Lane 2) were analysed on SDS-PAGE and detected by Simply Blue Safe-Stain. (b) 0.1 μg of biotin-CD40L (Lane 1) and 0.02 μg of biotin-CD40L (Lane 2) were detected by Western-blot probing with 1:5000 Streptavidin-HRP.
Figure 1B:
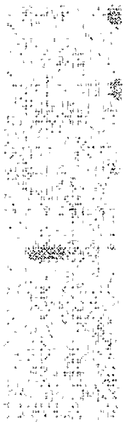

The biotinylated-CD40L was tested by receptor binding assay for binding to CD40/Fc to confirm its biological activity. Quality of biotin-CD40L was also monitored by analysing on a NuPaGE 4-12% Bis-Tris gel and detected by Simply Blue Safe-Stain (Invitrogen) (FIG. 1*a*), and western-blotting by probing with Streptavidin-HRP (FIG. 1*b*). The biotinylated-CD40L was further analysed by mass spectrometry with the majority of CD40L subunits containing 1 or 2 biotin moieties (data not shown).

TABLE 1

| Equipment/Reagent | Suggested or required supplier |
|---|---|
| Recombinant human soluble CD40 ligand/TRAP | PeproTech, Cat No: 310-02 Reconstituted in 5 mM Sodium phosphate, pH 5.0 to concentration of 0.5 mg/ml |
| EZ-Link ™ Sulfo-NHS-LC-Biotin | Pierce, Cat No: 21335 |
| Slide-A-Lyzer ® Dialysis Cassette | Pierce, Cat No: 66110 |

TABLE 1-continued

| Equipment/Reagent | Suggested or required supplier |
|---|---|
| Recombinant human CD40/Fc chimera | R&D Systems, Cat No: 1493-CD |
| NuPAGE ® 4-12% Bis-Tris gel | Invitrogen life technologies Ltd Cat. No NP0322 |
| Streptavidin-HRP | Amersham Biosciences Cat No: 1231V |
| Invitrogen ™ Simply Blue Safe-stain | Invitrogen Cat No: LC6065 |

Example 2

Phase Selections Using Biotinylated Antigen

The Domain Antibody (dAb) libraries are based on a single human framework for the $V_H$ (DP47 and JH4b) and for the VK (DPK9 and JK1) with side chain diversity incorporated at positions in the antigen binding site that make contact with antigen in known molecular structures and mirror residues diversified in the human antibody repertoire. The antibodies are displayed as fusion proteins covalently linked to the N-terminus of the Fd-phage protein pill, using the phage vector pDOM4 (Fd-Tet) with encodes the Fd phage genome with dAb expression under the control of the gene-III promoter. The dAb cassette consists of (5' to 3'): eukaryotic leader sequence, dAb, myc tag, gIII. The vector contains both the M13 and colE1 origins of replication and is selectable using tetracycline. The $V_H$ and $V_\kappa$ libraries each have a calculated size of over $1\times10^{10}$ molecules. Reagents, equipment and sources from which they are available are provided in Table 2.

Approximately $1\times10^{11}$ phage from the each of the Domantis dAb libraries were incubated in a final volume of 1 ml PBS containing 2% Marvel™ at room temperature for 1 h. Biotinylated antigen was added to the blocked phage such that the phage antigen mixture had a final concentration of 2% Marvel™ in PBS. The antigen concentration used for the first round of selection was 60 nM; the antigen concentration was decreased to 6 nM for round 2, and to 0.6 nM for round 3. The antigen/phage mix was incubated for 1 h at room temperature with rotation at 40 rpm.

For each selection, 100 μl of streptavidin-coated paramagnetic beads (Dynal Biotech) were prepared by washing once in 1 ml of PBS containing 0.1% Tween-20 followed by a second wash in 1 ml of PBS. The beads were then blocked in 1 ml of PBS containing 2% Marvel™ in a 2 ml eppendorf tube at room temperature on a rotating wheel for 1 h.

The tube containing the blocked streptavidin-coated magnetic beads was placed into a magnetic holder, enabling capture of the magnetic beads. The supernatant was removed and the beads resuspended in the antigen/phage mix. This mixture was rotated for 10 min to allow for bead capture of phage/antigen complexes.

The beads were captured using a magnetic holder and repeatedly washed 19 times using 1 ml of PBS containing 0.1% Tween-20, followed by a final wash of 1 ml PBS. The eppendorf tubes were changed following washing steps 3, 9, 15 and 19 to minimise background phage carryover.

The washed beads were then recaptured and all washing solution removed. The phage were eluted through resuspension in 500 μl of trypsin solution (50 μl of 10 mg/ml trypsin stock solution added to 450 μl PBS, freshly diluted) and rotated for 10 min at room temperature. The eluted phage were recovered by capturing the beads using the magnetic holder and the liquid containing the eluted phage recovered. The eluted phage were used to infect *E. coli* TG1 to prepare phage for a further round of selection.

The eluted phage (250 μl) were mixed with 1.75 ml of log phase *E. coli* TG1 ($OD_{600}$ between 0.3 and 0.6) and infection allowed to occur for 30 min at 37° C. without shaking. The infected *E. coli* TG1 culture was centrifuged at 11,600 g in a micro centrifuge for 1 min at room temperature. The pelleted bacteria were resuspended in 100 μl of 2xTY and plated on regular 9 cm diameter plates containing TYE supplemented with 15 μg/ml tetracycline. Plates were grown at 37° C. overnight.

After overnight growth, 2 ml of 2xTY containing 15% glycerol was added to the culture plates and cells loosened with a spreader, ensuring the cells were thoroughly mixed. Two millilitres of the culture were recovered by pipetting into a cryo-vial, from which 50 μl was used to inoculate 50 ml of 2xTY supplemented with 15 μg/ml tetracycline. The remaining cells in the cryo-vial were stored at −80° C.

The 50 ml culture was grown at 37° C. for 16 to 24 hours with shaking at 250 rpm.

Following overnight growth, the culture was centrifuged at 3,300 g for 15 min to pellet the bacteria. The phage were then precipitated from the supernatant through the addition of 10 ml of PEG/NaCl to 40 ml of clarified supernatant. The phage/PEG solution was mixed and incubated on ice for at least 1 h. To pellet the phage, the solution was centrifuged at 3,300 g for 30 min at 4° C. The supernatant was decanted and any remaining supernatant removed by aspiration.

The resulting phage pellet was resuspended in 2 ml PBS and centrifuged at 11,600 g for 10 min in a micro centrifuge to remove any remaining bacterial debris. The supernatant was filtered through a 0.45 μm filter (Sartorius, Minisart). The resuspended phage solution was used for the next round of selection.

TABLE 2

| Equipment/Reagent | Suggested or required supplier | Instrument setting, reagent preparation |
|---|---|---|
| Dynabeads ® M-280 Streptavidin (Prod. No.: 112.05) | Dynal Biotech UK 11 Bassendale Road, Croft Business Park, Bromborough, Wirral CH62 3QL UK | Resuspend thoroughly through repeated pipetting. |
| Tween 20 | Sigma Chemical Company Ltd. | 0.1% in PBS. |
| 99.5% dried skim milk powder | Marvel ™ (premier brands) from supermarkets. | 2% in PBS (prepare fresh and do not store). |
| Trypsin (T-8642) Type XIII from Bovine Pancreas. | Sigma Chemical Company Ltd. Fancy Road Dorset BH17 7NH U.K Tel +44 1202 733114 Fax +44 1202 715460 | made up in 50 mM Tris-HCl pH 7.4; 1 mM $CaCl_2$ and stored at −20° C. The trypsin stock solution should be stored aliquotted at −20° C. to avoid autoproteolysis. |
| PEG/NaCl | Sigma Chemical Company Ltd. | 20% Polyethylene glycol 8000 [formally known as 6000], 2.5 M NaCl pre-chilled to 4° C. |
| Dynal MPC-S magnetic particle concentrator (Prod. No.: 120.20) | Dynal Biotech UK 11 Bassendale Road, Croft Business Park, Bromborough, Wirral CH62 3QL UK | |

TABLE 2-continued

| Equipment/Reagent | Suggested or required supplier | Instrument setting, reagent preparation |
|---|---|---|
| 2xTY | | 16 g Tryptone, 10 g Yeast Extract and 5 g NaCl in 1 litre. Autoclave (121° C., 15 min) and store at RT |

Example 3

Cloning Enriched Phage Selection Outputs into the Soluble dAb Expression Vector pDOM5

Following the second and third rounds of selection, *E. coli* cells infected with the enriched dAb displaying fd-phage populations were obtained. An aliquot of these cells was used to prepare phage DNA and the enriched V-genes excised by digestion using the restriction endonucleases, SalI and NotI. The purified V-genes were ligated into the corresponding sites of pDOM5 (expression vector derived from pUC119 with LacZ promoter, eukaryotic leader, dAb cloning site, myc tag), and the ligated DNA used to electro-transform *E. coli* HB32151 cells which were grown overnight on agar plates containing the antibiotic carbenicillin. The resulting colonies were induced to express dAb protein either as 200 μl microcultures or 50 ml cultures. The resulting dAb was analysed for inhibitory activity using the CD40L receptor binding assay.

Following selection of phage, pDOM4 DNA was purified from the cell pellet obtained from a 50 ml overnight *E. coli* culture using the QIAfilter Plasmid Midi DNA purification kit from Qiagen, following the manufacturer's instructions. The dAb genes were excised from the pDOM4 vector by mixing: 10 μl of 10× SalI buffer; 1 μl of 100×BSA; 20 μg of purified DNA fragment; 2.5 μl of SalI enzyme (10 U/μl); 2.5 μl of NotI enzyme (10 μl); the digestion mix was made up to a final volume of 100 μl using sterile water. The digestion mix was incubated for 5 hours at 37° C.

The digested DNA samples were electrophoresed on a 1.5% agarose gel and the band corresponding to the dAb V-genes (~324 bp to 372 bp) was excised from the gel. The dAb gene DNA was purified from the gel slice using the QIAquick Gel Extraction kit from Qiagen, following the manufacturer's instructions.

The expression vector pDOM5 was digested with SalI and NotI as follows: 10 μl of 10× SalI buffer; 1 μl of 100×BSA; 20 μg of plasmid pDOM5; 1.5 μl of SalI enzyme (10 U/μl); 1.5 μl of NotI enzyme (10 U/μl); the digestion mix was made up to a final volume of 100 μl using sterile water. The digestion mix was incubated for 2 hours at 37° C. The digested vector fragment was purified using the QIAquick PCR Purification Kit.

The digested pDOM5 and digested dAb genes were ligated by mixing: 2 μl of 10× T4 DNA ligase buffer; 400 ng of digested pDOM5 vector; 100 ng of digested dAb genes; 1 μl of T4 DNA ligase (400 U/μl); the ligation mix was made up to 20 μl with sterile water. The ligation mixes were incubated for 2 hours at 25° C.

Two microlitres of the ligation mix was transferred to the bottom of a pre-chilled (on ice) 0.2 cm electroporation cuvette to which 100 μl of electrocompetent *E. coli* HB32151 cells were added. The DNA/cell mixture was incubated on ice for 1-2 min, then electroporated at 2.5 kV (25 μF, 200Ω). One millilitre of 2xTY was immediately added to the cuvette and the cells gently resuspended. The resuspended cells were transferred to a 14 ml disposable culture tube and incubated for 1 hour at 37° C. with shaking at 250 rpm. Dilutions of the cells from $10^{-0}$ to $10^{-3}$ were plated on regular 9 cm diameter plates containing TYE supplemented with 5% glucose and 50 μg/ml carbenicillin. The cells are incubated overnight at 37° C. in an inverted position. Reagents, equipment and sources from which they are available are provided in Table 3.

TABLE 3

| Equipment/Reagent | Suggested or required supplier | Instrument setting, reagent preparation |
|---|---|---|
| QIAfilter Plasmid Midi DNA purification kit | Qiagen Ltd Cat. No.: 12143 | Supplied as kit |
| SalI restriction endonuclease + 10 × SalI buffer | New England Biolabs Cat. No.: R0138S | |
| NotI restriction endonuclease + 10 × NotI buffer + 100 × BSA | New England Biolabs Cat. No.: R0189S | |
| QIAquick Gel Extraction kit | Qiagen Ltd Cat. No.: 28706 | Supplied as kit |
| Expression plasmid pDOM5 | | |
| T4 DNA ligase + 10 × T4 DNA ligase buffer | New England Biolabs Cat. No.: M0202L | The T4 DNA ligase buffer should be stored aliquotted at −20° C. Repeated freeze-thawing should be avoided to minimise the hydrolysis of ATP in the buffer. |

Example 4

Microwell Expression of Soluble dAbs

Following cloning of the selected phage dAb outputs into pDOM5, individual bacterial colonies were inoculated as microwell cultures and induced using IPTG to express dAb protein which was analysed for inhibitory activity using the CD40L receptor binding assay. Reagents, equipment and sources from which they are available are provided in Table 4.

Individual bacterial colonies were carefully picked to ensure that contamination from neighbouring colonies was avoided. The picked colonies were used to inoculate 96 well cell culture plates containing 100 μl per well of 2xTY supplemented with 5% glucose and 50 μg/ml carbenicillin. The lids were placed on the cell culture plates which were incubated overnight in a HiGro orbital shaker (GeneMachines, 935 Washington St, San Carlos, Calif. 94070, USA) under a humidified atmosphere at 37° C. with shaking at 450 rpm (4 mm shaking orbital diameter), with gas (30% $O_2$+70% $N_2$) pulsed for 10 seconds every 5 minutes at a flow rate of 5 SLPM (standard litres per minute). [These plates are referred to as Master Plates].

Following overnight growth, a 96 well transfer device was used to transfer between 1-5 μl of the bacterial culture into a fresh 96 well culture plate containing 100 μl per well of 2xTY supplemented with 0.1% glucose and 50 μg/ml carbenicillin.

The freshly inoculated plates were incubated at 37° C. for 3 to 4 h (shaking at 450 rpm, gas (30% $O_2$+70% $N_2$) pulsed for 10 seconds every 5 minutes at a flow rate of 5 SLPM) until the culture $OD_{600}$ reached approximately 1.0. The cultures were then induced by the addition of 100 μl per well of 2xTY containing 50 μg/ml carbenicillin and 2 mM IPTG (final IPTG concentration of 1 mM) and incubated overnight at 30° C. with shaking at 450 rpm, with gas (30% $O_2$+70% $N_2$) pulsed for 10 seconds every 5 minutes at a flow rate of 5 SLPM. [These plates are referred to a Induction Plates].

Glycerol stocks of the original Master Plates were made by the addition of 100 μl per well of 2xTY containing 50% sterile glycerol. These plates were stored at −80° C.

Following overnight incubation of the Induction Plates, the bacterial cells were pelleted by centrifugation at 1,800 g for 10 min at 4° C. The supernatant (containing expressed dAb) was then analysed to determine if dAbs were capable of inhibiting binding of CD40L to CD40-Fc fusion in a receptor binding assay.

TABLE 4

| Equipment/Reagent | Suggested or required supplier | Instrument setting, reagent preparation |
|---|---|---|
| 96 Well Cell Culture Cluster with round bottom and lid, Non-pyrogenic, Polystyrene | Corning Incorporated, Costar. Number: 3799 | |
| 2 × TY | | 16 g Tryptone, 10 g Yeast Extract and 5 g NaCl in 1 litre. Autoclave (121° C., 15 min) and store at RT |

Example 5

Expression of dAb in *E. coli* at 50 ml

To generate greater quantities of dAb protein for analysis, 50 ml cultures were used for induction. A single colony of the desired dAb (for example DOM-24) grown on TYE plates was inoculated into 10 ml 2xTY supplemented with 5% glucose and 50 μg/ml carbenicillin in a 30 ml universal tube and grown overnight at 37° C. with shaking at 250 rpm. Five hundred microlitres of the overnight culture was added into 50 ml of 2xTY supplemented with 0.1% glucose and 50 μg/ml carbenicillin and grown at 37° C. with shaking at 250 rpm. The $OD_{600}$ of the culture was monitored regularly in comparison with sterile 2xTY and at an $OD_{600}$ of 0.9 the culture was induced by the addition of 1 M IPTG to a final concentration of 1 mM. The inoculated culture was incubated at 30° C. with shaking at 250 rpm overnight. The next day, the culture was centrifuged at 6000 g for 15 min at 4° C. and the clarified supernatant mixed with 100 μl of protein-A streamline or protein-L agarose (pre-washed with 5 mM $MgSO_4$) overnight at 4° C. The supernatant/bead mixture was then centrifuged at 180 g at 4° C. for 2 minutes. The supernatant was decanted and the retained beads washed with 10 ml of PBS containing 0.5M NaCl. The bead solution was transferred into a 96 well Whatman filter plate and the beads washed once with 400 μl of PBS containing 0.5M NaCl, then once with 400 μl of PBS, followed by centrifugation for 2 minutes at 180 g after each washing step. dAb protein was eluted using 70 μl of 0.1 M glycine (pH 2.0) and the solution neutralised by the addition of 40 μl of 1 M Tris-HCl (pH 8.0). The purified dAb concentration was determinate by $OD_{280}$.

Reagents, equipment and sources from which they are available are provided in Table 5.

TABLE 5

| Equipment/Reagent | Suggested or required supplier | Instrument setting, reagent preparation |
|---|---|---|
| TYE | | 15 g Bacto-Agar, 8 g NaCl, 10 g Tryptone, 5 g Yeast Extract in 1 litre water. Autoclave (121° C., 15 min) and store at RT |
| 2 × TY | | 16 g Tryptone, 10 g Yeast Extract and 5 g NaCl in 1 litre. Autoclave (121° C., 15 min) and store at RT |
| 1 M IPTG | | stock made up in MQ water is sterile filtered through 0.22 μM filter and stored in aliquots at −20° C. |
| Carbenicillin | | 50 mg/ml stock made in water, 0.2 μm filter sterilised and stored in aliquots at −20° C. |
| 40% glucose solution | | 0.2 μm filter sterilise, store at RT |
| 5 mM $MgSO_4$ | | prepare fresh from 1 M stock solution, 0.2 μm filter sterilise and store at RT |
| 0.5M NaCl/PBS | | Autoclave or 0.2 μm filter sterilise and store at RT |
| Protein A agarose | Sigma P3476 | store 4° C. |
| Protein L agarose | Sigma P3351 | store 4° C. |
| Streamline rProtein A | Amersham Biosciences, cat no. 17-1281-02 (300 ml) | store 4° C. |
| 1 M Tris-HCl, pH 8.0 | | 0.2 μm filter sterilise or autoclave and store at RT |
| 0.2 M Glycine, pH2.0 | | 0.2 μm filter sterilise and store at 4° C. |

Example 6

CD40L Receptor Binding Assay

The CD40L assay was used to measure the binding of CD40L to CD40 and the ability of binding entities (eg, monovalent antibody fragments such a dAbs) to block this interaction, as described below and shown schematically in FIG. 7. (The soluble proteins from R&D Systems are CD40/Fc=homodimer and CD40L homotrimer).

A 96 well Nunc Maxisorp assay plate was coated overnight at 4° C. with 100 μl per well of recombinant human CD40/Fc (R&D Systems) at 0.5 μg/ml in carbonate buffer. The plate was washed 3 times with 300 μl of 0.05% Tween/PBS and 3 times with 300 μl of PBS using a Tecan plate washer. The wells were blocked using 200 μl of PBS containing 2% (w/v) BSA and incubated for a minimum of 1 h at room temperature. The wells were washed as above, then 50 μl of purified dAb protein (or unpurified supernatant containing dAb from a micro-culture expression) was added to each well. To each well 50 μl of CD40L, at 6 ng/ml in diluent (for a final concentration of 3 ng/ml), was also added and the plate incubated for 1 hr at room temperature.

The plate was washed as described previously and 100 μl biotinylated anti-CD40L antibody, 0.5 μg/ml in diluent, was added and incubated for 1 hr at room temperature. The plate was washed as described above, then 100 μl HRP conjugated anti-biotin antibody (1:5000 dilution in diluent) added to each well and the plate incubated for 1 hr at room temperature. The plate was washed again as described above using a Tecan plate washer and the assay developed using 100 μl of Sure-Blue 1-Component TMB MicroWell Peroxidase solution (the plate was left at room temperature for up to 20 min). The reaction was stopped by the addition of 100 μl M hydrochloric acid. The $OD_{450nm}$ of the plate was assayed within 30 minutes of acid addition. The $OD_{450nm}$ is proportional to the amount of bound streptavidin-HRP conjugate, therefore the greater the degree of dAb inhibition the lower the $OD_{450nm}$ of the resulting signal. Reagents, equipment and sources from which they are available are provided in Table 6.

Controls

The following controls were included:

0 ng/ml CD40L (diluent only)

3 ng/ml CD40L 3 ng/ml CD40L with 1 μg/ml anti-CD40L antibody

TABLE 6

| Equipment/Reagent | Suggest or required supplier (specify) | Reagent preparation |
|---|---|---|
| F96 Maxisorp 96 well immunoplate | Nunc, Cat No: 439454 | |
| 0.2M sodium carbonate bicarbonate buffer pH9.4 | Pierce, Cat No: 28382 | Dissolve 1 sachet in 500 ml deionised water and keep solution at 4° C. |
| Recombinant human CD40/Fc chimera | R&D Systems, Cat No: 1493-CD | Stock 50 μg/ml at −80° C. |
| Phosphate buffered saline (PBS) | Sigma, Cat No: P4417 | 10x solution100 tablets/L water. |
| Wash buffer | | 0.05% Tween-20/PBS |
| Diluent | | 0.1% BSA, 0.05% Tween-20 in PBS |
| Block | | 2% BSA in PBS |
| Recombinant human CD40L | R&D Systems, Cat No: 617-CL | Stock 50 μg/ml at −80° C. |
| Neutralising anti-CD40L antibody | Calbiochem, Cat No: 217595 | Stock 1 mg/ml at 4° C. |
| Biotinylated anti-CD40L antibody | R&D Systems, Cat No: BAF617 | Stock 50 μg/ml at −80° C. |
| Anti-biotin-HRP conjugate | Stratech, Cat No: 200-032-096 | Stock 800 μg/ml at −80 C., diluted 1:5000 in antibody diluent. Keep for 1 week only. |
| SureBlue TMB 1-component microwell peroxidase substrate | KPL, Cat No: 52-00-00 | at 4° C. |

Example 7

Results

Receptor binding data for the most potent inhibitors is summarised in FIGS. 2, 3, and 4, and in Table 7, below. Table 8, below, provides DNA and translated amino acid sequence of unique dAbs identified in the receptor binding assay as inhibiting CD40L binding to CD40.

Figure 2:
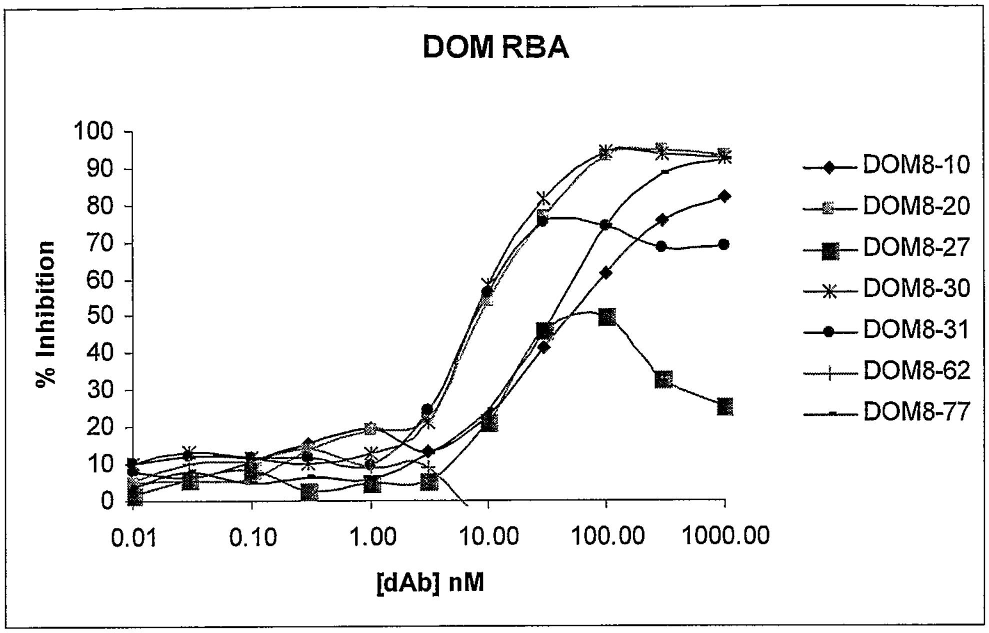
FIG. 2 shows a graphical representation of a dose response receptor binding assay (RBA) readout, analysing the inhibition of CD40L binding to CD40-Fc by dAbs DOM-10, -20, -27, -30, -31, -62, -77, titrated from 1 μM down to 10 pM. dAbs DOM-20, -30, and -31 are the most potent with $IC_{50}$ values of approximately 8 nM.

FIG. 2 shows a dose response receptor binding assay (RBA) readout, analysing the inhibition of CD40L binding to CD40-Fc by dAbs DOM-10, -20, -27, -30, -31, -62, -77, titrated from 1 μM down to 10 pM. dAbs DOM-20, -30, and -31 are the most potent, with $IC_{50}$ values of approximately 8 nM.

Figure 3:
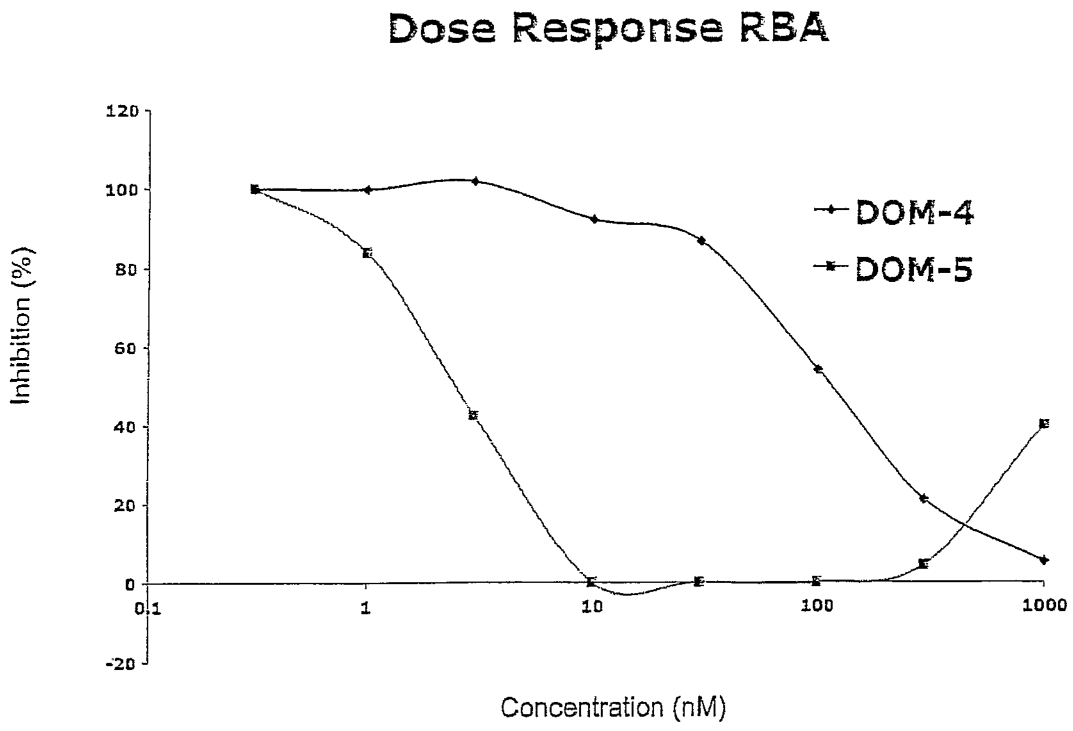
FIG. 3 shows a graphical representation of a dose response receptor binding assay readout, analysing the inhibition of CD40L binding to CD40-Fc by dAbs DOM-4 and DOM-5, titrated from 1 μM down to 500 pM. The $IC_{50}$ values for dAbs DOM-5 and DOM-4 are approximately 3 nM and 100 nM respectively.

FIG. 3 shows a dose response receptor binding assay readout, analysing the inhibition of CD40L binding to CD40-Fc by dAbs DOM-4 and DOM-5, titrated from 1 μM down to 500 pM. The $IC_{50}$ values for dAbs DOM-5 and DOM-4 are approximately 3 nM and 100 nM respectively.

Figure 4:
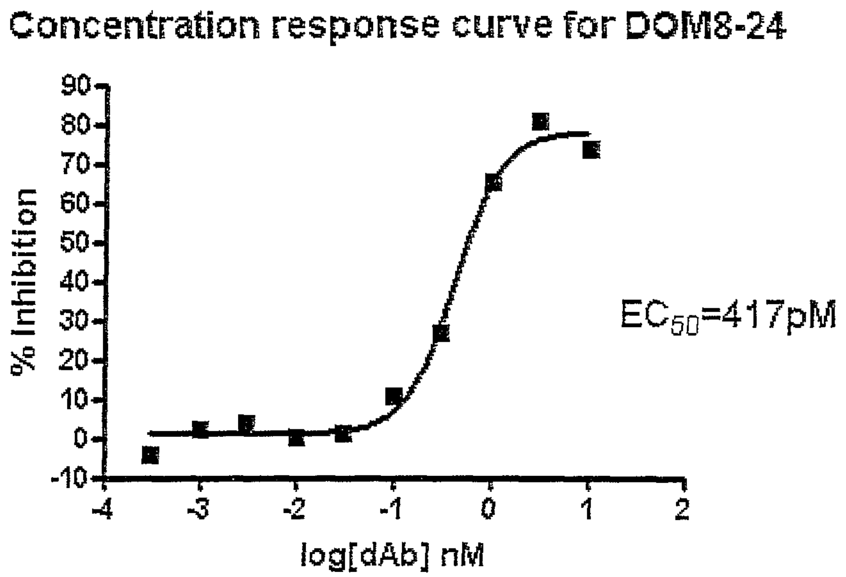
FIG. 4 shows a graphical representation of a dose response receptor binding assay readout, analysing the inhibition of CD40L binding to CD40-Fc by dAb DOM-24, titrated from 100 nM down to 0.5 pM. The data were curve-fitted using GraphPad Prism software.

FIG. 4 shows a dose response receptor binding assay readout, analysing the inhibition of CD40L binding to CD40-Fc by dAb DOM-24, titrated from 100 nM down to 0.5 pM. The data were curve-fitted using GraphPad Prism software.

TABLE 7

| Clone Name | dAb Type | $IC_{50}$ (nM) |
|---|---|---|
| DOM-2 | VH | 800 |
| DOM-4 | VH | 100 |
| DOM-5 | VH | 3 |
| DOM-7 | VH | 1500 |
| DOM-8 | VK | 900 |
| DOM-10 | VH | 50 |
| DOM-20 | VH | 8 |
| DOM-24 | VH | 0.417 |
| DOM-27 | VH | 100 approx. |
| DOM-30 | VH | 8 |
| DOM-31 | VH | 8 |
| DOM-77 | VH | 40 |

TABLE 8

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
DOM-2 SEQ ID NO: 7
     E V Q L L E S G G G L V Q P G G S L R L S C A A S G F T F S D
     Y E M .

   1 GAGGTGCAGC TGTTGGAGTC TGGGGGAGGC TTGGTACAGC CTGGGGGGTC CCTGCGTCTC TCCTGTGCAG
     CCTCCGGATT CACCTTTTCT GATTATGAGA

     CTCCACGTCG ACAACCTCAG ACCCCCTCCG AACCATGTCG GACCCCCCAG GGACGCAGAG AGGACACGTC
     GGAGGCCTAA GTGGAAAAGA CTAATACTCT

     . M W V R Q A P G K G L E W V S T I T S D G I S T Y Y A D S V
     K G R .

 101 TGATGTGGGT CCGCCAGGCT CCAGGGAAGG GTCTAGAGTG GGTCTCAACT ATTACTTCGG ATGGTATTTC
     TACATACTAC GCAGACTCCG TGAAGGGCCG

     ACTACACCCA GGCGGTCCGA GGTCCCTTCC CAGATCTCAC CCAGAGTTGA TAATGAAGCC TACCATAAAG
     ATGTATGATG CGTCTGAGGC ACTTCCCGGC

     . F T I F R D N S K N T L Y L Q M N S L R A E D T A V Y Y C A
     K S G

 201 GTTCACCATC TTCCGCGACA ATTCCAAGAA CACGCTGTAT CTGCAAATGA ACAGCCTGCG TGCCGAGGAT
     ACCGCGGTAT ATTACTGTGC GAAAAGTGGG

     CAAGTGGTAG AAGGCGCTGT TAAGGTTCTT GTGCGACATA GACGTTTACT TGTCGGACGC ACGGCTCCTA
     TGGCGCCATA TAATGACACG CTTTTCACCC

     R F F D Y W G Q G T L V T V S S

 301 AGGTTTTTTG ACTACTGGGG TCAGGGAACC CTGGTCACCG TCTCGAGC                (SEQ ID NO: 94)

     TCCAAAAAAC TGATGACCCC AGTCCCTTGG GACCAGTGGC AGAGCTCG                (SEQ ID NO: 95)

DOM-4 SEQ ID NO: 8
     E V Q L L E S G G G L V G Q P G G S L R L S C A A S G F T F D N
     Y E M .

   1 GAGGTGCAGC TGTTGGAGTC TGGGGGAGGC TTGGTACAGC CTGGGGGGTC CCTGCGTCTC TCCTGTGCAG
     CCTCCGGATT CACCTTTGAT AATTATGAGA

     CTCCACGTCG ACAACCTCAG ACCCCCTCCG AACCATGTCG GACCCCCCAG GGACGCAGAG AGGACACGTC
     GGAGGCCTAA GTGGAAACTA TTAATACTCT

     . T W V R Q A P G K G L E W V S S I T S D G T S T Y Y A D S V
     K G R .

 101 TGACGTGGGT CCGCCAGGCT CCAGGGAAGG GTCTAGAGTG GGTCTCATCT ATTACGAGTG ATGGTACTTC
     GACATACTAC GCAGACTCCG TGAAGGGCCG

     ACTGCACCCA GGCGGTCCGA GGTCCCTTCC CAGATCTCAC CCAGAGTAGA TAATGCTCAC TACCATGAAG
     CTGTATGATG CGTCTGAGGC ACTTCCCGGC

     . F T I S R D N S K N T L Y L Q M N S L R A E D T A V Y Y C A
     K P N
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
201 GTTCACCATC TCCCGCGACA ATTCCAAGAA CACGCTGTAT CTGCAAATGA ACAGCCTGCG TGCCGAGGAT
    ACCGCGGTAT ATTACTGTGC GAAACCTAAT

    CAAGTGGTAG AGGGCGCTGT TAAGGTTCTT GTGCGACATA GACGTTTACT TGTCGGACGC ACGGCTCCTA
    TGGCGCCATA TAATGACACG CTTTGGATTA

    P P F D Y W G Q G T L V T V S S

301 CCGCCGTTTG ACTACTGGGG TCAGGGAACC CTGGTCACCG TCTCGAGC                    (SEQ ID NO: 96)

    GGCGGCAAAC TGATGACCCC AGTCCCTTGG GACCAGTGGC AGAGCTCG                    (SEQ ID NO: 97)

DOM-5 SEQ ID NO: 9
    E V Q L L E S G G G L V Q P G G S L R L S C A A S G F T F D G
    Y E M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGAT GGGTATGAGA

    CTCCACGTCG ACAACCTCAG ACCCCCTCCG AACCATGTCG GACCCCCCAG GGACGCAGAG AGGACACGTC
    GGAGGCCTAA GTGGAAACTA CCCATACTCT

    . A W V R Q A P G K G L E W V S S I T S D G T S T Y Y A D S V
    K G R .

101 TGGCGTGGGT CCGCCAGGCT CCAGGGAAGG GTCTAGAGTG GGTCTCATCT ATTACGAGTG ATGGTACGAG
    TACATACTAC GCAGACTCCG TGAAGGGCCG

    ACCGCACCCA GGCGGTCCGA GGTCCCTTCC CAGATCTCAC CCAGAGTAGA TAATGCTCAC TACCATGCTC
    ATGTATGATG CGTCTGAGGC ACTTCCCGGC

    . F T I S R D N S K N T L Y L Q M N S L R A E D T A V Y Y C A
    K P G

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAACCGGGG

    CAAGTGGTAG AGGGCGCTGT TAAGGTTCTT GTGCGACATA GACGTTTACT TGTCGGACGC ACGGCTCCTG
    TGGCGCCATA TAATGACACG CTTTGGCCCC

    L R F D Y W G Q G T L V T V S S

301 CTGCGTTTTG ACTACTGGGG TCAGGGAACC CTGGTCACCG TCTCGAGC                    (SEQ ID NO: 98)

    GACGCAAAAC TGATGACCCC AGTCCCTTGG GACCAGTGGC AGAGCTCG                    (SEQ ID NO: 99)

DOM-7 SEQ ID NO: 10
    E V Q L L E S G G G L V Q P G G S L R L S C A A S G F T F N L
    Y E M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTAAT TTGTATGAGA

    CTCCACGTCG ACAACCTCAG ACCCCCTCCG AACCATGTCG GACCCCCCAG GGACGCAGAG AGGACACGTC
    GGAGGCCTAA GTGGAAATTA AACATACTCT

    . T W V R Q A P G K G L E W V S S I T S D G V S T Y Y A D S V
    K G R .

101 TGACTTGGGT CCGCCAGGCT CCAGGGAAGG GTCTAGAGTG GGTCTCATCT ATTACTAGTG ATGGTGTTTC
    TACATACTAC GCAGACTCCG TGAAGGGCCG

    ACTGAACCCA GGCGGTCCGA GGTCCCTTCC CAGATCTCAC CCAGAGTAGA TAATGATCAC TACCACAAAG
    ATGTATGATG CGTCTGAGGC ACTTCCCGGC

    . F T I S R D N S K N T L Y L Q M N S L R A E D T A V Y Y C A
    K A G

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAAGCTGGG

    CAAGTGGTAG AGGGCGCTGT TAAGGTTCTT GTGCGACATA GACGTTTACT TGTCGGACGC ACGGCTCCTG
    TGGCGCCATA TAATGACACG CTTTCGACCC

    V I F D Y W G Q G T L V T V S S
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
301 GTGATTTTTG ACTACTGGGG TCAGGGAACC CTGGTCACCG TCTCGAGC                    (SEQ ID NO: 100)

    CACTAAAAAC TGATGACCCC AGTCCCTTGG GACCAGTGGC AGAGCTCG                    (SEQ ID NO: 101)

DOM-8 SEQ ID NO: 11
    D I Q M T Q S P S S L S A S V G D R V T I T C R A S Q F I D T
    S L E .

  1 GACATCCAGA TGACCCAGTC TCCATCCTCC CTGTCTGCAT CTGTAGGAGA CCGTGTCACC ATCACTTGCC
    GGGCAAGTCA GTTTATTGAT ACGTCGTTAG

    CTGTAGGTCT ACTGGGTCAG AGGTAGGAGG GACAGACGTA GACATCCTCT GGCACAGTGG TAGTGAACGG
    CCCGTTCAGT CAAATAACTA TGCAGCAATC

    . W Y Q Q K P G K A P K L L I Y D G S H L Q S G V P S R F S G
    S G S .

101 AGTGGTATCA GCAGAAACCA GGGAAAGCCC CTAAGCTCCT GATCTATGAT GGGTCCCATT TGCAAAGTGG
    GGTCCCATCA CGTTTCAGTG GCAGTGGATC

    TCACCATAGT CGTCTTTGGT CCCTTTCGGG GATTCGAGGA CTAGATACTA CCCAGGGTAA ACGTTTCACC
    CCAGGGTAGT GCAAAGTCAC CGTCACCTAG

    . G T D F T L T I S S L Q P E D L A T Y Y C Q Q Y W V L P L T
    F G Q

201 TGGGACAGAT TTCACTCTCA CCATCAGCAG TCTGCAACCT GAAGATTTAG CTACGTACTA CTGTCAACAG
    TATTGGGTTC TTCCTCTGAC GTTCGGCCAA

    ACCCTGTCTA AAGTGAGAGT GGTAGTCGTC AGACGTTGGA CTTCTAAATC GATGCATGAT GACAGTTGTC
    ATAACCCAAG AAGGAGACTG CAAGCCGGTT

    G T K V E I K R

301 GGGACCAAGG TGGAAATCAA ACGG                                              (SEQ ID NO: 102)

    CCCTGGTTCC ACCTTTAGTT TGCC                                              (SEQ ID NO: 103)

DOM-10 SEQ ID NO: 12
    E V Q L L E S G G G L V Q P G G S L R L S C A A S G F T F I A
    Y D M .

  1 GAGGTGCAGC TGTTGGAGTC TGGGGGAGGC TTAGTACAGC CTGGGGGGTC CCTGCGTCTC TCCTGTGCAG
    CCTCCGGATT CACCTTTATT GCTTATGATA

    CTCCACGTCG ACAACCTCAG ACCCCCTCCG AATCATGTCG GACCCCCCAG GGACGCAGAG AGGACACGTC
    GGAGGCCTAA GTGGAAATAA CGAATACTAT

    . S W V R Q A P G K G L E W V S W I D E W G L Q T Y Y A D S V
    K G R .

101 TGAGTTGGGT CCGCCAGGCT CCAGGGAAGG GTCTGGAGTG GGTCTCATGG ATTGATGAGT GGGGTCTGCA
    GACATACTAC GCAGACTCCG TGAAGGGCCG

    ACTCAACCCA GGCGGTCCGA GGTCCCTTCC CAGACCTCAC CCAGAGTACC TAACTACTCA CCCCAGACGT
    CTGTATGATG CGTCTGAGGC ACTTCCCGGC

    . F T I S R D N S K N T L Y L Q M N S L R A E D T A V Y Y C A
    K K T

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAAAAGACG

    CAAGTGGTAG AGGGCGCTGT TAAGGTTCTT GTGCGACATA GACGTTTACT TGTCGGACGC ACGGCTCCTG
    TGGCGCCATA TAATGACACG CTTTTTCTGC

    P E E F D Y W G Q G T L V T V S S

301 CCTGAGGAGT TTGACTACTG GGGTCAGGGA ACCCTGGTCA CCGTCTCGAG C                 (SEQ ID NO: 104)

    GGACTCCTCA AACTGATGAC CCCAGTCCCT TGGGACCAGT GGCAGAGCTC G                 (SEQ ID NO: 105)
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
DOM-11 SEQ ID NO: 13
     E V Q L L E S G G G L V Q P G G S L R L S C A A S G F T F G D
     Y E M .

   1 GAGGTGCAGC TGTTGGAGTC TGGGGGAGGC TTGGTACAGC CTGGGGGGTC CCTGCGTCTC TCCTGTGCAG
     CCTCCGGATT CACCTTTGGT GATTATGAGA

     CTCCACGTCG ACAACCTCAG ACCCCCTCCG AACCATGTCG GACCCCCCAG GGACGCAGAG AGGACACGTC
     GGAGGCCTAA GTGGAAACCA CTAATACTCT

     . S W V R Q A P G K G L E W V S G I D G E G S D T Y Y A D S V
     K G R .

 101 TGAGTTGGGT CCGCCAGGCT CCAGGGAAGG GTCTAGAGTG GGTCTCAGGG ATTGATGGTG AGGGTTCTGA
     TACATACTAC GCAGACTCCG TGAAGGGCCG

     ACTCAACCCA GGCGGTCCGA GGTCCCTTCC CAGATCTCAC CCAGAGTCCC TAACTACCAC TCCCAAGACT
     ATGTATGATG CGTCTGAGGC ACTTCCCGGC

     . F T I S R D N S K N T L Y L Q M N S L R A E D T A V Y Y Y C A
     K P G

 201 GTTCACCATC TCCCGCGACA ATTCCAAGAA CACGCTGTAT CTGCAAATGA ACAGCCTGCG TGCCGAGGAT
     ACCGCGGTAT ATTACTGTGC GAAACCGGG

     CAAGTGGTAG AGGGCGCTGT TAAGGTTCTT GTGCGACATA GACGTTTACT TGTCGGACGC ACGGCTCCTA
     TGGCGCCATA TAATGACACG CTTTGGCCCC

     R S F D Y W G Q G T L V T V S S

 301 AGGAGTTTTG ACTACTGGGG TCAGGGAACC CTGGTCACCG TCTCGAGC                    (SEQ ID NO: 106)

     TCCTCAAAAC TGATGACCCC AGTCCCTTGG GACCAGTGGC AGAGCTCG                    (SEQ ID NO: 107)

DOM-12 SEQ ID NO: 14
     E V Q L L E S G G G L V Q P G G S L R L S C A A S G F T F R L
     Y E M .

   1 GAGGTGCAGC TGTTGGAGTC TGGGGGAGGC TTGGTACAGC CTGGGGGGTC CCTGCGTCTC TCCTGTGCAG
     CCTCCGGATT CACCTTTAGG TTGTATGAGA

     CTCCACGTCG ACAACCTCAG ACCCCCTCCG AACCATGTCG GACCCCCCAG GGACGCAGAG AGGACACGTC
     GGAGGCCTAA GTGGAAATCC AACATACTCT

     . A W V R Q A P G K G L E W V S G I D I L G S R T Y Y A D S V
     K G R .

 101 TGGCGTGGGT CCGCCAGGCT CCAGGGAAGG GTCTAGAGTG GGTCTCAGGG ATTGATATTT TGGGTTCGAG
     GACATACTAC GCAGACTCCG TGAAGGGCCG

     ACCGCACCCA GGCGGTCCGA GGTCCCTTCC CAGATCTCAC CCAGAGTCCC TAACTATAAA ACCCAAGCTC
     CTGTATGATG CGTCTGAGGC ACTTCCCGGC

     . F T I S R D N S K N T L Y L Q M N S L R A E D T A V Y C A
     K D L

 201 GTTCACCATC TCCCGCGACA ATTCCAAGAA CACGCTGTAT CTGCAAATGA ACAGCCTGCG TGCCGAGGAT
     ACCGCGGTAT ATTACTGTGC GAAAGATCTG

     CAAGTGGTAG AGGGCGCTGT TAAGGTTCTT GTGCGACATA GACGTTTACT TGTCGGACGC ACGGCTCCTA
     TGGCGCCATA TAATGACACG CTTTCTAGAC

     S W Q G F D Y W G Q G T L V T V S S

 301 TCGTGGCAGG GTTTTGACTA CTGGGGTCAG GGAACCCTGG TCACCGTCTC GACC             (SEQ ID NO: 108)

     AGCACCGTCC CAAAACTGAT GACCCCAGTC CCTTGGGACC AGTGGCAGAG CTCG             (SEQ ID NO: 109)

DOM-13 SEQ ID NO: 15
     E V Q L L E S G G G L V Q P G G S L R L S C A A S G F T F S Y
     Y S M .

   1 GAGGTGCAGC TGTTGGAGTC TGGGGGAGGC TTGGTACAGC CTGGGGGGTC CCTGCGTCTC TCCTGTGCAG
     CCTCCGGATT CACCTTTTCT TATTATTCGA
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
    CTCCACGTCG ACAACCTCAG ACCCCCTCCG AACCATGTCG GACCCCCCAG GGACGCAGAG AGGACACGTC
    GGAGGCCTAA GTGGAAAAGA ATAATAAGCT

    . Y W V R Q A P G K G L E W V S S I S P F G W G T Y Y A D S V
    K G R .

101 TGTATTGGGT CCGCCAGGCT CCAGGGAAGG GTCTAGAGTG GGTCTCATCG ATTTCGCCTT TTGGTTGGGG
    TACATACTAC GCAGACTCCG TGAAGGGCCG

    ACATAACCCA GGCGGTCCGA GGTCCCTTCC CAGATCTCAC CCAGAGTAGC TAAAGCGGAA AACCAACCCC
    ATGTATGATG CGTCTGAGGC ACTTCCCGGC

    . F T I S R D N S K D T L Y L Q M N S L R A E D T A V Y Y C A
    K Y G

201 GTTCACCATC TCCCGCGACA ATTCCAAGGA CACGCTGTAT CTGCAAATGA ACAGCCTGCG TGCCGAGGAC
    ACCGCGGTAT ATTACTGTGC GAAATATGGG

    CAAGTGGTAG AGGGCGCTGT TAAGGTTCCT GTGCGACATA GACGTTTACT TGTCGGACGC ACGGCTCCTG
    TGGCGCCATA TAATGACACG CTTTATACCC

    E T S G P I S E N F D Y W G Q G T L V T V S S

351 GAGACGAGTG GTCCGATTTC TGAGAATTTT GACTACTGGG GTCAGGGAAC CCTGGTCACC GTCTCGAGC      (SEQ ID NO: 110)

    CTCTGCTCAC CAGGCTAAAG ACTCTTAAAA CTGATGACCC CAGTCCCTTG GGACCAGTGG CAGAGCTCG      (SEQ ID NO: 111)

DOM-14 SEQ ID NO: 16
    E V Q L L E S G G G L V Q P G G S L R L S C A A S G F T F W S
    Y D M .

  1 GAGGTGCAGC TGTTGGACTC TGGGGGAGGC TTGGTACAGC CTGGGGGGTC CCTGCGTCTC TCCTGTGCAG
    CCTCCGGATT CACCTTTTGG TCTTATGATA

    CTCCACGTCG ACAACCTCAG ACCCCCTCCG AACCATGTCG GACCCCCCAG GGACGCAGAG AGGACACGTC
    GGAGGCCTAA GTGGAAAACC AGAATACTAT

    . T W V R Q A P G K G L E W V S S I M A S G D D T Y Y A D S V
    K G R .

101 TGACGTGGGT CCGCCAGGCT CCAGGGAAGG GTCTAGAGTG GGTCTCATCT ATTATGGCTT CGGGTGATGA
    TACATACTAC GCAGACTCCG TGAAGGGCCG

    ACTGCACCCA GGCGGTCCGA GGTCCCTTCC CAGATCTCAC CCAGAGTAGA TAATACCGAA GCCCACTACT
    ATGTATGATG CGTCTGAGGC ACTTCCCGGC

    . F T I S R D N S K N T L Y L Q M N S L R A E D T A V Y Y C A
    K W D

201 GTTCACCATC TCCCGCGACA ATTCCAAGAA CACGCTGTAT CTGCAAATGA ACAGCCTGCG TGCCGAGGAT
    ACCGCGGTAT ATTACTGTGC GAAATGGGAT

    CAAGTGGTAG AGGGCGCTGT TAAGGTTCTT GTGCGACATA GACGTTTACT TGTCGGACGC ACGGCTCCTA
    TGGCGCCATA TAATGACACG CTTTACCCTA

    R D F D Y W G Q G T L V T V S S

301 CGGGATTTTG ACTACTGGGG TCAGGGAACC CTGGTCACCG TCTCGAGC                            (SEQ ID NO: 112)

    GCCCTAAAAC TGATGACCCC AGTCCCTTGG GACCAGTGGC AGAGCTCG                            (SEQ ID NO: 113)

DOM-15 SEQ ID NO: 17
    E V Q L L E S G G G L V Q P G G S L R L S C A A S G F T F E E
    Y V M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGAG GAGTATGTTA

    CTCCACGTCG ACAACCTCAG ACCCCCTCCG AACCATGTCG GACCCCCCAG GGACGCAGAG AGGACACGTC
    GGAGGCCTAA GTGGAAACTC CTCATACAAT

    . S W V R Q A P G K G L E W V S T I S P I G L T T Y Y A D S V
    K G R .
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
101 TGTCGTGGGT CCGCCAGGCT CCAGGGAAGG GTCTGGAGTG GGTCTCAACT ATTTCTCCTA TTGGTCTGAC
    TACATACTAC GCAGACTCCG TGAAGGGCCG

    ACAGCACCCA GGCGGTCCGA GGTCCCTTCC CAGACCTCAC CCAGAGTTGA TAAAGAGGAT AACCAGACTG
    ATGTATGATG CGTCTGAGGC ACTTCCCGGC

    . F T I S R D N S K N T L Y L Q M N S L R A E D T A V Y Y C A
    E F P

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GGAATTTCCT

    CAAGTGGTAG AGGGCGCTGT TAAGGTTCTT GTGCGACATA GACGTTTACT TGTCGGACGC ACGGCTCCTG
    TGGCGCCATA TAATGACACG CCTTAAAGGA

    L I I L P D F D Y W G Q G T L V T V S S

301 TTGATTATTC TTCCTGATTT TGACTACTGG GGTCAGGGAA CCCTGGTCAC CGTCTCGAGC         (SEQ ID NO: 114)

    AACTAATAAG AAGGACTAAA ACTGATGACC CCAGTCCCTT GGGACCAGTG GCAGAGCTCG         (SEQ ID NO: 115)

DOM-16 SEQ ID NO: 18
    E V Q L L E S G G G L V Q P G G S L R L S C A A S G F T F M E
    Y A M .

  1 GAGGTGCAGC TGTTGGAGTC TGGGGGAGGC CTGGTACAGC CTGGGGGGTC CCTGCGTCTC TCCTGTGCAG
    CCTCCGGATT CACCTTTATG GAGTATGCGA

    CTCCACGTCG ACAACCTCAG ACCCCCTCCG GACCATGTCG GACCCCCCAG GGACGCAGAG AGGACACGTC
    GGAGGCCTAA GTGGAAATAC CTCATACGCT

    . I W V R Q A P G K G L E W V S I I S P L G L S T Y Y A D S V
    K G R .

101 TGATTTGGGT CCGCCAGGCT CCAGGGAAGG GTCTAGAGTG GGTCTCAATT ATTTCTCCGC TTGGTTTGTC
    TACATACTAC GCAGACTCCG TGAAGGGCCG

    ACTAAACCCA GGCGGTCCGA GGTCCCTTCC CAGATCTCAC CCAGAGTTAA TAAAGAGGCG AACCAAACAG
    ATGTATGATG CGTCTGAGGC ACTTCCCGGC

    . F T I S R D N S K N T L Y L Q M N S L R A E D T A V Y Y C A
    K Y Q

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAATATCAG

    CAAGTGGTAG AGGGCGCTGT TAAGGTTCTT GTGCGACATA GACGTTTACT TGTCGGACGC ACGGCTCCTG
    TGGCGCCATA TAATGACACG CTTTATAGTC

    D S S D S Q Y T N F D Y W G Q G T L V T V S S

301 GATTCGTCTG ATAGTCAGTA TACGAATTTT GACTACTGGG GTCAGGGAAC CCTGGTCACC GTCTCGAGC   (SEQ ID NO: 116)

    CTAAGCAGAC TATCAGTCAT ATGCTTAAAA CTGATGACCC CAGTCCCTTG GGACCAGTGG CAGAGCTCG   (SEQ ID NO: 117)

DOM-17 SEQ ID NO: 19
    E V Q L L E S G G G L V Q P G G S L R L S C A A S G F T F E D
    Y G M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGAG GATTATGGGA

    CTCCACGTCG ACAACCTCAG ACCCCCTCCG AACCATGTCG GACCCCCCAG GGACGCACAG AGGACACGTC
    GGAGGCCTAA GTGGAAACTC CTAATACCCT

    . G W A R Q A P G K G L E W V S S I G P L G L W T Y Y A D S A
    K G R .

101 TGGGGTGGGC CCGCCAGGCT CCAGGGAAGG GTCTAGAGTG GGTCTCAAGT ATTGGTCCTC TGGGTCTTTG
    GACATACTAC GCAGACTCCG CGAAGGGCCG

    ACCCCACCCG GGCGGTCCGA GGTCCCTTCC CAGATCTCAC CCAGAGTTCA TAACCAGGAG ACCCAGAAAC
    CTGTATGATG CGTCTGAGGC GCTTCCCGGC
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
     . F T I S R D N S K N T L Y L Q M N S L R A E D T A V Y Y C A
     K S P

 201 GTTCACCATC TCCCGCGACA ATTCCAAGAA CACGCTGTAT CTGCAAATGA ACAGCCTGCG TGCCGAGGAC
     ACCGCGGTAT ATTACTGTGC GAAATCTCCG

     CAAGTGGTAG AGGGCGCTGT TAAGGTTCTT GTGCGACATA GACGTTTACT TGTCGGACGC ACGGCTCCTG
     TGGCGCCATA TAATGACACG CTTTAGAGGC

     L E G L I T N F D Y W G Q G T L V T V S S

 301 CTTGAGGGTT TGATTACGAA TTTTGACTAC TGGGGTCAGG GAACCCTGGT CACCGTCTCG AGC           (SEQ ID NO: 118)

     GAACTCCCAA ACTAATGCTT AAAACTGATG ACCCCAGTCC CTTGGGACCA GTGGCAGAGC TCG           (SEQ ID NO: 119)

DOM-18 SEQ ID NO: 20
     E V Q L L E S G G G L V Q P G G S L R L S C A A S G F T F P E
     Y D M .

   1 GAGGTGCAGC TGTTGGAGTC TGGGGGAGGC TTGGTACAGC CTGGGGGGTC CCTGCGTCTC TCCTGTGCAG
     CCTCCGGATT CACCTTTCCT GAGTATGATA

     CTCCACGTCG ACAACCTCAG ACCCCCTCCG AACCATGTCG GACCCCCCAG GGACGCAGAG AGGACACGTC
     GGAGGCCTAA GTGGAAAGGA CTCATACTAT

     . T W V R Q A P G K G L E W V S Y I S S D G Y S T Y Y A D S V
     K G R .

 101 TGACGTGGGT CCGCCAGGCT CCAGGGAAGG GTCTGGAGTG GGTCTCATAT ATTAGTTCTG ATGGTTATTC
     TACATACTAC GCAGACTCCG TGAAGGGCCG

     ACTGCACCCA GGCGGTCCGA GGTCCCTTCC CAGACCTCAC CCAGAGTATA TAATCAAGAC TACCAATAAG
     ATGTATGATG CGTCTGAGGC ACTTCCCGGC

     . F T I S R D N S K N T L Y L Q M N S L R A E D T A V Y Y C A
     K P H

 201 GTTCACCATC TCCCGCGACA ATTCCAAGAA CACGCTGTAT CTGCAAATGA ACAGCCTGCG TGCCGAGGAC
     ACCGCGGTAT ATTACTGTGC GAAACCGCAT

     CAAGTGGTAG AGGGCGCTGT TAAGGTTCTT GTGCGACATA GACGTTTACT TGTCGGACGC ACGGCTCCTG
     TGGCGCCATA TAATGACACG CTTTGGCGTA

     G S P R E F D Y W G Q G T L V T V S S

 301 GGGAGTCCGC GGGAGTTTGA CTACTGGGGT CAGGGAACCC TGGTCACCGT CTCGAGC               (SEQ ID NO: 120)

     CCCTCAGGCG CCCTCAAACT GATGACCCCA GTCCCTTGGG ACCAGTGGCA GAGCTCG               (SEQ ID NO: 121)

DOM-19 SEQ ID NO: 21
     E V Q L L E S G G G L V Q P G G S L R L S C A A S G F P F P Q
     Y Q M .

   1 GAGGTGCAGC TGTTGGAGTC TGGGGGAGGC TTGGTACAGC CTGGGGGGTC CCTGCGTCTC TCCTGTGCAG
     CCTCCGGATT CCCCTTTCCG CAGTATCAGA

     CTCCACGTCG ACAACCTCAG ACCCCCTCCG AACCATGTCG GACCCCCCAG GGACGCAGAG AGGACACGTC
     GGAGGCCTAA GGGGAAAGGC GTCATAGTCT

     . A W V R Q A P G K G L E W V S M I T S D G L D T Y Y A D S V
     K G R .

 101 TGGCGTGGGT CCGCCAGGCT CCAGGGAAGG GTCTAGAGTG GGTCTCAATG ATTACTTCTG ATGGTCTTGA
     TACATATTAC GCAGACTCCG TGAAGGGCCG

     ACCGCACCCA GGCGGTCCGA GGTCCCTTCC CAGATCTCAC CCAGAGTTAC TAATGAAGAC TACCAGAACT
     ATGTATAATG CGTCTGAGGC ACTTCCCGGC

     . F T I S R D N S K N T L Y L Q M N S L R A E D T A V Y Y C A
     K P E

 201 GTTCACCATC TCCCGCGACA ATTCCAAGAA CACGCTGTAT CTGCAAATGA ACAGCCTGCG TGCCGAGGAT
     ACCGCGGTAT ATTACTGTGC GAAACCTGAG
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
    CAAGTGGTAG AGGGCGCTGT TAAGGTTCTT GTGCGACATA GACGTTTACT TGTCGGACGC ACGGCTCCTA
    TGGCGCCATA TAATGACACG CTTTGGACTC

    P L F D Y W G Q G T L V T V S S

301 CCTCTTTTTG ACTACTGGGG TCAGGGAACC CTGGTCACCG TCTCGAGC          (SEQ ID NO: 122)

    GGAGAAAAAC TGATGACCCC AGTCCCTTGG GACCAGTGGC AGAGCTCG          (SEQ ID NO: 123)

DOM-20 SEQ ID NO: 22
    E V Q L L E S G G G L V Q P G G S L R L S C A A S G F T F S G
    Y Q M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTTCG GGTTATCAGA

    CTCCACGTCG ACAACCTCAG ACCCCCTCCG AACCATGTCG GACCCCCCAG GGACGCAGAG AGGACACGTC
    GGAGGCCTAA GTGGAAAAGC CCAATAGTCT

    . A W V R Q A P G K G L E W V S G I S S E G L T T Y Y A D S V
    K G R .

101 TGGCTTGGGT CCGCCAGGCT CCAGGGAAGG GTCTAGAGTG GGTCTCAGGT ATTAGTTCGG AGGGTCTTAC
    TACATACTAC GCAGACTCCG TGAAGGGCCG

    ACCGAACCCA GGCGGTCCGA GGTCCCTTCC CAGATCTCAC CCAGAGTCCA TAATCAAGCC TCCCAGAATG
    ATGTATGATG CGTCTGAGGC ACTTCCCGGC

    . F T I S R D N S K N T L Y L Q M N S L R A E D T A V Y Y C A
    K L G

201 GTTCACCATC TCCCGCGACA ATTCCAAGAA GACGCTGTAT CTGCAAATGA ACAGCCTGCG TGCCGAGGAC
    ACCGCGGTAT ATTACTGTGC GAAATTGGGG

    CAAGTGGTAG AGGGCGCTGT TAAGGTTCTT GTGCGACATA GACGTTTACT TGTCGGACGC ACGGCTCCTG
    TGGCGCCATA TAATGACACG CTTTAACCCC

    R R F D Y W G Q G T L V T V S S

301 CGTAGGTTTG ACTACTGGGG TCAGGGAACC CTGGTCACCG TCTCGAGC          (SEQ ID NO: 124)

    GCATCCAAAC TGATGACCCC AGTCCCTTGG GACCAGTGGC AGAGCTCG          (SEQ ID NO: 125)

DOM-21 SEQ ID NO: 23
    E V Q L L E S G G G L V Q P G G S L R L S C A A S G F T F A N
    Y E M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGCG AATTATGAGA

    CTCCACGTCG ACAACCTCAG ACCCCCTCCG AACCATGTCG GACCCCCCAG GGACGCAGAG AGGACACGTC
    GGAGGCCTAA GTGGAAACGC TTAATACTCT

    . G W A R Q A P G K G L E W V S V I S E W G Y S T Y Y A D S A
    K G R .

101 TGGGGTGGGC CCGCCAGGCT CCAGGGAAGG GTCTAGAGTG GGTCTCAGTT ATTTCTGAGT GGGGTTATTC
    TACATACTAC GCAGACTCCG CGAAGGGCCG

    ACCCCACCCG GGCGGTCCGA GGTCCCTTCC CAGATCTCAC CCAGAGTCAA TAAAGACTCA CCCCAATAAG
    ATGTATGATG CGTCTGAGGC GCTTCCCGGC

    . F T I S R D N S K N T L Y L Q M N S L R A E D T A V Y Y C A
    K L V

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAACTTGTG

    CAAGTGGTAG AGGGCGCTGT TAAGGTTCTT GTGCGACATA GACGTTTACT TGTCGGACGC ACGGCTCCTG
    TGGCGCCATA TAATGACACG CTTTGAACAC

    G G T Q Y E F D Y W G Q G T L V T V S S

301 GGTGGGACTC AGTATGAGTT TGACTACTGG GGTCAGGGAA CCCTGGTCAC CGTCTCGAGC          (SEQ ID NO: 126)
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
     CCACCCTGAG TCATACTCAA ACTGATGACC CCAGTCCCTT GGGACCAGTG GCAGAGCTCG              (SEQ ID NO: 127)

DOM-22 SEQ ID NO: 24
     E V Q L L E S G G G L V Q P G G S L R L S C A A S G F T F H N
     Y E M .

   1 GAGGTGCAGC TGTTGGAGTC TGGGGGAGGC TTGGTACAGC CTGGGGGGTC CCTGCGTCTC TCCTGTGCAG
     CCTCCGGATT CACCTTTCAT AATTATGAGA

     CTCCACGTCG ACAACCTCAG ACCCCCTCCG AACCATGTCG GACCCCCCAG GGACGCAGAG AGGACACGTC
     GGAGGCCTAA GTGGAAAGTA TTAATACTCT

     . S W V R Q A P G K G L E W V S S I S S G G S S T Y Y A D S V
     K G R .

 101 TGTCGTGGGT CCGCCAGGCT CCAGGGAAGG GTCTAGAGTG GGTCTCAAGT ATTTCTTCGG GTGGTTCTTC
     TACATACTAC GCAGACTCCG TGAAGGGCCG

     ACAGCACCCA GGCGGTCCGA GGTCCCTTCC CAGATCTCAC CCAGAGTTCA TAAAGAAGCC CACCAAGAAG
     ATGTATGATG CGTCTGAGGC ACTTCCCGGC

     . F T I S R D N S K N T L Y L Q M N S L R A E D T A V Y Y C A
     K P G

 201 GTTCACCATC TCCCGCGACA ATTCCAAGAA CACGCTGTAT CTGCAAATGA ACAGCCTGCG TGCCGAGGAC
     ACCGCGGTAT ATTACTGTGC GAAACCGGGG

     CAAGTGGTAG AGGGCGCTGT TAAGGTTCTT GTGCGACATA GACGTTTACT TGTCGGACGC ACGGCTCCTG
     TGGCGCCATA TAATGACACG CTTTGGCCCC

     V K F D Y W G Q G T L V T V S S

 301 GTTAAGTTTG ACTACTGGGG TCAGGGAACC CTGGTCACCG TCTCGAGC                        (SEQ ID NO: 128)

     CAATTCAAAC TGATGACCCC AGTCCCTTGG GACCAGTGGC AGAGCTCG                        (SEQ ID NO: 129)

DOM-23 SEQ ID NO: 25
     E V Q L L E S G G G L V Q P G G S L R L S C A A S G F T F G L
     Y E M .

   1 GAGGTGCAGC TGTTGGAGTC CGGGGGAGGC TTGGTACAGC CTGGGGGGTC CCTGCGTCTC TCCTGTGCAG
     CCTCCGGATT CACCTTTGGG CTGTATGAGA

     CTCCACGTCG ACAACCTCAG GCCCCCTCCG AACCATGTCG GACCCCCCAG GGACGCAGAG AGGACACGTC
     GGAGGCCTAA GTGGAAACCC GACATACTCT

     . T W V R Q A P G K G L E W V S S I T G D G I S T Y Y A D S V
     K G R .

 101 TGACGTGGGT CCGCCAGGCT CCAGGGAAGG GTCTAGAGTG GGTCTCAAGT ATTACGGGTG ATGGTATTTC
     GACATACTAC GCAGACTCCG TGAAGGGCCG

     ACTGCACCCA GGCGGTCCGA GGTCCCTTCC CAGATCTCAC CCAGAGTTCA TAATGCCCAC TACCATAAAG
     CTGTATGATG CGTCTGAGGC ACTTCCCGGC

     . F T I S R D N S R N T L Y L Q M N S L R A E D T A V Y Y C A
     K A G

 201 GTTCACCATC TCCCGCGACA ATTCCAGGAA CACGCTGTAT CTGCAAATGA ACAGCCTGCG TGCCGAGGAC
     ACCGCGGTAT ATTACTGTGC GAAAGCTGGG

     CAAGTGGTAG AGGGCGCTGT TAAGGTCCTT GTGCGACATA GACGTTTACT TGTCGGACGC ACGGCTCCTG
     TGGCGCCATA TAATGACACG CTTTCGACCC

     R K F D Y W G Q G T L V T V S S

 301 AGGAAGTTTG ACTACTGGGG TCAGGGAACC CTGGTCACCG TCTCGAGC                        (SEQ ID NO: 130)

     TCCTTCAAAC TGATGACCCC AGTCCCTTGG GACCAGTGGC AGAGCTCG                        (SEQ ID NO: 131)

DOM-24 SEQ ID NO: 26
     E V Q L L E S G G G L V Q P G G S L R L S C A A S G F T F S N
     Y Q M .
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
  1 GAGGTGCAGC TGTTGGAGTC TGGGGGAGGC TTGGTACAGC CTGGGGGGTC CCTGCGTCTC TCCTGTGCAG
    CCTCCGGATT CACCTTTAGT AATTATCAGA

    CTCCACGTCG ACAACCTCAG ACCCCCTCCG AACCATGTCG GACCCCCCAG GGACGCAGAG AGGACACGTC
    GGAGGCCTAA GTGGAAATCA TTAATAGTCT

    . A W V R Q A P G K G L E W V S S I T S E G G S T Y Y A D S V
    K G R .

101 TGGCGTGGGT CCGCCAGGCT CCAGGGAAGG GTCTAGAGTG GGTCTCAAGT ATTACTAGTG AGGGTGGTTC
    GACATACTAC GCAGACTCCG TGAAGGGCCG

    ACCGCACCCA GGCGGTCCGA GGTCCCTTCC CAGATCTCAC CCAGAGTTCA TAATGATCAC TCCCACCAAG
    CTGTATGATG CGTCTGAGGC ACTTCCCGGC

    . F T I S R D N S K N T L Y L Q M N S L R A E D T A V Y Y C A
    K P G

201 GTTCACCATC TCCCGCGACA ATTCCAAGAA CACACTGTAT CTGCAAATGA ACAGCCTGCG TGCCGAGGAC
    ACCGCGGTAT ATTACTGTGC GAAACCGGGT

    CAAGTGGTAG AGGGCGCTGT TAAGGTTCTT GTGTGACATA GACGTTTACT TGTCGGACGC ACGGCTCCTG
    TGGCGCCATA TAATGACACG CTTTGGCCCA

    K N F D Y W G Q G T L V T V S S

301 AAGAATTTTG ACTACTGGGG TCAGGGAACC CTGGTCACCG TCTCGAGC                (SEQ ID NO: 132)

    TTCTTAAAAC TGATGACCCC AGTCCCTTGG GACCAGTGGC AGAGCTCG                (SEQ ID NO: 133)

DOM-25 SEQ ID NO: 27
    E V Q L L E S G G G L V Q P G G S L R L S C A A S G F T F D N
    Y E M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGAT AATTATGAGA

    CTCCACGTCG ACAACCTCAG ACCCCCTCCG AACCATGTCG GACCCCCCAG GGACGCAGAG AGGACACGTC
    GGAGGCCTAA GTGGAAACTA TTAATACTCT

    . T W V R Q A P G K G L E W V S T I T S Q G T S T Y Y A D S V
    K G R .

101 TGACGTGGGT CCGCCAGGCT CCAGGGAAGG GTCTAGAGTG GGTCTCAACT ATTACGTCGC AGGGTACTAG
    TACATACTAC GCAGACTCCG TGAAGGGCCG

    ACTGCACCCA GGCGGTCCGA GGTCCCTTCC CAGATCTCAC CCAGAGTTGA TAATGCAGCG TCCCATGATC
    ATGTATGATG CGTCTGAGGC ACTTCCCGGC

    . F T I S R D N S K N T L Y L Q M N S L R A E D T A V Y Y C A
    K P D

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAACCTGAT

    CAAGTGGTAG AGGGCGCTGT TAAGGTTCTT GTGCGACATA GACGTTTACT TGTCGGACGC ACGGCTCCTG
    TGGCGCCATA TAATGACACG CTTTGGACTA

    R S F D Y W G Q G T L V T V S S

301 CGTTCTTTTG ACTACTGGGG TCAGGGAACC CTGGTCACCG TCTCGAGC                (SEQ ID NO: 134)

    GCAAGAAAAC TGATGACCCC AGTCCCTTGG GACCAGTGGC AGAGCTCG                (SEQ ID NO: 135)

DOM-26 SEQ ID NO: 28
    E V Q L L E S G G G L V Q P G G S L R L S C A A S G F T F R S
    Y E M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTCGT AGTTATGAGA

    CTCCACGTCG ACAACCTCAG ACCCCCTCCG AACCATGTCG GACCCCCCAG GGACGCAGAG AGGACACGTC
    GGAGGCCTAA GTGGAAAGCA TCAATACTCT
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
     . T W V R Q A P G K G L E W V S S I T S D G G T T Y Y A D S V
     K G R .

 101 TGACTTGGGT CCGCCAGGCT CCAGGGAAGG GTCTGGAGTG GGTCTCATCT ATTACGTCGG ATGGTGGTAC
     TACATACTAC GCAGACTCCG TGAAGGGCCG

     ACTGAACCCA GGCGGTCCGA GGTCCCTTCC CAGACCTCAC CCAGAGTAGA TAATGCAGCC TACCACCATG
     ATGTATGATG CGTCTGAGGC ACTTCCCGGC

     . F T I S R D N S K N T L Y L Q M N S L R A E D T A V Y Y C A
     K P D

 201 GTTCACCATC TCCCGCGACA ATTCCAAGAA CACGCTGTAT CTGCAAATGA ACAGCCTGCG TGCCGAGGAC
     ACCGCGGTAT ATTACTGTGC GAAACCTGAT

     CAAGTGGTAG AGGGCGCTGT TAAGGTTCTT GTGCGACATA GACGTTTACT TGTCGGACGC ACGGCTCCTG
     TGGCGCCATA TAATGACACG CTTTGGACTA

     K T F D Y W G Q G T L V T V S S

 301 AAGACGTTTG ACTACTGGGG TCAGGGAACC CTGGTCACCG TCTCGAGC                (SEQ ID NO: 136)

     TTCTGCAAAC TGATGACCCC AGTCCCTTGG GACCAGTGGC AGAGCTCG                (SEQ ID NO: 137)

DOM-27 SEQ ID NO: 29
     E V Q L L E S G G G L V Q P G G S L R L S C A A S G F T F N L
     Y E M .

   1 GAGGTGCAGC TGTTGGAGTC TGGGGGAGGC TTGGTACAGC CTGGGGGGTC CCTGCGTCTC TCCTGTGCAG
     CCTCCGGATT CACCTTTAAT TTGTATGAGA

     CTCCACGTCG ACAACCTCAG ACCCCCTCCG AACCATGTCG GACCCCCCAG GGACGCAGAG AGGACACGTC
     GGAGGCCTAA GTGGAAATTA AACATACTCT

     . T W V R Q A P G K G L E W V S S I T S D G V S T Y Y A D S V
     K G R .

 101 TGACTTGGGT CCGCCAGGCT CCAGGGAAGG GTCTAGAGTG GGTCTCATCT ATTACTAGTG ATGGTGTTTC
     TACATACTAC GCAGACTCCG TGAAGGGCCG

     ACTGAACCCA GGCGGTCCGA GGTCCCTTCC CAGATCTCAC CCAGAGTAGA TAATGATCAC TACCACAAAG
     ATGTATGATG CGTCTGAGGC ACTTCCCGGC

     . F T I S R D N S K N T L Y L Q M N S L R A E D T A V Y Y C A
     K P D

 201 GTTCACCATC TCCCGCGACA ATTCCAAGAA CACGCTGTAT CTGCAAATGA ACAGCCTGCG TGCCGAGGAC
     ACCGCGGTAT ATTACTGTGC GAAACCGGAT

     CAAGTGGTAG AGGGCGCTGT TAAGGTTCTT GTGCGACATA GACGTTTACT TGTCGGACGC ACGGCTCCTG
     TGGCGCCATA TAATGACACG CTTTGGCCTA

     S P F D Y W G Q G T L V T V S S

 301 TCTCCGTTTG ACTACTGGGG TCAGGGAACC CTGGTCACCG TCTCGAGC                (SEQ ID NO: 138)

     AGAGGCAAAC TGATGACCCC AGTCCCTTGG GACCAGTGGC AGAGCTCG                (SEQ ID NO: 139)
DOM-28 SEQ ID NO: 30
     E V Q L L E S G G G L V Q P G G S L R L S C A A S G F T F G H
     Y D M .

   1 GAGGTGCAGC TGTTGGAGTC TGGGGGAGGC TTGGTACAGC CTGGGGGGTC CCTGCGTCTC TCCTGTGCAG
     CCTCCGGATT CACCTTTGGG CATTATGATA

     CTCCACGTCG ACAACCTCAG ACCCCCTCCG AACCATGTCG GACCCCCCAG GGACGCAGAG AGGACACGTC
     GGAGGCCTAA GTGGAAACCC GTAATACTAT

     . A W V R Q A P G K G L E W V S T I S D N G N G T Y Y A D S V
     K G R .

 101 TGGCTTGGGT CCGCCAGGCT CCAGGGAAGG GTCTAGAGTG GGTCTCAACT ATTAGTGATA ATGGTAATGG
     GACATACTAC GCAGACTCCG TGAAGGGCCG

     ACCGAACCCA GGCGGTCCGA GGTCCCTTCC CAGATCTCAC CCAGAGTTGA TAATCACTAT TACCATTACC
     CTGTATGATG CGTCTGAGGC ACTTCCCGGC
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
    . F T I S R D N S K N T L Y L Q M N S L R A E D T A V Y Y C A
    K P G

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAACCGGGG

    CAAGTGGTAG AGGGCGCTGT TAAGGTTCTT GTGCGACATA GACGTTTACT TGTCGGACGC ACGGCTCCTG
    TGGCGCCATA TAATGACACG CTTTGGCCCC

    R D F D Y W G Q G T L V T V S S

301 CGTGATTTTG ACTACTGGGG TCAGGGAACC CTGGTCACCG TCTCGAGC          (SEQ ID NO: 140)

    GCACTAAAAC TGATGACCCC AGTCCCTTGG GACCAGTGGC AGAGCTCG          (SEQ ID NO: 141)

DOM-29 SEQ ID NO: 31
    E V Q L L E S G G G L V Q P G G S L R L S C A A S G F T F G R
    Y Q M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGGT CGTTATCAGA

    CTCCACGTCG ACAACCTCAG ACCCCCTCCG AACCATGTCG GACCCCCCAG GGACGCAGAG AGGACACGTC
    GGAGGCCTAA GTGGAAACCA GCAATAGTCT

    . A W V R Q A P G K G L E W V S S I S S D G G G T Y Y A D S V
    K G R .

101 TGGCTTGGGT CCGCCAGGCT CCAGGGAAGG GTCTAGAGTG GGTCTCATCT ATTTCTTCTG ATGGTGGGGG
    GACATACTAC GCAGACTCCG TGAAGGGCCG

    ACCGAACCCA GGCGGTCCGA GGTCCCTTCC CAGATCTCAC CCAGAGTAGA TAAAGAAGAC TACCACCCCC
    CTGTATGATG CGTCTGAGGC ACTTCCCGGC

    . F T I S R D N S K N T L Y L Q M N S L R A E D T A V Y Y C A
    K P G

201 GTTCACCATC TCCCGCGACA ATTCCAAGAA CACGCTGTAT CTGCAAATGA ACAGCCTGCG TGCCGAGGAT
    ACCGCGGTAT ATTACTGTGC GAAACCTGGG

    CAAGTGGTAG AGGGCGCTGT TAAGGTTCTT GTGCGACATA GACGTTTACT TGTCGGACGC ACGGCTCCTA
    TGGCGCCATA TAATGACACG CTTTGGACCC

    R A F D Y W G Q G T L V T V S S

301 CGGGCGTTTG ACTACTGGGG TCAGGGAACC CTGGTCACCG TCTCGAGC          (SEQ ID NO: 142)

    GCCCGCAAAC TGATGACCCC AGTCCCTTGG GACCAGTGGC AGAGCTCG          (SEQ ID NO: 143)

DOM-30 SEQ ID NO: 32
    E V Q L L E S G G G L V Q P G G S L R L S C A A S G F T F A R
    Y Q M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGCG AGGTATCAGA

    CTCCACGTCG ACAACCTCAG ACCCCCTCCG AACCATGTCG GACCCCCCAG GGACGCAGAG AGGACACGTC
    GGAGGCCTAA GTGGAAACGC TCCATAGTCT

    . A W V R Q A P G K G L E W V S T I S D D G D S T Y Y A D S V
    K G R .

101 TGGCTTGGGT CCGCCAGGCT CCAGGGAAGG GTCTGGAGTG GGTCTCAACT ATTTCTGATG ATGGTGATTC
    GACATACTAC GCAGACTCCG TGAAGGGCCG

    ACCGAACCCA GGCGGTCCGA GGTCCCTTCC CAGACCTCAC CCAGAGTTGA TAAAGACTAC TACCACTAAG
    CTGTATGATG CGTCTGAGGC ACTTCCCGGC

    . F T I S R D N S K N T L Y L Q M N S L R A E D T A V Y Y C A
    K L D

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAACTGGAT
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
     CAAGTGGTAG AGGGCGCTGT TAAGGTTCTT GTGCGACATA GACGTTTACT TGTCGGACGC ACGGCTCCTG
     TGGCGCCATA TAATGACACG CTTTGACCTA

     K L F D Y W G Q G T L V T V S S

 301 AAGTTGTTTG ACTACTGGGG TCAGGGAACC CTGGTCACCG TCTCGAGC                          (SEQ ID NO: 144)

     TTCAACAAAC TGATGACCCC AGTCCCTTGG GACCAGTGGC AGAGCTCG                          (SEQ ID NO: 145)
DOM-31 SEQ ID NO: 33
     E V Q L L E S G G G L V Q P G G S L R L S C A A S G F T F E E
     Y Q M .

   1 GAGGTGCAGC TGTTGGAGTC TGGGGGAGGC TTGGTACAGC CTGGGGGGTC CCTGCGTCTC TCCTGTGCAG
     CCTCCGGATT CACCTTTGAG GAGTATCAGA

     CTCCACGTCG ACAACCTCAG ACCCCCTCCG AACCATGTCG GACCCCCCAG GGACGCAGAG AGGACACGTC
     GGAGGCCTAA GTGGAAACTC CTCATAGTCT

     . A W V R Q A P G K G L E W V S T I S D D G S S T Y Y A D S V
     K G R .

 101 TGGCGTGGGT CCGCCAGGCT CCAGGGAAGG GTCTAGAGTG GGTCTCAACG ATTTCGGATG ATGGTTCTTC
     GACATACTAC GCAGACTCCG TGAAGGGCCG

     ACCGCACCCA GGCGGTCCGA GGTCCCTTCC CAGATCTCAC CCAGAGTTGC TAAAGCCTAC TACCAAGAAG
     CTGTATGATG CGTCTGAGGC ACTTCCCGGC

     . F T I S R D N S K N T L Y L Q M N S L R A E D T A V Y Y C A
     K P D

 201 GTTCACCATC TCCCGCGACA ATTCCAAGAA CACGCTGTAT CTGCAAATGA ACAGCCTGCG TGCCGAGGAC
     ACCGCGGTAT ATTACTGTGC GAAACCTGAT

     CAAGTGGTAG AGGGCGCTGT TAAGGTTCTT GTGCGACATA GACGTTTACT TGTCGGACGC ACGGCTCCTG
     TGGCGCCATA TAATGACACG CTTTGGACTA

     L Y F D Y W G Q G T L V T V S S

 301 CTTTATTTTG ACTACTGGGG TCAGGGAACC CTGGTCACCG TCTCGAGC                          (SEQ ID NO: 146)

     GAAATAAAAC TGATGACCCC AGTCCCTTGG GACCAGTGGC AGAGCTCG                          (SEQ ID NO: 147)

DOM-32 SEQ ID NO: 34
     E V Q L L E S G G G L V Q P G G S L R L S C A A S G F T F E V
     Y Q M .

   1 GAGGTGCAGC TGTTGGAGTC TGGGGGAGGC TTGGTACAGC CTGGGGGGTC CCTGCGTCTC TCCTGTGCAG
     CCTCCGGATT CACCTTTGAG GTGTATCAGA

     CTCCACGTCG ACAACCTCAG ACCCCCTCCG AACCATGTCG GACCCCCCAG GGACGCAGAG AGGACACGTC
     GGAGGCCTAA GTGGAAACTC CACATAGTCT

     . G W V R Q A P G K G L E W V S F I V P G G D L T Y Y A D S V
     K G R .

 101 TGGGTTGGGT CCGCCAGGCT CCAGGGAAGG GTCTAGAGTG GGTCTCATTT ATTGTGCCTG GGGGTGATTT
     GACATACTAC GCAGACTCCG TGAAGGGCCG

     ACCCAACCCA GGCGGTCCGA GGTCCCTTCC CAGATCTCAC CCAGAGTAAA TAACACGGAC CCCCACTAAA
     CTGTATGATG CGTCTGAGGC ACTTCCCGGC

     . F T I S R D N S K N T L Y L Q M N S L R A E D T A V Y Y C A
     E T W

 201 GTTCACCATC TCCCGCGACA ATTCCAAGAA CACGCTGTAT CTGCAAATGA ACAGCCTGCG TGCCGAGGAC
     ACCGCGGTAT ATTACTGTGC GGAAACGTGG

     CAAGTGGTAG AGGGCGCTGT TAAGGTTCTT GTGCGACATA GACGTTTACT TGTCGGACGC ACGGCTCCTG
     TGGCGCCATA TAATGACACG CCTTTGCACC

     P E F D Y W G Q G T L V T V S S

 301 CCGGAGTTTG ACTACTGGGG TCAGGGAACC CTGGTCACCG TCTCGAGC                          (SEQ ID NO: 148)

     GGCCTCAAAC TGATGACCCC AGTCCCTTGG GACCAGTGGC AGAGCTCG                          (SEQ ID NO: 149)
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
DOM-33 SEQ ID NO: 35
     D I Q M T Q S P S S L S A S V G D R V T I T C R A S Q T I G E
     S L H .

   1 GACATCCAGA TGACCCAGTC TCCATCCTCC CTGTCTGCAT CTGTAGGAGA CCGTGTCACC ATCACTTGCC
     GGGCAAGTCA GACGATTGGG GAGAGTTTAC

     CTGTAGGTCT ACTGGGTCAG AGGTAGGAGG GACAGACGTA GACATCCTCT GGCACAGTGG TAGTGAACGG
     CCCGTTCAGT CTGCTAACCC CTCTCAAATG

     . W Y Q Q K P G K A P R L L I Y F A S L L Q S G V P S R F S G
     S G S .

 101 ATTGGTACCA GCAGAAACCA GGGAAAGCCC CTAGGCTCCT GATCTATTTT GCTTCCCTGT TGCAAAGTGG
     GGTCCCATCG CGTTTCAGTG GCAGTGGATC

     TAACCATGGT CGTCTTTGGT CCCTTTCGGG GATCCGAGGA CTAGATAAAA CGAAGGGACA ACGTTTCACC
     CCAGGGTAGC GCAAAGTCAC CGTCACCTAG

     . G T D F T L T I S S L Q P E D F A T Y Y C Q Q H H M L P S T
     F G Q

 201 TGGGACAGAT TTTACTCTCA CCATCAGCAG TCTGCAACCT GAAGATTTTG CTACGTACTA CTGTCAACAG
     CATCATATGC TTCCTTCTAC GTTCGGCCAA

     ACCCTGTCTA AAATGAGAGT GGTAGTCGTC AGACGTTGGA CTTCTAAAAC GATGCATGAT GACAGTTGTC
     GTAGTATACG AAGGAAGATG CAAGCCGGTT

     G T K V E I K R

 301 GGGACCAAGG TGGAAATCAA ACGG                                            (SEQ ID NO: 150)

     CCCTGGTTCC ACCTTTAGTT TGCC                                            (SEQ ID NO: 151)

DOM-34 SEQ ID NO: 36
     D I Q M T Q S P S S L S A S V G D R V T I T C R A S Q W I G D
     S L S .

   1 GACATCCAGA TGACCCAGTC TCCATCCTCC CTGTCTGCAT CTGTAGGAGA CCGTGTCACC ATCACTTGCC
     GGGCAAGTCA GTGGATTGGT GATAGTTTAT

     CTGTAGGTCT ACTGGGTCAG AGGTAGGAGG GACAGACGTA GACATCCTCT GGCACAGTGG TAGTGAACGG
     CCCGTTCAGT CACCTAACCA CTATCAAATA

     . W Y Q Q K P G K A P K L L I Y F A S Y L Q S G V P T R F S G
     S G S .

 101 CTTGGTACCA GCAGAAACCA GGGAAAGCCC CTAAGCTCCT GATCTATTTT GCTTCCTATT TGCAAAGTGG
     GGTCCCAACA CGTTTCAGTG GCAGTGGATC

     GAACCATGGT CGTCTTTGGT CCCTTTCGGG GATTCGAGGA CTAGATAAAA CGAAGGATAA ACGTTTCACC
     CCAGGGTTGT GCAAAGTCAC CGTCACCTAG

     . G T D F T L T I S S L Q P E D F A T Y Y C Q Q Y F E N P V T
     F G Q

 201 TGGGACAGAT TTCACTCTCA CCATCAGCAG TCTGCAACCT GAAGATTTTG CTACGTACTA CTGTCAACAG
     TATTTTGAGA ATCCTGTTAC GTTCGGCCAA

     ACCCTGTCTA AAGTGAGAGT GGTAGTCGTC AGACGTTGGA CTTCTAAAAC GATGCATGAT GACAGTTGTC
     ATAAAACTCT TAGGACAATG CAAGCCGGTT

     G T K V G I K R

 301 GGGACCAAGG TGGGAATCAA ACGG                                            (SEQ ID NO: 152)

     CCCTGGTTCC ACCCTTAGTT TGCC                                            (SEQ ID NO: 153)

DOM-35 SEQ ID NO: 37
     D I Q M T Q S P S S L S A S V G D R V T I T C R A S Q F I G D
     S L S .

   1 GACATCCAAA TGACCCAGTC TCCATCCTCC CTGTCTGCAT CTGTAGGAGA CCGTGTCACC ATCACTTGCC
     GGGCAAGTCA GTTTATTGGT GATTCTTTAT
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
    CTGTAGGTTT ACTGGGTCAG AGGTAGGAGG GACAGACGTA GACATCCTCT GGCACAGTGG TAGTGAACGG
    CCCGTTCAGT CAAATAACCA CTAAGAAATA

    . W Y Q Q K P G K A P K L L I Y F S S I L Q S G V P S R F S G
    S G S .

101 CTTGGTACCA GCAGAAACCA GGGAAAGCCC CTAAGCTCCT GATCTATTTT TCTTCCATTT TGCAAAGTGG
    GGTCCCATCA CGTTTCAGTG GCAGTGGATC

    GAACCATGGT CGTCTTTGGT CCCTTTCGGG GATTCGAGGA CTAGATAAAA AGAAGGTAAA ACGTTTCACC
    CCAGGGTAGT GCAAAGTCAC CGTCACCTAG

    . G T D F T L T I S S L Q P E D F A T Y Y C Q Q Y M D I P I T
    F G Q

201 TGGGACAGAT TTCACTCTCA CCATCAGCAG TCTGCAACCT GAAGATTTTG CTACGTACTA CTGTCAACAG
    TATATGGATA TTCCTATTAC GTTCGGCCAA

    ACCCTGTCTA AAGTGAGAGT GGTAGTCGTC AGACGTTGGA CTTCTAAAAC GATGCATGAT GACAGTTGTC
    ATATACCTAT AAGGATAATG CAAGCCGGTT

    G T K V E I K R

301 GGGACCAAGG TGGAAATCAA ACGG                                  (SEQ ID NO: 154)

    CCCTGGTTCC ACCTTTAGTT TGCC                                  (SEQ ID NO: 155)

DOM-36 SEQ ID NO: 38
    D I Q M T Q S P S S L S A S V G D R V T I T C R A S Q D I D H
    N L E .

  1 GACATCCAGA TGACCCAGTC TCCATCCTCC CTGTCTGCAT CTGTAGGAGA CCGTGTCACC ATCACTTGCC
    GGGCAAGTCA GGATATTGAT CATAATTTAG

    CTGTAGGTCT ACTGGGTCAG AGGTAGGAGG GACAGACGTA GACATCCTCT GGCACAGTGG TAGTGAACGG
    CCCGTTCAGT CCTATAACTA GTATTAAATC

    . W Y Q Q K P G K A P K L L I Y D S S M L Q S G V P S R F S G
    S G S .

101 AGTGGTATCA GCAGAAACCA GGGAAAGCCC CTAAGCTCCT GATCTATGAT AGTTCCATGT TGCAAAGTGG
    GGTCCCATCA CGTTTCAGTG GCAGTGGATC

    TCACCATAGT CGTCTTTGGT CCCTTTCGGG GATTCGAGGA CTAGATACTA TCAAGGTACA ACGTTTCACC
    CCAGGGTAGT GCAAAGTCAC CGTCACCTAG

    . G T D F T L T I S S L Q P E D F A T Y Y C Q Q Y H S I P V T
    F G Q

201 TGGGACAGAT TTCACTCTCA CCATCAGCAG TCTGCAACCT GAAGATTTTG CTACGTACTA CTGTCAACAG
    TATCATTCTA TTCCTGTTAC GTTCGGCCAA

    ACCCTGTCTA AAGTGAGAGT GGTAGTCGTC AGACGTTGGA CTTCTAAAAC GATGCATGAT GACAGTTGTC
    ATAGTAAGAT AAGGACAATG CAAGCCGGTT

    G T K V E I K R

301 GGGACCAAGG TGGAAATCAA ACGG                                  (SEQ ID NO: 156)

    CCCTGGTTCC ACCTTTAGTT TGCC                                  (SEQ ID NO: 107)

DOM-37 SEQ ID NO: 39
    D I Q M T Q S P S S L S A S V G D R V T I T C R A S Q Q I E T
    N L E .

  1 GACATCCAGA TGACCCAGTC TCCATCCTCC CTGTCTGCAT CTGTAGGAGA CCGTGTCACC ATCACTTGCC
    GGGCAAGTCA GCAGATTGAG ACGAATTTAG

    CTGTAGGTCT ACTGGGTCAG AGGTAGGAGG GACAGACGTA GACATCCTCT GGCACAGTGG TAGTGAACGG
    CCCGTTCAGT CGTCTAACTC TGCTTAAATC

    . W Y Q Q K P G K A P K L L I Y D G S W L Q S G V P S R F S G
    S G S .
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
101 AGTGGTATCA GCAGAAACCA GGGAAAGCCC CTAAGCTCCT GATCTATGAT GGTTCCTGGT TGCAAAGTGG
    GGTCCCATCA CGTTTCAGTG GCAGTGGATC

    TCACCATAGT CGTCTTTGGT CCCTTTCGGG GATTCGAGGA CTAGATACTA CCAAGGACCA ACGTTTCACC
    CCAGGGTAGT GCAAAGTCAC CGTCACCTAG

    . G T D F T L T I S S L Q P E D F A T Y Y C Q Q Y H S L P A T
    F G Q

201 TGGGACAGAT TTCACTCTCA CCATCAGCAG TCTGCAACCT GAAGATTTTG CTACGTACTA CTGTCAACAG
    TATCATAGTT TGCCTGCTAC GTTCGGCCAA

    ACCCTGTCTA AAGTGAGAGT GGTAGTCGTC AGACGTTGGA CTTCTAAAAC GATGCATGAT GACAGTTGTC
    ATAGTATCAA ACGGACGATG CAAGCCGGTT

    G T K V E I K R

301 GGGACCAAGG TGGAAATCAA ACGG                                     (SEQ ID NO: 158)

    CCCTGGTTCC ACCTTTAGTT TGCC                                     (SEQ ID NO: 159)

DOM-38 SEQ ID NO: 40
    D I Q M T Q S P S S L S A S V G D R V T I T C R A S Q D I G N
    N L E .

  1 GACATCCAGA TGACCCAGTC TCCATCCTCC CTGTCTGCAT CTGTAGGAGA CCGTGTCACC ATCACTTGCC
    GGGCAAGTCA GGATATTGGT AATAATTTAG

    CTGTAGGTCT ACTGGGTCAG AGGTAGGAGG GACAGACGTA GACATCCTCT GGCACAGTGG TAGTGAACGG
    CCCGTTCAGT CCTATAACCA TTATTAAATC

    . W Y Q Q K P G K A P R L L I Y H G S W L Q S G V P S R F S G
    S G S .

101 AGTGGTACCA GCAGAAACCA GGGAAAGCCC CTAGGCTCCT GATCTATCAT GGGTCCTGGT TGCAAAGTGG
    GGTCCCATCG CGTTTCAGTG GCAGTGGATC

    TCACCATGGT CGTCTTTGGT CCCTTTCGGG GATCCGAGGA CTAGATAGTA CCCAGGACCA ACGTTTCACC
    CCAGGGTAGC GCAAAGTCAC CGTCACCTAG

    . G T D F T L T I S S L Q P E D F A T Y Y C Q Q Y D F N P T T
    F G Q

201 TGGGACAGAT TTCACTCTTA CCATCAGCAG TCTGCAACCT GAAGATTTTG CTACGTACTA CTGTCAACAG
    TATGATTTTA ATCCTACTAC GTTCGGCCAA

    ACCCTGTCTA AAGTGAGAAT GGTAGTCGTC AGACGCTTGGA CTTCTAAAAC GATGCATGAT GACAGTTGTC
    ATACTAAAAT TAGGATGATG CAAGCCGGTT

    G T K V E I K R

301 GGGACCAAGG TGGAAATCAA ACGG                                     (SEQ ID ND: 160)

    CCCTGGTTCC ACCTTTAGTT TGCC                                     (SEQ ID NO: 161)

DOM-39 SEQ ID NO: 41
    D I Q M T Q S P S S L S A S V G D C V T I T C R A S Q N I D G
    L L W .

  1 GACATCCAGA TGACCCAGTC TCCATCCTCC CTGTCTGCAT CTGTAGGAGA CTGTGTCACC ATCACTTGCC
    GGGCAAGTCA GAATATTGAT GGTCTGTTAT

    CTGTAGGTCT ACTGGGTCAG AGGTAGGAGG GACAGACGTA GACATCCTCT GACACAGTGG TAGTGAACGG
    CCCGTTCAGT CTTATAACTA CCAGACAATA

    . W Y Q Q K P G K A P K L L I Y A G S G L Q S G V P S R F S G
    S G S .

101 GGTGGTATCA GCAGAAACCA GGGAAAGCCC CTAAGCTCCT GATCTATGCG GGGTCCGGGT TGCAAAGTGG
    GGTCCCATCA CGTTTCAGTG GCAGTGGATC

    CCACCATAGT CGTCTTTGGT CCCTTTCGGG GATTCGAGGA CTAGATACGC CCCAGGCCCA ACGTTTCACC
    CCAGGGTAGT GCAAAGTCAC CGTCACCTAG
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
     . G T D F T L T I S S L Q P E D F A T Y Y C Q Q K A F E P F T
     F G Q

 201 TGGGACAGAT TTCACTCTCA CCATCAGCAG TCTGCAACCT GAAGATTTTG CTACGTACTA CTGTCAACAG
     AAGGCTTTTG AGCCTTTTAC GTTCGGCCAA

     ACCCTGTCTA AAGTGAGAGT GGTAGTCGTC AGACGTTGGA CTTCTAAAAC GATGCATGAT GACAGTTGTC
     TTCCGAAAAC TCGGAAAATG CAAGCCGGTT

     G T K V E I K R

 301 GGGACCAAGG TGGAAATCAA ACGG                                      (SEQ ID NO: 162)

     CCCTGGTTCC ACCTTTAGTT TGCC                                      (SEQ ID NO: 163)

DOM-40 SEQ ID NO: 42
     E V Q L L E S G G G L V Q P G G S L R L S C A A S G F T F K A
     Y D M .

   1 GAGGTGCAGC TGTTGGAGTC TGGGGGAGGC TTGGTACAGC CTGGGGGGTC CCTGCGTCTC TCCTGTGCAG
     CCTCCGGATT CACCTTTAAG GCGTATGATA

     CTCCACGTCG ACAACCTCAG ACCCCCTCCG AACCATGTCG GACCCCCCAG GGACGCAGAG AGGACACGTC
     GGAGGCCTAA GTGGAAATTC CGCATACTAT

     . G W V R Q A P G K G L E W V S Q I G R D G S F T Y Y A D S V
     K G R .

 101 TGGGTTGGGT CCGCCAGGCT CCAGGGAAGG GTCTAGAGTG GGTCTCACAG ATTGGGAGGG ATGGTTCTTT
     TACATACTAC GCAGACTCCG TGAAGGGCCG

     ACCCAACCCA GGCGGTCCGA GGTCCCTTCC CAGATCTCAC CCAGAGTGTC TAACCCTCCC TACCAAGAAA
     ATGTATGATG CGTCTGAGGC ACTTCCCGGC

     . F T I S R D N S K N T L Y L Q M N S L R A E D T A V Y Y C A
     K P R

 201 GTTCACCATC TCCCGCGACA ATTCCAAGAA CACGCTGTAT CTGCAAATGA ACAGCCTGCG TGCCGAGGAC
     ACCGCGGTAT ATTACTGTGC GAAACCTCGT

     CAAGTGGTAG AGGGCGCTGT TAAGGTTCTT GTGCGACATA GACGTTTACT TGTCGGACGC ACGGCTCCTG
     TGGCGCCATA TAATGACACG CTTTGGAGCA

     R Y A I F T F D R G Q G T L V T V S S

 301 CGGTATGCTA TTTTTACTTT TGATCGGGGT CAGGGAACCC TGGTCACCGT CTCGAGC  (SEQ ID NO: 164)

     GCCATACGAT AAAAATGAAA ACTAGCCCCA GTCCCTTGGG ACCAGTGGCA GAGCTCG  (SEQ ID NO: 165)

DOM-41 SEQ ID NO: 43
     E V Q L L E S G G G L V Q P G G S L R L S C A A S G F T F F E
     Y E M .

   1 GAGGTGCAGC TGTTGGAGTC TGGGGGAGGC TTGGTACAGC CTGGGGGGTC CCTGCGTCTC TCCTGTGCAG
     CCTCCGGATT CACCTTTTTT GAGTATGAGA

     CTCCACGTCG ACAACCTCAG ACCCCCTCCG AACCATGTCG GACCCCCCAG GGACGCAGAG AGGACACGTC
     GGAGGCCTAA GTGGAAAAAA CTCATACTCT

     . T W V R Q A P G K G L E W V S S I A N D G S T T Y Y A D S V
     K G R .

 101 TGACGTGGGT CCGCCAGGCT CCAGGGAAGG GTCTAGAGTG GGTCTCATCT ATTGCGAATG ATGGTTCGAC
     TACATACTAC GCAGACTCCG TGAAGGGCCG

     ACTGCACCCA GGCGGTCCGA GGTCCCTTCC CAGATCTCAC CCAGAGTAGA TAACGCTTAC TACCAAGCTG
     ATGTATGATG CGTCTGAGGC ACTTCCCGGC

     . F T I S R D N S K N T L Y L Q M N S L R A E D T A V Y Y C A
     K P D

 201 GTTCACCATC TCCCGCGACA ATTCCAAGAA CACGCTGTAT CTGCAAATGA ACAGCCTGCG TGCCGAGGAC
     ACCGCGGTAT ATTACTGTGC GAAACCTGAT
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
    CAAGTGGTAG AGGGCGCTGT TAAGGTTCTT GTGCGACATA GACGTTTACT TGTCGGACGC ACGGCTCCTG
    TGGCGCCATA TAATGACACG CTTTGGACTA

    R Q F D Y W G Q G T L V T V S S

301 CGGCAGTTTG ACTACTGGGG TCAGGGAACC CTGGTCACCG TCTCGAGC                (SEQ ID NO: 166)

    GCCGTCAAAC TGATGACCCC AGTCCCTTGG GACCAGTGGC AGAGCTCG                (SEQ ID NO: 167)

DOM-42 SEQ ID NO: 44
    E V Q L L E S G G G L V Q P G G S L R L S C A A S G F T F G P
    Y E M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGGT CCGTATGAGA

    CTCCACGTCG ACAACCTCAG ACCCCCTCCG AACCATGTCG GACCCCCCAG GGACGCAGAG AGGACACGTC
    GGAGGCCTAA GTGGAAACCA GGCATACTCT

    . T W V R Q A P G K G L E W V S S I V G D G L D T Y Y A D S V
    K G R .

101 TGACTTGGGT CCGCCAGGCT CCAGGGAAGG GTCTAGAGTG GGTCTCATCG ATTGTTGGTG ATGGTCTGGA
    TACATACTAC GCAGACTCCG TGAAGGGCCG

    ACTGAACCCA GGCGGTCCGA GGTCCCTTCC CAGATCTCAC CCAGAGTAGC TAACAACCAC TACCAGACCT
    ATGTATGATG CGTCTGAGGC ACTTCCCGGC

    . F T I S R D N S K N T L Y L Q M N S L R A E D T A V Y Y C A
    K P D

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAACCGGAT

    CAAGTGGTAG AGGGCGCTGT TAAGGTTCTT GTGCGACATA GACGTTTACT TGTCGGACGC ACGGCTCCTG
    TGGCGCCATA TAATGACACG CTTTGGCCTA

    R V F D Y W G Q G T L V T V S S

301 CGGGTTTTTG ACTACTGGGG TCAGGGAACC CTGGTCACCG TCTCGAGC                (SEQ ID NO: 168)

    GCCCAAAAAC TGATGACCCC AGTCCCTTGG GACCAGTGGC AGAGCTCG                (SEQ ID NO: 169)

DOM-43 SEQ ID NO: 45
    E V Q L L E S G G G L V Q P G G S L R L S C A A S G F T F A S
    Y E M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGCT TCTTATGAGA

    CTCCACGTCG ACAACCTCAG ACCCCCTCCG AACCATGTCG GACCCCCCAG GGACGCAGAG AGGACACGTC
    GGAGGCCTAA GTGGAAACGA AGAATACTCT

    . A W V R Q A P G K G L E W V S S I G S D G G P T Y Y A D S V
    K G R .

101 TGGCGTGGGT CCGCCAGGCT CCAGGGAAGG GTCTAGAGTG GGTCTCATCG ATTGGTAGTG ATGGTGGGCC
    GACATACTAC GCAGACTCCG TGAAGGGCCG

    ACCGCACCCA GGCGGTCCGA GGTCCCTTCC CAGATCTCAC CCAGAGTAGC TAACCATCAC TACCACCCGG
    CTGTATGATG CGTCTGAGGC ACTTCCCGGC

    . F T I S R D N S K N T L Y L Q M N S L R A E D S A V Y Y C A
    K P D

201 GTTCACCATC TCCCGCGACA ATTCCAAGAA CACGCTGTAT CTGCAAATGA ACAGCCTGCG TGCCGAGGAC
    TCCGCGGTAT ATTACTGTGC GAAACCTGAT

    CAAGTGGTAG AGGGCGCTGT TAAGGTTCTT GTGCGACATA GACGTTTACT TGTCGGACGC ACGGCTCCTG
    AGGCGCCATA TAATGACACG CTTTGGACTA

    R A F D Y W G Q G T L V T V S S

301 AGGGCTTTTG ACTACTGGGG TCAGGGAACC CTGGTCACCG TCTCGAGC                (SEQ ID NO: 170)
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
     TCCCGAAAAC TGATGACCCC AGTCCCTTGG GACCAGTGGC AGAGCTCG                 (SEQ ID NO: 171)

DOM-44 SEQ ID NO: 46
     E V Q L L E S G G G L V Q P G G S L R L S C A A S G F T F T S
     Y E M .

   1 GAGGTGCAGC TGTTGGAGTC TGGGGGAGGC TTGGTACAGC CTGGGGGGTC CCTGCGTCTC TCCTGTGCAG
     CCTCCGGATT CACCTTTACG TCTTATGAGA

     CTCCACGTCG ACAACCTCAG ACCCCCTCCG AACCATGTCG GACCCCCCAG GGACGCAGAG AGGACACGTC
     GGAGGCCTAA GTGGAAATGC AGAATACTCT

     . G W V R Q A P G K G L E W V S S I E P T G I T T Y Y A D S V
     K G R .

 101 TGGGGTGGGT CCGCCAGGCT CCAGGGAAGG GTCTAGAGTG GGTCTCATCT ATTGAGCCTA CTGGTATTAC
     GACATACTAC GCAGACTCCG TGAAGGGCCG

     ACCCCACCCA GGCGGTCCGA GGTCCCTTCC CAGATCTCAC CCAGAGTAGA TAACTCGGAT GACCATAATG
     CTGTATGATG CGTCTGAGGC ACTTCCCGGC

     . F T I S R D N S K N T L Y L Q M N S L R A E D T A V Y Y C A
     K P H

 201 GTTCACCATC TCCCGCGACA ATTCCAAGAA CACGCTGTAT CTGCAAATGA ACAGCCTGCG TGCCGAGGAC
     ACCGCGGTAT ATTACTGTGC GAAACCTCAT

     CAAGTGGTAG AGGGCGCTGT TAAGGTTCTT GTGCGACATA GACGTTTACT TGTCGGACGC ACGGCTCCTG
     TGGCGCCATA TAATGACACG CTTTGGAGTA

     F T E L G F D Y W G Q G T L V T V S S

 301 TTTACTGAGC TTGGTTTTGA CTACTGGGGT CAGGGAACCC TGGTCACCGT CTCGAGC       (SEQ ID NO: 172)

     AAATGACTCG AACCAAAACT GATGACCCCA GTCCCTTGGG ACCAGTGGCA GAGCTCG       (SEQ ID NO: 173)

DOM-45 SEQ ID NO: 47
     E V Q L L E S G G G L V Q P G G S L R L S C A A S G F T F G N
     Y A M .

   1 GAGGTGCAGC TGTTGGAGTC TGGGGGAGGC TTGGTACAGC CTGGGGGGTC CCTGCGTCTC TCCTGTGCAG
     CCTCCGGATT CACCTTTGGT AATTATGCGA

     CTCCACGTCG ACAACCTCAG ACCCCCTCCG AACCATGTCG GACCCCCCAG GGACGCAGAG AGGACACGTC
     GGAGGCCTAA GTGGAAACCA TTAATACGCT

     . A W V R Q A P G K G L E W V S K I G A Q G L H T Y Y A G S V
     K G R .

 101 TGGCGTGGGT CCGCCAGGCT CCAGGGAAGG GTCTAGAGTG GGTCTCAAAG ATTGGGGCGC AGGGTCTTCA
     TACATACTAC GCAGGCTCCG TGAAGGGCCG

     ACCGCACCCA GGCGGTCCGA GGTCCCTTCC CAGATCTCAC CCAGAGTTTC TAACCCCGCG TCCCAGAAGT
     ATGTATGATG CGTCCGAGGC ACTTCCCGGC

     . F T I S R D N S K N T L Y L Q M N S L R A E D T A V Y Y C A
     K Q T

 201 GTTCACCATC TCCCGCGACA ATTCCAAGAA CACGCTGTAT CTGCAAATGA ACAGCCTGCG TGCCGAGGAC
     ACCGCGGTAT ATTACTGTGC GAAACAGACG

     CAAGTGGTAG AGGGCGCTGT TAAGGTTCTT GTGCGACATA GACGTTTACT TGTCGGACGC ACGGCTCCTG
     TGGCGCCATA TAATGACACG CTTTGTCTGC

     T M D Y E R F D Y W G Q G T L V T V S S

 301 ACGATGGATT ATGAGAGGTT TGACTACTGG GGTCAGGGAA CCCTGGTCAC CGTCTCGAGC    (SEQ ID NO: 174)

     TGCTACCTAA TACTCTCCAA ACTGATGACC CCAGTCCCTT GGGACCAGTG GCAGAGCTCG    (SEQ ID NO: 175)

DOM-46 SEQ ID NO: 48
     E V Q L L E S G G G L V Q P G G S L R L S C A A S G F T F E L
     Y A M .
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGAG TTGTATGCTA

    CTCCACGTCG ACAACCTCAG ACCCCCTCCG AACCATGTCG GACCCCCCAG GGACGCAGAG AGGACACGTC
    GGAGGCCTAA GTGGAAACTC AACATACGAT

    . A W V R Q A P G K G L E W V S G I G A V G E T T Y Y A D S V
    K G R .

101 TGGCGTGGGT CCGCCAGGCT CCAGGGAAGG GTCTAGAGTG GGTCTCAGGT ATTGGTGCTG TGGGTGAGAC
    TACATACTAC GCAGACTCCG TGAAGGGCCG

    ACCGCACCCA GGCGGTCCGA GGTCCCTTCC CAGATCTCAC CCAGAGTCCA TAACCACGAC ACCCACTCTG
    ATGTATGATG CGTCTGAGGC ACTTCCCGGC

    . F T I S R D N S K N T L Y L Q M N S L R A E D T A V Y Y C A
    K E A

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAAGAGGCT

    CAAGTGGTAG AGGGCGCTGT TAAGGTTCTT GTGCGACATA GACGTTTACT TGTCGGACGC ACGGCTCCTG
    TGGCGCCATA TAATGACACG CTTTCTCCGA

    N N L S D N L V F D Y W G Q G T L V T V S S

301 AATAATCTTT CTGATAATCT TGTGTTTGAC TACTGGGGTC AGGGAACCCT GGTCACCGTC TCGAGC         (SEQ ID NO: 176)

    TTATTAGAAA GACTATTAGA ACACAAACTG ATGACCCCAG TCCCTTGGGA CCAGTGGCAG AGCTCG         (SEQ ID NO: 177)

DOM-47 SEQ ID NO: 49
    D I Q M T Q S P S S L S A S V G D R V T I T C R A S Q W I G D
    S L S .

  1 GACATCCAGA TGACCCAGTC TCCATCCTCC CTGTCTGCAT CTGTAGGAGA CCGTGTCACC ATCACTTGCC
    GGGCAAGTCA GTGGATTGGG GATTCGTTAA

    CTGTAGGTCT ACTGGGTCAG AGGTAGGAGG GACAGACGTA GACATCCTCT GGCACAGTGG TAGTGAACGG
    CCCGTTCAGT CACCTAACCC CTAAGCAATT

    . W Y Q Q K P G K A P K L L I Y F G S Y L Q S G V P S R F S G
    S G S .

101 GTTGGTACCA GCAGAAACCA GGGAAAGCCC CTAAGCTCCT GATCTATTTT GGTTCCTATT TGCAAAGTGG
    GGTCCCATCA CGTTTCAGTG GCAGTGGATC

    CAACCATGGT CGTCTTTGGT CCCTTTCGGG GATTCGAGGA CTAGATAAAA CCAAGGATAA ACGTTTCACC
    CCAGGGTAGT GCAAAGTCAC CGTCACCTAG

    . G T D F T L T I S S L Q P E D F A T Y Y C Q Q Y L H T P S T
    F G Q

201 TGGGACAGAT TTCACTCTCA CCATCAGCAG TCTGCAACCT GAAGATTTTG CTACGTACTA CTGTCAACAG
    TATTTGCATA CTCCTTCGAC GTTCGGCCAA

    ACCCTGTCTA AAGTGAGAGT GGTAGTCGTC AGACGTTGGA CTTCTAAAAC GATGCATGAT GACAGTTGTC
    ATAAACGTAT GAGGAAGCTG CAAGCCGGTT

    G T K V E I K R

301 GGGACCAAGG TGGAAATCAA ACGG                                                       (SEQ ID NO: 178)

    CCCTGGTTCC ACCTTTAGTT TGCC                                                       (SEQ ID NO: 179)

DOM-48 SEQ ID NO: 50
    D I Q M T Q S P S S L S A S V G D R V T I T C R A S Q W I G D
    S L S .

  1 GACATCCAGA TGACCCAGTC TCCATCCTCC CTGTCTGCAT CTGTAGGAGA CCGTGTCACC ATCACTTGCC
    GGGCAAGGTCA GTGGATTGGG GATTCGTTAA

    CTGTAGGTCT ACTGGGTCAG AGGTAGGAGG GACAGACGTA GACATCCTCT GGCACAGTGG TAGTGAACGG
    CCCGTTCAGT CACCTAACCC CTAAGCAATT
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
    . W Y Q Q K P G K A P K L L I Y F G S Y L Q N G V P S R F S G
    S G S .

101 GTTGGTACCA GCAGAAACCA GGGAAAGCCC CTAAGCTCCT GATCTATTTT GGTTCCTATT TGCAAAATGG
    GGTCCCATCA CGTTTCAGTG GCAGTGGATC

    CAACCATGGT CGTCTTTGGT CCCTTTCGGG GATTCGAGGA CTAGATAAAA CCAAGGATAA ACGTTTTACC
    CCAGGGTAGT GCAAAGTCAC CGTCACCTAG

    . G T D F T L T I S S L Q P E D F A T Y Y C Q Q Y M I T P T T
    F G Q

201 TGGGACAGAT TTCACTCTCA CCATCAGCAG TCTGCAACCT GAAGATTTTG CTACGTACTA CTGTCAACAG
    TATATGATTA CTCCTACTAC GTTCGGCCAA

    ACCCTGTCTA AAGTGAGAGT GGTAGTCGTC AGACGTTGGA CTTCTAAAAC GATGCATGAT GACAGTTGTC
    ATATACTAAT GAGGATGATG CAAGCCGGTT

    G T K V E I K R

301 GGGACCAAGG TGGAAATCAA ACGG                                 (SEQ ID NO: 180)

    CCCTGGTTCC ACCTTTAGTT TGCC                                 (SEQ ID NO: 181)

DOM-49 SEQ ID NO: 51
    D V Q M T Q S P S S L S A S V G D R V T I T C R A S Q W I G D
    S L S .

  1 GACGTCCAGA TGACCCAGTC TCCATCCTCC CTGTCTGCAT CTGTAGGAGA CCGTGTCACC ATCACTTGCC
    GGGCAAGTCA GTGGATTGGG GATTCGTTAA

    CTGCAGGTCT ACTGGGTCAG AGGTAGGAGG GACAGACGTA GACATCCTCT GGCACAGTGG TAGTGAACGG
    CCCGTTCAGT CACCTAACCC CTAAGCAATT

    . W Y Q Q K P G K A P K L L I Y F G S Y L Q S G V P S R F S G
    S G S .

101 GTTGGTACCA GCAGAAACCA GGGAAAGCCC CTAAGCTCCT GATCTATTTT GGTTCCTATT TGCAAAGTGG
    GGTCCCATCA CGTTTCAGTG GCAGTGGATC

    CAACCATGGT CGTCTTTGGT CCCTTTCGGG GATTCGAGGA CTAGATAAAA CCAAGGATAA ACGTTTCACC
    CCAGGGTAGT GCAAAGTCAC CGTCACCTAG

    . G T D F T L T I S S L Q P E D F A T Y Y C Q Q Y M S A P S T
    F G Q

201 TGGGACAGAT TTCACTCTCA CCATCAGCAG TCTGCAACCT GAAGATTTTG CTACGTACTA CTGTCAACAG
    TATATGAGTG CTCCTTCTAC GTTCGGCCAA

    ACCCTGTCTA AAGTGAGAGT GGTAGTCGTC AGACGTTGGA CTTCTAAAAC GATGCATGAT GACAGTTGTC
    ATATACTCAC GAGGAAGATG CAAGCCGGTT

    G T K V E I K R

301 GGGACCAAGG TGGAAATCAA ACGG                                 (SEQ ID NO: 182)

    CCCTGGTTCC ACCTTTAGTT TGCC                                 (SEQ ID NO: 183)

DOM-50 SEQ ID NO: 52
    D I Q M T Q S P S S L S A S V G D R V T I T C R A S Q W I G D
    S L S .

  1 GACATCCAGA TGACCCAGTC TCCATCCTCC CTGTCTGCAT CTGTAGGAGA CCGTGTCACC ATCACTTGCC
    GGGCAAGTCA GTGGATTGGG GATTCGTTAA

    CTGTAGGTCT ACTGGGTCAG AGGTAGGAGG GACAGACGTA GACATCCTCT GGCACAGTGG TAGTGAACGG
    CCCGTTCAGT CACCTAACCC CTAAGCAATT

    . W Y Q Q K P G K A P K L L I Y F G S Y L Q S G V P S R F S G
    S G S .

101 GTTGGTACCA GCAGAAACCA GGGAAAGCCC CTAAGCTCCT GATCTATTTT GGTTCCTATT TGCAAAGTGG
    GGTCCCATCA CGTTTCAGTG GCAGTGGATC
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
    CAACCATGGT CGTCTTTGGT CCCTTTCGGG GATTCGAGGA CTAGATAAAA CCAAGGATAA ACGTTTCACC
    CCAGGGTAGT GCAAAGTCAC CGTCACCTAG

    . G T D F T L T I S S L Q P E D S A T Y Y C Q Q Y Q Y V P S T
    F G Q

201 TGGGACAGAT TTCACTCTCA CCATCAGCAG TCTGCAACCT GAAGATTCTG CTACGTACTA CTGTCAACAG
    TATCAGTATG TTCCTTCTAC GTTCGGCCAA

    ACCCTGTCTA AAGTGAGAGT GGTAGTCGTC AGACGTTGGA CTTCTAAGAC GATGCATGAT GACAGTTGTC
    ATAGTCATAC AAGGAAGATG CAAGCCGGTT

    G T K V E I K Q

301 GGGACCAAGG TGGAAATCAA ACAG                                  (SEQ ID NO: 184)

    CCCTGGTTCC ACCTTTAGTT TGTC                                  (SEQ ID NO: 185)

DOM-51 SEQ ID NO: 53
    D I Q M T Q S P S S L S A S V G D R V T I T C R A S Q P I V D
    E L D .

  1 GACATCCAGA TGACCCAGTC TCCATCCTCC CTGTCTGCAT CTGTAGGAGA CCGTGTCACC ATCACTTGCC
    GGGCAAGTCA GCCTATTGTT GATGAGTTAG

    CTGTAGGTCT ACTGGGTCAG AGGTAGGAGG GACAGACGTA GACATCCTCT GGCACAGTGG TAGTGAACGG
    CCCGTTCAGT CGGATAACAA CTACTCAATC

    . W Y Q Q K P G K A P K L L I Y A A S I L Q S G V P S R F S G
    S G S .

101 ATTGGTACCA GCAGAAACCA GGGAAAGCCC CTAAGCTCCT GATCTATGCT GCGTCCATTT TGCAAAGTGG
    GGTCCCATCA CGTTTCAGTG GCAGTGGATC

    TAACCATGGT CGTCTTTGGT CCCTTTCGGG GATTCGAGGA CTAGATACGA CGCAGGTAAA ACGTTTCACC
    CCAGGGTAGT GCAAAGTCAC CGTCACCTAG

    . G T D F T L T I S S L Q P E D F A T Y Y C H Q W S T Y P T T
    F G Q

201 TGGGACAGAT TTCACTCTCA CCATCAGCAG TCTGCAACCT GAAGATTTTG CTACGTACTA CTGTCATCAG
    TGGTCTACTT ATCCTACGAC GTTCGGCCAA

    ACCCTGTCTA AAGTGAGAGT GGTAGTCGTC AGACGTTGGA CTTCTAAAAC GATGCATGAT GACAGTAGTC
    ACCAGATGAA TAGGATGCTG CAAGCCGGTT

    G T K V E I K R

301 GGGACCAAGG TGGAAATTAA ACGG                                  (SEQ ID NO: 186)

    CCCTGGTTCC ACCTTTAATT TGCC                                  (SEQ ID NO: 187)

DOM-52 SEQ ID NO: 54
    D I Q M T Q S P S S L S A S V G D R V T I T C R A S Q D I G S
    A L R .

  1 GACATCCAGA TGACCCAGTC TCCATCCTCC CTGTCTGCAT CTGTAGGTGA CCGTGTCACC ATCACTTGCC
    GGGCAAGTCA GGATATTGGG TCTGCGTTAA

    CTGTAGGTCT ACTGGGTCAG AGGTAGGAGG GACAGACGTA GACATCCACT GGCACAGTGG TAGTGAACGG
    CCCGTTCAGT CCTATAACCC AGACGCAATT

    . W Y Q Q K P G K A P K L L I Y L G S D L Q S G V P S R F S G
    S G S .

101 GGTGGTATCA GCAGAAACCA GGGAAAGCCC CTAAGCTCCT GATCTATTTG GGTTCCGATT TGCAAAGTGG
    GGTCCCATCA CGTTTCAGTG GCAGTGGATC

    CCACCATAGT CGTCTTTGGT CCCTTTCGGG GATTCGAGGA CTAGATAAAC CCAAGGCTAA ACGTTTCACC
    CCAGGGTAGT GCAAAGTCAC CGTCACCTAG

    . G T D F T L T I S S L Q P E D F A T Y Y C Q Q T Q Y F P T T
    F G Q
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
201 TGGGACAGAT TTCACTCTCA CCATCAGCAG TCTGCAACCT GAAGATTTTG CTACGTACTA CTGTCAACAG
    ACGCAGTATT TTCCTACGAC GTTCGGCCAA

    ACCCTGTCTA AAGTGAGAGT GGTAGTCGTC AGACGTTGGA CTTCTAAAAC GATGCATGAT GACAGTTGTC
    TGCGTCATAA AAGGATGCTG CAAGCCGGTT

    G T K V E I K R

301 GGGACCAAGG TGGAAATCAA ACGG                                        (SEQ ID NO: 188)

    CCCTGGTTCC ACCTTTAGTT TGCC                                        (SEQ ID NO: 185)
DOM-53 SEQ ID NO: 55
    D I Q M T Q S P S S L S A S V G D R V T I T C R A S Q A I Y G
    G L R .

  1 GACATCCAGA TGACCCAGTC TCCATCCTCC CTGTCTGCAT CTGTAGGAGA CCGTGTCACC ATCACTTGCC
    GGGCAAGTCA GGCGATTTAT GGGGGGTTAC

    CTGTAGGTCT ACTGGGTCAG AGGTAGGAGG GACAGACGTA GACATCCTCT GGCACAGTGG TAGTGAACGG
    CCCGTTCAGT CCGCTAAATA CCCCCCAATG

    . W Y Q Q K P G K A P K L L I Y G E S M L Q S G V P S R F S G
    S G S .

101 GGTGGTACCA GCAGAAACCA GGGAAAGCCC CTAAGCTCCT GATCTATGGG GAGTCCATGT TGCAAAGTGG
    GGTCCCATCA CGTTTCAGTG GCAGTGCATC

    CCACCATGGT CGTCTTTGGT CCCTTTCGGG GATTCGAGGA CTAGATACCC CTCAGGTACA ACGTTTCACC
    CCAGGGTAGT GCAAAGTCAC CGTCACCTAG

    . G T D F T L T I S S L H P E D F A T Y Y C Q Q V Y H K P F T
    F G Q

201 TGGGACAGAT TTCACTCTCA CCATCAGCAG TCTGCATCCT GAAGATTTTG CTACGTACTA CTGTCAACAG
    GTTTATCATA AGCCTTTTAC GTTCGGCCAA

    ACCCTGTCTA AAGTGAGAGT GGTAGTCGTC AGACGTAGGA CTTCTAAAAC GATGCATGAT GACAGTTGTCX
    CCTCCGGATT CACCTTTACG CAAGCCGGTT

    G T K V E I K R

301 GGGACCAAGG TGGAAATCAA ACGG                                        (SEQ ID NO: 190)

    CCCTGGTTCC ACCTTTAGTT TGCC                                        (SEQ ID NO: 191)

DOM-54 SEQ ID NO: 56
    E V Q L L E S G G G L V Q P G G S L R L S C A A S G F T F T A
    Y R M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTACG GCGTATAGGA

    CTCCACGTCG ACAACCTCAG ACCCCCTCCG AACCATGTCG GACCCCCCAG GGACGCAGAG AGGACACGTC
    GGAGGCCTAA GTGGAAATGC CGCATATCCT

    . A W V R Q A P G K G L E W V S W I S P S G S G T Y Y A D S V
    K G R .

101 TGGCTTGGGT CCGCCAGGCT CCAGGGAAGG GTCTAGAGTG GGTCTCATGG ATTTCGCCTT CTGGTTCGGG
    GACATACTAC GCAGACTCCG TGAAGGGCCG

    ACCGAACCCA GGCGGTCCGA GGTCCCTTCC CAGATCTCAC CCAGAGTACC TAAAGCGGAA GACCAAGCCC
    CTGTATGATG CGTCTGAGGC ACTTCCCGGC

    . F T I S R D N S K N T L Y L Q M N S L R A E D T A V Y Y C A
    K T L

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAAACTTTG

    CAAGTGGTAG AGGGCGCTGT TAAGGTTCTT GTGCGACATA GACGTTTACT TGTCGGACGC ACGGCTCCTG
    TGGCGCCATA TAATGACACG CTTTTGAAAC
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
    T D S P S G H Y E F D Y W G Q G T L V T V S S

301 ACGGATTCGC CGTCGGGGCA TTATGAGTTT GACTACTGGG GTCAGGGAAC CCTGGTCACC GTCTCGAGC      (SEQ ID NO: 192)

    TGCCTAAGCG GCAGCCCCGT AATACTCAAA CTGATGACCC CAGTCCCTTG GGACCAGTGG CAGAGCTCG      (SEQ ID NO: 193)

DOM-55 SEQ ID NO: 57
    E V Q L L E S G G G L V Q P G G S L R L S C A A S G F T F A R
    Y E M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGCG CGGTATGAGA

    CTCCACGTCG ACAACCTCAG ACCCCCTCCG AACCATGTCG GACCCCCCAG GGACGCAGAG AGGACACGTC
    GGAGGCCTAA GTGGAAACGC GCCATACTCT

    . G W V R Q A P G K G L E W V S R I T A Q G L G T Y Y A D S V
    K G R .

101 TGGGGTGGGT CCGCCAGGCT CCAGGGAAGG GTCTAGAGTG GGTCTCACGG ATTACTGCTC AGGGTCTTGG
    GACATACTAC GCAGACTCCG TGAAGGGCCG

    ACCCCACCCA GGCGGTCCGA GGTCCCTTCC CAGATCTCAC CCAGAGTGCC TAATGACGAG TCCCAGAACC
    CTGTATGATG CGTCTGAGGC ACTTCCCGGC

    . F T I S R D N S K N T L Y L Q M N S L R A E D T A V Y Y C A
    K Y L

201 GTTCACCATC TCCCGCGACA ACTCCAAGAA CACGCTGTAT CTGCAAATGA ACAGCCTGCG TGCCGAGGAT
    ACCGCGGTAT ATTACTGTGC GAAATATCTT

    CAAGTGGTAG AGGGCGCTGT TGAGGTTCTT GTGCGACATA GACGTTTACT TGTCGGACGC ACGGCTCCTA
    TGGCGCCATA TAATGACACG CTTTATAGAA

    T D F S S G H Q E F D Y W G Q G T L V T V S S

301 ACTGATTTTA GTAGTGGGCA TCAGGAGTTT GACTACTGGG GTCAGGGAAC CCTGGTCACC GTCTCGAGC      (SEQ ID NO: 194)

    TGACTAAAAT CATCACCCGT AGTCCTCAAA CTGATGACCC CAGTCCCTTG GGACCAGTGG CAGAGCTCG      (SEQ ID NO: 195)

DOM-56 SEQ ID NO: 58
    E V Q L L E S G G G L V Q P G G S L R L S C A A S G F T F N D
    Y T M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTAAT GATTATACTA

    CTCCACGTCG ACAACCTCAG ACCCCCTCCG AACCATGTCG GACCCCCCAG GGACGCAGAG AGGACACGTC
    GGAGGCCTAA GTGGAAATTA CTAATATGAT

    . G W V R Q A P G K G L E W V S W I H G T G G Q T Y Y A D S V
    K G R .

101 TGGGTTGGGT CCGCCAGGCT CCAGGGAAGG GTCTAGAGTG GGTCTCATGG ATTCATGGGA CTGGTGGTCA
    GACATACTAC GCAGACTCCG TGAAGGGCCG

    ACCCAACCCA GGCGGTCCGA GGTCCCTTCC CAGATCTCAC CCAGAGTACC TAAGTACCCT GACCACCAGT
    CTGTATGATG CGTCTGAGGC ACTTCCCGGC

    . F T I S R D N S K N T L Y L Q M N S L R A E D T A V Y Y C A
    K A L

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAAGCTTTG

    CAAGTGGTAG AGGGCGCTGT TAAGGTTCTT GTGCGACATA GACGTTTACT TGTCGGACGC ACGGCTCCTG
    TGGCGCCATA TAATGACACG CTTTCGAAAC

    A D R S G G V V E F D Y W G Q G T L V T V S S

301 GCTGATAGGA GTGGGGGGGT TGTTGAGTTT GACTACTGGG GTCAGGGAAC CCTGGTCACC GTCTCGAGC      (SEQ ID NO: 196)

    CGACTATCCT CACCCCCCCA ACAACTCAAA CTGATGACCC CAGTCCCTTG GGACCAGTGG CAGAGCTCG      (SEQ ID NO: 197)
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
DOM-57 SEQ ID NO: 59
     E V Q L L E S G G G L V Q P G G S L R L S C A A S G F T F S E
     Y D M .

   1 GAGGTGCAGC TGTTGGAGTC TGGGGGAGGC TTGGTACAGC CTGGGGGGTC CCTGCGTCTC TCCTGTGCAG
     CCTCCGGATT CACCTTTTCT GAGTATGATA

     CTCCACGTCG ACAACCTCAG ACCCCCTCCG AACCATGTCG GACCCCCCAG GGACGCAGAG AGGACACGTC
     GGAGGCCTAA GTGGAAAAGA CTCATACTAT

     . Y W V R Q A P G K G L E W V S W I D T D G G D T Y Y A D S V
     K G R .

 101 TGTATTGGGT CCGCCAGGCT CCAGGGAAGG GTCTAGAGTG GGTCTCATGG ATTGATACTG ATGGTGGGGA
     TACATACTAC GCAGACTCCG TGAAGGGCCG

     ACATAACCCA GGCGGTCCGA GGTCCCTTCC CAGATCTCAC CCAGAGTACC TAACTATGAC TACCACCCCT
     ATGTATGATG CGTCTGAGGC ACTTCCCGGC

     . F T I S R D N S K N T L Y L Q M N S L R A E D T A V Y Y C A
     K P G

 201 GTTCACCATC TCCCGCGACA ATTCCAAGAA CACGCTGTAT CTGCAAATGA ACAGCCTGCG TGCCGAGGAC
     ACCGCGGTAT ATTACTGTGC GAAACCTGGT

     CAAGTGGTAG AGGGCGCTGT TAAGGTTCTT GTGCGACATA GACGTTTACT TGTCGGACGC ACGGCTCCTG
     TGGCGCCATA TAATGACACG CTTTGGACCA

     L K F D Y W G Q G T L V T V S S

 301 CTGAAGTTTG ACTACTGGGG TCAGGGAACC CTGGTCACCG TCTCGAGC                (SEQ ID NO: 198)
     GACTTCAAAC TGATGACCCC AGTCCCTTGG GACCAGTGGC AGAGCTCG                (SEQ ID NO: 199)

DOM-58 SEQ ID NO: 60
     E V Q L L E S G G G L V Q P G G S L R L S C A A S G F T F E V
     Y T M .

   1 GAGGTGCAGC TGTTGGAGTC TGGGGGAGGC TTGGTACAGC CTGGGGGGTC CCTGCGTCTC TCCTGTGCAG
     CCTCCGGATT CACCTTTGAG GTTTATACTA

     CTCCACGTCG ACAACCTCAG ACCCCCTCCG AACCATGTCG GACCCCCCAG GGACGCAGAG AGGACACGTC
     GGAGGCCTAA GTGGAAACTC CAAATATGAT

     . A W V R Q A P G K G L E W V S T I D E S G R D T Y Y A D S V
     K G R .

 101 TGGCGTGGGT CCGCCAGGCT CCAGGGAAGG GTCTGGAGTG GGTCTCAACG ATTGATGAGT CTGGTCGTGA
     TACATACTAC GCAGACTCCG TGAAGGGCCG

     ACCGCACCCA GGCGGTCCGA GGTCCCTTCC CAGACCTCAC CCAGAGTTGC TAACTACTCA GACCAGCACT
     ATGTATGATG CGTCTGAGGC ACTTCCCGGC

     . F T I S R D N S K N T L Y L Q M N S L R A E D T A V Y Y C A
     K P G

 201 GTTCACCATC TCCCGCGACA ATTCCAAGAA CACGCTGTAT CTGCAAATGA ACAGCCTGCG TGCCGAGGAC
     ACCGCGGTAT ATTACTGTGC GAAACCTGGT

     CAAGTGGTAG AGGGCGCTGT TAAGGTTCTT GTGCGACATA GACGTTTACT TGTCGGACGC ACGGCTCCTG
     TGGCGCCATA TAATGACACG CTTTGGACCA

     V W F D Y W G Q G T L V T V S S

 301 GTTTGGTTTG ACTACTGGGG TCAGGGAACC CTGGTCACCG TCTCGAGC                (SEQ ID NO: 200)

     CAAACCAAAC TGATGACCCC AGTCCCTTGG GACCAGTGGC AGAGCTCG                (SEQ ID NO: 201)

DOM-59 SEQ ID NO: 61
     E V Q L L E S G G G L V Q P G G S L R L S C A A S G F T F L D
     Y A M .

   1 GAGGTGCAGC TGTTGGAGTC TGGGGGAGGC TTGGTACAGC CTGGGGGGTC CCTGCGTCTC TCCTGTGCAG
     CCTCCGGATT CACCTTTCTG GATTATGCGA
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

CTCCACGTCG ACAACCTCAG ACCCCCTCCG AACCATGTCG GACCCCCCAG GGACGCAGAG AGGACACGTC
GGAGGCCTAA GTGGAAAGAC CTAATACGCT

. G W V R Q A P G K G L E W V S T I S P M G M G T Y Y A D S V
K G R .

101 TGGGTTGGGT CCGCCAGGCT CCAGGGAAGG GTCTGGAGTG GGTCTCAACT ATTTCTCCGA TGGGTATGGG
TACATACTAC GCAGACTCCG TGAAGGGCCG

ACCCAACCCA GGCGGTCCGA GGTCCCTTCC CAGACCTCAC CCAGAGTTGA TAAAGAGGCT ACCCATACCC
ATGTATGATG CGTCTGAGGC ACTTCCCGGC

. F T I S R D N S K N T L Y L Q M N S L R A E D T A V Y Y C A
K S S

201 GTTCACCATC TCCCGCGACA ATTCCAAGAA CACGCTGTAT CTGCAAATGA ACAGCCTGCG TGCCGAGGAC
ACCGCGGTAT ATTACTGTGC GAAATCGAGT

CAAGTGGTAG AGGGCGCTGT TAAGGTTCTT GTGCGACATA GACGTTTACT TGTCGGACGC ACGGCTCCTG
TGGCGCCATA TAATGACACG CTTTAGCTCA

A I S F T S D I S N F D Y W G Q G T L V T V S S

301 GCTATTTCGT TTACTTCTGA TATTTCTAAT TTTGACTACT GGGGTCAGGG AACCCTGGTC ACCGTCTCGA GC (SEQ ID NO: 202)
CGATAAAGCA AATGAAGACT ATAAAGATTA AAACTGATGA CCCCAGTCCC TTGGGACCAG TGGCAGAGCT CG (SEQ ID NO: 203)

DOM-61 SEQ ID NO: 62
E V Q L L E S G G G L V Q P G G S L R L S C A A S G F T F A A
Y A M .

1 GAGGTGCAGC TGTTGGAGTC TGGGGGAGGC TTGGTACAGC CTGGGGGGTC CCTGCGTCTC TCCTGTGCAG
CCTCCGGATT CACCTTTGCT GCTTATGCTA

CTCCACGTCG ACAACCTCAG ACCCCCTCCG AACCATGTCG GACCCCCCAG GGACGCAGAG AGGACACGTC
GGAGGCCTAA GTGGAAACGA CGAATACGAT

. T W V R Q A P G K G L E W V S Y I S P N G T A T Y Y A D S V
K G R .

101 TGACGTGGGT CCGCCAGGCT CCAGGGAAGG GTCTAGAGTG GGTCTCATAT ATTAGTCCGA ATGGTACGGC
GACATACTAC GCAGACTCCG TGAAGGGCCG

ACTGCACCCA GGCGGTCCGA GGTCCCTTCC CAGATCTCAC CCAGAGTATA TAATCAGGCT TACCATGCCG
CTGTATGATG CGTCTGAGGC ACTTCCCGGC

. F T I S R D N S K N T L Y L Q M N S L R A E D T A V Y Y C A
E Y V

201 GTTCACCATC TCCCGCGACA ATTCCAAGAA CACGCTGTAT CTGCAAATGA ACAGCCTGCG TGCCGAGGAC
ACCGCGGTAT ATTACTGTGC GGAATATGTG

CAAGTGGTAG AGGGCGCTGT TAAGGTTCTT GTGCGACATA GACGTTTACT TGTCGGACGC ACGGCTCCTG
TGGCGCCATA TAATGACACG CCTTATACAC

G M R W N S F D Y W G Q G T L V T V S S

301 GGGATGCGTT GGAATTCTTT TGACTACTGG GGTCAGGGAA CCCTGGTCAC CGTCTCGAGC (SEQ ID NO: 204)

CCCTACGCAA CCTTAAGAAA ACTGATGACC CCAGTCCCTT GGGACCAGTG GCAGAGCTCG (SEQ ID NO: 205)

DOM-62 SEQ ID NO: 63
E V Q L L E S G G G L V Q P G G S L R L S C A A S G F T F S S
Y E M .

1 GAGGTGCAGC TGTTGGAGTC TGGGGGAGGC TTGGTACAGC CTGGGGGGTC CCTGCGTCTC TCCTGTGCAG
CCTCCGGATT CACCTTTTCG AGTTATGAGA

CTCCACGTCG ACAACCTCAG ACCCCCTCCG AACCATGTCG GACCCCCCAG GGACGCAGAG AGGACACGTC
GGAGGCCTAA GTGGAAAAGC TCAATACTCT

. A W V R Q A P G K G L E W V S S I T S L G T S T Y Y A D S V
K G R .

101 TGGCTTGGGT CCGCCAGGCT CCAGGGAAGG GTCTAGAGTG GGTCTCATCT ATTACGAGTC TTGGTACTTC
TACATACTAC GCAGACTCCG TGAAGGGCCG

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
    ACCGAACCCA GGCGGTCCGA GGTCCCTTCC CAGATCTCAC CCAGAGTAGA TAATGCTCAG AACCATGAAG
    ATGTATGATG CGTCTGAGGC ACTTCCCGGC

    . F T I S R D N S K N T L Y L Q M N S L R A E D T A V Y Y C A
    K P G

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAACCGGGT

    CAAGTGGTAG AGGGCGCTGT TAAGGTTCTT GTGCGACATA GACGTTTACT TGTCGGACGC ACGGCTCCTG
    TGGCGCCATA TAATGACACG CTTTGGCCCA

    R K F D Y W G Q G T L V T V S S

301 AGGAAGTTTG ACTACTGGGG TCAGGGAACC CTGGTCACCG TCTCGAGC              (SEQ ID NO: 206)

    TCCTTCAAAC TGATGACCCC AGTCCCTTGG GACCAGTGGC AGAGCTCG              (SEQ ID NO: 207)

DOM-65 SEQ ID NO: 64
    E V Q L L E S G G G L V Q P G G S L R L S C A A S G F T F N E
    Y E M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTAAT GAGTATGAGA

    CTCCACGTCG ACAACCTCAG ACCCCCTCCG AACCATGTCG GACCCCCCAG GGACGCAGAG AGGACACGTC
    GGAGGCCTAA GTGGAAATTA CTCATACTCT

    . T W V R Q A P G K G L E W V S T I T S E G S G T Y Y A D S V
    K G R .

101 TGACGTGGGT CCGCCAGGCT CCAGGGAAGG GTCTAGAGTG GGTCTCAACG ATTACTAGTG AGGGTAGTGG
    GACATACTAC GCAGACTCCG TAAAGGGCCG

    ACTGCACCCA GGCGGTCCGA GGTCCCTTCC CAGATCTCAC CCAGAGTTGC TAATGATCAC TCCCATCACC
    CTGTATGATG CGTCTGAGGC ATTTCCCGGC

    . F T I S R D N S K N T L Y L Q M N S L R A E D T A V Y Y C A
    K P N

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAACCTAAT

    CAAGTGGTAG AGGGCGCTGT TAAGGTTCTT GTGCGACATA GACGTTTACT TGTCGGACGC ACGGCTCCTG
    TGGCGCCATA TAATGACACG CTTTGGATTA

    G K F D Y W G Q G T L V T V S S

301 GGTAAGTTTG ACTACTGGGG TCAGGGAACC CTGGTCACCG TCTCGAGC              (SEQ ID NO: 208)

    CCATTCAAAC TGATGACCCC AGTCCCTTGG GACCAGTGGC AGAGCTCG              (SEQ ID NO: 209)

DOM-66 SEQ ID NO: 65
    E V Q L L E S G G G L V Q P G G S L R L S C A A S G F T F S D
    Y E M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTTCT GATTATGAGA

    CTCCACGTCG ACAACCTCAG ACCCCCTCCG AACCATGTCG GACCCCCCAG GGACGCAGAG AGGACACGTC
    GGAGGCCTAA GTGGAAAAGA CTAATACTCT

    . L W V R Q A P G K G L E W V S T I T S E G H S T Y Y A D S V
    K G R .

101 TGTTGTGGGT CCGCCAGGCT CCAGGGAAGG GTCTGGAGTG GGTCTCAACT ATTACTAGTG AGGGTCATTC
    TACATACTAC GCAGACTCCG TGAAGGGCCG

    ACAACACCCA GGCGGTCCGA GGTCCCTTCC CAGACCTCAC CCAGAGTTGA TAATGATCAC TCCCAGTAAG
    ATGTATGATG CGTCTGAGGC ACTTCCCGGC

    . F T I S R D N S K N T L Y L Q M N S L R A E D T A V Y Y C A
    K P G
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAACCTGGG

    CAAGTGGTAG AGGGCGCTGT TAAGGTTCTT GTGCGACATA GACGTTTACT TGTCGGACGC ACGGCTCCTG
    TGGCGCCATA TAATGACACG CTTTGGACCC

    T S F D Y W G Q G T L V T V S S

301 ACTTCGTTTG ACTACTGGGG TCAGGGAACC CTGGTCACCG TCTCGAGC                  (SEQ ID NO: 210)

    TGAAGCAAAC TGATGACCCC AGTCCCTTGG GACCAGTGGC AGAGCTCG                  (SEQ ID NO: 211)

DOM-67 SEQ ID NO: 66
    E V Q L L E S G G G L V Q P G G S L R L S C A A S G F T F S D
    Y E M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTAGT GATTATGAGA

    CTCCACGTCG ACAACCTCAG ACCCCCTCCG AACCATGTCG GACCCCCCAG GGACGCAGAG AGGACACGTC
    GGAGGCCTAA GTGGAAATCA CTAATACTCT

    . S W V R Q A P G K G L E W V S T I D S D G S F T Y Y A D S V
    K G R .

101 TGAGTTGGGT CCGCCAGGCT CCAGGGAAGG GTCTAGAGTG GGTCTCAACG ATTGATTCTG ATGGTAGTTT
    TACATACTAC GCAGACTCCG TGAAGGGCCG

    ACTCAACCCA GGCGGTCCGA GGTCCCTTCC CAGATCTCAC CCAGAGTTGC TAACTAAGAC TACCATCAAA
    ATGTATGATG CGTCTGAGGC ACTTCCCGGC

    . F T I S R D N S K N T L Y L Q M N S L R A E D T A V Y Y C A
    K P G

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAACCGGGT

    CAAGTGGTAG AGGGCGCTGT TAAGGTTCTT GTGCGACATA GACGTTTACT TGTCGGACGC ACGGCTCCTG
    TGGCGCCATA TAATGACACG CTTTGGCCCA

    V K F D Y W G Q G T L V T V S S

301 GTGAAGTTTG ACTACTGGGG TCAGGGAACC CTGGTCACCG TCTCGAGC                  (SEQ ID NO: 212)

    CACTTCAAAC TGATGACCCC AGTCCCTTGG GACCAGTGGC AGAGCTCG                  (SEQ ID NO: 213)

DOM-68 SEQ ID NO: 67
    E V Q L L E S G G G L V Q P G G S L R L S C A A S G F T F K D
    Y E M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTAAG GATTATGAGA

    CTCCACGTCG ACAACCTCAG ACCCCCTCCG AACCATGTCG GACCCCCCAG GGACGCAGAG AGGACACGTC
    GGAGGCCTAA GTGGAAATTC CTAATACTCT

    . T W V R Q A P G K G L E W V S S I S S T G Q S T Y Y A D S V
    K G R .

101 TGACTTGGGT CCGCCAGGCT CCAGGGAAGG GTCTAGAGTG GGTCTCATCT ATTTCTTCTA CTGGTCAGTC
    TACATACTAC GCAGACTCCG TGAAGGGCCG

    ACTGAACCCA GGCGGTCCGA GGTCCCTTCC CAGATCTCAC CCAGAGTAGA TAAAGAAGAT GACCAGTCAG
    ATGTATGATG CGTCTGAGGC ACTTCCCGGC

    . F T I S R D N S K N T L Y L Q M N S L R A E D T A V Y Y C A
    K P G

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAACCGGGT

    CAAGTGGTAG AGGGCGCTGT TAAGGTTCTT GTGCGACATA GACGTTTACT TGTCGGACGC ACGGCTCCTG
    TGGCGCCATA TAATGACACG CTTTGGCCCA

    N K F D Y W G Q G T L V T V S S
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
301 AATAAGTTTG ACTACTGGGG TCAGGGAACC CTGGTCACCG TCTCGAGC                       (SEQ ID NO: 214)

    TTATTCAAAC TGATGACCCC AGTCCCTTGG GACCAGTGGC AGAGCTCG                       (SEQ ID NO: 215)

DOM-69 SEQ ID NO: 68
    E V Q L L E S G G G L V Q P G G S L R L S C A A S G F T F L D
    Y G M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTCTT GATTATGGTA

    CTCCACGTCG ACAACCTCAG ACCCCCTCCG AACCATGTCG GACCCCCCAG GGACGCAGAG AGGACACGTC
    GGAGGCCTAA GTGGAAAGAA CTAATACCAT

    . A W V R Q A P G K G L E W V S A I S P L G L S T Y Y A D S V
    K S R .

101 TGGCTTGGGT CCGCCAGGCT CCAGGGAAGG GTCTAGAGTG GGTCTCAGCT ATTTCGCCTC TTGGTCTTAG
    TACATACTAC GCAGACTCCG TGAAGAGCCG

    ACCGAACCCA GGCGGTCCGA GGTCCCTTCC CAGATCTCAC CCAGAGTCGA TAAAGCGGAG AACCAGAATC
    ATGTATGATG CGTCTGAGGC ACTTCTCGGC

    . F T I S R D N S K N T L Y L Q M N S L R A E D T A V Y Y C A
    K E V

201 GTTCACCATC TCCCGCGACA ATTCCAAGAA CACGCTGTAT CTGCAAATGA ACAGCCTGCG TGCCGAGGAT
    ACCGCGGTAT ATTACTGTGC GAAAGAGGTG

    CAAGTGGTAG AGGGCGCTGT TAAGGTTCTT GTGCGACATA GACGTTTACT TGTCGGACGC ACGGCTCCTA
    TGGCGCCATA TAATGACACG CTTTCTCCAC

    R V G R G V H P P K F D Y W G Q G T L V T V S S

301 AGGGTGGGTA GGGGTGTTCA TCCTCCGAAG TTTGACTACT GGGGTCAGGG AACCCTGGTC ACCGTCTCGA GC   (SEQ ID NO: 216)

    TCCCACCCAT CCCCACAAGT AGGAGGCTTC AAACTGATGA CCCCAGTCCC TTGGGACCAG TGGCAGAGCT CG   (SEQ ID NO: 217)

DOM-70 SEQ ID NO: 69
    E V Q L L E S G G G L V Q P G G S L R L S C A A S G F T F E N
    Y A M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGAG AATTATGCTA

    CTCCACGTCG ACAACCTCAG ACCCCCTCCG AACCATGTCG GACCCCCCAG GGACGCAGAG AGGACACGTC
    GGAGGCCTAA GTGGAAACTC TTAATACGAT

    . S W V R Q A P G K G L E W V S T I A P L G V P T Y Y A D S V
    K G R .

101 TGTCGTGGGT CCGCCAGGCT CCAGGGAAGG GTCTAGAGTG GGTCTCAACG ATTGCTCCGC TGGGTGTTCC
    GACATACTAC GCAGACTCCG TGAAGGGCCG

    ACAGCACCCA GGCGGTCCGA GGTCCCTTCC CAGATCTCAC CCAGAGTTGC TAACGAGGCG ACCCACAAGG
    CTGTATGATG CGTCTGAGGC ACTTCCCGGC

    . F T I S R D N S K N T L Y L Q M N S L R A E D T A V Y Y C A
    K K K

201 GTTCACCATC TCCCGCGACA ATTCCAAGAA CACGCTGTAT CTGCAAATGA ACAGCCTGCG TGCCGAGGAT
    ACCGCGGTAT ATTACTGTGC GAAAAAGAAG

    CAAGTGGTAG AGGGCGCTGT TAAGGTTCTT GTGCGACATA GACGTTTACT TGTCGGACGC ACGGCTCCTA
    TGGCGCCATA TAATGACACG CTTTTTCTTC

    V G A W L Q S R S F D Y W G Q G T L V T V S S

301 GTTGGGGCGT GGCTGCAGTC GCGGAGTTTT GACTACTGGG GTCAGGGAAC CCTGGTCACC GTCTCGAGC      (SEQ ID NO: 218)

    CAACCCCGCA CCGACGTCAG CGCCTCAAAA CTGATGACCC CAGTCCCTTG GGACCAGTGG CAGAGCTCG      (SEQ ID NO: 219)
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
DOM-71 SEQ ID NO: 70
     E V Q L L E S G G G L V Q P G G S L R L S C A A S G F T F E G
     Y P M .

   1 GAGGTGCAGC TGTTGGAGTC TGGGGGAGGC TTGGTACAGC CTGGGGGGTC CCTGCGTCTC TCCTGTGCAG
     CCTCCGGATT CACCTTTGAG GGTTATCCTA

     CTCCACGTCG ACAACCTCAG ACCCCCTCCG AACCATGTCG GACCCCCCAG GGACGCAGAG AGGACACGTC
     GGAGGCCTAA GTGGAAACTC CCAATAGGAT

     . S W V R Q A P G K G L E W V S T I S P L G P D T Y Y A D S V
     K G R .

 101 TGTCGTGGGT CCGCCAGGCT CCAGGGAAGG GTCTAGAGTG GGTCTCAACT ATTAGTCCTT TGGGTCCTGA
     TACATACTAC GCAGACTCCG TGAAGGGCCG

     ACAGCACCCA GGCGGTCCGA GGTCCCTTCC CAGATCTCAC CCAGAGTTGA TAATCAGGAA ACCCAGGACT
     ATGTATGATG CGTCTGAGGC ACTTCCCGGC

     . F T I S R D N S K N T L Y L Q M N S L R A E D T A V Y Y C A
     K L L

 201 GTTCACCATC TCCCGCGACA ATTCCAAGAA CACGCTGTAT CTGCAAATGA ACAGCCTGCG TGCCGAGGAT
     ACCGCGGTAT ATTACTGTGC GAAACTGTTG

     CAAGTGGTAG AGGGCGCTGT TAAGGTTCTT GTGCGACATA GACGTTTACT TGTCGGACGC ACGGCTCCTA
     TGGCGCCATA TAATGACACG CTTTGACAAC

     M G E Y L N S R T F D Y W G Q G T L V T V S S

 301 ATGGGGGAGT ATTTGAATTC TAGGACGTTT GACTACTGGG GTCAGGGAAC CCTGGTCACC GTCTCGAGC       (SEQ ID NO: 220)

     TACCCCCTCA TAAACTTAAG ATCCTGCAAA CTGATGACCC CAGTCCCTTG GGACCAGTGG CAGAGCTCG       (SEQ ID NO: 221)

DOM-72 SEQ ID NO: 71
     E V Q L L E S G G G L V Q P G G S L R L S C A A S G F T F E A
     Y P M .

   1 GAGGTGCAGC TGTTGGAGTC TGGGGGAGGC TTGGTACAGC CTGGGGGGTC CCTGCGTCTC TCCTGTGCAG
     CCTCCGGATT CACCTTTGAG GCGTATCCTA

     CTCCACGTCG ACAACCTCAG ACCCCCTCCG AACCATGTCG GACCCCCCAG GGACGCAGAG AGGACACGTC
     GGAGGCCTAA GTGGAAACTC CGCATAGGAT

     . S W V R Q A P G K G L E W V S S I S P L G L W T Y Y A D S V
     K G R .

 101 TGTCGTGGGT CCGCCAGGCT CCAGGGAAGG GTCTAGAGTG GGTCTCAAGT ATTTCCCCTC TTGGTTTGTG
     GACATACTAC GCAGACTCCG TGAAGGGCCG

     ACAGCACCCA GGCGGTCCGA GGTCCCTTCC CAGATCTCAC CCAGAGTTCA TAAAGGGGAG AACCAAACAC
     CTGTATGATG CGTCTGAGGC ACTTCCCGGC

     . F T I S R D N S K N T L Y L Q M N S L R A E D T A V Y Y C A
     K L S

 201 GTTCACCATC TCCCGCGACA ATTCCAAGAA CACGCTGTAT CTGCAAATGA ACAGCCTGCG TGCCGAGGAC
     ACCGCGGTAT ATTACTGTGC GAAACTTAGT

     CAAGTGGTAG AGGGCGCTGT TAAGGTTCTT GTGCGACATA GACGTTTACT TGTCGGACGC ACGGCTCCTG
     TGGCGCCATA TAATGACACG CTTTGAATCA

     A G A E T H V Y R L F D Y W G Q G T L V T V S S

 301 GCTGGGGCGG AGACTCATGT TTATCGGCTT TTTGACTACT GGGGTCAGGG AACCCTGGTC ACCGTCTCGA GC   (SEQ ID NO: 222)

     CGACCCCGCC TCTGAGTACA AATAGCCGAA AAACTGATGA CCCCAGTCCC TTGGGACCAG TGGCAGAGCT CG   (SEQ ID NO: 223)

DOM-73 SEQ ID NO: 72
     E V Q L L E S G G G L V Q P G G S L R L S C A A S G F T F S K
     Y D M .

   1 GAGGTGCAGC TGTTGGAGTC TGGGGGAGGC TTGGTACAGC CTGGGGGGTC CCTGCGTCTC TCCTGTGCAG
     CCTCCGGATT CACCTTTTCT AAGTATGATA
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
    CTCCACGTCG ACAACCTCAG ACCCCCTCCG AACCATGTCG GACCCCCCAG GGACGCAGAG AGGACACGTC
    GGAGGCCTAA GTGGAAAAGA TTCATACTAT

    . S W V R Q A P G K G L E W V S T I L E D G L T T Y Y A D S V
    K G R .

101 TGTCTTGGGT CCGCCAGGCT CCAGGGAAGG GTCTAGAGTG GGTCTCAACT ATTCTGGAGG ATGGTCTGAC
    TACATACTAC GCAGACTCCG TGAAGGGCCG

    ACAGAACCCA GGCGGTCCGA GGTCCCTTCC CAGATCTCAC CCAGAGTTGA TAAGACCTCC TACCAGACTG
    ATGTATGATG CGTCTGAGGC ACTTCCCGGC

    . F T I S R D N S K N T L Y L Q M N S L R A E D T A V Y Y C A
    K P G

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAACCGGGG

    CAAGTGGTAG AGGGCGCTGT TAAGGTTCTT GTGCGACATA GACGTTTACT TGTCGGACGC ACGGCTCCTG
    TGGCGCCATA TAATGACACG CTTTGGCCCC

    R L F D Y W G Q G T L V T V S S

301 CGTTTGTTTG ACTACTGGGG TCAGGGAACC CTGGTCACCG TCTCGAGC            (SEQ ID NO: 224)

    GCAAACAAAC TGATGACCCC AGTCCCTTGG GACCAGTGGC AGAGCTCG            (SEQ ID NO: 225)

DOM-74 SEQ ID NO: 73
    E V Q L L E S G G G L V Q P G G S L R L S C A A S G F T F S D
    Y P M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTTCG GATTATCCTA

    CTCCACGTCG ACAACCTCAG ACCCCCTCCG AACCATGTCG GACCCCCCAG GGACGCAGAG AGGACACGTC
    GGAGGCCTAA GTGGAAAAGC CTAATAGGAT

    . T W V R Q A P G K G L E W V S T I L S P G T E T Y Y A D S V
    K G R .

101 TGACGTGGGT CCGCCAGGCT CCAGGGAAGG GTCTGGAGTG GGTCTCAACT ATTCTGTCTC CGGGTACGGA
    GACATACTAC GCAGACTCCG TGAAGGGCCG

    ACTGCACCCA GGCGGTCCGA GGTCCCTTCC CAGACCTCAC CCAGAGTTGA TAAGACAGAG GCCCATGCCT
    CTGTATGATG CGTCTGAGGC ACTTCCCGGC

    . F T I S R D N S K N T L Y L Q M N S L R A E D T A V Y Y C A
    K A E

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAAGCTGAG

    CAAGTGGTAG AGGGCGCTGT TAAGGTTCTT GTGCGACATA GACGTTTACT TGTCGGACGC ACGGCTCCTG
    TGGCGCCATA TAATGACACG CTTTCGACTC

    K D F D Y W G Q G T L V T V S S

301 AAGGATTTTG ACTACTGGGG TCAGGGAACC CTGGTCACCG TCTCGAGC            (SEQ ID NO: 226)

    TTCCTAAAAC TGATGACCCC AGTCCCTTGG GACCAGTGGC AGAGCTCG            (SEQ ID NO: 227)

DOM-75 SEQ ID NO: 74
                                                  AvaI
                                                 ------
    E V Q L L E S G G G L V Q P G G S L R L S C A A S G F T F L Q
    Y P M .

  1 GAGGTGCAGC TGTTGGAGTC TGGGGGAGGC TTGGTACAGC CTGGGGGGTC CCTGCGTCTC TCCTGTGCAG
    CCTCGGGATT CACCTTTTTG CAGTATCCGA

    CTCCACGTCG ACAACCTCAG ACCCCCTCCG AACCATGTCG GACCCCCCAG GGACGCAGAG AGGACACGTC
    GGAGCCCTAA GTGGAAAAAC GTCATAGGCT

    . G W V R Q A P G K G L E W V S T I S P V G L T T Y Y A D S V
    K G R .
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
101 TGGGTTGGGT CCGCCAGGCT CCAGGGAAGG GTCTAGAGTG GGTCTCAACT ATTTCTCCTG TTGGTTTGAC
    TACATACTAC GCAGACTCCG TGAAGGGCCG

    ACCCAACCCA GGCGGTCCGA GGTCCCTTCC CAGATCTCAC CCAGAGTTGA TAAAGAGGAC AACCAAACTG
    ATGTATGATC CGTCTGAGGC ACTTCCCGGC

    . F T I S R D N S K N T L Y L Q M N S L R A E D T A V Y Y C A
    K L F

201 GTTCACCATC TCCCGCGACA ATTCCAAGAA CACGCTGTAT CTGCAAATGA ACAGCCTGCG TGCCGAGGAT
    ACCGCGGTAT ATTACTGTGC GAAATTGTTT

    CAAGTGGTAG AGGGCGCTGT TAAGGTTCTT GTGCGACATA GACGTTTACT TGTCGGACGC ACGGCTCCTA
    TGGCGCCATA TAATGACACG CTTTAACAAA

    E G S R I Q R D V G F D Y W G Q G T L V T V S S

301 GAGGGGTCGA GGATTCAGCG TGATGTGGGT TTTGACTACT GGGGTCAGGG AACCCTGGTC ACCGTCTCGA GC   (SEQ ID NO: 228)

    CTCCCCAGCT CCTAAGTCGC ACTACACCCA AAACTGATGA CCCCAGTCCC TTGGGACCAG TGGCAGAGCT CG   (SEQ ID NO: 229)

DOM-77 SEQ ID NO: 75
    E V Q L L E S G G G L V Q P G G S L R L S C A A S G F T F E E
    Y G M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGAG GAGTATGGTA

    CTCCACGTCG ACAACCTCAG ACCCCCTCCG AACCATGTCG GACCCCCCAG GGACGCAGAG AGGACACGTC
    GGAGGCCTAA GTGGAAACTC CTCATACCAT

    . A W V R Q A P G K G L E W V S T I S P L G I S T Y Y A D S V
    K G R .

101 TGGCGTGGGT CCGCCAGGCT CCAGGGAAGG GTCTAGAGTG GGTCTCAACT ATTTCTCCGC TGGGTATTTC
    GACATACTAC GCAGACTCCG TGAAGGGCCG

    ACCGCACCCA GGCGGTCCGA GGTCCCTTCC CAGATCTCAC CCAGAGTTGA TAAAGAGGCG ACCCATAAAG
    CTGTATGATG CGTCTGAGGC ACTTCCCGGC

    . F T I S R D N S K N T L Y L Q M N S L R A E D T A V Y Y C A
    K H A

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAACATGCT

    CAAGTGGTAG AGGGCGCTGT TAAGGTTCTT GTGCGACATA GACGTTTACT TGTCGGACGC ACGGCTCCTG
    TGGCGCCATA TAATGACACG CTTTGTACGA

    T S Q E S L R S F D Y W G Q G T L V T V S S

301 ACGTCTCAGG AGTCTTTGCG GTCTTTTGAC TACTGGGGTC AGGGAACCCT GGTCACCGTC TCGAGC         (SEQ ID NO: 230)

    TGCAGAGTCC TCAGAAACGC CAGAAAACTG ATGACCCCAG TCCCTTGGGA CCAGTGGCAG AGCTCG         (SEQ ID NO: 231)

DOM-78 SEQ ID NO: 76
    E V Q L L E S G G G L V Q P G G S L R L S C A A S G F T F E R
    Y Q M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGAG AGGTATCAGA

    CTCCACGTCG ACAACCTCAG ACCCCCTCCG AACCATGTCG GACCCCCCAG GGACGCAGAG AGGACACGTC
    GGAGGCCTAA GTGGAAACTC TCCATAGTCT

    . A W V R Q A P G K G L E W V S T I S S D G G G T Y Y A D S V
    K G R .

101 TGGCGTGGGT CCGCCAGGCT CCGGGGAAGG GTCTAGAGTG GGTCTCAACG ATTAGTTCTG ATGGTGGGGG
    GACATACTAC GCAGACTCCG TGAAGGGCCG

    ACCGCACCCA GGCGGTCCGA GGCCCCTTCC CAGATCTCAC CCAGAGTTGC TAATCAAGAC TACCACCCCC
    CTGTATGATC CGTCTGAGGC ACTTCCCGGC
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
    . F T I S R D N S K N T L Y L Q M N S L R A E D T A V Y Y C A
    K P G

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAACCTGGT

    CAAGTGGTAG AGGGCGCTGT TAAGGTTCTT GTGCGACATA GACGTTTACT TGTCGGACGC ACGGCTCCTG
    TGGCGCCATA TAATGACACG CTTTGGACCA

    H R F D Y W G Q G T L V T V S S

301 CATCGGTTTG ACTACTGGGG TCAGGGAACC CTGGTCACCG TCTCGAGC              (SEQ ID NO: 232)

    GTAGCCAAAC TGATGACCCC AGTCCCTTGG GACCAGTGGC AGAGCTCG              (SEQ ID NO: 233)

DOM-80 SEQ ID NO: 77
    E V Q L L E S G G G L V Q P G G S L R L S C A A S G F T F G R
    Y Q M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGGT CGTTATCAGA

    CTCCACGTCG ACAACCTCAG ACCCCCTCCG AACCATGTCG GACCCCCCAG GGACGCAGAG AGGACACGTC
    GGAGGCCTAA GTGGAAACCA GCAATAGTCT

    . A W V R Q A P G K G L E W V S S I S S D G G G T Y Y A D S V
    K G R .

101 TGGCTTGGGT CCGCCAGGCT CCAGGGAAGG GTCTAGAGTC GGTCTCATCT ATTTCTTCTG ATGGTGGGGG
    GACATACTAC GCAGACTCCG TGAAGGGCCG

    ACCGAACCCA GGCGGTCCGA GGTCCCTTCC CAGATCTCAC CCAGAGTAGA TAAAGAAGAC TACCACCCCC
    CTGTATGATG CGTCTGAGGC ACTTCCCGGC

    . F T I S R D N S K N T L Y L Q M N S L R A E D T A V Y Y C A
    K P S

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAACCGTCT

    CAAGTGGTAG AGGGCGCTGT TAAGGTTCTT GTGCGACATA GACGTTTACT TGTCGGACGC ACGGCTCCTG
    TGGCGCCATA TAATGACACG CTTTGGCAGA

    R R F D Y W G Q G T L V T V S S

301 CGTCGGTTTG ACTACTGGGG TCAGGGAACC CTGGTCACCG TCTCGAGC              (SEQ ID NO: 234)

    GCAGCCAAAC TGATGACCCC AGTCCCTTGG GACCAGTGGC AGAGCTCG              (SEQ ID NO: 235)

DOM-81 SEQ ID NO: 78
    E V Q L L E S G G G L V Q P G G F L R L S C A A S G F T F E L
    Y P M .

  1 GAGGTGCAGC TGTTGGAGTC TGGGGGAGGC TTGGTACAGC CTGGGGGGTT CCTGCGTCTC TCCTGTGCAG
    CCTCCGGATT CACCTTTGAG TTGTATCCGA

    CTCCACGTCG ACAACCTCAG ACCCCCTCCG AACCATGTCG GACCCCCCAA GGACGCAGAG AGGACACGTC
    GGAGGCCTAA GTGGAAACTC AACATAGGCT

    . A W V R Q A P G K G L E W V S S I S P V G F L T Y Y A D S V
    K G R .

101 TGGCGTGGGT CCGCCAGGCT CCAGGGAAGG GTCTGGAGTG GGTCTCATCG ATTTCTCCGG TTGGTTTTCT
    GACATACTAC GCAGACTCCG TGAAGGGCCG

    ACCGCACCCA GGCGGTCCGA GGTCCCTTCC CAGACCTCAC CCAGAGTAGC TAAAGAGGCC AACCAAAAGA
    CTGTATGATG CGTCTGAGGC ACTTCCCGGC

    . F T I S R D N S K N T L Y L Q M N S L R A E D T A V Y Y C A
    K G H

201 GTTCACCATC TCCCGCGACA ATTCCAAGAA CACGCTGTAT CTGCAAATGA ACAGCCTGCG TGCCGAGGAT
    ACCGCGGTAT ATTACTGTGC GAAAGGGCAT
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
    CAAGTGGTAG AGGGCGCTGT TAAGGTTCTT GTGCGACATA GACGTTTACT TGTCGGACGC ACGGCTCCTA
    TGGCGCCATA TAATGACACG CTTTCCCGTA

    E G S Y T P R S A F D Y W G Q G T L V T V S S

301 GAGGGGTCGT ATACTCCGCG GTCGGCTTTT GACTACTGGG GTCAGGGAAC CCTGGTCACC GTCTCGAGC     (SEQ ID NO: 236)

    CTCCCCAGCA TATGAGGCGC CAGCCGAAAA CTGATGACCC CAGTCCCTTG GGACCAGTGG CAGAGCTCG     (SEQ ID NO: 237)

DOM-82 SEQ ID NO: 79
    E V Q L L E S G G G L V Q P G G S L R L S C A A S G F T F V A
    Y P M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGTG GCGTATCCTA

    CTCCACGTCG ACAACCTCAG ACCCCCTCCG AACCATGTCG GACCCCCCAG GGACGCAGAG AGGACACGTC
    GGAGGCCTAA GTGGAAACAC CGCATAGGAT

    . A W V R Q A P G K G L E W V S T I A P L G G N T Y Y A D S V
    K G R .

101 TGGCGTGGGT CCGCCAGGCT CCAGGGAAGG GTCTGGAGTG GGTCTCAACT ATTGCGCCTC TGGGTGGTAA
    TACATACTAC GCAGACTCCG TGAAGGGCCG

    ACCGCACCCA GGCGGTCCGA GGTCCCTTCC CAGACCTCAC CCAGAGTTGA TAACGCGGAG ACCCACCATT
    ATGTATGATG CGTCTGAGGC ACTTCCCGGC

    . F T I S R D N S K N T L Y L Q M N S L R A E D T A V Y Y C A
    K R P

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAACGGCCG

    CAAGTGGTAG AGGGCGCTGT TAAGGTTCTT GTGCGACATA GACGTTTACT TGTCGGACGC ACGGCTCCTG
    TGGCGCCATA TAATGACACG CTTTGCCGGC

    E G L Q I D S Q N F D Y W G Q G T L V T V S S

301 GAGGGGCTGC AGATTGATTC TCAGAATTTT GACTACTGGG GTCAGGGAAC CCTGGTCACC GTCTCGAGC     (SEQ ID NO: 238)

    CTCCCCGACG TCTAACTAAG AGTCTTAAAA CTGATGACCC CAGTCCCTTG GGACCAGTGG CAGAGCTCG     (SEQ ID NO: 239

DOM-83 SEQ ID NO: 80
    E V Q L L E S G G G L V Q P G G S L R L S C A A S G F T F A L
    Y Q M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGCG TTGTATCAGA

    CTCCACGTCG ACAACCTCAG ACCCCCTCCG AACCATGTCG GACCCCCCAG GGACGCAGAG AGGACACGTC
    GGAGGCCTAA GTGGAAACGC AACATAGTCT

    . A W V R Q A P G K G L E W V S S I D S S G S D T Y Y A D S V
    K G R .

101 TGGCTTGGGT CCGCCAGGCT CCAGGGAAGG GTCTAGAGTG GGTCTCATCG ATTGATTCTT CTGGTAGTGA
    TACATACTAC GCAGACTCCG TGAAGGGCCG

    ACCGAACCCA GGCGGTCCGA GGTCCCTTCC CAGATCTCAC CCAGAGTAGC TAACTAAGAA GACCATCACT
    ATGTATGATG CGTCTGAGGC ACTTCCCGGC

    . F T I S R D N S K N T L Y L Q M N S L R A E D T A V Y Y C A
    K P E

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAACCTGAG

    CAAGTGGTAG AGGGCGCTGT TAAGGTTCTT GTGCGACATA GACGTTTACT TGTCGGACGC ACGGCTCCTG
    TGGCGCCATA TAATGACACG CTTTGGACTC

    R D F D Y W G Q G T L V T V S S
```

TABLE 8-continued

| Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below: |
|---|

```
301 CGTGATTTTG ACTACTGGGG TCAGGGAACC CTGGTCACCG TCTCGAGC          (SEQ ID NO: 240)

    GCACTAAAAC TGATGACCCC AGTCCCTTGG GACCAGTGGC AGAGCTCG          (SEQ ID NO: 241)

DOM-84 SEQ ID NO: 81
    E V Q L L E S G G G L V Q P G G S L R L S C A A S G F T F R Q
    Y Q M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTAGG CAGTACCAGA

    CTCCACGTCG ACAACCTCAG ACCCCCTCCG AACCATGTCG GACCCCCCAG GGACGCAGAG AGGACACGTC
    GGAGGCCTAA GTGGAAATCC GTCATGGTCT

    . A W A R Q A P G K G L E W V S T I A S D G V S T Y Y A D S V
    K G R .

101 TGGCTTGGGC CCGCCAGGCT CCAGGGAAGG GTCTAGAGTG GGTCTCAACG ATTGCGTCGG ATGGTGTTTC
    TACATACTAC GCAGACTCCG TGAAGGGCCG

    ACCGAACCCG GGCGGTCCGA GGTCCCTTCC CAGATCTCAC CCAGAGTTGC TAACGCAGCC TACCACAAAG
    ATGTATGATG CGTCTGAGGC ACTTCCCGGC

    . F T I S R D N S K N T L Y L Q M N S L R A E D T A V Y Y C A
    K V G

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAAGTTGGT

    CAAGTGGTAG AGGGCGCTGT TAAGGTTCTT GTGCGACATA GACGTTTACT TGTCGGACGC ACGGCTCCTG
    TGGCGCCATA TAATGACACG CTTTCAACCA

    R D F D Y W G Q G T L V T V S S

301 CGTGATTTTG ACTACTGGGG TCAGGGAACC CTGGTCACCG TCTCGAGC          (SEQ ID NO: 242)

    GCACTAAAAC TGATGACCCC AGTCCCTTGG GACCAGTGGC AGAGCTCG          (SEQ ID NO: 243)

DOM-116 SEQ ID NO: 82
    D I Q M T Q S P S S L S A S V G D R V T I T C R A S Q P I G P
    D L L .

  1 GACATCCAGA TGACCCAGTC TCCATCCTCC CTGTCTGCAT CTGTAGGAGA CCGTGTCACC ATCACTTGCC
    GGGCAAGTCA GCCTATTGGT CCTGATTTAC

    CTGTAGGTCT ACTGGGTCAG AGGTAGGAGG GACAGACGTA GACATCCTCT GGCACAGTGG TAGTGAACGG
    CCCGTTCAGT CGGATAACCA GGACTAAATG

    . W Y Q Q K P G K A P K L L I Y Q T S I L Q S G V P S R F S G
    S G S .

101 TGTGGTACCA GCAGAAACCA GGGAAAGCCC CTAAGCTCCT GATCTATCAG ACGTCCATTT TGCAAAGTGG
    GGTCCCATCA CGTTTCAGTG GCAGTGGATC

    ACACCATGGT CGTCTTTGGT CCCTTTCGGG GATTCGAGGA CTAGATAGTC TGCAGGTAAA ACGTTTCACC
    CCAGGGTAGT GCAAAGTCAC CGTCACCTAG

    . G T D F T L T I S S L Q P E D F A T Y Y C Q Q Y W A F P V T
    F G Q

201 TGGGACAGAT TTCACTCTCA CCATCAGCAG TCTGCAACCT GAAGATTTTG CTACGTACTA CTGTCAACAG
    TATTGGGCTT TTCCTGTGAC GTTCGGCCAA

    ACCCTGTCTA AAGTGAGAGT GGTAGTCGTC AGACGTTGGA CTTCTAAAAC GATGCATGAT GACAGTTGTC
    ATAACCCGAA AAGGACACTG CAAGCCGGTT

    G T K V E I K R

301 GGGACCAAGG TGGAAATCAA ACGG                                      (SEQ ID NO: 244)

    CCCTGGTTCC ACCTTTAGTT TGCC                                      (SEQ ID NO: 245)--

DOM-85 - SEQ ID NO.: 246
    E V Q L L E S G G G L V Q P G G S L R L S C A A S G F T
    F E Q Y D M .
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGAG CAGTATGATA

    . R W V R Q A P G K G L E W V S W I D E A G H E T Y Y A D
    S V K G R .

101 TGAGGTGGGT CCGCCAGGCT CCAGGGAAGG GTCTAGAGTG GGTCTCATGG ATTGATGAGG CGGGTCATGA
    GACATACTAT GCAGACTCCG TGAAGGGCCG

    . F T I S R D N S R N T L Y L Q M N S L R A E D T A V Y Y
    C A K G M

201 GTTCACCATC TCCCGCGACA ATTCCAGGAA CACGCTGTAT CTGCAAATGA ACAGCCTGCG TGCCGAGGAC
    ACCGCGGTAT ATTACTGTGC GAAAGGGATG

    D G F D Y W G Q G T L V T V S S

301 GATGGGTTTG ACTACTGGGG TCAGGGAACC CTGGTCACCG TCTCGAGC -          SEQ ID NO.: 361

DOM-86 - SEQ ID NO.: 247
    D I Q M T Q S P S S L S A S V G D R V T I T C R A S Q D
    I G D A L F .

  1 GACATCCAGA TGACCCAGTC TCCATCCTCC CTGTCTGCAT CTGTAGGAGA CCGTGTCACC ATCACTTGCC
    GGGCAAGTCA GGATATTGGG GATGCTTTAT

    . W Y Q Q K P G K A P K L L I Y Y S S M L Q S G V P S R F
    S G G G S .

101 TTTGGTACCA GCAGAAACCA GGGAAAGCCC CTAAGCTCCT GATCTATTAT TCTTCCATGT TGCAAAGTGG
    GGTCCCATCA CGTTTCAGTG GCGGTGGATC

    . G T D F T L T I S S L Q P E D F A T Y Y C Q Q R H S T P
    A T F G Q

201 TGGGACAGAT TTCACTCTCA CCATCAGCAG TCTGCAACCT GAAGATTTTG CTACGTACTA CTGTCAACAG
    CGGCATAGTA CTCCTGCTAC GTTCGGCCAA

    G T K V E I K R

301 GGGACCAAGG TGGAAATCAA ACGG -                                   SEQ ID NO.: 362

DOM-87 - SEQ ID NO.: 248
    D I Q M T Q S P S S L S A S V G D R V T I T C R A S Q D
    I D E S L M .

  1 GACATCCAGA TGACCCAGTC TCCATCCTCC CTGTCTGCAT CTGTAGGAGA CCGTGTCACC ATCACTTGCC
    GGGCAAGTCA GGATATTGAT GAGTCTTTAA

    . W Y Q Q K P G K A P R L L I Y G V S Y L Q S G V P S R F
    S G S G S .

101 TGTGGTACCA GCAGAAACCA GGGAAAGCCC CTAGGCTCCT GATCTATGGG GTGTCCTATT TGCAAAGTGG
    GTCCCATCA CGTTTCAGTG GCAGTGGATC

    . G T D F T L T I S S L Q P E D F A T Y Y C Q Q R W K A P
    F T F G Q

201 TGGGACAGAT TTCACTCTCA CCATCAGCAG TCTGCAACCT GAAGATTTCG CTACGTACTA CTGTCAACAG
    CGGTGGAAGG CTCCTTTTAC GTTCGGCCAA

    G T K V E I K R -                                             SEQ ID NO.: 363

DOM.88 - SEQ ID NO.: 249
    D I Q M T Q S P S S L S A S V G D R V T I T C R A S Q E
    I V E D L Y .

  1 GACATCCAGA TGACCCAGTC TCCATCCTCC CTGTCTGCAT CTGTAGGAGA CCGTGTTACC ATCACTTGCC
    GGGCAAGTCA GGAGATTGTG GAGGATTTAT

    . W Y Q Q K P G K A A K L L I Y G A S W L Q S G V P S R F
    S G S G S .
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
101 ATTGGTATCA GCAGAAACCA GGGAAAGCCG CTAAGCTCCT GATCTATGGT GCGTCCTGGT TGCAAAGTGG
    GGTCCCATCA CGTTTCAGTG GCAGTGGATC

    . G T D F T L T I S S L Q P E D F A T Y Y C Q Q T R R R P
    Y T F G Q

201 TGGGACAGAT TTCACTCTCA CCATCAGCAG TCTGCAACCT GAAGATTTTG CTACGTACTA CTGTCAACAG
    ACGCGTAGGC GTCCTTATAC GTTCGGCCAA

    G T K V E I K R

301 GGGACCAAGG TGGAAATCAA ACGG -                                     SEQ ID NO.: 364

DOM.89 - SEQ ID NO.: 250
    D I Q M T Q S P A S L S A S V G D R V T I T C R A S Q D
    I D P M L R .

  1 GACATCCAGA TGACCCAGTC TCCAGCCTCC CTGTCTGCAT CTGTAGGAGA CCGTGTCACC ATCACTTGCC
    GGGCAAGTCA GGATATTGAT CCTATGTTAA

    . W Y Q Q K P G K A P K L L I Y A G S I L Q S G V P S R F
    S G S G S .

101 GGTGGTACCA GCAGAAACCA GGGAAAGCCC CTAAGCTCCT GATCTATGCG GGTTCCATTT TGCAAAGTGG
    GGTCCCATCA CGTTTCAGTG GCAGTGGATC

    . G T D F T L T I S S L Q P E D F A T Y Y C Q Q T L V T P
    Y T F G Q

201 TGGGACAGAT TTCACTCTCA CCATCAGCAG TCTGCAACCT GAAGATTTTG CTACGTACTA CTGTCAACAG
    ACGCTGGTGA CTCCTTATAC GTTCGGCCAA

    G T K V E I K R

301 GGGACCAAGG TGGAAATCAA ACGG -                                     SEQ ID NO.: 365

DOM.90 - SEQ ID NO.: 251
    D I Q M T Q S P S S L S A S V G D R V T I T C R A S Q S
    I S D A L F .

  1 GACATCCAGA TGACCCAGTC TCCATCCTCC CTGTCTGCAT CTGTAGGAGA CCGTGTCACC ATCACTTGCC
    GGGCAAGTCA GTCGATTTCG GATGCGTTAT

    . W Y Q Q K P G K A P R L L I Y Y G S V L Q S G V P S R F
    S G S G S .

101 TTTGGTACCA GCAGAAACCA GGGAAAGCCC CTAGGCTCCT GATCTATTAT GGTTCCGTTT TGCAAAGTGG
    GGTCCCATCA CGTTTCAGTG GCAGTGGATC

    . G T D F T L T I S S L Q P E D F A T Y Y C Q Q R F Q E P
    V T F G Q

201 TGGGACAGAT TTCACTCTCA CCATCAGCAG TCTGCAACCT GAAGATTTTG CTACGTACTA CTGTCAACAG
    CGTTTTCAGG AGCCTGTGAC GTTCGGCCAA

    G T K V E I K R

301 GGGACCAAGG TGGAAATCAA ACGG -                                     SEQ ID NO.: 366
DOM.91 - SEQ ID NO.: 252
    D I Q M T Q S P S S L S A S V G D R V T I T C R A S Q Q
    I S D E L N .

  1 GACATCCAGA TGACCCAGTC TCCATCCTCC CTGTCCGCAT CTGTAGGAGA CCGTGTCACC ATCACTTGCC
    GGGCAAGTCA GCAGATTAGT GATGAGTTAA

    . W Y Q Q K P G K A P K L L I Y A V S I L Q S G V P S R F
    S G S G S .

101 ATTGGTATCA GCAGAAACCA GGGAAAGCCC CTAAGCTCCT GATCTATGCT GTGTCCATTT TGCAAAGTGG
    GGTCCCATCA CGTTTCAGTG GCAGTGGATC

    . G T D F T L T I S S L Q P E D F A T Y Y C Q Q W L S F P
    S T F G Q
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
 201 TGGGACAGAT TTCACTCTCA CCATCAGCAG TCTGCAACCT GAAGATTTTG CTACGTACTA CTGTCAACAG
     TGGTTGAGTT TTCCTTCGAC GTTTGGCCAA

     G T K V E I K R

 301 GGGACCAAGG TGGAAATCAA ACGG -                                        SEQ ID NO.: 367

DOM.92 - SEQ ID NO.: 253
     E V Q L L E S G G G L V Q P G G S L R L S C A A S G F T
     F V D Y P M .

   1 GAGGTGCAGC TGTTGGAGTC TGGGGGAGGC TTGGTACAGC CTGGGGGGTC CCTGCGTCTC TCCTGTGCAG
     CCTCCGGATT CACCTTTGTT GATTATCCGA

     . G W V R Q A P G K G L E W V S T I S T G G F S T Y Y A D
     S V K G R .

 101 TGGGTTGGGT CCGCCAGGCT CCAGGGAAGG GTCTAGAGTG GGTCTCAACG ATTTCTACGG GGGGTTTTTC
     GACATACTAC GCAGACTCCG TGAAGGGCCG

     . F T I S R D N S K N T L Y L Q M N S L R A E D T A V Y Y
     C A K A R

 201 GTTCACCATC TCCCGCGACA ATTCCAAGAA CACGCTGTAT CTGCAAATGA ACAGCCTGCG TGCCGAGGAC
     ACCGCGGTAT ATTACTGTGC GAAAGCGCGG

     Y Y Y L S Q I K N F D Y W G Q G T L V T V S S

 301 TATTATTATC TTAGTCAGAT TAAGAATTTT GACTACTGGG GTCAGGGAAC CCTGGTCACC GTCTCGAGC -     SEQ ID NO.: 368

DOM.93 - SEQ ID NO.: 254
     E V Q L L E S G G G L V Q P G G S L R L S C A A S G F T
     F D I Y G M .

   1 GAGGTGCAGC TGTTGGAGTC TGGGGGAGGC TTGGTACAGC CTGGGGGGTC CCTGCGTCTC TCCTGTGCAG
     CCTCCGGATT CACCTTTGAT ATTTATGGGA

     . T W V R Q A P G K G L E W V S S I S P L G L V T Y Y A D
     P V K G R .

 101 TGACTTGGGT CCGCCAGGCT CCAGGGAAGG GTCTGGAGTG GGTCTCAAGT ATTTCGCCTC TTGGTCTTGT
     TACATACTAC GCAGACCCCG TGAAGGGCCG

     . F T I S R D N S K N T L Y L Q M N S L R A E D T A V Y Y
     C A K L K

 201 GTTCACCATC TCCCGCGACA ATTCCAAGAA CACGCTGTAT CTGCAAATGA ACAGCCTGCG TGCCGAGGAC
     ACCGCGGTAT ATTACTGTGC GAAACTGAAG

     E H G D V P F D Y W G Q G T L V T V S S

 301 GAGCATGGGG ATGTTCCTTT TGACTACTGG GGTCAGGGAA CCCTGGTCAC CGTCTCGAGC -         SEQ ID NO.: 369

DOM.94 - SEQ ID NO.: 255
     E V Q L L E S G G G L V Q P G G S L R L S C A A S G F T
     F E L Y P M .

   1 GAGGTGCAGC TGTTGGAGTC TGGGGGAGGC TTGGTACAGC CTGGGGGGTC CCTGCGTCTC TCCTGTGCAG
     CCTCCGGATT CACCTTTGAG CTTTATCCGA

     . S W V R Q A P G K G L E W V S T I S P T G L L T Y Y A D
     S V K G R .

 101 TGAGTTGGGT CCGCCAGGCT CCAGGGAAGG GTCTAGAGTG GGTCTCAACT ATTTCTCCTA CGGGTTTGTT
     GACATACTAC GCAGACTCCG TGAAGGGCCG

     . F T I S R D N S K N T L Y L Q M N S L R A E D T A V Y Y
     C A K F K

 201 GTTCACCATC TCCCGCGACA ATTCCAAGAA CACGCTGTAT CTGCAAATGA ACAGCCTGCG TGCCGAGGAC
     ACCGCGGTAT ATTACTGTGC GAAATTTAAG

     R S G K T D D T N F D Y W G Q G T L V T V S S
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
301 AGGAGTGGGA AGACTGATGA TACTAATTTT GACTACTGGG GTCAGGGAAC CCTGGTCACC GTCTCGAGC -     SEQ ID NO.: 370

DOM.95 - SEQ ID NO.: 256
    E V Q L L E S G G G L V Q P G G S L R L S C A A S G F T
    F R E Y D M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTCGG GAGTATGATA

    . L W V R Q A P G K G L E W V S T I V G D G N G T Y Y A D
    S V K G R .

101 TGCTGTGGGT CCGCCAGGCT CCAGGGAAGG GTCTAGAGTG GGTCTCAACG ATTGTGGGGG ATGGTAATGG
    TACATACTAC GCAGACTCCG TGAAGGGCCG

    . F T I S R D N S K N T L Y L Q M N S L R A E D T A V Y Y
    C A K Q D

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAACAGGAT

    R Q F D Y W G Q G T L V T V S S

301 CGTCAGTTTG ACTACTGGGG TCAGGGAACC CTGGTCACCG TCTCGAGC -                            SEQ ID NO.: 371

DOM.96 - SEQ ID NO.: 257
    E V Q P L E S G G G L V Q P G G S L R L S C A A S G F T
    F T D Y K M .

  1 GAGGTGCAGC CGTTGGAGTC TGGGGGAGGC TTGGTACAGC CTGGGGGGTC CCTGCGTCTC TCCTGTGCAG
    CCTCCGGATT CACCTTTACT GATTATTAGA

    . L W V R Q A P G K G L E W V S S I S P S G R W T Y Y A D
    S V K G R .

101 TGCTTTGGGT CCGCCAGGCT CCAGGGAAGG GTCTAGAGTG GGTCTCAAGT ATTTCTCCTA GTGGTCGTTG
    GACATACTAC GCAGACTCCG TGAAGGGCCG

    . F T I S R D N S K N T L Y L Q M N S L R A E D T A V Y Y
    C A K S L

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAAAGTCTT

    F E G S F D Y W G Q G T L V T V S S

301 TTTGAGGGTA GTTTTGACTA CTGGGGTCAG GGAACCCTGG TCACCGTCTC GAGC -                     SEQ ID NO.: 372

DOM.97 - SEQ ID NO.: 258
    E V Q L L E S G G G L V Q P G G S L R L S C A A S G F T
    F E E Y G M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGAG GAGTATGGTA

    . S W V R Q A P G K G L E W V S T I S P I G V T T Y Y A D
    S V K G R .

101 TGAGTTGGGT CCGCCAGGCT CCAGGGAAGG GTCTAGAGTG GGTCTCAACG ATTTCGCCTA TTGGTGTTAC
    TACATACTAC GCAGACTCCG TGAAGGGCCG

    . F T I S R D N S K N T L Y L Q M N S L R A E D T A V Y Y
    C A K N A

201 GTTCACCATC TCCCGCGACA ATTCCAAGAA CACGCTGTAT CTGCAAATGA ACAGCCTGCG TGCCGAGGAT
    ACCGCGGTAT ATTACTGTGC GAAAAATGCT

    Y D R K S N F D Y W G Q G T L V T V S S

301 TATGATCGGA AGTCTAATTT TGACTACTGG GGTCAGGGAA CCCTGGTCAC CGTCTCGAGC -               SEQ ID NO.: 373

DOM.98 - SEQ ID NO.: 259
    E V Q L L E S G G G L V Q P G G S L R L S C A A S G F T
    F D R Y V M .
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGAT CGGTATGTGA

    . V W V R Q A P G K D L E W V S G I T P S G R R T Y Y A D
    S V K G R .

101 TGGTGTGGGT CCGCCAGGCT CCAGGGAAGG ATCTAGAGTG GGTCTCAGGT ATTACTCCGA GTGGTAGGAG
    GACATACTAC GCAGACTCCG TGAAGGGCCG

    . F T I S R D N S K D T L Y L Q M N S L R A E D T A V Y Y
    C A K V L

201 GTTCACCATC TCCCGCGACA ATTCCAAGGA CACGCTGTAT CTGCAAATGA ACAGCCTGCG TGCCGAGGAC
    ACCGCGGTAT ATTACTGTGC GAAAGTGTTG

    G R H F D P L L P S F D Y W G Q G T L V T V S S

301 GGGCGTCATT TTGATCCTCT TCTGCCTTCG TTTGACTACT GGGGTCAGGG AACCCTGGTC ACCGTCTCGA GC - SEQ ID NO.: 374

DOM.99 - SEQ ID NO.: 260
    E V Q L L E S G G G L V Q P G G S L R L S C A A S G F T
    F E D Y A M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGAG GATTATGCTA

    . S W V R Q A P G K G L E W V S T I T P G G F W T Y Y A D
    S V K G R .

101 TGAGTTGGGT CCGCCAGGCT CCAGGGAAGG GTCTAGAGTG GGTCTCAACT ATTACTCCGG GTGGTTTTTG
    GACATACTAC GCAGACTCCG TGAAGGGCCG

    . F T I S R D N S K N T L Y L Q M N S L R A E D T A V Y Y
    C A K T S

201 GTTCACCATC TCCCGCGACA ATTCCAAGAA CACGCTGTAT CTGCAAATGA ACAGCCTGCG TGCCGAGGAT
    ACCGCGGTAT ATTACTGTGC GAAAACGTCT

    S G E L Q L V E D F D Y W G Q G T L V T V S S

301 AGTGGGGAGT TGCAGTTGGT TGAGGATTTT GACTACTGGG GTCAGGGAAC CCTGGTCACC GTCTCGAGC -     SEQ ID NO.: 375

DOM.100 - SEQ ID NO.: 261
    D I Q M T Q S P S S L S A S V G D R V T I T C R A S Q N
    I K H S L R .

  1 GACATCCAGA TGACCCAGTC TCCATCCTCC CTGTCTGCAT CTGTAGGAGA CCGTGTCACC ATCACTTGCC
    GAGCAAGTCA GAATATTAAG CATTCGTTAC

    . W Y Q Q K P G K A P R L L I Y H R S Q L Q S G V P S R F
    S G S G S .

101 GGTGGTACCA GCAGAAACCA GGGAAAGCCC CTAGGCTCCT GATCTATCAT CGTTCCCAGT TGCAAAGTGG
    GGTCCCATCA CGTTTCAGTG GCAGTGGATC

    . G T D F T L T I S S L Q P E D F A T Y Y C Q Q V R H R P
    Y T F G Q

201 TGGGACAGAT TTCACTCTCA CCATCAGCAG TCTGCAACCT GAAGATTTTG CTACGTACTA CTGTCAACAG
    GTTAGGCATC GTCCTTATAC GTTCGGCCAA

    G T K V E I K R

301 GGGACCAAGG TGGAAATCAA ACGG -                                                 SEQ ID NO.: 376

DOM.101 - SEQ ID NO.: 262
    D I Q M T Q S P S S L S A S V G D R V T I T C R A S Q A
    I G H R L R .

  1 GACATCCAGA TGACCCAGTC TCCATCCTCT CTGTCTGCAT CTGTAGGAGA CCGTGTCACC ATCACTTGCC
    GGGCAAGTCA GGCTATTGGG CATCGGTTAC

    . W Y Q Q K P G K A P K L L I Y H R S K L Q S G V P S R F
    S G S G S .
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
101 GTTGGTATCA GCAGAAACCA GGGAAAGCCC CTAAGCTCCT GATCTATCAT CGGTCCAAGT TGCAAAGTGG
    GGTCCCATCA CGTTTCAGTG GCAGTGGATC

    . G T D F T L T I S S L Q P E D F A T Y Y C Q Q V A L F P
    Y T F G Q

201 TGGGACAGAT TTCACTCTCA CCATCAGCAG TCTGCAACCT GAAGATTTTG CTACGTACTA CTGTCAACAG
    GTTGCTTTGT TTCCCTATAC GTTCGGCCAA

    G T K V E I K R

301 GGGACCAAGG TGGAAATCAA ACGG -                                  SEQ ID NO.: 377

DOM.102 - SEQ ID NO.: 263
    D I Q M T Q S P S S L S A S V G D R V T I T C R A S Q H
    I G H H L R .

  1 GACATCCAGA TGACCCAGTC TCCATCCTCC CTGTCTGCAT CTGTAGGAGA CCGTGTCACC ATCACTTGCC
    GGGCAAGTCA GCATATTGGT CATCATTTAA

    . W Y Q Q K P G K A P K L L I Y H R S H L Q S G V P S R F
    S G S G S .

101 GGTGGTACCA GCAGAAACCA GGGAAAGCCC CCAAGCTCCT GATCTATCAT AGGTCCCATT TGCAAAGTGG
    GGTCCCATCA CGTTTCAGTG GCAGTGGATC

    . G T D F T L T I S S L Q P E D S A T Y Y C Q Q W D R P P
    Y T F G Q

201 TGGGACAGAT TTCACTCTCA CCATCAGCAG TCTGCAACCT GAAGATTCTG CTACGTACTA CTGTCAACAG
    TGGGATAGGC CGCCTTATAC GTTCGGCCAA

    G T K V E I K R

301 GGGACCAAGG TGGAAATCAA ACGG -                                  SEQ ID NO.: 378

DOM.103 - SEQ ID NO.: 264
    D I Q M T Q S P S S L S A S V G D R V T I T C R A S Q A
    I G H R L R .

  1 GACATCCAGA TGACCCAGTC CCCATCCTCC CTGTCTGCAT CTGTAGGAGA CCGTGTCACC ATCACTTGCC
    GGGCAAGTCA GGCTATTGGG CATCGGTTAC

    . W Y Q Q K P G K A P K L L I Y H R S K L Q S G V P S R F
    S G S G S .

101 GTTGGTATCA GCAGAAACCA GGGAAAGCCC CTAAGCTCCT GATCTATCAT CGGTCCAAGT TGCAAAGTGG
    GGTCCCATCA CGTTTCAGTG GCAGTGGATC

    . G T D F T L T I S S L Q P E D F A T Y Y C Q Q V R A V P
    Y T F G Q

201 TGGGACAGAT TTCACTCTCA CCATCAGCAG TCTGCAACCT GAAGATTTTG CTACGTACTA CTGTCAACAG
    GTGCGGGCTG TGCCTTATAC GTTTGGCCAA

    G T K V E I K R

301 GGGACCAAGG TGGAAATTAA ACGG -                                  SEQ ID NO.: 379

DOM.104 - SEQ ID NO.: 265
    D I Q M T Q S P S S L S A S V G D R V T I T C R A S Q A
    I G H R L R .

  1 GACATCCAGA TGACCCAGTC TCCATCCTCC CTGTCTGCAT CTGTAGGAGA CCGTGTCACC ATCACTTGCC
    GGGCAAGTCA GGCTATTGGG CATCGGTTAC

    . W Y Q Q K P G K A P K L L I Y H R S K L Q S G V P S R F
    S G S G S .

101 GTTGGTATCA GCAGAAACCA GGGAAAGCCC CTAAGCTCCT GATCTATCAT CGGTCCAAGT TGCAAAGTGG
    GGTCCCATCA CGTTTCAGTG GCAGTGGATC

    . G T D F T L T I S S L Q P E D F A T Y Y C Q Q V R F S P
    Y T F G Q
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
201 TGGGACAGAT TTCACTCTCA CCATCAGCAG TCTGCAACCT GAAGATTTTG CTACGTACTA CTGTCAACAG
    GTTCGTTTTT CTCCTTATAC GTTCGGCCAA

    G T K V E I K R

301 GGGACCAAGG TGGAAATCAA ACGG -                                       SEQ ID NO.: 380

DOM.105 - SEQ ID NO.: 266
    D I Q M T Q S P S S L S A S V G D R V T I T C R A S Q A
    I G H R L R .

  1 GACATCCAGA TGACCCAGTC TCCATCCTCC CTGTCTGCAT CTGTAGGAGA CCGTGTCACC ATCACTTGCC
    GGGCAAGTCA GGCTATTGGG CATCGGTTAC

    . W Y Q Q K P G K A P K L L I Y H R S K L Q S G V P S R F
    S G S G S .

101 GTTGGTATCA GCAGAAACCA GGGAAAGCCC CTAAGCTCCT GATCTATCAT CGGTCCAAGT TGCAAAGTGG
    GGTCCCATCA CGTTTCAGTG GCAGTGGATC

    . G T D F T L T I S S L Q P E D F A T Y Y C Q Q S Y A R P
    V T F G Q

201 TGGGACAGAT TTCACTCTCA CCATCAGCAG TCTGCAACCT GAAGATTTTG CTACGTACTA CTGTCAACAG
    TCTTATGCTA GGCCTGTGAC GTTCGGCCAA

    G T K V E I K R

301 GGGACCAAGG TGGAAATCAA ACGG -                                       SEQ ID NO.: 381

DOM.106 - SEQ ID NO.: 267
    D I Q M T Q S P S S L S A S V G D R V T I T C R A S Q S
    I N H R L Y .

  1 GACATCCAGA TGACCCAGTC TCCATCCTCC CTGTCTGCAT CTGTAGGAGA CCGTGTCACC ATCACTTGCC
    GGGCAAGTCA AAGTATTAAT CATAGGTTAT

    . W Y Q Q K P G K A P K L L I Y H R S R L Q S G V P S R F
    S G S G S .

101 ATTGGTACCA GCAGAAACCA GGGAAAGCCC CTAAGCTCCT GATCTATCAT CGGTCCAGGT TGCAAAGTGG
    GGTCCCATCA CGTTTCAGTG GCAGTGGATC

    . G T D F T L T I S S L Q P E D F A T Y Y C Q Q Y K V R P
    N T F G Q

201 TGGGACAGAT TTCACTCTCA CCATCAGCAG TCTGCAACCT GAGGATTTTG CTACGTACTA CTGTCAACAG
    TATAAGGTTA GGCCTAATAC GTTCGGCCAA

    G T K V E I K R

301 GGGACCAAGG TGGAAATCAA ACGG -                                       SEQ ID NO.: 382

DOM.107 - SEQ ID NO.: 268
    D I Q M T Q S P S S L S A S V G D R V T I T C R A S Q A
    I G H R L R .

  1 GACATCCAGA TGACCCAGTC TCCATCCTCC CTGTCTGCAT CTGTAGGAGA CCGTGTCACC ATCACTTGCC
    GGGCAAGTCA GGCTATTGGG CATCGGTTAC

    . W Y Q Q K P G K A P K L L I Y H R S K L Q S G V P S R F
    S G S G S .

101 GTTGGTATCA GCAGAAACCA GGGAAAGCCC CTAAGCTCCT GATTTATCAT CGGTCCAAGT TGCAAAGTGG
    GGTCCCATCA CGTTTCAGTG GCAGTGGATC

    . G T D F T L T I S S L Q P E D F A T Y Y C Q Q T Y S S P
    H T F G Q

201 TGGGACAGAT TTCACTCTCA CCATCAGCAG TCTGCAACCT GAAGATTTTG CTACGTACTA CTGTCAACAG
    ACTTATTCGT CTCCTCATAC GTTCGGCCAA

    G T K V E I K R
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
 301 GGGACCAAGG TGGAAATCAA ACGG -                                         SEQ ID NO.: 383

DOM.108 - SEQ ID NO.: 269
     D I Q M T Q S P S S L S A S V G D R V T I T C R A S Q A
     I G H R L R .

   1 GACATCCAGA TGACCCAGTC TCCATCCTCC CTGTCTGCAT CTGTAGGAGA CCGTGTCACC ATCACTTGCC
     GGGCAAGTCA GGCTATTGGG CATCGGTTAC

     . W Y Q Q K P G K A P K L L I Y H R S K L Q S G V P S R F
     S G S G S .

 101 GTTGGTATCA GCAGAAACCA GGGAAAGCCC CTAAGCTCCT GATCTATCAT CGGTCCAAGT TGCAAAGTGG
     GGTCCCATCA CGTTTCAGTG GCAGTGGATC

     . G T D F T L T I S S L Q P E D F A T Y Y C Q Q R A V R P
     F T F G Q

 201 TGGGACAGAT TTCACTCTCA CCATCAGCAG TCTACAACCT GAAGATTTTG CTACGTACTA CTGTCAACAG
     AGGGCGGTGA GGCCTTTTAC GTTCGGCCAA

     G T K V E I K R

 301 GGGACAAAAG TGGAAATCAA ACGG -                                         SEQ ID NO.: 384

DOM.109 - SEQ ID NO.: 270
     D I Q M T Q S P S S L S A S V G D R V T I T C R A S Q A
     I G H R L R .

   1 GACATCCAGA TGACCCAGTC TCCATCCTCC CTGTCTGCAT CTGTAGGAGA CCGTGTCACC ATCACTTGCC
     GGGCAAGTCA GGCTATTGGG CATCGGTTAC

     . W Y Q Q K P G K A P K L L I Y H R S K L Q S G V P S R F
     S G S G S .

 101 GTTGGTATCA GCAGAAACCA GGGAAAGCCC CTAAGCTCCT GATCTATCAT CGGTCCAAGT TGCAAAGTGG
     GGTCCCATCA CGTTTCAGTG GCAGTGGATC

     . G T D F T L T I S S L Q P E D F A T Y Y C Q Q T Y Y R P
     L T F G Q

 201 TGGGACAGAT TTCACTCTCA CCATCAGCAG TCTGCAACCT GAAGATTTTG CTACGTACTA CTGTCAACAG
     ACTTATTATC GTCCTCTTAC GTTCGGCCAA

     G T K V E I K R

 301 GGGACCAAGG TGGAAATCAA ACGG -                                         SEQ ID NO.: 385

DOM.110 - SEQ ID NO.: 271
     D I Q M T Q S P A S L S A S V G D R V T I T C R A S Q D
     I D P M L R .

   1 GACATCCAGA TGACCCAGTC TCCAGCCTCC CTGTCTGCAT CTGTAGGAGA CCGTGTCACC ATCACTTGCC
     GGGCAAGTCA GGATATTGAT CCTATGTTAA

     . W Y Q Q K P G K A P K L L I Y A G S I L Q S G V P S R F
     S G S G S .

 101 GGTGGTACCA GCAGAAACCA GGGAAAGCCC CTAAGCTCCT GATCTATGCG GGTTCCATTT TGCAAAGTGG
     GGTCCCATCA CGTTTCAGTG GCAGTGGATC

     . G T D F T L T I S S L Q P E D F A T Y Y C Q Q T S I R P
     Y T F G Q

 201 TGGGACAGAT TTCACTCTCA CCATCAGCAG TCTGCAACCT GAAGATTTTG CTACGTACTA CTGTCAACAG
     ACTAGTATTA GGCCTTATAC GTTCGGCCAA

     G T K V E I K R

 301 GGGACCAAGG TGGAAATCAA ACGG -                                         SEQ ID NO.: 386

DOM8.111 - SEQ ID NO.: 272
     E V Q L L E S G G G L V Q P G G S L R L S C A A S G F T
     F E R Y P M .
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGAG CGTTATCCTA

    . T W V R Q A P G K G L E W V S T I H G S G S A T Y Y A D
    S V K G R .

101 TGACGTGGGT CCGCCAGGCT CCAGGGAAGG GTCTAGAGTG GGTCTCAACG ATTCATGGTT CTGGTAGTGC
    TACATACTAC GCAGACTCCG TGAAGGGCCG

    . F T I S R D N S K N T L Y L Q M N S L R A E D T A V Y Y
    C A K G P

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAAGGGCCG

    Y T S R H N S L G H F D Y W G Q G T L V T V S S

301 TATACTAGTC GGCATAATAG TCTTGGGCAT TTTGACTACT GGGGTCAGGG AACCCTGGTC ACCGTCTCGA GC - SEQ ID NO.: 387

DOM.112 - SEQ ID NO.: 273
    E V Q L L E S G G G L V Q P G G S L R L S C A A S G F T
    F M D Y P M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTATG GATTATCCTA

    . G W V R Q A P G K G L E W V S S I G P V G M S T Y Y A D
    S V K G R .

101 TGGGGTGGGT CCGCCAGGCT CCAGGGAAGG GTCTAGAGTG GGTCTCATCT ATTGGGCCTG TTGGTATGAG
    TACATACTAC GCAGACTCCG TGAAGGGCCG

    . F T I S R D N S K N T L Y L Q M N S L R A E D T A V Y Y
    C A K Y G

201 GTTCACCATC TCCCGCGACA ATTCCAAGAA CACGCTGTAT CTGCAAATGA ACAGCCTGCG TGCCGAGGAT
    ACCGCGGTAT ATTACTGTGC GAAATATGGG

    G T S G R H N T K F D Y W G Q G T L V T V S S

301 GGGACTAGTG GTAGGCATAA TACTAAGTTT GACTACTGGG GTCAGGGAAC CCTGGTCACC GTCTCGAGC -     SEQ ID NO.: 388

DOM.113 - SEQ ID NO.: 274
    E V Q L L E S G G G L V Q P G G S L R L S C A A S G F T
    F T E Y P M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTACT GAGTATCCTA

    . S W V R Q A P G K G L E W V S V I S P L G F T T Y Y A D
    S V K G R .

101 TGAGTTGGGT CCGCCAGGCT CCAGGGAAGG GTCTAGAGTG GGTCTCAGTT ATTTCTCCTC TTGGTTTTAC
    GACATACTAC GCAGACTCCG TGAAGGGCCG

    . F T I S R D N S K N T L Y L Q M N S L R A E D T A V Y Y
    C A K W T

201 GTTCACCATC TCCCGCGACA ATTCCAAGAA CACGCTGTAT CTGCAAATGA ACAGCCTGCG TGCCGAGGAT
    ACCGCGGTAT ATTACTGTGC GAAATGGACT

    G G S G I L N S S F D Y W G Q G T L V T V S S

301 GGTGGGAGTG GTATTTTGAA TTCTTCTTTT GACTACTGGG GTCAGGGAAC CCTGGTCACC GTCTCGAGC -     SEQ ID NO.: 389

DOM.114 - SEQ ID NO.: 275
    E V Q L L E S G G G L V Q P G G S L R L S C A A S G F R
    V S N Y D L .

  1 GAGGTGCAGC TGTTGGAGTC TGGGGGAGGC TTGGTACAGC CTGGGGGGTC CCTGCGTCTC TCCTGTGCAG
    CCTCCGGATT TAGGGTTAGC AATTACGATT

    . T W V R Q A P G K G L E W V S T I S A T N G S T Y Y A D
    S V K G R .
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
101 TGACCTGGGT CCGCCAGGCT CCAGGGAAGG GTCTAGAGTG GGTATCAACC ATTAGTGCCA CAAACGGTAG
    CACATACTAC GCAGACTCCG TGAAGGGCCG

    . F T I S R D N S K N T L Y L Q M N S L R A E D T A V Y Y
    C A A V T

201 GTTCACCATC TCCCGTGACA ATTCCAAGAA CACGCTGTAT CTGCAAATGA ACAGCCTGCG TGCCGAGGAC
    ACCGCGGTAT ATTATTGCGC GGCAGTGACG

    W W L L R H N D N L G F W G Q G T L V T V S S

301 TGGTGGTTGT TGCGTCATAA CGACAACTTG GGGTTTTGGG GTCAGGGAAC CCTGGTCACC GTCTCGAGC -     SEQ ID NO.: 390

DOM.115 - SEQ ID NO.: 276
    E V Q L L E S G G G L V Q P G G S L R L S C A A S G F S
    I S Y K N M .

  1 GAGGTGCAGC TGTTGGAGTC TGGGGGAGGC TTGGTACAGC CTGGGGGGTC CCTGCGTCTC TCCTGTGCAG
    CCTCCGGATT TAGCATTAGC TATAAGAATA

    . A W V R Q A P G K G L E W V S A I K A A N G S T Y Y A D
    S V K G R .

101 TGGCCTGGGT CCGCCAGGCT CCAGGGAAGG GTCTAGAGTG GGTATCAGCC ATTAAGGCGG CAAACGGTAG
    CACATACTAC GCAGACTCCG TGAAGGGCCG

    . F T I S R D N S K N T L Y L Q M N S L R A E D T A V Y Y
    C A T G S

201 GTTCACCATC TCCCGTGACA ATTCCAAGAA CACGCTGTAT CTGCAAATGA ACAGCCTGCG TGCCGAGGAC
    ACCGCGGTAT ATTATTGCGC GACAGGGAGT

    Q K K R T Y T F D F W G Q G T L V T V S S

301 CAGAAGAAGC GGACCTACAC GTTCGACTTT TGGGGTCAGG GAACCCTGGT CACCGTCTCG AGC -          SEQ ID NO.: 391

DOM.120 - SEQ ID NO.: 277
    E V Q L L E S G G G L V Q P G G S L R L S C A A S G F T
    F R S Y T M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTAGG TCTTATACGA

    . G W V R Q A P G K G L E W V S S I N P M G Y Q T Y Y A D
    S V K G R .

101 TGGGTTGGGT CCGCCAGGCT CCAGGGAAGG GTCTAGAGTG GGTCTCATCT ATTAATCCTA TGGGTTATCA
    GACATACTAC GCAGACTCCG TGAAGGGCCG

    . F T I S R D N S K N T L Y L Q M N S L R A E D T A V Y Y
    C A K H G

201 GTTCACCATC TCCCGCGACA ATTCCAAGAA CACGCTGTAT CTGCAAATGA ACAGCCTGCG TGCCGAGGAT
    ACCGCGGTAT ATTACTGTGC GAAACATGGG

    V G K G T K P H N F D Y W G Q G T L V T V S S

301 GTGGGGAAGG GTACTAAGCC GCATAATTTT GACTACTGGG GTCAGGGAAC CCTGGTCACC GTCTCGAGC -     SEQ ID NO.: 392

DOM.121 - SEQ ID NO.: 278
    E V Q L L E S G G G L V Q P G G S L R L S C A A S G F T
    F E L Y R M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGAG CTGTATAGGA

    . S W V R Q A P G K G L E W V S E I S G S G F P T Y Y A D
    S V K G R .

101 TGTCTTGGGT CCGCCAGGCT CCAGGGAAGG GTCTAGAGTG GGTCTCAGAG ATTAGTGGTA GTGGTTTTCC
    TACATACTAC GCAGACTCCG TGAAGGGCCG

    . F T I S R D N S K N T L Y L Q M N S L R A E D T A V Y Y
    C A K S L
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAAAGTCTG

    H D K T Q H H Q E F D Y W G Q G T L V T V S S

301 CATGATAAGA CTCAGCATCA TCAGGAGTTT GACTACTGGG GTCAGGGAAC CCTGGTCACC GTCTCGAGC -     SEQ ID NO.: 393

DOM.123 - SEQ ID NO.: 279
    E V Q L L E S G G G L V Q P G G S L R L S C A A S G F T
    F I E Y P M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTATT GAGTATCCTA

    . R W V R Q A P G K G L E W V S L I S P S G V F T Y Y A D
    S V K G R .

101 TGCGGTGGGT CCGCCAGGCT CCAGGGAAGG GTCTAGAGTG GGTCTCACTT ATTTCTCCGT CTGGTGTGTT
    TACATACTAC GCAGACTCCG TGAAGGGCCG

    . F T I S R D N S K N T L Y L Q M N S L R A E D T A V Y Y
    C A K G D

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAAGGGGAT

    E S S T F D Y W G Q G T L V T V S S

301 GAGTCTAGTA CTTTTGACTA CTGGGGTCAG GGAACCCTGG TCACCGTCTC GAGC -                   SEQ ID NO.: 394

DOM.124 - SEQ ID NO.: 280
    E V Q L L E S G G G L V Q P G G S L R L S C A A S G F T
    F K R Y D M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTAAG CGGTATGATA

    . D W V R Q A P G K G L E W V S T I G S S G Y P T Y Y A D
    S V K G R .

101 TGGATTGGGT CCGCCAGGCT CCAGGGAAGG GTCTAGAGTG GGTCTCAACG ATTGGGAGTT CGGGTTATCC
    GACATACTAC GCAGACTCCG TGAAGGGCCG

    . F T I S R D N S K N T L Y L Q M N S L R A E D T A V Y Y
    C A E R M

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GGAAAGGATG

    P G Y F P G F A R Q F D Y W G Q G T L V T V S S

301 CCTGGTTATT TTCCTGGGTT TGCTCGGCAG TTTGACTACT GGGGTCAGGG AACCCTGGTC ACCGTCTCGA GC - SEQ ID NO.: 395

DOM.125 - SEQ ID NO.: 281
    E V Q L L E S G G G L V Q P G G S L R L S C A A S G F T
    F W R Y A M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTTGG CGGTATGCTA

    . G W V R Q A P G K G L E W V S T I N D E G R E T Y Y A D
    S V K G R .

101 TGGGGTGGGT CCGCCAGGCT CCAGGGAAGG GTCTAGAGTG GGTCTCAACG ATTAATGATG AGGGTCGGGA
    GACATACTAC GCAGACTCCG TGAAGGGCCG

    . F T I S R D N S K N T L Y L Q M N S L R A E D T A V Y Y
    C A K K R

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAAAAGCGG

    V S S S V N A P Y E F D Y W G Q G T L V T V S S
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
 301 GTGTCTAGTT CTGTGAATGC TCCGTATGAG TTTGACTACT GGGGTCAGGG AACCCTGGTC ACCGTCTCGA GC - SEQ ID NO.: 396

DOM.126 - SEQ ID NO.: 282
     E V Q L L E S G G G L V Q P G G S L R L S C A A S G F T
     F A N Y S M .

   1 GAGGTGCAGC TGTTGGAGTC TGGGGGAGGC TTGGTACAGC CTGGGGGGTC CCTGCGTCTC TCCTGTGCAG
     CCTCCGGATT CACCTTTGCG AATTATAGTA

     . S W V R Q A P G K G L E W V S S I D R L G T H T Y Y A D
     S V K G R .

 101 TGAGTTGGGT CCGCCAGGCC CCAGGGAAGG GTCTAGAGTG GGTCTCATCG ATTGATCGTC TTGGTACGCA
     TACATACTAC GCAGACTCCG TGAAGGGCCG

     . F T I S R D N S K N T L Y L Q M N S L R A E D T A V Y Y
     C A K V L

 201 GTTCACCATC TCCCGCGACA ATTCCAAGAA TACGCTGTAT CTGCAAATGA ACAGCCTGCG TGCCGAGGAT
     ACCGCGGTAT ATTACTGTGC GAAAGTGCTG

     A D L I A G H A E F D Y W G Q G T L V T V S S

 301 GCTGATCTTA TTGCTGGGCA TGCGGAGTTT GACTACTGGG GTCAGGGAAC CCTGGTCACC GTCTCGAGC -     SEQ ID NO.: 397

DOM.127 - SEQ ID NO.: 283
     E V Q L L E S G G G L V Q P G G S L R L S C A A S G F T
     F P S Y D M .

   1 GAGGTGCAGC TGTTGGAGTC TGGGGGAGGC TTGGTACAGC CTGGGGGGTC CCTGCGTCTC TCCTGTGCAG
     CCTCCGGATT CACCTTTCCG TCGTATGATA

     . A W V R Q A P G K G L E W V S G I S R S G S M T Y Y A D
     S V K G R .

 101 TGGCGTGGGT CCGCCAGGCT CCAGGGAAGG GTCTAGAGTG GGTCTCAGGG ATTTCGAGGT CTGGTTCTAT
     GACATACTAC GCAGACTCCG TGAAGGGCCG

     . F T I S R D N S K N T L Y L Q M N S L R A E D T A V Y Y
     C A K G V

 201 GTTCACCATC TCCCGCGACA ATTCCAAGAA CACGCTGTAT TTGCAAATGA ACAGCCTGCG TGCCGAGGAC
     ACCGCGGTAT ATTACTGTGC GAAAGGTGTT

     D A H V Y Y M E P F F D Y W G Q G T L V T V S S

 301 GATGCGCATG TTTATTATAT GGAGCCTTTT TTTGACTACT GGGGTCAGGG AACCCTGGTC ACCGTCTCGA GC - SEQ ID NO.: 398

DOM.128 - SEQ ID NO.: 284
     E V Q L L E S G G G L V Q P G G S L R L S C A A S G F T
     F E R Y Q M .

   1 GAGGTGCAGC TGTTGGAGTC TGGGGGAGGC TTGGTACAGC CTGGGGGGTC CCTGCGTCTC TCCTGTGCAG
     CCTCCGGATT CACCTTTGAG AGGTATCAGA

     . A W V R Q A P G K G L E W V S T I S S D G G G T Y Y A D
     S V K G R .

 101 TGGCGTGGGT CCGCCAGGCT CCAGGGAAGG GTCTAGAGTG GGTCTCAACG ATTAGTTCTG ATGGTGGGGG
     GACATACTAC GCAGACTCCG TGAAGGGCCG

     . F T I S R D N S K N T L Y L Q M N S L R A E D T A V Y Y
     C A K P G

 201 GTTCACCATC TCCCGCGACA ATTCCAAGAA CACGCTGTAT CTGCAAATGA ACAGCCTGCG TGCCGAGGAC
     ACCGCGGTAT ATTACTGTGC GAAACCGGGT

     T V F D Y W G Q G T L V T V S S

 301 ACTGTTTTTG ACTACTGGGG TCAGGGAACC CTGGTCACCG TCTCGAGC -                            SEQ ID NO.: 399

DOM.129 - SEQ ID NO.: 285
     E V Q L L E S G G G L V Q P G G S L R L S C A A S G F T
     F P K Y E M .
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
  1 GAGGTGCAGC TGTTGGAGTC TGGGGGAGGC TTGGTACAGC CTGGGGGGTC CCTGCGTCTC TCCTGTGCAG
    CCTCCGGATT CACATTTCCG AAGTATGAGA

    . A W V R Q A P G K G L E W V S S I D G D G K S T Y Y A D
    S V K G R .

101 TGGCGTGGGT CCGCCAGGCT CCAGGGAAGG GTCTAGAGTG GGTCTCATCT ATTGATGGTG ATGGTAAGTC
    TACATACTAC GCAGACTCCG TGAAGGGCCG

    . F T I S R D N S K N T L Y L Q M N S L R A E D T A V Y Y
    C A K P D

201 GTTCACCATC TCCCGCGACA ATTCCAAGAA CACGCTGTAT CTGCAAATGA ACAGCCTGCG TGCCGAGGAT
    ACCGCGGTAT ATTACTGTGC GAAACCGGAT

    Q F F D Y W G Q G T L V T V S S

301 CAGTTTTTTG ACTACTGGGG TCAGGGAACC CTGGTCACCG TCTCGAGC -          SEQ ID NO.: 400

DOM.130 - SEQ ID NO.: 286
    E V Q L L E S G G G L V Q P G G S L R L S C T A S G F T
    F A G Y Q M .

  1 GAGGTGCAGC TGTTGGAGTC TGGGGGAGGC TTGGTACAGC CTGGGGGGTC CCTGCGTCTC TCCTGTACAG
    CCTCCGGATT CACCTTTGCG GGTTATCAGA

    . S W V R Q A P G K G L E W V S S I T N E G V S T Y Y A D
    S V K G R .

101 TGTCGTGGGT CCGCCAGGCT CCAGGGAAGG GTCTAGAGTG GGTCTCAAGT ATTACTAATG AGGGTGTTTC
    TACATACTAC GCAGACTCCG TGAAGGGCCG

    . F T I S R D N S K N T L Y L Q M N S L R A E D T A V Y Y
    C A K P G

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAACCGGGG

    K Y F D Y W G Q G T L V T V S S

301 AAGTATTTTG ACTACTGGGG TCAGGGAACC CTGGTCACCG TCTCGAGC -          SEQ ID NO.: 401

DOM.131 - SEQ ID NO.: 287
    E V Q L L E S G G G L V Q P G G S L R L S C A A S G F T
    F G E Y E M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGGG GAGTATGAGA

    . V W V R Q A P G K G L E W V S S I T S D G L S T Y Y A D
    S V K G R .

101 TGGTGTGGGT CCGCCAGGCT CCAGGGAAGG GTCTGGAGTG GGTCTCATCT ATTACGTCGG ATGGTCTGAG
    TACATACTAC GCAGACTCCG TGAAGGGCCG

    . F T I S R D N S K N T L Y L Q M N S L R A E D T A V Y Y
    C A K P G

201 GTTCACCATC TCCCGCGACA ATTCCAAGAA CACGCTGTAT CTGCAAATGA ACAGCCTGCG TGCTGAGGAC
    ACCGCGGTAT ATTACTGTGC GAAACCGGGT

    I R F D Y W G Q G T L V T V S S

301 ATTCGTTTTG ACTACTGGGG TCAGGGAACC CTGGTCACCG TCTCGAGC -          SEQ ID NO.: 402

DOM.132 - SEQ ID NO.: 288
    E V Q L L E S G G G L V Q P G G S L R L S C A A S G F T
    F A D Y D M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGCT GATTATGATA

    . A W V R Q A P G K G L E W V S G I V D D G L M T Y Y A D
    S V K G R .
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
101 TGGCTTGGGT CCGCCAGGCT CCAGGGAAGG GTCTAGAGTG GGTCTCAGGT ATTGTTGATG ATGGTCTTAT
    GACATACTAC GCAGACTCCG TGAAGGGCCG

    . F T I S R D N S K N T L Y L Q M N S L R A E D T A V Y Y
    C A K P D

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAACCGGAT

    V A F D Y W G Q G T L V T V S N

301 GTTGCTTTTG ACTACTGGGG TCAGGGGACC CTGGTCACCG TCTCGAAC -                SEQ ID NO.: 403

DOM.133 - SEQ ID NO.: 289
    E V Q L L E S G G G L V Q P G G S L R L S C A A S G F T
    F I G Y A M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTATT GGTTATGCTA

    . A W V R Q A P G K G L E W V S S I G P L G A T T Y Y A D
    S V K G R .

101 TGGCGTGGGT CCGCCAGGCT CCAGGGAAGG GTCTAGAGTG GGTCTCAAGT ATTGGTCCTT TGGGTGCGAC
    TACATACTAC GCAGACTCCG TGAAGGGCCG

    . F T I S R D N S K N T L Y L Q M N S L R A E D T A V Y Y
    C A K L P

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAATTGCCT

    A G T S S H S V D F D Y W G Q G T L V T V S S

301 GCTGGTACGA GTAGTCATAG TGTGGATTTT GACTACTGGG GTCAGGGAAC CCTGGTCACC GTCTCGAGC -     SEQ ID NO.: 404

DOM.134 - SEQ ID NO.: 290
    E V Q L L E S G G G L V Q P G G S L R L S C A A S G F T
    F A D Y E M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGCG GATTATGAGA

    . T W V R Q A P G K G L E W V S S I T S D G V S T Y Y A D
    S V K G R .

101 TGACTTGGGT CCGCCAGGCT CCAGGGAAGG GTCTAGAGTG GGTCTCATCT ATTACTAGTG ATGGTGTTTC
    TACATACTAC GCAGACTCCG TGAAGGGCCG

    . F T I S R D N S K N T L Y L Q M N S L R A E D T A V Y Y
    C A K P S

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAACCGTCG

    V Q F D Y W G Q G T L V T V S S

301 GTTCAGTTTG ACTACTGGGG TCAGGGAACC CTGGTCACCG TCTCGAGC -                SEQ ID NO.: 405

DOM.135 - SEQ ID NO.: 291
    E V Q L L E S G G G L V Q P G G S L R L S C A A S G F T
    F R R Y V M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTCGT AGGTATGTTA

    . G W V R Q A P G K G L E W V S W I E A D G R T T Y Y A D
    S V K G R .

101 TGGGGTGGGT CCGCCAGGCT CCAGGGAAGG GTCTAGAGTG GGTCTCATGG ATTGAGGCTG ATGGTCGTAC
    GACATACTAC GCAGACTCCG TGAAGGGCCG

    . F T I S R D N S K N T L Y L Q M N S L R A E D T A V Y Y
    C A K G L
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAAGGGCTT

    T D Q H V I E F D Y W G Q G T L V T V S S

301 ACGGATCAGC ATGTTATTGA GTTTGACTAC TGGGGTCAGG GAACCCTGGT CACCGTCTCG AGC -          SEQ ID NO.: 406

DOM.136 - SEQ ID NO.: 292
    E V Q L L E S G G G L V Q P G G S L R L S C A A S G F T
    F D G Y R M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGAT GGTTATCGTA

    . G W V R Q A P G K G L E W V S S I A P D G N Y T Y Y A D
    S V K G R .

101 TGGGGTGGGT CCGCCAGGCT CCAGGGAAGG GTCTAGAGTG GGTCTCATCG ATTGCTCCGG ATGGTAATTA
    TACATACTAC GCAGACTCCG TGAAGGGCCG

    . F T I S R D N S K N T L Y L Q M N S L R A E D T A V Y Y
    C A K F W

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAATTTTGG

    G M Q F D Y W G Q G T L V T V S S

301 GGGATGCAGT TTGACTACTG GGGTCAGGGA ACCCTGGTCA CCGTCTCGAG C -                       SEQ ID NO.: 407

DOM.137 - SEQ ID NO.: 293
    E V Q L L E S G G G L V Q P G G S L R L S C A A S G F T
    F A S Y P M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGCT TCGTATCCGA

    . G W V R Q A P G K G L E W V S S I G P I G F T T Y Y A D
    S V K G R .

101 TGGGTTGGGT CCGCCAGGCT CCAGGGAAGG GTCTAGAGTG GGTCTCAAGT ATTGGTCCTA TTGGTTTTAC
    TACATACTAC GCAGACTCCG TGAAGGGCCG

    . F T I S R D N S K N T L Y L Q M N S L R A E D T A V Y Y
    C A E M K

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GGAAATGAAG

    S P Y K P Q F D Y W G Q G T L V T V S S

301 TCGCCTTATA AGCCGCAGTT TGACTACTGG GGTCAGGGAA CCCTGGTCAC CGTCTCGAGC -              SEQ ID NO.: 408

DOM.138 - SEQ ID NO.: 294
    E V Q L L E S G G G L V Q P G G S L R L S C A A S G F T
    F L A Y W M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTTTG GCTTATTGGA

    . V W V R Q A P G K G L E W V S S I S P S G T H T Y Y A D
    S V K G R .

101 TGGTTTGGGT CCGCCAGGCT CCAGGGAAGG GTCTAGAGTG GGTCTCATCT ATTTCTCCGT CGGGTACGCA
    TACATACTAC GCAGACTCCG TGAAGGGCCG

    . F T I S R D N S K N T L Y L Q M N S L R V E D T A V Y Y
    C A K Y T

201 GTTCACCATC TCCCGCGACA ATTCCAAGAA CACGCTGTAT CTGCAAATGA ACAGCCTGCG TGTCGAGGAC
    ACCGCGGTAT ATTACTGTGC GAAATATACT

    E P G L G S F D Y W G Q G T L V T V S S
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
301 GAGCCGGGGT TGGGTTCTTT TGACTACTGG GGTCAGGGAA CCCTGGTCAC CGTCTCGAGC -             SEQ ID NO.: 409

DOM.139 - SEQ ID NO.: 295
    E V Q L L E S G G G L V Q P G G S L R L S C A A S G F T
    F S N Y E M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTTCG AATTATGAGA

    . G W V R Q A P G K G L E W V S V I S E V G S L T Y Y A D
    S V K G R .

101 TGGGGTGGGT CCGCCAGGCT CCAGGGAAGG GTCTAGAGTG GGTCTCAGTG ATTTCTGAGG TGGGTTCTCT
    GACATACTAC GCAGACTCCG TGAAGGGCCG

    . F T I S R D N S K N T L Y L Q M N S L R A E D T A V Y Y
    C A K P H

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAACCTCAT

    D S S I G F D Y W G Q G T L V T V S S

301 GATAGTTCGA TTGGGTTTGA CTACTGGGGT CAGGGAACCC TGGTCACCGT CTCGAGC -                SEQ ID NO.: 410

DOM.141 - SEQ ID NO.: 296
    D I Q M T Q S P S S L S A S V G D R V T I T C R A S Q W
    I G D T L T .

  1 GACATCCAGA TGACCCAGTC TCCATCCTCC CTGTCTGCAT CTGTAGGAGA CCGTGTCACC ATCACTTGCC
    GGGCAAGTCA GTGGATTGGG GATACGTTAA

    . W Y Q Q K L G K A P K L L I Y G G S E L Q S G V P P R F
    S G S G S .

101 CGTGGTACCA GCAGAAACTA GGGAAAGCCC CTAAGCTCCT GATCTATGGT GGTTCCGAGT TGCAAAGTGG
    GGTCCCACCA CGTTTCAGTG GCAGTGGATC

    . G T D F T L T I S S L Q P E D F A T Y Y C Q Q C I S S P
    C T F G Q

201 TGGGACAGAT TTCACTCTCA CCATCAGCAG TCTGCAACCT GAAGATTTTG CTACGTACTA CTGTCAACAG
    TGTATTAGTA GTCCTTGTAC GTTCGGCCAA

    G T K V E I K R

301 GGGACCAAGG TGGAAATCAA ACGG -                                                     SEQ ID NO.: 411

DOM.142 - SEQ ID NO.: 297
    D I Q M T Q S P S S L S A S V G D R V T I T C R A S Q F
    I G D S L S .

  1 GACATCCAGA TGACCCAGTC TCCATCCTCC CTGTCTGCAT CTGTAGGAGA CCGTGTCACC ATCACTTGCC
    GGGCAAGTCA GTTTATTGGT GATTCTTTAT

    . W Y Q Q K P G K A P K L L I Y F S S I L Q S G V P S R F
    S G S G S .

101 CTTGGTACCA GCAGAAACCA GGGAAAGCCC CTAAGCTCCT GATCTATTTT TCTTCCATTT TGCAAAGTGG
    GGTCCCATCA CGTTTCAGTG GCAGTGGATC

    . G T D F T L T I S S L Q P E D F A T Y Y C Q Q Y H T S P
    T T F G R

201 TGGGACAGAT TTCACTCTCA CCATCAGCAG TCTGCAACCT GAAGATTTTG CTACGTACTA CTGTCAACAG
    TATCATACTT CGCCTACTAC GTTCGGCCGA

    G T K V K I K R

301 GGGACCAAGG TGAAAATCAA ACGG -                                                     SEQ ID NO.: 412

DOM.143 - SEQ ID NO.: 298
    D I Q M T Q S P S S L S A S V G D R V T I T C R A S Q T
    I E T N L E .
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
  1 GACATCCAGA TGACCCAGTC TCCATCCTCC CTGTCCGCAT CTGTAGGAGA CCGTGTCACC ATCACTTGCC
    GGGCAAGTCA GACTATTGAG ACTAATTTAG

    . W Y Q Q K P G K A P K L L I Y D S S Q L Q S G V P S R F
    S G S G S .

101 AGTGGTACCA GCAGAAACCA GGGAAAGCCC CTAAGCTCCT GATCTATGAT TCTTCCCAGT TGCAAAGTGG
    GGTCCCATCA CGTTTCAGTG GCAGTGGATC

    . G T D F T L T I S S L Q P E D L A T Y Y C Q Q Y H G Y P
    T T F G Q

201 TGGGACAGAT TTTACTCTCA CCATCAGCAG TCTGCAACCT GAAGATTTAG CTACGTACTA CTGTCAACAG
    TATCATGGGT ATCCTACGAC GTTCGGCCAA

    G T K V E I K R

301 GGGACCAAGG TGGAAATCAA ACGG -                                      SEQ ID NO.: 413

DOM.144 - SEQ ID NO.: 299
    D I Q M T Q S P S S L S A S V G D R V T I T C R A S Q M
    I D Q D L E .

  1 GACATCCAGA TGACCCAGTC TCCATCCTCC CTGTCTGCAT CTGTAGGAGA CCGTGTCACC ATCACTTGCC
    GGGCAAGTCA GATGATTGAT CAGGATTTAG

    . W Y Q Q K P G K A P K L L I Y N A S W L Q S G V P S R F
    S G S G S .

101 AGTGGTACCA GCAGAAACCA GGGAAAGCCC CTAAGCTCCT GATCTATAAT GCGTCCTGGT TGCAAAGTGG
    GGTCCCATCA CGTTTCAGCG GCAGTGGATC

    . G T D F T L T I S S L Q P E D F A T Y Y C Q Q Y H G Y P
    I T F G Q

201 TGGGACAGAT TTCACTCTCA CCATCAGCAG TCTGCAACCT GAAGATTTTG CTACGTACTA CTGTCAACAG
    TATCATGGTT ATCCTATTAC GTTCGGCCAA

    G T K V E I K R

301 GGGACCAAGG TGGAAATCAA ACGG -                                      SEQ ID NO.: 414

DOM.145 - SEQ ID NO.: 300
    D I Q M T Q S P S S L S A S V G D R V T I T C R A S Q T
    I Y T S L S .

  1 GACATCCAGA TGACCCAGTC TCCATCCTCC CTGTCTGCAT CTGTAGGAGA CCGTGTCACC ATCACTTGCC
    GGGCAAGTCA GACGATTTAT ACTTCGTTAA

    . W Y Q Q K P G K A P K L L I H Y G S V L Q S G V P S R F
    S G S G S .

101 GTTGGTATCA GCAGAAACCA GGGAAAGCCC CTAAGCTCCT GATCCATTAT GGTTCCGTGT TGCAAAGTGG
    GGTCCCATCA CGTTTCAGTG GCAGTGGATC

    . G T D F T L T I S S L Q P E D S A T Y Y C Q Q V H Q A P
    T T F G Q

201 TGGGACAGAT TTCACTCTCA CCATCAGCAG TCTGCAACCT GAAGATTCTG CTACGTACTA CTGTCAACAG
    GTTCATCAGG CTCCTACGAC GTTCGGCCAA

    G T K V E I K R

301 GGGACCAAGG TGGAAATCAA ACGG -                                      SEQ ID NO.: 415

DOM.146 - SEQ ID NO.: 301
    D I R M T Q S P S S L S A S V G D R V T I T C R A S Q W
    I G D S L A .

  1 GACATCCGGA TGACCCAGTC TCCATCCTCC CTGTCTGCAT CTGTAGGAGA CCGTGTCACC ATCACTTGCC
    GGGCAAGTCA GTGGATTGGG GATTCTTTAG

    . W Y Q Q K P G K A P K L L I Y G I S E L Q S G V P S R F
    S G S G S .
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
101 CGTGGTACCA GCAGAAGCGA GGGAAAGCCC CTAAGCTCCT GATCTATGGT ATTTCCGAGT TGCAAAGTGG
    GGTCCCATCA CGTTTCAGTG GCAGTGGATC

    . G T D F T L T I S S L Q P E D S A T Y Y C Q L S S S M P
    H T F G Q

201 TGGGACAGAT TTCACTCTCA CCATCAGCAG TCTGCAACCT GAAGATTCTG CTACGTACTA CTGTCAACTG
    TCTAGTAGTA TGCCTCATAC GTTCGGCCAA

    G T K V E I K R

301 GGGACCAAGG TGGAAATCAA ACGG -                                   SEQ ID NO.: 416

DOM.147 - SEQ ID NO.: 302
    D I Q M T Q S P S S L S A S V G D R V T I T C R A S Q E
    I E T N L E .

  1 GACATCCAGA TGACCCAGTC TCCATCCTCC CTGTCTGCAT CTGTAGGAGA CCGTGTCACC ATCACTTGCC
    GGGCAAGTCA GGAGATTGAG ACGAATTTAG

    . W Y Q Q K P G K A P K L L I Y D S S H L Q S G V P S R F
    S G S G S .

101 AGTGGTACCA GCAGAAACCA GGGAAAGCCC CTAAGCTCCT GATCTATGAT TCGTCCCATT TGCAAAGTGG
    GGTCCCATCA CGTTTCAGTG GCAGTGGATC

    . G T D F T L T I S S L Q P E D F A T Y Y C Q Q Y H Q N P
    P T F G Q

201 TGGGACAGAT TTCACTCTCA CCATCAGCAG TCTGCAACCT GAAGATTTTG CTACGTACTA CTGTCAACAG
    TATCATCAGA ATCCTCCGAC GTTCGGCCAA

    G T K V E I K R

301 GGAACCAAGG TGGAAATCAA ACGG -                                   SEQ ID NO.: 417

DOM.149 - SEQ ID NO.: 303
    D I Q M T Q S P S S L S A S V G D R V T I T C R A S Q W
    I G R Q L V .

  1 GACATCCAGA TGACCCAGTC TCCATCCTCC CTGTCTGCAT CTGTAGGAGA CCGTGTCACC ATCACTTGCC
    GGGCAAGTCA GTGGATTGGG AGGCAGTTAG

    . W Y Q Q K P G K A P K L L I Y G A T E L Q S G V P S R F
    S G S G S .

101 TTTGGTACCA GCAGAAACCA GGGAAAGCCC CTAAGCTCCT GATCTATGGG GCGACCGAGT TGCAAAGTGG
    GGTCCCATCA CGTTTTAGTG GCAGTGGATC

    . G T D F T L T I S S L Q P E D F A T Y Y C Q Q Q S K G P
    L T F G H

201 TGGGACAGAT TTCACTCTCA CCATCAGCAG TCTGCAACCT GAAGATTTTG CTACGTACTA CTGTCAACAG
    CAGTCGAAGG GTCCTCTTAC GTTCGGCCAT

    G T K V E I K R

301 GGGACCAAGG TGGAAATCAA ACGG -                                   SEQ ID NO.: 418

DOM.150 - SEQ ID NO.: 304
    D I Q M T Q S P S S L S A S V G D R V T I T C R A S Q G
    I G T D L N .

  1 GACATCCAA TGACCCAGTC TCCATCCTCC CTGTCTGCAT CTGTAGGAGA CCGTGTCACC ATCACTTGCC
    GGGCAAGTCA GGGGATTGGT ACTGATTTAA

    . W Y Q Q K P G K A P K L L I Y M G S Y L Q S G V P S R F
    S G S G S .

101 ATTGGTATCA GCAGAAACCA GGGAAAGCCC CTAAGCTCCT GATCTATATG GGTTCCTATT TSCAAAGTGG
    GGTCCCATCA CGTTTCAGTG GCAGTGGATC

    . G T D F T L T I S S L Q P E D F A T Y Y C Q Q I Y S F P
    I T F G Q
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
201 TGGGACAGAT TTCACTCTCA CCATCAGCAG TCTGCAACCT GAAGATTTTG CTACGTACTA CTGTCAACAG
    ATTTATTCTT TTCCTATTAC GTTCGGCCAA

    G T K V E I K R

301 GGGACCAAGG TGGAAATCAA ACGG -                                    SEQ ID NO.: 419

DOM.154 - SEQ ID NO.: 305
    D I Q M T Q S P S S L S A S V G D R V T I T C R A S Q D
    I E E M L H .

  1 GACATCCAGA TGACCCAGTC TCCATCCTCC CTGTCTGCAT CTGTAGGAGA CCGTGTCACC ATCACTTGCC
    GGGCAAGTCA GGATATTGAG GAGATGTTAC

    . W Y Q Q K P G K A P K L L I Y F G S L L Q S G V P S R F
    S G S R S .

101 ATTGGTATCA GCAGAAACCA GGGAAAGCCC CTAAGCTCCT GATCTATTTT GGTTCCCTGT TGCAAAGTGG
    GGTCCCATCA CGTTTCAGTG GCAGTAGATC

    . G T D F T L T I S S L Q P E D F A T Y Y C Q Q H H T R P
    Y T F G Q

201 TGGGACAGAT TTCACTCTCA CCATCAGCAG TCTGCAACCT GAAGATTTTG CTACGTACTA CTGTCAACAG
    CATCATACTC GTCCTTATAC GTTCGGCCAA

    G T K V E I K R

301 GGGACCAAGG TGGAAATCAA ACGG -                                    SEQ ID NO.: 420

DOM.155 - SEQ ID NO.: 306
    D I Q M T Q S P S S L S A S V G D R V T I T C R A S Q D
    I G M D L E .

  1 GACATCCAGA TGACCCAGTC TCCATCCTCC CTGTCTGCAT CTGTAGGAGA CCGTGTCACC ATCACTTGCC
    GGGCAAGTCA GGATATTGGG ATGGATTTAG

    . W Y Q Q I P G K V P K L L I Y D A S Y L Q S G V P S R F
    S G S G S .

101 AGTGGTACCA GCAGATACCA GGGAAAGTCC CTAAGCTCCT GATCTATGAT GCGTCCTATT TGCAAAGTGG
    GGTCCCATCA CGTTTCAGTG GCAGTGGATC

    . G T D F T L T I S S L Q P E D F A T Y Y C Q Q Y H K L P
    A T F G Q

201 TGGGACAGAT TTCACTCTCA CCATCAGCAG TCTGCAACCT GAAGATTTTG CTACGTACTA CTGTCAACAG
    TATCATAAGC TTCCTGCGAC GTTTGGCCAA

    G T K V E I K R

301 GGGACCAAGG TGGAAATCAA ACGG -                                    SEQ ID NO.: 421

DOM.156 - SEQ ID NO.: 307
    D I Q M T Q S P S S L S A S V G D R V T I T C R A S Q D
    I M D N L E .

  1 GACATCCAGA TGACCCAGTC TCCATCCTCC CTGTCTGCAT CTGTAGGAGA CCGTGTCACC ATCACTTGCC
    GGGCAAGTCA GGATATTATG GATAATTTAG

    . W Y Q Q K P G K A P K L L I Y A A S W L Q S G V P S R F
    S G S G S .

101 AGTGGTATCA GCAGAAACCA GGGAAAGCCC CTAAGCTCCT GATCTATGCG GCGTCCTGGT TGCAAAGTGG
    GGTCCCATCA CGTTTCAGTG GCAGTGGATC

    . G T D F T L T I S S L Q P E D F A T Y Y C Q Q Y H K L P
    V T F G Q

201 TGGGACAGAT TTCACTCTCA CCATCAGCAG TCTGCAACCT GAAGATTTTG CTACGTACTA CTGTCAACAG
    TATCATAAGT TGCCTGTGAC GTTCGGCCAA

    G T K V E I K R
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
 301 GGGACCAAGG TGGAAATCAA ACGG -                                              SEQ ID NO.: 422

DOM.157 - SEQ ID NO.: 308
     D I Q M T Q S P S S L S A S V G D R V T I T C R A S Q N
     I G E D L E .

   1 GACATCCAGA TGACCCAGTC TCCATCCTCC CTGTCTGCAT CTGTAGGAGA CCGTGTCACC ATCACTTGCC
     GAGCAAGTCA GAATATTGGG GAGGATTTAG

     . W Y Q Q K P G N A P K L L I Y S A S H L Q S G V P S R F
     S G S G S .

 101 AGTGGTACCA GCAGAAACCA GGGAATGCCC CTAAGCTCCT GATCTATAGT GCGTCCCATT TGCAAAGTGG
     GGTCCCATCA CGTTTCAGTG GCAGTGGATC

     . G T D F T L T I S S L Q P E D F A T Y Y C Q Q Y S S Y P
     V T F G Q

 201 TGGGACAGAT TTCACTCTCA CCATCAGCAG TCTGCAACCT GAAGATTTTG CTACGTACTA CTGTCAACAG
     TATTCTAGTT ATCCTGTTAC GTTCGGCCAA
     G T K V E I K R

 301 GGGACCAAGG TGGAAATCAA ACGG -                                              SEQ ID NO.: 423

DOM.158 - SEQ ID NO.: 309
     D I Q M T Q S P S S L S A S V G D R V T I T C R A S Q P
     I D E D L E .

   1 GACATCCAGA TGACCCAGTC TCCATCCTCC CTGTCTGCAT CCGTAGGAGA CCGTGTCACC ATCACTTGCC
     GGGCAAGTCA GCCGATTGAT GAGGATTTAG

     . W Y Q Q K P G N A P K L L I Y S A S Y L Q S G V P S R F
     S G S G S .

 101 AGTGGTACCA GCAGAAACCA GGGAATGCCC CTAAGCTCCT GATCTATAGT GCGTCCTATT TGCAAAGTGG
     GGTCCCATCA CGTTTCAGTG GCAGTGGATC

     . G T D F T L T I S R L Q P E D F A T Y Y C Q Q Y H L L P
     A T F G Q

 201 TGGGACAGAT TTCACTCTCA CCATCAGCAG ACTGCAACCT GAAGATTTTG CTACGTACTA CTGTCAACAG
     TATCATCTTC TGCCTGCTAC GTTCGGCCAA

     G T K V E I K R

 301 GGGACCAAGG TGGAAATCAA ACGG -                                              SEQ ID NO.: 424

DOM.159 - SEQ ID NO.: 310
     D I Q M I Q S P S S L S A S V G D R V T I T C R A S Q D
     I N E D L E .

   1 GACATCCAGA TGATCCAGTC TCCATCCTCC CTGTCTGCAT CTGTAGGAGA CCGTGTCACC ATCACTTGCC
     GGGCAAGTCA GGATATTAAT GAGGATTTAG

     . W Y Q Q K P G K A P K L L I Y N A S M L Q S G V P S R F
     S G S G S .

 101 AGTGGTATCA GCAGAAACCA GGGAAAGCCC CTAAGCTCCT GATCTATAAT GCTTCCATGT TGCAAAGCGG
     GGTCCCATCA CGTTTCAGTG GCAGTGGATC

     . G T D F T L T I S S L Q P K D F A T Y Y C Q Q Y H T N P
     T T F G Q

 201 TGGGACAGAT TTCACTCTCA CCATCAGCAG TCTGCAACCT AAAGATTTTG CTACGTACTA CTGTCAACAG
     TATCATACTA ATCCTACTAC GTTCGGCCAA

     G T K V E I K R

 301 GGGACCAAGG TGGAAATCAA ACGG -                                              SEQ ID NO.: 425

DOM.160 - SEQ ID NO.: 311
     D I Q M T Q S P S S L S A S V G D R V T I T C R A S Q D
     I E A D L E .
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
  1 GACATCCAGA TGACCCAGTC TCCATCCTCC CTGTCTGCAT CTGTAGGAGA CCGTGTCACC ATCACTTGCC
    GGGCAAGTCA GGATATTGAG GCGGATTTAG

    . W Y Q Q K P G K A P K L L I Y H S S E L Q S G V P S R F
    S G S G S .

101 AGTGGTACCA GCAGAAACCA GGGAAAGCCC CTAAGCTCCT GATCTATCAT TCTTCCGAGT TGCAAAGTGG
    GGTCCCATCA CGTTTCAGTG GAAGTGGATC

    . G T D F T L T I S S L Q P E D F A T Y Y C Q Q Y H M S P
    V T F G Q

201 TGGGACAGAT TTCACTCTCA CCATCAGCAG TCTGCAACCT GAAGATTTTG CTACGTACTA CTGTCAACAG
    TATCATATGT CGCCTGTGAC GTTCGGCCAA

    G T K V E I K R

301 GGGACCAAGG TGGAAATCAA ACGG -                                       SEQ ID NO.: 426

DOM.161 - SEQ ID NO.: 312
    D I Q M T Q S P S S L S A S V G D R V T I T C R A S Q D
    I D S D L E .

  1 GACATCCAGA TGACCCAGTC TCCATCCTCC CTGTCTGCAT CTGTAGGAGA CCGTGTCACC ATCACTTGCC
    GGGCAAGTCA GGATATTGAT AGTGATTTAG

    . W Y Q Q K P G K A P M L L I Y S S S D L Q S G V P S R F
    S G S G S .

101 AGTGGTACCA GCAGAAACCA GGGAAAGCCC CTATGCTCCT GATCTATTCT TCGTCCGATT TGCAAAGTGG
    GGTCCCATCA CGTTTCAGTG GCAGTGGATC

    . G T D F T L T I S S L Q P E D F A T Y Y C Q Q Y H S L P
    V T F G Q

201 TGGGACAGAT TTCACTCTCA CCATCAGCAG TCTGCAACCT GAAGATTTTG CTACGTACTA CTGTCAACAG
    TATCATAGTC TGCCTGTTAC GTTCGGCCAA

    G T K V E I K R

301 GGGACCAAGG TGGAAATCAA ACGG -                                       SEQ ID NO.: 427

DOM.162 - SEQ ID NO.: 313
    D I Q M T Q S P S S L S A S V G D R V T I T C R A S Q D
    I S D D L E .

  1 GACATCCAGA TGACCCAGTC TCCATCCTCC CTGTCTGCAT CTGTAGGAGA CCGTGTCACC ATCACTTGCC
    GGGCAAGTCA GGATATTTCG GATGATTTAG

    . W Y Q Q K P G K A P K L L I Y N S S F L Q S G V P S R F
    S G S G S .

101 AGTGGTACCA GCAGAAACCA GGGAAAGCCC CTAAGCTCCT GATCTATAAT TCGTCCTTTT TGCAAAGTGG
    GGTCCCATCA CGTTTCAGTG GCAGTGGATC

    . G A D F T L T I S S L Q P E D F A T Y Y C Q Q Y H S L P
    V T F G Q

201 TGGGGCAGAT TTCACTCTCA CCATCAGCAG TCTGCAACCT GAAGATTTTG CTACGTACTA CTGTCAACAG
    TATCATAGTT TGCCTGTTAC GTTCGGCCAA

    G T K V E I K R

301 GGGACCAAGG TGGAAATCAA ACGG -                                       SEQ ID NO.: 428

DOM.163 - SEQ ID NO.: 314
    D I Q M T Q S P S S L S A S V G D R V T I T C R A S Q D
    I E G N L E .

  1 GACATCCAGA TGACCCAGTC TCCATCCTCC CTGTCTGCAT CTGTAGGAGA CCGTGTCACC ATCACTTGCC
    GGGCAAGTCA GGATATTGAG GGTAATTTAG

    . W Y Q Q K P G K A P K L L I Y D S S Q L Q S G V P S R F
    S G S G S .
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

101 AGTGGTACCA GCAGAAACCA GGGAAAGCCC CTAAGCTCCT GATCTATGAT TCGTCCCAGT TGCAAAGTGG
GGTCCGATCA CGTTTCAGTG GCAGTGGGTC

. G T D F T L T I S S L Q P E D F A T Y Y C Q Q Y H H L P
T T F G Q

201 TGGGACAGAT TTCACTCTCA CCATCAGCAG TCTGCAACCT GAAGATTTTG CTACGTACTA CTGTCAACAG
TATCATCATC TTCCTACGAC GTTCGGCCAA

G T K V E I K R

301 GGGACCAAGG TGGAAATCAA ACGG - SEQ ID NO.: 429

DOM.164 - SEQ ID NO.: 315
D I Q M T Q S P S S L S A S V G D R V T I T C R A S Q S
I D T D L E .

1 GACATCCAGA TGACCCAGTC TCCATCCTCC CTGTCTGCAT CTGTAGGAGA CCGTGTCACC ATCACTTGCC
GGGCAAGTCA GAGTATTGAT ACGGATTTAG

. W Y Q Q K P G K A P K L L I Y D G S W L Q S G V P S R F
S G S G S .

101 AGTGGTATCA GCAGAAACCA GGGAAAGCCC CTAAGCTCCT GATCTATGAT GGGTCCTGGT TGCAAAGTGG
GGTCCCATCA CGTTTCAGTG GCAGTGGATC

. G T D F T L T I S S L Q P E D F A T Y Y C Q Q Y R W I P
V T F G Q

201 TGGGACAGAT TTTACTCTCA CCATCAGCAG TCTGCAACCT GAAGATTTTG CTACGTACTA CTGTCAACAG
TATCGGTGGA TTCCTGTTAC GTTCGGCCAA

G T K V E I K R

301 GGGACCAAGG TGGAAATCAA ACGG - SEQ ID NO.: 430

DOM.165 - SEQ ID NO.: 316
D I Q M T Q S P S S L S A S V G D R V T I T C R A S Q S
I S T D L E .

1 GACATCCAGA TGACCCAGTC TCCATCCTCC CTGTCTGCAT CTGTAGGAGA CCGTGTCACC ATCACTTGCC
GGGCAAGTCA GAGTATTGAT ACTGATTTAG

. W Y Q Q K L G K A P K L L I Y D A S L L Q S G V P S R F
S G S G S .

101 AGTGGTACCA GCAGAAACTA GGGAAAGCCC CTAAGCTCCT GATCTATGAT GCTTCCCTTT TGCAAAGTGG
GGTCCCATCA CGTTTCAGTG GCAGTGGATC

. G T D F T L T I S S L Q P E D F A T Y Y C Q Q Y S S L P
V T F G Q

201 TGGGACAGAT TTCACTCTCA CCATCAGCAG TCTGCAACCT GAAGATTTTG CTACGTACTA CTGTCAACAG
TATTCGAGTC TGCCTGTTAC GTTCGGCCAA

G T K V E I K R

301 GGGACCAAGG TGGAAATCAA ACGG - SEQ ID NO.: 431

DOM.166 - SEQ ID NO.: 317
D I Q M T Q S P S S L S A S V G D R V T I T C R A S Q P
I T T S L E .

1 GACATCCAGA TGACCCAGTC TCCATCCTCC CTGTCTGCAT CTGTAGGAGA CCGTGTCACC ATCACTTGCC
GGGCAAGTCA GCCTATTACG ACGTCTTTAG

. W Y Q Q K P G K A P K L L I Y D A S M L Q S G V P S R F
S G S G S .

101 AGTGGTACCA GCAGAAACCA GGGAAAGCCC CTAAGCTCCT GATCTATGAT GCGTCCATGT TGCAAAGTGG
GGTCCCATCA CGTTTCAGTG GCAGTGGATC

. G T D F T L T I S S L Q P E D F A T Y Y C Q Q Y W V T P
V T F G Q

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
201 TGGGACAGAT TTCACTCTCA CCATCAGCAG TCTGCAACCT GAAGATTTTG CTACGTACTA CTGTCAACAG
    TATTGGGTTA CGCCTGTTAC GTTCGGCCAA

    G T K V E I K R

301 GGGACCAAGG TGGAAATCAA ACGG -                                    SEQ ID NO.: 432

DOM.167 - SEQ ID NO.: 318
    D I Q M T Q S P S S L S A S V G D R V T I T C R A S Q N
    I H T N L E .

  1 GACATCCAGA TGACCCAGTC TCCATCCTCC CTGTCTGCAT CTGTAGGAGA CCGTGTCACC ATCACTTGCC
    GGGCAAGTCA GAATATTCAT ACGAATTTAG

    . W Y Q Q K P G K A P K L L I Y D G S M L Q S G V P S R F
    S G S G S .

101 AGTGGTATCA GCAGAAACCA GGGAAAGCCC CTAAGCTCCT GATCTATGAT GGTTCCATGT TGCAAAGTGG
    GGTCCCATCA CGTTTCAGTG GCAGTGGATC

    . G T D F T L T I S S L Q P E D F A T Y Y C Q Q Y S A N P
    V T F G Q

201 TGGGACAGAT TTCACTCTCA CCATCAGCAG TCTGCAACCT GAAGATTTTG CTACGTACTA CTGTCAACAG
    TATTCGGCTA ATCCTGTTAC GTTCGGCCAA

    G T K V G I K R

301 GGGACCAAGG TGGGAATCAA ACGG -                                    SEQ ID NO.: 433

DOM.168 - SEQ ID NO.: 319
    D I Q M T Q S P S S L S A S V G D R V T I T C R A S Q W
    I H T D L E .

  1 GACATCCAGA TGACCCAGTC TCCATCCTCC CTGTCTGCAT CTGTAGGAGA CCGTGTCACC ATCACTTGCC
    GGGCAAGTCA GTGGATTCAT ACGGATTTAG

    . W Y Q Q K P G K A P K L L I Y D G S M L Q S G V P S R F
    S G S G S .

101 AGTGGTATCA GCAGAAACCA GGGAAAGCCC CTAAGCTCCT GATCTATGAT GGTTCCATGT TGCAAAGTGG
    GGTCCCATCA CGTTTCAGTG GCAGTGGATC

    . G T D F T L T I S S L Q P E D F A T Y Y C Q Q Y S V S P
    V T F G Q

201 TGGGACAGAT TTCACTCTCA CCATCAGCAG TCTGCAACCT GAAGATTTTG CTACGTACTA CTGTCAACAG
    TATAGTGTGT CGCCTGTTAC GTTCGGCCAA

    G T K V E I K R

301 GGGACCAAGG TGGAAATCAA ACGG -                                    SEQ ID NO.: 434

DOM.169 - SEQ ID NO.: 320
    D I Q M T Q S P S S L S A S V G D R V T I T C R A S Q S
    I D N N L E .

  1 GACATCCAGA TGACCCAGTC TCCATCCTCC CTGTCTGCAT CTGTAGGAGA CCGTGTCACC ATCACTTGCC
    GGGCAAGTCA GAGTATTGAT AATAATTTAG

    . W Y Q Q K P G E A P K L L I Y D G S L L Q S G V P S R F
    S G S G S .

101 AGTGGTACCA GCAGAAACCA GGGGAAGCCC CTAAGCTCCT GATCTATGAT GGGTCCCTTT TGCAAAGTGG
    GGTCCCATCA CGTTTCAGTG GCAGTGGATC

    . G T D F T L T I S S L Q P E D F A T Y Y C Q Q Y H L H P
    V T F G Q

201 TGGGACAGAT TTCACTCTTA CCATCAGCAG TCTGCAACCT GAAGATTTTG CTACGTACTA CTGTCAACAG
    TATCATCTTC ATCCTGTTAC GTTCGGCCAA

    G T K V E I K R
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
301 GGGACCAAGG TGGAAATCAA ACGG -                                      SEQ ID NO.: 435

DOM.170 - SEQ ID NO.: 321
    D I Q M T Q S P S S L S A S V G D R V T I T C R A S Q D
    I D T N L E .

  1 GACATCCAGA TGACCCAGTC TCCATCCTCC CTGTCTGCAT CTGTAGGAGA CCGTGTCACC ATCACTTGCC
    GGGCAAGTCA GGATATTGAT ACGAATTTAG

    . W Y Q Q K P G E A P K L L I Y D R S T L Q S G V P S R F
    S G S G S .

101 AGTGGTATCA GCAGAAACCA GGGAAAGCCC CTAAGCTCCT GATCTATGAT CGTTCCACGT TGCAAAGTGG
    GGTCCCATCA CGTTTCAGTG GCAGTGGATC

    . G T D F T L T I S S L Q P E D F A T Y Y C Q Q Y D S Y P
    V T F G Q

201 TGGGACAGAT TTCACTCTCA CCATCAGCAG TCTGCAACCT GAAGATTTTG CTACGTACTA CTGTCAACAG
    TATGATTCTT ATCCTGTGAC GTTCGGCCAA

    G T K V E I K R

301 GGGACCAAGG TGGAAATCAA ACGG -                                      SEQ ID NO.: 436

DOM.171 - SEQ ID NO.: 322
    D I Q M T Q S P S S L S A S V G D R V T I T C R A S Q S
    I E S N L E .

  1 GACATCCAGA TGACCCAGTC TCCATCCTCC CTGTCTGCAT CTGTAGGAGA CCGTGTCACC ATCACTTGCC
    GGGCAAGTCA GTCTATTGAG TCTAATTTAG

    . W Y Q Q K P G K A P K L L I Y N A S E L Q S G V P S R F
    S G S G S .

101 AGTGGTACCA GCAGAAACCA GGGAAAGCCC CTAAGCTCCT GATCTATAAT GCGTCCGAGT TGCAAAGTGG
    GGTCCCATCA CGTTTCAGTG GCAGTGGATC

    . G T D F T L T I S S L R P E D F A T Y Y C Q Q Y D Q W P
    T T F G Q

201 TGGGACAGAT TTCACTCTCA CCATCAGCAG TCTGCGACCT GAAGATTTTG CTACGTACTA CTGTCAACAG
    TATGATCAGT GGCCTACGAC GTTCGGCCAA

    G T K V E I K R

301 GGGACCAAGG TGGAAATCAA ACGG -                                      SEQ ID NO.: 437

DOM.172 - SEQ ID NO.: 323
    D I Q M T Q S P S S L S A S V G D R V T I T C R A S Q A
    I G N T L R .

  1 GACATCCAGA TGACCCAGTC TCCATCCTCC CTGTCTGCAT CTGTAGGAGA CCGTGTCACT ATCACTTGCC
    GGGCAAGTCA GGCTATTGGT AATACTTTAC

    . W Y Q Q K P G K A P K L L I Y L S S R L Q S G V P S R F
    S G S G S .

101 GGTGGTACCA GCAGAAACCA GGGAAAGCCC CTAAGCTCCT GATCTATCTT AGTTCCAGGT TGCAAAGTGG
    GGTCCCATCA CGTTTCAGTG GCAGTGGATC

    . G T D F T L T I S S L Q P E D F A T Y Y C Q Q L K K P P
    Y T F G Q

201 TGGGACAGAT TTTACTCTCA CCATCAGCAG TCTGCAACCT GAAGATTTTG CTACGTACTA CTGTCAACAG
    CTGAAGAAGC CTCCTTATAC GTTCGGCCAA

    G T K V E I K R

301 GGGACCAAGG TGGAAATCAA ACGG -                                      SEQ ID NO.: 438

DOM.173 - SEQ ID NO.: 324
    D I Q M T Q S P S S L S A S V G D R V T I T C R A S Q K
    I K N R L A .
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
  1 GACATCCAGA TGACCCAGTC TCCATCCTCC CTGTCTGCAT CTGTAGGAGA CCGTGTCACC ATCACTTGCC
    GGGCAAGTCA GAAGATTAAG AATCGGTTAG

    . W Y Q Q K P G K A P K L L I Y E V S H L Q S G V P S R F
    S G S G S .

101 CGTGGTACCA GCAGAAACCA GGGAAAGCCC CTAAGCTCCT GATCTATGAG GTTTCCCATT TGCAAAGTGG
    GGTCCCATCA CGTTTCAGTG GCAGTGGATC

    . G T D F T L T I G S L Q P E D F A T Y Y C Q Q R R Q S P
    Y T F G Q

201 TGGGACAGAT TTCACTCTCA CCATCGGCAG TCTGCAACCT GAAGATTTTG CTACGTACTA CTGTCAACAG
    AGGAGGCAGT CGCCTTATAC GTTCGGCCAA

    G T K V E I K R

301 GGGACCAAGG TGGAAATCAA ACGG -                                      SEQ ID NO.: 439

DOM.174 - SEQ ID NO.: 325
    D I Q M T Q S P S S L S A S V G D R V T I T C R A S E D
    I G E E L F .

  1 GACATCCAGA TGACCCAGTC TCCATCCTCC CTGTCTGCAT CTGTAGGAGA CCGTGTCACC ATCACTTGCC
    GGGCAAGTGA GGATATTGGG GAGGAGTTAT

    . W Y Q Q K P G K A P K L L I Y S A S T L Q S E V P S R F
    S G S G S .

101 TTTGGTATCA GCAGAAACCA GGGAAAGCCC CTAAGCTCCT GATCTATTCG GCGTCCACGT TGCAAAGTGA
    GGTCCCATCA CGTTTCAGTG GCAGTGGATC

    . G T D F T L T I S S L Q H E D F A T Y Y C Q Q V Y E W P
    Y T F G Q

201 TGGGACAGAT TTCACTCTCA CCATCAGCAG TCTGCAACAT GAASATTTTG CTACGTACTA CTGTCAACAG
    GTTTATGAGT GGCCTTATAC GTTCGGCCAA

    G T K V E I K R

301 GGGACCAAGG TGGAAATCAA ACGG -                                      SEQ ID NO.: 440

DOM.175 - SEQ ID NO.: 326
    D I Q M T Q S P S S L S A S V G D R V T I T C R A S Q P
    I S G G L R .

  1 GACATCCAGA TGACCCAGTC TCCATCCTCC CTGTCTGCAT CTGTAGGAGA CCGTGTCACC ATCACTTGCC
    GGGCAAGTCA GCCTATTTCT GGGGGTTTAA

    . W Y Q Q K P G K A P K L L I Y S T S M L Q S G V P S R F
    S G S G S .

101 GGTGGTACCA GCAGAAACCA GGGAAAGCCC CTAAGCTCCT GATCTATTCT ACTTCCATGT TGCAAAGTGG
    GGTCCCATCA CGTTTCAGTG GCAGTGGATC

    . G T D F T L T I S S L Q P E D F A T Y Y C Q Q L Y S A P
    Y T F G Q

201 TGGGACAGAT TTCACTCTCA CCATCAGCAG TCTGCAACCT GAAGATTTTG CTACGTACTA CTGTCAACAG
    CTTTATTCTG CTCCTTATAC GTTCGGCCAA

    G T K V E I K R

301 GGGACCAAGG TGGAAATCAA ACGG -                                      SEQ ID NO.: 441

DOM.176 - SEQ ID NO.: 327
    E V Q L L E S G G G L V Q P G G S L R L S C A A S G F T
    F D A Y E M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGAT GCGTATGAGA

    . G W V R Q A P G K G L E W V S I I D W D G N S T Y Y A D
    S V K G R .
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
101 TGGGGTGGGT CCGCCAGGCT CCAGGGAAGG GTCTAGAGTG GGTCTCAATT ATTGATTGGG ATGGTAATTC
    TACATACTAC GCAGACTCCG TGAAGGGCCG

    . F T I S R D N S K N T L Y L Q M N S L R A E D T A V Y Y
    C A K P G

201 GTTCACCATC TCCCGCGACA ATTCCAAGAA CACGCTGTAT CTGCAAATGA ACAGCCTGCG TGCCGAGGAT
    ACCGCGGTAT ATTACTGTGC GAAACCTGGG

    D N V G I F D Y W G Q G T L V T V S S

301 GATAATGTTG GTATTTTTGA CTACTGGGGT CAGGGAACCC TGGTCACCGT CTCGAGC -        SEQ ID NO.: 442

DOM.177 - SEQ ID NO.: 328
    E V Q L L E S G G G L V Q P G G S L R L S C A A S G F T
    F S N Y Y M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGAT AATTATTATA

    . V W V R Q A P G K G L E W V S A I D E W G F A T Y Y A D
    S V K G R .

101 TGGTGTGGGT CCGCCAGGCT CCAGGGAAGG GTCTAGAGTG GGTCTCAGCG ATTGATGAGT GGGGTTTTGC
    GACATACTAC GCAGACTCCG TGAAGGGCCG

    . F T I S R D N S K N T L Y L Q M N S L R A E D T A V Y Y
    C A K H W

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAACATTGG

    E F T S D T S R F D Y W G Q G T L V T V S S

301 GAGTTTACGT CTGATACGTC GCGTTTTGAC TACTGGGGTC AGGGAACCCT GGTCACCGTC TCGAGC -        SEQ ID NO.: 443

DOM.178 - SEQ ID NO.: 329
    E V Q L L E S G G G L V Q P G G S L R L S C A A S G F T
    F E D F D M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGAG GATTTTGATA

    . A W V R Q A P G K G L E W V S S I N D Q G S L T Y Y A D
    S V K G R .

101 TGGCTTGGGT CCGCCAGGCT CCAGGGAAGG GTCTAGAGTG GGTCTCATCT ATTAATGATC AGGGTTCTCT
    GACATACTAC GCAGACTCCG TGAAGGGCCG

    . F T I S R D N S K N T L Y L Q M N S L R A E D T A V Y Y
    C A K P D

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAACCGGAT

    Q F F D Y W G Q G T L V T V S S

301 CAGTTTTTTG ACTACTGGGG TCAGGGAACC CTGGTCACCG TCTCGAGC -        SEQ ID NO.: 444

DOM.179 - SEQ ID NO.: 330
    E V Q L L E S G G G L V Q P G G S L R L S C A A S G F T
    F S A Y D M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTAGT GCTTATGATA

    . M W V R Q A P G K G L E W V S R I S P Q G Q R T Y Y A D
    S V K G R .

101 TGATGTGGGT CCGCCAGGCT CCAGGGAAGG GTCTAGAGTG GGTCTCACGG ATTAGTCCTC AGGGTCAGCG
    GACATACTAC GCAGACTCCG TGAAGGGCCG

    . F T I S R D N S K N T L Y L Q M N S L R A E D T A V Y Y
    C A K I R
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAAATTCGT

    G Q S R I P M R F D Y W G Q G T L V

301 GGGCAGTCGC GGATTCCTAT GAGGTTTGAC TACTGGGGTC AGGGAACCCT GGTC -          SEQ ID NO.: 445

DOM.180 - SEQ ID NO.: 331
    E V Q L L E S G G G L V Q P G G S L R L S C A A S G F T
    F T D Y E M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTACG GATTATGAGA

    . G W V R Q A P G K G L E W V S T I T S L G E S T Y A D
    S V K G R .

101 TGGGGTGGGT CCGCCAGGCT CCAGGGAAGG GTCTAGAGTG GGTCTCAACG ATTACTAGTT TGGGTGAGAG
    TACATACTAC GCAGACTCCG TGAAGGGCCG

    . F T I S R D N S K N T L Y L Q M N S L R A E D T A V Y Y
    C A K P G

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAACCTGGT

    R I F D Y W G Q G T L V T V S S

301 CGTATTTTG ACTACTGGGG TCAGGGAACC CTGGTCACCG TCTCGAGC -                  SEQ ID NO.: 446

DOM.181 - SEQ ID NO.: 332
    E V Q L L E S G G G L V Q P G G S L R L S C A A S G F T
    F A F Y P M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGCT TTTTATCCTA

    . M W V R Q A P G K G L E W V S W I D A T G T R T Y Y A D
    S V K G R .

101 TGATGTGGGT CCGCCAGGCT CCAGGGAAGG GTCTAGAGTG GGTCTCATGG ATTGATGCTA CGGGTACGAG
    GACATACTAC GCAGACTCCG TGAAGGGCCG

    . F T I S R D N S K N T L Y L Q M N S L R A E D T A V Y Y
    C A E G N

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GGAAGGTAAT

    Y G S S Y T M G V F D Y W G Q G T L V T V S S

301 TATGGGAGTT CGTATACTAT GGGGGTTTTT GACTACTGGG GTCAGGGAAC CCTGGTCACC GTCTCGAGC -     SEQ ID NO.: 447

DOM.182 - SEQ ID NO.: 333
    E V Q L L E S G G G L V Q P G G S L R L S C A A S G F T
    F D E Y P M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGAT GAGTATCCGA

    . Y W V R Q A P G K G L E W V S S I G P S G P N T Y Y A D
    S V K G R .

101 TGTATTGGGT CCGCCAGGCT CCAGGGAAGG GTCTAGAGTG GGTCTCATCG ATTGGTCCTT CTGGTCCGAA
    TACATACTAC GCAGACTCCG TGAAGGGCCG

    . F T I S R D N S K N T L Y L Q M N S L R A E D T A V Y Y
    C A K S P

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAATCTCCG

    Y F D V I P S Y F D Y W G Q G T L V T V S S
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
301 TATTTTGATG TTATTCCTAG TTATTTTGAC TACTGGGGTC AGGGAACCCT GGTCACCGTC TCGAGC -       SEQ ID NO.: 448

DOM.183 - SEQ ID NO.: 334
    E V Q L L E S G G G L V Q P G G S L R L S C A A S G F T
    F A D Y G M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGCG GATTACGGTA

    . G W V R Q A P G K G L E W V S S I Q S S G L R T Y Y A D
    S V K G R .

101 TGGGTTGGGT CCGCCAGGCT CCAGGGAAGG GTCTAGAGTG GGTCTCATCT ATTCAGTCGT CGGGTTTGCG
    GACATACTAC GCAGACTCCG TGAAGGGCCG

    . F T I S R D N S K N T L Y L Q M N S L R A E D T A V Y Y
    C A K R A

201 GTTCACCATC TCCCGCGACA ATTCCAAGAA CACGCTGTAT CTGCAAATGA ACAGCCTGCG TGCCGAGGAT
    ACCGCGGTAT ATTACTGTGC GAAACGGGCT

    N S R R G F D Y W G Q G T L V T V S S

301 AATTCTCGTA GGGGTTTTGA CTACTGGGGT CAGGGAACCC TGGTCACCGT CTCGAGC -                SEQ ID NO.: 449

DOM.184 - SEQ ID NO.: 335
    E V Q L L E S G G G L V Q P G G S L R L S C A A S G F T
    F S D Y E M .

  1 GAGGTGCAGC TGTTGGAGTC TGGGGGAGGC TTGGTACAGC CTGGGGGGTC CCTGCGTCTC TCCTGTGCAG
    CCTCCGGATT

    CACCTTTTCT GATTATGAGA

    . M W V R Q A P G K G L E W V S S I T S H G G S T Y Y A D
    S V K G R .

101 TGATGTGGGT CCGCCAGGCT CCAGGGAAGG GTCTAGAGTG GGTCTCATCT ATTACTAGTC ATGGTGGGTC
    TACATACTAC GCAGACTCCG TGAAGGGCCG

    . F T I S R D N S K N T L Y L Q M N S L R A E D T A V Y Y
    C A K P D

201 GTTCACCATC TCCCGCGACA ATTCCAAGAA CACGCTGTAT CTGCAAATGA ACAGCCTGCG TGCCGAGGAT
    ACCGCGGTAT ATTACTGTGC GAAACCTGAT

    K D F D Y W G Q G T L V T V S S

301 AAGGATTTTG ACTACTGGGG TCAGGGAACC CTGGTCACCG TCTCGAGC -                           SEQ ID NO.: 450

DOM.185 - SEQ ID NO.: 336
    E V Q L L E S G G G L V Q P G G S L R L S C A A S G F T
    F A H Y P M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGCG CATTATCCGA

    . S W V R Q A P G K G L E W V S S I G R L G N R T Y Y A D
    S V K G R .

101 TGTCGTGGGT CCGCCAGGCT CCAGGGAAGG GTCTAGAGTG GGTCTCATCG ATTGGTAGGC TGGGTAATCG
    TACATACTAC GCAGACTCCG TGAAGGGCCG

    . F T I S R D N S K N T L Y L Q M N S L R A E D T A V Y Y
    C A K R A

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAACGTGCT

    T P V P I K G L F D Y W G Q G T L V T V S S
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
 301 ACGCCTGTGC CGATTAAGGG TTTGTTTGAC TACTGGGGTC AGGGAACCCT GGTCACCGTC TCGAGC -       SEQ ID NO.: 451

DOM.186 - SEQ ID NO.: 337
     E V Q L L E S G G G L V Q P G G S L R L S C A A S G L T
     F G R Y E M .

   1 GAGGTGCAGC TGTTGGAGTC TGGGGGAGGC TTGGTACAGC CTGGGGGGTC CCTGCGTCTC TCCTGTGCAG
     CCTCCGGACT CACCTTTGGG AGGTATGAGA

     . A W V R Q A P G K G L E W V S S I D S D G W V T Y Y A D
     S V K G R .

 101 TGGCGTGGGT CCGCCAGGCT CCAGGGAAGG GTCTAGAGTG GGTCTCAAGT ATTGATTCGG ATGGTTGGGT
     GACATACTAC GCAGACTCCG TGAAGGGCCG

     . F T I S R D N S K N T L Y L Q M N S L R A E D T A V Y Y
     C A Q P D

 201 GTTCACCATC TCCCGCGACA ATTCCAAGAA CACGCTGTAT CTGCAAATGA ACAGCCTGCG TGCCGAGGAC
     ACCGCGGTAT ATTACTGTGC GCAACCGGAT

     S L F D Y W G Q G T L V T V S S

 301 TCGTTGTTTG ACTACTGGGG TCAGGGAACC CTGGTCACCG TCTCGAGC -                          SEQ ID NO.: 452

DOM.187 - SEQ ID NO.: 338
     E V Q L L E S G G G L V Q P G G S L R L S C A A S G F T
     F S S Y S M .

   1 GAGGTGCAGC TGTTGGAGTC TGGGGGAGGC TTGGTACAGC CTGGGGGGTC CCTGCGTCTC TCCTGTGCAG
     CCTCCGGATT CACCTTTTCT AGTTATTCTA

     . V W V R Q A P G K G L E W V S G I N R G G T R T Y Y A D
     S V K G R .

 101 TGGTGTGGGT CCGCCAGGCT CCAGGGAAGG GTCTAGAGTG GGTCTCAGGT ATTAATCGGG GTGGTACTCG
     TACATACTAC GCAGACTCCG TGAAGGGCCG

     . F T I S R D N S K N T L Y L Q M N S L R A E D T A V Y Y
     C A K G W

 201 GTTCACCATC TCCCGCGACA ATTCCAAGAA CACGCTGTAT CTGCAAATGA ACAGCCTGCG TGCCGAGGAC
     ACCGCGGTAT ATTACTGTGC GAAAGGTTGG

     R R G F D Y W G Q G T L V T V S S

 301 AGGAGGGGGT TTGACTACTG GGGTCAGGGA ACCCTGGTCA CCGTCTCGAG C -                      SEQ ID NO.: 453

DOM.188 - SEQ ID NO.: 339
     E V Q L L E S G G G L V Q P G G S L R L S C A A S G F T
     F T R Y R M .

   1 GAGGTGCAGC TGTTGGAGTC TGGGGGAGGC TTGGTACAGC CTGGGGGGTC CCTGCGTCTC TCCTGTGCAG
     CCTCCGGATT CACCTTTACG CGTTATAGGA

     . S W V R Q A P G K G L E W V S G I S R D G Y R T Y Y A D
     S V K G R .

 101 TGTCTTGGGT CCGCCAGGCT CCAGGGAAGG GTCTGGAGTG GGTCTCAGGG ATTTCGAGGG ATGGTTATCG
     GACATACTAC GCAGACTCCG TGAAGGGCCG

     . F T I S R D N S K N T L Y L Q M N S L R A E D T A V Y Y
     C A K G M

 201 GTTCACCATC TCCCGCGACA ATTCCAAGAA CACGCTGTAT CTGCAAATGA ACAGCCTGCG TGCCGAGGAC
     ACCGCGGTAT ATTACTGTGC GAAAGGTATG

     T A S F D Y W G Q G T L V T V S S

 301 ACTGCGTCGT TTGACTACTG GGGTCAGGGA ACCCTGGTCA CCGTCTCGAG C -                      SEQ ID NO.: 454

DOM.189 - SEQ ID NO.: 340
     E V Q L L E S G G G L V Q P G G S L R L S C A A S G F T
     F Q M Y P M .
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
  1 GAGGTGCAGC TGTTGGAGTC TGGGGGAGGC TTGGTACAGC CTGGGGGGTC CCTGCGTCTC TCCTGTGCAG
    CCTCCGGATT CACCTTTCAG ATGTATCCGA

    . G W V R Q A P G K G L E W V S M I E P A G D L T Y Y A D
    S V K G R .

101 TGGGGTGGGT CCGCCAGGCT CCAGGGAAGG GTCTAGAGTG GGTCTCAATG ATTGAGCCGG CTGGTGATCT
    TACATACTAC GCAGACTCCG TGAAGGGCCG

    . F T I S R D N S K N T L Y L Q M N S L R A E D T A V Y Y
    C A K Y Q

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAATATCAG

    E Q P W F D Y W G Q G T L V T V S S

301 GAGCAGCCTT GGTTTGACTA CTGGGGTCAG GGAACCCTGG TCACCGTCTC GAGC -        SEQ ID NO.: 455

DOM.190 - SEQ ID NO.: 341
    E V Q L L E S G G G L V Q P G G S L R L S C A A S G F T
    F S M Y D M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTAGT ATGTATGATA

    . H W V R Q A P G K G L E W V S T I L S D G T D T Y Y A D
    S V K G R .

101 TGCATTGGGT CCGCCAGGCT CCAGGGAAGG GTCTAGAGTG GGTCTCAACG ATTTTGTCTG ATGGTACGGA
    TACATACTAC GCAGACTCCG TGAAGGGCCG

    . F T I S R D N S K N T L Y L Q M N S L R A E D T A V Y Y
    C A K Y G

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAATATGGG

    A M F D Y W G Q G T L V T V S S

301 GCTATGTTTG ACTACTGGGG TCAGGGAACC CTGGTCACCG TCTCGAGC -              SEQ ID NO.: 456

DOM.191 - SEQ ID NO.: 342
    E V Q L L E S G G G L V Q P G G S L R L S C A A S G F T
    F K L Y P M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTAAG TTGTATCCGA

    . T W V R Q A P G K G L E W V S S I D A G G H E T Y Y A D
    S V K G R .

101 TGACGTGGGT CCGCCAGGCT CCAGGGAAGG GTCTAGAGTG GGTCTCATCT ATTGATGCGG GGGGTCATGA
    GACATACTAC GCAGACTCCG TGAAGGGCCG

    . F T I S R D N S K N T L Y L Q M N S L R A E D T A V Y Y
    C A K D W

201 GTTCACCATC TCCCGCGACA ATTCCAAGGA CACGCTGTAT CTGCAAATGA ACAGCCTGCG TGCCGAGGAT
    ACCGCGGTAT ATTACTGTGC GAAAGATTGG

    W D Y L F D Y W G Q G T L V T V S S

301 TGGGATTATC TGTTTGACTA CTGGGGTCAG GGAACCCTGG TCACCGTCTC GAGC -        SEQ ID NO.: 457

DOM.192 - SEQ ID NO.: 343
    E V Q L L E S G G G L V Q P G G S L R L S C A A S G F T
    F S R Y P M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTTCG CGGTATCCGA

    . S W V R Q A P G K G L E W V S S I N R S G M R T Y Y A D
    S V K G R .
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
101 TGAGTTGGGT CCGCCAGGCT CCAGGGAAGG GTCTAGAGTG GGTCTCATCT ATTAATCGTT CGGGTATGCG
    GACATACTAC GCAGACTCCG TGAAGGGCCG

    . F T I S R D N S K N T L Y L Q M N S L R A E D T A V Y Y
    C A E G H

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GGAAGGGCAT

    Q A P F D Y W G Q G T L V T V S S

301 CAGGCGCCGT TTGACTACTG GGGTCAGGGA ACCCTGGTCA CCGTCTCGAG C -            SEQ ID NO.: 458

DOM.193 - SEQ ID NO.: 344
    E V Q L L E S G G G L V Q P G G S L R L S C A A S G F T
    F T G Y A M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTACG GGGTATGCTA

    . S W V R Q A P G K G L E W V S T I N A N G I R T Y Y A D
    S V K G R .

101 TGTCTTGGGT CCGCCAGGCT CCAGGGAAGG GTCTAGAGTG GGTCTCAACT ATTAATGCGA ATGGTATTCG
    GACATACTAC GCCGACTCCG TGAAGGGCCG

    . F T I S R D N S K N T L Y L Q M N G L R A E D T A V Y Y
    C A K G G

201 GTTCACCATC TCCCGCGACA ATTCCAAGAA CACGCTGTAT CTGCAAATGA ACGGCCTGCG TGCCGAGGAC
    ACCGCGGTAT ATTACTGTGC GAAAGGGGGG

    V W R W G T G H K F D Y W G Q G T L V T V S S

301 GTTTGGAGGT GGGGGACTGG GCATAAGTTT GACTACTGGG GTCAGGGAAC CCTGGTCACC GTCTCGAGC -   SEQ ID NO.: 459

DOM.194 - SEQ ID NO.: 345
    E V Q L L E S G G G L V Q P G G S L R L S C A A S G F T
    F K Q Y D M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTAAG CAGTATGATA

    . R W V R Q A P G K G L E W V S T I S Q N G T K T Y Y A D
    S V K G R .

101 TGCGGTGGGT CCGCCAGGCT CCAGGGAAGG GTCTAGAGTG GGTCTCAACG ATTTCGCAGA ATGGTACTAA
    GACATACTAC GCAGACTCCG TGAAGGGCCG

    . F T I S R D N S K N T L Y L Q M N S L R A E D T A V Y Y
    C A K S R

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAATCGAGG

    T G R Y F D Y W G Q G T L V T V S S

301 ACTGGTAGGT ATTTTGACTA CTGGGGTCAG GGAACCCTGG TCACCGTCTC GAGC -          SEQ ID NO.: 460

DOM.195 - SEQ ID NO.: 346
    E V Q L L E S G G G L V Q P G G S L R L S C A A S G F T
    F G T Y D M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGGG ACTTATGATA

    . G W V R Q A P G K G L E W V S R I N W Q G D R T Y Y A D
    S V K G R .

101 TGGGGTGGGT CCGCCAGGCT CCAGGGAAGG GTCTAGAGTG GGTCTCAAGG ATTAATTGGC AGGGTGATCG
    TACATACTAC GCAGACTCCG TGAAGGGCCG

    . F T I S R D N S K N T L Y L Q M N S L R A E D T A V Y Y
    C A K A G
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

```
201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAAGCGGGG

    F G H Y V D G L G F D Y W G Q G T L V T V S S

301 TTTGGTCATT ATGTTGATGG TCTTGGGTTT GACTACTGGG GTCAGGGAAC CCTGGTCACC GTCTCGAGC -     SEQ ID NO.: 461

DOM.196 - SEQ ID NO.: 347
    E V Q L L E S G G G L V Q P G G S L R L S C A A S G F T
    F S G Y E M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTAGT GGGTATGAGA

    . A W V R Q A P G K G L E W V S S I T D M G D S T Y Y A D
    S V K G R .

101 TGGCGTGGGT CCGCCAGGCT CCAGGGAAGG GTCTAGAGTG GGTCTCATCT ATTACTGATA TGGGTGATTC
    TACATACTAC GCAGACTCCG TGAAGGGCCG

    . F T I S R D N S K N T L Y L Q M N S L R A E D T A V Y Y
    C A K P G

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAACCTGGG

    T A F D Y W G P G T L V T V S S

301 ACTGCGTTTG ACTACTGGGG TCCGGGAACC CTGGTCACCG TCTCGAGC -                            SEQ ID NO.: 462

DOM.197 - SEQ ID NO.: 348
    E V Q L L E S G G G L V Q P G G S L R L S C A A S G F T
    F A K Y K M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGCG AAGTATAAGA

    . W W V R Q A P G K G L E W V S S I T P K G H S T Y Y A D
    S V K G R .

101 TGTGGTGGGT CCGCCAGGCT CCAGGGAAGG GTCTAGAGTG GGTCTCAAGT ATTACTCCGA AGGGTCATTC
    TACATACTAC GCAGACTCCG TGAAGGGCCG

    . F T I S R D N S K N T L Y L Q M N S L R A E D T A V Y Y
    C A K R P

201 GTTCACCATC TCCCGCGACA ATTCCAAGAA CACGCTGTAT CTGCAAATGA ACAGCCTGCG TGCCGAGGAT
    ACCGCGGTAT ATTACTGTGC GAAAAGGCCG

    M T P F D Y W G Q G T L V T V S S

301 ATGACTCCGT TTGACTACTG GGGTCAGGGA ACCCTGGTCA CCGTCTCGAG C -                        SEQ ID NO.: 463

DOM.198 - SEQ ID NO.: 349
    E V Q L L E S G G G L V Q P G G S L R L S C A A S G F T
    F E R Y N M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGAG CGGTATAATA

    . S W V R Q A P G K G L E W V S S I R P R G G K T Y Y A D
    S V K G R .

101 TGTCTTGGGT CCGCCAGGCT CCAGGGAAGG GTCTAGAGTG GGTCTCATCT ATTCGGCCGC GGGGTGGGAA
    GACATACTAC GCAGACTCCG TGAAGGGCCG

    . F T I S R D N S K N T L Y L Q M N S L R A E D T A V Y Y
    C A K W R

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAATGGCGG

    R E G Y T G S K F D Y W G Q G T L V T V S S
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
301 CGGGAGGGGT ATACTGGTTC TAAGTTTGAC TACTGGGGTC AGGGAACCCT GGTCACCGTC TCGAGC -        SEQ ID NO.: 464

DOM.199 - SEQ ID NO.: 350
    E V Q L L E S G G G L V Q P G G S L R L S C A A S G F T
    F E R Y G M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGAG AGGTATGGTA

    . T W V R Q A P G K G L E W V S S I W P R G Q K T Y Y A D
    S V K G R .

101 TGACTTGGGT CCGCCAGGCT CCAGGGAAGG GTCTGGAGTG GGTCTCAAGT ATTTGGCCGA GGGGTCAGAA
    GACATACTAC GCAGACTCCG TGAAGGGCCG

    . F T I S R D N S K N T L Y L Q M N S L R A E D T A V Y Y
    C A K G N

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAAGGGAAT

    S R Y V F D Y W G Q G T L V T V S S

301 AGTCGGTATG TTTTTGACTA CTGGGGTCAG GGAACCCTGG TCACCGTCTC GAGC -        SEQ ID NO.: 465

DOM.200 - SEQ ID NO.: 351
    E V Q L L E S G G G L V Q P G G S L R L S C A A S G F T
    F T N Y S M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTACT AATTATAGTA

    . G W V R Q A P G K G L E W V S T I R P N G T K T Y Y A D
    S V K G R .

101 TGGGTTGGGT CCGCCAGGCT CCAGGGAAGG GTCTAGAGTG GGTCTCAACT ATTCGTCCTA ATGGTACTAA
    GACATACTAC GCAGACTCCG TGAAGGGCCG

    . F T I S R D N S K N T L Y L Q M N S L R A E D T A V Y Y
    C A K R S

201 GTTCACCATC TCCCGCGACA ATTCCAAGAA CACGCTGTAT CTGCAAATGA ACAGCCTGCG TGCCGAGGAT
    ACCGCGGTAT ATTACTGTGC GAAACGGTCG

    S A H L Q R F D Y W G Q G T L V T V S S

301 TCTGCGCATC TTCAGAGGTT TGACTACTGG GGTCAGGGAA CCCTGGTCAC CGTCTCGAGC -        SEQ ID NO.: 466

DOM.201 - SEQ ID NO.: 352
    E V Q L L E S G G G L V Q P G G S L R L S C A A S G F T
    F G N Y S M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGGT AATTATTCGA

    . G W V R Q A P G K G L E W V S S I G R H G G R T Y Y A D
    S V K G R .

101 TGGGTTGGGT CCGCCAGGCT CCAGGGAAGG GTCTAGAGTG GGTCTCATCG ATTGGTCGTC ATGGTGGGCG
    TACATACTAC GCAGACTCCG TGAAGGGCCG

    . F T I S R D N S K N T L Y L Q M N S L R A E D T A V Y Y
    C A K K G

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAAAAGGGG

    S T Y P R F D Y W G Q G T L V T V S S

301 AGTACTTATC CTAGGTTTGA CTACTGGGGT CAGGGAACCC TGGTCACCGT CTCGAGC -        SEQ ID NO.: 467

DOM.202 - SEQ ID NO.: 353
    E V Q L L E S G G G L V Q P G G S L R L S C T A S G F T
    F S H Y E M .
```

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
  1 GAGGTGCAGC TGTTGGAGTC TGGGGGAGGC TTGGTACAGC CTGGGGGGTC CCTGCGTCTC TCCTGTACAG
    CCTCCGGATT CACCTTTTCG CATTATGAGA

    . G W V R Q A P G K G L E W V S S I E P F G G G T Y Y A D
    S V K G R .

101 TGGGGTGGGT CCGCCAGGCT CCAGGGAAGG GTCTAGAGTG GGTCTCAAGT ATTGAGCCTT TTGGTGGTGG
    GACATACTAC GCAGACTCCG TGAAGGGCCG

    . F T I S R D N S K N T L Y L Q M N S L R A E D T A V Y Y
    C A K V Y

201 GTTCACCATC TCCCGCGACA ATTCCAAGAA CACGCTGTAT CTGCAAATGA ACAGCCTGCG TGCCGAGGAT
    ACCGCGGTAT ATTACTGTGC GAAAGTGTAT

    P Q G S F D Y W G Q G T L V T V S S

301 CCTCAGGGTT CTTTTGACTA CTGGGGTCAG GGAACCCTGG TCACCGTCTC GAGC -          SEQ ID NO.: 468

DOM.203 - SEQ ID NO.: 354
    E V Q L L E S G G G L V Q P G G S L R L S C A A S G F T
    F S N Y T M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTAGT AATTATACTA

    . G W V R Q A P G K G L E W V S S I R P D G K I T Y Y A D
    S V K G R .

101 TGGGGTGGGT CCGTCAGGCT CCAGGGAAGG GTCTAGAGTG GGTCTCATCT ATTCGGCCTG ATGGTAAGAT
    TACATACTAC GCAGACTCCG TGAAGGGCCG

    . F T I S R D N S K N T L Y L Q M N S L R A E D T A V Y Y
    C A E V Y

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GGAAGTTTAT

    S S C A M C T P L L F D Y W G Q G T L V T V S S

301 TCTTCGTGTG CGATGTGTAC TCCGCTTTTG TTTGACTACT GGGGTCAGGG AACCCTGGTC ACCGTCTCGA GC - SEQ ID NO.: 469

DOM.204 - SEQ ID NO.: 355
    E V Q L L E S G G G L V Q P G G S L R L S C A A S G F T
    F K R Y S M .

  1 GAGGTGCAGC TGTTGGAGTC TGGGGGGGGC TTGGTACAGC CTGGGGGGTC CCTGCGTCTC TCCTGTGCAG
    CCTCCGGATT CACCTTTAAG CGGTATTCGA

    . A W V R Q A P G K G L E W V S D I G P R G F S T Y Y A D
    S V K G R .

101 TGGCGTGGGT CCGCCAGGCT CCAGGGAAGG GTCTAGAGTG GGTCTCAGAT ATTGGGCCGA GGGGTTTTTC
    GACATACTAC GCAGACTCCG TGAAGGGCCG

    . F T I S R D N S K N T L Y L Q M N S L R A E D T A V Y Y
    C A K V G

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAAGTGGGT

    R G Q R D T S Q P F D Y W G Q G T L V T V S S

301 CGTGGTCAGC GTGATACTAG TCAGCCGTTT GACTACTGGG GTCAGGGAAC CCTGGTCACC GTCTCGAGC -     SEQ ID NO.: 470

DOM.205 - SEQ ID NO.: 356
    E V Q L L E S G G G L V Q P G G S L R L S C A A S G F T
    F A S Y Q M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGCT TCTTATCAGA

    . A W V R Q A P G K G L E W V S G I T S G G L S T Y Y A D
    S V K G R .
```

TABLE 8-continued

Summary of dAbs exhibiting a range of CD40L inhibitory $IC_{50}$ values as determined using the CD40L/CD40-Fc receptor inhibition assay.
The DNA and translated amino acid sequence of unique dAbs identified in the receptor binding assay as inhibiting CD40L binding to CD40 are detailed below:

101 TGGCTTGGGT CCGCCAGGCT CCAGGGAAGG GTCTAGAGTG GGTCTCAGGG ATTACTTCGG GTGGTCTTAG
TACGTACTAC GCAGACTCCG TGAAGGGCCG

. F T I S R D N S K N T L Y L Q M N S L R A E D T A V Y Y
C A K P G

201 GTTCACCATC TCCCGCGACA ATTCCAAGAA CACGCTGTAT CTGCAAATGA ACAGCCTGCG TGCCGAGGAC
ACCGCGGTAT ATTACTGTGC GAAACCGGGG

R G F D Y W G Q G T L V T V S S

301 AGGGGTTTTG ACTACTGGGG TCAGGGAACC CTGGTCACCG TCTCGAGC - SEQ ID NO.: 471

DOM.206 - SEQ ID NO.: 357
E V Q L L E S G G G L V Q P G G S L R L S C A A S G F T
F A S Y E M .

1 GAGGTGCAGC TGTTGGAGTC TGGGGGAGGC TTGGTACAGC CTGGTGGGTC CCTGCGTCTC TCCTGTGCAG
CCTCCGGATT CACCTTTGCT TCTTATGAGA

. T W V R Q A P G K G L E W V S G I S S D G L S T Y Y A D
S V K G R .

101 TGACTTGGGT CCGCCAGGCT CCAGGGAAGG GTCTAGAGTG GGTCTCAGGG ATTTCTTCTG ATGGTCTGTC
TACATACTAC GCAGACTCCG TGAAGGGCCG

. F T I S R D N S K N T L Y L Q M N S L R A E D T A V Y Y
C A K P G

201 GTTCACCATC TCCCGCGACA ATTCCAAGAA CACGCTGTAT CTGCAAATGA ACAGCCTGCG TGCCGAGGAC
ACCGCGGTAT ATTACTGTGC GAAACCGGGG

V L F D Y W G Q G T L V T V S S

301 GTGTTGTTTG ACTACTGGGG TCAGGGAACC CTGGTCACCG TCTCGAGC - SEQ ID NO.: 472

DOM.207 - SEQ ID NO.: 358
E V Q L L E S G G G L V Q P G G S L R L S C A A S G F T
F D K Y L M .

1 GAGGTGCAGC TGTTGGAGTC TGGGGGAGGC TTGGTACAGC CTGGGGGGTC CCTGCGTCTC TCCTGTGCAG
CCTCTGGATT CACCTTTGAT AAGTATTTGA

. S W V R Q A P G K G L E W V S G I E P L G D V T Y Y A D
S V K G R .

101 TGTCGTGGGT CCGCCAGGCT CCAGGGAAGG GTCTGGAGTG GGTCTCAGGT ATTGAGCCTC TGGGTGATGT
TACATACTAC GCAGACTCCG TGAAGGGCCG

. F T I S R D N S K N T L Y L Q M N S L R A E D T A V Y Y
C A K E A

201 GTTCACCATC TCCCGCGACA ATTCCAAGAA CACGCTGTAT CTGCAAATGA ACAGCCTGCG TGCCGAGGAC
ACCGCGGTAT ATTACTGTGC GAAAGAGGCT

S G D F D Y W G Q G T L V T V S S

301 TCGGGGGATT TTGACTACTG GGGTCAGGGA ACCCTGGTCA CCGTCTCGAG C - SEQ ID NO.: 473

DOM.208 - SEQ ID NO.: 359
E V Q L L E S G G G L V Q P G G S L R L S C A A S G F T
F T E Y E M .

1 GAGGTGCAGC TGTTGGAGTC TGGGGGAGGC TTGGTACAGC CTGGGGGGTC CCTGCGTCTC TCCTGTGCAG
CCTCCGGGTT CACCTTTACT GAGTATGAGA

. S W V R Q A P G K G L E W V S S I D N V G S S T Y Y A D
S V K G R .

101 TGTCTTGGGT CCGCCAGGCT CCAGGGAAGG GTCTAGAGTG GGTCTCAAGT ATTGATAATG TGGGTAGTAG
TACATACTAC GCAGACTCCG TGAAGGGCCG

. F T I S R D N S K N T L Y L Q M N S L R A E D T A V Y Y
C A K P G

TABLE 8-continued

Summary of dAbs exhibiting a range of CD40L inhibitory $IC_{50}$ values as determined using the CD40L/CD40-Fc receptor inhibition assay. The DNA and translated amino acid sequence of unique dAbs identified in the receptor binding assay as inhibiting CD40L binding to CD40 are detailed below:

```
201 GTTCACCATC TCCCGCGACA ATTCCAAGAA CACGCTGTAT CTGCAAATGA ACAGCCTGCG TGCCGAGGAT
    ACCGCGGTAT ATTACTGTGC GAAACCTGGG

    K L F D Y W G Q G T L V T V S S

301 AAGCTTTTTG ACTACTGGGG TCAGGGAACC CTGGTCACCG TCTCGAGC -              SEQ ID NO.: 474

DOM.209 - SEQ ID NO.: 360
    E V Q L L E S G G G L V Q P G G S L R L S C A A S G F T
    F A D Y E M .

  1 GAGGTGCAGC TGTTGGAGTC TGGGGGAGGC TTGGTACAGC CTGGGGGGTC CCTGCGTCTC TCCTGTGCAG
    CCTCCGGATT CACCTTTGCT GATTATGAGA

    . W W V R Q A P G K G L E W V S A I S R Q G F A T Y Y A D
    S V K G R .

101 TGTGGTGGGT CCGCCAGGCT CCAGGGAAGG GTCTAGAGTG GGTCTCAGCG ATTTCTAGGC AGGGTTTTGC
    TACATACTAC GCAGACTCCG TGAAAGGCCG

    . F T I S R D N S K N T L Y L Q M N S L R A E D T A V Y Y
    C A K D L

201 GTTCACCATC TCCCGCGACA ATTCCAAGAA CACGCTGTAT CTGCAAATGA ACAGCCTGCG TGCCGAGGAC
    ACCGCGGTAT ATTACTGTGC GAAAGATCTG

    E R D D F D Y W G Q G T L V T V S S

301 GAGCGGGATG ATTTTGACTA CTGGGGTCAG GGAACCCTGG TCACCGTCTC GAGC -         SEQ ID NO.: 475
```

Among the DOM clones described, a number of observations have been made regarding homology among clones, and properties of amino acids predicted at particular positions in the anti-CD40L dAbs. These are shown in Tables 9 and 10 below:

TABLE 9

Predictions for anti-VH CD40L clones: (using standard single letter amino acid code)

| Predicted amino acid number relative to dummy sequence | Predicted Kabat numbering | Predicted dummy amino acid at this position | Properties of amino acids frequently fount at the designated position in anti-CD40L dAbs | Amino acid frequently fount at the designated position in anti-CD40L dAbs |
|---|---|---|---|---|
| 30 | 30 | S | acidic; small | D, E, A, G |
| 33 | 33 | A | mix | Q, E, P, G |
| 35 | 35 | S | mix | A, M, G, T |
| 50 | 50 | A | nucleophilic; or G, W | S, T, G, W |
| 52 | 52 | S | hydrophilic; or G, D, N | T, S, G, D, N |
| 53 | 53 | G | mix | P, R, S, D |
| 54 | 54 | S | acidic; or L, I, Q | D, E, L, I, Q |
| 99* | 95 | S | hydrophobic; or P, G | P, G, V, L |
| 100 | 96 | Y | mix | G, D, R, L |

*If amino acid at position 99 (dummy) is P then G or D is frequently found at position 100.

TABLE 10

Predictions for anti-VK CD40L clones:

| Predicted amino acid number relative to dummy sequence | Predicted Kabat numbering | Predicted dummy amino acid at this position | Properties of amino acids frequently fount at the designated position in anti-CD40L dAbs | Amino acid frequently fount at the designated position in anti-CD40L dAbs |
|---|---|---|---|---|
| 28* | 28 | S | mix | A, D, W, P |
| 30 | 30 | S | acidic; or G | G, D, E |
| 32 | 32 | Y | mix | R, S, D, N |
| 34** | 34 | N | acidic or basic | R, E |
| 50 | 50 | A | mix | H, D, G, S |
| 51 | 51 | A | mix | S, G, R |
| 53 | 53 | S | hydrophobic; or K, E | I, L, M, K, E, W |
| 91 | 91 | S | mix | Y, R, V |
| 92 | 92 | Y | basic; or S, W | H, S, W, R |
| 96 | 96 | N | mix | Y, V, A, T |

*If amino acid at position 28 (dummy) is D then E is frequently found at position 34.

**If amino acid at position 34 (dummy) is E then Y is frequently found at position 91 and H or D at position 92.

Example 8

PEGylation of DOM8-24

Site specific maleimide-PEGylation of DOM48-24 requires a solvent accessible cysteine to be provided on the surface of the protein, in this example, at the C-terminus. The cysteine residue, once reduced to give the free thiol, can then be used to specifically couple the protein to PEG via a wide range of chemistries such as maleimide or another thiol to give a disulphide. A wide range of chemical modified PEGs of different sizes and branched formats are available from Nektar (formally known as Shearwater Corp). This allows the basic dab-cys monomer to be formatted in a variety of ways for example as a PEGylated monomer, dimer, trimer, tetramer etc. The size of the PEGs is given in kDa but can also be referred to as K (i.e. "40K PEG"=40 kDa PEG).

PCR Construction of DOM8-24cys

The site of attachment for the PEG may be placed elsewhere on the surface of the dAb as long as the targeted amino acid is solvent accessible and the resultant PEGylated protein still maintains antigen binding. Thus it is also possible to engineer the cys into any one of frameworks 1-4 of the dAb for PEGylation and still maintain some antigen binding. The following oligonucleotides were used to specifically PCR DOM8-24 with a SalI and BamHI sites for cloning and also to introduce a C-terminal cysteine residue.

```
        SalI
        ~~~~~~~~
    Ala Ser Thr Glu Val Gln Leu Leu Glu Ser Gly Gly Gly Leu Val (SEQ ID NO: 85)
 1 GCG TCG ACG GAG GTG CAG CTG TTG GAG TCT GGG GGA GGC TTG GTA (SEQ ID NO: 83)
   CGC AGC TGC CTC CAC GTC GAC AAC CTC AGA CCC CCT CCG AAC CAT (SEQ ID NO: 84)

    Gln Pro Gly Gly Ser Leu Arg Leu Ser Cys Ala Ala Ser Gly Phe
46 CAG CCT GGG GGG TCC CTG CGT CTC TCC TGT GCA GCC TCC GGA TTC
   GTC GGA CCC CCC AGG GAC GCA GAG AGG ACA CGT CGG AGG CCT AAG

    Thr Phe Ser Asn Tyr Gln Met Ala Trp Val Arg Gln Ala Pro Gly
91 ACC TTT AGT AAT TAT CAG ATG GCG TGG GTC CGC CAG GCT CCA GGG
   TGG AAA TCA TTA ATA GTC TAC CGC ACC CAG GCG GTC CGA GGT CCC

    Lys Gly Leu Glu Trp Val Ser Ser Ile Thr Ser Glu Gly Gly Ser
136 AAG GGT CTA GAG TGG GTC TCA AGT ATT ACT AGT GAG GGT GGT TCG
    TTC CCA GAT CTC ACC CAG AGT TCA TAA TGA TCA CTC CCA CCA AGC

    Thr Tyr Tyr Ala Asp Ser Val Lys Gly Arg Phe Thr Ile Ser Arg
181 ACA TAC TAC GCA GAC TCC GTG AAG GGC CGG TTC ACC ATC TCC CGC
    TGT ATG ATG CGT CTG AGG CAC TTC CCG GCC AAG TGG TAG AGG GCG

    Asp Asn Ser Lys Asn Thr Leu Tyr Leu Gln Met Asn Ser Leu Arg
226 GAC AAT TCC AAG AAC ACA CTG TAT CTG CAA ATG AAC AGC CTG CGT
    CTG TTA AGG TTC TTG TGT GAC ATA GAC GTT TAC TTG TCG GAC GCA

    Ala Glu Asp Thr Ala Val Tyr Tyr Cys Ala Lys Pro Gly Lys Asn
271 GCC GAG GAC ACC GCG GTA TAT TAC TGT GCG AAA CCG GGT AAG AAT
    CGG CTC CTG TGG CGC CAT ATA ATG ACA CGC TTT GGC CCA TTC TTA

    Phe Asp Tyr Trp Gly Gln Gly Thr Leu Val Thr Val Ser Cys ***
316 TTT GAC TAC TGG GGT CAG GGA ACC CTG GTC ACC GTC TCG TGC TAA
    AAA CTG ATG ACC CCA GTC CCT TGG GAC CAG TGG CAG AGC ACG ATT

         BamHI
         ~~~~~~~
    *** Gly Ser
361 TAA GGA TCC
    ATT CCT AGG
```

The DNA sequence of the PCR primers used to amplify the engineered dAb are shown below.

```
Forward primer
                                         (SEQ ID NO: 86)
5'-AGTGCGTCGACGGAGGTGCAGCTGTTGGAGTCT-3'

Reverse primer
                                         (SEQ ID NO: 87)
5'-AAAGGATCCTTATTAGCACGAGACGGTGACCAGGGTTCCCTG-3'
```

The PCR reaction (50 μL volume) was set up as follows: 200 μM dNTP's, 0.4 μM of each primer, 5 μL of 10×PfuTurbo buffer (Stratagene), 100 ng of template plasmid (DOM8-24), 1 μL of PfuTurbo enzyme (Stratagene) and the volume adjusted to 50 μL using sterile water. The following PCR conditions were used: initial denaturing step 94° C. for 2 mins, then 25 cycles of 94° C. for 30 secs, 64° C. for 30 sec and 72° C. for 30 sec. A final extension step was also included of 72° C. for 5 mins. The PCR product was purified and digested with SalI and BamHI and ligated into the vector (pDOM5) which had also been cut with the same restriction enzymes. Correct clones were verified by DNA sequencing.

Expression and Purification of DOM8-24

DOM8-24 vector was transformed into HB2151 electrocompetent cells. Cells carrying the dAb plasmid were selected for using 100 μg/mL carbenicillin. Cultures were set up in 2 L baffled flasks containing 500 mL of terrific broth (Sigma-Aldrich) and 100 μg/mL carbenicillin. The cultures were grown at 30° C. at 200 rpm to an O.D.600 of 1-1.5 and then induced with 1 mM IPTG (isopropyl-beta-D-thiogalactopyranoside, from Melford Laboratories). The expression of the dAb was allowed to continue for 12-16 hrs at 30° C. It was found that most of the dAb was present in the culture media. Therefore, the cells were separated from the media by centrifugation (8,000×g for 30 mins), and the supernatant used to purify the dAb. Per litre of supernatant, 10 mL of Streamline Protein A (Amersham Biosciences) was added and the dAb allowed to batch bind with stirring for 3 hours at room temperature, or overnight at 4° C. The resin was then allowed to settle under gravity for an hour before the supernatant removed. The agarose was then packed into a XK 16 column (Amersham Pharmacia) and was washed with 10 column volumes of 2×PBS. The bound dAb was eluted with 100 mM glycine pH 3.0 and protein containing fractions were then neutralized by the addition of ⅕ volume of 1 M Tris pH 8.0.

PEGylation of DOM8-24cys Using MAL Activated PEG

Monomer PEGylation

The cysteine residue which had been engineered onto the surface of the VH dAb was specifically modified with a single linear or branched PEG-MAL to give monomeric modified protein. mPEG-MAL formats which may be used to PEGylate a monomeric VH or Vk dAb. The PEGs may be of MW from 500 to 60,000 (eg, from 2,000 to 40,000) in size.

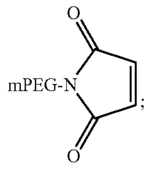

mPEG-MAL

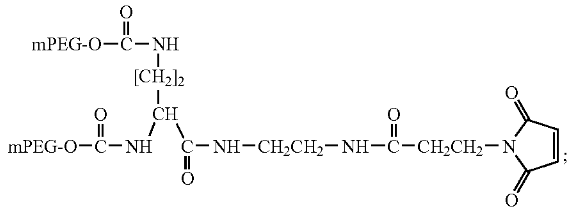

mPEG2-MAL 2.5 ml of 500 μM DOM8-24cys was reduced with 5 mM dithiothreitol and left at room temperature for 20 minutes. The sample was then buffer exchanged using a PD-10 column (Amersham Pharmacia). The column had been pre-equilibrated with 5 mM EDTA, 20 mM sodium phosphate pH 6.5, 10% glycerol, and the sample applied and eluted following the manufactures guidelines. The eluted sample (3.5 ml of ~360 SUM dAb) was placed on ice until required. A four fold molar excess of 30K PEG-MAL or 40K PEG2-MAL (Nektar) was weighed out and added directly to the reduced dAb solution and gently mixed until the polymer had dissolved. The reaction was left to proceed at room temperature for 3 hours.

Purification of 30K and 40K PEGylated DOM8-24cys Monomer

The PEGylated dAb was purified using cation exchange chromatography as the isoelectric point (pI) of the protein is ~8.40 μL of 40% glacial acetic acid was added per mL of the 30K or 40K PEG DOM8-24cys reaction to reduce the pH to ~4. The sample was then applied to a 1 mL Resource S cation exchange column (Amersham Pharmacia), which had been pre-equilibrated with 50 mM sodium acetate pH 4.0. The PEGylated material was separated from the unmodified dAb by running a linear sodium chloride gradient from 0 to 500 mM over 20 column volumes. Fractions containing PEGylated dAb only were identified using SDS-PAGE and then pooled and the pH increased to 8 by the addition of ⅕ volume of 1M Tris pH 8.0

In Vitro Functional Binding Assay: CD40 Ligand Receptor Assay (CD40L RBA)

Figure 7:
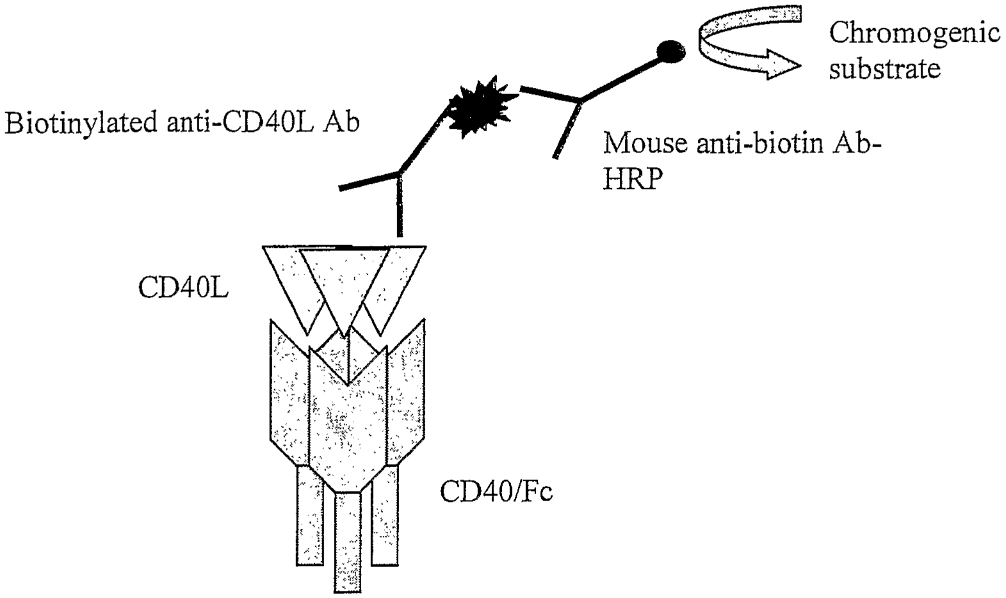
FIG. 7 shows a schematic representation of the CD40L binding assay used herein, e.g., in Example 6.

The CD40L assay was used to measure the binding of CD40L to CD40 and the ability of binding entities (including monovalent antibody fragments such a dabs) to block this interaction, as shown FIG. 7.

A 96 well Nunc Maxisorp assay plate was coated overnight at 4° C. with 100 μl per well of recombinant human CD40/Fc (R&D Systems) at 0.5 μg/ml in carbonate buffer. The plate was washed 3 times with 300 μl of 0.05% Tween/PBS and 3 times with 300 μl of PBS using a Tecan plate washer. The wells were blocked using 200 μl of PBS containing 2% (w/v) BSA and incubated for a minimum of 1 h at room temperature. The wells were washed as above, then 50 μl of purified dAb protein was added to each well. To each well 50 μl of CD40L, at 6 ng/ml in diluent (for a final concentration of 3 ng/ml), was also added and the plate incubated for 1 hr at room temperature. The plate was washed as described previously and 100 μl biotinylated anti-CD40L antibody, 0.5 μg/ml in diluent, was added and incubated for 1 hr at room temperature. The plate was washed as described above, then 100 μl HRP conjugated anti-biotin antibody (1:5000 dilution in diluent) added to each well and the plate incubated for 1 hr at room temperature. The plate was washed again as described above using a Tecan plate washer and the assay developed using 100 μl of SureBlue 1-Component TMB MicroWell Peroxidase solution (the plate was left at room temperature for up to 20 min). The reaction was stopped by the addition of 100 μl M hydrochloric acid. The $OD_{450nm}$ of the plate was assayed within 30 minutes of acid addition. The $OD_{450nm}$ is proportional to the amount of bound streptavidin-HRP conjugate, therefore the greater the degree of dAb inhibition the lower the $OD_{450nm}$ of the resulting signal. The following controls were included; 0 ng/ml CD40L (diluent only), 3 ng/ml CD40L and 3 ng/ml CD40L with 1 μg/ml anti-CD40L antibody.

The results of the CD40L RBA are shown in FIG. 9. It can be seen that PEGylated DOM8-24cys has a similar affinity for CD40L as the unmodified protein. The size of the polymer attached (either 30 or 40K) does not seem to significantly affect the IC 50 of ~1 nM.

Example 9

Generation and Expression of a Dual Specific dAb Dimer (DOM7h-26-DOM-24)

A dual specific dAb dimer was constructed essentially as described in WO2004/003019 and as described below.

A PCR fragment introducing 5' NotI and 3' EcoRI restriction sites into the DOM-24 DNA sequence was generated using the primers VH-5'-NotI (5'-GTATGTCTGGCGGCCG-CAGAGGTGCAGCTGTTGGAGTCTGGGG-GAGGCTTG-3'; SEQ ID NO: 90) and VH—NO-XhoI (5'-TAGAATTCTTATTAGCTGGAGACGGTGACCAGGGT-3'; SEQ ID NO: 91). The PCR product was electrophoresed on a 1% agarose gel and the appropriate band was excised and gel cleaned using the Qiagen Gel Extraction Kit. The purified DNA was digested with NotI and EcoRI for 1 hour at 37° C. and then the digested DNA fragment purified using the Qiagen PCR Cleanup Kit. The digested PCR product was ligated using T4 DNA ligase into the vector pCH3, derived from pPICz-alpha (Invitrogen Ltd, Paisley, UK), which had been previously been digested with NotI and EcoRI, thereby enabling the ligation of the DOM-24 DNA sequence 3' relative to the anti-human serum albumin dAb DNA sequence (DOM7h-26). One micro-litre of the ligation mix was used to electroporate 50 μl of *E. coli* TOP10F' (0.2 mm diameter cuvettes; 25 μFD; 200Ω; 2.500 kV) using a Biorad Genepulser II with pulse controller module. The electroporated cells were immediately resuspended in 1 ml low salt LB medium (10 g/l tryptone; 5 g/l yeast extract; 5 g/l NaCl; pH to 7.5 with 4 M NaOH; then autoclaved at 121° C. for 15 min) and 100 μl of the cell suspension plated onto low salt LB agar plates (10 g/l tryptone; 5 g/l yeast extract; 5 g/l NaCl; pH to 7.5 with 4 M NaOH; 15 g/l agar; then autoclaved at 121° C. for 15 min) supplemented with 25 μg/ml zeocin (Invitrogen Ltd, Paisley, UK) and grown at 37° C. overnight.

Several individual clones from the overnight growth plate were analysed by DNA sequencing using the alpha-factor sequencing primer (5'-TACTATTGCCAGCATTGCTGC-3'; SEQ ID NO: 92) and the reverse 3' AOX1 primer (5'-GCAAATGGCATTCTGACATCC-3'; SEQ ID NO: 93). A plasmid prep derived from a single clone containing the desired DNA sequence was made by inoculating 100 ml of low salt LB medium supplemented with 25 μg/ml zeocin and grown overnight at 37° C. with shaking at 250 rpm, followed by purification of the plasmid DNA using a Qiagen Plasmid Midi Prep Kit (Qiagen).

The concentration and purity of the DNA was determined by measuring the absorbance at 280 nm and 260 nm. Between 10 and 50 μg of DNA was digested with PmeI, SacI or BstXI restriction enzymes and the DNA digestion confirmed by analysis on a 0.8% agarose gel. The digested DNA was purified using the Qiagen Qiaex II Kit (Qiagen) and the DNA eluted into 10 μl purified water per 20 μl of Qiaex II resin.

Competent yeast cells were made by streaking the wild type *Pichia pastoris* strain X33 onto a YPD agar plate (for 1 litre of media: 20 g peptone from meat type 1; 10 g yeast extract; 20 g agar dissolved in 900 ml water and sterilise by autoclaving at 121° C. for 15 minutes; followed by the aseptic addition of 100 ml of 20% dextrose and the desired amount of zeocin once the media had cooled below 50° C.) and grown at 30° C. for 36-48 h until colonies appeared. A single colony was inoculated into 5 ml of YPD medium (as for YPD agar, without the addition of 20 g agar) and grown overnight in a 50 ml baffled flask at 30° C. with shaking at 250 rpm. Five hundred millilitres of YPD medium in a 21 baffled flask was inoculated with 0.1-0.5 ml of the overnight culture and grown at 30° C. with shaking at 250 rpm overnight to an OD600 of approximately 1.3-1.5. The culture was cooled on ice then the *Pichia* harvested by centrifugation at 1500 g for 5 min at 4° C. The supernatant was discarded and the pellet resuspended in 500 ml ice cold ultrapure water. The *Pichia* were recovered again by centrifugation at 1500 g for 5 min at 4° C. The pellet was resuspended and centrifuged for a further three times, the first time in 250 ml ice cold ultrapure water, then twice in 20 ml ice cold 1M sorbitol. The competent *Pichia* were kept on ice for up to 6 hours prior to use.

To transform the *Pichia* by electroporation, between 10 to 20 μg of linearised vector in 10 μl of water was mixed with 80 μl of competent *Pichia* in a precooled microfuge tube and incubate on ice for 5 min. The *Pichia* mixture was then transferred to a precooled 0.2 cm gap electroporation cuvette, and electroporated: 25 μF, resistance set to infinity, 0.54 kV in a Biorad Genepulser II with pulse controller module. Immediately 1 ml ice cold 1 M sorbitol was added to the electroporation cuvette and the electroporated *Pichia* transferred into a 15 ml polypropylene tube. This culture was incubated at 30° C. without shaking for 2 hours to allow the cells to recover. The cells were then plated onto YPDS agar plates (YPD agar supplemented with 1 M sorbitol) and zeocin added to final concentrations of 100 μg/ml, 500 μg/ml, 1000 μg/ml, and 2000 μg/ml. The plates were incubated at 30° C. in the dark for 2-10 days until colonies appeared. Several clones were picked from each plate and restreaked onto YPD plates supplemented with the same amount of zeocin as they were originally selected against. For small to medium scale shaking flask expression the Mut status of each X33 clone was not determined.

Individual restreaked colonies were used to inoculate 50 ml of BMGY medium (for 1 litre of medium: 20 g peptone from meat type 1; 10 g yeast extract were dissolved in 700 ml with water and sterilise by autoclaving at 121° C. for 15 minutes; followed by the aseptic addition of 100 ml 1 M KPO4 pH 6.0; 100 ml 10% glycerol; and 100 ml 10xYNB (Yeast Nitrogen Base); 2 ml of 500× biotin) in a 250 ml flask and grown at 30° C. with shaking at 250 rpm until an OD600 of 2 to 6 was attained. The *Pichia* was recovered by centrifugation at 1500 g for 5 min at room temperature. The resulting pellet was resuspended in 20 ml BMMH medium (as for BMGY medium except the 100 ml 10% glycerol was replaced with 100 ml of 5% methanol), and returned to a fresh 250 ml baffled flask and incubated at 30° C. with shaking at 250 rpm for up to 5 days post induction. At 24 h intervals, 0.5 ml samples were recovered and assessed by analysis of the supernatant by SDS-PAGE.

Dimer dAb was purified from the culture supernatant using Streamline protein-A matrix (Amersham Biosciences). Following binding of the dimer dAb, the matrix was transferred to an empty 20 ml chromatography column containing a frit and the supernatant allowed to flow through the column, retaining the matrix. The matrix was washed with 10 times the matrix volume of high salt buffer (10 mM Phosphate buffer, 2.7 mM KCl, 487 mM NaCl, pH 7.4). The bound protein was eluted with 0.1 M glycine pH 3 supplemented with 0.15 M NaCl and 0.8 ml fractions were collected which were immediately neutralised with the addition of 0.2 ml of 1 M Tris-HCl pH 8.0.

Simultaneous Antigen Binding of the Dual Specific dAb Dimer

To demonstrate that the dual specific dimeric dAb was functional and could bind both antigens simultaneously, an antigen binding ELISA was performed. Fifty microlitres per well of human serum albumin at 100 μg/ml in PBS was coated on to a Maxisorb ELISA plate (Nunc) overnight at 4° C. The plate was washed 3 times with 250 μl/well of PBS supplemented with 0.1% (v/v) Tween 20 (Sigma). The plate was then blocked for 1 h at room temperature with 200 μl per well of PBSM (PBS supplemented with 2% (w/v) low fat milk powder). The plate was washed as before, then 50 μl per well of doubling dilutions of the dimer dAb in PBSM were added and incubated for 1 hour at room temperature. The plate was washed as before then 50 μl per well of a 5 nM solution of biotinylated CD40L in PBSM added and incubated for 1 hour at room temperature. The plate was washed as before then 50 μl per well of streptavidin-HRP (Amersham Biosciences) diluted 1 in 4000 in PBSM was added and incubated for 1 hour at room temperature. The plate was washed 4 times with 250 μl/well of PBS supplemented with 0.1% (v/v) Tween 20, followed by two washes with 250 μl/well of PBS. The ELISA was developed by adding 50 μl per well of SureBlue 1-Component TMB MicroWell Peroxidase solution (KPL, Gaithersberg, Md.) and incubated at room temperature for several minutes until the desired colour intensity was obtained. The reaction was stopped by the addition of 100 μl of 1 M hydrochloric acid and read at 450 nm (FIG. 10).

Generation and Expression of a Dual Specific Fab (DOM7h-2:CK DOM-24:CH)

The produce a dual specific Fab the method used was essentially the same method as described for the dual specific dAb dimer (DOM7h-26-DOM-24) except that the DNA for the DOM7h-2 and DOM-24 dAbs were cloned into separate pPICz-alpha based vectors containing the human CK or human CH1 domain respectively. Each of the two vectors were designed to enable the expression of a single polypeptide consisting of the CH1 or CK domain fused in frame to the 3' end of the appropriate dAb. To obtain expression of the complete Fab fragment, competent *Pichia pastoris* strain X33 were cotransformed with two linearised vectors. Purification was as described for the dimer Fab.

Simultaneous Antigen Binding of the Dual Specific Fab

The simultaneous antigen binding of the dual specific Fab was carried out using the same assay as described for the dual specific dAb dimmer above. The results are shown in FIG. 11.

Inhibition of CD40 Mediated CD54 Upregulation Disruption of CD40/CD40L Interaction in L3055 Cells.

Monomeric dAb molecules were assayed for their ability to disrupt the binding of cellularly associated CD40L to CD40. This was determined by measuring the level inhibition of CD40 mediated CD54 upregulation on group 1 Burkitt lymphoma cell line L3055 by FACS. CD40 displayed on the L3055 cells was stimulated by CD40L expressed on the surface of fibroblasts (typically mouse L-cells) transfected with the CD40L gene as previously described by Garrone et al., 1995 (Garrone P., Neidhardt E. V., Garcia E., Galibert L., van Kooten C., Banchereau J. (1995) J Exp Med 182, 1265-1273.)

Samples containing the dAbs were preincubated with the L-cells cells for 1 hour prior to the addition of the L3055 cells. Both cell lines were co-cultured for 22 hours following which the L-cells were stained for FACS analysis, as described by Baker et al., 1998 (Baker, M. P., Eliopoulos, A. G., Young, L. S., Armitage, R. J., Gregory, C. D., Gordon, J. (1998) Blood, 92 (8), 2830-2843) and by Challa et al., 2002 (Challa, A., Eliopoulos, A. G., Holder, M. J., Burguete, A. S., Pound, J. D., Chamba, A., Grafton, G., Armitage, R. J., Gregory, C. D., Martinez-Valdez, H., Young, L. and Gordon, J. (2002) Blood, 99 (9), 3411-3418.

The FACS analysis of DOM-24 (monomeric form) at a concentration of 12 μm showed inhibition.

FACS analysis of the Vk DOM-116 at a concentration of 9 μM showed inhibition compared with a control blank dAb and the stimulated cell trace (FIG. 13).

Effect of Anti-CD40L Therapy on Primary Immune Response to KLH Immunisation.

To show the effect of anti-CD40L therapy on the primary immune response to KLH immunization a similar study to that described by Gobburu, J. V. S. et al., 1998 can be carried out (Gobburu, J. V. S., Tenhoor, C., Rogge, M. C., Frazier, D. E., Thomas, D., Benjamin, C., Hess, D. M., & Jusko, W. J. (1998) JPET, 286, 925-930.

A study example could be as follows: Cynomolgus monkeys are injected with an anti-CD40L antibody or dAb format at a dosing of 10 mg/kg at time 0 h, 168 h and 336 h. At 24 h the animals receive a single intradermal injection of 100 μg highly purified keyhole limpet hemocyanin (KLH). The serum is tested for a KLH response prior to the start and following completion of the study. The animals are allowed to recover for a suitable time to ensure that the dAb molecule has cleared the circulation, then injected with KLH (without dAb) to determine if the animal can raise an immune response against KLH. Alternative antigens can be used for the study if an earlier response to KLH is detected prior to the start of the study.

The immune response to KLH will be measured by a suitable ELISA, RIA or antibody titer assay. It is anticipated that the results would show that that the PEglyated monomeric DOM-24 would suppress the animals immune response to KLH. This would be shown in the reduction of the antibody titer compared to a positive control. The results could be normalized such that the positive control was deemed to be 100 and the reduction in immune response after the administration of the dAbs would be in the range of 10 to 90% ie 90 to 10 units.

```
Sequence of the DOM7h-26-DOM-24
                                          (SEQ ID NO: 88)
LEKREVQLLESGGGLVQPGGSLRLSCTASGFTFDEYNMSWVRQAPGKGLE

WVSTILPHGDRTYYADSVKGRFTISRDNSKNTLYLQMNSLRAEDTAVYYC

AKQDPLYRFDYWGQGTLVTVSSAAAEVQLLESGGGLVQPGGSLRLSCAAS

GFTFSNYQMAWVRQAPGKGLEWVSSITSEGGSTYYADSVKGRFTISRDNS

KNTLYLQMNSLRAEDTAVYYCAKPGKNFDYWGQGTLVTVSS

Sequence of the DOM7h-26
                                          (SEQ ID NO: 89)
DIQMTQSPSSLSASVGDRVTITCRASQKIATYLNWYQQKPGKAPKLLIYR

SSSLQSAVPSRFSGSGSGTVFTLTISSLQPEDFATYYCQQTYAVPPTFGQ

GTKVEIKR
```

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

Annex 1; Polypeptides Which Enhance Half-Life In Vivo.

Alpha-1 Glycoprotein (Orosomucoid) (AAG)
Alpha-1 Antichyromotrypsin (ACT)
Alpha-1 Antitrypsin (AAT)
Alpha-1 Microglobulin (Protein HC) (AIM)
Alpha-2 Macroglobulin (A2M)
Antithrombin III (AT III)
Apolipoprotein A-1 (Apo A-1)
Apoliprotein B (Apo B)
Beta-2-microglobulin (B2M)
Ceruloplasmin (Cp)
Complement Component (C3)
Complement Component (C4)
C1 Esterase Inhibitor (C1 INH)
C-Reactive Protein (CRP)
Cystatin C (Cys C)
Ferritin (FER)
Fibrinogen (FIB)
Fibronectin (FN)
Haptoglobin (Hp)
Hemopexin (HPX)
Immunoglobulin A (IgA)
Immunoglobulin D (IgD)
Immunoglobulin E (IgE)
Immunoglobulin G (IgG)
Immunoglobulin M (IgM)
Immunoglobulin Light Chains (kappa/lambda)
Lipoprotein(a) [Lp(a)]
Mannose-binding protein (MBP)
Myoglobin (Myo)
Neonatal Fc (FcRn)
Plasminogen (PSM)
Prealbumin (Transthyretin) (PAL)
Retinol-binding protein (RBP)
Rheomatoid Factor (RF)
Serum Amyloid A (SAA)
Soluble Transferrin Receptor (sTfR)
Transferrin (Tf)

| Annex 2 | |
|---|---|
| Pairing | Therapeutic relevant references. |
| TNF ALPHA/TGF-β | TGF-b and TNF when injected into the ankle joint of collagen induced arthritis model significantly enhanced joint inflammation. In non-collagen challenged mice there was no effect. |
| TNF ALPHA/IL-1 | TNF and IL-1 synergize in the pathology of uveitis.<br>TNF and IL-1 synergize in the pathology of malaria (hypoglycaemia, NO).<br>TNF and IL-1 synergize in the induction of polymorphonuclear (PMN) cells migration in inflammation.<br>IL-1 and TNF synergize to induce PMN infiltration into the peritoneum.<br>IL-1 and TNF synergize to induce the secretion of IL-1 by endothelial cells. Important in inflammation.<br>IL-1 or TNF alone induced some cellular infiltration into knee synovium. IL-1 induced PMNs, TNF - monocytes. Together they induced a more severe infiltration due to increased PMNs.<br>Circulating myocardial depressant substance (present in sepsis) is low levels of IL-1 and TNFacting synergistically. |
| TNF ALPHA/IL-2 | Most relating to synergisitic activation of killer T-cells. |
| TNF ALPHA/IL-3 | Synergy of interleukin 3 and tumor necrosis factor alpha in stimulating clonal growth of acute myelogenous leukemia blasts is the result of induction of secondary hematopoietic cytokines by tumor necrosis factor alpha.<br>Cancer Res. 1992 Apr 15; 52(8): 2197-201. |
| TNF ALPHA/IL-4 | IL-4 and TNF synergize to induce VCAM expression on endothelial cells. Implied to have a role in asthma. Same for synovium - implicated in RA.<br>TNF and IL-4 synergize to induce IL-6 expression in keratinocytes.<br>Sustained elevated levels of VCAM-1 in cultured fibroblast-like synoviocytes can be achieved by TNF-alpha in combination with either IL-4 or IL-13 through increased mRNA stability. Am J Pathol. 1999 Apr; 154(4): 1149-58 |
| TNF ALPHA/IL-5 | Relationship between the tumor necrosis factor system and the serum interleukin-4, interleukin-5, interleukin-8, eosinophil cationic protein, and immunoglobulin E levels in the bronchial hyperreactivity of adults and their children. Allergy Asthma Proc. 2003 Mar-Apr; 24(2): 111-8. |
| TNF ALPHA/IL-6 | TNF and IL-6 are potent growth factors for OH-2, a novel human myeloma cell line. Eur J Haematol. 1994 Jul; 53(1): 31-7. |
| TNF ALPHA/IL-8 | TNF and IL-8 synergized with PMNs to activate platelets.<br>Implicated in Acute Respiratory Distress Syndrome.<br>See IL-5/TNF (asthma). Synergism between interleukin-8 and tumor necrosis factor-alpha for neutrophil-mediated platelet activation. Eur Cytokine Netw. 1994 Sep-Oct; 5(5): 455-60. (adult respiratory distress syndrome (ARDS)) |
| TNF ALPHA/IL-9 | |
| TNF ALPHA/IL-10 | IL-10 induces and synergizes with TNF in the induction of HIV expression in chronically infected T-cells. |
| TNF ALPHA/IL-11 | Cytokines synergistically induce osteoclast differentiation: support by immortalized or normal calvarial cells. Am J Physiol Cell Physiol. 2002 Sep; 283(3): C679-87. (Bone loss) |
| TNF ALPHA/IL-12 | |
| TNF ALPHA/IL-13 | Sustained elevated levels of VCAM-1 in cultured fibroblast-like synoviocytes can be achieved by TNF-alpha in combination with either IL-4 or IL-13 through increased mRNA stability. Am J Pathol. 1999 Apr; 154(4): 1149-58.<br>Interleukin-13 and tumour necrosis factor-alpha synergistically induce eotaxin production in human nasal fibroblasts. Clin Exp Allergy. 2000 Mar; 30(3): 348-55.<br>Interleukin-13 and tumour necrosis factor-alpha synergistically induce eotaxin production in human nasal fibroblasts. Clin Exp Allergy. 2000 Mar; 30(3): 348-55 (allergic inflammation)<br>Implications of serum TNF-beta and IL-13 in the treatment response of childhood nephrotic syndrome. Cytokine. 2003 Feb 7; 21(3): 155-9. |
| TNF ALPHA/IL-14 | Effects of inhaled tumour necrosis factor alpha in subjects with mild asthma. Thorax. 2002 Sep; 57(9): 774-8. |
| TNF ALPHA/IL-15 | Effects of inhaled tumour necrosis factor alpha in subjects with mild asthma. Thorax. 2002 Sep; 57(9): 774-8. |
| TNF | Tumor necrosis factor-alpha-induced synthesis of interleukin- |

-continued

| Annex 2 | |
|---|---|
| Pairing | Therapeutic relevant references. |
| ALPHA/IL-16 | 16 in airway epithelial cells: priming for serotonin stimulation. Am J Respir Cell Mol Biol. 2003 Mar; 28(3): 354-62. (airway inflammation)<br>Correlation of circulating interleukin 16 with proinflammatory cytokines in patients with rheumatoid arthritis. Rheumatology (Oxford). 2001 Apr; 40(4): 474-5. No abstract available.<br>Interleukin 16 is up-regulated in Crohn's disease and participates in TNBS colitis in mice. Gastroenterology. 2000 Oct; 119(4): 972-82. |
| TNF ALPHA/IL-17 | Inhibition of interleukin-17 prevents the development of arthritis in vaccinated mice challenged with Borrelia burgdorferi. Infect Immun. 2003 Jun; 71(6): 3437-42.<br>Interleukin 17 synergises with tumour necrosis factor alpha to induce cartilage destruction in vitro. Ann Rheum Dis. 2002 Oct; 61(10): 870-6.<br>A role of GM-CSF in the accumulation of neutrophils in the airways caused by IL-17 and TNF-alpha. Eur Respir J. 2003 Mar; 21(3): 387-93. (Airway inflammation)<br>Abstract Interleukin-1, tumor necrosis factor alpha, and interleukin-17 synergistically up-regulate nitric oxide and prostaglandin E2 production in explants of human osteoarthritic knee menisci. Arthritis Rheum. 2001 Sep; 44(9): 2078-83. |
| TNF ALPHA/IL-18 | Association of interleukin-18 expression with enhanced levels of both interleukin-1beta and tumor necrosis factor alpha in knee synovial tissue of patients with rheumatoid arthritis. Arthritis Rheum. 2003 Feb; 48(2): 339-47.<br>Abstract Elevated levels of interleukin-18 and tumor necrosis factor-alpha in serum of patients with type 2 diabetes mellitus: relationship with diabetic nephropathy. Metabolism. 2003 May; 52(5): 605-8. |
| TNF ALPHA/IL-19 | Abstract IL-19 induces production of IL-6 and TNF-alpha and results in cell apoptosis through TNF-alpha. J Immunol. 2002 Oct 15; 169(8): 4288-97. |
| TNF ALPHA/IL-20 | Abstract Cytokines: IL-20-a new effector in skin inflammation. Curr Biol. 2001 Jul 10; 11(13): R531-4 |
| TNF ALPHA/Complement | Inflammation and coagulation: implications for the septic patient. Clin Infect Dis. 2003 May 15; 36(10): 1259-65. Epub 2003 May 08. Review. |
| TNF ALPHA/IFN-γ | MHC induction in the brain.<br>Synergize in anti-viral response/IFN-β induction.<br>Neutrophil activation/respiratory burst.<br>Endothelial cell activation<br>Toxicities noted when patients treated with TNF/IFN-γ as anti-viral therapy<br>Fractalkine expression by human astrocytes.<br>Many papers on inflammatory responses - i.e. LPS, also macrophage activation.<br>Anti-TNF and anti-IFN-γ synergize to protect mice from lethal endotoxemia. |
| TGF-β/IL-1 | Prostaglndin synthesis by osteoblasts<br>IL-6 production by intestinal epithelial cells (inflammation model)<br>Stimulates IL-11 and IL-6 in lung fibroblasts (inflammation model)<br>IL-6 and IL-8 production in the retina |
| TGF-β/IL-6 | Chondrocarcoma proliferation |
| IL-1/IL-2 | B-cell activation<br>LAK cell activation<br>T-cell activation<br>IL-1 synergy with IL-2 in the generation of lymphokine activated killer cells is mediated by TNF-alpha and beta (lymphotoxin). Cytokine. 1992 Nov; 4(6): 479-87. |
| IL-1/IL-3 | |
| IL-1/IL-4 | B-cell activation<br>IL-4 induces IL-1 expression in endothelial cell activation. |
| IL-1/IL-5 | |
| IL-1/IL-6 | B cell activation<br>T cell activation (can replace accessory cells)<br>IL-1 induces IL-6 expression<br>C3 and serum amyloid expression (acute phase response)<br>HIV expression<br>Cartilage collagen breakdown. |
| IL-1/IL-7 | IL-7 is requisite for IL-1-induced thymocyte proliferation.<br>Involvement of IL-7 in the synergistic effects of granulocyte- |

-continued

| Annex 2 | |
|---|---|
| Pairing | Therapeutic relevant references. |
| | macrophage colony-stimulating factor or tumor necrosis factor with IL-1. J Immunol. 1992 Jan 1; 148(1): 99-105. |
| IL-1/IL-8 | |
| IL-1/IL-10 | |
| IL-1/IL-11 | Cytokines synergistically induce osteoclast differentiation: support by immortalized or normal calvarial cells. Am J Physiol Cell Physiol. 2002 Sep; 283(3): C679-87. (Bone loss) |
| IL-1/IL-16 | Correlation of circulating interleukin 16 with proinflammatory cytokines in patients with rheumatoid arthritis. Rheumatology (Oxford). 2001 Apr; 40(4): 474-5. No abstract available. |
| IL-1/IL-17 | Inhibition of interleukin-17 prevents the development of arthritis in vaccinated mice challenged with Borrelia burgdorferi. Infect Immun. 2003 Jun; 71(6): 3437-42.<br>Contribution of interleukin 17 to human cartilage degradation and synovial inflammation in osteoarthritis. Osteoarthritis Cartilage. 2002 Oct; 10(10): 799-807.<br>Abstract Interleukin-1, tumor necrosis factor alpha, and interleukin-17 synergistically up-regulate nitric oxide and prostaglandin E2 production in explants of human osteoarthritic knee menisci. Arthritis Rheum. 2001 Sep; 44(9): 2078-83. |
| IL-1/IL-18 | Association of interleukin-18 expression with enhanced levels of both interleukin-1beta and tumor necrosis factor alpha in knee synovial tissue of patients with rheumatoid arthritis. Arthritis Rheum. 2003 Feb; 48(2): 339-47. |
| IL-1/IFN-g | |
| IL-2/IL-3 | T-cell proliferation<br>B cell proliferation |
| IL-2/IL-4 | B-cell proliferation<br>T-cell proliferation<br>(selectively inducing activation of CD8 and NK lymphocytes)IL-2R beta agonist P1-30 acts in synergy with IL-2, IL-4, IL-9, and IL-15: biological and molecular effects. J Immunol. 2000 Oct 15; 165(8): 4312-8. |
| IL-2/IL-5 | B-cell proliferation/Ig secretion<br>IL-5 induces IL-2 receptors on B-cells |
| IL-2/IL-6 | Development of cytotoxic T-cells |
| IL-2/IL-7 | |
| IL-2/IL-9 | See IL-2/IL-4 (NK-cells) |
| IL-2/IL-10 | B-cell activation |
| IL-2/IL-12 | IL-12 synergizes with IL-2 to induce lymphokine-activated cytotoxicity and perforin and granzyme gene expression in fresh human NK cells. Cell Immunol. 1995 Oct 1; 165(1): 33-43. (T-cell activation) |
| IL-2/IL-15 | See IL-2/IL-4 (NK cells)<br>(T cell activation and proliferation) IL-15 and IL-2: a matter of life and death for T cells in vivo. Nat Med. 2001 Jan; 7(1): 114-8. |
| IL-2/IL-16 | Synergistic activation of CD4+ T cells by IL-16 and IL-2. J Immunol. 1998 Mar 1; 160(5): 2115-20. |
| IL-2/IL-17 | Evidence for the early involvement of interleukin 17 in human and experimental renal allograft rejection. J Pathol. 2002 Jul; 197(3): 322-32. |
| IL-2/IL-18 | Interleukin 18 (IL-18) in synergy with IL-2 induces lethal lung injury in mice: a potential role for cytokines, chemokines, and natural killer cells in the pathogenesis of interstitial pneumonia. Blood. 2002 Feb 15; 99(4): 1289-98. |
| IL-2/TGF-β | Control of CD4 effector fate: transforming growth factor beta 1 and interleukin 2 synergize to prevent apoptosis and promote effector expansion. J Exp Med. 1995 Sep 1; 182(3): 699-709. |
| IL-2/IFN-γ | Ig secretion by B-cells<br>IL-2 induces IFN-γ expression by T-cells |
| IL-2/IFN-α/β | None |
| IL-3/IL-4 | Synergize in mast cell growth<br>Synergistic effects of IL-4 and either GM-CSF or IL-3 on the induction of CD23 expression by human monocytes: regulatory effects of IFN-alpha and IFN-gamma. Cytokine. 1994 Jul; 6(4): 407-13. |
| IL-3/IL-5 | |
| IL-3/IL-6 | |
| IL-3/IFN-γ | IL-4 and IFN-gamma synergistically increase total polymeric IgA receptor levels in human intestinal epithelial cells. Role of protein tyrosine kinases. J Immunol. 1996 Jun 15; 156(12): 4807-14. |
| IL-3/GM-CSF | Differential regulation of human eosinophil IL-3, IL-5, and GM-CSF receptor alpha-chain expression by cytokines: IL-3, IL-5, and GM-CSF down-regulate IL-5 receptor alpha |

-continued

Annex 2

| Pairing | Therapeutic relevant references. |
|---|---|
| | expression with loss of IL-5 responsiveness, but up-regulate IL-3 receptor alpha expression. J Immunol. 2003 Jun 1; 170(11): 5359-66. (allergic inflammation) |
| IL-4/IL-2 | IL-4 synergistically enhances both IL-2- and IL-12-induced IFN-{gamma} expression in murine NK cells. Blood. 2003 Mar 13 [Epub ahead of print] |
| IL-4/IL-5 | Enhanced mast cell histamine etc. secretion in response to IgE A Th2-like cytokine response is involved in bullous pemphigoid. the role of IL-4 and IL-5 in the pathogenesis of the disease. Int J Immunopathol Pharmacol. 1999 May-Aug; 12(2): 55-61. |
| IL-4/IL-6 | |
| IL-4/IL-10 | |
| IL-4/IL-11 | Synergistic interactions between interleukin-11 and interleukin-4 in support of proliferation of primitive hematopoietic progenitors of mice. Blood. 1991 Sep 15; 78(6): 1448-51. |
| IL-4/IL-12 | Synergistic effects of IL-4 and IL-18 on IL-12-dependent IFN-gamma production by dendritic cells. J Immunol. 2000 Jan 1; 164(1): 64-71. (increase Th1/Th2 differentiation) IL-4 synergistically enhances both IL-2- and IL-12-induced IFN-{gamma} expression in murine NK cells. Blood. 2003 Mar 13 [Epub ahead of print] |
| IL-4/IL-13 | Abstract Interleukin-4 and interleukin-13 signaling connections maps. Science. 2003 Jun 6; 300(5625): 1527-8. (allergy, asthma) Inhibition of the IL-4/IL-13 receptor system prevents allergic sensitization without affecting established allergy in a mouse model for allergic asthma. J Allergy Clin Immunol. 2003 Jun; 111(6): 1361-1369. |
| IL-4/IL-16 | (asthma) Interleukin (IL)-4/IL-9 and exogenous IL-16 induce IL-16 production by BEAS-2B cells, a bronchial epithelial cell line. Cell Immunol. 2001 Feb 1; 207(2): 75-80 |
| IL-4/IL-17 | Interleukin (IL)-4 and IL-17 synergistically stimulate IL-6 secretion in human colonic myofibroblasts. Int J Mol Med. 2002 Nov; 10(5): 631-4. (Gut inflammation) |
| IL-4/IL-24 | IL-24 is expressed by rat and human macrophages. Immunobiology. 2002 Jul; 205(3): 321-34. |
| IL-4/IL-25 | Abstract New IL-17 family members promote Th1 or Th2 responses in the lung: in vivo function of the novel cytokine IL-25. J Immunol. 2002 Jul 1; 169(1): 443-53. (allergic inflammation) Abstract Mast cells produce interleukin-25 upon Fcepsilon RI-mediated activation. Blood. 2003 May 1; 101(9): 3594-6. Epub 2003 Jan 02. (allergic inflammation) |
| IL-4/IFN-γ | Abstract Interleukin 4 induces interleukin 6 production by endothelial cells: synergy with interferon-gamma. Eur J Immunol. 1991 Jan; 21(1): 97-101. |
| IL-4/SCF | Regulation of human intestinal mast cells by stem cell factor and IL-4. Immunol Rev. 2001 Feb; 179: 57-60. Review. |
| IL-5/IL-3 | Differential regulation of human eosinophil IL-3, IL-5, and GM-CSF receptor alpha-chain expression by cytokines: IL-3, IL-5, and GM-CSF down-regulate IL-5 receptor alpha expression with loss of IL-5 responsiveness, but up-regulate IL-3 receptor alpha expression. J Immunol. 2003 Jun 1; 170(11): 5359-66. (Allergic inflammation see abstract) |
| IL-5/IL-6 | |
| IL-5/IL-13 | Inhibition of allergic airways inflammation and airway hyperresponsiveness in mice by dexamethasone: role of eosinophils, IL-5, eotaxin, and IL-13. J Allergy Clin Immunol. 2003 May; 111(5): 1049-61. |
| IL-5/IL-17 | Interleukin-17 orchestrates the granulocyte influx into airways after allergen inhalation in a mouse model of allergic asthma. Am J Respir Cell Mol Biol. 2003 Jan; 28(1): 42-50. |
| IL-5/IL-25 | Abstract New IL-17 family members promote Th1 or Th2 responses in the lung: in vivo function of the novel cytokine IL-25. J Immunol. 2002 Jul 1; 169(1): 443-53. (allergic inflammation) Abstract Mast cells produce interleukin-25 upon Fcepsilon RI-mediated activation. Blood. 2003 May 1; 101(9): 3594-6. Epub 2003 Jan 02. (allergic inflammation) |
| IL-5/IFN-γ | |
| IL-5/GM-CSF | Differential regulation of human eosinophil IL-3, IL-5, and GM-CSF receptor alpha-chain expression by cytokines: IL-3, IL-5, and GM-CSF down-regulate IL-5 receptor alpha expression with loss of IL-5 responsiveness, but up-regulate |

-continued

| Annex 2 | |
|---|---|
| Pairing | Therapeutic relevant references. |
| | IL-3 receptor alpha expression. J Immunol. 2003 Jun 1; 170(11): 5359-66. (Allergic inflammation) |
| IL-6/IL-10 | |
| IL-6/IL-11 | |
| IL-6/IL-16 | Interleukin-16 stimulates the expression and production of pro-inflammatory cytokines by human monocytes. Immunology. 2000 May; 100(1): 63-9. |
| IL-6/IL-17 | Stimulation of airway mucin gene expression by interleukin (IL)-17 through IL-6 paracrine/autocrine loop. J Biol Chem. 2003 May 9; 278(19): 17036-43. Epub 2003 Mar 06. (airway inflammation, asthma) |
| IL-6/IL-19 | Abstract IL-19 induces production of IL-6 and TNF-alpha and results in cell apoptosis through TNF-alpha. J Immunol. 2002 Oct 15; 169(8): 4288-97. |
| IL-6/IFN-g | |
| IL-7/IL-2 | Interleukin 7 worsens graft-versus-host disease. Blood. 2002 Oct 1; 100(7): 2642-9. |
| IL-7/IL-12 | Synergistic effects of IL-7 and IL-12 on human T cell activation. J Immunol. 1995 May 15; 154(10): 5093-102. |
| IL-7/IL-15 | Interleukin-7 and interleukin-15 regulate the expression of the bcl-2 and c-myb genes in cutaneous T-cell lymphoma cells. Blood. 2001 Nov 1; 98(9): 2778-83. (growth factor) |
| IL-8/IL-11 | Abnormal production of interleukin (IL)-11 and IL-8 in polycythaemia vera. Cytokine. 2002 Nov 21; 20(4): 178-83. |
| IL-8/IL-17 | The Role of IL-17 in Joint Destruction. Drug News Perspect. 2002 Jan; 15(1): 17-23. (arthritis)<br>Abstract Interleukin-17 stimulates the expression of interleukin-8, growth-related oncogene-alpha, and granulocyte-colony-stimulating factor by human airway epithelial cells. Am J Respir Cell Mol Biol. 2002 Jun; 26(6): 748-53. (airway inflammation) |
| IL-8/GSF | Interleukin-8: an autocrine/paracrine growth factor for human hematopoietic progenitors acting in synergy with colony stimulating factor-1 to promote monocyte-macrophage growth and differentiation. Exp Hematol. 1999 Jan; 27(1): 28-36. |
| IL-8/VGEF | Intracavitary VEGF, bFGF, IL-8, IL-12 levels in primary and recurrent malignant glioma. J Neurooncol. 2003 May; 62(3): 297-303. |
| IL-9/IL-4 | Anti-interleukin-9 antibody treatment inhibits airway inflammation and hyperreactivity in mouse asthma model. Am J Respir Crit Care Med. 2002 Aug 1; 166(3): 409-16. |
| IL-9/IL-5 | Pulmonary overexpression of IL-9 induces Th2 cytokine expression, leading to immune pathology. J Clin Invest. 2002 Jan; 109(1): 29-39.<br>Th2 cytokines and asthma. Interleukin-9 as a therapeutic target for asthma. Respir Res. 2001; 2(2): 80-4. Epub 2001 Feb 15. Review.<br>Abstract Interleukin-9 enhances interleukin-5 receptor expression, differentiation, and survival of human eosinophils. Blood. 2000 Sep 15; 96(6): 2163-71 (asthma) |
| IL-9/IL-13 | Anti-interleukin-9 antibody treatment inhibits airway inflammation and hyperreactivity in mouse asthma model. Am J Respir Crit Care Med. 2002 Aug 1; 166(3): 409-16.<br>Direct effects of interleukin-13 on epithelial cells cause airway hyperreactivity and mucus overproduction in asthma. Nat Med. 2002 Aug; 8(8): 885-9. |
| IL-9/IL-16 | See IL-4/IL-16 |
| IL-10/IL-2 | The interplay of interleukin-10 (IL-10) and interleukin-2 (IL-2) in humoral immune responses: IL-10 synergizes with IL-2 to enhance responses of human B lymphocytes in a mechanism which is different from upregulation of CD25 expression. Cell Immunol. 1994 Sep; 157(2): 478-88. |
| IL-10/IL-12 | |
| IL-10/TGF-β | IL-10 and TGF-beta cooperate in the regulatory T cell response to mucosal allergens in normal immunity and specific immunotherapy. Eur J Immunol. 2003 May; 33(5): 1205-14. |
| IL-10/IFN-γ | |
| IL-11/IL-6 | Interleukin-6 and interleukin-11 support human osteoclast formation by a RANKL-independent mechanism. Bone. 2003 Jan; 32(1): 1-7. (bone resorption in inflammation) |
| IL-11/IL-17 | Polarized in vivo expression of IL-11 and IL-17 between acute and chronic skin lesions. J Allergy Clin Immunol. 2003 Apr; 111(4): 875-81. (allergic dermatitis)<br>IL-17 promotes bone erosion in murine collagen-induced |

-continued

Annex 2

| Pairing | Therapeutic relevant references. |
|---|---|
| | arthritis through loss of the receptor activator of NF-kappa B ligand/osteoprotegerin balance. J Immunol. 2003 Mar 1; 170(5): 2655-62. |
| IL-11/TGF-β | Polarized in vivo expression of IL-11 and IL-17 between acute and chronic skin lesions. J Allergy Clin Immunol. 2003 Apr; 111(4): 875-81. (allergic dermatitis) |
| IL-12/IL-13 | Relationship of Interleukin-12 and Interleukin-13 imbalance with class-specific rheumatoid factors and anticardiolipin antibodies in systemic lupus erythematosus. Clin Rheumatol. 2003 May; 22(2): 107-11. |
| IL-12/IL-17 | Upregulation of interleukin-12 and -17 in active inflammatory bowel disease. Scand J Gastroenterol. 2003 Feb; 38(2): 180-5. |
| IL-12/IL-18 | Synergistic proliferation and activation of natural killer cells by interleukin 12 and interleukin 18. Cytokine. 1999 Nov; 11(11): 822-30. |
| | Inflammatory Liver Steatosis Caused by IL-12 and IL-18. J Interferon Cytokine Res. 2003 Mar; 23(3); 155-62. |
| IL-12/IL-23 | nterleukin-23 rather than interleukin-12 is the critical cytokine for autoimmune inflammation of the brain. Nature. 2003 Feb 13; 421(6924): 744-8. |
| | Abstract A unique role for IL-23 in promoting cellular immunity. J Leukoc Biol. 2003 Jan; 73(1): 49-56. Review. |
| IL-12/IL-27 | Abstract IL-27, a heterodimeric cytokine composed of EBI3 and p28 protein, induces proliferation of naive CD4(+) T cells. Immunity. 2002 Jun; 16(6): 779-90. |
| IL-12/IFN-γ | IL-12 induces IFN-γ expression by B and T-cells as part of immune stimulation. |
| IL-13/IL-5 | See IL-5/IL-13 |
| IL-13/IL-25 | Abstract New IL-17 family members promote Th1 or Th2 responses in the lung: in vivo function of the novel cytokine IL-25. J Immunol. 2002 Jul 1; 169(1): 443-53. (allergic inflammation) |
| | Abstract Mast cells produce interleukin-25 upon Fcepsilon RI-mediated activation. Blood. 2003 May 1; 101(9): 3594-6. Epub 2003 Jan 02. (allergic inflammation) |
| IL-15/IL-13 | Differential expression of interleukins (IL)-13 and IL-15 in ectopic and eutopic endometrium of women with endometriosis and normal fertile women. Am J Reprod Immunol. 2003 Feb; 49(2): 75-83. |
| IL-15/IL-16 | IL-15 and IL-16 overexpression in cutaneous T-cell lymphomas: stage-dependent increase in mycosis fungoides progression. Exp Dermatol. 2000 Aug; 9(4): 248-51. |
| IL-15/IL-17 | Abstract IL-17, produced by lymphocytes and neutrophils, is necessary for lipopolysaccharide-induced airway neutrophilia: IL-15 as a possible trigger. J Immunol. 2003 Feb 15; 170(4): 2106-12. (airway inflammation) |
| IL-15/IL-21 | IL-21 in Synergy with IL-15 or IL-18 Enhances IFN-gamma Production in Human NK and T Cells. J Immunol. 2003 Jun 1; 170(11): 5464-9. |
| IL-17/IL-23 | Interleukin-23 promotes a distinct CD4 T cell activation state characterized by the production of interleukin-17. J Biol Chem. 2003 Jan 17; 278(3): 1910-4. Epub 2002 Nov 03 |
| IL-17/TGF-β | Polarized in vivo expression of IL-11 and IL-17 between acute and chronic skin lesions. J Allergy Clin Immunol. 2003 Apr; 111(4): 875-81. (allergic dermatitis) |
| IL-18/IL-12 | Synergistic proliferation and activation of natural killer cells by interleukin 12 and interleukin 18. Cytokine. 1999 Nov; 11(11): 822-30. |
| | Abstract Inhibition of in vitro immunoglobulin production by IL-12 in murine chronic graft-vs.-host disease: synergism with IL-18. Eur J Immunol. 1998 Jun; 28(6): 2017-24. |
| IL-18/IL-21 | IL-21 in Synergy with IL-15 or IL-18 Enhances IFN-gamma Production in Human NK and T Cells. J Immunol. 2003 Jun 1; 170(11): 5464-9. |
| IL-18/TGF-β | Interleukin 18 and transforming growth factor betal in the serum of patients with Graves' ophthalmopathy treated with corticosteroids. Int Immunopharmacol. 2003 Apr; 3(4): 549-52. |
| IL-18/IFN-γ | |
| Anti-TNF ALPHA/anti-CD4 | Synergistic therapeutic effect in DBA/1 arthritic mice. |

-continued

Annex 3: Oncology combinations

| Target | Disease | Pair with |
|---|---|---|
| CD89* | Use as cytotoxic cell recruiter | all |
| CD19 | B cell lymphomas | HLA-DR<br>CD5 |
| HLA-DR | B cell lymphomas | CD89<br>CD19<br>CD5 |
| CD38 | Multiple myeloma | CD138<br>CD56<br>HLA-DR |
| CD138 | Multiple myeloma | CD38<br>CD56<br>HLA-DR |
| CD138 | Lung cancer | CD56<br>CEA |
| CD33 | Acute myelod lymphoma | CD34<br>HLA-DR |
| CD56 | Lung cancer | CD138<br>CEA |
| CEA | Pan carcinoma | MET receptor |
| VEGF | Pan carcinoma | MET receptor |
| VEGF receptor | Pan carcinoma | MET receptor |
| IL-13 | Asthma/pulmonary inflammation | IL-4<br>IL-5<br>Eotaxin(s)<br>MDC<br>TARC<br>TNFα<br>IL-9<br>EGFR<br>CD40L<br>IL-25<br>MCP-1<br>TGFβ |
| IL-4 | Asthma | IL-13<br>IL-5<br>Eotaxin(s)<br>MDC<br>TARC<br>TNFα<br>IL-9<br>EGFR<br>CD40L<br>IL-25<br>MCP-1<br>TGFβ |
| Eotaxin | Asthma | IL-5<br>Eotaxin-2<br>Eotaxin-3 |
| EGFR | cancer | HER2/neu<br>HER3<br>HER4 |
| HER2 | cancer | HER3<br>HER4 |
| TNFR1 | RA/Crohn's disease | IL-1R<br>IL-6R<br>IL-18R |
| TNFα | RA/Crohn's disease | IL-1α/β<br>IL-6<br>IL-18<br>ICAM-1<br>IL-15<br>IL-17 |
| IL-1R | RA/Crohn's disease | IL-6R<br>IL-18R |
| IL-18R | RA/Crohn's disease | IL-6R |

The invention claimed is:

1. A method of antagonizing an activity of CD40 or CD40L in an individual having an autoimmune disease, comprising administering to said individual, a polypeptide comprising a single immunoglobulin variable domain, wherein said single immunoglobulin variable domain specifically binds CD40L independently of an additional antibody VH or VL domain and antagonizes an activity of CD40L and/or antagonizes an activity of CD40 mediated by an interaction between CD40 and CD40L, wherein said single immunoglobulin variable domain consists of an amino acid sequence which is 85% identical to a sequence selected from the group consisting of SEQ ID NOS: 7-82 and SEQ ID NOS: 246-360.

2. The method according to claim 1 wherein said autoimmune disease is selected from the group consisting of systemic lupus erythematosis, multiple sclerosis, and rheumatoid arthritis, and diabetes.

3. The method according to claim 1 wherein said single immunoglobulin variable domain inhibits the binding of CD40L to CD40.

4. The method according to claim 1 wherein said single immunoglobulin variable domain is human.

5. The method according to claim 1 wherein said single immunoglobulin variable domain consists of an amino acid sequence selected from the group consisting of SEQ ID NOS: 7-82 and SEQ ID NOS: 246-360.

6. The method according to claim 1 wherein said single immunoglobulin variable domain consists of an amino acid sequence that is at least 80% homologous to SEQ ID NO: 26.

7. The method according to claim 5 wherein said single immunoglobulin variable domain consists of an amino acid sequence that is identical to SEQ ID NO: 26.

8. The method according to claim 1 wherein binding of said single immunoglobulin variable domain to CD40L does not substantially agonize CD40 and/or CD40L activity.

9. The method according to claim 1 wherein the presence of said polypeptide in a standard platelet aggregation assay is correlated with 25% or less aggregation over the aggregation level observed in a negative control assay.

10. The method of claim 3, wherein said single immunoglobulin variable domain inhibits binding of CD40L to CD40 with an IC50 in the range of 20 pM to 1.5 μM inclusive.

11. The method of claim 2, wherein polypeptide is PEG-linked, optionally via linkage at a cysteine or lysine residue on said polypeptide.

12. The method of claim 11, wherein said PEG-linked polypeptide has a hydrodynamic size of at least 24 kD.

13. The method of claim 11 wherein the total PEG size is from 20 to 60 kD, inclusive.

14. The method of claim 11 wherein said PEG-linked polypeptide has a hydrodynamic size of at least 200 kD.

15. The method of claim 11 wherein said PEG-linked polypeptide has an increased in vivo half-life relative to the same polypeptide lacking linked polyethylene glycol.

16. The method of claim 15 wherein the tα-half life of the polypeptide is increased by 10% or more.

17. The method of claim 15 wherein tα-half life of the polypeptide is in the range of 0.25 minutes to 12 hours.

18. The method of claim 15 wherein tα-half life of the polypeptide-is increased by 10% or more.

19. The method of claim 15 wherein the tα-half life of the polypeptide is in the range of 12 to 48 hours.

20. The method of claim 1, wherein said single immunoglobulin variable domain is linked to an antibody Fc region.

21. The method of claim 20, wherein said Fc region comprises one or both of CH2 and CH3 domains, and optionally a hinge region.

22. The method of claim 1, wherein said polypeptide is linked to an antibody Fc region.

23. The method of claim 22, wherein said Fc region comprises one or both of CH2 and CH3 domains, and optionally a hinge region.

24. A method of antagonizing an activity of CD40 or CD40L in an individual having a disease or disorder selected from the group consisting of allograft rejection, xenograft transplant rejection, and graft vs. host disease, comprising administering to said individual a polypeptide comprising a single immunoglobulin variable domain, wherein said single immunoglobulin variable domain specifically binds CD40L independently of an additional antibody VH or VL domain and antagonizes the activity of CD40L and/or antagonizes an activity of CD40 mediated by an interaction between CD40 and CD40L, wherein said single immunoglobulin variable domain consists of an amino acid sequence which is 85% identical to a sequence selected from the group consisting of SEQ ID NOS: 7-82 and SEQ ID NOS: 246-360.

25. The method according to claim 24, wherein said single immunoglobulin variable domain inhibits the binding of CD40L to CD40.

26. The method according to claim 24 wherein said single immunoglobulin variable domain is human.

27. The method according to claim 24 wherein said single immunoglobulin variable domain consists of an amino acid sequence selected from the group consisting of SEQ ID NOS: 7-82 and SEQ ID NOS: 246-360.

28. The method according to claim 27 wherein said single immunoglobulin variable domain consists of an amino acid sequence that is at least 80% homologous to SEQ ID NO: 26.

29. The method according to claim 27 wherein said single immunoglobulin variable domain consists of an amino acid sequence that is identical to SEQ ID NO: 26.

30. The method according to claim 24 wherein binding of said single immunoglobulin variable domain to CD40L does not substantially agonize CD40 and/or CD40L activity.

31. The method according to claim 24 wherein the presence of said polypeptide in a standard platelet aggregation assay is correlated with 25% or less aggregation over the aggregation level observed in a negative control assay.

32. The method of claim 25, wherein said single immunoglobulin variable domain inhibits binding of CD40L to CD40 with an 1050 in the range of 20 pM to 1.5 μM, inclusive.

33. The method of claim 24, wherein said polypeptide is PEG-linked, optionally via linkage at a cysteine or lysine residue on said polypeptide.

34. The method of claim 33, wherein said PEG-linked polypeptide has a hydrodynamic size of at least 24 kD.

35. The method of claim 34 wherein the total PEG size is from 20 to 60 kD, inclusive.

36. The method of claim 34 wherein said PEG-linked polypeptide has a hydrodynamic size of at least 200 kD.

37. The method of claim 34 wherein said PEG-linked polypeptide has an increased in vivo half-life relative to the same polypeptide lacking linked polyethylene glycol.

38. The method of claim 37 wherein the tα-half life of the polypeptide is increased by 10% or more.

39. The method of claim 37 wherein the tα-half life of the polypeptide is in the range of 0.25 minutes to 12 hours.

40. The method of claim 37 wherein the tα-half life of the polypeptide-is increased by 10% or more.

41. The method of claim 37 wherein the tα-half life of the polypeptide is in the range of 12 to 48 hours.

42. The method of claim 24, wherein said single immunoglobulin variable domain is linked to an antibody Fc region.

43. The method of claim 42, wherein said Fc region comprises one or both of CH2 and CH3 domains, and optionally a hinge region.

* * * * *

UNITED STATES PATENT AND TRADEMARK OFFICE

CERTIFICATE OF CORRECTION

PATENT NO. : 8,524,236 B2
APPLICATION NO. : 11/663247
DATED : September 3, 2013
INVENTOR(S) : Grant et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1765 days.

Signed and Sealed this
Fifteenth Day of September, 2015

Michelle K. Lee
*Director of the United States Patent and Trademark Office*